US008536306B2

(12) United States Patent
Stevens et al.

(10) Patent No.: US 8,536,306 B2
(45) Date of Patent: Sep. 17, 2013

(54) HUMAN $A_{2A}$ ADENOSINE RECEPTOR CRYSTALS AND USES THEREOF

(75) Inventors: Raymond C. Stevens, La Jolla, CA (US); Michael A. Hanson, San Marcos, CA (US); Vadim Cherezov, San Diego, CA (US); Mark Griffith, San Diego, CA (US); Veli-Pekka Jaakola, San Diego, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 13/121,923

(22) PCT Filed: Oct. 1, 2009

(86) PCT No.: PCT/US2009/059289
§ 371 (c)(1),
(2), (4) Date: Oct. 13, 2011

(87) PCT Pub. No.: WO2010/040003
PCT Pub. Date: Apr. 8, 2010

(65) Prior Publication Data
US 2012/0123092 A1 May 17, 2012

Related U.S. Application Data

(60) Provisional application No. 61/194,961, filed on Oct. 1, 2008.

(51) Int. Cl.
*C07K 14/705* (2006.01)
(52) U.S. Cl.
USPC .......................................................... 530/350
(58) Field of Classification Search
None
See application file for complete search history.

(56) References Cited

U.S. PATENT DOCUMENTS

| | | | |
|---|---|---|---|
| 6,448,377 B1 | 9/2002 | Kobilka et al. | |
| 6,555,545 B2 | 4/2003 | Cronstein et al. | |
| 7,790,850 B2 | 9/2010 | Kobilka et al. | |
| 2004/0137518 A1 | 7/2004 | Lambert, III et al. | |
| 2005/0124792 A1 | 6/2005 | Palczewski et al. | |
| 2005/0220799 A1 | 10/2005 | Sitkovsky et al. | |
| 2006/0094119 A1 | 5/2006 | Ismagilov et al. | |
| 2006/0188964 A1 | 8/2006 | Mancia et al. | |
| 2007/0020684 A1 | 1/2007 | Bledsoe et al. | |
| 2007/0031926 A1 | 2/2007 | Linden et al. | |
| 2008/0124808 A1 | 5/2008 | Rodgers et al. | |
| 2008/0201123 A1* | 8/2008 | Cosgrove | 703/11 |
| 2011/0031438 A1* | 2/2011 | Stevens et al. | 252/182.12 |

FOREIGN PATENT DOCUMENTS
WO WO 2006/036772 A2 6/2006

OTHER PUBLICATIONS

Doré et al., "Structure of the Adenosine A2A Receptor in Complex with ZM241385 and the Xanthines XAC and Caffeine", Structure 19:1283-1293, 2011.*
Lebon et al., "Agonist-bound adenosine A2A receptor structures reveal common features of GPCR activation", Nature 474:, 521-526, 2011.*
Supplementary Information to Lebon et al., "Agonist-bound adenosine A2A receptor structures reveal common features of GPCR activation", Nature 474:, 521-526, 2011, 11 pages.*
Angers, S. et al., "Detection of $\beta_2$-Adrenergic Receptor Dimerization in Living Cells Using Bioluminescence Resonance Energy Transfer (BRET)," Proc. Natl. Acad. Sci., Mar. 28, 2000, pp. 3684-3689, vol. 97, No. 7.
Audet, M. et al., "Insights Into Signaling from the $\beta_2$-Adrenergic Receptor," Nature Chemical Biology, Jul. 2008, pp. 397-403, vol. 4, No. 7.
Basheer, R. et al., "Adenosine and Sleep-Wake Regulation," Progress in Neurobiology, 2004, pp. 379-396, vol. 73.
Benarroch, E. E., "Adenosine and its Receptors," Neurology, Jan. 15, 2008, pp. 231-236, vol. 70.
Birnbaumer, L. et al., "Studies on the Intrinsic Activity (Efficacy) of Human Adrenergic Receptors," Texas Heart Institute Journal, 1994, pp. 16-21, vol. 21, No. 1.
Bissantz, C. et al., "Protein-Based Virtual Screening of Chemical Databases. II. Are Homology Models of G-Protein Coupled Receptors Suitable Targets?" Protein: Structure, Function, and Genetics, 2003, pp. 5-25, vol. 50.
Blum, D. et al., "Adenosine Receptors and Huntington's Disease: Implications for Pathogenesis and Therapeutics," The Lancet Neurology, Jun. 2003, pp. 366-374, vol. 2.
Brown, R. A. et al., "Adenosine Receptors and Asthma," British Journal of Pharmacology, 2008, pp. S446-S456, vol. 153, Suppl 1.
Burstein, E. S. et al., "The Second Intracellular Loop of the m5 Muscarinic Receptor is the Switch Which Enables G-Protein Coupling," The Journal of Biological Chemistry, Sep. 18, 1998, pp. 24322-24327, vol. 273, No. 38.
Caffrey, M., "A Lipid's Eye View of Membrane Protein Crystallization in Mesophases," Current Opinion in Structural Biology, 2000, pp. 486-497. vol. 10.
Caron, M.C. et al., "Catecholamine Receptors: Structure, Function, and Regulation," Recent Progress in Hormone Research, 1993, pp. 277-290, vol. 48.
Chelikani, P. et al., "Role of Group-Conserved Residues in the Helical Core of $\beta_2$-Adrenergic Receptor," PNAS, Apr. 24, 2007, pp. 7027-7032, vol. 104, No. 17.

(Continued)

*Primary Examiner* — David J Steadman
(74) *Attorney, Agent, or Firm* — Fenwick & West LLP

(57) ABSTRACT

The invention provides the structure of human $A_{2A}$ adenosine receptor protein bound to an antagonist. Methods of using one or more binding sites and other features of this G-protein coupled receptor to develop new therapeutics are also disclosed.

4 Claims, 19 Drawing Sheets

(56) References Cited

OTHER PUBLICATIONS

Cheng, A. et al., "A Simple Mechanical Mixer for Small Viscous Lipid-Containing Samples," Chemistry and Physics of Lipids, 1998, pp. 11-21, vol. 95.

Cherezov, V. et al., "High Resolution Crystal Structure of an Engineered Human $\beta_2$-Adrenergic G Protein-Coupled Receptor," Author Manuscript, Published in final edited form as: Science, Nov. 23, 2007, pp. 1258-1265, vol. 318, No. 5854.

Cherezov, V. et al., "High Resolution Crystal Structure of an Engineered Human $\beta_2$-Adrenergic G Protein-Coupled Receptor," Science, Nov. 23, 2007, pp. 1258-1265, vol. 318, No. 5854.

Cherezov, V. et al., "In *Meso* Structure of the Cobalamin Transporter, BtuB, at 1.95 Å Resolution," J. Mol. Biol., 2006, pp. 716-734, vol. 364.

Cherezov, V. et al., "Membrane Protein Crystallization in Meso: Lipid Type-Tailoring of the Cubic Phase," Biophysical Journal, Dec. 2002, pp. 3393-3407, vol. 83.

Cherezov, V. et al., "Nano-Volume Plates with Excellent Optical Properties for Fast, Inexpensive Crystallization Screening of Membrane Proteins," Journal of Applied Crystallography, 2003, pp. 1372-1377, vol. 36.

Cherezov, V. et al., "A Robotic System for Crystallizing Membrane and Soluble Proteins in Lipidic Mesophases," Acta Crystallographica Section D, Biological Crystallography, 2004, pp. 1795-1807, vol. D 60.

Cherezov, V. et al., "Room to Move: Crystallizing Membrane Proteins in Swollen Lipidic Mesophases," J. Mol. Biol., 2006, pp. 1605-1618, vol. 357.

Cohen, B. E. et al., "A Fluorescent Probe Designed for Studying Protein Conformational Change," Proc Natl Acad Sci U S A, Jan. 25, 2005, pp. 965-970, vol. 102, No. 4.

Deisenhofer, J., "The Photosynthetic Reaction Centre from the Purple Bacterium *Rhodopseudomonas viridis*," The EMBO Journal, 1989, pp. 2149-2170, vol. 8, No. 8.

Deupi, X. et al., "Activation of G Protein-Coupled Receptors," Advances in Protein Chemistry, 2007, pp. 137-166, vol. 74.

Dunwiddie, T. V. et al., "The Role and Regulation of Adenosine in the Central Nervous System," Annu. Rev. Neurosci., 2001, pp. 31-55, vol. 24.

During, M. J. et al., "Adenosine: A Potential Mediator of Seizure Arrest and Postictal Refractoriness," Annals of Neurology, Nov. 1992, pp. 618-624, vol. 32, No. 5.

Engel, C.K. et al., "Insertion of Carrier Proteins into Hydrophilic Loops of the *Escherichia coli* Lactose Permease," Biochimica et Biophysica Acta, 2002, pp. 38-46, vol. 1564, Issue 1.

European Extended Search Report, European Application No. 08841630.0, Jul. 18, 2011, 7 pages.

Ferre, S. et al., "Adenosine $A_1$-$A_{2A}$ Receptor Heteromers: New Targets for Caffeine in the Brain," Frontiers in Bioscience, Jan. 1, 2008, pp. 2391-2399, vol. 13.

Ferre, S., "An Update on the Mechanisms of the Psychostimulant Effects of Caffeine," Journal of Neurochemistry, 2008, pp. 1067-1079, vol. 105.

Freddolino, P.L. et al., "Predicted 3D Structure for the Human $\beta_2$ Adrenergic Receptor and Its Binding Site for Agonists and Antagonists," PNAS, Mar. 2, 2004, pp. 2736-2741, vol. 101, No. 9.

Fredholm, B. B. et al., "Actions of Adenosine at Its Receptors in the CNS: Insights from Knockouts and Drugs," Annu. Rev. Pharmacol. Toxicol., 2005, pp. 385-412, vol. 45.

Fredholm, B. B. et al., "International Union of Pharmacology. XXV. Nomenclature and Classification of Adenosine Receptors," Pharmacological Reviews, 2001, pp. 527-552, vol. 53, No. 4.

Fredriksson, R. et al., "The G-Protein-Coupled Receptors in the Human Genome Form Five Main Families. Phylogenetic Analysis, Paralogon Groups, and Fingerprints," Molecular Pharmacology, 2003, pp. 1256-1272, vol. 63, No. 6.

Furse, K.E. et al., "Three-Dimensional Models for $\beta$-Adrenergic Receptor Complexes with Agonists and Antagonists," J. Med. Chem., 2003, pp. 4450-4462, vol. 46.

Gouldson, P.R. et al., "Toward the Active Conformations of Rhodopsin and the $\beta_2$-Adrenergic Receptor," Proteins: Structure, Function, and Bioinformatics, 2004, pp. 67-84, vol. 56.

Hanson et al., "A Specific Cholesterol Binding Site is Established by the 2.8A Structure of the Human Beta-2-Andrenergic Receptor in an Alternate Crystal Form," Structure, Jun. 2008, pp. 897-905, vol. 16, No. 6.

Hein, L. et al., "Adrenergic Receptors, From Molecular Structure to in vivo Function," Trends Cardiovasc. Med., 1997, pp. 137-145, vol. 7, No. 5.

Horn, F. et al., "GPCRDB Information System for G Protein-Coupled Receptors," Nucleic Acids Research, 2003, pp. 294-297, vol. 31, No. 1.

Jaakola, B. et al., "The 2.6 Angstrom Crystal Structure of a Human $A_{2A}$ Adenosine Receptor Bound to an Antagonist," Science, Nov. 21, 2008, pp. 1211-1217, vol. 322, No. 5905.

Jaakola V. P. et al., "G Protein-Coupled Receptors Show Unusual Patterns of Intrinsic Unfolding," Protein Engineering, Design & Selection, 2005, pp. 103-110, vol. 18, No. 2.

Jacobson, K. A. et al., "Adenosine Receptors as Therapeutic Targets," Nature Reviews Drug Discovery, Mar. 2006, pp. 247-264, vol. 5.

Javitch, J.A., "The Ants Go Marching Two by Two: Oligomeric Structure of G-Protein-Coupled Receptors," Molecular Pharmacology, 2004, pp. 1077-1082, vol. 66, No. 5.

Jiang, Q. et al., "Mutagenesis Reveals Structure—Activity Parallels Between Human $A_{2A}$ Adenosine Receptors and Biogenic Amine G Protein-Coupled Receptors," J Med Chem, 1997, pp. 2588-2595, vol. 40.

Katona, G. et al., "Lipidic Cubic Phase Crystal Structure of the Photosynthetic Reaction Centre from *Rhodobacter sphaeroides* at 2.35Å Resolution," Journal of Molecular Biology, Aug. 15, 2003, pp. 681-692, vol. 331, No. 3.

Katragadda, M. et al., "Structural Studies of the Putative Helix 8 in the Human $\beta_2$ Adrenergic Receptor: an NMR Study," Biochimica et Biophysica Acta, 2004, pp. 74-81, vol. 1663.

Kim, J. et al., "Glutamate Residues in the Second Extracellular Loop of the Human $A_{2a}$ Adenosine Receptor Are Required for Ligand Recognition," Molecular Pharmacology, 1996, pp. 683-691, vol. 49.

Kim, J. et al., "Site-Directed Mutagenesis Identifies Residues Involved in Ligand Recognition in the Human $A_{2a}$ Adenosine Receptor," The Journal of Biological Chemistry, Jun. 9, 1995, pp. 13987-13997, vol. 270, No. 23.

Kobilka, B., Adrenergic Receptors as Models for G Protein-Coupled Receptors, Annu. Rev. Neurosci., 1992, pp. 87-114, vol. 15.

Kobilka, B.K. et al, "Conformational Complexity of G-Protein-Coupled Receptors," Trends in Pharmacological Sciences, Epub Jul. 13, 2007, Aug. 2007, pp. 397-406, vol. 28, No. 8.

Kobilka, B.K., "G Protein Coupled Receptor Structure and Activation," Biochimica et Biophysica Acta, Epub Nov. 15, 2006, 2007, pp. 794-807, vol. 1768, No. 4.

Lahiri, S. et al., "Purines, the Carotid Body and Respiration," Respir Physiol Neurobiol., Jul. 1, 2007, pp. 123-129, vol. 157, No. 1.

Landau, E.M. et al., "Lipidic Cubic Phases: A Novel Concept for the Crystallization of Membrane Proteins," Proc. Natl. Acad. Sci., Dec. 1996, pp. 14532-14535, vol. 93.

Lefkowitz, R.J., "The Superfamily of Heptahelical Receptors," Nature Cell Biology, Jul. 2000, pp. E133-E136, vol. 2.

Luecke, H. et al., "Crystal Structure of Sensory Rhodopsin II at 2.4 A: Insights into Color Tuning and Transducer Interaction," Sciencexpress, Jul. 21, 2001, 8 pages.

Magnani, F. et al., "Co-Evolving Stability and Conformational Homogeneity of the Human Adenosine $A_{2a}$ Receptor," PNAS, Aug. 5, 2008, pp. 10750-10755, vol. 105, No. 31.

Mantri M. et al., "2-Amino-6-furan-2-yl-4-substituted Nicotinonitriles as $A_{2A}$ Adenosine Receptor Antagonists," *J. Med. Chem.*, 2008, pp. 4449-4455, vol. 51.

Martinelli, A. et al., "Molecular Modeling of Adenosine Receptors: New Results and Trends," Medicinal Research Reviews, 2008, pp. 247-277, vol. 28, No. 2.

Mercier, J-F. et al., "Quantitative Assessment of $\beta_1$- and $\beta_2$-Adrenergic Receptor Homo- and Heterodimerization by Bioluminescence Resonance Energy Transfer," The Journal of Biological Chemistry, Nov. 22, 2002, pp. 44925-44931, vol. 277, No. 47.

Mialet-Perez, J. et al., "A Primate-Dominant Third Glycosylation Site of the β₂-Adrenergic Receptor Routes Receptors to Degradation During Agonist Regulation," The Journal of Biological Chemistry, Sep. 10, 2004, pp. 38603-38607, vol. 279, No. 37.

Moro, S. et al., "Demystifying the Three Dimensional Structure of G Protein-Coupled Receptors (GPCRs) with the Aid of Molecular Modeling," Chem. Commun. (Camb), 2003, pp. 2949-2956.

Murakami, M. et al., "Crystal Structure of Squid Rhodopsin," Nature, May 2008, pp. 363-368, vol. 453.

Navarro, J. et al., "Receptor-Dependent G-Protein Activation in Lipidic Cubic Phase," Biopolymers, Jan. 2002, pp. 167-177, vol. 67, No. 3.

Ongini, E. et al., "Comparison of CGS 15943, ZM 241385 and SCH 58261 as Antagonists at Human Adenosine Receptors," Naunyn-Schmiedebergs Arch Pharmacol, 1999, pp. 7-10, vol. 359.

Ostrom, R.S. et al., "The Evolving Role of Lipid Rafts and Caveolae in G Protein-Coupled Receptor Signaling: Implications for Molecular Pharmacology," British Journal of Pharmacology, Sep. 2004, pp. 235-245, vol. 143.

Palczewski, K. et al., "Crystal Structure of Rhodopsin: A G Protein-Coupled Receptor," Science, Aug. 4, 2000, pp. 739-745, vol. 289.

Palczewski, K., "G Protein-Coupled Receptor Rhodopsin," Annu Rev Biochem., 2006, pp. 743-767, vol. 75.

Pardo, L. et al., "The Role of Internal Water Molecules in the Structure and Function of the Rhodopsin Family of G Protein-Coupled Receptors," ChemBioChem, 2007, pp. 19-24, vol. 8.

PCT International Search Report and Written Opinion, PCT Application No. PCT/US2009/059289, Oct. 4, 2010, 10 pages.

PCT International Search Report and Written Opinion, PCT Application No. PCT/US08/80847, Sep. 10, 2009, 12 pages.

PCT International Search Report and Written Opinion, PCT Application No. PCT/US08/80844, 9 pages.

Pierce, K.L. et al., "Seven-Transmembrane Receptors," Nature Reviews Molecular Cell Biology, Sep. 2002, pp. 639-650, vol. 3.

Poucher, S. M. et al., "The in Vitro Pharmacology of ZM 241385, a Potent, Non-Xanthine, $A_{2a}$ Selective Adenosine Receptor Antagonist," British Journal of Pharmacology, 1995, pp. 1096-1102, vol. 115.

Rasmussen, S.G.F. et al., "Crystal Structure of the human β₂ Adrenergic G-Protein-Coupled Receptor," Nature, Nov. 15, 2007, pp. 383-388, vol. 450.

Rasmussen, S.G.F. et al., "Crystal Structure of the human β₂ Adrenergic G-Protein-Coupled Receptor—Online Methods," 2 pages, [Online] [Retrieved on Mar. 15, 2011] Retrieved from the Internet<URL:www.nature.com>.

Rasmussen, S.G.F. et al., "Crystal Structure of the human β₂ Adrenergic G-Protein-Coupled Receptor—Supplementary Information," pp. 1-8, [Online] [Retrieved on Mar. 15, 2011] Retrieved from the Internet<URL:www.nature.com>.

Rohrer, D.K., "Physiological Consequences of β-Adrenergic Receptor Disruption," J. Mol. Med., 1998, pp. 764-772, vol. 76.

Rosenbaum, D.M. et al., "GPCR Engineering Yields High-Resolution Structural Insights into β₂- Adrenergic Receptor Function," Science, Epub Oct. 25. 2007, pp. 1266-1273 vol. 318.

Rummel, G., "Lipidic Cubic Phases: New Matrices for the Three-Dimensional Crystallization of Membrane Proteins," Journal of Structural Biology, Jan. 1998, pp. 82-91, vol. 121, No. 2.

Salom, D. et al., "Crystal Structure of a Photoactivated Deprotonated Intermediate of Rhodopsin," PNAS, Oct. 13, 2006, pp. 16123-16128, vol. 103, No. 44.

Sawynok, J. et al., "Adenosine in the Spinal Cord and Periphery: Release and Regulation of Pain," Progress in Neurobiology, 2003, pp. 313-340, vol. 69.

Schapira, A. H. et al., "Novel Pharmacological Targets for the Treatment of Parkinson's Disease," Nature Reviews Drug Discovery, Oct. 2006, pp. 845-854, vol. 5.

Schertler, G. FX., "Structure of Rhodopsin and the Metarhodopsin I Photointermediate," Current Opinion in Structural Biology, 2005, pp. 408-415, vol. 15.

Schwartz, T.W. et al., "Molecular Mechanism of 7TM Receptor Activation—A Global Toggle Switch Model," Annu. Rev. Pharmacol. Toxicol., 2006, pp. 481-519, vol. 46.

Schwarzschild, M. A. et al., "Targeting Adenosine A2A Receptors in Parkinson's Disease," Trends in Neuroscience, 2006, pp. 647-954, vol. 29, No. 11.

Serrano-Vega, M. J. et al., "Conformational Thermostabilization of the β1-Adrenergic Receptor in a Detergent-Resistant Form," Proc Natl Acad Sci USA, Jan. 22, 2008, pp. 877-882, vol. 105, No. 3.

Shi, Y. et al., "Interaction of Mechanisms Involving Epoxyeicosatrienoic Acids, Adenosine Receptors, and Metabotropic Glutamate Receptors in Neurovascular Coupling in Rat Whisker Barrel Cortex," Journal of Cerebral Blood Flow Metabolism, 2008, pp. 111-125, vol. 28.

Shi, L. et al., "β₂ Adrenergic Receptor Activation," The Journal of Biological Chemistry, Oct. 25, 2002, pp. 40989-10996, vol. 277, No. 43.

Smyth, D.R. et al., "Crystal Structures of Fusion Proteins with Large-Affinity Tags," Protein Science, 2003, pp. 1313-1322, vol. 12.

Sprang, S.R., "A Receptor Unlocked," Nature, Nov. 15, 2007, pp. 355-356, vol. 450.

Strosberg, A.D., "Structure, Function, and Regulation of Adrenergic Receptors," Protein Science, 1993, pp. 1198-1209, vol. 2.

Sugimoto, Y. et al., "β₁-Selective Agonist (−)-1-(3,4-Dimethoxyphenetylamino)-3-(3,4-dihydroxy)-2-propanol [(−)-RO363] Differentially Interacts with Key Amino Acids Responsible for β₁-Selective Binding in Resting and Active States," The Journal of Pharmacology and Experminetal Therapeutics, 2002, pp. 51-58, vol. 301, No. 1.

United States Office Action, U.S. Appl. No. 12/739,134, Mar. 22, 2011, 8 pages.

Wadsten, P. et al., "Lipidic Sponge Phase Crystallization of Membrane Proteins," J. Mol. Biol., 2006, pp. 44-53, vol. 364.

Warne, T. et al., "Structure of a β₁-Adrenergic G-Protein-Coupled Receptor," Nature, Jul. 24, 2008, pp. 486-492, vol. 454.

Wieland, K. et al., "Involvement of Asn-293 in Stereospecific Agonist Recognition and in Activation of the β₂-Adrenergic Receptor," Proc. Natl. Acad. Sci., Aug. 1996, pp. 9276-9281, vol. 93.

Xiang, Y. et al., "The β-Adrenergic Receptors," Chapter 10, The Adrenergic Receptors, 2006, ed. D. Perez, pp. 267-291.

Xiang, Y. et al., "Caveolar Localization Dictates Physiologic Signaling of β₂-Adrenoceptors in Neonatal Cardiac Myocytes," The Journal of Biological Chemistry, Sep. 13, 2002, pp. 34280-34286, vol. 277, No. 37.

Yohannan, S. et al., "The Evolution of Transmembrane Helix Kinks and the Structural Diversity of G Protein-Coupled Receptors," PNAS, Jan. 27, 2004, pp. 959-963, vol. 101, No. 4.

Yuzlenko, O. et al., "Molecular Modeling of $A_1$ and $A_{2A}$ Adenosine Receptors: Comparison of Rhodopsin- and β₂-Adrenergic-Based Homology Models Through the Docking Studies," J Comput Chem, 2009, pp. 14-32, vol. 30.

Zezula, J. et al., "The $A_{2A}$-Adenosine Receptor: a GPCR with Unique Features?" British Journal of Pharmacology, 2008, pp. S184-S190, vol. 153 Suppl 1.

Zhang, Y. et al., "Structure Modeling of All Identified G Protein-Coupled Receptors in the Human Genome," PLoS Comput Biol, 2006, pp. 88-99, vol. 2, Issue 2, e13.

Canadian Office Action, Canadian Application No. 2,701,283, Mar. 27, 2012, 4 pages.

Arora, A. et al. "Biophysical Approaches to Membrane Protein Structure Determination," Current Opinion in Structural Biology, 2001, pp. 540-547, vol. 11, Issue 5.

"Ballestero-Weinstein index GPCR" (last viewed on Nov. 15, 2012), 2 pages [Online] [Retrieved on Nov. 15, 2012] Retrieved from the Internet<URL:http://www.cs.cmu.edu/~blmt/Seminar/SeminarMaterials/GPCRnumbers.html>.

Drenth, J. "Principles of Protein X-Ray Crystallography", 2nd Edition, 1999, Springer-Verlag New York Inc., pp. 1-21.

"Drug Design Cutting Edge Approaches," Flower D.R. (ed.), The Royal Society of Chemistry, 2002, p. 21-27.

Hegyi, H. et al., "The Relationship Between Protein Structure and Function: a Comprehensive Survey with Application to the Yeast Genome," J Mol Biol., 1999, pp. 147-164, vol. 288.

Klyushnichenko, V., "Protein Crystallization: From HTS to Kilogram-Scale," Current Opinion in Drug Discovery, 2003, pp. 848-854, vol. vol. 6, No. 6.

Kobilka, B. et al., "New G-Protein-Coupled Receptor Crystal Structures: Insights and Limitations," Trends Pharmacological Sciences, 2008, pp. 79-83, vol. 29, No. 2.

Reggio, P., "Computational Methods in Drug Design: Modeling G Protein-Coupled Receptor Monomers, Dimers, and Oligomers," The AAPS Journal, 2006, pp. E322-E336, vol. 8, No. 2.

Weber, P.C., "Overview of Crystallization Methods. Methods," in Enzymology, 1997 pp. 13-22, vol. 276.

Yang, M.X. et al., "Crystalline Monoclonal Antibodies for Subcutaneous Delivery," PNAS Jun. 10, 2003, pp. 6934-6939, vol. 100.

United States Office Action, U.S. Appl. No. 12/739,133, Nov. 26, 2012, 51 pages.

European Examination Report, European Application No. 08841630.0, Mar. 20, 2013, 4 pages.

Canadian Office Action, Canadian Application No. 2,701,283, Apr. 9, 2013, 2 pages.

* cited by examiner

Fig. 8(A)

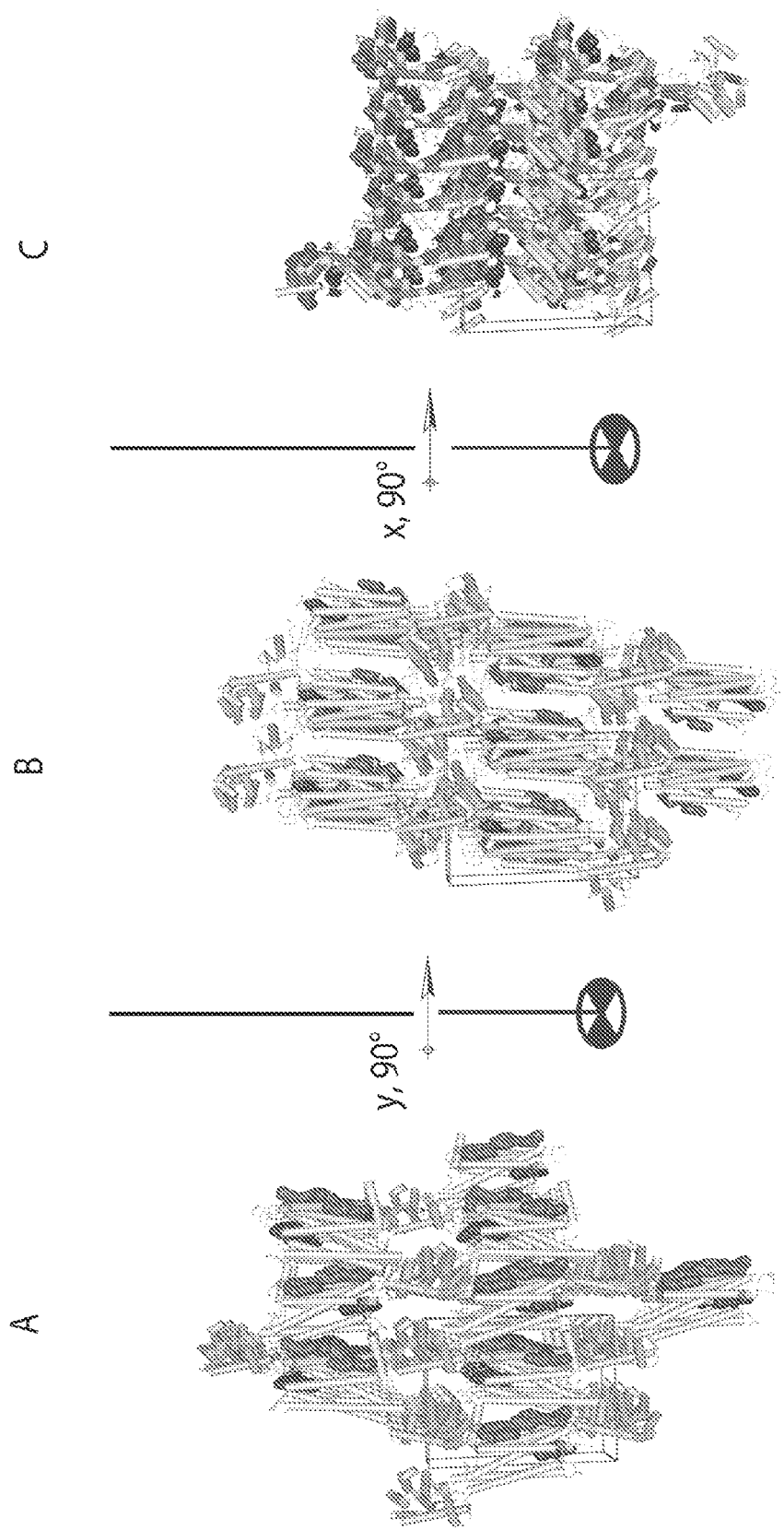
Fig. 1(A)-(C)

Orientation of T4L

HUMAN $A_{2A}$ ADENOSINE RECEPTOR CRYSTALS AND USES THEREOF

RELATED APPLICATIONS

This applications claims the benefit of U.S. provisional application 61/194,961, filed Oct. 1, 2008, and incorporated herein by reference for all purposes.

STATEMENT REGARDING FEDERALLY SPONSORED RESEARCH OR DEVELOPMENT

This invention was made with government support under Grant Nos. GM073197 and GM074961 awarded by the National Institutes of Health. The government has certain rights in the invention.

REFERENCE TO SEQUENCE LISTING

This specification includes a sequence listing submitted electronically as a text file named "16086_US_Sequence Listing.txt", created Mar. 30, 2011, with a size of 84 kb. The sequence listing consists of 36 sequences and is incorporated by reference.

BACKGROUND OF THE INVENTION

1. Field of the Invention

The invention relates to the fields of chemistry, and biophysics.

2. Description of the Related Art

G-protein coupled receptors (GPCRs) comprise a broad class of membrane-bound proteins that share a variety of structural and functional attributes. See Friedricksson et al. *Mol Pharmacol* (63)6: p. 1256-1272, 2003; and Friedricksson et al. *Mol Pharmacol* (67)5: p. 1414-1425, 2005. GPCRs are classified into 1 of 6 classes: A, B, C, D, E, and F, see Friedricksson et al. (2003) and Friedricksson et al. (2005). GPCRs comprise seven transmembrane helical regions, as well as an extracellular portion that binds endogenous ligands.

Extracellular adenosine plays an important role in physiology and initiates most of its effects through the activation of four GPCR subtypes, $A_1$, $A_{2A}$, $A_{2B}$ and $A_3$ (B. B. Fredholm et al., *Annu Rev Pharmacol Toxicol* 45, 385 (2005); B. B. Fredholm et al., *Pharmacol Rev* 53, 527 (2001)). Each of these four receptor subtypes plays an essential role in responding to adenosine in the central nervous system (T. V. Dunwiddie et al., *Annu Rev Neurosci* 24, 31 (2001); K. A. Jacobson et al., *Nat Rev Drug Discov* 5, 247 (2006)) regulating pain (J. Sawynok, X. J. Liu, *Prog Neurobiol* 69, 313 (2003)), cerebral blood flow (Y. Shi et al., *J Cereb Blood Flow Metab* 28, 111 (2008)), basal ganglia functions (M. A. Schwarzschild et al., *Trends Neurosci* 29, 647 (2006)), respiration (S. Lahiri et al., *Respir Physiol Neurobiol* 157, 123 (2007)) and sleep (R. Basheer et al., *Prog Neurobiol* 73, 379 (2004)). These receptor subtypes are primarily coupled to the cAMP second messenger system and each has its own unique pharmacological profile. The $A_{2A}$ adenosine subtype is linked to $G_s$ and $G_{olf}$ proteins and upon receptor activation, the intracellular levels of cAMP increase. At least three of the four adenosine receptor subtypes ($A_1$, $A_{2A}$ and $A_{2B}$) are blocked by naturally occurring methylxanthines, such as caffeine, with modest affinity. Interestingly, strong epidemiological evidence suggests that coffee drinkers have a lower risk of Parkinson's disease (M. A. Hernan et al., *Ann Neurol* 52, 276 (2002)). This effect has been linked to caffeine's interaction with the $A_{2A}$ adenosine receptor, which controls locomotor behavior in basal ganglia together with dopamine $D_2$ and metabotropic glutamate mGluR receptors (S. Ferre, *J Neurochem* 105, 1067 (2008); S. Ferre et al., *Front Biosci* 13, 2391 (2008)). Development of more selective compounds for adenosine receptor subtypes could provide a class of therapeutics for treating numerous human maladies, such as pain (J. Sawynok et al., *Prog Neurobiol* 69, 313 (2003)), Parkinson's disease (M. A. Schwarzschild et al., *Trends Neurosci* 29, 647 (2006); A. H. Schapira et al., *Nat Rev Drug Discov* 5, 845 (2006)), Huntington disease (D. Blum et al., S. N. Schiffmann, *Lancet Neurol* 2, 366 (2003)), asthma (R. A. Brown et al., *Br J Pharmacol* 153 Suppl 1, S446 (2008)), seizures (M. J. During et al., *Ann Neurol* 32, 618 (1992)) and many other neurological disorders (D. Blum et al., *Lancet Neurol* 2, 366 (2003); E. E. Benarroch, *Neurology* 70, 231 (2008)).

SUMMARY OF THE INVENTION

Described herein is the structure of the human $A_{2A}$ adenosine receptor in complex with the subtype selective high affinity antagonist (4-(2-[7-amino-2-(2-furyl)-[1,2,4]triazolo-[2,3-a][1,3,5]triazin-5-ylamino]ethyl)-phenol (ZM241385) (E. Ongini et al., *Naunyn Schmiedebergs Arch Pharmacol* 359, 7 (1999); S. M. Poucher et al., *Br J Pharmacol* 115, 1096 (1995)). The basis for this compound's selectivity over the adenosine $A_1$ and $A_3$ receptors can now be analyzed in the context of its molecular interactions with the $A_{2A}$ receptor along with previously reported mutagenesis data. With an additional human GPCR structure, the analysis of structural differences as they pertain to receptor pharmacology, receptor activation, ligand recognition and ligand engineering is facilitated for all members of the class A receptor family.

In one embodiment, the invention provides a crystalline form of a human $A_{2A}$ adenosine receptor protein having an atomic arrangement of coordinates comprising the coordinates set forth in Table 6. In another embodiment, the invention provides a crystalline form of a human $A_{2A}$ adenosine receptor protein, where said form has unit cell dimensions of a=47.7±0.5 Angstroms, b=76.9±0.5 Angstroms, and c=86.8±0.5 Angstroms. In still another embodiment, the invention provides a crystalline form of a human $A_{2A}$ adenosine receptor protein, wherein said space group of said crystalline form is $P2_1$. In yet another embodiment, the invention provides a crystalline form of a human $A_{2A}$ adenosine receptor protein, wherein said crystalline form diffracts X-rays to a resolution of 2.6 Angstroms. In an embodiment related to the crystalline forms described above, the human $A_{2A}$ adenosine receptor protein is a chimeric receptor or fusion protein comprising a human $A_{2A}$ adenosine receptor protein and T4 lysozyme. In yet another related embodiment, a crystalline form such as that described above may comprise a xanthine ligand. In certain embodiments, the xanthine ligand is a ligand such as theophylline, xanthine, theobromine and caffeine. In still other embodiments, the crystalline human $A_{2A}$ adenosine receptor protein comprises a bound non-xanthine ligand, such as ZM241385.

In another related embodiment, the invention provides a crystalline form of human $A_{2A}$ adenosine receptor protein or a portion thereof, wherein said human $A_{2A}$ adenosine receptor protein or portion thereof comprises a binding pocket I site, and wherein said binding pocket I comprises a plurality of amino acid residues selected from the group consisting of Phe168[5.29], Ile274[7.39], Glu169[5.30], Leu249[6.51], and Asn253[6.55]. In a related embodiment, binding pocket I comprises a non-xanthine antagonist (e.g., ZM241385) in binding pocket I. In yet another embodiment, the invention provides a crystalline form of human $A_{2A}$ adenosine receptor protein or a portion thereof, wherein said human $A_{2A}$ adenosine receptor protein or portion thereof comprises a binding pocket II site, and wherein said binding pocket II comprises amino acid residues Phe62$^{2.60}$, Ile66$^{2.64}$, Ile80$^{3.28}$, Val84$^{3.32}$, Phe168$^{5.29}$, Leu249$^{6.51}$, Ile274$^{7.39}$ and His278$^{7.43}$. In a related embodiment, a xanthine ligand is bound by binding pocket II in the in the crystalline human $A_{2A}$ adenosine receptor. In yet another embodiment, the invention provides crystalline form of human $A_{2A}$ adenosine receptor protein or a portion thereof, wherein said human $A_{2A}$ adenosine receptor protein or portion thereof comprises a binding pocket III site, and wherein said binding pocket III site comprises a plurality of amino acid residues selected from the group consisting of Leu48$^{2.46}$, Ala51$^{2.49}$, Asp52$^{2.50}$, Val55$^{2.53}$, Val84$^{3.32}$, Leu87$^{3.35}$, Thr88$^{3.36}$, Ser91$^{3.39}$, Leu95$^{3.43}$, Ile238$^{6.40}$, Phe242$^{6.44}$, Trp246$^{6.48}$, Ser277$^{7.42}$, His278$^{7.43}$, Asn280$^{7.45}$, Ser281$^{7.46}$ and Asn284$^{7.49}$.

In another embodiment, the invention provides methods for identifying a compound that binds to a ligand binding site of a human $A_{2A}$ adenosine receptor protein by comparing a set of three-dimensional structures representing a set of candidate compounds with a three-dimensional molecular model of said ligand binding site, comprising: receiving a three-dimensional model of a ligand binding site on said human $A_{2A}$ adenosine receptor protein, wherein said three-dimensional model of said ligand binding site comprises atomic co-ordinates for a plurality of ligand-binding residues; determining, for each of the set of compound three-dimensional models, a plurality of distance values indicating distances between said atomic co-ordinates of said candidate compound of the set of candidate compounds and said atomic coordinates of said ligand-binding residues comprising said ligand binding site; determining, for each of the set of compound three-dimensional models, a binding strength value based on the plurality of distance values determined for the compound three-dimensional model, wherein the binding strength value indicates the stability of a complex formed by said human $A_{2A}$ adenosine receptor protein and a compound represented by the compound three-dimensional model; and storing or displaying a set of results indicating whether each candidate compound binds to the three-dimensional model based on the binding strength values. Displaying can include displaying all or a portion of the results on a monitor or on a printed sheet of paper. In certain related embodiments of the method, the set of candidate compounds or the set of three-dimensional structures or both contains one member, or more. The candidate compounds may include compounds derived from one or more known GPCR ligands, or they may be designed de novo based on the three-dimensional molecular model of the ligand binding site, e.g., the model described herein or a portion thereof. The invention also provides a related embodiment of the above-described method wherein the plurality of ligand-binding residues comprises residues that form a binding pocket, e.g., binding pocket I, binding pocket II, or binding pocket III of said human $A_2$a adenosine receptor.

In another related embodiment of the above-described method for identifying a compound that binds to a ligand binding site of a human $A_{2A}$ adenosine receptor protein, the ligand-binding residues comprise a plurality of residues selected from the group consisting of Phe168$^{5.29}$, Ile274$^{7.39}$, Glu169$^{5.30}$, Leu249$^{6.51}$, and Asn253$^{6.55}$. In yet another related embodiment of the method, the ligand-binding residues comprise a plurality of residues selected from the group consisting of Phe62$^{2.60}$, Ile66$^{2.64}$, Ile80$^{3.28}$, Val84$^{3.32}$, Phe168$^{5.29}$, Leu249$^{6.51}$, Ile274$^{7.39}$ and His278$^{7.43}$. In still another related embodiment, the ligand-binding residues comprise a plurality of residues selected from the group consisting of Leu48$^{2.46}$, Ala51$^{2.49}$, Asp52$^{2.50}$, Val55$^{2.53}$, Val84$^{3.32}$, Leu87$^{3.35}$, Thr88$^{3.36}$, Ser91$^{3.39}$, Leu95$^{3.43}$, Ile238$^{6.40}$, Phe242$^{6.44}$, Trp246$^{6.48}$, Ser277$^{7.42}$, His278$^{7.43}$, Asn280$^{7.45}$, Ser281$^{7.46}$ and Asn284$^{7.49}$.

In another related embodiment of the above-described method for identifying a compound that binds to a ligand binding site of a human $A_{2A}$ adenosine receptor protein, binding strength value is based on one or more of a hydrogen bonding strength, a hydrophobic interaction strength, or a Coulombic interaction binding strength. In related variations of the method, one or more of the steps of receiving, determining, or storing are carried out using a commercially-available software program. Example of appropriate programs include DOCK, QUANTA, Sybyl, CHARMM, AMBER, GRID, MCSS, AUTODOCK, CERIUS II, Flexx, CAVEAT, MACCS-3D, HOOK, LUDI, LEGEND, Leap-Frog, Gaussian 92, QUANTA/CHARMM, Insight II/Discover, and ICM.

In yet another related embodiment of the above-described method for identifying a compound that binds to a ligand binding site of a human $A_{2A}$ adenosine receptor protein, the method comprises an additional step of contacting a human $A_{2A}$ adenosine receptor protein with a molecule comprising an identified candidate compound. In some embodiments, the molecule comprising an identified candidate compound additionally comprises a moiety capable of competitively displacing a ligand from a human $A_{2A}$ adenosine receptor protein, e.g., a ligand that binds to binding pocket I, II or III of a human $A_{2A}$ adenosine receptor protein. The invention provides another related embodiment of the method for identifying a compound that binds to a ligand binding site of a human $A_{2A}$ adenosine receptor protein, wherein the method further comprising characterizing a binding interaction between the human $A_{2A}$ adenosine receptor protein and the molecule comprising the identified candidate compound, and storing the result of that characterization, e.g., storing a measured value representative of the binding interaction. The characterization step of this embodiment may comprise, for example, determining an activation of a function of the human $A_{2A}$ adenosine receptor protein, an inhibition of a function of said human $A_{2A}$ adenosine receptor protein, an increase in expression of said human $A_{2A}$ adenosine receptor protein, a decrease in expression of said human $A_{2A}$ adenosine receptor protein, a displacement of a ligand bound to said ligand binding site, or a stability measure for said human $A_{2A}$ adenosine receptor protein, or a combination of one or more of these determinations. In addition or in the alternative to these characterizations, an association constant may be determined.

The invention also provides a human $A_{2A}$ adenosine receptor fusion protein, wherein said fusion protein comprises the amino acid sequence of T4 lysozyme, wherein said fusion protein comprises a deletion in the $A_{2A}$ adenosine receptor sequence between Leu209$^{5.70}$ and Ala221$^{6.23}$. In a related embodiment, the invention provides a fusion protein composition with an amino acid sequence at least 95%, 96%, 97%, 98%, 99% or 100% identical to SEQ ID NO:1. In yet another embodiment, the invention provides an isolated nucleic acid comprising a sequence encoding the above-described fusion protein, wherein the nucleic acid sequence encodes proteins whose primary sequence is at least 95%, 96%, 97%, 98%, 99% or 100% identical to the sequence of SEQ ID NO:1.

These and other features, aspects, and advantages of the present invention will become better understood with regard to the following description, and accompanying drawings.

BRIEF DESCRIPTION OF THE SEVERAL VIEWS OF THE DRAWINGS

FIG. 7A shows that when His$278^{7.43}$ is protonated and positively charged, caffeine binds adjacent to binding pocket I in a xanthine-binding site defined by hydrophobic interactions with: Phe$62^{2.60}$, Ile$66^{2.64}$, Ile$80^{3.28}$, Val$84^{3.32}$, Phe$168^{5.29}$, Leu$249^{6.51}$, Ile$274^{7.39}$ and forming polar interactions with His$278^{7.43}$. FIG. 7B: When His$278^{7.43}$ is deprotonated, caffeine binds in a location similar to binding pocket I.

FIGS. 8A and 8B. Sequence alignment between human Adenosine receptor subtypes $A_1$ (SEQ ID NO: 29), $A_{2A}$ (SEQ ID NO: 2), $A_{2B}$ (SEQ ID NO: 30), $A_3$ (SEQ ID NO: 31) and $A_{2A}$-T4L-ΔC constructs (SEQ ID NO: 28) (A) and comparison of $A_{2A}$ from different species (Human (SEQ ID NO: 2), *Rattus norvegicus* (SEQ ID NO: 32), Mus musculus (SEQ ID NO: 33), *Macaca mulatta* (SEQ ID NO: 34) and *Danio rerio*

(SEQ ID NO: 35)) (B). The residues within 4.5 Å from the ligand binding site of ZM241385 are indicated by an asterix. Ballesteros and Weinstein (S. C. Sealfon et al., *J Biol Chem* 270, 16683 (1995)) numbering is shown for each transmembrane region. The amino and carboxyl terminal purification tags and the T4L tag are also indicated. The assigned secondary structural elements are shown as alpha helix (α), beta-sheet (β) or turns (T). Residues which are conserved in other human subtypes, species and their level of conservation appear in boxes. Dark boxes indicate identical residues. Four disulfide bonds are numbered from 1 to 4.

FIG. 9A-C. Pharmacological validation of $A_{2A}$-T4L-ΔC constructs. 9A. cAMP determination in HEK293T cells transfected with $A_{2A}$ constructs; $A_{2A}$-WT and $A_{2A}$-T4L or $A_{2A}$-T4L-ΔC. Data from untransfected HEK293T cells is not shown but is equivalent to the data from $A_{2A}$-T4L or $A_{2A}$-T4L-ΔC. HEK293T (B) and Sf9 (C) cellular localization/trafficking 9B. Whole HEK293T cell ELISA experiment using a monoclonal anti-FLAG (M2) antibody demonstrates cell surface expression of the $A_{2A}$-WT and $A_{2A}$-T4L constructs but not the $A_{2A}$-T4L-ΔC construct. 9C. Similar results were obtained from Sf9 cells using a monoclonal anti-FLAG (M2) antibody (M. A. Hanson et al., *Protein Expr Purif,* 56, 85 (2007)). For total expression cells were permeabilized with 0.15% TRITON X-100.

FIG. 10 A-D. Indirect evidence of receptor stabilization by ligands or allosteric modulators such as sodium ions or lipids: Effects of NaCl, cholesterol and ligands on $A_{2A}$-T4L-wt and $A_{2A}$-T4L-ΔC receptor thermal stability and conformation. A. Effect of NaCl on $A_{2A}$-T4L-ΔC receptor thermal stability. Representative melting curves of 5 μg $A_{2A}$-T4L receptor in 0.05% DDM in purification buffer containing 0, 150, 400, 800, 2000 and 4000 mM NaCl. Calculated $T_m$ values in order of increasing salt concentration are: 45° C., 40° C., 50° C., 53 and 54° C. B. Effects of cholesterol-hemi-succinate and C. Synthetic cholesterol (Sigma) on $A_{2A}$-T4L receptor thermal stability in low and high NaCl concentration. D. Effect of unligated, theophylline, ZM241385, SCH422416, SCH58261 and p-DITC-APEC on $A_{2A}$-T4L-ΔC in high concentration. Calculated $T_m$ values in order of affinity unligated, theophylline, p-DITC-APEC, SCH58261, ZM241385, and SCH422416 are 45° C., 42° C., 60° C., 40° C., 62 and 50° C., respectively. Data points are means of at least duplicate, in most case triplicate samples. The assay was done as in Alexandrov et al, *Structure* 16, 351 (2008).

Figure 11D:
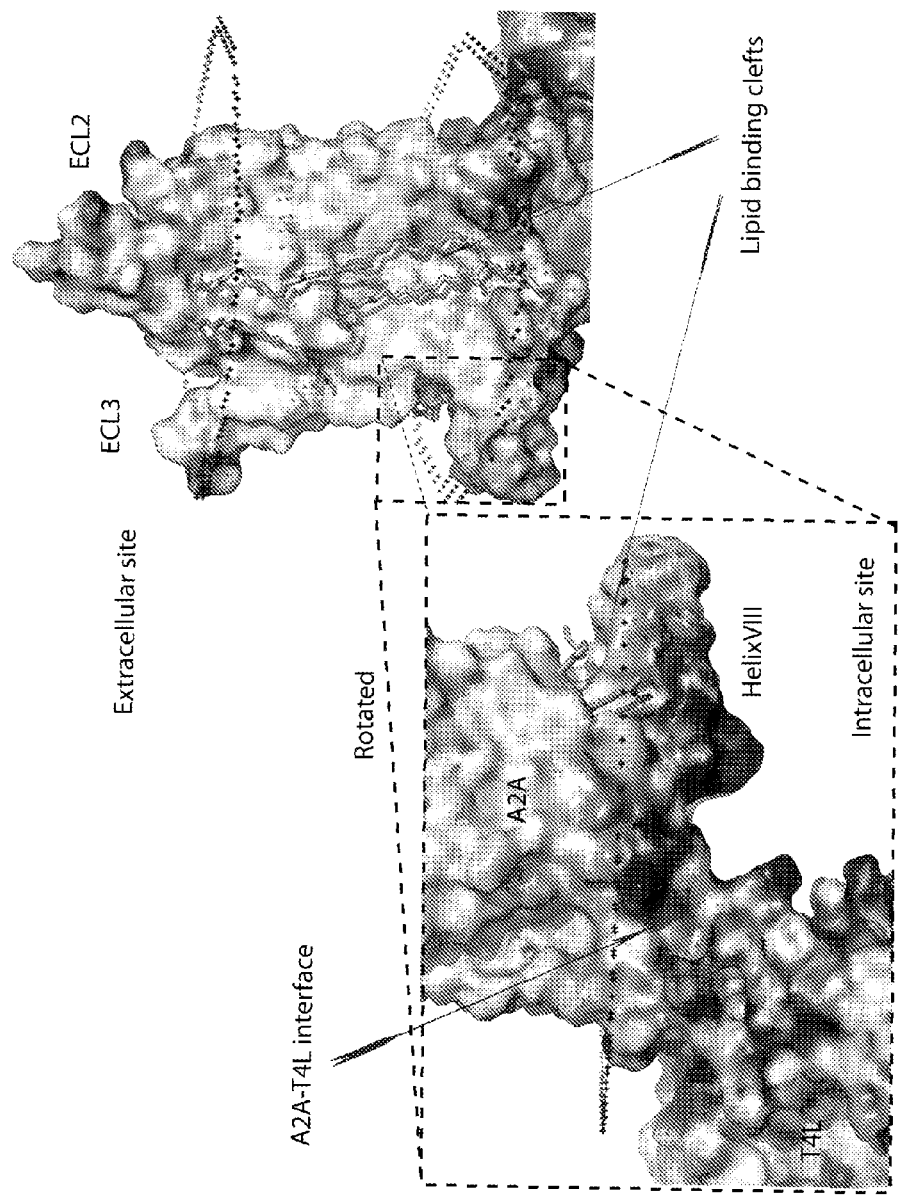
Figure 11E:
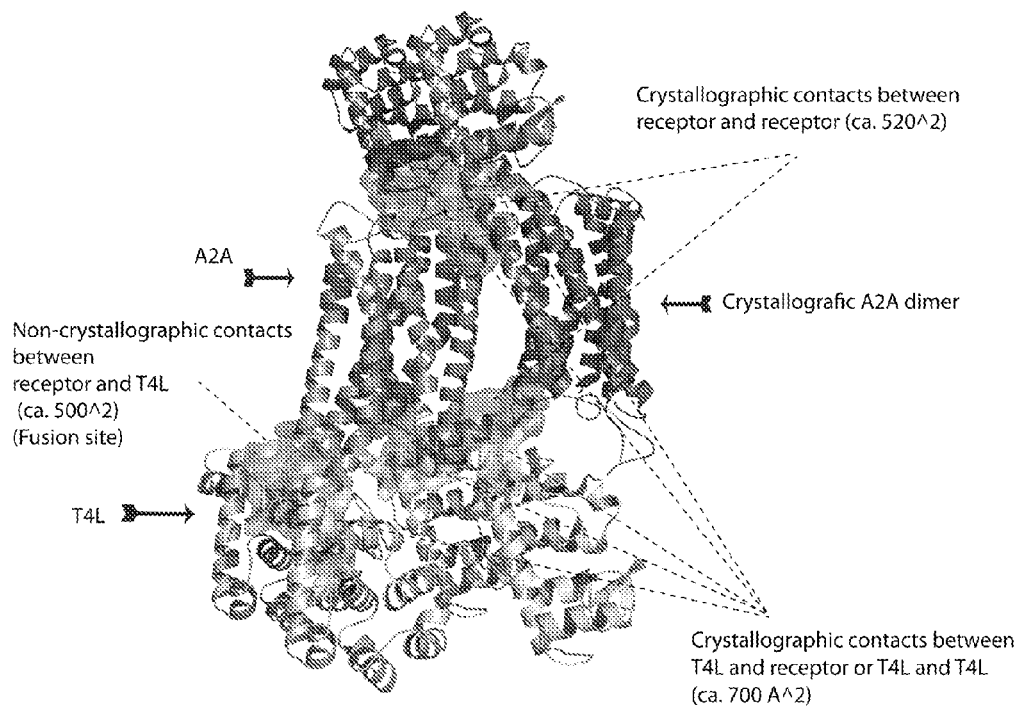
Figure 11F:
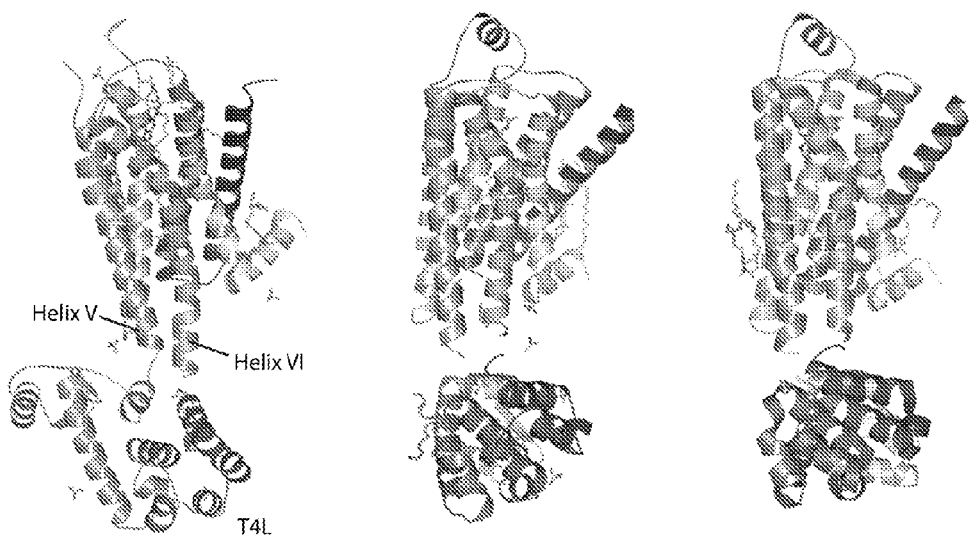

FIG. 11A-F. Crystal packing and protein-lipids interactions in the in meso grown crystal of $A_{2A}$-T4L-ΔC-ZM241385. A. Crystal packing. Note that the images in 11B and 11C are rotated 90° around x and y axis from A. FIG. 11D shows detailed crystallographic and non-crystallographic interactions. The values of interface areas and distances between interacting residues are given in Table 4. The interfaces are indicated by arrows and transparent surfaces. For clarity, the lipids are not-shown in this figure, but included in E. The main lipid binding site occurs at the crystallographic interface between two receptor monomers and is mediated by the lipid-lipid and lipid-receptor interactions. E. Closer view of the lipid binding site and the positively charged intracellular environment. The receptor surface is shaded according to calculated charge with the darkest regions corresponding to (−20 kbT/ec; e.g., the darkened regions near the ECL2 cleft) or (+20 kbT/ec; e.g., the surface of Helix VIII and the A2A-T4L interface) using dielectric constant of 80 using program APBS as implemented in the program PyMOL. F. Comparison of T4L orientation between Adenosine $A_{2A}$-T4L and two $β_2$-AR-T4L structures.

Figure 12:
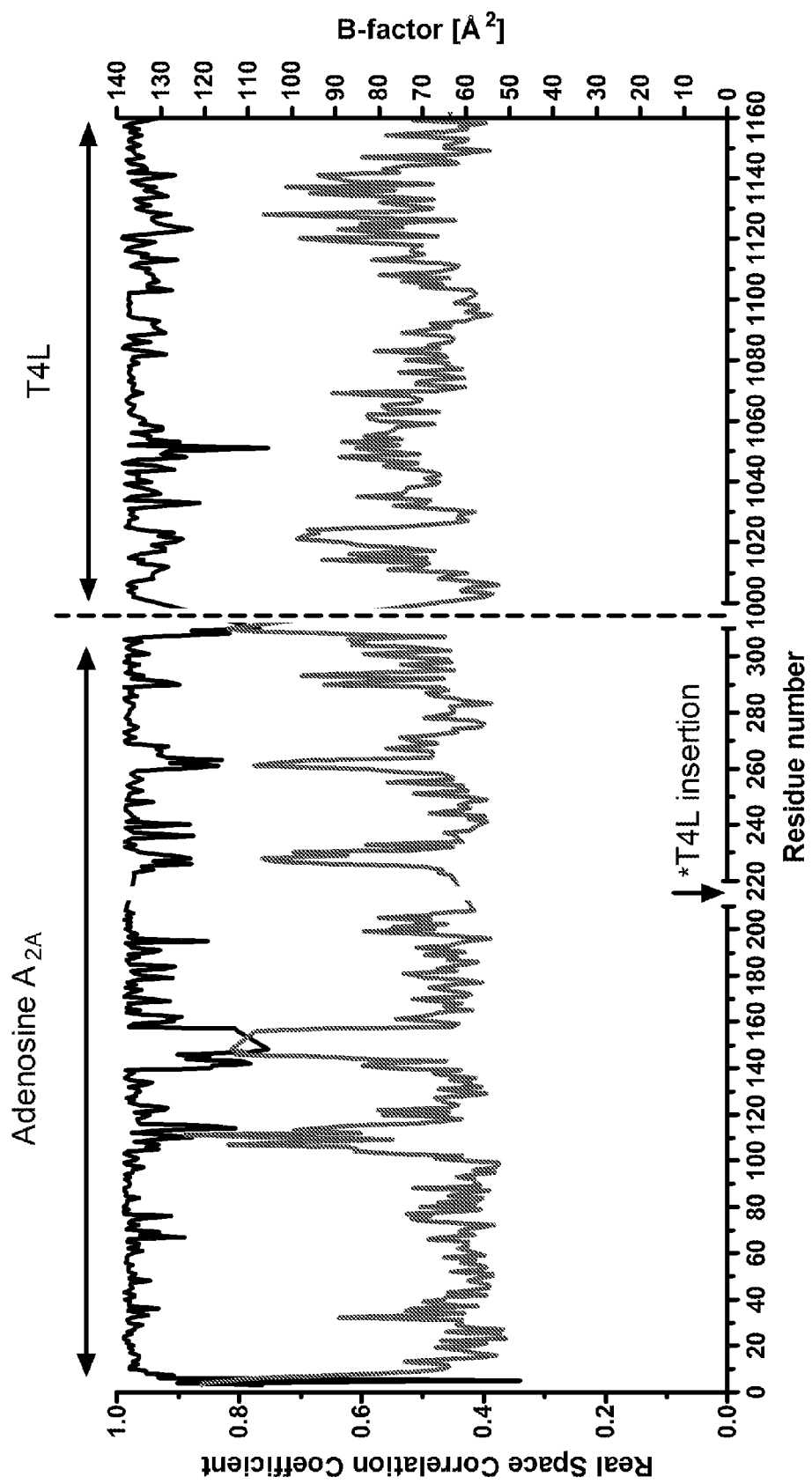

FIG. 12. Per-residue real space correlation coefficient and crystallographic B-factor for the final model.

Figure 13B:
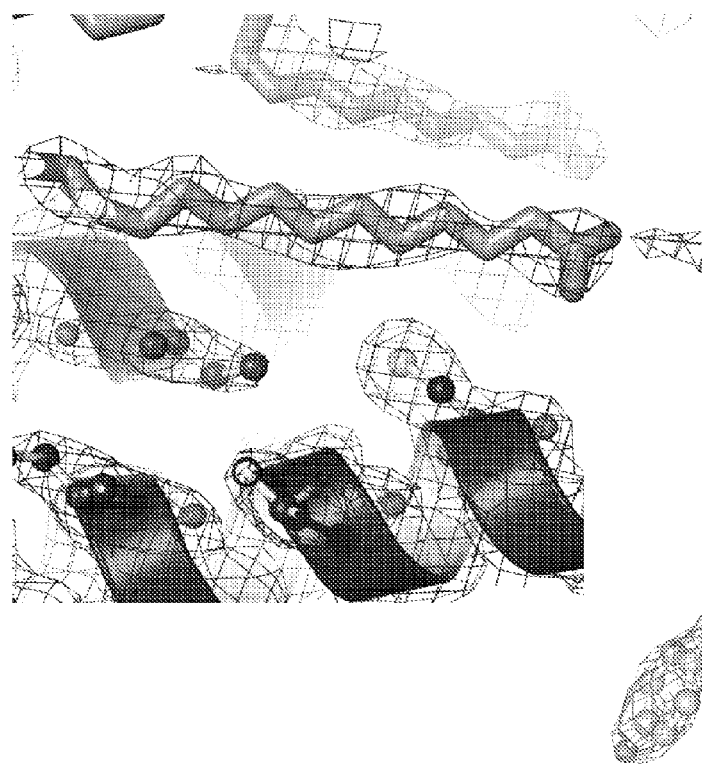
Figure 13C:
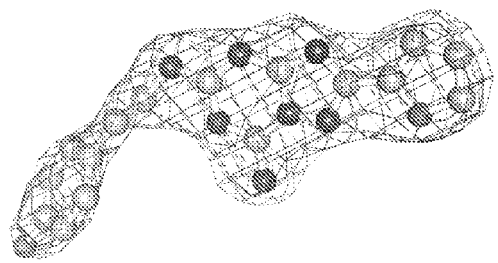
Figure 13A:
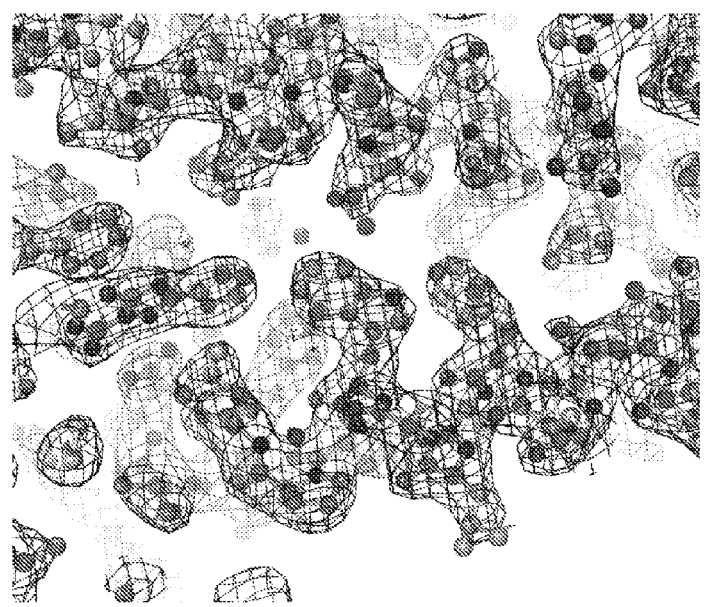

FIG. 13A-C. Examples of the electron density in a σ-A weighted $2F_o$-$F_c$ map calculated from the refined model for $A_{2A}$-T4L-ΔC. A. Electron density of helices VI and VII. B. Electron density associated with some lipids and helix interactions. Density from the final σ-A weighted $2F_o$-$F_c$ map is contoured at 1.4σ. C. The $2F_o$-$F_c$σ-A weighted and $F_o$-$F_c$ omit electron density maps of the Adenosine A2A antagonist ZM241385. Electron density is contoured at 1.4σ and 4σ from the $2F_o$-$F_c$ and $F_o$-$F_c$ omit maps, respectively, and calculated without the contribution of ZM241385.

Additional information related to the forgoing Figures may be found in U.S. provisional application 61/194,961, filed Oct. 1, 2008, and in the paper by Jaakola et al., *Science* (2008) 322, 1211-1217.

DETAILED DESCRIPTION OF THE INVENTION

Advantages and Utility

Briefly, and as described in more detail below, described herein is the 2.6 Angstrom resolution structure of the human A2A adenosine receptor in complex with a high affinity subtype-selective antagonist, ZM241385. Advantages of this invention can include the ability to create or identify compounds with increased specificity and functionality with respect to this protein and with respect to related proteins. While much of the disclosure that follows deals specifically with the human A2A adenosine receptor, the invention contemplates and encompasses the application of findings and observations developed using this receptor to similar GPCRs.

Definitions

Terms used in the claims and specification are defined as set forth below unless otherwise specified.

As used herein, the term "binding site" or "binding pocket" refers to a region of a protein that binds or interacts with a particular compound.

As used herein, the terms "binding" or "interaction" refers to a condition of proximity between a chemical entity, compound, or portions thereof, with another chemical entity, compound or portion thereof. The association or interaction can be non-covalent—wherein the juxtaposition is energetically favored by hydrogen bonding or van der Waals or electrostatic interactions—or it can be covalent.

As used herein, the term "residue" refers to an amino acid residue is one amino acid that is joined to another by a peptide bond. Residue is referred to herein to describe both an amino acid and its position in a polypeptide sequence.

As used herein, the term "surface residue" refers to a surface residue is a residue located on a surface of a polypeptide. In contrast, a buried residue is a residue that is not located on the surface of a polypeptide. A surface residue usually includes a hydrophilic side chain. Operationally, a surface residue can be identified computationally from a structural model of a polypeptide as a residue that contacts a sphere of hydration rolled over the surface of the molecular structure. A surface residue also can be identified experimentally through the use of deuterium exchange studies, or accessibility to various labeling reagents such as, e.g., hydrophilic alkylating agents.

As used herein, the term "polypeptide" refers to a single linear chain of 2 or more amino acids. A protein is an example of a polypeptide.

As used herein, the term "homolog" refers to a gene related to a second gene by descent from a common ancestral DNA sequence. The term, homolog, can apply to the relationship between genes separated by the event of speciation or to the relationship between genes separated by the event of genetic duplication.

As used herein, the term "conservation" refers to conservation a high degree of similarity in the primary or secondary structure of molecules between homologs. This similarity is thought to confer functional importance to a conserved region of the molecule. In reference to an individual residue or amino acid, conservation is used to refer to a computed likelihood of substitution or deletion based on comparison with homologous molecules.

As used herein, the term "distance matrix" refers to the method used to present the results of the calculation of an optimal pairwise alignment score. The matrix field (i,j) is the score assigned to the optimal alignment between two residues (up to a total of i by j residues) from the input sequences. Each entry is calculated from the top-left neighboring entries by way of a recursive equation.

As used herein, the term "substitution matrix" refers to a matrix that defines scores for amino acid substitutions, reflecting the similarity of physicochemical properties, and observed substitution frequencies. These matrices are the foundation of statistical techniques for finding alignments.

As used herein, the term "pharmacophore" refers to an ensemble of steric and electronic features that is necessary to ensure the optimal supramolecular interactions with a specific biological target structure and to trigger or block a biological response. A pharmacophore can be used to design one or more candidate compounds that comprise all or most of the ensemble of steric and electronic features present in the pharmacophore and that are expected to bind to a site and trigger or block a biological response.

As used herein, the term "atomic co-ordinates" refers to a set of three-dimensional co-ordinates for atoms within a molecular structure. In one embodiment, atomic-co-ordinates are obtained using X-ray crystallography according to methods well-known to those of ordinarily skill in the art of biophysics. Briefly described, X-ray diffraction patterns can be obtained by diffracting X-rays off a crystal. The diffraction data are used to calculate an electron density map of the unit cell comprising the crystal; said maps are used to establish the positions of the atoms (i.e., the atomic co-ordinates) within the unit cell. Those of skill in the art understand that a set of structure co-ordinates determined by X-ray crystallography contains standard errors. In other embodiments, atomic co-ordinates can be obtained using other experimental biophysical structure determination methods that can include electron diffraction (also known as electron crystallography) and nuclear magnetic resonance (NMR) methods. In yet other embodiments, atomic co-ordinates can be obtained using molecular modeling tools which can be based on one or more of ab initio protein folding algorithms, energy minimization, and homology-based modeling. These techniques are well known to persons of ordinary skill in the biophysical and bioinformatic arts, and are described in greater detail below.

Atomic co-ordinates for binding pockets, such as, e.g., binding pockets I, II and III of the human $A_{2A}$ adenosine receptor and it subtypes, and/or agonist/antagonist binding sites of the present invention are intended to encompass those co-ordinates set out in the .pdb file (Table 6) incorporated into this specification, as well as co-ordinates that are substantially equivalent. Substantially equivalent co-ordinates are those that can be related to a reference set of co-ordinates by transformation reflecting differences in the choice of origin or inter-axis angels for one or more axes used to define the coordinate system. Operationally, co-ordinates are "substantially equivalent" when the structures represented by those co-ordinates can be superimposed in a manner such that root mean square deviations (RMSD) of atomic positions for the structures differs by less than a predetermined threshold. In some embodiments that threshold is less than about 5 Angstroms, or less than about 4 Angstroms, or less than about 3 Angstroms, or less than about 2 Angstroms, or less than about 1 Angstrom, or less than about 0.9 Angstrom, or less than about 0.8 Angstrom, or less than about 0.7 Angstrom, or less than about 0.6 Angstrom, or less than about 0.5 Angstrom, or less than about 0.4 Angstrom, or less than about 0.3 Angstrom. Preferably, co-ordinates are considered "substantially equivalent" when the RMSD is less than about 1 Angstrom. Methods for structure superpositioning and RMSD calculations are well known to those of ordinary skill in the art, and can be carried out using programs such as, e.g., the programs listed in Table 5 below.

Structural similarity can be inferred from, e.g., sequence similarity, which can be determined by one of ordinary skill through visual inspection and comparison of the sequences, or through the use of well-known alignment software programs such as CLUSTAL (Wilbur et al., *Proc. Natl. Acad. Sci. USA*, 80, 726-730 (1983)) or CLUSTALW (Thompson et al., *Nucleic Acids Research*, 22:4673 4680 (1994)) or BLAST® (Altschul et al., *J Mol. Biol.*, October 5; 215(3):403 10 (1990)), a set of similarity search programs designed to explore all of the available sequence databases regardless of whether the query is protein or DNA. CLUSTAL W is available at the EMBL-EBI website (found on the web at the site: ebi.ac.uk/clustalw); BLAST is available from the National Center for Biotechnology website (found on the web at the site: ncbi.nlm.nih.gov/BLAST). A residue within a first protein or nucleic acid sequence corresponds to a residue within a second protein or nucleic acid sequence if the two residues occupy the same position when the first and second sequences are aligned.

The term "a set" refers to a collection of one or more objects.

The term percent "identity," in the context of two or more nucleic acid or polypeptide sequences, refer to two or more sequences or subsequences that have a specified percentage of nucleotides or amino acid residues that are the same, when compared and aligned for maximum correspondence, as measured using one of the sequence comparison algorithms described below (e.g., BLASTP and BLASTN or other algorithms available to persons of skill) or by visual inspection. Depending on the application, the percent "identity" can exist over a region of the sequence being compared, e.g., over a functional domain, or, alternatively, exist over the full length of the two sequences to be compared.

For sequence comparison, typically one sequence acts as a reference sequence to which test sequences are compared. When using a sequence comparison algorithm, test and reference sequences are input into a computer, subsequence co-ordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (NCBI web-site)

The term "sterol" refers to a subgroup of steroids with a hydroxyl group at the 3-position of the A-ring (Subramaniam et al., *J. Lipid Res.* 46 (5):839-861 (2005)). Sterols are amphipathic lipids synthesized from acetyl-coenzyme A via the HMG-CoA reductase pathway. The overall molecule is quite flat. Sterols can include, e.g., cholesterol or CHS.

The term "atomic co-ordinates for residues" refers to co-ordinates for all atoms associated with a residue, or for some of the atoms such as, e.g., side chain atoms.

The term "atomic co-ordinates of a candidate compound" refers to co-ordinates for all atoms comprising the compound or a subset of atoms comprising the compound.

The term "characterizing a binding interaction" refers to characterizing any observable property of a first molecule and determining an whether there is a change in that observable property after contacting the first molecule with a second molecule under conditions in which said first and second molecules can potentially bind.

Ballesteros-Weinstein numbering is used throughout the text as superscripts to the protein numbering. Within each helix is a single most conserved residue among the class A GPCRs. This residue is designated X.50, where x is the number of the transmembrane helix. All other residues on that helix are numbered relative to this conserved position.

It must be noted that, as used in the specification and the appended claims, the singular forms "a," "an" and "the" include plural referents unless the context clearly dictates otherwise.

Introduction

G-protein coupled receptors are cell surface receptors that indirectly transduce extracellular signals to downstream effectors, e.g., intracellular signaling proteins, enzymes, or channels. G-protein coupled receptor membrane proteins are grouped into one of 6 classes: A, B, C, D, E, and F. The interaction between the receptor and the downstream effector is mediated by a G-protein, a heterotrimeric protein that binds GTP. Examples of mammalian G proteins include Gi, Go, Gq, Gs, and Gt. Changes in the activity of the G proteins then mediate subsequent cellular events.

G-protein coupled receptors (GPCRs) typically have seven transmembrane regions, along with an extracellular domain and a cytoplasmic tail at the C-terminus. These receptors form a large superfamily of related receptor molecules that play a key role in many signaling processes, such as sensory and hormonal signal transduction. An example of a mammalian G-protein coupled receptor is the adenosine $A_{2A}$ receptor, a receptor in the Class A subfamily of GPCRs.

Class A GPCRs function in a variety of physiological processes such as vasodilation, bronchodilation, neurotransmitter signaling, stimulation of endocrine secretions, gut peristalsis, development, mitogenesis, cell proliferation, cell migration, immune system function, and oncogenesis. Accordingly, class A GPCRs can be used as screening targets to identify modulators of these processes which can then function to ameliorate diseases associated with these processes, e.g., cancer and autoimmunity. A 2.8 Å resolution crystal structure of a thermally-stabilized human $\beta_2$-adrenergic receptor bound to cholesterol and the partial inverse agonist timolol has been previously described (see, e.g., D. M. Rosenbaum et al., *Science* 318: 1266 (2007); V. Cherezov et al., *Science* 318: 1258 (2007); U.S. Prov. App. No. 60/999,51, filed Oct. 22, 2007; U.S. Prov. App. No. 61/000,325, filed Oct. 24, 2007; and U.S. Prov. App. No. 61,0606,107, filed Jun. 9, 2008). That work indicated a structurally relevant cholesterol binding site between helices I, II, III, and IV. Thermal stability analysis using isothermal denaturation confirmed that cholesterol enhances the stability of the $\beta_2$-adrenergic receptor and identified a consensus binding site.

The Crystal Structure Co-Ordinates of the Human Adenosine $A_{2A}$ Receptor Bound to ZM241385

The 2.6 Angstrom structure of human $A_{2A}$ adenosine receptor bound to ZM241385 can be used as a model for rationally designing pharmacophore and/or candidate compounds, either de novo or by modification of known compounds. As noted below, the multiple ligand binding sites in this structure include amino acids that are highly conserved across a large number of class A G protein coupled receptors (GPCRs) indicating that the 2.6 Angstrom structure of human $A_{2A}$ adenosine receptor can be used for the rational designing of ligands (e.g., therapeutic compounds) that bind to this receptor and others. Pharmacophore and candidate compounds identified through the use of the crystal structure co-ordinates will have utility as pharmaceuticals due to their ability to alter the structure and/or binding properties of the $A_{2A}$ adenosine receptor. Pharmacophores and candidate compounds can be determined according to any method known in the art, including the methods described in U.S. Pat. No. 5,888,738 to Hendry, and the methods described in U.S. Pat. No. 5,856,116 to Wilson et al. the disclosures of which both are incorporated by reference in their entirety for all purposes.

The structure data provided herein can be used in conjunction with computer-modeling techniques to develop models of sites on the human $A_{2A}$ adenosine receptor or related GPCRs selected by analysis of the crystal structure data. The site models characterize the three-dimensional topography of site surface, as well as factors including van der Waals contacts, electrostatic interactions, and hydrogen-bonding opportunities. Computer simulation techniques can be used to map interaction positions for functional groups including protons, hydroxyl groups, amine groups, divalent cations, aromatic and aliphatic functional groups, amide groups, alcohol groups, etc. that are designed to interact with the model site. These groups can be designed into a pharmacophore or candidate compound with the expectation that the candidate compound will specifically bind to the site. Pharmacophore design thus involves a consideration of the ability of the candidate compounds falling within the pharmacophore to interact with a site through any or all of the available types of chemical interactions, including hydrogen bonding, van der Waals, electrostatic, and covalent interactions, although, in general, and preferably, pharmacophores interact with a site through non-covalent mechanisms.

The ability of a pharmacophore or candidate compound to bind to the human $A_{2A}$ adenosine receptor can be analyzed prior to actual synthesis using computer modeling techniques. Only those candidates that are indicated by computer modeling to bind the target with sufficient binding energy (i.e., binding energy corresponding to a dissociation constant with the target on the order of $10^{-2}$ M or tighter) can be synthesized and tested for their ability to bind to the human $A_{2A}$ adenosine receptor using binding assays or functional assays known to those of skill in the art. The computational evaluation step thus avoids the unnecessary synthesis of compounds that are unlikely to bind the human $A_{2A}$ adenosine receptor or one or more of its constitutive binding sites, or the related binding sites of another GPCR with adequate affinity.

A human $A_{2A}$ adenosine receptor or candidate compound(s) can be computationally evaluated and designed by means of a series of steps in which chemical entities or fragments are screened and selected for their ability to associate with individual binding target sites on the human $A_{2A}$ adenosine receptor or binding site thereof, including, but not limited to binding pockets I, II, and III of the human $A_{2A}$ adenosine receptor. One skilled in the art can use one of several methods to screen chemical entities or fragments for their ability to associate with one or more of these human $A_{2A}$ adenosine receptor binding sites. For example, increased affinity and specificity may be designed into caffeine and other xanthine molecules by combining interactions with both xanthine and non-xanthine binding sites.

The process can begin by visual inspection of, for example a target site on a computer screen, based on the human $A_{2A}$ adenosine receptor co-ordinates, or a subset of those co-ordinates (e.g., binding Pockets I, II or III), as set forth in Table 6. Selected fragments or chemical entities can then be positioned in a variety of orientations or "docked" within a target site of the human $A_{2A}$ adenosine receptor as defined from analysis of the crystal structure data. Docking can be accomplished using software such as Quanta (Molecular Simulations, Inc., San Diego, Calif.) and Sybyl (Tripos, Inc. St. Louis, Mo.) followed by energy minimization and molecular dynamics with standard molecular mechanics forcefields such as CHARMM (Molecular Simulations, Inc., San Diego, Calif.), ICM (Molsoft, San Diego, Calif.), and AMBER (University of California, San Francisco).

Specialized computer programs can also assist in the process of selecting fragments or chemical entities. These include but are not limited to: GRID (Goodford et al., *J. Med. Chem.*, 28, pp. 849 857 (1985)); GRID is available from Oxford University, Oxford, UK; MCSS (Miranker, A. and M. Karplus, *Proteins: Structure, Function and Genetics*, 11, pp. 29 34 (1991)); MCSS is available from Molecular Simulations, Inc., San Diego, Calif.; AUTODOCK (Goodsell, D. S, and A. J. Olsen, *Proteins: Structure, Function, and Genetics*, 8, pp. 195 202 (1990)); AUTODOCK is available from Scripps Research Institute, La Jolla, Calif.; DOCK (Kuntz, I. D., et al., *J. Mol. Biol.*, 161, pp. 269 288 (1982)); DOCK is available from University of California, San Francisco, Calif.; CERIUS II (available from Molecular Simulations, Inc., San Diego, Calif.); and Flexx (Raret et al., *J. Mol. Biol.*, 261, pp. 470 489 (1996)).

After selecting suitable chemical entities or fragments, they can be assembled into a single compound. Assembly can proceed by visual inspection of the relationship of the fragments to each other on a three-dimensional image of the fragments in relation to the human $A_{2A}$ adenosine receptor or its binding sites or those of a related GPCR receptor structure or portion thereof displayed on a computer screen. Visual inspection can be followed by manual model building using software such as the Quanta or Sybyl programs described above.

Software programs also can be used to aid one skilled in the art in connecting the individual chemical entities or fragments. These include, but are not limited to CAVEAT (Bartlett, P. A., et al. "CAVEAT: A Program to Facilitate the Structure-Derived Design of Biologically Active Molecules" In "Molecular Recognition in Chemical and Biological Problems," Special Publ, Royal Chem. Soc., 78, pp. 182-196 (1989)); CAVEAT is available from the University of California, Berkeley, Calif.; 3D Database systems such as MACCS-3D (MDL Information Systems, San Leandro, Calif.); this area is reviewed in Martin, Y. C., *J. Med. Chem.*, 35:2145 2154 (1992)); and HOOK (available from Molecular Simulations Inc., San Diego, Calif.).

As an alternative to building candidate pharmacophores or candidate compounds up from individual fragments or chemical entities, they can be designed de novo using the structure of the $A_{2A}$ adenosine receptor, its constituent binding pockets I, II and III, or the homologous cavities in a related GPCR, optionally, including information from co-factor(s) or known activators or inhibitor(s) that bind to the target site. De novo design can be implemented by programs including, but not limited to LUDI (Bohm, H. J., *J. Comp. Aid. Molec. Design*, 6, pp. 61 78 (1992)); LUDI is available from Molecular Simulations, Inc., San Diego, Calif.; LEGEND (Nishibata, Y., and Itai, A., *Tetrahedron* 47, p. 8985 (1991); LEGEND is available from Molecular Simulations, San Diego, Calif.; and LeapFrog (available from Tripos Associates, St. Louis, Mo.).

The functional effects of known $A_{2A}$ adenosine receptor ligands also can be altered through the use of the molecular modeling and design techniques described herein. This can be carried out by docking the structure of the known ligand on a human $A_{2A}$ adenosine receptor or a model structure of one or more binding sites of the human $A_{2A}$ adenosine receptor (e.g., binding pockets I, II and/or III describes herein) and modifying the shape and charge distribution of the ligand or protein model structure to optimize the binding interactions between the ligand and protein. The modified structure can be synthesized or obtained from a library of compounds and tested for its binding affinity and/or effect on ribosome function. Of course, where the crystal structure of a complex between a human $A_{2A}$ adenosine receptor (or subunit thereof) and a ligand is known, comparisons between said complex and the structures of the present invention can be made to gain additional information about alterations in human $A_{2A}$ adenosine receptor conformation that occur upon ligand binding. This information can be used in design of optimized ligands. Compounds that interfere or activate human $A_{2A}$ adenosine receptor function (e.g., by interacting with binding pockets I, II or III) are especially well suited for the docking, co-crystallization, and optimization applications of the present invention.

Additional molecular modeling techniques also can be employed in accordance with the invention. See, e.g., Cohen, N. C., et al. *J. Med. Chem.*, 33, pp. 883 894 (1990); Hubbard, Roderick E., *Curr. Opin. Biotechnol.* 8, pp. 696-700 (1997); and Afshar, et al. "Structure-Based and Combinatorial Search for New RNA-Binding Drugs," *Curr. Opin. Biotechnol.* 10, pp. 59-63 (1999).

Following pharmacophore or candidate compound design or selection according to any of the above methods or other methods known to one skilled in the art, the efficiency with which a candidate compound falling within the pharmacophore definition binds to the human $A_{2A}$ adenosine receptor or at least one its three preferred binding sites, or alternatively binds to a related GPCR or homologous portions thereof, can be tested and optimized using computational evaluation. A candidate compound can be optimized, e.g., so that in its bound state it would preferably lack repulsive electrostatic interaction with the target site. These repulsive electrostatic interactions include repulsive charge-charge, dipole-dipole, and charge-dipole interactions. It is preferred that the sum of all electrostatic interactions between the candidate compound and the human $A_{2A}$ adenosine receptor, including its binding pockets I, II, and/or III (collectively "target") when the candidate compound is bound to the target make a neutral or favorable contribution to the binding enthalpy or free energy.

Specific computer software is available in the art to evaluate compound deformation energy and electrostatic interactions. Examples of programs designed for such uses include, but are not limited to Gaussian 92, revision C (Frisch, M. J., Gaussian, Inc., Pittsburgh, Pa. (1992)); AMBER, version 4.0 (Kollman, P. A., University of California at San Francisco, (1994)); QUANTA/CHARMM (Molecular Simulations, Inc., San Diego, Calif. (1994)); and Insight II/Discover (Biosym Technologies Inc., San Diego, Calif. (1994)). These programs can be run, using, e.g., a Silicon Graphics workstation, Indigo, 02-R10000 or IBM RISC/6000 workstation model 550. Other hardware and software combinations can be used to carry out the above described functions, and are known to those of skill in the art. In general, the methods described herein, particularly computer-implemented methods, comprise a step of recording or storing data onto a medium, wherein the medium can include a computer-readable medium. Additionally, or alternatively, the methods comprise a step of reporting or communicating the data to a user of interest, e.g., an operator of the device and/or computer that is employed in the method; or the computer can perform an additional useful task, e.g., alert the operator of the computer that a function has been completed, upon completing one or more determining steps of the method.

Once a pharmacophore or candidate compound has been optimally selected or designed, as described above, substitutions can then be made in some of its atoms or side groups to improve or modify its binding properties. Generally, initial substitutions are conservative in that the replacement group will have approximately the same size, shape, hydrophobicity and charge as the original group. Components known in the art to alter conformation should be avoided in making substitutions. Substituted candidates can be analyzed for efficiency of fit to the human $A_{2A}$ adenosine receptor (or one or more binding sites selected from binding pockets I, II and III of the human $A_{2A}$ adenosine receptor) using the same methods described above.

Assays

Any one of a number of assays of function known to those of skill in the art can be used to determine the biological activity of candidate compounds.

Candidate compound interaction with the human $A_{2A}$ adenosine receptor (or one or more binding sites selected from binding pockets I, II and III of the human $A_{2A}$ adenosine receptor) or to a related GPCR or portion thereof can be evaluated using direct binding assays including filter binding assays, such as are known to those skilled in the art. Binding assays can be modified to evaluate candidate compounds that competitively inhibit the binding of, e.g., known human $A_{2A}$ adenosine receptor binding compounds including xanthine and xanthine-based compounds such as theophylline, theobromine and caffeine. These and other assays are described in International Publication WO 00/69391, the entire disclosure of which is incorporated by reference in its entirety for all purposes. Methods of assaying for modulators of ligand binding and signal transduction include in vitro ligand binding assays using GPCRs, such as human $A_{2A}$ adenosine receptor (or one or more binding sites selected from the binding pockets I, II and III of the human $A_{2A}$ adenosine receptor), portions thereof such as the extracellular domain, or chimeric proteins comprising one or more domains of a GPCR, oocyte GPCR expression or tissue culture cell GPCR expression, either naturally occurring or recombinant; membrane expression of a GPCR, either naturally occurring or recombinant; tissue expression of a GPCR; expression of a GPCR in a transgenic animal, etc.

As noted above, GPCRs and their alleles and polymorphic variants are G-protein coupled receptors that participate in signal transduction and are associated with cellular function in a variety of cells, e.g., neurons, immune system cells, kidney, liver, colon, adipose, and other cells. The activity of GPCR polypeptides can be assessed using a variety of in vitro and in vivo assays to determine functional, chemical, and physical effects, e.g., measuring ligand binding, (e.g., radioactive ligand binding), second messengers (e.g., cAMP, cGMP, $IP_3$, DAG, or $Ca^{2+}$), ion flux, phosphorylation levels, transcription levels, neurotransmitter levels, and the like. Such assays can be used to test for inhibitors and activators of a GPCR. In particular, the assays can be used to test for compounds that modulate natural ligand-induced GPCR activity, for example, by modulating the binding of the natural ligand to the receptor and/or by modulating the ability of the natural ligand to activate the receptor. Typically in such assays, the test compound is contacted with the GPCR in the presence of the natural ligand. The natural ligand can be added to the assay before, after, or concurrently with the test compound. The results of the assay, for example, the level of binding, calcium mobilization, etc. is then compared to the level in a control assay that comprises the GPCR and natural ligand in the absence of the test compound.

Screening assays of the invention are used to identify modulators that can be used as therapeutic agents, e.g., antagonists of GPCR activity. For example, ZM241385 is a known high-affinity specific antagonist of the human $A_{2A}$ adenosine receptor.

The effects of test compounds upon the function of the GPCR polypeptides can be measured by examining any of the parameters described above. Any suitable physiological change that affects GPCR activity can be used to assess the influence of a test compound on the GPCRs and natural ligand-mediated GPCR activity. When the functional consequences are determined using intact cells or animals, one can also measure a variety of effects such as transmitter release, hormone release, transcriptional changes to both known and uncharacterized genetic markers (e.g., northern blots), changes in cell metabolism such as cell growth or pH changes, and changes in intracellular second messengers such as $Ca^{2+}$, $IP_3$ or cAMP.

For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., *Nature* 348:125-32 (1990); Pitcher et al., *Annu. Rev. Biochem.* 67:653-92 (1998).

Modulators of GPCR activity are tested using GPCR polypeptides, either recombinant or naturally occurring. The protein can be isolated, expressed in a cell, expressed in a membrane derived from a cell, expressed in tissue or in an animal, either recombinant or naturally occurring. For example, neurons, cells of the immune system, adipocytes, kidney cells, transformed cells, or membranes can be used. Modulation is tested using one of the in vitro or in vivo assays described herein or others as generally known in the art. Signal transduction can also be examined in vitro with soluble or solid state reactions, using a chimeric molecule such as an extracellular domain of a receptor covalently linked to a heterologous signal transduction domain, or a heterologous extracellular domain covalently linked to the transmembrane and or cytoplasmic domain of a receptor. Furthermore, ligand-binding domains of the protein of interest can be used in vitro in soluble or solid state reactions to assay for ligand binding.

Ligand binding to a human $A_{2A}$ adenosine receptor (or one or more binding sites selected from binding pockets I, II and III of the human $A_{2A}$ adenosine receptor) or a chimeric protein derivative can be tested in a number of formats. For example, binding can be performed in solution, in a bilayer membrane, attached to a solid phase, in a lipid monolayer, or in vesicles. Typically, in an assay of the invention, the binding of the natural ligand to its receptor is measured in the presence of a candidate modulator. Alternatively, the binding of the candidate modulator can be measured in the presence of the natural ligand. Often, competitive assay that measure the ability of a compound to compete with binding of the natural ligand to the receptor are used. Binding can be measured by assessing GPCR activity or by other assays: binding can be tested by measuring e.g., changes in spectroscopic characteristics (e.g., fluorescence, absorbance, refractive index), hydrodynamic (e.g., shape) changes, or changes in chromatographic or solubility properties.

Receptor-G-protein interactions can also be used to assay for modulators. For example, in the absence of GTP, binding of an activator such as the natural ligand will lead to the formation of a tight complex of a G protein (all three subunits) with the receptor. This complex can be detected in a variety of ways, as noted above. Such an assay can be modified to search for inhibitors. For example, a ligand can be added to the human $A_{2A}$ adenosine receptor and G protein in the absence of GTP to form a tight complex Inhibitors can be identified by looking at dissociation of the receptor-G protein complex. In the presence of GTP, release of the alpha subunit of the G protein from the other two G protein subunits serves as a criterion of activation.

An activated or inhibited G-protein will in turn alter the properties of downstream effectors such as proteins, enzymes, and channels. The classic examples are the activation of cGMP phosphodiesterase by transducin in the visual system, adenylate cyclase by the stimulatory G-protein, phospholipase C by $G_q$ and other cognate G proteins, and modulation of diverse channels by Gi and other G proteins. Downstream consequences such as generation of diacyl glycerol and $IP_3$ by phospholipase C, and in turn, for calcium mobilization e.g., by $IP_3$ can also be examined. Thus, modulators can be evaluated for the ability to stimulate or inhibit ligand-mediated downstream effects. In other examples, the ability of a modulator to activate a GPCR expressed in adipocytes in comparison to the ability of a natural ligand, can be determined using assays such as lipolysis (see, e.g., WO01/61359).

Activated GPCRs become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. The kinase/arrestin pathway plays a key role in the desensitization of many GPCR receptors. Modulators can therefore also be identified using assays involving beta-arrestin recruitment. Beta-arrestin serves as a regulatory protein that is distributed throughout the cytoplasm in unactivated cells. Ligand binding to an appropriate GPCR is associated with redistribution of beta-arrestin from the cytoplasm to the cell surface, where it associates with the GPCR. Thus, receptor activation and the effect of candidate modulators on ligand-induced receptor activation, can be assessed by monitoring beta-arrestin recruitment to the cell surface. This is frequently performed by transfecting a labeled beta-arrestin fusion protein (e.g., beta-arrestin-green fluorescent protein (GFP)) into cells and monitoring its distribution using confocal microscopy (see, e.g., Groarke et al., *J. Biol. Chem.* 274(33):23263-69 (1999)).

Receptor internalization assays can also be used to assess receptor function. Upon ligand binding, the G-protein coupled receptor—ligand complex is internalized from the plasma membrane by a clathrin-coated vesicular endocytic process; internalization motifs on the receptors bind to adaptor protein complexes and mediate the recruitment of the activated receptors into clathrin-coated pits and vesicles. Because only activated receptors are internalized, it is possible to detect ligand-receptor binding by determining the amount of internalized receptor. In one assay format, cells are transiently transfected with radiolabeled receptor and incubated for an appropriate period of time to allow for ligand binding and receptor internalization. Thereafter, surface-bound radioactivity is removed by washing with an acid solution, the cells are solubilized, and the amount of internalized radioactivity is calculated as a percentage of ligand binding. See, e.g., Vrecl et al., *Mol. Endocrinol.* 12:1818-29 (1988) and Conway et al., *J. Cell Physiol.* 189(3):341-55 (2001). In addition, receptor internalization approaches have allowed real-time optical measurements of GPCR interactions with other cellular components in living cells (see, e.g., Barak et al., *Mol. Pharmacol.* 51(2)177-84 (1997)). Modulators can be identified by comparing receptor internalization levels in control cells and cells contacted with candidate compounds. For example, candidate modulators the human $A_{2A}$ adenosine receptor are assayed by examining their effects on receptor internalization upon binding of the natural ligand, e.g., adenosine.

Another technology that can be used to evaluate GPCR-protein interactions in living cells involves bioluminescence resonance energy transfer (BRET). A detailed discussion regarding BRET can be found in Kroeger et al., *J. Biol. Chem.*, 276(16):12736-43 (2001).

Receptor-stimulated guanosine 5'-O-(.gamma.-Thio)-Triphosphate ([$^{35}$S]GTP.gamma.S) binding to G-proteins can also be used as an assay for evaluating modulators of GPCRs. [$^{35}$S]GTPγS is a radiolabeled GTP analog that has a high affinity for all types of G-proteins, is available with a high specific activity and, although unstable in the unbound form, is not hydrolyzed when bound to the G-protein. Thus, it is possible to quantitatively assess ligand-bound receptor by comparing stimulated versus unstimulated [$^{35}$S]GTP.gamma.S binding utilizing, for example, a liquid scintillation counter. Inhibitors of the receptor-ligand interactions would result in decreased [$^{35}$S]GTPγS binding. Descriptions of [$^{35}$S]GTPγS binding assays are provided in Traynor and Nahorski, *Mol. Pharmacol.* 47(4):848-54 (1995) and Bohn et al., *Nature* 408:720-23 (2000).

The ability of modulators to affect ligand-induced ion flux can also be determined. Ion flux can be assessed by determining changes in polarization (i.e., electrical potential) of the cell or membrane expressing a GPCR. One means to determine changes in cellular polarization is by measuring changes in current (thereby measuring changes in polarization) with voltage-clamp and patch-clamp techniques, e.g., the "cell-attached" mode, the "inside-out" mode, and the "whole cell" mode (see, e.g., Ackerman et al., *New Engl. J. Med.* 336:1575-1595 (1997)). Whole cell currents are conveniently determined using the standard methodology (see, e.g., Hamil et al., *Pflügers. Archiv.* 391:85 (1981). Other known assays include: radiolabeled ion flux assays and fluorescence assays using voltage-sensitive dyes (see, e.g., Vestergarrd-Bogind et al., *J. Membrane Biol.* 88:67-75 (1988); Gonzales & Tsien, *Chem. Biol.* 4:269-277 (1997); Daniel et al., *J. Pharmacol. Meth.* 25:185-193 (1991); Holevinsky et al., *J.*

*Membrane Biology* 137:59-70 (1994)). Generally, the compounds to be tested are present in the range from 1 pM to 100 mM.

Preferred assays for G-protein coupled receptors include cells that are loaded with ion or voltage sensitive dyes to report receptor activity. Assays for determining activity of such receptors can also use known agonists and antagonists for other G-protein coupled receptors and the natural ligands disclosed herein as negative or positive controls to assess activity of tested compounds. In assays for identifying modulatory compounds (e.g., agonists, antagonists), changes in the level of ions in the cytoplasm or membrane voltage are monitored using an ion sensitive or membrane voltage fluorescent indicator, respectively. Among the ion-sensitive indicators and voltage probes that can be employed are those disclosed in the Molecular Probes 1997 Catalog. For G-protein coupled receptors, promiscuous G-proteins such as $G\alpha 15$ and $G\alpha 16$ can be used in the assay of choice (Wilkie et al., *Proc. Nat'l Acad. Sci. USA* 88:10049-10053 (1991)). Such promiscuous G-proteins allow coupling of a wide range of receptors to signal transduction pathways in heterologous cells.

Receptor activation by ligand binding typically initiates subsequent intracellular events, e.g., increases in second messengers such as $IP_3$, which releases intracellular stores of calcium ions. Activation of some G-protein coupled receptors stimulates the formation of inositol triphosphate ($IP_3$) through phospholipase C-mediated hydrolysis of phosphatidylinositol (Berridge & Irvine, *Nature* 312:315-21 (1984)). $IP_3$ in turn stimulates the release of intracellular calcium ion stores. Thus, a change in cytoplasmic calcium ion levels, or a change in second messenger levels such as $IP_3$ can be used to assess G-protein coupled receptor function. Cells expressing such G-protein coupled receptors can exhibit increased cytoplasmic calcium levels as a result of contribution from both intracellular stores and via activation of ion channels, in which case it can be desirable although not necessary to conduct such assays in calcium-free buffer, optionally supplemented with a chelating agent such as EGTA, to distinguish fluorescence response resulting from calcium release from internal stores.

Other assays can involve determining the activity of receptors which, when activated by ligand binding, result in a change in the level of intracellular cyclic nucleotides, e.g., cAMP or cGMP, by activating or inhibiting downstream effectors such as adenylate cyclase. There are cyclic nucleotide-gated ion channels, e.g., rod photoreceptor cell channels and olfactory neuron channels that are permeable to cations upon activation by binding of cAMP or cGMP (see, e.g., Altenhofen et al., *Proc. Natl. Acad. Sci. U.S.A.* 88:9868-9872 (1991) and Dhallan et al., *Nature* 347:184-187 (1990)). In cases where activation of the receptor results in a decrease in cyclic nucleotide levels, it can be preferable to expose the cells to agents that increase intracellular cyclic nucleotide levels, e.g., forskolin, prior to adding a receptor-activating compound to the cells in the assay. Cells for this type of assay can be made by co-transfection of a host cell with DNA encoding a cyclic nucleotide-gated ion channel, GPCR phosphatase and DNA encoding a receptor (e.g., certain glutamate receptors, muscarinic acetylcholine receptors, dopamine receptors, serotonin receptors, and the like), which, when activated, causes a change in cyclic nucleotide levels in the cytoplasm.

In one embodiment, changes in intracellular cAMP or cGMP can be measured using immunoassays. The method described in Offermanns & Simon, *J. Biol. Chem.* 270:15175-15180 (1995) can be used to determine the level of cAMP. Also, the method described in Felley-Bosco et al., *Am. J. Resp. Cell and Mol. Biol.* 11:159-164 (1994) can be used to determine the level of cGMP. Further, an assay kit for measuring cAMP and/or cGMP is described in U.S. Pat. No. 4,115,538, herein incorporated by reference.

In another embodiment, phosphatidyl inositol (PI) hydrolysis can be analyzed according to U.S. Pat. No. 5,436,128, herein incorporated by reference. Briefly, the assay involves labeling of cells with $^3$H-myoinositol for 48 or more hrs. The labeled cells are treated with a test compound for one hour. The treated cells are lysed and extracted in chloroform-methanol-water after which the inositol phosphates are separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which can or can not contain an agonist).

In another embodiment, transcription levels can be measured to assess the effects of a test compound on ligand-induced signal transduction. A host cell containing the protein of interest is contacted with a test compound in the presence of the natural ligand for a sufficient time to effect any interactions, and then the level of gene expression is measured. The amount of time to effect such interactions can be empirically determined, such as by running a time course and measuring the level of transcription as a function of time. The amount of transcription can be measured by using any method known to those of skill in the art to be suitable. For example, mRNA expression of the protein of interest can be detected using northern blots or their polypeptide products can be identified using immunoassays. Alternatively, transcription based assays using reporter genes can be used as described in U.S. Pat. No. 5,436,128, herein incorporated by reference. The reporter genes can be, e.g., chloramphenicol acetyltransferase, firefly luciferase, bacterial luciferase, beta-galactosidase and alkaline phosphatase. Furthermore, the protein of interest can be used as an indirect reporter via attachment to a second reporter such as green fluorescent protein (see, e.g., Mistili & Spector, *Nature Biotechnology* 15:961-964 (1997)).

The amount of transcription is then compared to the amount of transcription in either the same cell in the absence of the test compound, or it can be compared with the amount of transcription in a substantially identical cell that lacks the protein of interest. A substantially identical cell can be derived from the same cells from which the recombinant cell was prepared but which had not been modified by introduction of heterologous DNA. Any difference in the amount of transcription indicates that the test compound has in some manner altered the activity of the protein of interest.

Samples that are treated-with a potential GPCR inhibitor or activator are compared to control samples comprising the natural ligand without the test compound to examine the extent of modulation. Control samples (untreated with activators or inhibitors) are assigned a relative GPCR activity value of 100 Inhibition of a GPCR is achieved when the GPCR activity value relative to the control is about 90%, optionally 50%, optionally 25-0%. Activation of a GPCR is achieved when the GPCR activity value relative to the control is 110%, optionally 150%, 200-500%, or 1000-2000%.

In one embodiment the invention provides soluble assays using molecules such as a domain, e.g., a ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; a GPCR; or a cell or tissue expressing a GPCR, either naturally occurring or recombinant. In another embodiment, the invention provides solid phase based in vitro assays in a high throughput format, where the domain, chimeric molecule, GPCR, or cell or tissue expressing a GPCR is attached to a solid phase substrate.

Certain screening methods involve screening for a compound that modulates the expression of the GPCRs described herein, or the levels of natural ligands, e.g., ASP and stanniocalcins. Such methods generally involve conducting cell-based assays in which test compounds are contacted with one or more cells expressing the GPCR or ligand and then detecting an increase or decrease in expression (either transcript or translation product). Such assays are typically performed with cells that express the endogenous GPCR or ligand.

Expression can be detected in a number of different ways. As described herein, the expression levels of the protein in a cell can be determined by probing the mRNA expressed in a cell with a probe that specifically hybridizes with a transcript (or complementary nucleic acid derived therefrom) of the GPCR or protein ligand. Probing can be conducted by lysing the cells and conducting Northern blots or without lysing the cells using in situ-hybridization techniques (see above). Alternatively, protein can be detected using immunological methods in which a cell lysate is probed with antibodies that specifically bind to the protein.

Other cell-based assays are reporter assays conducted with cells that do not express the protein. Certain of these assays are conducted with a heterologous nucleic acid construct that includes a promoter that is operably linked to a reporter gene that encodes a detectable product. A number of different reporter genes can be utilized. Some reporters are inherently detectable. An example of such a reporter is green fluorescent protein that emits fluorescence that can be detected with a fluorescence detector. Other reporters generate a detectable product. Often such reporters are enzymes. Exemplary enzyme reporters include, but are not limited to, beta-glucuronidase, CAT (chloramphenicol acetyl transferase), luciferase, beta-galactosidase and alkaline phosphatase.

In these assays, cells harboring the reporter construct are contacted with a test compound. A test compound that either modulates the activity of the promoter by binding to it or triggers a cascade that produces a molecule that modulates the promoter causes expression of the detectable reporter. Certain other reporter assays are conducted with cells that harbor a heterologous construct that includes a transcriptional control element that activates expression of the GPCR or ligand and a reporter operably linked thereto. Here, too, an agent that binds to the transcriptional control element to activate expression of the reporter or that triggers the formation of an agent that binds to the transcriptional control element to activate reporter expression, can be identified by the generation of signal associated with reporter expression.

In one embodiment the invention provides soluble assays using molecules such as a domain, e.g., a ligand binding domain, an extracellular domain, a transmembrane domain (e.g., one comprising seven transmembrane regions and cytosolic loops), the transmembrane domain and a cytoplasmic domain, an active site, a subunit association region, etc.; a domain that is covalently linked to a heterologous protein to create a chimeric molecule; a GPCR; or a cell or tissue expressing a GPCR, either naturally occurring or recombinant. In another embodiment, the invention provides solid phase based in vitro assays in a high throughput format, where the domain, chimeric molecule, GPCR, or cell or tissue expressing a GPCR is attached to a solid phase substrate.

In the high throughput assays of the invention, it is possible to screen up to several thousand different modulators or ligands in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-1500 different compounds. It is possible to assay several different plates per day; assay screens for up to about 6,000-20,000 different compounds are possible using the integrated systems of the invention.

The molecule of interest can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest (e.g., the signal transduction molecule of interest) is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.). Antibodies to molecules with natural binders such as biotin are also widely available and are appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherin family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., Clinical Chemistry 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Modulators

Inhibitors and/or activators identified according to the methods of the invention can be provided from libraries of compounds available from a number of sources or can be derived by combinatorial chemistry approaches known in the art. Such libraries include but are not limited to the available Chemical Director, Maybridge, and natural product collections. In one embodiment of the invention libraries of compounds with known or predicted structures can be docked to the human $A_{2A}$ adenosine receptor structures of the invention. In another embodiment, the libraries for ligands binding to binding pockets I, II and/or III can include xanthines and xanthine derivatives. In another embodiment, the libraries can include a linker component or moiety. In some embodiments, the linker can include from about 10-22 atoms and can include one or more of C, O, N, S, and/or H atoms. In another embodiment, the libraries can include a ligand binding site (also known as the ligand, agonist, or antagonist binding pocket) component or moiety. In some embodiments, the libraries can include drug-like molecules, i.e., molecules having structural attributes of one or more compounds known to bind to and/or affect a physiologic function of a GPCR.

In some embodiments, the invention includes compounds that can be tested as modulators of GPCR activity. Compounds tested as modulators of GPCRs can be any small chemical compound or biological entity. Typically, test compounds will be small chemical molecules and peptides. Essentially any chemical compound can be used as a potential modulator or ligand in the assays of the invention, although most often compounds can be dissolved in aqueous or organic (especially DMSO-based) solutions. The assays are designed to screen large chemical libraries by automating the assay steps. The assays are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial chemical or peptide library containing a large number of potential therapeutic compounds (potential modulator or ligand compounds). Such "combinatorial chemical libraries" or ligand libraries are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Russell & Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. Nos. 5,506,337; benzodiazepines, 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

It is noted that modulators that compete with the binding and/or activity of the known ligands for binding pockets I, II and III of the human $A_{2A}$ adenosine receptor can be used to treat various diseases including, but not limited to, coronary artery disease, atherosclerosis, thrombosis, obesity, diabetes, stroke, and other diseases.

In one embodiment, a modulator binds to a site on a GPCR, e.g., a human $A_{2A}$ adenosine receptor. In one aspect, the site is a xanthine binding site, e.g., the protonated form of binding pocket II. In another aspect, the site is a non-xanthine binding site, e.g., binding pocket I or the non-protonated form of binding pocket II. In another aspect, the site is an approximately 29 Angstrom$^3$ cavity site corresponding to binding pocket III. In another aspect, the site is a ligand binding site. In another aspect, the modulator has a first moiety that binds to one of the binding sites (e.g., binding pocket I, II or III). In another aspect, the first moiety is connected to a linker. In another aspect, the first moiety and the linker are connected to at least one additional moiety that binds to a site other than that bound by the first moiety. In another aspect, the two or more moieties are not connected by a linker and are both present in a composition.

Computer-based Modeling of Adenosine $A_{2A}$ Receptors

Protein-ligand docking aims to employ principles by which protein receptors, e.g., human $A_{2A}$ adenosine receptors, recognize, interact, and associate with molecular substrates and compounds to predict the structure arising from the association between a given compound and a target protein of known three-dimensional structure.

In protein-ligand docking, the search algorithm can allow the degrees of freedom of the protein-ligand system to be sampled sufficiently as to include the true binding modes. Three general categories of algorithms have been developed to address this problem of ligand flexibility: systematic methods; random or stochastic methods; and simulation methods.

Systematic search algorithms attempt to explore all degrees of freedom in a molecule. These algorithms can be further divided into three types: conformational search methods, fragmentation methods, and database methods.

In conformational search methods, all rotatable bonds in the ligand are systematically rotated through 360° using a fixed increment, until all possible combinations have been generated and evaluated. As the number of structures generated increases immensely with the number of rotatable bonds (combinatorial explosion), the application of this type of method, in its purest form, is very limited.

Fragmentation methods use two different approaches to incrementally grow the ligands into the active site. One approach is by docking the several fragments into a site, e.g., a xanthine binding site (such as the protonated form of binding pocket II) or non-xanthine binding site of a human $A_{2A}$ adenosine receptor, and linking them covalently to recreate the initial ligand ("the place-and-join approach"). Another approach is by dividing the ligand into a rigid core-fragment that is docked in first place and flexible regions that are subsequently and successively added ("the incremental approach"). DOCK (see above) is an example of s docking programs that use a fragmentation search method.

Database methods using libraries of pre-generated conformations or conformational ensembles to address the combinatorial explosion problem. A example of a docking program using database methods is FLOG which generates a small set of 25 database conformations per molecule based on distance geometry, that are subsequently subject to a rigid docking protocol.

Random search algorithms sample the conformational space by performing random changes to a single ligand or a population of ligands. At each step, the alteration performed is accepted or rejected based on a predefined probability function. There are three basic types of methods based on random algorithms: Monte Carlo methods (MC), Genetic Algorithm methods (GA), and Tabu Search methods.

Simulation methods employ a rather different approach to the docking problem, based on the calculation of the solutions to Newton's equations of motion. Two major types exist: molecular dynamics (MD) and pure energy minimization methods.

Scoring functions normally employed in protein-ligand docking are generally able to predict binding free energies within 7-10 kJ/mol and can be divided into three major classes: force field-based, empirical, and knowledge-based scoring functions.

In force-field based scoring, standard force fields quantify the sum of two energies: the interaction energy between the receptor and the ligand, and the internal energy of the ligand. The energies are normally accounted through a combination of a van der Waals with an electrostatic energy terms. A Lennard-Jones potential is used to describe the van der Waals energy term, whereas the electrostatic term is given by a Coulombic formulation with a distance-dependent dielectric function that lessens the contribution from charge-charge interactions.

Empirical scoring functions are based on the idea that binding energies can be approximated by a sum of several individual uncorrelated terms. Experimentally determined binding energies and sometimes a training set of experimentally resolved receptor-ligand complexes are used to determine the coefficients for the various terms by means of a regression analysis.

Knowledge-based scoring functions focus on following the rules and general principles statistically derived that aim to reproduce experimentally determined structures, instead of binding energies, trying to implicitly capture binding effects that are difficult to model explicitly. Typically, these methods use very simple atomic interactions-pair potentials, allowing large compound databases to be efficiently screened. These potentials are based on the frequency of occurrence of different atom-atom pair contacts and other typical interactions in large datasets of protein-ligand complexes of known structure. Therefore, their derivation is dependent on the information available in limited sets of structures.

Consensus Scoring combines the information obtained from different scores to compensate for errors from individual scoring functions, therefore improving the probability of finding the correct solution. Several studies have demonstrated the success of consensus scoring methods in relation to the use of individual functions schemes.

Using the Protein-ligand docking methods described above, a predicted association can be made between a selected chemical library compound (see above for examples) and the binding sites in the human $A_{2A}$ adenosine structure described in Table 6. These methods will therefore allow the generation of a binding profile for any known compound in any of the binding sites or cavities of the human $A_{2A}$ adenosine receptor based on the simulated docking of the compound.

In another embodiment, a form of computer-assisted drug design is employed in which a computer system is used to generate a three-dimensional structure of the candidate class A GPCR based on the structural information encoded by the amino acid sequence. This will allow use of the methods described above to identify candidate compounds based on their ability to dock in one or more of the predicted GPCR structure binding sites. In one aspect, the input amino acid sequence of the GPCR interacts directly and actively with a pre-established algorithm in a computer program to yield secondary, tertiary, and quaternary structural models of the class A GPCR. The models of the class A GPCR structure are then examined to identify the position and structure of the binding sites, e.g., binding pocket I, II and/or III. The position and structure of the predicted binding site(s) is then used to identify various compounds that modulate ligand-receptor binding using the methods described above.

The three-dimensional structural model of the GPCR is generated by entering protein amino acid sequences of at least 10 amino acid residues or corresponding nucleic acid sequences encoding a GPCR polypeptide into the computer system. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the GPCR is then generated by the interaction of the amino acid sequence and the computer system, using software known to those of skill in the art. Any method of protein structure modeling such as ab-initio modeling, threading or sequence-sequence based methods of fold recognition. In one embodiment, the AS2TS system of protein structure modeling is used. In other embodiments, a sequence alignment in combination with a threshold protein sequence similarity to determine a set of protein sequences for which to model protein structure is used. In one aspect, sequence alignments are generated for the set of sequences to be modeled with sequences of proteins with solved empirical structure in a protein structure databank known to one of skill in the art. If the sequences to be modeled have a sufficient similarity to one or more sequences with known protein structure, then the three dimensional structure of the sequence can be modeled.

The amino acid sequence represents a primary structure that encodes the information necessary to form the secondary, tertiary and quaternary structure of the GPCR of interest. In one embodiment, software can look at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

In another embodiment, protein structure alignments can be used to determine the structure of GPCRs using the known structure of the human $A_{2A}$ adenosine receptor (Table 6). Protein structure alignments preferably are sets of correspondences between spatial co-ordinates of sets of carbon alpha atoms which form the 'backbone' of the three-dimensional structure of polypeptides, although alignments of other backbone or side chain atoms also can be envisioned. These correspondences are generated by computationally aligning or superimposing two sets of atoms order to minimize distance between the two sets of carbon alpha atoms. The root mean square deviation (RMSD) of all the corresponding carbon alpha atoms in the backbone is commonly used as a quantitative measure of the quality of alignment. Another quantitative measure of alignment is the number of equivalent or structurally aligned residues.

In another embodiment, a GPCR structure is calculated based on the solved structure of the human $A_{2A}$ adenosine receptor by computationally aligning or superimposing two sets of atoms to minimize distance between the two sets of carbon alpha atoms (i.e., the alpha carbon atoms of the human $A_{2A}$ adenosine receptor and an unknown GPCR structure), followed by one or more of simulated annealing and energy minimization. The result of this calculation is a computed structure for a GPCR that provides atomic co-ordinates for the alpha carbon backbone as well as side chain atoms.

A variety of methods for generating an optimal set of correspondences can be used in the present invention. Some methods use the calculation of distance matrices to generate an optimal alignment. Other methods maximize the number of equivalent residues while RMSD is kept close to a constant value.

In the calculation of correspondences, various cutoff values can be specified to increase or decrease the stringency of the alignment. These cutoffs can be specified using distance in Angstroms. Depending on the level of stringency employed in the present invention, the distance cutoff used is less than 10 Angstroms or less than 5 Angstroms, or less than 4 Angstroms, or less than 3 Angstroms. One of ordinary skill will recognize that the utility of stringency criterion depends on the resolution of the structure determination.

In another embodiment of the present invention, the set of residue-residue correspondences are created using a local-global alignment (LGA), as described in US Patent Publication Number 2004/0185486. In this method, a set of local superpositions are created in order to detect regions which are most similar. The LGA scoring function has two components, LCS (longest continuous segments) and GDT (global distance test), established for the detection of regions of local and global structure similarities between proteins. In comparing two protein structures, the LCS procedure is able to localize and superimpose the longest segments of residues that can fit under a selected RMSD cutoff. The GDT algorithm is designed to complement evaluations made with LCS searching for the largest (not necessary continuous) set of 'equivalent' residues that deviate by no more than a specified distance cutoff.

Using the protein structure alignments described above, the structure of human $A_{2A}$ adenosine receptor in Table 6 can be used as a model on which to discern the structure of other GPCRs and/or their predicted ligand-binding sites, e.g., binding pockets I, II, and III.

Once the GPCR structure has been generated, binding pockets I, II, and III are identified by the computer system. Computational models seek to identify the regions by characterization of the three dimensional structure of the GPCR.

Some methods of identifying binding pockets I, II, and III use triangulation such as weighted Delaunay triangulation to determine pocket volumes (castP). Other methods use spheres to determining protein pocket volumes (Q-sitefinder, UniquePocket).

Figure 8A:
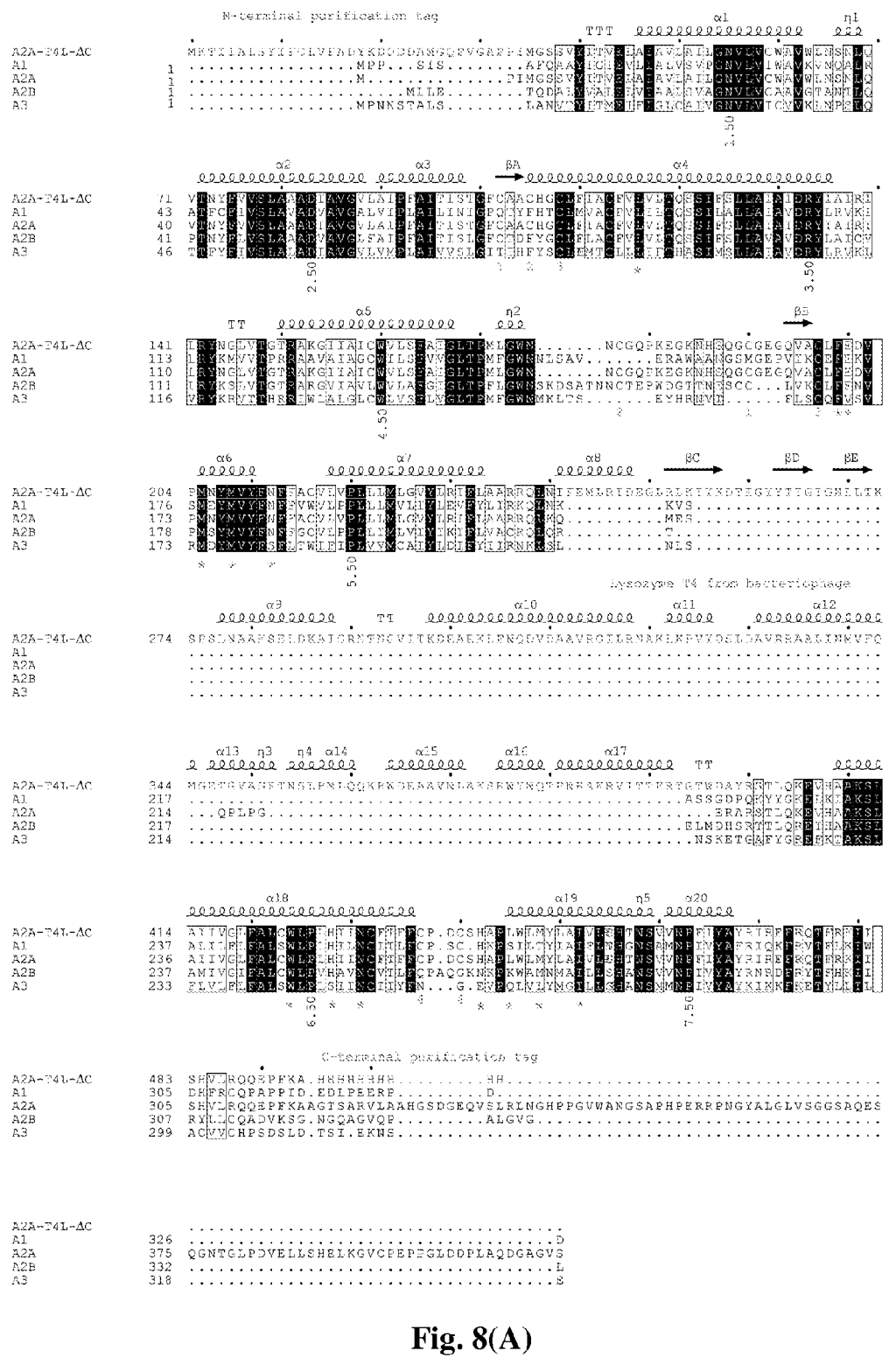
Figure 8B:
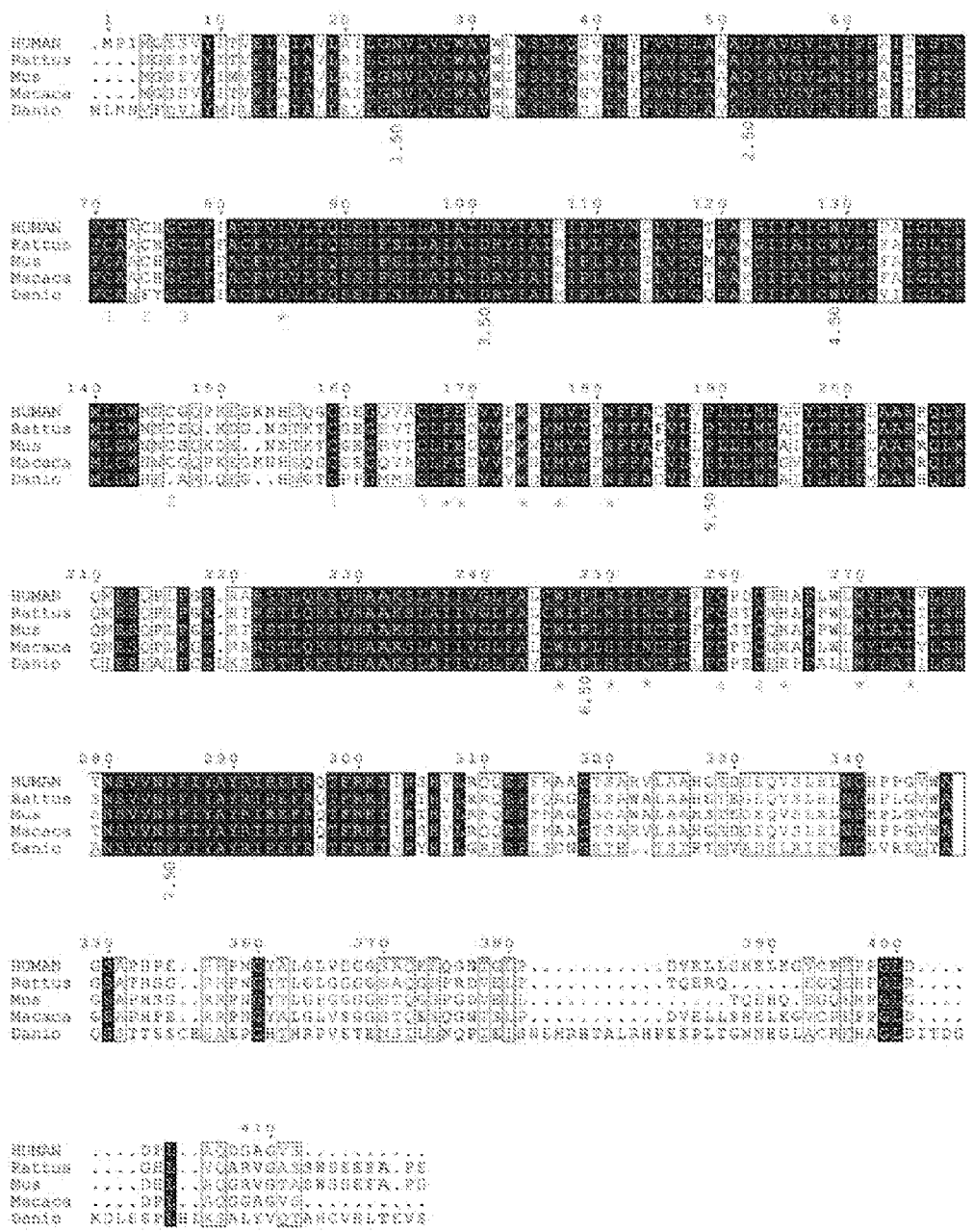

Conserved binding-site identification seeks to identify conserved regions such as binding pockets I, II, and III through associating the residues which form the aforementioned regions with conserved residues in homologous protein sequences or structures, e.g., see the alignments in FIG. 8.

One method of identifying binding pockets I, II, and III in a GPCR entails filling the three dimensional protein structures with spheres, creating a "negative image" of the structure. A cutoff distance, such as 8 Angstroms, is used to determine spheres which interact with residues. Spheres are labeled as conserved or not-conserved based on their interaction with residues which form a conserved binding site. The conserved spheres are clustered based on their three dimensional co-ordinates to identify a set of spheres with interact with conserved residues and are proximal in three dimensional space forming a cluster. Three-dimensional structures for potential compounds are generated by entering chemical formulas of compounds. The three-dimensional structure of the potential compound is then compared to that of the GPCR protein ligand-binding site(s) (e.g., binding pockets I, II or III) to identify compounds that bind to the GPCR binding site(s). Binding affinity between the GPCR binding site(s) and the compound is determined using energy terms to determine which ligands have an enhanced probability of binding to the protein.

While the invention has been particularly shown and described with reference to a preferred embodiment and several alternate embodiments, it will be understood by persons skilled in the relevant art that various changes in form and details can be made therein without departing from the spirit and scope of the invention.

It should be noted that the language used in the specification has been principally selected for readability and instructional purposes, and can not have been selected to delineate or circumscribe the inventive subject matter. Accordingly, the disclosure of the present invention is intended to be illustrative, but not limiting, of the scope of the invention, which is set forth in the claims.

The following examples are set forth so that the invention can be understood more fully. The examples are for illustrative purposes only and are not to be construed as limiting this invention in any manner.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ Ed. (Plenum Press) Vols. A and B (1992).

Methods

Molecular biology for generation of mammalian and *Spodoptera frugiperda*(Sf9) expression $A_{2A}$-WT, $A_{2A}$-T4L-WT and $A_{2A}$-T4L-AC constructs. The commercially available pBac5 vector (EMD biosciences was modified as follows to generate pBac5b. The 5' coding region of pBac5 was eliminated by digesting the vector with restriction enzyme NcoI (New England Biolabs) followed by generation of a blunt end by digestion with Mung Bean nuclease (New England Biolabs). The resulting linear DNA was further digested with SmaI to eliminate the N-terminal tags associated with the pBac5 vector. The resulting linear DNA was recirculated by ligation to generate pBac5b. Expression cassettes containing hemagluttinin signal sequence, FLAG epitope tag, precission protease site and 10x histidine tag (SEQ ID NO: 36) were sub cloned into pBac5b using the BamHI and HindIII restriction sites to yield the expression vector pBac5b-830400. Construction of $A_{2A}$-WT was completed utilizing standard PCR techniques to amplify the wild type $A_{2A}$ (found on the web at the site: cDNA.org) gene using modified PCR primers encoding exogenous restriction sites AscI at the 5', GGC GCG CCG CCC ATC ATG GGC TCC TCG GTG TAC ATC A (SEQ ID NO: 13), and FseI at the 3', AGG CCG GCC GGA CAC TCC TGC TCC ATC CTG GGC fSEQ ID NO: 14), termini, which was sub-cloned into a pBac5b-830400 vector using the aforementioned restriction sites. Subcloning into pcDNA3.1(-) was achieved using PCR with primer pairs encoding endogenous restriction sites BamHI at the 5', GGA TCC ATG AAG ACG ATC ATC GCC CTG AGC TAC ATC TTC TG (SEQ ID NO: 15), and HindIII at the 3', AAG CTT CTA ATG GTG ATG GTG ATG GTG ATG GTG ATG GTG AGG fSEQ ID NO: 16), termini of pBac5b+830400+$A_{2A}$ with subsequent ligation into the corresponding restriction sites found in pcDNA3.1(-).

$A_{2A}$-T4L-WT construction involved a two-step cloning strategy with the first step using splicing by overlap extension (SOE) PCR (K. L. Heckman, L. R. Pease, *Nat Protoc* 2, 924 (2007)) to insert a modified (Cysteines were mutated to Serines) bacteriophage T4 lysozyme (D. M. Rosenbaum et al., *Science* 318, 1266 (2007)) within the wild type $A_{2A}$ ICL3 region. The second step utilized standard PCR techniques to amplify the resulting $A_{2A}$-T4L fusion using PCR primers encoding exogenous restriction sites BamHI at the 5' GGA TCC ATG AAG ACG ATC ATC GCC CTG AGC TAC ATC TTC TG fSEQ ID NO: 15) and HindIII at the 3' AGG CCG GCC GGA CAC TCC TGC TCC ATC CTG GGC fSEQ ID NO: 14) termini. This allowed for standard subcloning into the pBac5b vector. Subcloning into pcDNA3.1(-) was achieved using PCR with primer pairs encoding endogenous restriction sites BamHI at the 5', GGA TCC ATG AAG ACG ATC ATC GCC CTG AGC TAC ATC TTC TG fSEQ ID NO: 15), and HindIII at the 3', AAG CTT CTA ATG GTG ATG GTG ATG GTG ATG GTG AGG (SEQ ID NO: 16), termini of pBac5b-830400- $A_{2A}$-T4L with subsequent ligation into the corresponding restriction sites found in pcDNA3.1(-).

$A_{2A}$-T4L-ΔC is the result of a ligation between $A_{2A}$-T4L and $A_{2A}$-ΔC (Δ317-412). $A_{2A}$-ΔC (Δ317-412) was constructed by using PCR with primers encoding exogenous restriction sites BamHI at the 5', GGA TCC ATG AAG ACG ATC ATC GCC CTG AGC TAC ATC TTC TG (SEQ ID NO: 15) and HindIII at the 3', AAG CTT TCA GTG ATG GTG ATG GTG ATG GTG ATG GTG TGC CTT GAA AGG TTC (SEQ ID NO: 17). Both $A_{2A}$-T4L and $A_{2A}$-ΔC (Δ317-412) were digested in two separate restriction digest reactions using Bsu36I and PciI restriction enzymes. After digestion the larger fragment of $A_{2A}$-T4L, which contained the $A_{2A}$-T4L fusion, was treated as the vector while the smaller fragment of $A_{2A}$-ΔC (Δ317-412), containing a C-terminal truncation, was used as the insert. Standard cloning methods were implemented and after the resulting $A_{2A}$-T4L-ΔC fusion was DNA sequence verified, subcloning into pcDNA3.1(−) was performed using PCR with primer pairs encoding endogenous restriction sites NheI at the 5', GCTA GCA TGA AGA CGA TCA TCG CCC TGA GCT ACA TCT TCT G (SEQ ID NO: 18), and HindIII at the 3', AAG CTT TCA GTG ATG GTG ATG GTG ATG GTG ATG GTG GT (SEQ ID NO: 19), termini of the resultant $A_{2A}$-T4L-$\Delta$C fusion.

Purification of $A_{2A}$-T4L Constructs

High-titer recombinant baculovirus (>10$^8$ viral particles per ml) was obtained following transfection protocol from Expression Systems (found on the web at the site: expression-systems.com/). Briefly, recombinant baculoviruses were generated by co-transfecting 2 µg of transfer plasmid containing the target coding sequence with 0.5 µg of Sapphire™ baculovirus DNA (Orbigen) into Sf9 cells using 6 µl of FuGENE 6 Transfection Reagent (Roche) and Transfection Medium (Expression Systems). Cell suspension was incubated for 4 days while shaking at 27° C. P0 viral stock was isolated after 4 days and used to produce high-titer baculovirus stock. Expression of gp64 was detected by staining with gp64-PE. Viral titers were performed by flow cytometric method (M. A. Hanson et al., *Protein Expr Purif* 56, 85 (2007)).

Insect cell membranes were initially disrupted by nitrogen cavitation pump in a hypotonic buffer containing 10 mM HEPES (pH 7.5), 20 mM KCl, and 10 mM MgCl$_2$. Extensive washing of the isolated raw membranes was performed by repeated centrifugation (typically six-to-nine times) in a high osmotic buffer containing 1.0 M NaCl, 10 mM HEPES (pH 7.5), 10 mM MgCl$_2$, 20 mM KCl, and protease inhibitor cocktail (Roche), followed by Dounce homogenization to resuspend the membranes in fresh wash buffer thereby separating soluble and membrane associated proteins from integral transmembrane proteins. Highly purified membranes were resuspended in 10 mM HEPES (pH 7.5), 10 mM MgCl$_2$, 20 mM KCl, and 40% glycerol then flash-frozen with liquid nitrogen and stored at −80° C. until further use.

Prior to solubilization, purified membranes were thawed on ice in the presence of 4 mM theophylline, 2.0 mg/ml iodoacetamide (Sigma), and protease inhibitor cocktail. Membranes were then solubilized by incubation in the presence of 0.5% (w/v) DDM (Anatrace) and 0.01% (w/v) cholesteryl hemisuccinate (CHS) (Sigma) for two to three hours at 4° C. After solubilization, the unsolubilized material was removed by centrifugation at 150,000×g for 45 minutes. The supernatant was separated, supplemented with fresh ligand, 25 mM buffered imidazole and incubated with TALON IMAC resin (Clontech) overnight at 4° C.; typically 1.5 ml of resin per one liter of original culture volume was used. After binding the resin was washed with ten column volumes of 25 mM HEPES (pH 7.5), 800 mM NaCl, 10% (v/v) glycerol, 55 mM imidazole, 4.0 mM theophyline, 0.05% (w/v) DDM and 0.001% (w/v) CHS, followed by four column volume of 25 mM HEPES (pH 7.5), 800 mM NaCl, 10% (v/v) glycerol, 25 mM imidazole, 4.0 mM theophyline, 0.05% (w/v) DDM, 0.001% (w/v) CHS, 8 mM ATP (Sigma) and 10 mM MgCl$_2$. The receptor was eluted with 25 mM HEPES (pH 7.5), 800 mM NaCl, 10% (v/v) glycerol, 4.0 mM theophyline, 0.05% (w/v) DDM, 0.001% (w/v) CHS, 10 mM ATP (Sigma) and 10 mM MgCl$_2$. The ATP and MgCl$_2$ were removed by PD10 buffer exchange columns (GE Lifescience). An additional Ni IMAC (GE LifeScience) column step after desalting was used to concentrate, deglycosylate (PNGase F, New England Biolab) and exchange the ligand to 200 µM ZM241385 (Tocris). Ni IMAC column was washed with 4 column volumes of 25 mM HEPES (pH 7.5), 800 mM NaCl, 10% (v/v) glycerol, 55 mM imidazole, 200 µM ZM241385, 0.05% (w/v) DDM and 0.001% (w/v) CHS and receptor was eluted with 25 mM HEPES (pH 7.5), 800 mM NaCl, 10% (v/v) glycerol, 200 mM imidazole, 200 µM ZM241385, 0.05% (w/v) DDM and 0.001% (w/v) CHS. Receptor was concentrated from ~3 mg/ml to 70 mg/ml with a 100 kDa molecular weight cut-off Vivaspin concentrator (Vivascience). Receptor purity and monodispersity was followed using SDS-PAGE, Maldi-TOF and analytical size-exclusion chromatography (aSEC).

In Meso Crystallization of $A_{2A}$-T4L-$\Delta$C with ZM241385

For lipidic cubic phase (LCP) crystallization, nanovolume robotic trials were carried-out using an in meso crystallization robot as previously described (V. Cherezov, A. Peddi, L. Muthusubramaniam, Y. F. Zheng, M. Caffrey, *Acta Crystallogr D Biol Crystallogr,* 60, 1795 (2004)). Glass sandwich plates (V. Cherezov, et al., *Acta Crystallogr D Biol Crystallogr,* 60, 1795 (2004)) were filled with 50 nl receptor-cholesterol-monoolein LCP drops overlaid by 0.8 µl of precipitant solution in each well and sealed with a glass coverslip. Lipid:receptor LCP mixture typically contained monoolein:cholesterol (54%:6% (w/w)) and receptor (40% (w/w)). Crystallization set-ups were performed at ambient temperature (22±2° C.). Plates were incubated and imaged at 20° C. using an automated incubator/imager (RockImager 1000, Formulatrix). Data-collection quality crystals (~100 µm×10 µm×5 µm) were obtained in 30% (v/v) PEG 400 (range of 28-32%), 186 mM Lithium sulfate (range of 180 to 220 mM), 100 mM Sodium citrate (pH 6.5) (Range of 5.5 to 6.5) and 200 µM ZM241385. The protein crystallized in the primitive monoclinic space group P2$_1$ with one molecule per asymmetric unit and an estimated solvent content of 52%.

Data Collection and Structure Solution

Crystallographic data were collected on the 23ID-B beamline (GM/CA CAT) at the Advanced Photon Source, Argonne, Ill. using a 10 µm minibeam (wavelength 1.0332 Å) and a MarMosaic 300 CCD detector. Crystals were invisible after flash-freezing into liquid nitrogen, and a similar alignment and data-collection strategy was followed as has been previously described (M. A. Hanson et al., *Structure* 16, 897 (2008); V. Cherezov et al., *Science* 318, 1258 (2007)). A nearly complete dataset was collected from a single crystal at 3.5 Å resolution using 20× attenuated beam, 3 s exposure and 1° oscillation per frame. High-resolution data was obtained by collecting 10-15° wedges from 13 crystals, 2-5 s exposure with 1× attenuated beam and optimizing the data collection strategy using the software program XDS (W. Kabsch, *J. Appl. Cryst.* 26 (1993)). High resolution frames were merged and scaled using the lower resolution dataset as a reference for scaling to obtain a complete 2.6 Å data using the software program XDS (Table 2).

Initial phase information was obtained by molecular replacement using the receptor and T4L portion of β$_2$AR-T4L (PDB-code: 2RH1) independently with the program Phaser (A. J. McCoy, R. W. Grosse-Kunstleve, L. C. Storoni, R. J. Read, *Acta Crystallogr D Biol Crystallogr* 61, 458 (2005)). Initial refinement was performed iteratively using the Phenix software suite (P. D. Adams et al., *Acta Crystallogr D Biol Crystallogr* 58, 1948 (2002)), Lafire software suite (M. Yao, Y. Zhou, I. Tanaka, *Acta Crystallogr D Biol Crystallogr* 62, 189 (2006)) and Refmac5 software suite (G. N. Murshudov, A. A. Vagin, E. J. Dodson, *Acta Crystallogr D Biol Crystallogr* 53, 240 (1997)) followed by manual examination and rebuilding of the refined coordinates in program Coot (P. Emsley, K. Cowtan, *Acta Crystallogr D Biol Crystallogr* 60, 2126 (2004)) using both |2F$_o$-F$_c$| sigma-A weighted and |F$_o$-F$_c$| maps, as well as omit maps calculated using programs Bhat's (T. N. Bhat, *Acta Crystallogr A* 45 (Pt 1), 145 (1989)) and CNS1.2 (A. T. Brunger et al., *Acta Crystallogr D Biol Crystallogr* 54, 905 (1998)).

Ligand Binding Assays and Functional Assays Using Sf9 and HEK293 Membranes

Saturation Isotherm using Sf9 membranes: Cell pellets of $A_{2A}$-WT, $A_{2A}$-T4L-WT and $A_{2A}$-T4L-ΔC constructs were suspended in ice-cold 25 mM Hepes, pH 7.5 as a lysis buffer, containing protease inhibitors (Complete protease inhibitor cocktail tablet, Roche Applied Science, USA) and homogenized with 20 strokes using a Dounce homogenizer. Cellular debris and nucleoli were removed by centrifugation at 400×g for 5 minutes at 4° C., and the supernatants were collected. Crude plasma membranes were isolated by centrifugation of the supernatants at 150,000×g for 60 minutes at 4° C., and crude plasma membranes were further washed three times by repeat centrifugation and resuspension in 25 mM Hepes, 1000 mM NaCl, pH 7.5, and containing protease inhibitors. Prior to the ligand binding assays, the membrane pellets were resuspended in ligand binding buffer either low salts buffer (TME: 50 mM Tris-HCl, 10 mM $MgCl_2$, 0.5 mM EDTA, pH 7.4) or high salt buffer TME supplemented with 1000 mM NaCl. The samples were tested for binding with [2-$^3$H]-4-(2-[7-amino-2-{2-furyl}{1,2,4}triazolo{2,3-a}{1,3,5}triazin-5-yl amino]ethyl)phenol [$^3$H]ZM241385 (42.5 Ci/mmol, from Perkin Elmer Life Sciences). Crude plasma membranes (0.2 μg of total protein per reaction) were incubated for 30 min at room temperature with serial dilutions of the radioligand (0.05-10 nM). Incubations were rapidly terminated by filtration using a Tomtec Mach III cell harvester (Tomtec) through a 96-well GF/B filter plate (MultiScreen Harvest plate, Millipore Corp.), and rinsed five times with 500 μl of ice-cold buffer (50 mM Tris-HCl, pH 7.4). The harvest plates were dried, and 30 μl of OptiPhase "HiSafe" III scintillation liquid (Perkin-Elmer Life Sciences) were added. The bound radioactivity was measured using a Packard's TopCounter NTX. Nonspecific binding was determined in parallel reactions in the presence of an excess of Theophylline (100 μM, Sigma-Aldrich, USA), and specific binding was defined as the difference between total and nonspecific binding. Protein concentrations were determined with the BCA protein assay (Pierce, USA), using serum albumin as a reference. All incubations were performed in triplicate, and independent experiments were repeated at least two times. Equilibrium dissociation constants ($K_d$) and maximal receptor levels ($B_{max}$) were calculated from the results of saturation experiments using GraphPad Prism version 4 Software.

Competition Binding Assays using HEK membranes. [$^3$H] ZM241385 (27.4 Ci/mmol) was obtained from ARC Inc., St. Louis, USA. DPCPX and CGS21680 were obtained from Sigma. All other materials were purchased from commercial sources and were of the highest available purity. HEK293T cells were grown as monolayers in DMEM medium supplemented with 2 mM glutamine, 10% newborn calf serum at 37° C. in a moist, 7% $CO_2$ atmosphere. Cells were transfected with the indicated plasmids using the calcium phosphate precipitation method. Experiments were performed 48 h after transfection. Membranes were prepared as follows. Cells were detached from the plates by scraping them into 5 mL PBS, collected and centrifuged at 200×g for 5 minutes. Cell pellets were resuspended in 20 ml of ice-cold 50 mM Tris-HCl buffer, pH 7.4. An Ultra-turrax was used to homogenise the cell suspension. The cytosolic and membrane fractions were separated using a high speed centrifugation step of 100,000×g, (31,000 rpm in a Beckman Optima LE-80K ultracentrifuge) at 4° C. for 20 minutes. The pellet was resuspended in 10 mL of Tris buffer and the homogenisation and centrifugation step repeated. The resulting pellet was resuspended in 50 mM Tris-HCl buffer, pH7.4. Adenosine deaminase (ADA) was added to a final concentration of 0.8 IU/ml.

Binding assays were performed in a 100 μl reaction volume. The assay mixture contained 50 mM Tris-HCL buffer, pH 7.4, membrane protein (25 μg/assay point for single point assays, 5 μg/assay point for competition curves).

The ability of increasing concentrations of the antagonist ZM241385 and agonist CGS21680 to compete with [$^3$H] ZM241385 binding at the various $A_{2A}$ receptor constructs was tested in the absence or presence of 1M NaCl. Nonspecific binding was determined in the presence of an excess of CGS21680 (100 μM). The radioligand concentrations were close to equilibrium dissociation constants ($K_d$~1.0 nM). Incubation was for 2 hours at 25° C. Binding reactions were terminated by filtration through Whatman GF/B filters under reduced pressure using a MY-24 cell harvester (Brandell). Filters were washed three times with ice cold buffer and placed in scintillation vials. Radioactivity was determined using a Tri-Carb 2900TR liquid scintillation analyzer (Perkin Elmer, Shelton, Conn.).

Cell-surface Receptor Measurement and Enzyme-Linked Immunosorbent Assay. Twenty-four hours after transfection cells were split into 96-well poly-n-lysine-coated plates at a density of 100,000 cells per well. After an additional 24 h, cell-surface receptors were labeled with anti-FLAG (M2) antibody (Sigma) (1:1000) in growth medium for 30 min at 30° C. The cells were then washed once with 20 mM HEPES and Dulbecco's modified Eagle's medium and then incubated for another 30 min at 37° C. in growth medium supplemented with horseradish peroxidase-conjugated anti-mouse IgG (Sigma) (1:5000) as the secondary antibody. The cells were washed twice with phosphate-buffered saline. Finally, the cells were incubated with TMB for 5 min in the dark at room temperature and then the reaction stopped with 1M $H_3PO_4$ and the absorbance was read at 450 nm using a VICTOR$^2$ plate reader (PerkinElmer Life Sciences). Control experiments were performed in which no secondary or primary antibody was added. In both cases no absorbance was observed.

Demonstration of downstream signaling by intracellular cAMP determination. HEK293T cells were grown and transfected as described above. Experiments were performed 48 h after transfection. Cells were harvested, resuspended in 'stimulation buffer' and added to 384 well Optiplates at a concentration of 7500 cells/well. The assay was performed following the protocol recommended in the LANCE cAMP 384 kit (PerkinElmer Life and Analytical Sciences). The assay tracer, antibody and detection mix are components of the kit. Deviations from the kit protocol are as follows. The stimulation buffer used was PBS with the addition of 5 mM HEPES, 0.1% BSA, 50 μM rolipram, 50 μM cilostamide and 0.8 IU/ml adenosine deaminase. The assay was performed in white 384-well OptiPlates (PerkinElmer Life and Analytical Sciences). Treatment of cells with agonist or antagonist was for 45 min. Following addition of the detection/antibody mix plates were left for 3 h prior to reading using a VICTOR$^2$ plate reader (PerkinElmer Life Sciences).

Thermal stability assay. Thermal stability assays using a fluorescent probe was done as previously described (A. I. Alexandrov et al., *Structure* 16, 351 (2008)).

Example 1

Crystal Generation and Structure Solution

GPCRs possess numerous thermodynamic conformations (B. E. Cohen et al., *Proc Natl Acad Sci USA* 102, 965 (2005); B. K. Kobilka, X. Deupi, *Trends Pharmacol Sci* 28, 397 (2007)), implying an inherent structural flexibility (V. P. Jaakola, J. Prilusky, J. L. Sussman, A. Goldman, *Protein Eng Des Sel* 18, 103 (2005); S. G. Rasmussen et al., *Nature* 450, 383 (2007); D. M. Rosenbaum et al., *Science* 318, 1266 (2007)). This flexibility manifests itself as thermal instability upon detergent extraction from lipid membranes and is one of the primary challenges in generating crystals of GPCRs (F. Magnani, Y. Shibata, M. J. Serrano-Vega, C. G. Tate, *Proc Natl Acad Sci USA*, (2008); M. J. Serrano-Vega, F. Magnani, Y. Shibata, C. G. Tate, *Proc Natl Acad Sci USA* 105, 877 (2008)). In order to overcome this obstacle with the human $A_{2A}$ adenosine receptor, a T4L fusion strategy (D. M. Rosenbaum et al., *Science* 318, 1266 (2007); V. Cherezov et al., *Science* 318, 1258 (2007); C. K. Engel, L. Chen, G. G. Prive, *Biochim Biophys Acta* 1564, 38 (2002)) was applied. Specifically, most of the third cytoplasmic loop (Leu209$^{5.70}$-Ala221$^{6.23}$) was replaced with lysozyme from T4 bacteriophage. The carboxyl-terminal tail (Ala317-Ser412) was also. The resulting recombinant construct ($A_2A$-T4L-$\Delta C$) was further stabilized during purification with (i) sodium chloride, which has a beneficial effect on adenosine receptor stability, (ii) a saturating concentration of the nonspecific adenosine receptor antagonist theophylline (ZM241385 was exchanged from theophylline in the last purification step) and (iii) including cholesteryl hemisuccinate throughout the purification. Purified $A_{2A}$-T4L-$\Delta C$ bound to ZM241385 was crystallized using the in meso crystallization methodology where the lipid phase consisted of a mixture of monoolein and cholesterol.

Figure 1:
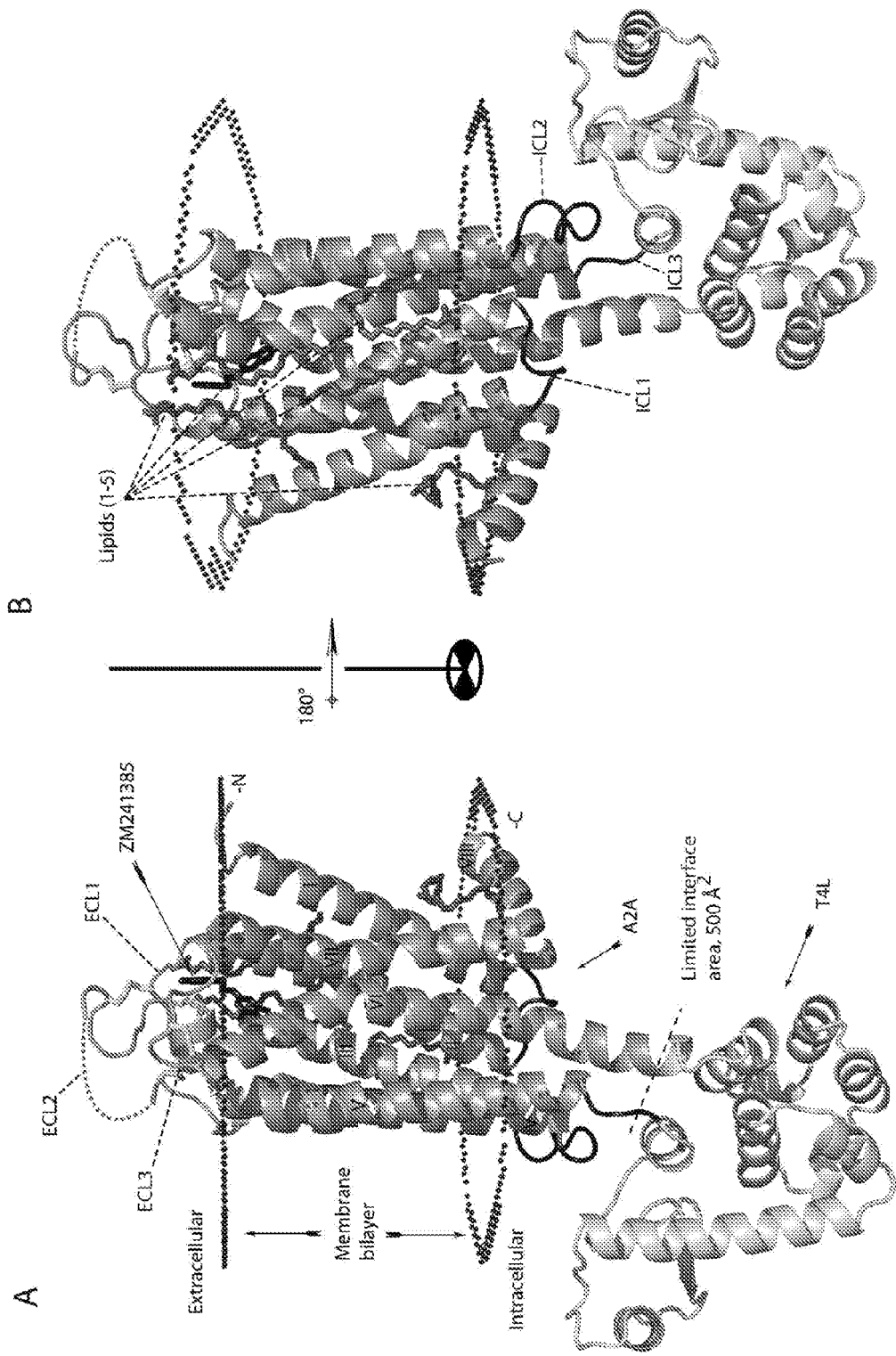
FIGS. 1A and 1B. Crystal structure of $A_{2A}$-T4L-ΔC. A. Overall topology of $A_{2A}$-T4L-ΔC. The transmembrane part of $A_{2A}$-ΔC structure includes helices I-VIII and the T4L is located intracellularly. The structure is viewed perpendicular to the plasma membrane. ZM241385, the four lipid molecules, and the four disulfide bonds are also shown. The sulfate ions are omitted. The extracellular loops are labeled ECL1-3 are labeled ICL1-3. The membrane boundaries are adapted from the OPM database (found on the web at the site: opm.phar.umich.edu) using $β_2$AR-T4L (2RH1) as a model. B. Rotated 180° around the x-axis. The images were created with PyMOL.

Diffraction data from thirteen of the best crystals were combined to yield a 2.6 Å dataset (Table 1). Phases were obtained by molecular replacement using the coordinates of the $\beta_2$-adrenergic receptor ($\beta_2$AR) fused to T4-lysozyme (PDB accession number, 2RH1). The final refined model includes residues Ile3 to Gln310 of the human $A_{2A}$ adenosine receptor, residues 2 to 161 of T4-lysozyme, five lipid hydrocarbon chains modeled as stearic acid, eight sulfate ions and the antagonist ZM241385 bound in the ligand binding cavity (FIG. 1). The experimental electron density for the amino (Met1-Pro2) and carboxyl (Glu311-Ala316) termini did not support modeling of these regions. In addition, the tip of second extracellular loop (Gln148-Ser156) was not modeled due to weak experimental electron density. Although cholesterol does have a significant stabilizing effect on the $A_{2A}$ adenosine receptor and was included in the crystallization trials, in contrast to the $\beta_2$-adrenergic receptor structure which had cholesterol bound in a pocket referred to as the cholesterol consensus motif (M. A. Hanson et al., *Structure* 16, 897 (2008)), the $A_{2A}$ adenosine receptor structure has phospholipid bound in the same area.

Example 2

Biochemical characterization of $A_{2A}$-T4L-$\Delta C$

Figure 9:
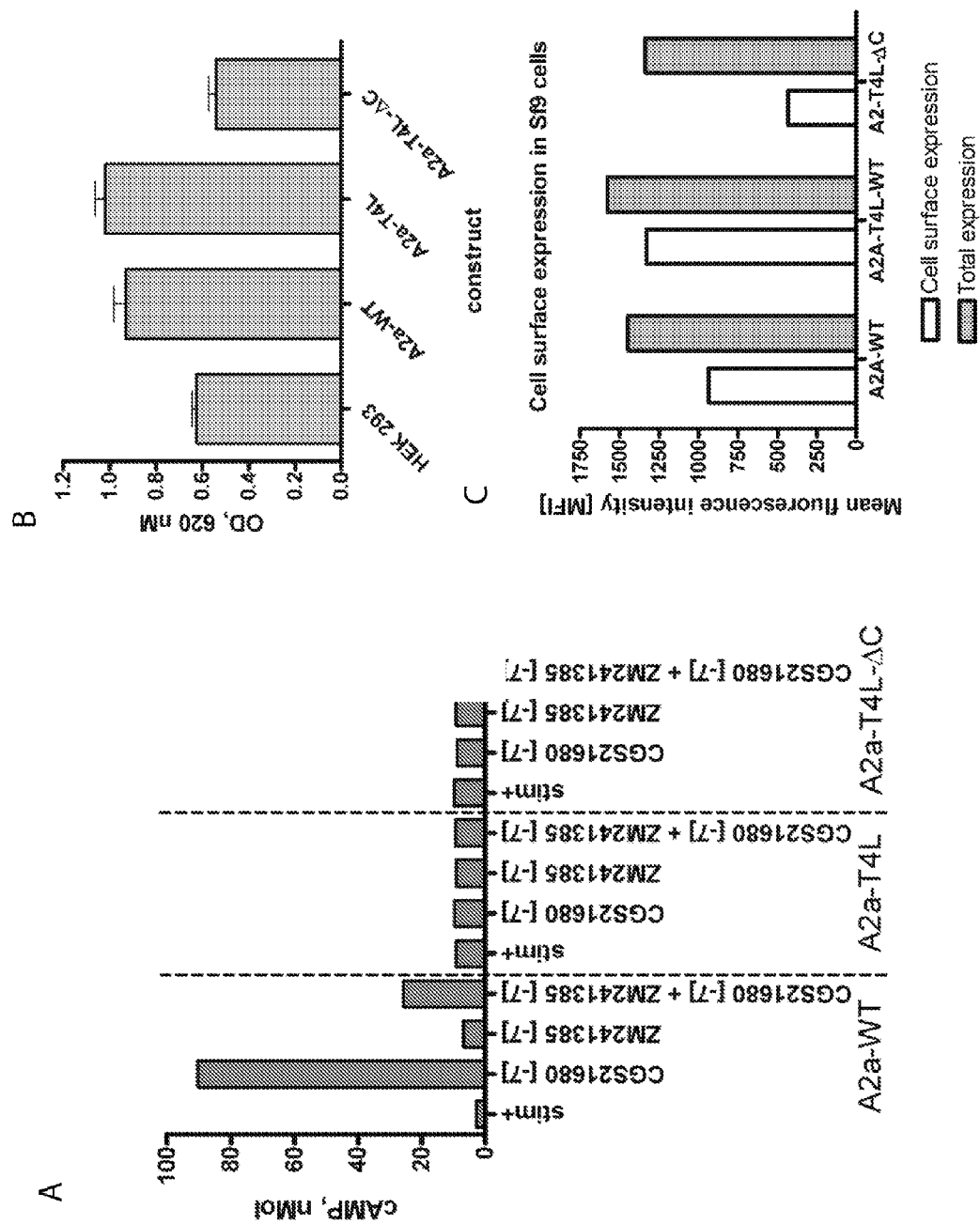
Figure 10A:
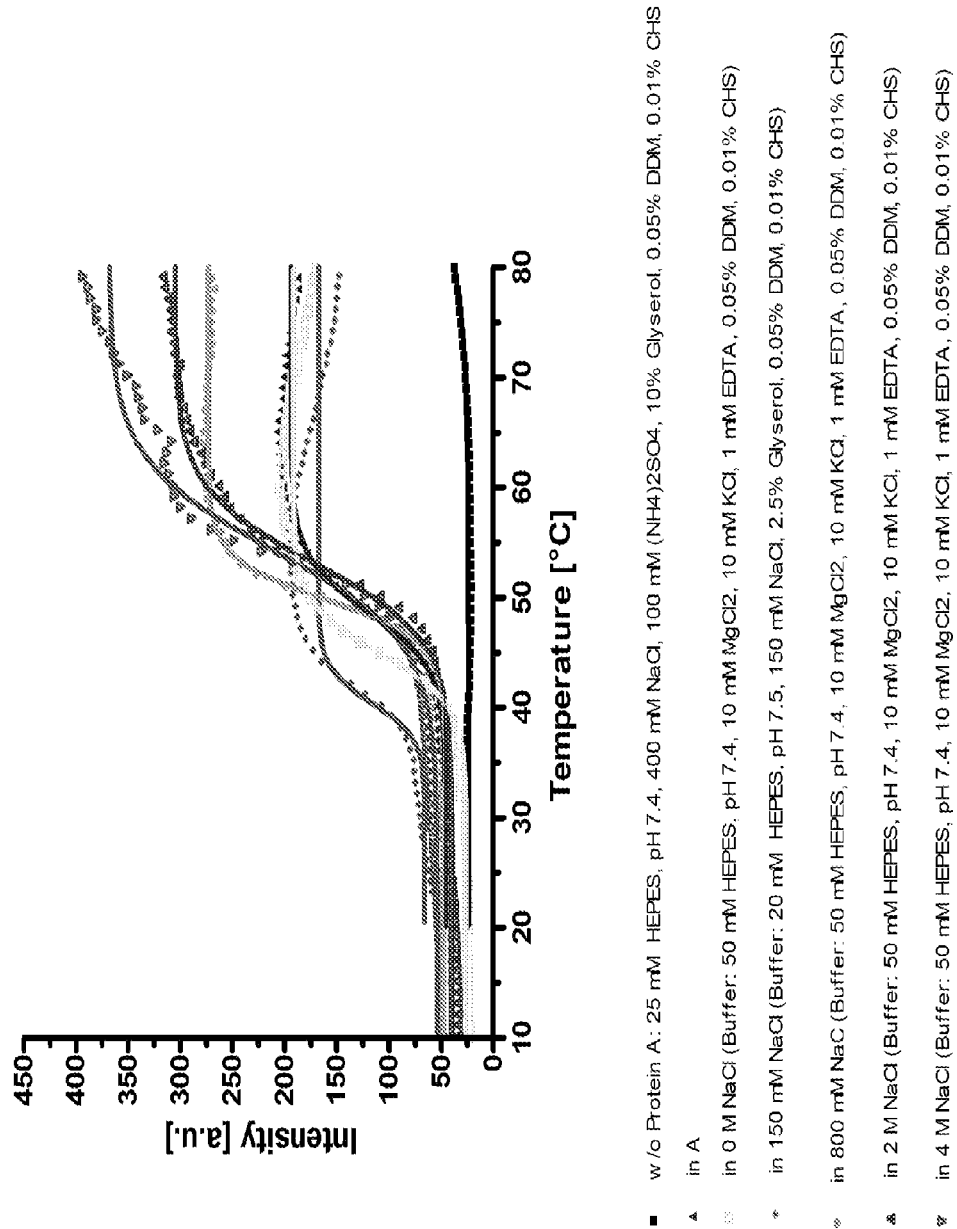
Figure 10B:
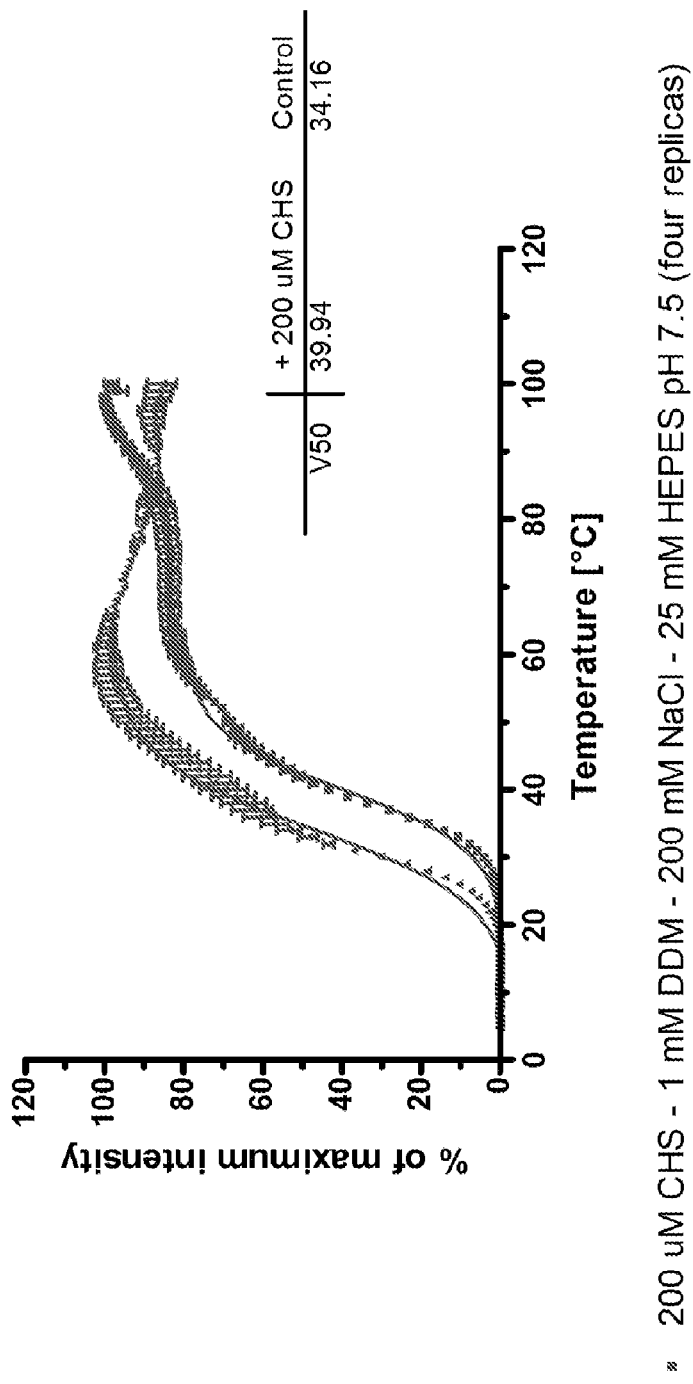
Figure 10C:
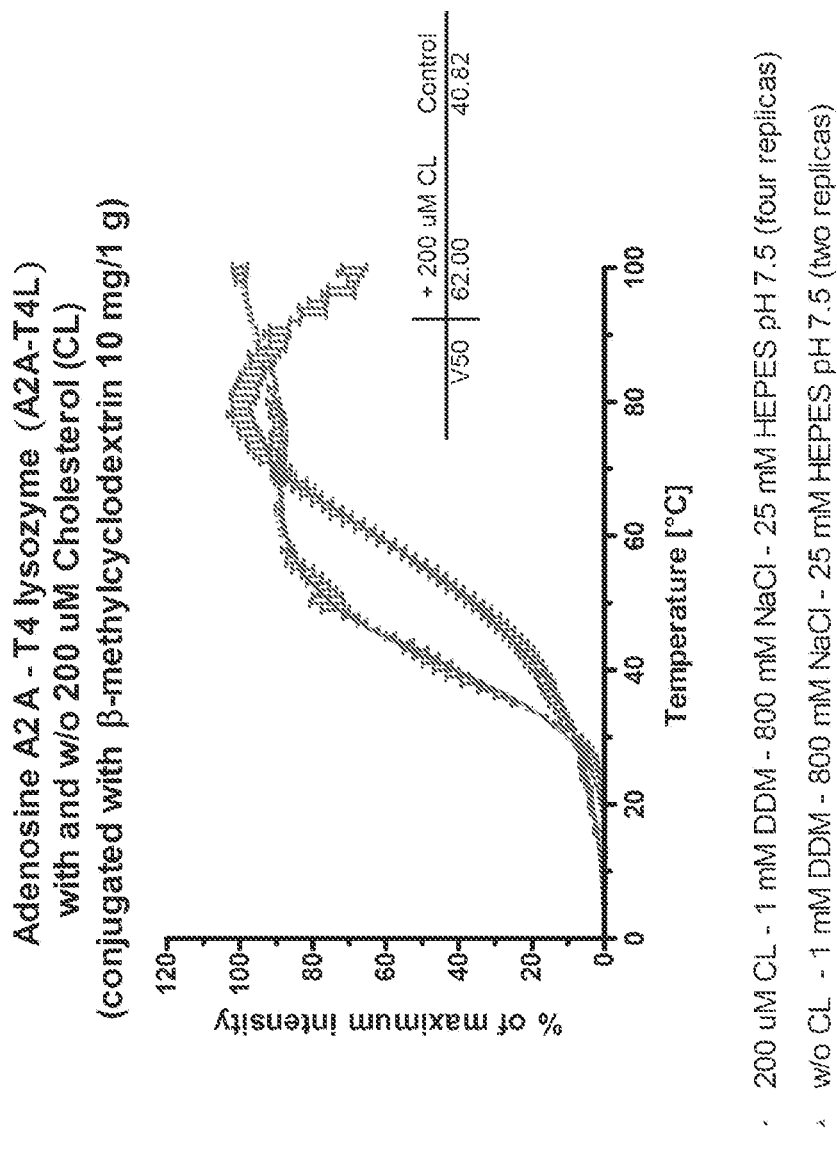
Figure 10D:
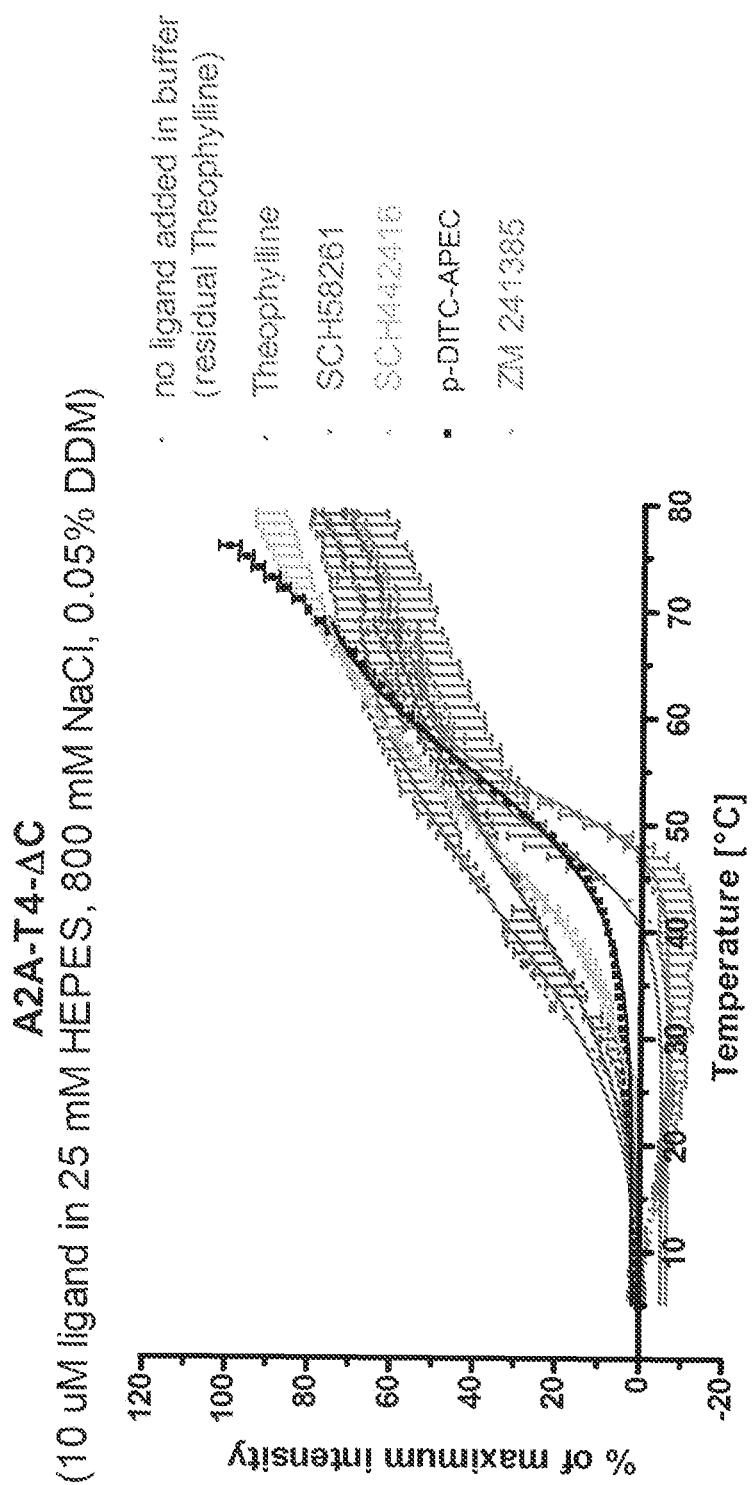

The functionality of $A_{2A}$-T4L-$\Delta C$ was verified by comparing its binding properties to $A_{2A}$-T4 and $A_{2A}$-WT. $A_{2A}$-T4 refers to a construct in which the third cytoplasmic loop (residues Leu208$^{5.69}$ to Ala221$^{6.23}$) was replaced with the lysozyme from T4 bacteriophage and the full carboxy terminus intact (Ala317 to Ser412). $A_{2A}$-WT refers to the wild-type construct without the T4 lysozyme. All constructs have a FLAG purification tag in the amino terminus and ten histidine residues (SEQ ID NO: 36) in the carboxy terminus. The $A_{2A}$-T4L-$\Delta C$, $A_{2A}$-T4 and $A_{2A}$-WT constructs expressed in Sf9 cells bind [$^3$H]ZM241385 with similar affinity as the same constructs transiently expressed in HEK293 as judged by radioligand saturation experiments. This finding was corroborated in competition binding assays, as the two $A_{2A}$-T4L constructs had IC$_{50}$ values similar to $A_{2A}$-WT for ZM241385 (FIG. 2; FIG. 9 and Table 3). However, $A_{2A}$-T4L and $A_{2A}$-T4L-$\Delta C$ displayed significantly higher affinity for the subtype-selective agonist CGS21680 as compared to the $A_{2A}$-WT construct, possibly indicating a shift toward the activated state induced by the incorporation of the T4L moiety. A comparable construct of the $\beta_2$AR behaved in a similar fashion (D. M. Rosenbaum et al., *Science* 318, 1266 (2007)); however, unlike $\beta_2$AR, the $A_{2A}$-WT has no associated basal activity (G protein signalling in the absence of agonist). The inclusion of a high concentration of sodium chloride in the assay medium induced a substantial decrease in the agonist affinity for all of the tested constructs (FIG. 2b) but did not appreciably affect antagonist affinity. The p$K_i$ values for the agonist in the presence of sodium chloride were virtually identical for all constructs tested (Table 3) indicating that sodium chloride induced a shift in receptor equilibrium to an inactive state (Z. G. Gao, A. P. Ijzerman, *Biochem Pharmacol* 60, 669 (2000)). In addition, sodium chloride induced a 10° C. increase in thermal stability for $A_{2A}$-T4L-$\Delta C$ solubilized in n-Dodecyl-$\beta$-D-maltoside (FIG. 10). Thus, radioligand binding experiments support the conclusion that the construct used for crystallization is a functional receptor with an increased affinity for agonist, and wild-type affinity for antagonist.

Example 3

Architecture of the Human $A_{2A}$ Adenosine Receptor

The residues constituting the transmembrane $\alpha$-helices are: Gly5$^{1.31}$-Trp32$^{1.58}$ (helix I); Thr41$^{2.39}$-Ser67$^{2.65}$ (helix II); His75$^{3.23}$-Arg107$^{3.55}$ (helix III); Thr119$^{4.40}$-Leu140$^{4.61}$ (helix IV); Asn175$^{5.36}$-Ala204$^{5.65}$ (helix V); Arg222$^{6.24}$-Phe258$^{6.60}$ (helix VI); Leu269$^{7.34}$-Arg291$^{7.56}$ (helix VII) (33). A small non-transmembrane helix is located at the membrane-cytoplasm interface and comprises Arg296$^{8.47}$-Leu308$^{8.59}$ (helix VIII). The $A_{2A}$ adenosine receptor does not contain the canonical palmitoylation site(s) found in the majority of GPCRs; instead, helix VIII is stabilized by interactions with helix I. In this crystal form, the crystallographic contacts are mostly driven by the T4L protein where receptor-to-lysozyme and lysozyme-to-lysozyme mainly form the lattice contacts. A relatively large receptor-to-receptor crystallographic interface (~520 Å$^2$) forms anti-parallel receptor dimers (FIG. 11). The total surface interface between receptor and T4L moieties is 1300 Å$^2$, whereas lysozyme-to-lysozyme is ~200 Å$^2$. The largest contact interface (~500 Å$^2$) between receptor and T4L is non-crystallographic, and is located in the cytoplasmic site, where receptor is fused to the T4L. The other receptor-to-lysozyme surface interfaces are crystallographic (260 Å$^2$). In comparison to the previously solved $\beta_2$AR-T4L fusion proteins, the T4L domain is significantly tilted from the membrane plane, and creates more surface interactions than seen in human $\beta_2$AR-T4L constructs that were solved in different space groups.

The residues defining intracellular and extracellular loops (ICLs and ECLs) are: Leu33$^{1.59}$-Val40$^{2.38}$ (ICL1); Ile108$^{3.56}$-Gly118$^{4.39}$ (ICL2); Leu208$^{5.69}$-Ala221$^{6.23}$ (ICL3); Thr68$^{2.66}$-Cys74$^{3.22}$ (ECL1); Leu141$^{4.62}$-Met174$^{5.35}$ (ECL2); Cys259$^{6.61}$-Trp268$^{7.33}$ (ECL3). In our structure ICL3 has been replaced by 160 residues from T4L lysozyme (see FIG. 8 and SEQ ID NO:1). Additionally, The N-linked glycan associated with Asn154$^{4.75}$ has been removed enzymatically to improve crystallization.

The crystallographic model of $A_{2A}$-T4L-$\Delta C$ bound to ZM241385 reveals three features distinct from the previously reported GPCR structures. First, the organization of the extracellular loops is markedly different from $\beta_1AR$, $\beta_2AR$ and bovine/squid rhodopsins (S. G. Rasmussen et al., *Nature* 450, 383 (2007); D. M. Rosenbaum et al., *Science* 318, 1266 (2007); M. A. Hanson et al., *Structure* 16, 897 (2008); M. Murakami, T. Kouyama, *Nature* 453, 363 (2008); K. Palczewski et al., *Science* 289, 739 (2000); T. Warne et al., *Nature* 454, 486 (2008)). Secondly, ZM241385 binds in an extended conformation perpendicular to the plane of the membrane and co-linear with transmembrane helix VII interacting with both ECL2 and ECL3. This is somewhat incongruous with earlier molecular modeling studies based on $\beta_2AR$ and rhodopsin homology models where ZM241385 and other antagonists were docked into a binding site emulating that of $\beta_2AR$ and rhodopsin (for examples see (A. Martinelli et al., *Med Res Rev* 28, 247 (2008); 0. Yuzlenko et al., *J Comput Chem*, (2008)), and references therein). Finally, a subtle divergence in the helical positions and orientations relative to rhodopsin and $\beta_2AR$ redefines the antagonist binding cavity so that it is located closer to helices VI and VII and allowing only limited interactions with helices III and V.

Example 4

Figure 3:
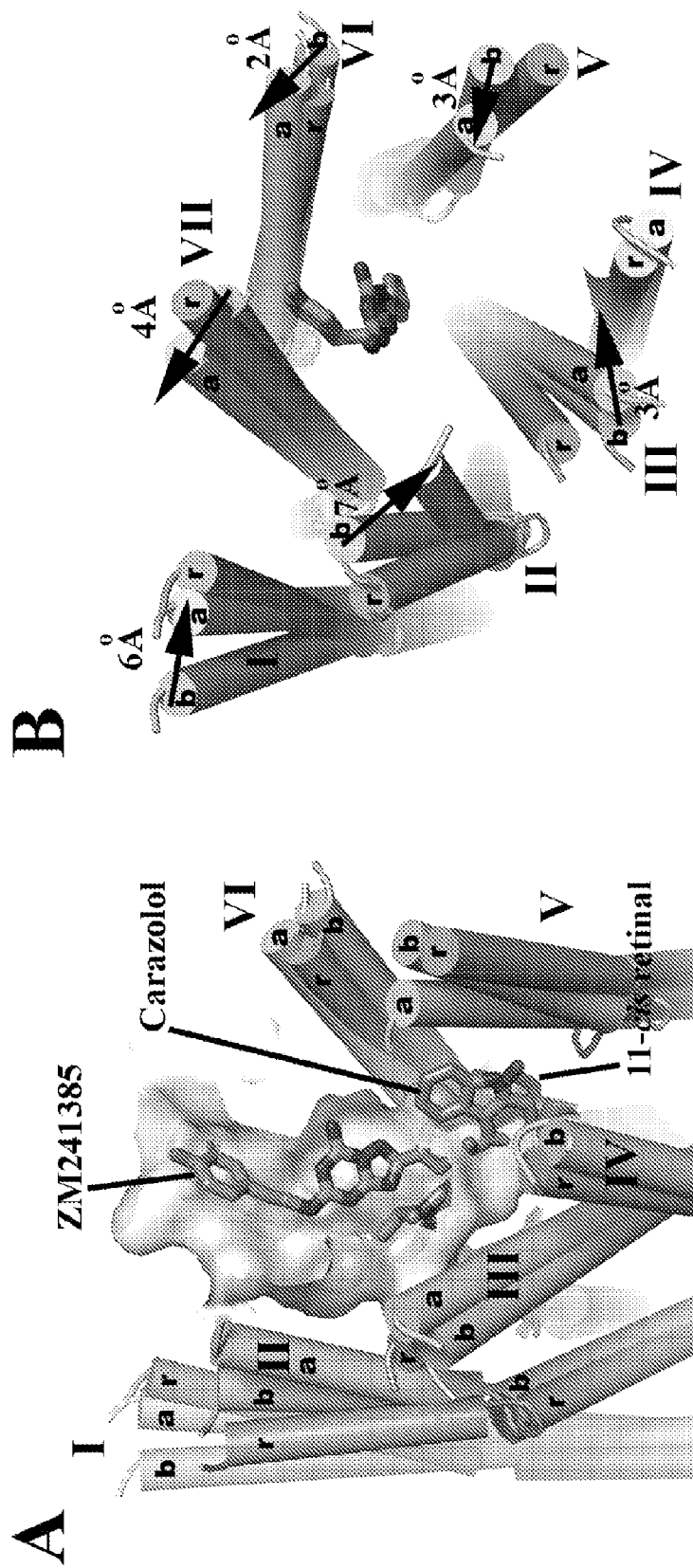
FIGS. 3A and 3B. Slight changes in helical positions alter the orientation of the ligand binding pocket. A. A surface rendering of the binding pocket for ZM241385 in the $A_{2A}$ adenosine receptor. Helical positions for $A_{2A}$ adenosine ("a"), $β_2$AR (pdbid: 2RH1) ("b") and rhodopsin (pdbid: 1U19) ("r") are shown after alignment with the FatCat server (found on the web at the site: fatcat.burnham.org/). Ligands for each receptor are shown to illustrate the differences in binding orientation and the differences in the adenosine $A_{2A}$ binding pocket. B. A top view of the helical bundle illustrating the maximal helical positional shifts of $A_{2A}$ relative to $β_2$AR.
Figure 4:
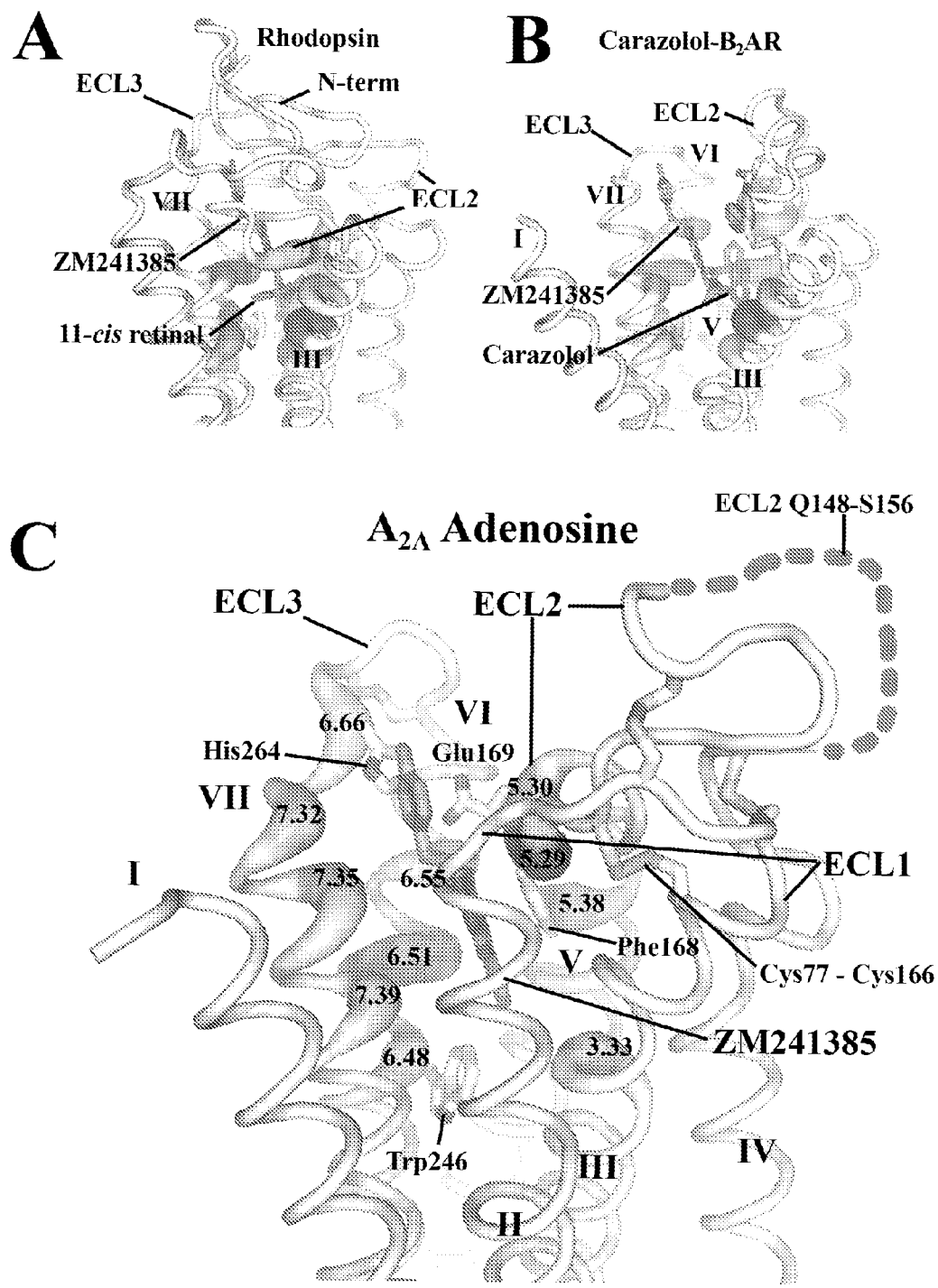
FIG. 4A-C. Normalized occluded surface (NOS) area changes due to ligand binding. Increases in occluded surface area are represented as thickened areas of the protein backbone chain. A. Rhodopsin (pdbid: 1U19) with retinal is shown along with the position of ZM241385 for comparison. Retinal makes extensive contact with helices III, V, VI and VII deep in the binding pocket. B. $β_2$AR bound to carazolol (pdbid: 2RH1) is shown along with the position of ZM241385 for comparison. Carazolol also makes extensive contacts with helices III, V, VI and VII deep in the binding pocket but is responsible for minimal changes in NOS of Trp $286^{6.48}$ the canonical "toggle switch". C. $A_{2A}$ adenosine receptor bound to ZM241385 has a very different binding orientation relative to rhodopsin and $β_2$AR having minimal interaction with helices III and V, but extensive interactions with helices VI and VII as well as residues in a ECL2 and ECL3. ZM241385 also forms significant contacts with Trp$246^{6.48}$. All interacting positions on the receptor are displayed as thick areas and labeled by their corresponding Ballesteros-Weinstein designation. The amino-acid numbering is based on the human $A_{2A}$ adenosine receptor primary sequence (SEQ ID NO: 2; accession number P29274). In addition to numbering residue positions in the primary amino acid sequence, the residues have numbers in superscripts (X.YY) that indicate their position in each transmembrane helix (X, helix number, from 1 to 8)), relative to the most conserved reference residue in that helix (YY). This residue is arbitrarily assigned the number 50, numbers decreasing towards N-terminus and increasing towards C-terminus However, the numbering is not used in loop regions beyond residues X.20 and/or X.80 or T4L FIG. 5A-D. A Comparison of interactions between helix III (E/DRY motif) and ICL2 for human $A_{2A}$-T4L-ΔC, human $β_2$AR-T4L (pdbid: 2RH1) and turkey $β_1$AR (pdbid 2VT4). A. $A_{2A}$-T4L-ΔC interactions. The DRY motif does not participate in any stabilizing ionic interactions similar to $β_2$AR and $β_1$AR. Instead Arg$102^{3.50}$ may play a role in shifting the pKa of the adjacent Asp$101^{3.49}$ allowing this residue to make stronger hydrogen bonding interactions with helix II and ICL2. B. Turkey $β_1$AR participates in similar interactions as $A_{2A}$-T4L-ΔC without the hydrogen bond to helix II. C. $β_2$AR does not contain a helical segment in ICL2 and has a modified set of interactions. D. The canonical "ionic lock" in rhodopsin.

Helical Position and Binding Pocket in the A2A Adenosine Receptor Versus Other Receptors Among the class A GPCRs, the sequence identity is highest within the α-helical transmembrane regions and ranges from 20-50% (P. Joost, A. Methner, *Genome Biol* 3, RESEARCH0063 (2002); D. K. Vassilatis et al., *Proc Natl Acad Sci USA* 100, 4903 (2003)). Not surprisingly, the helical arrangement is similar among the human $\beta_2AR$, turkey $\beta_1AR$ and squid/bovine rhodopsins structures determined to date. However, shifts in the relative positions of the various helices results in a root mean square deviation (RMSDs) between 2.0 to 2.5 Å (depending on how the alignment is carried out and which structures are being compared) that has structural, and biochemical implications. Most of the structural divergence arises in the extracellular portions of helices I, II, III and V, where the variation in the positions of helices II, III and V appears to redefine the location of the ligand binding pocket (the FatCat server (found on the web at the site: fatcat.burnham.org/) was used for structural alignment of the TMs with the rhodopsin structure 1U19 as a reference taken directly from that server: "It simultaneously addresses the two major goals of flexible structure alignment; optimizing the alignment and minimizing the number of rigid-body movements (twists) around pivot points (hinges) introduced in the reference structure"). However, comparisons between ground-state rhodopsin bound to retinal and $\beta_2AR$ bound to carazolol show minimal differences as the relative helical shifts are smaller (FIGS. 3a and 3b) (V. Cherezov et al., *Science* 318, 1258 (2007)). The position of the retinal and carazolol binding pocket is very similar and making most contact with helices III, V, VI (FIG. 3a and FIG. 4). The binding pocket of the $A_{2A}$ adenosine receptors is shifted closer to helices VI and VII which contribute the majority of the binding interactions associated with helical regions, as judged by occluded surface area calculations (G. S. Ratnaparkhi, R. Varadarajan, *Biochemistry* 39, 12365 (2000); the program occluded surface (OS) was used which calculates the occluded surface and atomic packing of protein model structures: found on the web at the site: csb.yale.edu/userguides/datamanip/os/ (FIG. 3b and FIG. 4). A concomitant shift of helices II and V (7 Å and 3 Å, respectively) toward the binding pocket, and a lateral shift of helix III toward helix V by 3 Å, compensates for the absence of ligand interactions in this region by increasing protein packing interactions (FIGS. 3a and 3b).

Example 5

Conformational Equilibrium and Receptor Activation

A common feature of the class A GPCRs is the presence of a tryptophan residue (at position 6.48) on helix VI whose rotameric position is thought to control the equilibrium between the active and inactive states of each receptor (it has been speculated that the general activation mechanism include following changes 6.47 (gauche+conformers)/6.48 (trans–conformers)/6.52 (trans–conformers) represent the active state (R*) and 6.47 (trans–conformers)/6.48 (gauche+ conformers)/6.52 (gauche+conformers) represent inactive state (R)). Based on the position of retinal in the rhodopsin structure it had been proposed that ligand interactions with this key residue could modulate receptor equilibrium (D. L. Farrens, C. Altenbach, K. Yang, W. L. Hubbell, H. G. Khorana, *Science* 274, 768 (1996)). Interestingly, the contact area between ligand and the "toggle switch" tryptophan residue at position 6.48 varies considerably among the solved receptor structures. For instance, rhodopsin and $\beta_2AR$ have a similar binding mode as noted; however, retinal in rhodopsin has a contact area of 36 Å$^2$, whereas carazolol bound to $\beta_2AR$ lacks any direct contact with Trp286$^{6.48}$ (V. Cherezov et al., *Science* 318, 1258 (2007)).

Basal or constitutive activity is the spontaneous production of cellular response in the absence of a ligand. Inverse agonist shifts the equilibrium towards inactive state. Agonist shifts the conformation towards the active state. Neutral antagonist binds to receptors and block the active site but not shift the equilibrium. A typical GPCRs can "dial" almost any conformational equilibrium between fully inactive and fully active therefore agonist/inverse agonist are classified as weak/partial/full. Depending on a receptor and cellular environment, the nature of an invert agonism and truly neutral antagonism can be difficult to detect. Ground-state rhodopsin has virtually no basal activity, whereas $\beta_2AR$ has a relatively high basal activity which is suppressed somewhat by carazolol as an inverse agonist (S. G. Rasmussen et al., *Nature* 450, 383 (2007)).

The observed increase in contact area may have direct implications for inverse agonist efficacy or suppressed basal activity by limiting the range of motion of the "toggle switch" tryptophan. The competitive antagonist ZM241385 has a 14 Å$^2$ contact area with Trp246$^{6.48}$ despite an altered binding mode relative to rhodopsin (FIG. 4c). This finding indicates that this ligand has the ability to stabilize the $A_{2A}$ adenosine receptor in an inactive state.

Figure 5:
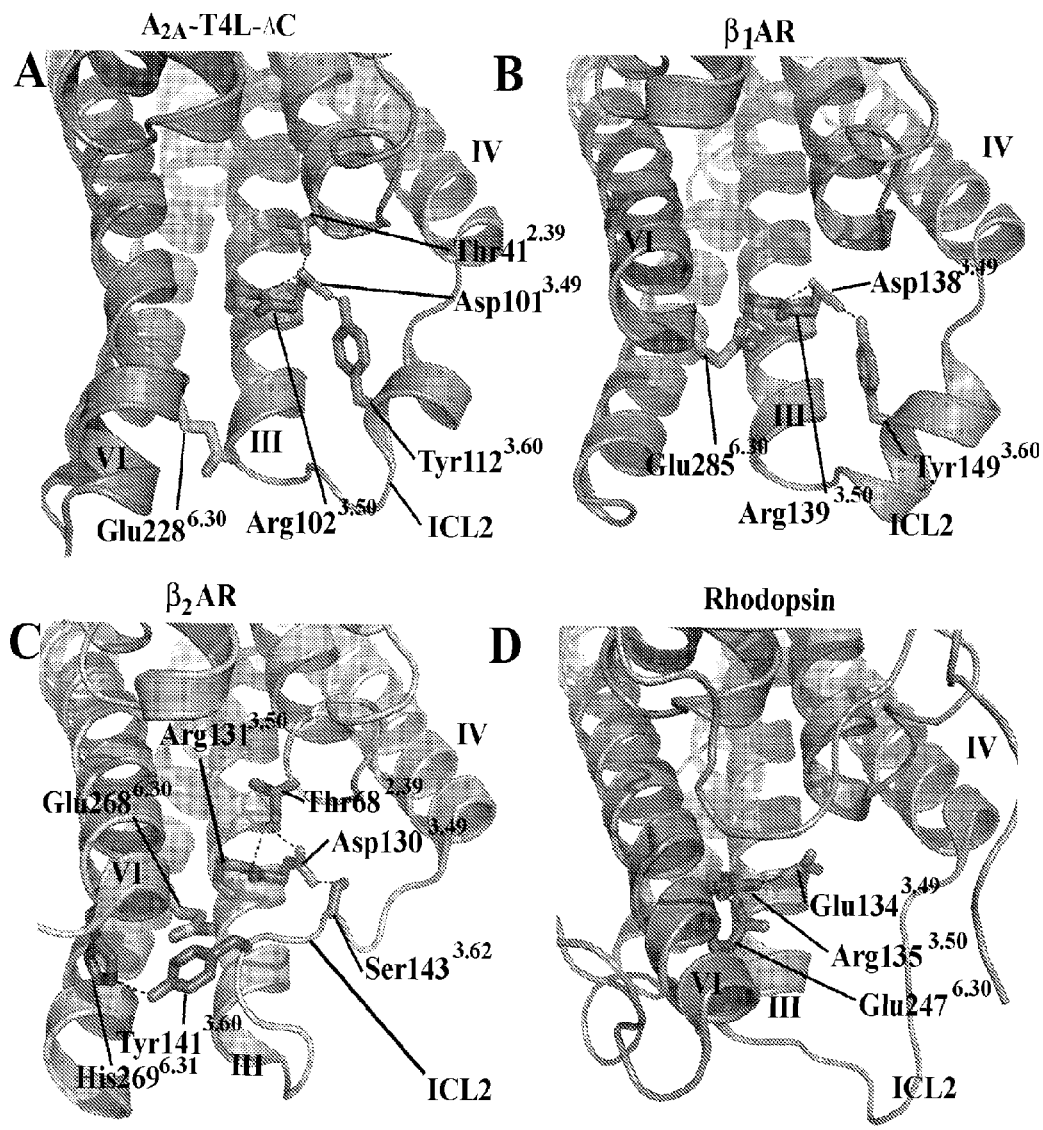

Interactions between the cytoplasmic end of helix III (conserved D/ERY (Asp$^{3.49}$ Arg$^{3.50}$ Tyr$^{3.51}$ sequence motif) and helix VI (Glu$^{6.30}$) have been proposed to constitute an "ionic-lock" that may play a role in restraining the fully inactive conformation of rhodopsin and other class A receptors (K. Palczewski et al., *Science* 289, 739 (2000); R. Vogel et al., *J Mol Biol* 380, 648 (2008); T. Okada et al., *J Mol Biol* 342, 571 (2004)). Of particular note is that with the exception of the rhodopsins, none of the GPCR structures solved to date have the ionic lock interaction, including the $A_{2A}$ adenosine receptor. Instead, as in $\beta_1AR$ and $\beta_2AR$, the D/ERY motif in the $A_{2A}$ adenosine receptor participates in interactions that restrain the conformation of ICL2. In the $A_{2A}$ adenosine receptor, Asp101$^{3.49}$ forms a hydrogen bond with Tyr112$^{3.60}$ in ICL2 and Thr41$^{2.39}$ at the base of helix II (FIG. 5a). Similar hydrogen bonding interactions were reported in the turkey β₁AR structure (T. Warne et al., *Nature* 454, 486 (2008)), but not in any of the β₂AR structures where Asp130$^{3.49}$ forms a hydrogen bond with Ser143$^{3.62}$ although there is a tyrosine at the 3.60 position (FIGS. 5b and 5c) (S. G. Rasmussen et al., *Nature* 450, 383 (2007); D. M. Rosenbaum et al., *Science* 318, 1266 (2007); M. A. Hanson et al., *Structure* 16, 897 (2008)). This discrepancy is caused by a short helical section in the ICL2 loop of both β₁AR and the A$_{2A}$ adenosine receptor that is not present in any of the β₂AR structures (FIG. 5). It has been proposed that ICL2 serves as a control switch facilitating G protein activation through a select set of interactions (E. S. Burstein, T. A. Spalding, M. R. Brann, *J Biol Chem* 273, 24322 (1998)). Interestingly the basal activity profile among the β₁AR, β₂AR and the A$_{2A}$ adenosine receptors correlates with the presence of this short helix in ICL2 and the presence of hydrogen bonding interactions between tyrosine at position 3.60 in ICL2 and Asp at position 3.49. In β₁AR and A$_{2A}$ adenosine receptor, both of which have low basal activity, this interaction is present (L. Birnbaumer, F. O. Levy, X. Zhu, A. J. Kaumann, *Texas Heart Inst J* 21, 16 (1994); J. Zezula, M. Freissmuth, *Br J Pharmacol* 153 Suppl 1, S184 (2008)). In contrast, β₂AR exhibits high basal activity and lacks helical structure within its ICL2 resulting in altered interactions with the DRY motif (L. Birnbaumer, F. O. Levy, X. Zhu, A. J. Kaumann, *Texas Heart Inst J* 21, 16 (1994)). Thus, instead of participating in an 'ionic lock' as in rhodopsin, the arginine residue in the D/ERY motif cam play a role in stabilizing the deprotonated state of the adjacent aspartate or glutamate residue, which would strengthen the polar interactions between the D/ERY motif and both ICL2, and helix II. This set of interactions may have direct implications in G protein activation (R. Vogel et al., *J Mol Biol* 380, 648 (2008)).

Example 5

Extracellular Loops: Mediation of Ligand Entry and Binding in the A2A Adenosine Receptor Versus other GPCRs The extracellular surface properties of the A$_{2A}$ adenosine receptor is largely dictated by its second extracellular loop (ECL2), which is considerably different from that of β₁AR, β₂AR and rhodopsin (FIG. 1 and FIG. 4). The ECL2 of the A$_{2A}$ adenosine receptor lacks the prominent secondary structural elements, such as β-sheet and α-helix, which were observed in the rhodopsin and β-adrenergic receptors, respectively. Instead, the ECL2 of the A$_{2A}$ adenosine receptor is mainly a spatially constrained random coil possessing three disulfide linkages with ECL1 (FIG. 4C). Two of the three disulfide bonds (Cys71$^{2.69}$-Cys159$^{5.20}$ and Cys74$^{3.22}$-Cys146$^{4.67}$) are unique to the A$_{2A}$ adenosine receptor while the third (Cys77$^{3.25}$-Cys166$^{5.27}$) is conserved among many class A GPCRs. In addition, a fourth intraloop disulfide bond is formed in ECL3 between Cys259$^{6.61}$ and Cys262$^{6.64}$ with the sequence CPDC which creates a kink in the loop that constrains the position of ECL3 and orients His264$^{6.66}$ at the top of the ligand binding site.

The extensive disulfide bond network forms a rigid, open structure exposing the ligand binding cavity to solvent and should allow free access for small molecule ligands. In addition, the family conserved disulfide bridge (Cys77$^{3.25}$-Cys166$^{5.27}$) is adjacent to a short helical segment that presents two crucial residues for ligand binding interactions (Phe 168$^{5.29}$ and Glu169$^{5.30}$). The missing tip of the loop (Gln148-Ser156) is spatially distinct from the ligand binding site, and therefore should not directly interact with the binding cavity. Mutation of Cys262$^{6.64}$ to Gly did not affect binding to radio-ligand agonist or antagonist, indicating that the kink in ECL3 is either unnecessary for receptor function or that the other disulfide bonds are sufficient to constrain extracellular loop architecture (D. J. Scholl, J. N. Wells, *Biochem Pharmacol* 60, 1647 (2000)). Mutational studies on the A₁ adenosine receptor indicate that these cysteine residues (Cys80$^{3.25}$-Cys169$^{5.27}$ in the A₁ receptor) (FIG. 8) are critical for expression due to a complete loss of radiolabeled antagonist binding in the absence of this disulfide bond.

Example 6

Binding of Non-Xanthine Antagonists by the Adenosine A2a Receptor

Prior to this invention, methods for generating structural and biophysical data relating to class A GPCRs with diffusible ligands have used primarily the biogenic amine receptors, e.g., the adrenergic, dopamine, and serotonin families. These amine ligands are all positively charged at physiologic pH and are known to interact with a key negatively charged aspartate residue (Asp$^{3.32}$) on helix III. Indeed, in all three of the available β-adrenergic structures, each co-crystallized ligand interacts with this residue and binds in a pocket quite similar to that of retinal in rhodopsin.

Figure 6:
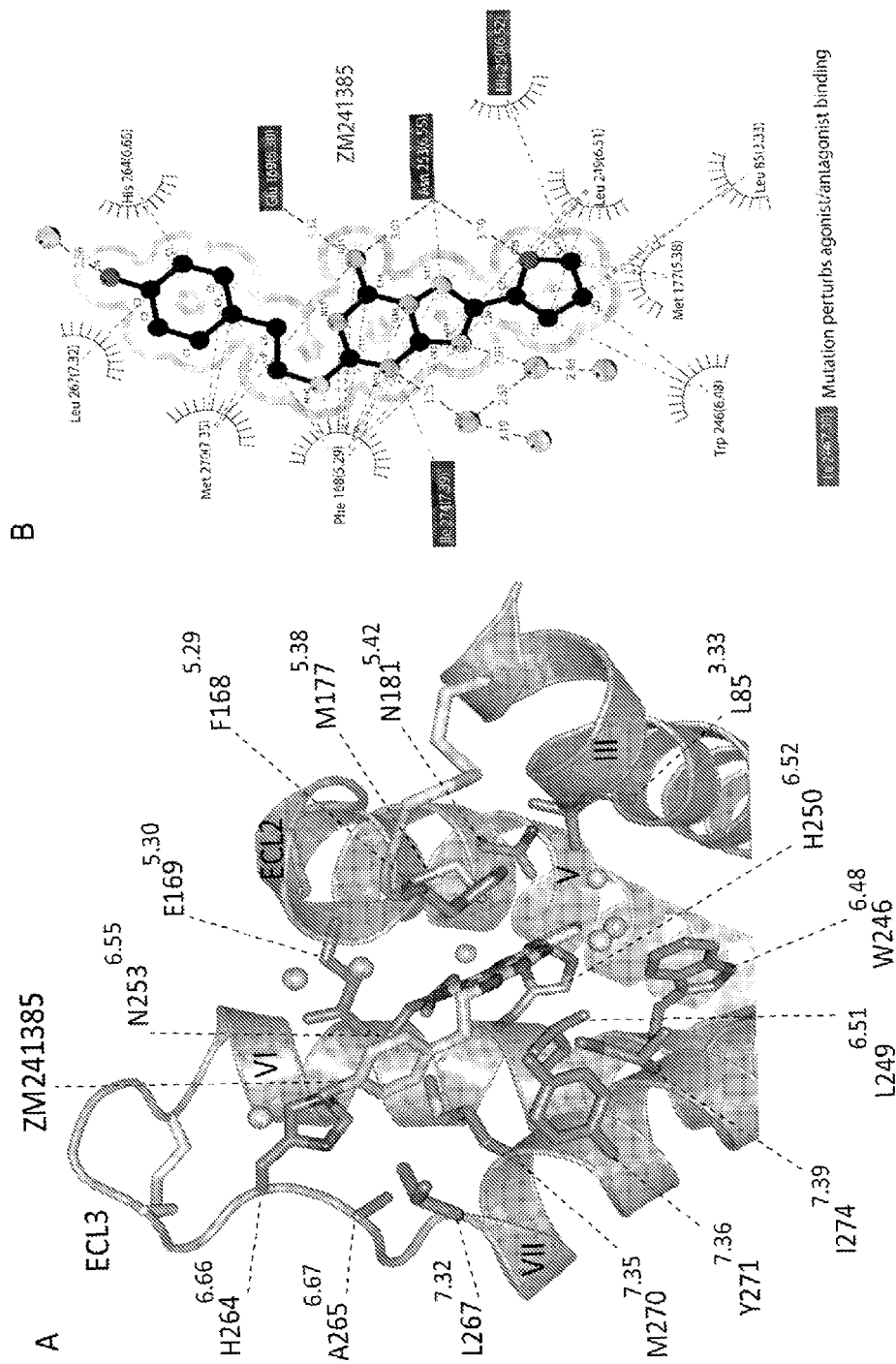
FIGS. 6A and 6B. Ligand binding cavity of $A_{2A}$-T4L-ΔC with ZM241385 bound. A. Residues within 5 Å of the ZM241385 are shown in stick representation. Only the interacting helices, ECL3 and the interacting part of ECL2 are shown. The two disulfide bridges in close proximity to the binding cavity are also shown. ZM241385 is positioned co-linear with respect to the transmembrane helices V, VI and VII, and the binding cavity is elongated to the ECL3 and helical ends of TM VI and VII. For comparison to retinal chromophore or beta-blockers binding site, see FIG. 3 for details. The Phe$168^{5.29}$ from ECL2 forms various aromatic stacking interactions with the bicyclic core of ZM241385. Trp$246^{6.48}$ associated with stabilizing the antagonist structure is at 3 Å distance from the furan ring of ZM241385. The binding cavity includes four ordered water molecules shown as light spheres. B. Schematic representation of the interactions between $A_{2A}$-T4L-ΔC and ZM241385 at the ligand binding cavity combined with mutation analysis for adenosine agonist/antagonists interactions. Mutations that are reported to disrupt antagonist and/or agonist binding are within darkened squares: Glu$169^{5.30}$, His$250^{6.25}$, Asn$253^{6.55}$ and Ile$274^{7.39}$.

In contrast to the 3-adrenergic ligands and retinal, ZM241385 bound to human A$_{2A}$ adenosine receptor occupies a significantly different position in the transmembrane network (FIG. 4) where its orientation is almost perpendicular to the membrane plane (FIGS. 4c and 6). The bicyclic triazolotriazine core of ZM241385 is anchored by an aromatic stacking interaction with Phe168$^{5.29}$, an aliphatic hydrophobic interaction with Ile274$^{7.39}$ and a hydrogen bonding interaction with Asn253$^{6.55}$ (FIG. 6). Adjacent to Phe168$^{5.29}$ a polar residue (Glu169$^{5.30}$) interacts with the exocyclic amino group (N15 atom) linked to the bicyclic core of ZM241385 (FIG. 6b). This binding pocket is referred to as binding pocket I.

Mutation of Glu169$^{5.30}$ to alanine reduces the affinity for both antagonists and agonists and causes a 1000-fold reduction in agonist efficacy (J. Kim et al., *Mol Pharmacol* 49, 683 (1996)). However, mutating this position to glutamine did not have a substantial impact on antagonist binding affinity, suggesting hydrogen bonding as the predominant means of interacting with N15 of ZM241385 as opposed to Coulombic interactions (FIG. 6b). Early studies indicate that mutation of Asn253$^{6.55}$ to alanine, which would disrupt an important polar contact with the exocyclic N15 atom of ZM241385, results in a complete loss of both agonist and antagonist binding (J. Kim, J. Wess, A. M. van Rhee, T. Schoneberg, K. A. Jacobson, *J Biol Chem* 270, 13987 (1995)). The structure also shows that Ile274$^{7.39}$ forms a hydrophobic contact with the C12 atom of ZM241385; accordingly mutation of Ile274$^{7.39}$ to alanine results in negligible antagonist binding and a 30-fold reduction in agonist potency (J. Kim, J. Wess, A. M. van Rhee, T. Schoneberg, K. A. Jacobson, *J Biol Chem* 270, 13987 (1995)). Phe168$^{5.29}$ and Leu249 both anchor the bicyclic ring of ZM241385 through π stacking and hydrophobic interactions, respectively, and are proposed to be involved in ligand binding (S. Moro et al., *Chem Commun* (Camb), 2949 (2003)). The phenolic hydroxyl group extending from the ethylamine chain of ZM241385 forms a hydrogen bond with an ordered water molecule. The phenyl ring forms hydrophobic interactions with Leu267$^{7.32}$ and Met270$^{7.35}$ that is consistent with hydrophobicity rather than aromaticity as means of interaction with the phenolic substituent, A ZM241385 derivative, with a cycloalkyl substituent (LUF5477) instead of phenylmethylene, also has high affinity for the $A_{2A}$ adenosine receptor. In a recent study on new antagonists for the $A_{2A}$ adenosine receptor it was demonstrated that tremendous substituent flexibility exists in this area of the pharmacophore (M. Mantri et al., *J Med Chem* 51, 4449 (2008)). This observation correlates well with the directionality of the phenylethylamine substituent in ZM241385 as it is directed towards the more solvent exposed extracellular region (ECL2 and ECL3) rather than towards the transmembrane domain of the receptor as was previously proposed (A. Martinelli, T. Tuccinardi, *Med Res Rev* 28, 247 (2008); O. Yuzlenko, K. Kiec-Kononowicz, *J Comput Chem*, (2008)). The other substituent in ZM241385 is the furan ring, a feature that occurs in many $A_{2A}$ adenosine receptor antagonists. This moiety is located deep in the ligand binding cavity and directed towards helices V and VII, where it hydrogen bonds to $Asn253^{6.55}$ and forms a water-mediated interaction with $His 250^{6.52}$ (FIG. 6A). Hydrophobic interactions of the furan ring system include $His250^{6.52}$ with C23 and $Leu249^{6.51}$ with the C22 and C21 atoms of ZM241385. Mutation of $His250^{6.52}$ to alanine completely abolishes ligand binding, whereas mutation to phenylalanine or tyrosine residues modestly affects agonist binding but not antagonist binding (J. Kim, J. Wess, A. M. van Rhee, T. Schoneberg, K. A. Jacobson, *J Biol Chem* 270, 13987 (1995); Q. Jiang, B. X. Lee, M. Glashofer, A. M. van Rhee, K. A. Jacobson, *J Med Chem* 40, 2588 (1997)); replacement with an asparagine slightly increases ligand affinity (Q. Jiang, B. X. Lee, M. Glashofer, A. M. van Rhee, K. A. Jacobson, *J Med Chem* 40, 2588 (1997)). The furan ring is approximately 3 Å away from the highly conserved $Trp246^{6.48}$, an important residue in receptor activation as discussed above (M. Audet, M. Bouvier, *Nat Chem Biol* 4, 397 (2008)). The hydrophobic interactions between ZM241385's furan ring and this residue are expected to hinder the structural rearrangements necessary for activation, constraining the receptor in an inactive state.

Example 7

Two Additional Binding Pockets in the Adenosine A2a Receptor

In addition to the empirically delineated binding site associated with ZM241385 (i.e., binding pocket I described above), the present invention provides a crystal structure comprising two additional water-filled binding sites in the general vicinity of the non-xanthine binding site that can be used for designing novel drugs.

Figure 7:
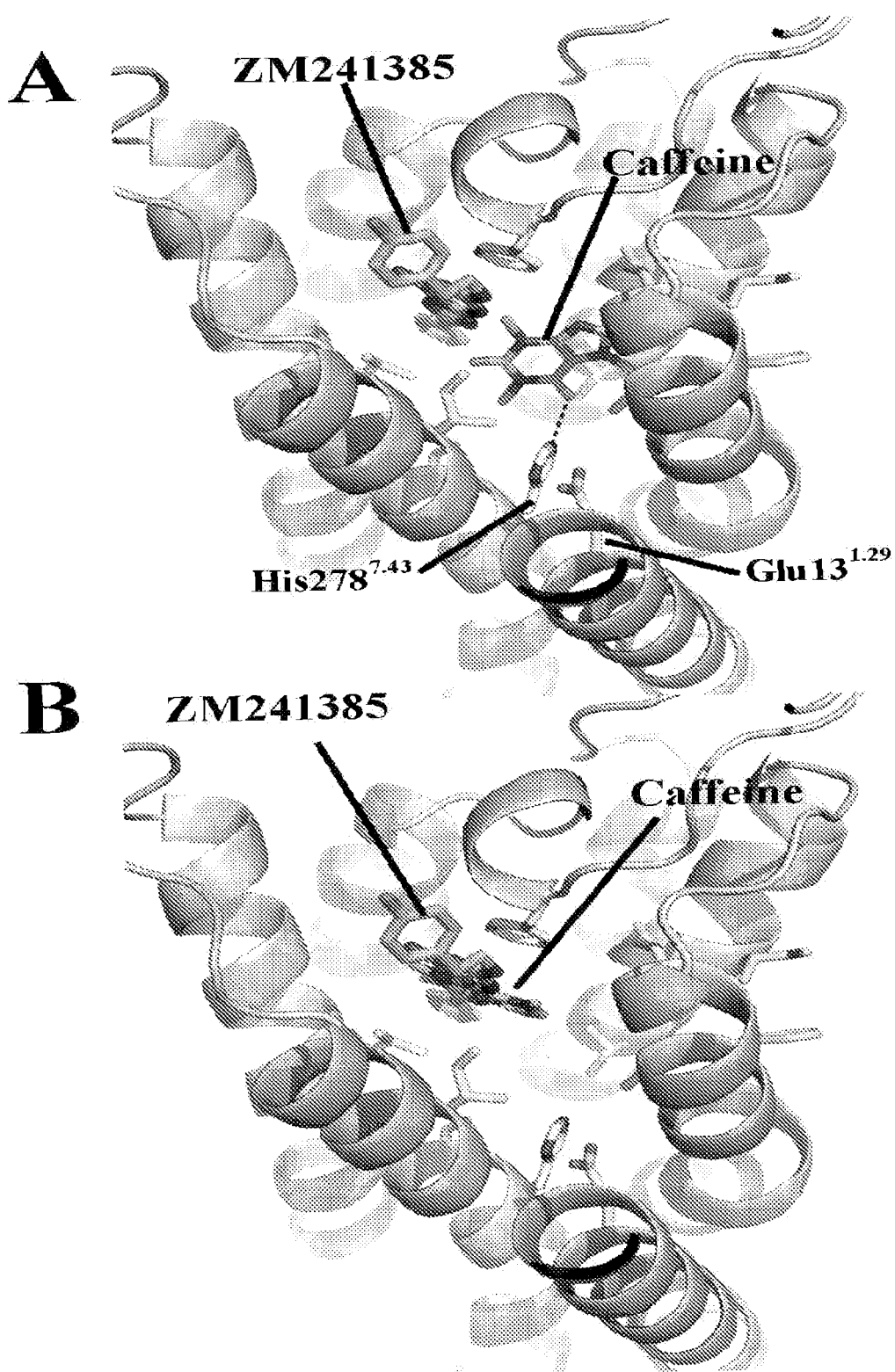
FIGS. 7A and 7B. In silico docking of caffeine to binding pocket II of human $A_{2A}$ adenosine receptor.

(1) Binding pocket II. In silico docking studies were carried out on the adenosine A2a structure using four xanthine-based ligands: theophylline, xanthine, theobromine and caffeine. The resulting binding interactions were similar for all four and the results for caffeine are presented herein. The location of the xanthine binding pocket (binding pocket II) appears to be dependent on the protonation state of $His278^{7.43}$. When this residue is protonated and positively charged, caffeine is expected to bind adjacent to the non-xanthine binding site defined by hydrophobic interactions with: $Phe62^{2.60}$, $Ile66^{2.64}$, $Ile80^{3.28}$, $Val84^{3.32}$, $Phe168^{5.29}$, $Leu249^{6.51}$, $Ile274^{7.39}$ and forming polar interactions with $His278^{7.43}$ (FIG. 7A). However, when $His278^{7.43}$ is deprotonated, the xanthine binding site is found in a location similar to the binding pocket I (FIG. 7B), a non-xanthine binding pocket. Physiologically, the protonated form of $His278^{7.43}$ will be more prevalent because of a charge coupling interaction with $Glu13^{1.29}$.

(2) Binding pocket III, the 29 Angstrom$^3$ lower binding cavity. The invention also provides an $A_{2A}$ adenosine receptor crystal structure comprising a third cavity, referred to herein as binding pocket III. This third cavity corresponds to the water filled cavity in $\beta_2$-AR and rhodopsin. However, in the case of the $A_{2A}$ adenosine receptor the water filled cavity is much larger (29 Angstroms$^3$) and shows some connectivity with the base of binding pocket I. In the model described herein, this binding cavity (binding pocket III) is formed by the following polar and hydrophobic amino acids: $Leu48^{2.46}$, $Ala51^{2.49}$, $Asp52^{2.50}$, $Val55^{2.53}$, $Val84^{3.32}$, $Leu87^{3.35}$, $Thr88^{3.36}$, $Ser91^{3.39}$, $Leu95^{3.43}$, $Ile238^{6.40}$, $Phe242^{6.44}$, $Trp246^{6.48}$, $Ser277^{7.42}$, $His278^{7.43}$, $Asn280^{7.45}$, $Ser281^{7.46}$ and $Asn284^{7.49}$. In certain embodiments, therefore, the invention provides methods for designing small molecules to bind selectively in this site and affect a response from the receptor. Because water bound in this area is likely to play a significant role in signal transduction, stabilizing the interactions in this site can provide a more effective intervention strategy than targeting the more canonical ligand binding sites of GPCRs.

The invention thus provides in certain embodiments the use of three binding sites, i.e., binding pockets I, II and/or III, for designing novel $A_{2A}$ adenosine receptor ligands. The invention provides methods of exploiting the xanthine binding site that lies adjacent to the site of ZM241385 to study the binding mode of caffeine and other xanthine molecules that differ significantly from the mode of binding observed in higher-affinity non-xanthine molecules. Increased affinity and specificity may be designed into existing ligands by combining interactions with both xanthine and non-xanthine binding sites (e.g., binding pockets I and II). The invention also provides methods for designing molecules that interact with the 29 Angstrom$^3$ ligand-binding cavity, which can be accessed from the extracellular space, thereby increasing the specificity and functionality of ligands that target the $A_{2A}$ adenosine receptor and other class A GPCRs with conserved sequences in this region.

All references, issued patents and patent applications cited within the body of the instant specification are hereby incorporated by reference in their entirety, for all purposes.

TABLE 1

| Data collection and refinement statistics | |
|---|---|
| | $A_{2A}$-T4L-$\Delta$C |
| Data collection (APS GM/CA CAT ID-B, 10 µm beam) | |
| Space group | P2$_1$ |
| Cell dimensions | |
| a, b, c (Å) | 47.7, 76.9, 86.6 |
| (°) | 101.3 |
| No. of reflections processed | 64,526 (8165) |
| No. unique reflections | 18,465 (356) |
| Resolution (Å) | 20.0-2.6 (2.8-2.6) |
| R$_{sym}$ | 9.8 (38.9) |
| Mean I/σ(I) | 7.0 (2.3) |
| Completeness (%) | 96.8 (93.9) |
| Multiplicity | 3.5 (2.3) |
| Refinement | |
| Resolution (Å) | 20.0-2.6 |
| No. reflections (reference set) | 18,461 (937) |
| R$_{crys}$/R$_{free}$ | 19.6/23.1 |
| No. atoms | 3769 |
| Protein | 3521 |

TABLE 1-continued

Data collection and refinement statistics

|  | $A_{24}$-T4L-$\Delta$C |
|---|---|
| Ions, lipids, ligand and other | 165 |
| Water oxygen | 83 |
| B-values (Å$^2$) | |
| All atoms | 70.6 |
| Protein | 69.4 |
| Ligand | 66.7 |
| Lipid | 94.4 |
| R.m.s deviations from ideality | |
| Bond lengths (Å) | 0.002 |
| Bond angles (°) | 0.78 |

TABLE 1-continued

Data collection and refinement statistics

|  | $A_{24}$-T4L-$\Delta$C |
|---|---|
| Ramachandran plot statistics (%) (excl. Gly, Pro): | |
| Most favored regions | 92.8 |
| Additionally allowed regions | 7.2 |
| Generously allowed regions | 0.0 |
| Disallowed regions | 0.0 |

*Highest resolution shell is shown in parenthesis.
$R_{sym} = 100 \, \Sigma_n (\Sigma_l |I_j - I|)/\Sigma_n (\Sigma I_j)$
$R_{crys} = 100 \, \Sigma_{hkl} |F_{obs} - F_{calc}|\Sigma_{hkl} F_{obs}$.
$R_{free}$ = test set 5%.

TABLE 2

Analysis of crystallographic data quality using the software program XDS (W. Kabsch, *J. Appl. Cryst.* 26 (1993)). Data was processed and merged together using data-sets collected from 13 individual crystals. A comparison is performed between the complete data set and data filtered by σ cut-off value. Cut-off value was not used in the structure solution or refinement process.

| Resolution [Å] | Number of reflections Observed | Unique | Multiplicity | Completeness [%] | R-factor $R_{sym}$ | I/σ | $R_{meas}$ | $R_{mrgd\text{-}F}$ |
|---|---|---|---|---|---|---|---|---|
| Signal/noise ≥ −3 | | | | | | | | |
| 10 | 1069 | 283 | 3.8 | 80.2 | 4.8 | 14.66 | 5.5 | 3.3 |
| 8 | 1200 | 324 | 3.7 | 97.3 | 5 | 14.03 | 5.8 | 3.7 |
| 6 | 3318 | 897 | 3.7 | 98.8 | 7.2 | 12.05 | 8.3 | 6 |
| 5 | 4250 | 1138 | 3.7 | 98.9 | 8.8 | 11.6 | 10.1 | 6.8 |
| 4.5 | 3688 | 978 | 3.8 | 98.1 | 9.2 | 12.23 | 10.6 | 7 |
| 4 | 5740 | 1529 | 3.8 | 98.3 | 10.3 | 11.29 | 11.9 | 8.1 |
| 3.5 | 9577 | 2508 | 3.8 | 97.7 | 13 | 9.18 | 15 | 11.1 |
| 3.2 | 8924 | 2336 | 3.8 | 97.5 | 19.2 | 6.75 | 22.1 | 16.9 |
| 3 | 8156 | 2143 | 3.8 | 97.8 | 26.8 | 4.87 | 30.8 | 26.2 |
| 2.8 | 10439 | 2769 | 3.8 | 97.9 | 35.5 | 3.78 | 40.9 | 36.2 |
| 2.6 | 8165 | 3560 | 2.3 | 93.9 | 38.9 | 2.32 | 48.8 | 57.1 |
| Σ | 64526 | 18465 | 3.5 | 96.8 | 9.8 | 7.03 | 11.3 | 12.9 |
| Signal/noise ≥ 0 | | | | | | | | |
| 10 | 1069 | 283 | 3.8 | 80.2 | 4.8 | 14.66 | 5.5 | 3.3 |
| 8 | 1200 | 324 | 3.7 | 97.3 | 5 | 14.03 | 5.8 | 3.7 |
| 6 | 3312 | 894 | 3.7 | 98.5 | 7.2 | 12.09 | 8.3 | 5.9 |
| 5 | 4238 | 1134 | 3.7 | 98.5 | 8.8 | 11.64 | 10.1 | 6.8 |
| 4.5 | 3679 | 974 | 3.8 | 97.7 | 9.2 | 12.28 | 10.6 | 6.9 |
| 4 | 5714 | 1521 | 3.8 | 97.8 | 10.3 | 11.35 | 11.9 | 7.9 |
| 3.5 | 9496 | 2486 | 3.8 | 96.8 | 13 | 9.26 | 14.9 | 10.8 |
| 3.2 | 8766 | 2284 | 3.8 | 95.3 | 19 | 6.91 | 21.9 | 15.8 |
| 3 | 7822 | 2042 | 3.8 | 93.2 | 26 | 5.13 | 29.9 | 23.6 |
| 2.8 | 10010 | 2633 | 3.8 | 93.1 | 34.3 | 4 | 39.5 | 32.8 |
| 2.6 | 7382 | 3157 | 2.3 | 83.3 | 35.8 | 2.69 | 44.8 | 47 |
| Σ | 62688 | 17732 | 3.5 | 93 | 9.7 | 7.35 | 11.2 | 12 |

$R_{sym} = 100 \, \Sigma_n (\Sigma_l |I_j - \hat{I}|)/\Sigma_n (\Sigma I_j)$ $R_{meas} = 100 \, n \, \Sigma_l |\hat{I} - I_j|/\Sigma_{hkl} (n - 1) \, \Sigma_l I_j$, where $\hat{I}$ is the mean intensity of symmetry-related reflections $R_{mrgd\text{-}F}$ as defined by (K. Diederichs, P. A. Karplus, *Nat Struct Biol* 4, 269 (1997)) is a quality measure of the reduced structure factor amplitudes $R = 100 \, \Sigma_{hkl} |F_{obs} - F_{calc}|\Sigma_{hkl} F_{obs}$.

Test set size 5%.

I/σ = mean of intensity/σ,

σ = standard deviation of reflection intensity I estimated from sample statistics

TABLE 3

Binding affinities of subtype specific agonists and antagonists for the wild-type $A_{2A}$-WT, full length fusion protein $A_{2A}$-T4L-WT and carboxy-terminally truncated $A_{2A}$-T4-ΔC in the presence and absence of NaCl as an allosteric modulator. The competition binding curves were fitted for one-site competition or two-site (only for agonists) binding models, using the program GraphPad Prism version 4. Apparent affinity ($K_i$) values were calculated using the Cheng-Prusoff equation as $K_i = IC_{50}/(1 + [\text{ligand}]/K_d)$. (A) Competition binding of [$^3$H]ZM241385 versus CGS21680: agonist affinity is decreased at both the wild type and modified $A_{2A}$ constructs in the presence of 1M NaCl. The modified $A_{2A}$ receptor constructs $A_{2A}$-T4L-WT and $A_{2A}$-T4-ΔC show a significantly higher affinity for the agonist CGS21680 than the wild type receptor. (B) Competition binding of [$^3$H]ZM241385 versus CGS21680: antagonist affinity is not affected by the presence of 1M NaCl at both the wild type $A_{2A}$ and modified $A_{2A}$ constructs. The modified $A_{2A}$ receptor constructs $A_{2A}$-T4L-WT and $A_{2A}$-T4-ΔC show a wild type affinity for the antagonist ZM241385.

(A)

| | CGS21680 | | CGS21680 + 1M NaCL | | Fold shift |
|---|---|---|---|---|---|
| Construct | pKi (±S.D.) | Ki, nM | pKi (±S.D) | Ki, nM | in affinity |
| $A_{2A}$-WT | 6.27 (0.1) | 545 | 5.35** | 4491 | 8 |
| $A_{2A}$-T4L-WT | 6.74 (0.06) τ | 181 | 5.36*** | 4327 | 24 |
| $A_{2A}$-T4-ΔC | 7.08 (0.21) τττ, ‡ | 83 | 5.28*** | 5204 | 63 |

(B)

| | ZM241385 | | ZM241385 + 1M NaCL | | Fold shift |
|---|---|---|---|---|---|
| Construct | pKi (±S.D.) | Ki, nM | pKi (±S.D) | Ki, nM | in affinity |
| $A_{2A}$-WT | 8.67 (0.21) | 2.13 | 8.9 | 1.27 | 1.7 |
| $A_{2A}$-T4L-WT | 8.74 (0.1) | 1.83 | 8.93 | 1.17 | 1.6 |
| $A_{2A}$-T4-ΔC | 8.87 (0.1) | 1.38 | 8.87 | 1.08 | 1.2 |

Figure 2:
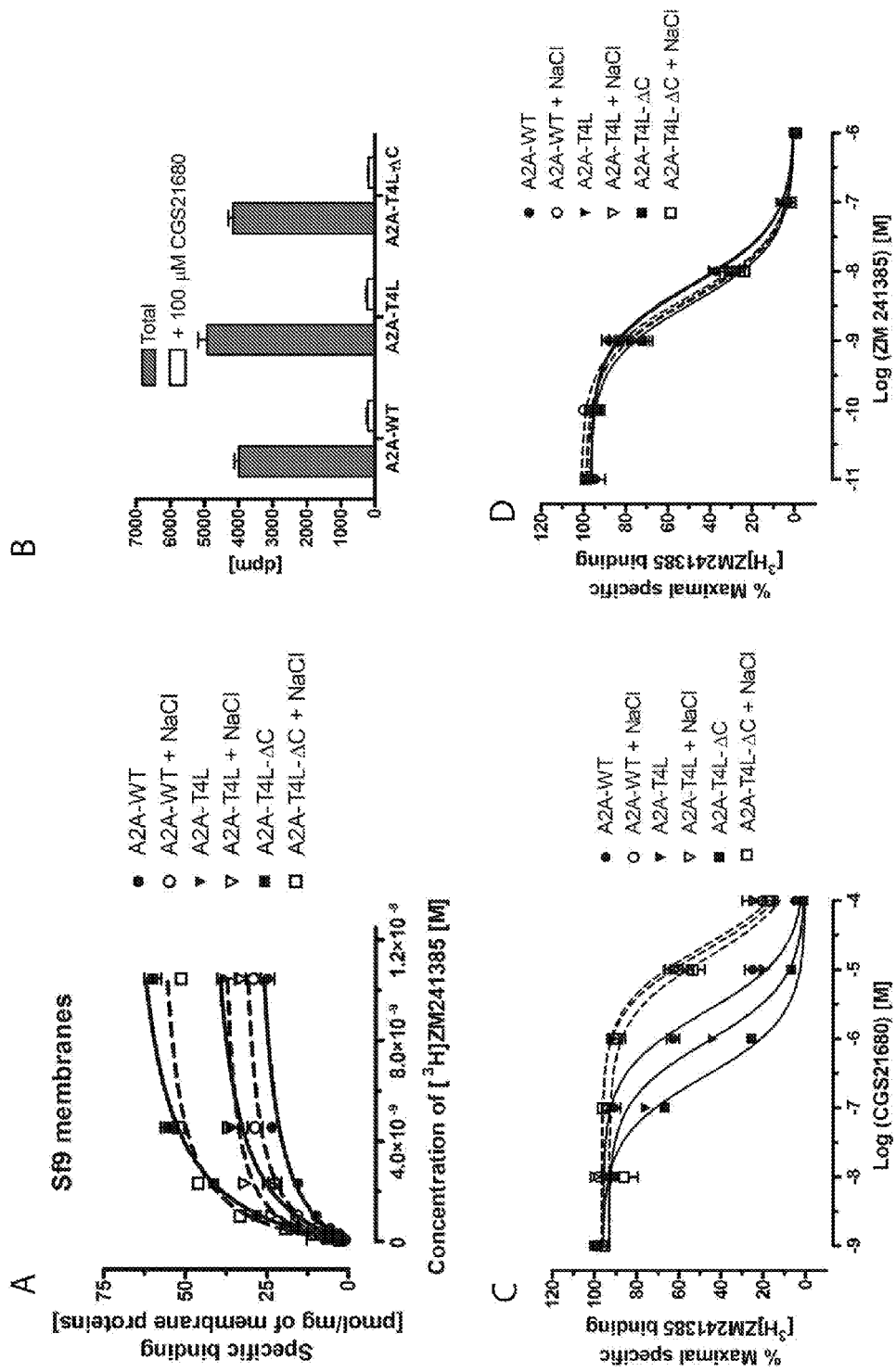
FIG. 2A-D. Ligand binding characteristics of $A_{2A}$-WT, $A_{2A}$-T4L and $A_{2A}$-T4L-ΔC. A. Saturation binding isotherm for the binding of [$^3$H]ZM241385 to different $A_{2A}$-WT, $A_{2A}$-T4L or $A_{2A}$-T4L-ΔC receptors confined in membranes of Sf9 cells. The indicated preparations of $A_{2A}$ receptors were incubated with different concentrations of [$^3$H]ZM241385 in the absence (filled shapes and solid lines) and presence (open shapes and dashed lines) of 1 M NaCl as described in SOM. The figure shown represents data combined from two separate experiments performed in triplicate. The equilibrium constant ($K_d$) values of [$^3$H]ZM241385 in the absence and the presence of 1 M NaCl were 2.1±0.7 nM, 1.3±0.2 nM for $A_{2A}$-WT; 2.0±0.3 nM, 0.9±0.1 nM for $A_{2A}$-T4L and 1.8±0.2 nM, 1.0±0.1 nM for $A_{2A}$-T4L-DC, respectively. B. One point binding assay demonstrating the binding of [$^3$H]ZM241385 to membranes (5 µg/assay point) of HEK 293T cells transfected with $A_{2A}$-WT, $A_{2A}$-T4L or $A_{2A}$-T4L-ΔC. [$^3$H] ZM241385 was used at a concentration equivalent to the previously observed equilibrium constant ($K_d$). Lower panels—the ability of increasing concentrations of C. the agonist CGS21680 or D. the antagonist ZM241385 to compete with [$^3$H]ZM241385 binding at $A_{2A}$-WT (circles), $A_{2A}$-T4L (triangles), $A_{2A}$-T4L-ΔC (squares) constructs in HEK293T cells was tested in the absence (filled shapes and solid lines) or presence (open shapes and dashed lines) of 1 M NaCl. The figure shown represents data combined from three separate experiments performed in duplicate.

Data relates to experiments described in FIG. 2.
The differences in pK$_i$ observed between control and + 1M NaCl conditions were analysed using a Student's t-test and significant differences noted as below (p < 0.01 = , p < 0.001 = *).
Differences in pK$_i$ observed between various $A_{2A}$ constructs was analysed using a one-way anova analysis followed by a bonferroni post-hoc test.
Significant differences were only observed in the control conditions and are noted as follows:
τ = pK$_i$ ($A_{2A}$-WT) > pK$_i$ ($A_{2A}$-T4L-WT) – p < 0.05,
τττ = pK$_i$ ($A_{2A}$-WT) > pK$_i$ ($A_{2A}$-T4L-ΔC) – p < 0.001,
‡ = pK$_i$ ($A_{2A}$-T4L-WT) > pK$_i$ ($A_{2A}$-T4L-ΔC*) – p < 0.05.
The differences in pK$_i$ observed between control and + 1M NaCl conditions were analysed using a Student's t-test.
Differences in pKi observed between various $A_{2A}$ constructs was analysed using a one way anova analysis followed by a bonferroni post-hoc test. Significant differences were not observed (ns).

TABLE 4

Molecular interactions in the $A_{2A}$-T4L-ΔC structure. Only a very limited number of interactions are present between $A_{2A}$ and T4L. Table 4A: The contact surfaces between receptor and T4L. The data was obtained using the PISA server (found on the web at the site: ebi.ac.uk) Table 4B: The atomic contacts between $A_{2A}$-T4L-ΔC and ZM241385 (ZMA), co-factors (SO$_4$) and various lipids (DGR) found in the structure. The results were obtained using WHAT IF server (found on the web at the site: swift.cmbi.ru.nl/servers/html/index.html).

Table 4A

| Domain 1 | | | | Domain 2 | | | Interface area, Å$^2$ | N$_{HB}$ | N$_{SB}$ |
|---|---|---|---|---|---|---|---|---|---|
| Range | $^iN_{at}$ | N$_{res}$ | | Range | $^iN_{at}$ | $^iN_{res}$ | | | |
| A2A | 59 | 21 | X | A2A | 55 | 15 | 517.8 | 5 | |
| T4L | 63 | 17 | NX | A2A | 46 | 11 | 500.1 | 8 | 2 |
| A2A | 42 | 13 | NX | T4L | 36 | 11 | 347.1 | 7 | |
| A2A | 24 | 9 | NX | T4L | 35 | 9 | 260.9 | 1 | |
| T4L | 20 | 6 | X | T4L | 22 | 7 | 189.5 | 2 | |
| A2A | 9 | 3 | X | T4L | 14 | 5 | 79.2 | | |
| A2A | 6 | 2 | NX | T4L | 8 | 3 | 68.8 | | |
| A2A | 2 | 1 | NX | T4L | 1 | 1 | 22.5 | | |

$^iN_{at}$: indicates the number of interfacing atoms in the corresponding structure
$^iN_{res}$: indicates the number of interfacing residues in the corresponding structure
N$_{HB}$: indicates the number of potential hydrogen bonds across the interface.
N$_{SB}$: indicates the number of potential salt bridges across the interface.
X: the interface is crystallographically related
NX: the interface is not crystallographically related TABLE 4-continued Table 4B

| Type | Protein residue and atoms | | | | <> | Co-factor residue and atom | | | Distance |
|---|---|---|---|---|---|---|---|---|---|
| (B-D) | 21 | GLY (23) | A | CA | <> | 454 | DRG (5) | D | CAN | D = 3.75 |
| (S-D) | 27 | TRP (29) | A | CZ3 | <> | 454 | DRG (5) | D | CAE | D = 3.53 |
| (S-D) | 44 | VAL (46) | A | CG1 | <> | 450 | DRG (1) | D | CAS | D = 3.64 |
| (S-D) | 44 | VAL (46) | A | CG1 | <> | 451 | DRG (2) | D | CAT | D = 3.74 |
| (S-D) | 48 | ALA (50) | A | CB | <> | 451 | DRG (2) | D | CAP | D = 3.72 |
| (S-D) | 51 | ILE (53) | A | CG2 | <> | 450 | DRG (1) | D | CAK | D = 3.80 |
| (S-D) | 55 | VAL (57) | A | CG1 | <> | 450 | DRG (1) | D | CAH | D = 3.50 |
| (S-D) | 55 | VAL (57) | A | CG1 | <> | 450 | DRG (1) | D | CAF | D = 3.75 |
| (B-D) | 55 | VAL (57) | A | O | <> | 452 | DRG (3) | D | CAI | D = 3.17 |
| (B-D) | 55 | VAL (57) | A | O | <> | 452 | DRG (3) | D | CAH | D = 2.86 |
| (S-D) | 56 | LEU (58) | A | CG | <> | 450 | DRG (1) | D | CAH | D = 3.67 |
| (S-D) | 56 | LEU (58) | A | CD1 | <> | 450 | DRG (1) | D | CAH | D = 3.49 |
| (S-D) | 56 | LEU (58) | A | CD2 | <> | 452 | DRG (3) | D | CAI | D = 3.71 |
| (S-D) | 56 | LEU (58) | A | CD1 | <> | 453 | DRG (4) | D | CAH | D = 3.65 |
| (S-D) | 60 | PHE (62) | A | CE1 | <> | 452 | DRG (3) | D | CAM | D = 3.53 |
| (S-D) | 72 | CYS (74) | A | CB | <> | 458 | SO4 (5) | E | O4 | D = 3.45 |
| (S-D) | 73 | HIS (75) | A | ND1 | <> | 458 | SO4 (5) | E | S | D = 3.77 |
| (S-D) | 73 | HIS (75) | A | CD1 | <> | 458 | SO4 (5) | E | O4 | D = 2.92 |
| (S-D) | 78 | ILE (80) | A | CD1 | <> | 452 | DRG (3) | D | CAP | D = 3.82 |
| (S-D) | 78 | ILE (80) | A | CD1 | <> | 453 | DRG (4) | D | CAT | D = 3.64 |
| (S-D) | 78 | ILE (80) | A | CD1 | <> | 453 | DRG (4) | D | CAS | D = 3.38 |
| (S-D) | 83 | LEU (85) | A | CD2 | <> | 449 | ZMA (1) | C | C22 | D = 3.84 |
| (S-D) | 83 | LEU (85) | A | CD2 | <> | 449 | ZMA (1) | C | C23 | D = 3.70 |
| (S-D) | 105 | ARG (107) | A | CG | <> | 457 | SO4 (3) | E | O3 | D = 3.40 |
| (S-D) | 105 | ARG (107) | A | CD | <> | 457 | SO4 (3) | E | O3 | D = 3.35 |
| (S-D) | 127 | TRP (129) | A | CD2 | <> | 451 | DRG (2) | D | CAK | D = 3.75 |
| (S-D) | 127 | TRP (129) | A | CE2 | <> | 451 | DRG (2) | D | CAO | D = 3.73 |
| (S-D) | 127 | TRP (129) | A | CE2 | <> | 451 | DRG (2) | D | CAM | D = 3.84 |
| (S-D) | 127 | TRP (129) | A | CE3 | <> | 451 | DRG (2) | D | CAK | D = 3.64 |
| (S-D) | 127 | TRP (129) | A | CZ2 | <> | 451 | DRG (2) | D | CAO | D = 3.72 |
| (S-D) | 127 | TRP (129) | A | CZ2 | <> | 451 | DRG (2) | D | CAM | D = 3.65 |
| (S-D) | 127 | TRP (129) | A | CZ3 | <> | 451 | DRG (2) | D | CAM | D = 3.71 |
| (S-D) | 127 | TRP (129) | A | CH2 | <> | 451 | DRG (2) | D | CAM | D = 3.57 |
| (S-D) | 159 | PHE (168) | A | CB | <> | 449 | ZMA (1) | C | C9 | D = 3.47 |
| (S-D) | 159 | PHE (168) | A | CB | <> | 449 | ZMA (1) | C | N10 | D = 3.26 |
| (S-D) | 159 | PHE (168) | A | CB | <> | 449 | ZMA (1) | C | C11 | D = 3.43 |
| (S-D) | 159 | PHE (168) | A | CB | <> | 449 | ZMA (1) | C | N13 | D = 3.75 |
| (S-D) | 159 | PHE (168) | A | CG | <> | 449 | ZMA (1) | C | N10 | D = 3.74 |
| (S-D) | 159 | PHE (168) | A | CG | <> | 449 | ZMA (1) | C | C11 | D = 3.37 |
| (S-D) | 159 | PHE (168) | A | CG | <> | 449 | ZMA (1) | C | N12 | D = 3.50 |
| (S-D) | 159 | PHE (168) | A | CG | <> | 449 | ZMA (1) | C | N13 | D = 3.62 |
| (S-D) | 159 | PHE (168) | A | CD1 | <> | 449 | ZMA (1) | C | N12 | D = 3.69 |
| (S-D) | 159 | PHE (168) | A | CD2 | <> | 449 | ZMA (1) | C | C11 | D = 3.51 |
| (S-D) | 159 | PHE (168) | A | CD2 | <> | 449 | ZMA (1) | C | N12 | D = 3.70 |
| (S-D) | 159 | PHE (168) | A | CD2 | <> | 449 | ZMA (1) | C | N13 | D = 3.26 |
| (S-D) | 159 | PHE (168) | A | CD2 | <> | 449 | ZMA (1) | C | C14 | D = 3.23 |
| (S-D) | 159 | PHE (168) | A | CD2 | <> | 449 | ZMA (1) | C | N16 | D = 3.43 |
| (S-D) | 159 | PHE (168) | A | CD2 | <> | 449 | ZMA (1) | C | C18 | D = 3.67 |
| (S-D) | 159 | PHE (168) | A | CE2 | <> | 449 | ZMA (1) | C | C14 | D = 3.47 |
| (S-D) | 159 | PHE (168) | A | CE2 | <> | 449 | ZMA (1) | C | N16 | D = 3.23 |
| (S-D) | 159 | PHE (168) | A | CE2 | <> | 449 | ZMA (1) | C | N17 | D = 3.46 |
| (S-D) | 159 | PHE (168) | A | CE2 | <> | 449 | ZMA (1) | C | C18 | D = 3.57 |
| (S-D) | 159 | PHE (168) | A | CZ | <> | 449 | ZMA (1) | C | C18 | D = 3.67 |
| (S-D) | 159 | PHE (168) | A | CZ | <> | 449 | ZMA (1) | C | N19 | D = 3.68 |
| (S-D) | 159 | PHE (168) | A | CZ | <> | 449 | ZMA (1) | C | C20 | D = 3.76 |
| (S-D) | 168 | MET (177) | A | CE | <> | 449 | ZMA (1) | C | C21 | D = 3.56 |
| (S-D) | 168 | MET (177) | A | CE | <> | 449 | ZMA (1) | C | C24 | D = 3.38 |
| (S-D) | 168 | MET (177) | A | CE | <> | 449 | ZMA (1) | C | O25 | D = 3.00 |
| (S-D) | 200 | ARG (222) | A | NH2 | <> | 455 | SO4 (1) | E | S | D = 3.31 |
| (S-D) | 200 | ARG (222) | A | NH2 | <> | 455 | SO4 (1) | E | O3 | D = 2.83 |
| (S-D) | 200 | ARG (222) | A | NH2 | <> | 455 | SO4 (1) | E | O4 | D = 2.72 |
| (S-D) | 224 | TRP (246) | A | CZ3 | <> | 449 | ZMA (1) | C | C22 | D = 3.72 |
| (S-D) | 224 | TRP (246) | A | CZ3 | <> | 449 | ZMA (1) | C | C23 | D = 3.40 |
| (S-D) | 227 | LEU (249) | A | CG | <> | 449 | ZMA (1) | C | C21 | D = 3.84 |
| (S-D) | 227 | LEU (249) | A | CD2 | <> | 449 | ZMA (1) | C | C20 | D = 3.51 |
| (S-D) | 227 | LEU (249) | A | CD2 | <> | 449 | ZMA (1) | C | C21 | D = 3.47 |
| (S-D) | 227 | LEU (249) | A | CD2 | <> | 449 | ZMA (1) | C | C22 | D = 3.76 |
| (S-D) | 228 | HIS (250) | A | CE1 | <> | 449 | ZMA (1) | C | C24 | D = 3.40 |
| (S-D) | 231 | ASN (253) | A | OD1 | <> | 449 | ZMA (1) | C | N15 | D = 3.01 |
| (S-D) | 231 | ASN (253) | A | ND2 | <> | 449 | ZMA (1) | C | N17 | D = 3.59 |
| (S-D) | 231 | ASN (253) | A | ND2 | <> | 449 | ZMA (1) | C | O25 | D = 3.30 |
| (S-D) | 242 | HIS (264) | A | CE1 | <> | 449 | ZMA (1) | C | C5 | D = 3.35 |
| (S-D) | 245 | LEU (267) | A | CD2 | <> | 449 | ZMA (1) | C | C5 | D = 3.82 |
| (S-D) | 248 | MET (270) | A | CG | <> | 449 | ZMA (1) | C | C6 | D = 3.06 |
| (S-D) | 248 | MET (270) | A | CG | <> | 449 | ZMA (1) | C | C8 | D = 3.83 |
| (S-D) | 248 | MET (270) | A | SD | <> | 449 | ZMA (1) | C | C6 | D = 3.93 |

TABLE 4-continued

| | | | | | | | | | | |
|---|---|---|---|---|---|---|---|---|---|---|
| (S-D) | 248 | MET (270) | A | CE | <> | 449 | ZMA (1) | C | N15 | D = 3.65 |
| (S-D) | 264 | PHE (286) | A | CD1 | <> | 454 | DRG (5) | D | CAQ | D = 3.81 |
| (S-D) | 274 | ARG (296) | A | NE | <> | 456 | SO4 (2) | E | O3 | D = 2.99 |
| (S-D) | 274 | ARG (296) | A | NH2 | <> | 456 | SO4 (2) | E | S | D = 3.88 |
| (S-D) | 274 | ARG (296) | A | NH2 | <> | 456 | SO4 (2) | E | O4 | D = 3.14 |
| (S-D) | 275 | GLN (297) | A | NE2 | <> | 456 | SO4 (2) | E | O1 | D = 2.96 |
| (S-D) | 277 | PHE (299) | A | CB | <> | 454 | DRG (5) | D | OAB | D = 2.94 |
| (S-D) | 278 | ARG (300) | A | NH2 | <> | 456 | SO4 (2) | E | S | D = 3.63 |
| (S-D) | 278 | ARG (300) | A | NH2 | <> | 456 | SO4 (2) | E | O3 | D = 2.72 |
| (B-D) | 301 | ARG (1014) | A | CA | <> | 462 | SO4 (9) | E | O2 | D = 3.44 |
| (B-D) | 301 | ARG (1014) | A | C | <> | 462 | SO4 (9) | E | O2 | D = 3.03 |
| (B-D) | 302 | LEU (1015) | A | N | <> | 462 | SO4 (9) | E | S | D = 3.34 |
| (B-D) | 302 | LEU (1015) | A | N | <> | 462 | SO4 (9) | E | O2 | D = 1.92 |
| (B-D) | 302 | LEU (1015) | A | CA | <> | 462 | SO4 (9) | E | S | D = 3.99 |
| (B-D) | 302 | LEU (1015) | A | CA | <> | 462 | SO4 (9) | E | O2 | D = 2.61 |
| (B-D) | 302 | LEU (1015) | A | C | <> | 462 | SO4 (9) | E | O2 | D = 2.99 |
| (S-D) | 302 | LEU (1015) | A | CB | <> | 462 | SO4 (9) | E | S | D = 3.91 |
| (S-D) | 302 | LEU (1015) | A | CB | <> | 462 | SO4 (9) | E | O2 | D = 2.88 |
| (B-D) | 303 | LYS (1016) | A | N | <> | 462 | SO4 (9) | E | S | D = 3.82 |
| (B-D) | 303 | LYS (1016) | A | N | <> | 462 | SO4 (9) | E | O2 | D = 2.73 |
| (S-D) | 303 | LYS (1016) | A | CG | <> | 462 | SO4 (9) | E | S | D = 4.03 |
| (S-D) | 363 | ARG (1076) | A | NH1 | <> | 461 | SO4 (8) | E | S | D = 3.12 |
| (S-D) | 363 | ARG (1076) | A | NH1 | <> | 461 | SO4 (8) | E | O2 | D = 3.15 |
| (S-D) | 363 | ARG (1076) | A | NH1 | <> | 461 | SO4 (8) | E | O3 | D = 2.89 |
| (S-D) | 363 | ARG (1076) | A | NH1 | <> | 461 | SO4 (8) | E | O4 | D = 2.88 |
| (S-D) | 367 | ARG (1080) | A | NH1 | <> | 461 | SO4 (8) | E | O4 | D = 3.15 |
| (S-D) | 367 | ARG (1080) | A | NH2 | <> | 461 | SO4 (8) | E | S | D = 3.92 |
| (S-D) | 367 | ARG (1080) | A | NH2 | <> | 461 | SO4 (8) | E | O2 | D = 3.24 |
| (B-D) | 401 | PHE (1114) | A | CA | <> | 460 | SO4 (7) | E | S | D = 3.98 |
| (B-D) | 401 | PHE (1114) | A | CA | <> | 460 | SO4 (7) | E | O1 | D = 3.29 |
| (B-D) | 401 | PHE (1114) | A | C | <> | 460 | SO4 (7) | E | O4 | D = 3.39 |
| (S-D) | 401 | PHE (1114) | A | CB | <> | 460 | SO4 (7) | E | O1 | D = 3.43 |
| (S-D) | 401 | PHE (1114) | A | CD2 | <> | 460 | SO4 (7) | E | O1 | D = 3.21 |
| (B-D) | 402 | THR (1115) | A | N | <> | 460 | SO4 (7) | E | O4 | D = 3.06 |
| (B-D) | 403 | ASN (1116) | A | N | <> | 460 | SO4 (7) | E | S | D = 3.83 |
| (B-D) | 403 | ASN (1116) | A | N | <> | 460 | SO4 (7) | E | O4 | D = 2.69 |
| (S-D) | 403 | ASN (1116) | A | CB | <> | 460 | SO4 (7) | E | S | D = 3.91 |
| (S-D) | 403 | ASN (1116) | A | CB | <> | 460 | SO4 (7) | E | O3 | D = 3.35 |
| (S-D) | 403 | ASN (1116) | A | CB | <> | 460 | SO4 (7) | E | O4 | D = 3.34 |
| (S-D) | 419 | ASN (1132) | A | ND2 | <> | 460 | SO4 (7) | E | O3 | D = 2.86 |
| (B-D) | 429 | THR (1142) | A | CA | <> | 459 | SO4 (6) | E | S | D = 4.03 |
| (B-D) | 429 | THR (1142) | A | CA | <> | 459 | SO4 (6) | E | O2 | D = 3.24 |
| (B-D) | 429 | THR (1142) | A | C | <> | 459 | SO4 (6) | E | O2 | D = 3.00 |
| (S-D) | 429 | THR (1142) | A | CB | <> | 459 | SO4 (6) | E | S | D = 3.97 |
| (B-D) | 430 | PRO (1143) | A | N | <> | 459 | SO4 (6) | E | O2 | D = 3.13 |
| (S-D) | 430 | PRO (1143) | A | CD | <> | 459 | SO4 (6) | E | O2 | D = 3.44 |
| (B-D) | 431 | ASN (1144) | A | N | <> | 459 | SO4 (6) | E | O2 | D = 2.73 |
| (B-D) | 431 | ASN (1144) | A | CA | <> | 459 | SO4 (6) | E | O2 | D = 3.38 |
| (S-D) | 431 | ASN (1144) | A | CB | <> | 459 | SO4 (6) | E | S | D = 3.74 |
| (S-D) | 431 | ASN (1144) | A | CB | <> | 459 | SO4 (6) | E | O2 | D = 3.22 |
| (S-D) | 431 | ASN (1144) | A | CB | <> | 459 | SO4 (6) | E | O3 | D = 3.26 |
| (S-D) | 431 | ASN (1144) | A | ND2 | <> | 459 | SO4 (6) | E | S | D = 3.93 |
| (S-D) | 431 | ASN (1144) | A | ND2 | <> | 459 | SO4 (6) | E | O3 | D = 2.88 |
| (S-D) | 444 | THR (1157) | A | CB | <> | 455 | SO4 (1) | E | S | D = 4.05 |
| (S-D) | 444 | THR (1157) | A | CB | <> | 455 | SO4 (1) | E | O3 | D = 3.36 |
| (B-D) | 445 | TRP (1158) | A | N | <> | 455 | SO4 (1) | E | S | D = 3.81 |
| (B-D) | 445 | TRP (1158) | A | N | <> | 455 | SO4 (1) | E | O3 | D = 2.87 |
| (S-D) | 445 | TRP (1158) | A | CD1 | <> | 455 | SO4 (1) | E | S | D = 3.64 |
| (S-D) | 445 | TRP (1158) | A | CD1 | <> | 455 | SO4 (1) | E | O1 | D = 3.39 |
| (S-D) | 445 | TRP (1158) | A | CD1 | <> | 455 | SO4 (1) | E | O4 | D = 3.16 |

Type: Indicator of the type of contact.
B stands for residue backbone;
S for residue side chain;
C for carbohydrate or sugar;
W for water,
D for ligand, drug, or ion.
DNA, RNA, and amino acids count as residues in this option.
A period is used for atoms that do not fall in any of the previously mentioned categories.

TABLE 5

Programs for structure superpositioning and RMSD calculations

| Name | Description | Author | Year |
|---|---|---|---|
| C-BOP | Coordinate-Based Organization of Proteins | E. Sandelin | 2005 |
| CAALIGN | Cα Align | T. J. Oldfield | 2007 |
| CBA | Consistency Based Alignment | J. Ebert | 2006 |
| CE/CE-MC | Combinatorial Extension - Monte Carlo | I. Shindyalov | 2000 |
| CLEMAPS | Conformation-based alphabet alignments | W-M. Zheng | 2007 |
| CTSS | Protein Structure Alignment Using Local Geometrical Features | T. Can | 2004 |
| CURVE | NA | D. Zhi | 2006 |
| DaliLite | Distance Matrix Alignment | L. Holm | 1993 |
| DEJAVU | NA | GJ. Kleywegt | 1997 |
| EXPRESSO | Fast Multiple Structural Alignment using T-Coffee and Sap | C. Notredame et al. | 2007 |
| FAST | FAST Alignment and Search Tool | J. Zhu | 2004 |
| FATCAT | Flexible Structure AlignmenT by Chaining Aligned Fragment Pairs Allowing Twists | Y. Ye & A. Godzik | 2003 |
| FLASH | Fast aLignment Algorithm for finding Structural Homology of proteins | E. S. C. Shih & M-J Hwang | 2003 |
| FlexProt | Flexible Alignment of Protein Structures | M. Shatsky & H. Wolfson | 2002 |
| GANGSTA | Genetic Algorithm for Nonsequential and Gapped STructural Alignment | B. Kolbeck et al. | 2006 |
| KENOBI/K2 | NA | Z. Weng | 2000 |
| LGA | Local-Global Alignment | A. Zemla | 2003 |
| LOCK | Hierarchical protein structure superposition | AP. Singh | 1997 |
| LOCK 2 | Improvements over LOCK | J. Shapiro | 2003 |
| LOVOALIGN | Low Order Value Optimization methods for Structural Alignment | Andreani et al. | 2006 |
| MALECON | NA | S. Wodak | 2004 |
| MAMMOTH | MAtching Molecular Models Obtained from Theory | AR. Ortiz | 2002 |
| MAMMOTH-mult | MAMMOTH-based multiple structure alignment | D. Lupyan | 2005 |
| MASS | Multiple Alignment by Secondary Structure | O. Dror & H. Wolfson | 2003 |
| MatAlign | Protein Structure Comparison by Matrix Alignment | Z. Aung & K. L. Tan | 2006 |
| Matchprot | Comparison of protein structures by growing neighborhood alignments | S. Bhattacharya et al. | 2007 |
| Matras | MArkovian TRAnsition of protein Structure | K. Nishikawa | 2000 |
| Matt | Multiple Alignment with Translations and Twists | M. Menke | 2008 |
| MolCom | NA | S. D. O'Hearn | 2003 |
| MultiProt | Multiple Alignment of Protein Structures | M. Shatsky & H. Wolfson | 2004 |
| MUSTANG | MUltiple STructural AligNment AlGorithm | A. S. Konagurthu et al. | 2005 |
| POSA | Partial Order Structure Alignment | Y. Ye & A. Godzik | 2005 |
| PRIDE | PRobaility of IDEntity | S. Pongor | 2002 |
| PrISM | Protein Informatics Systems for Modeling | B. Honig | 2000 |
| ProFit | Protein least-squares Fitting | ACR. Martin | 1996 |
| Protein3Dfit | NA | D. Schomburg | 1994 |
| PyMOL | "super" command does sequence-independent 3D alignment | W. L. DeLano | 2007 |
| RAPIDO | Rapid Alignment of Protein structures In the presence of Domain mOvements | R. Mosca & T. R. Schneider | 2008 |
| SARF2 | Spatial ARrangements of Backbone Fragments | N. Alexandrov | 1996 |
| SCALI | Structural Core ALIgnment of proteins | C. Bystroff | 2004 |
| SHEBA | Structural Homology by Environment-Based Alignment | B. Lee | 2000 |
| SSAP | Sequential Structure Alignment Program | C. Orengo & W. Taylor | 1989 |
| SSGS | Secondary Structure Guided Superimposition | G. Wainreb et al. | 2006 |
| SSM | Secondary Structure Matching | E. Krissinel | 2003 |
| STAMP | STructural Alignment of Multiple Proteins | R. Russell & G. Barton | 1992 |
| STRAP | STRucture based Alignment Program | C. Gille | 2006 |
| TALI | Torsion Angle ALIgnment | X. Mioa | 2006 |
| TetraDA | Tetrahedral Decomposition Alignment | J. Roach | 2005 |
| TM-align | TM-score based protein structure alignment | Y. Zhang & J. Skolnick | 2005 |
| TopMatch | Protein structure alignment and visualization of structural similarities | M. Sippl & M. Wiederstein | 2008 |
| TOPOFIT | Alignment as a superimposition of common volumes at a topomax point | VA. Ilyin | 2004 |
| UCSF Chimera | see MatchMaker tool and "matchmaker" command | E. Meng et al. | 2006 |
| URMS | Unit-vector RMSD | K. Kedem | 2003 |
| VAST | Vector Alignment Search Tool | S. Bryant | 1996 |
| Vorolign | Fast structure alignment using Voronoi contacts | F. Birzele et al. | 2007 |
| YAKUSA | Internal Co-ordinates and BLAST type algorithm | M. Carpentier et al. | 2005 |

TABLE 6

HUMAN A2A ADENOSINE STRUCTURE.PDB FILE
(Table 6: discloses SEQ ID NOS 20-27, respectively, in order of appearance.)

```
Appendix I
HEADER    MEMBRANE PROTEIN              24-SEP-08    3EML
TITLE     THE 2.6 A CRYSTAL STRUCTURE OF A HUMAN A2A ADENOSINE
TITLE    2 RECEPTOR BOUND TO ZM241385.
COMPND    MOL_ID: 1;
COMPND   2 MOLECULE: HUMAN ADENOSINE A2A RECEPTOR/T4 LYSOZYME CHIMERA;
COMPND   3 CHAIN: A;
COMPND   4 ENGINEERED: YES
SOURCE    MOL_ID: 1;
```

TABLE 6-continued

HUMAN A2A ADENOSINE STRUCTURE.PDB FILE
(Table 6: discloses SEQ ID NOS 20-27, respectively, in order of appearance.)

```
SOURCE     2 ORGANISM_SCIENTIFIC: HOMO SAPIENS, ENTEROBACTERIA PHAGE T4,
SOURCE     3 HOMO SAPIENS;
SOURCE     4 EXPRESSION_SYSTEM: SPODOPTERA FRUGIPERDA;
SOURCE     5 EXPRESSION_SYSTEM_VECTOR_TYPE: PLASMID;
SOURCE     6 EXPRESSION_SYSTEM_PLASMID: PBAC5B
KEYWDS       ADENOSINE, CAFFEINE, GPCR, MEMBRANE PROTEIN, RECEPTOR, LCP,
KEYWDS     2 MESOPHASE
EXPDTA       X-RAY DIFFRACTION
AUTHOR       V.-P. JAAKOLA, M. T. GRIFFITH, M. A. HANSON, V. CHEREZOV, E. Y. T. CHIEN,
AUTHOR     2 J. R. LANE, A. P. IJZERMAN, R. C. STEVENS
JRNL         AUTH       V.-P. JAAKOLA, M. T. GRIFFITH, M. A. HANSON, V. CHEREZOV,
JRNL         AUTH   2   E. Y. T. CHIEN, J. R. LANE, A. P. IJZERMAN, R. C. STEVENS
JRNL         TITL       THE 2.6 A CRYSTAL STRUCTURE OF A HUMAN A2A
JRNL         TITL   2   ADENOSINE RECEPTOR BOUND TO AN ANTAGONIST.
JRNL         REF        TO BE PUBLISHED
JRNL         REFN
REMARK   1
REMARK   2
REMARK   2 RESOLUTION. 2.60 ANGSTROMS.
REMARK   3
REMARK   3 REFINEMENT.
REMARK   3   PROGRAM     : PHENIX (PHENIX.REFINE)
REMARK   3   AUTHORS     : PAUL ADAMS, PAVEL AFONINE, VICENT CHEN, IAN
REMARK   3               : DAVIS, KRESHNA GOPAL, RALF GROSSE-
REMARK   3               : KUNSTLEVE, LI-WEI HUNG, ROBERT IMMORMINO,
REMARK   3               : TOM IOERGER, AIRLIE MCCOY, ERIK MCKEE, NIGEL
REMARK   3               : MORIARTY, REETAL PAI, RANDY READ, JANE
REMARK   3               : RICHARDSON, DAVID RICHARDSON, TOD ROMO, JIM
REMARK   3               : SACCHETTINI, NICHOLAS SAUTER, JACOB SMITH,
REMARK   3               : LAURENT STORONI, TOM TERWILLIGER, PETER
REMARK   3               : ZWART
REMARK   3
REMARK   3      REFINEMENT TARGET: ML
REMARK   3
REMARK   3    DATA USED IN REFINEMENT.
REMARK   3      RESOLUTION RANGE HIGH       (ANGSTROMS) : 2.60
REMARK   3      RESOLUTION RANGE LOW        (ANGSTROMS) : 19.42
REMARK   3      MIN(FOBS/SIGMA_FOBS)                    : 2.000
REMARK   3      COMPLETENESS FOR RANGE            (%)   : 97.1
REMARK   3      NUMBER OF REFLECTIONS                   : 18461
REMARK   3
REMARK   3    FIT TO DATA USED IN REFINEMENT.
REMARK   3      R VALUE          (WORKING + TEST SET) : 0.198
REMARK   3      R VALUE              (WORKING SET)    : 0.196
REMARK   3      FREE R VALUE                          : 0.231
REMARK   3      FREE R VALUE TEST SET SIZE    (%)     : 5.080
REMARK   3      FREE R VALUE TEST SET COUNT           : 937
REMARK   3
REMARK   3    FIT TO DATA USED IN REFINEMENT (IN BINS).
REMARK   3     BIN  RESOLUTION RANGE  COMPL.  NWORK  NFREE  RWORK   RFREE
REMARK   3      1   19.4211 -  4.9500   0.98   2595    127   0.1809  0.2180
REMARK   3      2    4.9500 -  3.9397   0.98   2526    120   0.1738  0.2070
REMARK   3      3    3.9397 -  3.4448   0.98   2533    142   0.1794  0.1950
REMARK   3      4    3.4448 -  3.1313   0.97   2477    145   0.2166  0.2329
REMARK   3      5    3.1313 -  2.9077   0.98   2510    143   0.2323  0.3127
REMARK   3      6    2.9077 -  2.7367   0.96   2472    120   0.2490  0.2816
REMARK   3      7    2.7367 -  2.6000   0.94   2411    140   0.2623  0.3054
REMARK   3
REMARK   3    BULK SOLVENT MODELLING.
REMARK   3      METHOD USED      : FLAT BULK SOLVENT MODEL
REMARK   3      SOLVENT RADIUS   : 1.11
REMARK   3      SHRINKAGE RADIUS : 0.90
REMARK   3      K_SOL            : 0.33
REMARK   3      B_SOL            : 78.49
REMARK   3
REMARK   3    ERROR ESTIMATES.
REMARK   3      COORDINATE ERROR (MAXIMUM-LIKELIHOOD BASED)      : 0.430
REMARK   3      PHASE ERROR (DEGREES, MAXIMUM-LIKELIHOOD BASED)  : NULL
REMARK   3
REMARK   3    B VALUES.
REMARK   3      FROM WILSON PLOT          (A**2) : NULL
REMARK   3      MEAN B VALUE      (OVERALL, A**2) : NULL
REMARK   3      OVERALL ANISOTROPIC B VALUE.
REMARK   3       B11 (A**2) : NULL
REMARK   3       B22 (A**2) : NULL
REMARK   3       B33 (A**2) : NULL
REMARK   3       B12 (A**2) : NULL
```

TABLE 6-continued

HUMAN A2A ADENOSINE STRUCTURE.PDB FILE
(Table 6: discloses SEQ ID NOS 20-27, respectively, in order of appearance.)

```
REMARK   3        B13 (A**2) : NULL
REMARK   3        B23 (A**2) : NULL
REMARK   3
REMARK   3     TWINNING INFORMATION.
REMARK   3      FRACTION: NULL
REMARK   3      OPERATOR: NULL
REMARK   3
REMARK   3     DEVIATIONS FROM IDEAL VALUES.
REMARK   3                   RMSD          COUNT
REMARK   3      BOND       : NULL         NULL
REMARK   3      ANGLE      : NULL         NULL
REMARK   3      CHIRALITY  : NULL         NULL
REMARK   3      PLANARITY  : NULL         NULL
REMARK   3      DIHEDRAL   : NULL         NULL
REMARK   3
REMARK   3     TLS DETAILS
REMARK   3      NUMBER OF TLS GROUPS   : NULL
REMARK   3
REMARK   3     NCS DETAILS
REMARK   3      NUMBER OF NCS GROUPS : NULL
REMARK   3
REMARK   3     OTHER REFINEMENT REMARKS: NULL
REMARK   4
REMARK   4 3EML COMPLIES WITH FORMAT V. 3.1, 01-AUG-2007
REMARK 100
REMARK 100 THIS ENTRY HAS BEEN PROCESSED BY RCSB.
REMARK 100 THE RCSB ID CODE IS RCSB049511.
REMARK 200
REMARK 200 EXPERIMENTAL DETAILS
REMARK 200   EXPERIMENT TYPE                : X-RAY DIFFRACTION
REMARK 200   DATE OF DATA COLLECTION        : 28-JUN-2008
REMARK 200   TEMPERATURE        (KELVIN)   : NULL
REMARK 200   PH                             : 6.5
REMARK 200   NUMBER OF CRYSTALS USED        : 13
REMARK 200
REMARK 200   SYNCHROTRON         (Y/N) : Y
REMARK 200   RADIATION SOURCE            : APS
REMARK 200   BEAMLINE                    : 23-ID-B
REMARK 200   X-RAY GENERATOR MODEL       : NULL
REMARK 200   MONOCHROMATIC OR LAUE  (M/L) : M
REMARK 200   WAVELENGTH OR RANGE      (A) : 1.0332
REMARK 200   MONOCHROMATOR               : DOUBLE CRYSTAL
REMARK 200   OPTICS                      : MIRRORS
REMARK 200
REMARK 200   DETECTOR TYPE               : CCD
REMARK 200   DETECTOR MANUFACTURER       : MARMOSAIC 300 MM CCD
REMARK 200   INTENSITY-INTEGRATION SOFTWARE  : XDS
REMARK 200   DATA SCALING SOFTWARE       : XSCALE
REMARK 200
REMARK 200   NUMBER OF UNIQUE REFLECTIONS   : 18465
REMARK 200   RESOLUTION RANGE HIGH      (A) : 2.600
REMARK 200   RESOLUTION RANGE LOW       (A) : 20.000
REMARK 200   REJECTION CRITERIA  (SIGMA(I)) : 2.000
REMARK 200
REMARK 200 OVERALL.
REMARK 200   COMPLETENESS FOR RANGE     (%) : 96.8
REMARK 200   DATA REDUNDANCY                : 3.400
REMARK 200   R MERGE                    (I) : NULL
REMARK 200   R SYM                      (I) : 9.80000
REMARK 200   <I/SIGMA(I)> FOR THE DATA SET  : 7.3500
REMARK 200
REMARK 200 IN THE HIGHEST RESOLUTION SHELL.
REMARK 200   HIGHEST RESOLUTION SHELL, RANGE HIGH  (A) : 2.60
REMARK 200   HIGHEST RESOLUTION SHELL, RANGE LOW   (A) : 2.80
REMARK 200   COMPLETENESS FOR SHELL     (%) : 93.9
REMARK 200   DATA REDUNDANCY IN SHELL       : 2.30
REMARK 200   R MERGE FOR SHELL          (I) : NULL
REMARK 200   R SYM FOR SHELL            (I) : 39.80000
REMARK 200   <I/SIGMA(I)> FOR SHELL         : 2.300
REMARK 200
REMARK 200 DIFFRACTION PROTOCOL: SINGLE WAVELENGTH
REMARK 200 METHOD USED TO DETERMINE THE STRUCTURE: MOLECULAR REPLACEMENT
REMARK 200 SOFTWARE USED: PHASER
REMARK 200 STARTING MODEL: PDB ENTRY 2RH1
REMARK 200
REMARK 200 REMARK: NULL
REMARK 280
```

TABLE 6-continued

HUMAN A2A ADENOSINE STRUCTURE.PDB FILE
(Table 6: discloses SEQ ID NOS 20-27, respectively, in order of appearance.)

```
REMARK  280 CRYSTAL
REMARK  280 SOLVENT CONTENT, VS     (%): 56.79
REMARK  280 MATTHEWS COEFFICIENT, VM (ANGSTROMS**3/DA): 2.85
REMARK  280
REMARK  280 CRYSTALLIZATION CONDITIONS: PEG400 30% V/V, LISO4 185 MM,
REMARK  280    NACITRATE 100 MM, PH 6.5, LIPIDIC MESOPHASE, TEMPERATURE 293 K
REMARK  290
REMARK  290 CRYSTALLOGRAPHIC SYMMETRY
REMARK  290 SYMMETRY OPERATORS FOR SPACE GROUP: P 1 21 1
REMARK  290
REMARK  290              SYMOP  SYMMETRY
REMARK  290             NNNMMM  OPERATOR
REMARK  290              1555   X, Y, Z
REMARK  290              2555   -X, 1//2 + Y, -Z
REMARK  290
REMARK  290    WHERE     NNN -> OPERATOR NUMBER
REMARK  290              MMM -> TRANSLATION VECTOR
REMARK  290
REMARK  290 CRYSTALLOGRAPHIC SYMMETRY TRANSFORMATIONS
REMARK  290 THE FOLLOWING TRANSFORMATIONS OPERATE ON THE ATOM/HETATM
REMARK  290 RECORDS IN THIS ENTRY TO PRODUCE CRYSTALLOGRAPHICALLY
REMARK  290 RELATED MOLECULES.
REMARK  290      SMTRY1   1   1.000000  0.000000   0.000000        0.00000
REMARK  290      SMTRY2   1   0.000000  1.000000   0.000000        0.00000
REMARK  290      SMTRY3   1   0.000000  0.000000   1.000000        0.00000
REMARK  290      SMTRY1   2  -1.000000  0.000000   0.000000        0.00000
REMARK  290      SMTRY2   2   0.000000  1.000000   0.000000       38.46600
REMARK  290      SMTRY3   2   0.000000  0.000000  -1.000000        0.00000
REMARK  290
REMARK  290 REMARK: NULL
REMARK  300
REMARK  300 BIOMOLECULE: 1
REMARK  300 SEE REMARK 350 FOR THE AUTHOR PROVIDED AND/OR PROGRAM
REMARK  300 GENERATED ASSEMBLY INFORMATION FOR THE STRUCTURE IN
REMARK  300 THIS ENTRY. THE REMARK MAY ALSO PROVIDE INFORMATION ON
REMARK  300 BURIED SURFACE AREA.
REMARK  350
REMARK  350 COORDINATES FOR A COMPLETE MULTIMER REPRESENTING THE KNOWN
REMARK  350 BIOLOGICALLY SIGNIFICANT OLIGOMERIZATION STATE OF THE
REMARK  350 MOLECULE CAN BE GENERATED BY APPLYING BIOMT TRANSFORMATIONS
REMARK  350 GIVEN BELOW. BOTH NON-CRYSTALLOGRAPHIC AND
REMARK  350 CRYSTALLOGRAPHIC OPERATIONS ARE GIVEN.
REMARK  350
REMARK  350 BIOMOLECULE: 1
REMARK  350 AUTHOR DETERMINED BIOLOGICAL UNIT: MONOMERIC
REMARK  350 SOFTWARE DETERMINED QUATERNARY STRUCTURE: MONOMERIC
REMARK  350 SOFTWARE USED: PISA
REMARK  350 APPLY THE FOLLOWING TO CHAINS: A
REMARK  350      BIOMT1   1   1.000000  0.000000   0.000000        0.00000
REMARK  350      BIOMT2   1   0.000000  1.000000   0.000000        0.00000
REMARK  350      BIOMT3   1   0.000000  0.000000   1.000000        0.00000
REMARK  465
REMARK  465 MISSING RESIDUES
REMARK  465 THE FOLLOWING RESIDUES WERE NOT LOCATED IN THE
REMARK  465 EXPERIMENT. (M = MODEL NUMBER; RES = RESIDUE NAME; C = CHAIN
REMARK  465 IDENTIFIER; SSEQ = SEQUENCE NUMBER; I = INSERTION CODE.)
REMARK  465
REMARK  465     M   RES   C   SSEQI
REMARK  465         ASP   A    -14
REMARK  465         TYR   A    -13
REMARK  465         LYS   A    -12
REMARK  465         ASP   A    -11
REMARK  465         ASP   A    -10
REMARK  465         ASP   A     -9
REMARK  465         ASP   A     -8
REMARK  465         ALA   A     -7
REMARK  465         MET   A     -6
REMARK  465         GLY   A     -5
REMARK  465         GLN   A     -4
REMARK  465         PRO   A     -3
REMARK  465         VAL   A     -2
REMARK  465         GLY   A     -1
REMARK  465         ALA   A      0
REMARK  465         PRO   A      1
REMARK  465         PRO   A      2
REMARK  465         PRO   A    149
REMARK  465         LYS   A    150
```

TABLE 6-continued

HUMAN A2A ADENOSINE STRUCTURE.PDB FILE
(Table 6: discloses SEQ ID NOS 20-27, respectively, in order of appearance.)

```
REMARK 465         GLU  A    151
REMARK 465         GLY  A    152
REMARK 465         LYS  A    153
REMARK 465         ASN  A    154
REMARK 465         HIS  A    155
REMARK 465         GLN  A    311
REMARK 465         GLU  A    312
REMARK 465         PRO  A    313
REMARK 465         PHE  A    314
REMARK 465         LYS  A    315
REMARK 465         ALA  A    316
REMARK 465         HIS  A    317
REMARK 465         HIS  A    318
REMARK 465         HIS  A    319
REMARK 465         HIS  A    320
REMARK 465         HIS  A    321
REMARK 465         HIS  A    322
REMARK 465         HIS  A    323
REMARK 465         HIS  A    324
REMARK 465         HIS  A    325
REMARK 465         HIS  A    326
REMARK 500
REMARK 500 GEOMETRY AND STEREOCHEMISTRY
REMARK 500 SUBTOPIC: CLOSE CONTACTS IN SAME ASYMMETRIC UNIT
REMARK 500
REMARK 500 THE FOLLOWING ATOMS ARE IN CLOSE CONTACT.
REMARK 500
REMARK 500    ATM1  RES  C   SSEQI ATM2  RES  C   SSEQI
REMARK 500    O     HOH  A    564   O    HOH  A    570            2.10
REMARK 500
REMARK 500 REMARK: NULL
REMARK 500
REMARK 500 GEOMETRY AND STEREOCHEMISTRY
REMARK 500 SUBTOPIC: CLOSE CONTACTS
REMARK 500
REMARK 500 THE FOLLOWING ATOMS THAT ARE RELATED BY CRYSTALLOGRAPHIC
REMARK 500 SYMMETRY ARE IN CLOSE CONTACT. AN ATOM LOCATED WITHIN 0.15
REMARK 500 ANGSTROMS OF A SYMMETRY RELATED ATOM IS ASSUMED TO BE ON A
REMARK 500 SPECIAL POSITION AND IS, THEREFORE, LISTED IN REMARK 375
REMARK 500 INSTEAD OF REMARK 500. ATOMS WITH NON-BLANK ALTERNATE
REMARK 500 LOCATION INDICATORS ARE NOT INCLUDED IN THE CALCULATIONS.
REMARK 500
REMARK 500 DISTANCE CUTOFF:
REMARK 500 2.2 ANGSTROMS FOR CONTACTS NOT INVOLVING HYDROGEN ATOMS
REMARK 500 1.6 ANGSTROMS FOR CONTACTS INVOLVING HYDROGEN ATOMS
REMARK 500
REMARK 500    ATM1  RES  C   SSEQI   ATM2 RES  C   SSEQI   SSYMOP DISTANCE
REMARK 500    O     PHE  A    257    NH2  ARG  A    309    2556    1.99
REMARK 500    O     PHE  A    257    NH1  ARG  A    309    2556    2.11
REMARK 500
REMARK 500 REMARK: NULL
REMARK 500
REMARK 500 GEOMETRY AND STEREOCHEMISTRY
REMARK 500 SUBTOPIC: TORSION ANGLES
REMARK 500
REMARK 500 TORSION ANGLES OUTSIDE THE EXPECTED RAMACHANDRAN REGIONS:
REMARK 500 (M = MODEL NUMBER; RES = RESIDUE NAME; C = CHAIN IDENTIFIER;
REMARK 500 SSEQ = SEQUENCE NUMBER; I = INSERTION CODE).
REMARK 500
REMARK 500 STANDARD TABLE:
REMARK 500 FORMAT: (10X, I3, 1X, A3, 1X, A1, I4, A1, 4X, F7.2, 3X, F7.2)
REMARK 500
REMARK 500 EXPECTED VALUES: GJ KLEYWEGT AND TA JONES (1996). PHI/PSI-
REMARK 500 CHOLOGY: RAMACHANDRAN REVISITED. STRUCTURE 4, 1395-1400
REMARK 500
REMARK 500   M RES CSSEQI           PSI       PHI
REMARK 500     PRO  A1037          32.24    -78.04
REMARK 500     VAL  A 229         -22.06   -141.91
REMARK 500
REMARK 500 REMARK: NULL
REMARK 800
REMARK 800 SITE
REMARK 800 SITE_IDENTIFIER: AC1
REMARK 800 SITE_DESCRIPTION: BINDING SITE FOR RESIDUE ZMA A 401
REMARK 800 SITE_IDENTIFIER: AC2
REMARK 800 SITE_DESCRIPTION: BINDING SITE FOR RESIDUE STE A 402
REMARK 800 SITE_IDENTIFIER: AC3
```

TABLE 6-continued

HUMAN A2A ADENOSINE STRUCTURE.PDB FILE
(Table 6: discloses SEQ ID NOS 20-27, respectively, in order of appearance.)

```
REMARK  800 SITE_DESCRIPTION: BINDING SITE FOR RESIDUE STE A 403
REMARK  800 SITE_IDENTIFIER: AC4
REMARK  800 SITE_DESCRIPTION: BINDING SITE FOR RESIDUE STE A 404
REMARK  800 SITE_IDENTIFIER: AC5
REMARK  800 SITE_DESCRIPTION: BINDING SITE FOR RESIDUE STE A 405
REMARK  800 SITE_IDENTIFIER: AC6
REMARK  800 SITE_DESCRIPTION: BINDING SITE FOR RESIDUE STE A 406
REMARK  800 SITE_IDENTIFIER: AC7
REMARK  800 SITE_DESCRIPTION: BINDING SITE FOR RESIDUE SO4 A 407
REMARK  800 SITE_IDENTIFIER: AC8
REMARK  800 SITE_DESCRIPTION: BINDING SITE FOR RESIDUE SO4 A 408
REMARK  800 SITE_IDENTIFIER: AC9
REMARK  800 SITE_DESCRIPTION: BINDING SITE FOR RESIDUE SO4 A 409
REMARK  800 SITE_IDENTIFIER: BC1
REMARK  800 SITE_DESCRIPTION: BINDING SITE FOR RESIDUE SO4 A 410
REMARK  800 SITE_IDENTIFIER: BC2
REMARK  800 SITE_DESCRIPTION: BINDING SITE FOR RESIDUE SO4 A 411
REMARK  800 SITE_IDENTIFIER: BC3
REMARK  800 SITE_DESCRIPTION: BINDING SITE FOR RESIDUE SO4 A 412
REMARK  800 SITE_IDENTIFIER: BC4
REMARK  800 SITE_DESCRIPTION: BINDING SITE FOR RESIDUE SO4 A 413
DBREF   3EML  A     2     208  UNP    P29274  AA2AR_HUMAN    2    208
DBREF   3EML  A  1002    1161  UNP    P00720  LYS_BPT4       2    161
DBREF   3EML  A   222     316  UNP    P29274  AA2AR_HUMAN  222    316
SEQADV  3EML  ASP  A   -14  UNP  P29274              EXPRESSION TAG
SEQADV  3EML  TYR  A   -13  UNP  P29274              EXPRESSION TAG
SEQADV  3EML  LYS  A   -12  UNP  P29274              EXPRESSION TAG
SEQADV  3EML  ASP  A   -11  UNP  P29274              EXPRESSION TAG
SEQADV  3EML  ASP  A   -10  UNP  P29274              EXPRESSION TAG
SEQADV  3EML  ASP  A    -9  UNP  P29274              EXPRESSION TAG
SEQADV  3EML  ASP  A    -8  UNP  P29274              EXPRESSION TAG
SEQADV  3EML  ALA  A    -7  UNP  P29274              EXPRESSION TAG
SEQADV  3EML  MET  A    -6  UNP  P29274              EXPRESSION TAG
SEQADV  3EML  GLY  A    -5  UNP  P29274              EXPRESSION TAG
SEQADV  3EML  GLN  A    -4  UNP  P29274              EXPRESSION TAG
SEQADV  3EML  PRO  A    -3  UNP  P29274              EXPRESSION TAG
SEQADV  3EML  VAL  A    -2  UNP  P29274              EXPRESSION TAG
SEQADV  3EML  GLY  A    -1  UNP  P29274              EXPRESSION TAG
SEQADV  3EML  ALA  A     0  UNP  P29274              EXPRESSION TAG
SEQADV  3EML  PRO  A     1  UNP  P29274              EXPRESSION TAG
SEQADV  3EML  HIS  A   317  UNP  P29274              EXPRESSION TAG
SEQADV  3EML  HIS  A   318  UNP  P29274              EXPRESSION TAG
SEQADV  3EML  HIS  A   319  UNP  P29274              EXPRESSION TAG
SEQADV  3EML  HIS  A   320  UNP  P29274              EXPRESSION TAG
SEQADV  3EML  HIS  A   321  UNP  P29274              EXPRESSION TAG
SEQADV  3EML  HIS  A   322  UNP  P29274              EXPRESSION TAG
SEQADV  3EML  HIS  A   323  UNP  P29274              EXPRESSION TAG
SEQADV  3EML  HIS  A   324  UNP  P29274              EXPRESSION TAG
SEQADV  3EML  HIS  A   325  UNP  P29274              EXPRESSION TAG
SEQADV  3EML  HIS  A   326  UNP  P29274              EXPRESSION TAG
SEQRES    1  A  488  ASP  TYR  LYS  ASP  ASP  ASP  ASP  ALA  MET  GLY  GLN  PRO  VAL
SEQRES    2  A  488  GLY  ALA  PRO  PRO  ILE  MET  GLY  SER  SER  VAL  TYR  ILE  THR
SEQRES    3  A  488  VAL  GLU  LEU  ALA  ILE  ALA  VAL  LEU  ALA  ILE  LEU  GLY  ASN
SEQRES    4  A  488  VAL  LEU  VAL  CYS  TRP  ALA  VAL  TRP  LEU  ASN  SER  ASN  LEU
SEQRES    5  A  488  GLN  ASN  VAL  THR  ASN  TYR  PHE  VAL  VAL  SER  LEU  ALA  ALA
SEQRES    6  A  488  ALA  ASP  ILE  ALA  VAL  GLY  VAL  LEU  ALA  ILE  PRO  PHE  ALA
SEQRES    7  A  488  ILE  THR  ILE  SER  THR  GLY  PHE  CYS  ALA  ALA  CYS  HIS  GLY
SEQRES    8  A  488  CYS  LEU  PHE  ILE  ALA  CYS  PHE  VAL  LEU  VAL  LEU  THR  GLN
SEQRES    9  A  488  SER  SER  ILE  PHE  SER  LEU  LEU  ALA  ILE  ALA  ILE  ASP  ARG
SEQRES   10  A  488  TYR  ILE  ALA  ILE  ARG  ILE  PRO  LEU  ARG  TYR  ASN  GLY  LEU
SEQRES   11  A  488  VAL  THR  GLY  THR  ARG  ALA  LYS  GLY  ILE  ILE  ALA  ILE  CYS
SEQRES   12  A  488  TRP  VAL  LEU  SER  PHE  ALA  ILE  GLY  LEU  THR  PRO  MET  LEU
SEQRES   13  A  488  GLY  TRP  ASN  ASN  CYS  GLY  GLN  PRO  LYS  GLU  GLY  LYS  ASN
SEQRES   14  A  488  HIS  SER  GLN  GLY  CYS  GLY  GLU  GLY  GLN  VAL  ALA  CYS  LEU
SEQRES   15  A  488  PHE  GLU  ASP  VAL  VAL  PRO  MET  ASN  TYR  MET  VAL  TYR  PHE
SEQRES   16  A  488  ASN  PHE  PHE  ALA  CYS  VAL  LEU  VAL  PRO  LEU  LEU  LEU  MET
SEQRES   17  A  488  LEU  GLY  VAL  TYR  LEU  ARG  ILE  PHE  LEU  ALA  ALA  ARG  ARG
SEQRES   18  A  488  GLN  LEU  ASN  ILE  PHE  GLU  MET  LEU  ARG  ILE  ASP  GLU  GLY
SEQRES   19  A  488  LEU  ARG  LEU  LYS  ILE  TYR  LYS  ASP  THR  GLU  GLY  TYR  TYR
SEQRES   20  A  488  THR  ILE  GLY  ILE  GLY  HIS  LEU  LEU  THR  LYS  SER  PRO  SER
SEQRES   21  A  488  LEU  ASN  ALA  ALA  LYS  SER  GLU  LEU  ASP  LYS  ALA  ILE  GLY
SEQRES   22  A  488  ARG  ASN  THR  ASN  GLY  VAL  ILE  THR  LYS  ASP  GLU  ALA  GLU
SEQRES   23  A  488  LYS  LEU  PHE  ASN  GLN  ASP  VAL  ASP  ALA  ALA  VAL  ARG  GLY
SEQRES   24  A  488  ILE  LEU  ARG  ASN  ALA  LYS  LEU  LYS  PRO  VAL  TYR  ASP  SER
SEQRES   25  A  488  LEU  ASP  ALA  VAL  ARG  ARG  ALA  ALA  LEU  ILE  ASN  MET  VAL
SEQRES   26  A  488  PHE  GLN  MET  GLY  GLU  THR  GLY  VAL  ALA  GLY  PHE  THR  ASN
SEQRES   27  A  488  SER  LEU  ARG  MET  LEU  GLN  GLN  LYS  ARG  TRP  ASP  GLU  ALA
```

TABLE 6-continued

HUMAN A2A ADENOSINE STRUCTURE.PDB FILE
(Table 6: discloses SEQ ID NOS 20-27, respectively, in order of appearance.)

| | | | | | | | | | | | | | | | | | | | |
|---|---|---|---|---|---|---|---|---|---|---|---|---|---|---|---|---|---|---|---|
| SEQRES | 28 | A | 488 | ALA | VAL | ASN | LEU | ALA | LYS | SER | ARG | TRP | TYR | ASN | GLN | THR | | | |
| SEQRES | 29 | A | 488 | PRO | ASN | ARG | ALA | LYS | ARG | VAL | ILE | THR | THR | PHE | ARG | THR | | | |
| SEQRES | 30 | A | 488 | GLY | THR | TRP | ASP | ALA | TYR | ARG | SER | THR | LEU | GLN | LYS | GLU | | | |
| SEQRES | 31 | A | 488 | VAL | HIS | ALA | ALA | LYS | SER | LEU | ALA | ILE | ILE | VAL | GLY | LEU | | | |
| SEQRES | 32 | A | 488 | PHE | ALA | LEU | CYS | TRP | LEU | PRO | LEU | HIS | ILE | ILE | ASN | CYS | | | |
| SEQRES | 33 | A | 488 | PHE | THR | PHE | PHE | CYS | PRO | ASP | CYS | SER | HIS | ALA | PRO | LEU | | | |
| SEQRES | 34 | A | 488 | TRP | LEU | MET | TYR | LEU | ALA | ILE | VAL | LEU | SER | HIS | THR | ASN | | | |
| SEQRES | 35 | A | 488 | SER | VAL | VAL | ASN | PRO | PHE | ILE | TYR | ALA | TYR | ARG | ILE | ARG | | | |
| SEQRES | 36 | A | 488 | GLU | PHE | ARG | GLN | THR | PHE | ARG | LYS | ILE | ILE | ARG | SER | HIS | | | |
| SEQRES | 37 | A | 488 | VAL | LEU | ARG | GLN | GLN | GLU | PRO | PHE | LYS | ALA | HIS | HIS | HIS | | | |
| SEQRES | 38 | A | 488 | HIS | HIS | HIS | HIS | HIS | HIS | | | | | | | | | | |
| HET | ZMA | A | 401 | | 25 | | | | | | | | | | | | | | |
| HET | STE | A | 402 | | 20 | | | | | | | | | | | | | | |
| HET | STE | A | 403 | | 20 | | | | | | | | | | | | | | |
| HET | STE | A | 404 | | 20 | | | | | | | | | | | | | | |
| HET | STE | A | 405 | | 20 | | | | | | | | | | | | | | |
| HET | STE | A | 406 | | 20 | | | | | | | | | | | | | | |
| HET | SO4 | A | 407 | | 5 | | | | | | | | | | | | | | |
| HET | SO4 | A | 408 | | 5 | | | | | | | | | | | | | | |
| HET | SO4 | A | 409 | | 5 | | | | | | | | | | | | | | |
| HET | SO4 | A | 410 | | 5 | | | | | | | | | | | | | | |
| HET | SO4 | A | 411 | | 5 | | | | | | | | | | | | | | |
| HET | SO4 | A | 412 | | 5 | | | | | | | | | | | | | | |
| HET | SO4 | A | 413 | | 5 | | | | | | | | | | | | | | |
| HETNAM | | ZMA | 4-{2-[(7-AMINO-2-FURAN-2-YL[1,2,4]TRIAZOLO[1,5-A][1,3, | | | | | | | | | | | | | | | | |
| HETNAM | 2 | ZMA | 5]TRIAZIN-5-YL)AMINO]ETHYL}PHENOL | | | | | | | | | | | | | | | | |
| HETNAM | | STE STEARIC ACID | | | | | | | | | | | | | | | | | |
| HETNAM | | SO4 SULFATE ION | | | | | | | | | | | | | | | | | |
| FORMUL | 2 | ZMA | C16H15N7O2 | | | | | | | | | | | | | | | | |
| FORMUL | 3 | STE | 5(C18H36O2) | | | | | | | | | | | | | | | | |
| FORMUL | 8 | SO4 | 7(O4S2−) | | | | | | | | | | | | | | | | |
| FORMUL | 5 | HOH | *77(H2O) | | | | | | | | | | | | | | | | |
| HELIX | 1 | 1 | SER | A | 6 | ASN | A | 34 | 1 | | | | | | | | | | 29 |
| HELIX | 2 | 2 | SER | A | 35 | GLN | A | 38 | 5 | | | | | | | | | | 4 |
| HELIX | 3 | 3 | VAL | A | 40 | LEU | A | 58 | 1 | | | | | | | | | | 19 |
| HELIX | 4 | 4 | LEU | A | 58 | SER | A | 67 | 1 | | | | | | | | | | 10 |
| HELIX | 5 | 5 | ALA | A | 73 | ARG | A | 107 | 1 | | | | | | | | | | 35 |
| HELIX | 6 | 6 | ILE | A | 108 | TYR | A | 112 | 5 | | | | | | | | | | 5 |
| HELIX | 7 | 7 | THR | A | 117 | LEU | A | 137 | 1 | | | | | | | | | | 21 |
| HELIX | 8 | 8 | THR | A | 138 | GLY | A | 142 | 5 | | | | | | | | | | 5 |
| HELIX | 9 | 9 | LEU | A | 167 | VAL | A | 172 | 1 | | | | | | | | | | 6 |
| HELIX | 10 | 10 | PRO | A | 173 | TYR | A | 179 | 1 | | | | | | | | | | 7 |
| HELIX | 11 | 11 | ASN | A | 181 | VAL | A | 186 | 1 | | | | | | | | | | 6 |
| HELIX | 12 | 12 | VAL | A | 186 | ARG | A | 205 | 1 | | | | | | | | | | 20 |
| HELIX | 13 | 13 | ASN | A | 1002 | GLU | A | 1011 | 1 | | | | | | | | | | 10 |
| HELIX | 14 | 14 | SER | A | 1038 | GLY | A | 1051 | 1 | | | | | | | | | | 14 |
| HELIX | 15 | 15 | THR | A | 1059 | ASN | A | 1081 | 1 | | | | | | | | | | 23 |
| HELIX | 16 | 16 | LYS | A | 1083 | LEU | A | 1091 | 1 | | | | | | | | | | 9 |
| HELIX | 17 | 17 | ASP | A | 1092 | GLY | A | 1107 | 1 | | | | | | | | | | 16 |
| HELIX | 18 | 18 | GLY | A | 1107 | ALA | A | 1112 | 1 | | | | | | | | | | 6 |
| HELIX | 19 | 19 | PHE | A | 1114 | GLN | A | 1123 | 1 | | | | | | | | | | 10 |
| HELIX | 20 | 20 | ARG | A | 1125 | ALA | A | 1134 | 1 | | | | | | | | | | 10 |
| HELIX | 21 | 21 | SER | A | 1136 | THR | A | 1142 | 1 | | | | | | | | | | 7 |
| HELIX | 22 | 22 | THR | A | 1142 | GLY | A | 1156 | 1 | | | | | | | | | | 15 |
| HELIX | 23 | 23 | TRP | A | 1158 | CYS | A | 259 | 1 | | | | | | | | | | 42 |
| HELIX | 24 | 24 | PRO | A | 266 | ILE | A | 292 | 1 | | | | | | | | | | 27 |
| HELIX | 25 | 25 | ILE | A | 292 | HIS | A | 306 | 1 | | | | | | | | | | 15 |
| SHEET | 1 | A | 2 | CYS | A | 71 | ALA | A | 72 | 0 | | | | | | | | | |
| SHEET | 2 | A | 2 | VAL | A | 164 | ALA | A | 165 | −1 | O | VAL | A | 164 | N | ALA | A | 72 | |
| SHEET | 1 | B | 3 | ARG | A1014 | LYS | A1019 | 0 | | | | | | | | | | | |
| SHEET | 2 | B | 3 | TYR | A1025 | GLY | A1028 | −1 | O | THR | A1026 | N | TYR | A1018 | | | | | |
| SHEET | 3 | B | 3 | HIS | A1031 | THR | A1034 | −1 | O | LEU | A1033 | N | TYR | A1025 | | | | | |
| SSBOND | 1 | CYS | A | 71 | CYS | A | 159 | | | | | 1555 | 1555 | 2.03 | | | | | |
| SSBOND | 2 | CYS | A | 74 | CYS | A | 146 | | | | | 1555 | 1555 | 2.03 | | | | | |
| SSBOND | 3 | CYS | A | 77 | CYS | A | 166 | | | | | 1555 | 1555 | 2.03 | | | | | |
| SSBOND | 4 | CYS | A | 259 | CYS | A | 262 | | | | | 1555 | 1555 | 2.03 | | | | | |
| SITE | 1 | AC1 | 11 | PHE | A | 168 | GLU | A | 169 | MET | A | 177 | TRP | A | 246 | | | | |
| SITE | 2 | AC1 | 11 | LEU | A | 249 | HIS | A | 250 | ASN | A | 253 | HIS | A | 264 | | | | |
| SITE | 3 | AC1 | 11 | MET | A | 270 | HOH | A | 519 | HOH | A | 559 | | | | | | | |
| SITE | 1 | AC2 | 4 | VAL | A | 57 | LEU | A | 58 | STE | A | 405 | HOH | A | 571 | | | | |
| SITE | 1 | AC3 | 1 | VAL | A | 46 | | | | | | | | | | | | | |
| SITE | 1 | AC4 | 3 | VAL | A | 57 | PHE | A | 62 | STE | A | 405 | | | | | | | |
| SITE | 1 | AC5 | 4 | GLY | A | 76 | ILE | A | 80 | STE | A | 402 | STE | A | 404 | | | | |
| SITE | 1 | AC6 | 3 | GLY | A | 23 | PHE | A | 299 | HOH | A | 562 | | | | | | | |
| SITE | 1 | AC7 | 5 | ARG | A | 222 | HOH | A | 506 | ASN | A1040 | THR | A1157 | | | | | | |
| SITE | 2 | AC7 | 5 | TRP | A1158 | | | | | | | | | | | | | | |
| SITE | 1 | AC8 | 3 | ARG | A | 296 | GLN | A | 297 | ARG | A | 300 | | | | | | | |

TABLE 6-continued

HUMAN A2A ADENOSINE STRUCTURE.PDB FILE
(Table 6: discloses SEQ ID NOS 20-27, respectively, in order of appearance.)

| | | | | | | | | | | | | |
|---|---|---|---|---|---|---|---|---|---|---|---|---|
| SITE | 1 | AC9 | 5 | ARG | A | 107 | ALA | A | 203 | ARG | A | 206 | HOH | A | 530 |
| SITE | 2 | AC9 | 5 | ARG | A1008 | | | | | | | |
| SITE | 1 | BC1 | 3 | ALA | A | 73 | CYS | A | 74 | HIS | A | 75 | | | |
| SITE | 1 | BC2 | 4 | THR | A1142 | | PRO | A1143 | | ASN | A1144 | | ARG | A1145 | |
| SITE | 1 | BC3 | 5 | PHE | A1114 | | THR | A1115 | | ASN | A1116 | | SER | A1117 | |
| SITE | 2 | BC3 | 5 | ASN | A1132 | | | | | | | |
| SITE | 1 | BC4 | 3 | HOH | A | 547 | ARG | A1076 | | ARG | A1080 | | | | |
| CRYST1 | 47.736 | | 76.932 | | 86.553 | | 90.00 | 101.32 | 90.00 | P 1 21 1 | | 2 |
| ORIGX1 | 1.000000 | | 0.000000 | | 0.000000 | | | 0.00000 | | | | |
| ORIGX2 | 0.000000 | | 1.000000 | | 0.000000 | | | 0.00000 | | | | |
| ORIGX3 | 0.000000 | | 0.000000 | | 1.000000 | | | 0.00000 | | | | |
| SCALE1 | 0.020949 | | 0.000000 | | 0.004192 | | | 0.00000 | | | | |
| SCALE2 | 0.000000 | | 0.012998 | | 0.000000 | | | 0.00000 | | | | |
| SCALE3 | 0.000000 | | 0.000000 | | 0.011783 | | | 0.00000 | | | | |
| ATOM | 1 | N | ILE | A | 3 | −30.582 | −20.763 | 57.829 | 1.00 | 115.32 | N |
| ATOM | 2 | CA | ILE | A | 3 | −29.314 | −20.499 | 57.159 | 1.00 | 116.02 | C |
| ATOM | 3 | C | ILE | A | 3 | −28.389 | −19.651 | 58.027 | 1.00 | 113.18 | C |
| ATOM | 4 | O | ILE | A | 3 | −28.839 | −18.751 | 58.736 | 1.00 | 111.11 | O |
| ATOM | 5 | CB | ILE | A | 3 | −29.525 | −19.801 | 55.801 | 1.00 | 122.12 | C |
| ATOM | 6 | CG1 | ILE | A | 3 | −30.369 | −18.537 | 55.975 | 1.00 | 127.32 | C |
| ATOM | 7 | CG2 | ILE | A | 3 | −30.184 | −20.750 | 54.811 | 1.00 | 119.11 | C |
| ATOM | 8 | CD1 | ILE | A | 3 | −30.644 | −17.800 | 54.681 | 1.00 | 127.54 | C |
| ATOM | 9 | N | MET | A | 4 | −27.095 | −19.947 | 57.964 | 1.00 | 114.09 | N |
| ATOM | 10 | CA | MET | A | 4 | −26.097 | −19.237 | 58.759 | 1.00 | 113.72 | C |
| ATOM | 11 | C | MET | A | 4 | −25.637 | −17.954 | 58.075 | 1.00 | 111.28 | C |
| ATOM | 12 | O | MET | A | 4 | −25.728 | −17.821 | 56.855 | 1.00 | 111.47 | O |
| ATOM | 13 | CB | MET | A | 4 | −24.892 | −20.141 | 59.029 | 1.00 | 114.23 | C |
| ATOM | 14 | CG | MET | A | 4 | −25.165 | −21.271 | 60.008 | 1.00 | 114.99 | C |
| ATOM | 15 | SD | MET | A | 4 | −25.242 | −20.704 | 61.718 | 1.00 | 176.57 | S |
| ATOM | 16 | CE | MET | A | 4 | −23.568 | −20.112 | 61.954 | 1.00 | 112.29 | C |
| ATOM | 17 | N | GLY | A | 5 | −25.139 | −17.013 | 58.871 | 1.00 | 108.62 | N |
| ATOM | 18 | CA | GLY | A | 5 | −24.637 | −15.757 | 58.348 | 1.00 | 113.00 | C |
| ATOM | 19 | C | GLY | A | 5 | −23.270 | −15.907 | 57.707 | 1.00 | 120.15 | C |
| ATOM | 20 | O | GLY | A | 5 | −22.728 | −14.954 | 57.146 | 1.00 | 122.73 | O |
| ATOM | 21 | N | SER | A | 6 | −22.710 | −17.110 | 57.793 | 1.00 | 121.00 | N |
| ATOM | 22 | CA | SER | A | 6 | −21.405 | −17.393 | 57.205 | 1.00 | 112.22 | C |
| ATOM | 23 | C | SER | A | 6 | −21.516 | −18.439 | 56.100 | 1.00 | 107.46 | C |
| ATOM | 24 | O | SER | A | 6 | −20.735 | −18.431 | 55.148 | 1.00 | 111.51 | O |
| ATOM | 25 | CB | SER | A | 6 | −20.418 | −17.860 | 58.278 | 1.00 | 103.57 | C |
| ATOM | 26 | OG | SER | A | 6 | −20.834 | −19.083 | 58.859 | 1.00 | 100.88 | O |
| ATOM | 27 | N | SER | A | 7 | −22.488 | −19.337 | 56.231 | 1.00 | 98.15 | N |
| ATOM | 28 | CA | SER | A | 7 | −22.729 | −20.351 | 55.212 | 1.00 | 92.91 | C |
| ATOM | 29 | C | SER | A | 7 | −23.089 | −19.692 | 53.886 | 1.00 | 87.40 | C |
| ATOM | 30 | O | SER | A | 7 | −22.962 | −20.298 | 52.823 | 1.00 | 82.75 | O |
| ATOM | 31 | CB | SER | A | 7 | −23.837 | −21.309 | 55.651 | 1.00 | 90.04 | C |
| ATOM | 32 | OG | SER | A | 7 | −23.450 | −22.041 | 56.801 | 1.00 | 91.37 | O |
| ATOM | 33 | N | VAL | A | 8 | −23.544 | −18.445 | 53.961 | 1.00 | 83.91 | N |
| ATOM | 34 | CA | VAL | A | 8 | −23.812 | −17.654 | 52.768 | 1.00 | 78.45 | C |
| ATOM | 35 | C | VAL | A | 8 | −22.500 | −17.121 | 52.210 | 1.00 | 68.73 | C |
| ATOM | 36 | O | VAL | A | 8 | −22.235 | −17.220 | 51.011 | 1.00 | 65.71 | O |
| ATOM | 37 | CB | VAL | A | 8 | −24.746 | −16.469 | 53.071 | 1.00 | 79.64 | C |
| ATOM | 38 | CG1 | VAL | A | 8 | −24.852 | −15.553 | 51.860 | 1.00 | 79.22 | C |
| ATOM | 39 | CG2 | VAL | A | 8 | −26.119 | −16.970 | 53.493 | 1.00 | 77.55 | C |
| ATOM | 40 | N | TYR | A | 9 | −21.682 | −16.557 | 53.094 | 1.00 | 60.14 | N |
| ATOM | 41 | CA | TYR | A | 9 | −20.372 | −16.044 | 52.715 | 1.00 | 61.91 | C |
| ATOM | 42 | C | TYR | A | 9 | −19.552 | −17.109 | 51.995 | 1.00 | 67.50 | C |
| ATOM | 43 | O | TYR | A | 9 | −18.914 | −16.835 | 50.978 | 1.00 | 68.07 | O |
| ATOM | 44 | CB | TYR | A | 9 | −19.614 | −15.550 | 53.949 | 1.00 | 58.73 | C |
| ATOM | 45 | CG | TYR | A | 9 | −18.146 | −15.294 | 53.694 | 1.00 | 65.03 | C |
| ATOM | 46 | CD1 | TYR | A | 9 | −17.730 | −14.172 | 52.991 | 1.00 | 68.96 | C |
| ATOM | 47 | CD2 | TYR | A | 9 | −17.176 | −16.176 | 54.155 | 1.00 | 66.40 | C |
| ATOM | 48 | CE1 | TYR | A | 9 | −16.391 | −13.933 | 52.755 | 1.00 | 74.95 | C |
| ATOM | 49 | CE2 | TYR | A | 9 | −15.832 | −15.947 | 53.922 | 1.00 | 65.41 | C |
| ATOM | 50 | CZ | TYR | A | 9 | −15.444 | −14.824 | 53.221 | 1.00 | 75.65 | C |
| ATOM | 51 | OH | TYR | A | 9 | −14.108 | −14.589 | 52.985 | 1.00 | 74.15 | O |
| ATOM | 52 | N | ILE | A | 10 | −19.579 | −18.326 | 52.528 | 1.00 | 68.00 | N |
| ATOM | 53 | CA | ILE | A | 10 | −18.808 | −19.429 | 51.967 | 1.00 | 63.94 | C |
| ATOM | 54 | C | ILE | A | 10 | −19.372 | −19.907 | 50.630 | 1.00 | 62.03 | C |
| ATOM | 55 | O | ILE | A | 10 | −18.619 | −20.204 | 49.703 | 1.00 | 68.15 | O |
| ATOM | 56 | CB | ILE | A | 10 | −18.730 | −20.611 | 52.951 | 1.00 | 63.47 | C |
| ATOM | 57 | CG1 | ILE | A | 10 | −18.048 | −20.170 | 54.247 | 1.00 | 66.00 | C |
| ATOM | 58 | CG2 | ILE | A | 10 | −17.982 | −21.777 | 52.327 | 1.00 | 65.06 | C |
| ATOM | 59 | CD1 | ILE | A | 10 | −17.993 | −21.246 | 55.307 | 1.00 | 68.16 | C |
| ATOM | 60 | N | THR | A | 11 | −20.695 | −19.981 | 50.531 | 1.00 | 61.30 | N |
| ATOM | 61 | CA | THR | A | 11 | −21.340 | −20.389 | 49.288 | 1.00 | 64.10 | C |
| ATOM | 62 | C | THR | A | 11 | −21.057 | −19.383 | 48.177 | 1.00 | 61.59 | C |
| ATOM | 63 | O | THR | A | 11 | −20.570 | −19.745 | 47.106 | 1.00 | 54.04 | O |

TABLE 6-continued

HUMAN A2A ADENOSINE STRUCTURE.PDB FILE
(Table 6: discloses SEQ ID NOS 20-27, respectively, in order of appearance.)

| ATOM | 64 | CB | THR | A | 11 | −22.866 | −20.533 | 49.455 | 1.00 | 67.09 | C |
|---|---|---|---|---|---|---|---|---|---|---|---|
| ATOM | 65 | OG1 | THR | A | 11 | −23.150 | −21.507 | 50.467 | 1.00 | 68.70 | O |
| ATOM | 66 | CG2 | THR | A | 11 | −23.507 | −20.970 | 48.144 | 1.00 | 53.89 | C |
| ATOM | 67 | N | VAL | A | 12 | −21.365 | −18.118 | 48.448 | 1.00 | 65.58 | N |
| ATOM | 68 | CA | VAL | A | 12 | −21.164 | −17.040 | 47.486 | 1.00 | 63.91 | C |
| ATOM | 69 | C | VAL | A | 12 | −19.753 | −17.054 | 46.912 | 1.00 | 67.80 | C |
| ATOM | 70 | O | VAL | A | 12 | −19.562 | −16.955 | 45.700 | 1.00 | 71.79 | O |
| ATOM | 71 | CB | VAL | A | 12 | −21.421 | −15.661 | 48.130 | 1.00 | 61.21 | C |
| ATOM | 72 | CG1 | VAL | A | 12 | −20.973 | −14.544 | 47.199 | 1.00 | 53.70 | C |
| ATOM | 73 | CG2 | VAL | A | 12 | −22.891 | −15.505 | 48.488 | 1.00 | 67.26 | C |
| ATOM | 74 | N | GLU | A | 13 | −18.767 | −17.184 | 47.792 | 1.00 | 66.46 | N |
| ATOM | 75 | CA | GLU | A | 13 | −17.369 | −17.098 | 47.389 | 1.00 | 69.25 | C |
| ATOM | 76 | C | GLU | A | 13 | −16.900 | −18.343 | 46.637 | 1.00 | 68.66 | C |
| ATOM | 77 | O | GLU | A | 13 | −15.990 | −18.271 | 45.812 | 1.00 | 66.95 | O |
| ATOM | 78 | CB | GLU | A | 13 | −16.486 | −16.837 | 48.607 | 1.00 | 69.29 | C |
| ATOM | 79 | CG | GLU | A | 13 | −15.232 | −16.053 | 48.291 | 1.00 | 76.14 | C |
| ATOM | 80 | CD | GLU | A | 13 | −14.751 | −15.258 | 49.479 | 1.00 | 74.21 | C |
| ATOM | 81 | OE1 | GLU | A | 13 | −15.593 | −14.923 | 50.333 | 1.00 | 78.41 | O |
| ATOM | 82 | OE2 | GLU | A | 13 | −13.540 | −14.968 | 49.560 | 1.00 | 78.21 | O |
| ATOM | 83 | N | LEU | A | 14 | −17.522 | −19.481 | 46.926 | 1.00 | 67.94 | N |
| ATOM | 84 | CA | LEU | A | 14 | −17.253 | −20.701 | 46.174 | 1.00 | 64.86 | C |
| ATOM | 85 | C | LEU | A | 14 | −17.828 | −20.588 | 44.768 | 1.00 | 63.34 | C |
| ATOM | 86 | O | LEU | A | 14 | −17.233 | −21.069 | 43.804 | 1.00 | 67.04 | O |
| ATOM | 87 | CB | LEU | A | 14 | −17.832 | −21.923 | 46.888 | 1.00 | 66.60 | C |
| ATOM | 88 | CG | LEU | A | 14 | −16.872 | −22.686 | 47.803 | 1.00 | 68.43 | C |
| ATOM | 89 | CD1 | LEU | A | 14 | −16.114 | −21.728 | 48.695 | 1.00 | 76.17 | C |
| ATOM | 90 | CD2 | LEU | A | 14 | −17.619 | −23.715 | 48.635 | 1.00 | 66.48 | C |
| ATOM | 91 | N | ALA | A | 15 | −18.990 | −19.951 | 44.659 | 1.00 | 54.24 | N |
| ATOM | 92 | CA | ALA | A | 15 | −19.610 | −19.714 | 43.362 | 1.00 | 54.16 | C |
| ATOM | 93 | C | ALA | A | 15 | −18.732 | −18.786 | 42.533 | 1.00 | 53.26 | C |
| ATOM | 94 | O | ALA | A | 15 | −18.501 | −19.023 | 41.347 | 1.00 | 57.84 | O |
| ATOM | 95 | CB | ALA | A | 15 | −20.998 | −19.124 | 43.536 | 1.00 | 56.06 | C |
| ATOM | 96 | N | ILE | A | 16 | −18.242 | −17.729 | 43.171 | 1.00 | 52.04 | N |
| ATOM | 97 | CA | ILE | A | 16 | −17.339 | −16.787 | 42.524 | 1.00 | 53.28 | C |
| ATOM | 98 | C | ILE | A | 16 | −16.086 | −17.491 | 42.013 | 1.00 | 53.42 | C |
| ATOM | 99 | O | ILE | A | 16 | −15.595 | −17.193 | 40.923 | 1.00 | 53.32 | O |
| ATOM | 100 | CB | ILE | A | 16 | −16.935 | −15.656 | 43.486 | 1.00 | 51.70 | C |
| ATOM | 101 | CG1 | ILE | A | 16 | −18.140 | −14.761 | 43.782 | 1.00 | 56.16 | C |
| ATOM | 102 | CG2 | ILE | A | 16 | −15.785 | −14.844 | 42.907 | 1.00 | 48.96 | C |
| ATOM | 103 | CD1 | ILE | A | 16 | −17.926 | −13.800 | 44.932 | 1.00 | 61.38 | C |
| ATOM | 104 | N | ALA | A | 17 | −15.577 | −18.431 | 42.803 | 1.00 | 48.45 | N |
| ATOM | 105 | CA | ALA | A | 17 | −14.378 | −19.178 | 42.438 | 1.00 | 53.75 | C |
| ATOM | 106 | C | ALA | A | 17 | −14.587 | −20.009 | 41.172 | 1.00 | 63.57 | C |
| ATOM | 107 | O | ALA | A | 17 | −13.728 | −20.041 | 40.292 | 1.00 | 69.25 | O |
| ATOM | 108 | CB | ALA | A | 17 | −13.934 | −20.068 | 43.594 | 1.00 | 49.57 | C |
| ATOM | 109 | N | VAL | A | 18 | −15.733 | −20.679 | 41.086 | 1.00 | 60.60 | N |
| ATOM | 110 | CA | VAL | A | 18 | −16.040 | −21.525 | 39.938 | 1.00 | 58.67 | C |
| ATOM | 111 | C | VAL | A | 18 | −16.102 | −20.719 | 38.642 | 1.00 | 60.19 | C |
| ATOM | 112 | O | VAL | A | 18 | −15.559 | −21.135 | 37.617 | 1.00 | 59.26 | O |
| ATOM | 113 | CB | VAL | A | 18 | −17.364 | −22.291 | 40.133 | 1.00 | 64.12 | C |
| ATOM | 114 | CG1 | VAL | A | 18 | −17.721 | −23.067 | 38.873 | 1.00 | 63.73 | C |
| ATOM | 115 | CG2 | VAL | A | 18 | −17.266 | −23.224 | 41.331 | 1.00 | 65.66 | C |
| ATOM | 116 | N | LEU | A | 19 | −16.764 | −19.566 | 38.689 | 1.00 | 56.71 | N |
| ATOM | 117 | CA | LEU | A | 19 | −16.861 | −18.700 | 37.517 | 1.00 | 58.49 | C |
| ATOM | 118 | C | LEU | A | 19 | −15.510 | −18.100 | 37.143 | 1.00 | 53.86 | C |
| ATOM | 119 | O | LEU | A | 19 | −15.165 | −18.018 | 35.964 | 1.00 | 53.92 | O |
| ATOM | 120 | CB | LEU | A | 19 | −17.892 | −17.590 | 37.734 | 1.00 | 67.30 | C |
| ATOM | 121 | CG | LEU | A | 19 | −19.324 | −17.907 | 37.298 | 1.00 | 76.63 | C |
| ATOM | 122 | CD1 | LEU | A | 19 | −19.913 | −19.038 | 38.129 | 1.00 | 79.95 | C |
| ATOM | 123 | CD2 | LEU | A | 19 | −20.196 | −16.665 | 37.381 | 1.00 | 75.91 | C |
| ATOM | 124 | N | ALA | A | 20 | −14.750 | −17.681 | 38.150 | 1.00 | 59.37 | N |
| ATOM | 125 | CA | ALA | A | 20 | −13.418 | −17.137 | 37.921 | 1.00 | 54.11 | C |
| ATOM | 126 | C | ALA | A | 20 | −12.584 | −18.117 | 37.105 | 1.00 | 54.81 | C |
| ATOM | 127 | O | ALA | A | 20 | −11.968 | −17.745 | 36.107 | 1.00 | 53.51 | O |
| ATOM | 128 | CB | ALA | A | 20 | −12.735 | −16.832 | 39.244 | 1.00 | 53.22 | C |
| ATOM | 129 | N | ILE | A | 21 | −12.580 | −19.374 | 37.534 | 1.00 | 51.11 | N |
| ATOM | 130 | CA | ILE | A | 21 | −11.829 | −20.421 | 36.850 | 1.00 | 44.22 | C |
| ATOM | 131 | C | ILE | A | 21 | −12.371 | −20.707 | 35.450 | 1.00 | 51.90 | C |
| ATOM | 132 | O | ILE | A | 21 | −11.644 | −20.606 | 34.463 | 1.00 | 62.45 | O |
| ATOM | 133 | CB | ILE | A | 21 | −11.822 | −21.726 | 37.668 | 1.00 | 51.90 | C |
| ATOM | 134 | CG1 | ILE | A | 21 | −11.099 | −21.513 | 39.000 | 1.00 | 56.33 | C |
| ATOM | 135 | CG2 | ILE | A | 21 | −11.168 | −22.847 | 36.878 | 1.00 | 52.44 | C |
| ATOM | 136 | CD1 | ILE | A | 21 | −11.218 | −22.678 | 39.961 | 1.00 | 53.18 | C |
| ATOM | 137 | N | LEU | A | 22 | −13.649 | −21.064 | 35.369 | 1.00 | 63.25 | N |
| ATOM | 138 | CA | LEU | A | 22 | −14.267 | −21.406 | 34.092 | 1.00 | 63.45 | C |
| ATOM | 139 | C | LEU | A | 22 | −14.160 | −20.273 | 33.076 | 1.00 | 59.45 | C |
| ATOM | 140 | O | LEU | A | 22 | −13.798 | −20.495 | 31.920 | 1.00 | 60.42 | O |

TABLE 6-continued

HUMAN A2A ADENOSINE STRUCTURE.PDB FILE
(Table 6: discloses SEQ ID NOS 20-27, respectively, in order of appearance.)

| ATOM | 141 | CB | LEU | A | 22 | −15.734 | −21.788 | 34.292 | 1.00 | 61.90 | C |
|---|---|---|---|---|---|---|---|---|---|---|---|
| ATOM | 142 | CG | LEU | A | 22 | −15.984 | −23.111 | 35.014 | 1.00 | 63.21 | C |
| ATOM | 143 | CD1 | LEU | A | 22 | −17.474 | −23.393 | 35.110 | 1.00 | 61.60 | C |
| ATOM | 144 | CD2 | LEU | A | 22 | −15.264 | −24.246 | 34.303 | 1.00 | 61.95 | C |
| ATOM | 145 | N | GLY | A | 23 | −14.477 | −19.060 | 33.512 | 1.00 | 49.29 | N |
| ATOM | 146 | CA | GLY | A | 23 | −14.455 | −17.910 | 32.630 | 1.00 | 41.16 | C |
| ATOM | 147 | C | GLY | A | 23 | −13.080 | −17.637 | 32.058 | 1.00 | 47.99 | C |
| ATOM | 148 | O | GLY | A | 23 | −12.926 | −17.447 | 30.853 | 1.00 | 52.04 | O |
| ATOM | 149 | N | ASN | A | 24 | −12.073 | −17.628 | 32.926 | 1.00 | 50.22 | N |
| ATOM | 150 | CA | ASN | A | 24 | −10.718 | −17.270 | 32.518 | 1.00 | 44.51 | C |
| ATOM | 151 | C | ASN | A | 24 | −9.942 | −18.401 | 31.843 | 1.00 | 50.67 | C |
| ATOM | 152 | O | ASN | A | 24 | −8.975 | −18.154 | 31.122 | 1.00 | 50.53 | O |
| ATOM | 153 | CB | ASN | A | 24 | −9.941 | −16.688 | 33.701 | 1.00 | 46.69 | C |
| ATOM | 154 | CG | ASN | A | 24 | −10.426 | −15.300 | 34.082 | 1.00 | 54.60 | C |
| ATOM | 155 | OD1 | ASN | A | 24 | −10.253 | −14.342 | 33.328 | 1.00 | 51.61 | O |
| ATOM | 156 | ND2 | ASN | A | 24 | −11.045 | −15.188 | 35.252 | 1.00 | 45.15 | N |
| ATOM | 157 | N | VAL | A | 25 | −10.363 | −19.639 | 32.076 | 1.00 | 45.08 | N |
| ATOM | 158 | CA | VAL | A | 25 | −9.825 | −20.758 | 31.316 | 1.00 | 47.66 | C |
| ATOM | 159 | C | VAL | A | 25 | −10.255 | −20.592 | 29.864 | 1.00 | 55.47 | C |
| ATOM | 160 | O | VAL | A | 25 | −9.499 | −20.884 | 28.936 | 1.00 | 60.83 | O |
| ATOM | 161 | CB | VAL | A | 25 | −10.324 | −22.116 | 31.852 | 1.00 | 47.32 | C |
| ATOM | 162 | CG1 | VAL | A | 25 | −10.178 | −23.193 | 30.789 | 1.00 | 43.42 | C |
| ATOM | 163 | CG2 | VAL | A | 25 | −9.559 | −22.507 | 33.109 | 1.00 | 38.82 | C |
| ATOM | 164 | N | LEU | A | 26 | −11.476 | −20.101 | 29.683 | 1.00 | 56.99 | N |
| ATOM | 165 | CA | LEU | A | 26 | −12.045 | −19.904 | 28.357 | 1.00 | 54.09 | C |
| ATOM | 166 | C | LEU | A | 26 | −11.273 | −18.847 | 27.570 | 1.00 | 56.51 | C |
| ATOM | 167 | O | LEU | A | 26 | −11.094 | −18.972 | 26.359 | 1.00 | 61.89 | O |
| ATOM | 168 | CB | LEU | A | 26 | −13.519 | −19.511 | 28.472 | 1.00 | 61.54 | C |
| ATOM | 169 | CG | LEU | A | 26 | −14.357 | −19.530 | 27.193 | 1.00 | 71.92 | C |
| ATOM | 170 | CD1 | LEU | A | 26 | −14.364 | −20.919 | 26.575 | 1.00 | 72.32 | C |
| ATOM | 171 | CD2 | LEU | A | 26 | −15.775 | −19.063 | 27.482 | 1.00 | 71.63 | C |
| ATOM | 172 | N | VAL | A | 27 | −10.817 | −17.807 | 28.262 | 1.00 | 57.29 | N |
| ATOM | 173 | CA | VAL | A | 27 | −10.052 | −16.742 | 27.620 | 1.00 | 48.64 | C |
| ATOM | 174 | C | VAL | A | 27 | −8.740 | −17.276 | 27.057 | 1.00 | 48.87 | C |
| ATOM | 175 | O | VAL | A | 27 | −8.377 | −16.979 | 25.919 | 1.00 | 55.75 | O |
| ATOM | 176 | CB | VAL | A | 27 | −9.759 | −15.577 | 28.592 | 1.00 | 46.54 | C |
| ATOM | 177 | CG1 | VAL | A | 27 | −8.709 | −14.647 | 28.004 | 1.00 | 43.30 | C |
| ATOM | 178 | CG2 | VAL | A | 27 | −11.035 | −14.813 | 28.912 | 1.00 | 39.25 | C |
| ATOM | 179 | N | CYS | A | 28 | −8.034 | −18.069 | 27.858 | 1.00 | 48.72 | N |
| ATOM | 180 | CA | CYS | A | 28 | −6.770 | −18.660 | 27.430 | 1.00 | 57.38 | C |
| ATOM | 181 | C | CYS | A | 28 | −6.984 | −19.673 | 26.309 | 1.00 | 59.99 | C |
| ATOM | 182 | O | CYS | A | 28 | −6.181 | −19.764 | 25.379 | 1.00 | 60.57 | O |
| ATOM | 183 | CB | CYS | A | 28 | −6.065 | −19.333 | 28.611 | 1.00 | 57.82 | C |
| ATOM | 184 | SG | CYS | A | 28 | −5.723 | −18.241 | 30.008 | 1.00 | 58.82 | S |
| ATOM | 185 | N | TRP | A | 29 | −8.071 | −20.435 | 26.411 | 1.00 | 57.26 | N |
| ATOM | 186 | CA | TRP | A | 29 | −8.408 | −21.451 | 25.419 | 1.00 | 57.95 | C |
| ATOM | 187 | C | TRP | A | 29 | −8.565 | −20.828 | 24.036 | 1.00 | 59.13 | C |
| ATOM | 188 | O | TRP | A | 29 | −8.090 | −21.373 | 23.039 | 1.00 | 56.47 | O |
| ATOM | 189 | CB | TRP | A | 29 | −9.707 | −22.157 | 25.811 | 1.00 | 62.93 | C |
| ATOM | 190 | CG | TRP | A | 29 | −9.935 | −23.460 | 25.103 | 1.00 | 61.45 | C |
| ATOM | 191 | CD1 | TRP | A | 29 | −9.324 | −23.894 | 23.962 | 1.00 | 61.41 | C |
| ATOM | 192 | CD2 | TRP | A | 29 | −10.861 | −24.488 | 25.478 | 1.00 | 61.95 | C |
| ATOM | 193 | NE1 | TRP | A | 29 | −9.801 | −25.134 | 23.612 | 1.00 | 58.38 | N |
| ATOM | 194 | CE2 | TRP | A | 29 | −10.747 | −25.520 | 24.525 | 1.00 | 59.99 | C |
| ATOM | 195 | CE3 | TRP | A | 29 | −11.771 | −24.638 | 26.528 | 1.00 | 65.86 | C |
| ATOM | 196 | CZ2 | TRP | A | 29 | −11.509 | −26.685 | 24.592 | 1.00 | 59.67 | C |
| ATOM | 197 | CZ3 | TRP | A | 29 | −12.527 | −25.796 | 26.593 | 1.00 | 61.08 | C |
| ATOM | 198 | CH2 | TRP | A | 29 | −12.390 | −26.804 | 25.630 | 1.00 | 55.39 | C |
| ATOM | 199 | N | ALA | A | 30 | −9.237 | −19.682 | 23.987 | 1.00 | 60.75 | N |
| ATOM | 200 | CA | ALA | A | 30 | −9.495 | −18.988 | 22.731 | 1.00 | 54.63 | C |
| ATOM | 201 | C | ALA | A | 30 | −8.209 | −18.494 | 22.078 | 1.00 | 53.63 | C |
| ATOM | 202 | O | ALA | A | 30 | −8.017 | −18.652 | 20.872 | 1.00 | 63.69 | O |
| ATOM | 203 | CB | ALA | A | 30 | −10.452 | −17.829 | 22.957 | 1.00 | 56.60 | C |
| ATOM | 204 | N | VAL | A | 31 | −7.334 | −17.892 | 22.876 | 1.00 | 53.18 | N |
| ATOM | 205 | CA | VAL | A | 31 | −6.073 | −17.364 | 22.364 | 1.00 | 58.61 | C |
| ATOM | 206 | C | VAL | A | 31 | −5.201 | −18.476 | 21.785 | 1.00 | 60.55 | C |
| ATOM | 207 | O | VAL | A | 31 | −4.472 | −18.267 | 20.816 | 1.00 | 65.47 | O |
| ATOM | 208 | CB | VAL | A | 31 | −5.292 | −16.606 | 23.459 | 1.00 | 61.76 | C |
| ATOM | 209 | CG1 | VAL | A | 31 | −3.897 | −16.235 | 22.968 | 1.00 | 60.52 | C |
| ATOM | 210 | CG2 | VAL | A | 31 | −6.059 | −15.364 | 23.893 | 1.00 | 53.64 | C |
| ATOM | 211 | N | TRP | A | 32 | −5.288 | −19.660 | 22.381 | 1.00 | 61.93 | N |
| ATOM | 212 | CA | TRP | A | 32 | −4.516 | −20.807 | 21.921 | 1.00 | 67.14 | C |
| ATOM | 213 | C | TRP | A | 32 | −5.058 | −21.346 | 20.596 | 1.00 | 64.28 | C |
| ATOM | 214 | O | TRP | A | 32 | −4.292 | −21.737 | 19.715 | 1.00 | 62.55 | O |
| ATOM | 215 | CB | TRP | A | 32 | −4.522 | −21.906 | 22.987 | 1.00 | 76.54 | C |
| ATOM | 216 | CG | TRP | A | 32 | −3.486 | −22.967 | 22.776 | 1.00 | 88.88 | C |
| ATOM | 217 | CD1 | TRP | A | 32 | −2.148 | −22.867 | 23.025 | 1.00 | 92.35 | C |

TABLE 6-continued

HUMAN A2A ADENOSINE STRUCTURE.PDB FILE
(Table 6: discloses SEQ ID NOS 20-27, respectively, in order of appearance.)

| ATOM | 218 | CD2 | TRP | A | 32 | −3.704 | −24.296 | 22.283 | 1.00 | 99.86 | C |
|---|---|---|---|---|---|---|---|---|---|---|---|
| ATOM | 219 | NE1 | TRP | A | 32 | −1.518 | −24.047 | 22.713 | 1.00 | 100.27 | N |
| ATOM | 220 | CE2 | TRP | A | 32 | −2.451 | −24.941 | 22.255 | 1.00 | 103.18 | C |
| ATOM | 221 | CE3 | TRP | A | 32 | −4.836 | −25.002 | 21.860 | 1.00 | 101.46 | C |
| ATOM | 222 | CZ2 | TRP | A | 32 | −2.298 | −26.257 | 21.822 | 1.00 | 104.81 | C |
| ATOM | 223 | CZ3 | TRP | A | 32 | −4.681 | −26.308 | 21.429 | 1.00 | 101.91 | C |
| ATOM | 224 | CH2 | TRP | A | 32 | −3.422 | −26.922 | 21.414 | 1.00 | 105.43 | C |
| ATOM | 225 | N | LEU | A | 33 | −6.380 | −21.355 | 20.459 | 1.00 | 60.82 | N |
| ATOM | 226 | CA | LEU | A | 33 | −7.026 | −21.875 | 19.257 | 1.00 | 64.06 | C |
| ATOM | 227 | C | LEU | A | 33 | −6.970 | −20.904 | 18.082 | 1.00 | 64.97 | C |
| ATOM | 228 | O | LEU | A | 33 | −6.647 | −21.294 | 16.960 | 1.00 | 59.60 | O |
| ATOM | 229 | CB | LEU | A | 33 | −8.486 | −22.234 | 19.544 | 1.00 | 68.79 | C |
| ATOM | 230 | CG | LEU | A | 33 | −8.760 | −23.526 | 20.312 | 1.00 | 72.17 | C |
| ATOM | 231 | CD1 | LEU | A | 33 | −10.256 | −23.783 | 20.379 | 1.00 | 73.45 | C |
| ATOM | 232 | CD2 | LEU | A | 33 | −8.044 | −24.696 | 19.658 | 1.00 | 66.75 | C |
| ATOM | 233 | N | ASN | A | 34 | −7.293 | −19.642 | 18.343 | 1.00 | 66.04 | N |
| ATOM | 234 | CA | ASN | A | 34 | −7.421 | −18.654 | 17.278 | 1.00 | 63.50 | C |
| ATOM | 235 | C | ASN | A | 34 | −6.139 | −17.866 | 17.023 | 1.00 | 73.73 | C |
| ATOM | 236 | O | ASN | A | 34 | −5.572 | −17.268 | 17.937 | 1.00 | 74.49 | O |
| ATOM | 237 | CB | ASN | A | 34 | −8.578 | −17.699 | 17.578 | 1.00 | 55.71 | C |
| ATOM | 238 | CG | ASN | A | 34 | −9.081 | −16.990 | 16.338 | 1.00 | 59.31 | C |
| ATOM | 239 | OD1 | ASN | A | 34 | −8.462 | −17.062 | 15.275 | 1.00 | 63.02 | O |
| ATOM | 240 | ND2 | ASN | A | 34 | −10.211 | −16.301 | 16.465 | 1.00 | 56.96 | N |
| ATOM | 241 | N | SER | A | 35 | −5.691 | −17.870 | 15.771 | 1.00 | 77.82 | N |
| ATOM | 242 | CA | SER | A | 35 | −4.483 | −17.149 | 15.380 | 1.00 | 75.43 | C |
| ATOM | 243 | C | SER | A | 35 | −4.709 | −15.641 | 15.381 | 1.00 | 69.77 | C |
| ATOM | 244 | O | SER | A | 35 | −3.775 | −14.863 | 15.580 | 1.00 | 66.19 | O |
| ATOM | 245 | CB | SER | A | 35 | −4.009 | −17.607 | 13.999 | 1.00 | 81.27 | C |
| ATOM | 246 | OG | SER | A | 35 | −2.862 | −16.883 | 13.586 | 1.00 | 89.74 | O |
| ATOM | 247 | N | ASN | A | 36 | −5.954 | −15.232 | 15.155 | 1.00 | 64.21 | N |
| ATOM | 248 | CA | ASN | A | 36 | −6.304 | −13.816 | 15.149 | 1.00 | 67.38 | C |
| ATOM | 249 | C | ASN | A | 36 | −6.389 | −13.231 | 16.557 | 1.00 | 67.33 | C |
| ATOM | 250 | O | ASN | A | 36 | −6.767 | −12.076 | 16.739 | 1.00 | 70.96 | O |
| ATOM | 251 | CB | ASN | A | 36 | −7.615 | −13.591 | 14.396 | 1.00 | 72.24 | C |
| ATOM | 252 | CG | ASN | A | 36 | −7.500 | −13.924 | 12.922 | 1.00 | 86.62 | C |
| ATOM | 253 | OD1 | ASN | A | 36 | −6.429 | −13.795 | 12.327 | 1.00 | 82.67 | O |
| ATOM | 254 | ND2 | ASN | A | 36 | −8.605 | −14.355 | 12.323 | 1.00 | 98.34 | N |
| ATOM | 255 | N | LEU | A | 37 | −6.037 | −14.041 | 17.550 | 1.00 | 62.99 | N |
| ATOM | 256 | CA | LEU | A | 37 | −5.965 | −13.579 | 18.930 | 1.00 | 60.03 | C |
| ATOM | 257 | C | LEU | A | 37 | −4.558 | −13.799 | 19.468 | 1.00 | 62.48 | C |
| ATOM | 258 | O | LEU | A | 37 | −4.329 | −13.732 | 20.674 | 1.00 | 70.21 | O |
| ATOM | 259 | CB | LEU | A | 37 | −6.979 | −14.315 | 19.808 | 1.00 | 51.98 | C |
| ATOM | 260 | CG | LEU | A | 37 | −8.463 | −14.209 | 19.453 | 1.00 | 50.41 | C |
| ATOM | 261 | CD1 | LEU | A | 37 | −9.273 | −15.208 | 20.263 | 1.00 | 45.06 | C |
| ATOM | 262 | CD2 | LEU | A | 37 | −8.987 | −12.797 | 19.668 | 1.00 | 47.06 | C |
| ATOM | 263 | N | GLN | A | 38 | −3.618 | −14.072 | 18.567 | 1.00 | 55.36 | N |
| ATOM | 264 | CA | GLN | A | 38 | −2.243 | −14.365 | 18.965 | 1.00 | 59.02 | C |
| ATOM | 265 | C | GLN | A | 38 | −1.308 | −13.184 | 18.723 | 1.00 | 62.89 | C |
| ATOM | 266 | O | GLN | A | 38 | −0.144 | −13.354 | 18.355 | 1.00 | 53.79 | O |
| ATOM | 267 | CB | GLN | A | 38 | −1.737 | −15.632 | 18.268 | 1.00 | 66.47 | C |
| ATOM | 268 | CG | GLN | A | 38 | −2.467 | −16.890 | 18.720 | 1.00 | 74.55 | C |
| ATOM | 269 | CD | GLN | A | 38 | −1.917 | −18.154 | 18.090 | 1.00 | 73.77 | C |
| ATOM | 270 | OE1 | GLN | A | 38 | −1.085 | −18.102 | 17.185 | 1.00 | 81.72 | O |
| ATOM | 271 | NE2 | GLN | A | 38 | −2.384 | −19.303 | 18.569 | 1.00 | 61.31 | N |
| ATOM | 272 | N | ASN | A | 39 | −1.836 | −11.985 | 18.941 | 1.00 | 70.86 | N |
| ATOM | 273 | CA | ASN | A | 39 | −1.044 | −10.767 | 18.906 | 1.00 | 66.48 | C |
| ATOM | 274 | C | ASN | A | 39 | −0.411 | −10.501 | 20.269 | 1.00 | 66.69 | C |
| ATOM | 275 | O | ASN | A | 39 | −0.720 | −11.183 | 21.246 | 1.00 | 64.50 | O |
| ATOM | 276 | CB | ASN | A | 39 | −1.918 | −9.589 | 18.482 | 1.00 | 65.45 | C |
| ATOM | 277 | CG | ASN | A | 39 | −3.222 | −9.523 | 19.255 | 1.00 | 69.71 | C |
| ATOM | 278 | OD1 | ASN | A | 39 | −3.228 | −9.332 | 20.472 | 1.00 | 76.47 | O |
| ATOM | 279 | ND2 | ASN | A | 39 | −4.336 | −9.683 | 18.550 | 1.00 | 64.47 | N |
| ATOM | 280 | N | VAL | A | 40 | 0.468 | −9.506 | 20.332 | 1.00 | 66.28 | N |
| ATOM | 281 | CA | VAL | A | 40 | 1.198 | −9.210 | 21.564 | 1.00 | 62.67 | C |
| ATOM | 282 | C | VAL | A | 40 | 0.282 | −8.719 | 22.684 | 1.00 | 57.05 | C |
| ATOM | 283 | O | VAL | A | 40 | 0.517 | −8.999 | 23.860 | 1.00 | 49.86 | O |
| ATOM | 284 | CB | VAL | A | 40 | 2.304 | −8.166 | 21.326 | 1.00 | 68.95 | C |
| ATOM | 285 | CG1 | VAL | A | 40 | 3.115 | −7.956 | 22.595 | 1.00 | 61.33 | C |
| ATOM | 286 | CG2 | VAL | A | 40 | 3.204 | −8.600 | 20.181 | 1.00 | 73.71 | C |
| ATOM | 287 | N | THR | A | 41 | −0.761 | −7.984 | 22.312 | 1.00 | 63.28 | N |
| ATOM | 288 | CA | THR | A | 41 | −1.683 | −7.422 | 23.291 | 1.00 | 65.30 | C |
| ATOM | 289 | C | THR | A | 41 | −2.338 | −8.506 | 24.145 | 1.00 | 69.65 | C |
| ATOM | 290 | O | THR | A | 41 | −2.532 | −8.326 | 25.348 | 1.00 | 72.53 | O |
| ATOM | 291 | CB | THR | A | 41 | −2.782 | −6.586 | 22.610 | 1.00 | 58.97 | C |
| ATOM | 292 | OG1 | THR | A | 41 | −2.191 | −5.719 | 21.634 | 1.00 | 56.89 | O |
| ATOM | 293 | CG2 | THR | A | 41 | −3.535 | −5.754 | 23.642 | 1.00 | 51.51 | C |
| ATOM | 294 | N | ASN | A | 42 | −2.675 | −9.630 | 23.519 | 1.00 | 59.31 | N |

TABLE 6-continued

HUMAN A2A ADENOSINE STRUCTURE.PDB FILE
(Table 6: discloses SEQ ID NOS 20-27, respectively, in order of appearance.)

| ATOM | 295 | CA | ASN | A | 42 | −3.326 | −10.731 | 24.226 | 1.00 | 54.96 | C |
|---|---|---|---|---|---|---|---|---|---|---|---|
| ATOM | 296 | C | ASN | A | 42 | −2.363 | −11.572 | 25.063 | 1.00 | 53.43 | C |
| ATOM | 297 | O | ASN | A | 42 | −2.785 | −12.466 | 25.796 | 1.00 | 58.46 | O |
| ATOM | 298 | CB | ASN | A | 42 | −4.116 | −11.609 | 23.254 | 1.00 | 54.51 | C |
| ATOM | 299 | CG | ASN | A | 42 | −5.357 | −10.916 | 22.729 | 1.00 | 55.48 | C |
| ATOM | 300 | OD1 | ASN | A | 42 | −5.981 | −10.123 | 23.434 | 1.00 | 55.74 | O |
| ATOM | 301 | ND2 | ASN | A | 42 | −5.721 | −11.209 | 21.486 | 1.00 | 60.06 | N |
| ATOM | 302 | N | TYR | A | 43 | −1.071 | −11.281 | 24.949 | 1.00 | 52.66 | N |
| ATOM | 303 | CA | TYR | A | 43 | −0.072 | −11.879 | 25.827 | 1.00 | 54.61 | C |
| ATOM | 304 | C | TYR | A | 43 | −0.313 | −11.417 | 27.260 | 1.00 | 51.58 | C |
| ATOM | 305 | O | TYR | A | 43 | −0.136 | −12.176 | 28.212 | 1.00 | 51.67 | O |
| ATOM | 306 | CB | TYR | A | 43 | 1.333 | −11.468 | 25.392 | 1.00 | 57.59 | C |
| ATOM | 307 | CG | TYR | A | 43 | 1.897 | −12.269 | 24.241 | 1.00 | 64.19 | C |
| ATOM | 308 | CD1 | TYR | A | 43 | 1.099 | −12.642 | 23.169 | 1.00 | 67.89 | C |
| ATOM | 309 | CD2 | TYR | A | 43 | 3.238 | −12.632 | 24.219 | 1.00 | 66.57 | C |
| ATOM | 310 | CE1 | TYR | A | 43 | 1.618 | −13.369 | 22.113 | 1.00 | 72.72 | C |
| ATOM | 311 | CE2 | TYR | A | 43 | 3.766 | −13.355 | 23.168 | 1.00 | 68.15 | C |
| ATOM | 312 | CZ | TYR | A | 43 | 2.953 | −13.722 | 22.118 | 1.00 | 73.46 | C |
| ATOM | 313 | OH | TYR | A | 43 | 3.479 | −14.444 | 21.072 | 1.00 | 75.89 | O |
| ATOM | 314 | N | PHE | A | 44 | −0.717 | −10.159 | 27.402 | 1.00 | 53.23 | N |
| ATOM | 315 | CA | PHE | A | 44 | −0.989 | −9.577 | 28.709 | 1.00 | 55.20 | C |
| ATOM | 316 | C | PHE | A | 44 | −2.386 | −9.941 | 29.198 | 1.00 | 53.59 | C |
| ATOM | 317 | O | PHE | A | 44 | −2.628 | −10.028 | 30.401 | 1.00 | 49.70 | O |
| ATOM | 318 | CB | PHE | A | 44 | −0.822 | −8.057 | 28.659 | 1.00 | 57.61 | C |
| ATOM | 319 | CG | PHE | A | 44 | 0.556 | −7.614 | 28.256 | 1.00 | 60.37 | C |
| ATOM | 320 | CD1 | PHE | A | 44 | 0.778 | −7.027 | 27.022 | 1.00 | 62.33 | C |
| ATOM | 321 | CD2 | PHE | A | 44 | 1.631 | −7.794 | 29.110 | 1.00 | 60.43 | C |
| ATOM | 322 | CE1 | PHE | A | 44 | 2.047 | −6.621 | 26.649 | 1.00 | 58.27 | C |
| ATOM | 323 | CE2 | PHE | A | 44 | 2.901 | −7.392 | 28.744 | 1.00 | 57.39 | C |
| ATOM | 324 | CZ | PHE | A | 44 | 3.110 | −6.805 | 27.513 | 1.00 | 58.99 | C |
| ATOM | 325 | N | VAL | A | 45 | −3.304 | −10.150 | 28.259 | 1.00 | 54.14 | N |
| ATOM | 326 | CA | VAL | A | 45 | −4.653 | −10.587 | 28.596 | 1.00 | 52.45 | C |
| ATOM | 327 | C | VAL | A | 45 | −4.613 | −11.992 | 29.190 | 1.00 | 51.25 | C |
| ATOM | 328 | O | VAL | A | 45 | −5.332 | −12.296 | 30.141 | 1.00 | 55.59 | O |
| ATOM | 329 | CB | VAL | A | 45 | −5.578 | −10.576 | 27.361 | 1.00 | 55.15 | C |
| ATOM | 330 | CG1 | VAL | A | 45 | −6.931 | −11.187 | 27.698 | 1.00 | 58.64 | C |
| ATOM | 331 | CG2 | VAL | A | 45 | −5.745 | −9.158 | 26.833 | 1.00 | 45.21 | C |
| ATOM | 332 | N | VAL | A | 46 | −3.760 | −12.841 | 28.625 | 1.00 | 51.50 | N |
| ATOM | 333 | CA | VAL | A | 46 | −3.592 | −14.209 | 29.107 | 1.00 | 54.61 | C |
| ATOM | 334 | C | VAL | A | 46 | −2.954 | −14.249 | 30.495 | 1.00 | 55.57 | C |
| ATOM | 335 | O | VAL | A | 46 | −3.410 | −14.980 | 31.376 | 1.00 | 51.94 | O |
| ATOM | 336 | CB | VAL | A | 46 | −2.749 | −15.050 | 28.129 | 1.00 | 57.81 | C |
| ATOM | 337 | CG1 | VAL | A | 46 | −2.243 | −16.312 | 28.809 | 1.00 | 56.04 | C |
| ATOM | 338 | CG2 | VAL | A | 46 | −3.561 | −15.388 | 26.884 | 1.00 | 51.86 | C |
| ATOM | 339 | N | SER | A | 47 | −1.897 | −13.465 | 30.685 | 1.00 | 61.87 | N |
| ATOM | 340 | CA | SER | A | 47 | −1.249 | −13.359 | 31.988 | 1.00 | 54.01 | C |
| ATOM | 341 | C | SER | A | 47 | −2.259 | −12.892 | 33.031 | 1.00 | 51.38 | C |
| ATOM | 342 | O | SER | A | 47 | −2.294 | −13.396 | 34.154 | 1.00 | 46.71 | O |
| ATOM | 343 | CB | SER | A | 47 | −0.069 | −12.387 | 31.926 | 1.00 | 51.97 | C |
| ATOM | 344 | OG | SER | A | 47 | 0.587 | −12.293 | 33.179 | 1.00 | 57.36 | O |
| ATOM | 345 | N | LEU | A | 48 | −3.082 | −11.924 | 32.644 | 1.00 | 54.76 | N |
| ATOM | 346 | CA | LEU | A | 48 | −4.141 | −11.421 | 33.508 | 1.00 | 58.61 | C |
| ATOM | 347 | C | LEU | A | 48 | −5.146 | −12.526 | 33.825 | 1.00 | 59.46 | C |
| ATOM | 348 | O | LEU | A | 48 | −5.596 | −12.662 | 34.963 | 1.00 | 59.35 | O |
| ATOM | 349 | CB | LEU | A | 48 | −4.846 | −10.241 | 32.840 | 1.00 | 65.92 | C |
| ATOM | 350 | CG | LEU | A | 48 | −5.938 | −9.529 | 33.637 | 1.00 | 66.12 | C |
| ATOM | 351 | CD1 | LEU | A | 48 | −5.381 | −8.991 | 34.944 | 1.00 | 56.59 | C |
| ATOM | 352 | CD2 | LEU | A | 48 | −6.548 | −8.411 | 32.808 | 1.00 | 67.97 | C |
| ATOM | 353 | N | ALA | A | 49 | −5.491 | −13.312 | 32.810 | 1.00 | 60.16 | N |
| ATOM | 354 | CA | ALA | A | 49 | −6.419 | −14.427 | 32.978 | 1.00 | 58.88 | C |
| ATOM | 355 | C | ALA | A | 49 | −5.838 | −15.486 | 33.910 | 1.00 | 56.89 | C |
| ATOM | 356 | O | ALA | A | 49 | −6.568 | −16.141 | 34.655 | 1.00 | 51.14 | O |
| ATOM | 357 | CB | ALA | A | 49 | −6.766 | −15.038 | 31.626 | 1.00 | 52.59 | C |
| ATOM | 358 | N | ALA | A | 50 | −4.520 | −15.651 | 33.859 | 1.00 | 50.59 | N |
| ATOM | 359 | CA | ALA | A | 50 | −3.834 | −16.597 | 34.729 | 1.00 | 49.49 | C |
| ATOM | 360 | C | ALA | A | 50 | −3.989 | −16.189 | 36.190 | 1.00 | 53.79 | C |
| ATOM | 361 | O | ALA | A | 50 | −4.272 | −17.020 | 37.052 | 1.00 | 63.67 | O |
| ATOM | 362 | CB | ALA | A | 50 | −2.363 | −16.690 | 34.356 | 1.00 | 44.53 | C |
| ATOM | 363 | N | ALA | A | 51 | −3.806 | −14.900 | 36.457 | 1.00 | 55.33 | N |
| ATOM | 364 | CA | ALA | A | 51 | −3.927 | −14.370 | 37.810 | 1.00 | 47.52 | C |
| ATOM | 365 | C | ALA | A | 51 | −5.332 | −14.574 | 38.369 | 1.00 | 53.37 | C |
| ATOM | 366 | O | ALA | A | 51 | −5.501 | −14.870 | 39.550 | 1.00 | 57.64 | O |
| ATOM | 367 | CB | ALA | A | 51 | −3.554 | −12.898 | 37.835 | 1.00 | 45.14 | C |
| ATOM | 368 | N | ASP | A | 52 | −6.338 | −14.415 | 37.514 | 1.00 | 57.53 | N |
| ATOM | 369 | CA | ASP | A | 52 | −7.728 | −14.560 | 37.933 | 1.00 | 50.75 | C |
| ATOM | 370 | C | ASP | A | 52 | −8.103 | −16.018 | 38.189 | 1.00 | 57.74 | C |
| ATOM | 371 | O | ASP | A | 52 | −8.948 | −16.308 | 39.035 | 1.00 | 62.76 | O |

TABLE 6-continued

HUMAN A2A ADENOSINE STRUCTURE.PDB FILE
(Table 6: discloses SEQ ID NOS 20-27, respectively, in order of appearance.)

| ATOM | 372 | CB | ASP | A | 52 | −8.670 | −13.933 | 36.904 | 1.00 | 54.25 | C |
|---|---|---|---|---|---|---|---|---|---|---|---|
| ATOM | 373 | CG | ASP | A | 52 | −8.633 | −12.416 | 36.930 | 1.00 | 64.00 | C |
| ATOM | 374 | OD1 | ASP | A | 52 | −8.476 | −11.844 | 38.030 | 1.00 | 69.09 | O |
| ATOM | 375 | OD2 | ASP | A | 52 | −8.761 | −11.794 | 35.856 | 1.00 | 57.84 | O |
| ATOM | 376 | N | ILE | A | 53 | −7.474 | −16.934 | 37.459 | 1.00 | 54.06 | N |
| ATOM | 377 | CA | ILE | A | 53 | −7.679 | −18.355 | 37.706 | 1.00 | 51.76 | C |
| ATOM | 378 | C | ILE | A | 53 | −7.096 | −18.723 | 39.064 | 1.00 | 56.19 | C |
| ATOM | 379 | O | ILE | A | 53 | −7.707 | −19.462 | 39.836 | 1.00 | 58.51 | O |
| ATOM | 380 | CB | ILE | A | 53 | −7.020 | −19.231 | 36.621 | 1.00 | 56.32 | C |
| ATOM | 381 | CG1 | ILE | A | 53 | −7.673 | −18.981 | 35.260 | 1.00 | 59.33 | C |
| ATOM | 382 | CG2 | ILE | A | 53 | −7.120 | −20.705 | 36.994 | 1.00 | 49.46 | C |
| ATOM | 383 | CD1 | ILE | A | 53 | −6.988 | −19.699 | 34.114 | 1.00 | 60.95 | C |
| ATOM | 384 | N | ALA | A | 54 | −5.910 | −18.195 | 39.351 | 1.00 | 52.48 | N |
| ATOM | 385 | CA | ALA | A | 54 | −5.230 | −18.470 | 40.611 | 1.00 | 50.78 | C |
| ATOM | 386 | C | ALA | A | 54 | −6.025 | −17.934 | 41.800 | 1.00 | 60.72 | C |
| ATOM | 387 | O | ALA | A | 54 | −5.917 | −18.448 | 42.913 | 1.00 | 60.49 | O |
| ATOM | 388 | CB | ALA | A | 54 | −3.824 | −17.886 | 40.594 | 1.00 | 44.14 | C |
| ATOM | 389 | N | VAL | A | 55 | −6.822 | −16.898 | 41.559 | 1.00 | 59.00 | N |
| ATOM | 390 | CA | VAL | A | 55 | −7.672 | −16.335 | 42.601 | 1.00 | 53.33 | C |
| ATOM | 391 | C | VAL | A | 55 | −8.742 | −17.337 | 43.012 | 1.00 | 54.00 | C |
| ATOM | 392 | O | VAL | A | 55 | −8.991 | −17.543 | 44.200 | 1.00 | 60.44 | O |
| ATOM | 393 | CB | VAL | A | 55 | −8.356 | −15.033 | 42.140 | 1.00 | 55.05 | C |
| ATOM | 394 | CG1 | VAL | A | 55 | −9.467 | −14.646 | 43.107 | 1.00 | 55.08 | C |
| ATOM | 395 | CG2 | VAL | A | 55 | −7.337 | −13.910 | 42.022 | 1.00 | 53.82 | C |
| ATOM | 396 | N | GLY | A | 56 | −9.371 | −17.960 | 42.022 | 1.00 | 51.21 | N |
| ATOM | 397 | CA | GLY | A | 56 | −10.411 | −18.936 | 42.280 | 1.00 | 58.11 | C |
| ATOM | 398 | C | GLY | A | 56 | −9.869 | −20.208 | 42.902 | 1.00 | 63.92 | C |
| ATOM | 399 | O | GLY | A | 56 | −10.535 | −20.845 | 43.718 | 1.00 | 62.56 | O |
| ATOM | 400 | N | VAL | A | 57 | −8.649 | −20.572 | 42.523 | 1.00 | 65.66 | N |
| ATOM | 401 | CA | VAL | A | 57 | −8.049 | −21.820 | 42.981 | 1.00 | 58.18 | C |
| ATOM | 402 | C | VAL | A | 57 | −7.416 | −21.721 | 44.370 | 1.00 | 58.97 | C |
| ATOM | 403 | O | VAL | A | 57 | −7.558 | −22.632 | 45.183 | 1.00 | 57.33 | O |
| ATOM | 404 | CB | VAL | A | 57 | −6.999 | −22.339 | 41.980 | 1.00 | 55.79 | C |
| ATOM | 405 | CG1 | VAL | A | 57 | −6.325 | −23.589 | 42.519 | 1.00 | 64.68 | C |
| ATOM | 406 | CG2 | VAL | A | 57 | −7.646 | −22.617 | 40.634 | 1.00 | 45.08 | C |
| ATOM | 407 | N | LEU | A | 58 | −6.723 | −20.619 | 44.645 | 1.00 | 58.83 | N |
| ATOM | 408 | CA | LEU | A | 58 | −5.983 | −20.492 | 45.900 | 1.00 | 60.87 | C |
| ATOM | 409 | C | LEU | A | 58 | −6.427 | −19.325 | 46.783 | 1.00 | 59.06 | C |
| ATOM | 410 | O | LEU | A | 58 | −6.700 | −19.507 | 47.969 | 1.00 | 61.62 | O |
| ATOM | 411 | CB | LEU | A | 58 | −4.479 | −20.389 | 45.628 | 1.00 | 70.55 | C |
| ATOM | 412 | CG | LEU | A | 58 | −3.797 | −21.628 | 45.044 | 1.00 | 70.44 | C |
| ATOM | 413 | CD1 | LEU | A | 58 | −2.334 | −21.341 | 44.750 | 1.00 | 69.14 | C |
| ATOM | 414 | CD2 | LEU | A | 58 | −3.933 | −22.812 | 45.987 | 1.00 | 73.02 | C |
| ATOM | 415 | N | ALA | A | 59 | −6.486 | −18.130 | 46.205 | 1.00 | 54.43 | N |
| ATOM | 416 | CA | ALA | A | 59 | −6.774 | −16.922 | 46.976 | 1.00 | 50.06 | C |
| ATOM | 417 | C | ALA | A | 59 | −8.086 | −17.009 | 47.750 | 1.00 | 59.55 | C |
| ATOM | 418 | O | ALA | A | 59 | −8.144 | −16.658 | 48.928 | 1.00 | 56.30 | O |
| ATOM | 419 | CB | ALA | A | 59 | −6.771 | −15.701 | 46.072 | 1.00 | 52.42 | C |
| ATOM | 420 | N | ILE | A | 60 | −9.138 | −17.472 | 47.083 | 1.00 | 56.07 | N |
| ATOM | 421 | CA | ILE | A | 60 | −10.452 | −17.575 | 47.713 | 1.00 | 56.71 | C |
| ATOM | 422 | C | ILE | A | 60 | −10.509 | −18.638 | 48.818 | 1.00 | 57.72 | C |
| ATOM | 423 | O | ILE | A | 60 | −11.054 | −18.383 | 49.893 | 1.00 | 51.88 | O |
| ATOM | 424 | CB | ILE | A | 60 | −11.567 | −17.800 | 46.673 | 1.00 | 60.41 | C |
| ATOM | 425 | CG1 | ILE | A | 60 | −11.807 | −16.512 | 45.881 | 1.00 | 58.94 | C |
| ATOM | 426 | CG2 | ILE | A | 60 | −12.846 | −18.258 | 47.353 | 1.00 | 51.36 | C |
| ATOM | 427 | CD1 | ILE | A | 60 | −12.829 | −16.646 | 44.774 | 1.00 | 52.17 | C |
| ATOM | 428 | N | PRO | A | 61 | −9.954 | −19.835 | 48.559 | 1.00 | 57.55 | N |
| ATOM | 429 | CA | PRO | A | 61 | −9.851 | −20.817 | 49.645 | 1.00 | 58.52 | C |
| ATOM | 430 | C | PRO | A | 61 | −9.028 | −20.281 | 50.817 | 1.00 | 62.38 | C |
| ATOM | 431 | O | PRO | A | 61 | −9.351 | −20.564 | 51.973 | 1.00 | 55.92 | O |
| ATOM | 432 | CB | PRO | A | 61 | −9.131 | −21.994 | 48.982 | 1.00 | 48.18 | C |
| ATOM | 433 | CG | PRO | A | 61 | −9.495 | −21.884 | 47.544 | 1.00 | 55.33 | C |
| ATOM | 434 | CD | PRO | A | 61 | −9.564 | −20.408 | 47.259 | 1.00 | 57.67 | C |
| ATOM | 435 | N | PHE | A | 62 | −7.981 | −19.517 | 50.522 | 1.00 | 54.81 | N |
| ATOM | 436 | CA | PHE | A | 62 | −7.181 | −18.891 | 51.569 | 1.00 | 51.86 | C |
| ATOM | 437 | C | PHE | A | 62 | −8.022 | −17.905 | 52.376 | 1.00 | 54.22 | C |
| ATOM | 438 | O | PHE | A | 62 | −7.931 | −17.856 | 53.603 | 1.00 | 62.37 | O |
| ATOM | 439 | CB | PHE | A | 62 | −5.961 | −18.176 | 50.981 | 1.00 | 61.40 | C |
| ATOM | 440 | CG | PHE | A | 62 | −4.856 | −19.103 | 50.554 | 1.00 | 65.62 | C |
| ATOM | 441 | CD1 | PHE | A | 62 | −4.850 | −20.429 | 50.954 | 1.00 | 59.06 | C |
| ATOM | 442 | CD2 | PHE | A | 62 | −3.807 | −18.638 | 49.777 | 1.00 | 66.19 | C |
| ATOM | 443 | CE1 | PHE | A | 62 | −3.829 | −21.278 | 50.568 | 1.00 | 54.74 | C |
| ATOM | 444 | CE2 | PHE | A | 62 | −2.783 | −19.482 | 49.391 | 1.00 | 60.74 | C |
| ATOM | 445 | CZ | PHE | A | 62 | −2.794 | −20.803 | 49.787 | 1.00 | 58.09 | C |
| ATOM | 446 | N | ALA | A | 63 | −8.839 | −17.122 | 51.679 | 1.00 | 53.63 | N |
| ATOM | 447 | CA | ALA | A | 63 | −9.700 | −16.141 | 52.330 | 1.00 | 52.19 | C |
| ATOM | 448 | C | ALA | A | 63 | −10.624 | −16.807 | 53.346 | 1.00 | 58.31 | C |

TABLE 6-continued

HUMAN A2A ADENOSINE STRUCTURE.PDB FILE
(Table 6: discloses SEQ ID NOS 20-27, respectively, in order of appearance.)

| ATOM | 449 | O   | ALA | A | 63 | −10.789 | −16.321 | 54.465 | 1.00 | 59.74 | O |
|------|-----|-----|-----|---|----|---------|---------|--------|------|-------|---|
| ATOM | 450 | CB  | ALA | A | 63 | −10.512 | −15.377 | 51.293 | 1.00 | 49.14 | C |
| ATOM | 451 | N   | ILE | A | 64 | −11.220 | −17.924 | 52.948 | 1.00 | 57.19 | N |
| ATOM | 452 | CA  | ILE | A | 64 | −12.141 | −18.655 | 53.810 | 1.00 | 58.02 | C |
| ATOM | 453 | C   | ILE | A | 64 | −11.425 | −19.250 | 55.017 | 1.00 | 53.50 | C |
| ATOM | 454 | O   | ILE | A | 64 | −11.937 | −19.216 | 56.136 | 1.00 | 51.96 | O |
| ATOM | 455 | CB  | ILE | A | 64 | −12.840 | −19.784 | 53.037 | 1.00 | 55.73 | C |
| ATOM | 456 | CG1 | ILE | A | 64 | −13.527 | −19.221 | 51.793 | 1.00 | 58.64 | C |
| ATOM | 457 | CG2 | ILE | A | 64 | −13.838 | −20.505 | 53.933 | 1.00 | 60.85 | C |
| ATOM | 458 | CD1 | ILE | A | 64 | −14.063 | −20.282 | 50.869 | 1.00 | 61.69 | C |
| ATOM | 459 | N   | THR | A | 65 | −10.239 | −19.800 | 54.780 | 1.00 | 52.08 | N |
| ATOM | 460 | CA  | THR | A | 65 | −9.437  | −20.399 | 55.838 | 1.00 | 54.83 | C |
| ATOM | 461 | C   | THR | A | 65 | −9.094  | −19.381 | 56.918 | 1.00 | 63.10 | C |
| ATOM | 462 | O   | THR | A | 65 | −9.188  | −19.669 | 58.112 | 1.00 | 59.03 | O |
| ATOM | 463 | CB  | THR | A | 65 | −8.124  | −20.972 | 55.275 | 1.00 | 53.32 | C |
| ATOM | 464 | OG1 | THR | A | 65 | −8.418  | −22.016 | 54.338 | 1.00 | 54.74 | O |
| ATOM | 465 | CG2 | THR | A | 65 | −7.259  | −21.528 | 56.394 | 1.00 | 56.55 | C |
| ATOM | 466 | N   | ILE | A | 66 | −8.703  | −18.187 | 56.485 | 1.00 | 60.54 | N |
| ATOM | 467 | CA  | ILE | A | 66 | −8.212  | −17.155 | 57.390 | 1.00 | 58.22 | C |
| ATOM | 468 | C   | ILE | A | 66 | −9.331  | −16.468 | 58.172 | 1.00 | 57.21 | C |
| ATOM | 469 | O   | ILE | A | 66 | −9.077  | −15.816 | 59.186 | 1.00 | 63.98 | O |
| ATOM | 470 | CB  | ILE | A | 66 | −7.388  | −16.097 | 56.624 | 1.00 | 67.42 | C |
| ATOM | 471 | CG1 | ILE | A | 66 | −6.508  | −15.298 | 57.586 | 1.00 | 72.00 | C |
| ATOM | 472 | CG2 | ILE | A | 66 | −8.300  | −15.178 | 55.822 | 1.00 | 69.57 | C |
| ATOM | 473 | CD1 | ILE | A | 66 | −5.644  | −14.265 | 56.900 | 1.00 | 73.41 | C |
| ATOM | 474 | N   | SER | A | 67 | −10.568 | −16.616 | 57.708 | 1.00 | 54.77 | N |
| ATOM | 475 | CA  | SER | A | 67 | −11.709 | −15.994 | 58.375 | 1.00 | 57.12 | C |
| ATOM | 476 | C   | SER | A | 67 | −12.046 | −16.690 | 59.693 | 1.00 | 63.98 | C |
| ATOM | 477 | O   | SER | A | 67 | −12.965 | −16.281 | 60.404 | 1.00 | 64.17 | O |
| ATOM | 478 | CB  | SER | A | 67 | −12.936 | −15.987 | 57.459 | 1.00 | 57.32 | C |
| ATOM | 479 | OG  | SER | A | 67 | −13.478 | −17.289 | 57.319 | 1.00 | 54.70 | O |
| ATOM | 480 | N   | THR | A | 68 | −11.300 | −17.742 | 60.014 | 1.00 | 64.00 | N |
| ATOM | 481 | CA  | THR | A | 68 | −11.515 | −18.483 | 61.251 | 1.00 | 53.90 | C |
| ATOM | 482 | C   | THR | A | 68 | −10.640 | −17.944 | 62.377 | 1.00 | 51.40 | C |
| ATOM | 483 | O   | THR | A | 68 | −10.957 | −18.109 | 63.555 | 1.00 | 47.76 | O |
| ATOM | 484 | CB  | THR | A | 68 | −11.219 | −19.981 | 61.070 | 1.00 | 56.20 | C |
| ATOM | 485 | OG1 | THR | A | 68 | −9.823  | −20.166 | 60.799 | 1.00 | 59.42 | O |
| ATOM | 486 | CG2 | THR | A | 68 | −12.040 | −20.551 | 59.921 | 1.00 | 48.56 | C |
| ATOM | 487 | N   | GLY | A | 69 | −9.535  | −17.302 | 62.009 | 1.00 | 55.64 | N |
| ATOM | 488 | CA  | GLY | A | 69 | −8.605  | −16.759 | 62.984 | 1.00 | 58.61 | C |
| ATOM | 489 | C   | GLY | A | 69 | −7.849  | −17.840 | 63.734 | 1.00 | 59.28 | C |
| ATOM | 490 | O   | GLY | A | 69 | −7.484  | −17.665 | 64.897 | 1.00 | 62.11 | O |
| ATOM | 491 | N   | PHE | A | 70 | −7.608  | −18.961 | 63.061 | 1.00 | 60.20 | N |
| ATOM | 492 | CA  | PHE | A | 70 | −6.950  | −20.108 | 63.679 | 1.00 | 59.57 | C |
| ATOM | 493 | C   | PHE | A | 70 | −5.500  | −19.809 | 64.058 | 1.00 | 50.81 | C |
| ATOM | 494 | O   | PHE | A | 70 | −4.888  | −18.877 | 63.537 | 1.00 | 49.57 | O |
| ATOM | 495 | CB  | PHE | A | 70 | −6.998  | −21.310 | 62.736 | 1.00 | 57.73 | C |
| ATOM | 496 | CG  | PHE | A | 70 | −6.149  | −21.148 | 61.510 | 1.00 | 62.68 | C |
| ATOM | 497 | CD1 | PHE | A | 70 | −6.544  | −20.306 | 60.484 | 1.00 | 65.58 | C |
| ATOM | 498 | CD2 | PHE | A | 70 | −4.954  | −21.837 | 61.383 | 1.00 | 66.10 | C |
| ATOM | 499 | CE1 | PHE | A | 70 | −5.762  | −20.153 | 59.354 | 1.00 | 65.37 | C |
| ATOM | 500 | CE2 | PHE | A | 70 | −4.168  | −21.690 | 60.256 | 1.00 | 65.32 | C |
| ATOM | 501 | CZ  | PHE | A | 70 | −4.573  | −20.846 | 59.240 | 1.00 | 61.83 | C |
| ATOM | 502 | N   | CYS | A | 71 | −4.958  | −20.610 | 64.969 | 1.00 | 48.00 | N |
| ATOM | 503 | CA  | CYS | A | 71 | −3.574  | −20.460 | 65.399 | 1.00 | 51.87 | C |
| ATOM | 504 | C   | CYS | A | 71 | −2.628  | −21.022 | 64.346 | 1.00 | 56.16 | C |
| ATOM | 505 | O   | CYS | A | 71 | −2.803  | −22.149 | 63.884 | 1.00 | 66.76 | O |
| ATOM | 506 | CB  | CYS | A | 71 | −3.345  | −21.179 | 66.730 | 1.00 | 48.71 | C |
| ATOM | 507 | SG  | CYS | A | 71 | −4.342  | −20.570 | 68.109 | 1.00 | 63.99 | S |
| ATOM | 508 | N   | ALA | A | 72 | −1.627  | −20.234 | 63.970 | 1.00 | 46.09 | N |
| ATOM | 509 | CA  | ALA | A | 72 | −0.642  | −20.672 | 62.988 | 1.00 | 46.80 | C |
| ATOM | 510 | C   | ALA | A | 72 | 0.710   | −20.010 | 63.220 | 1.00 | 52.70 | C |
| ATOM | 511 | O   | ALA | A | 72 | 0.801   | −18.982 | 63.895 | 1.00 | 58.22 | O |
| ATOM | 512 | CB  | ALA | A | 72 | −1.139  | −20.382 | 61.577 | 1.00 | 45.85 | C |
| ATOM | 513 | N   | ALA | A | 73 | 1.757   | −20.609 | 62.662 | 1.00 | 56.02 | N |
| ATOM | 514 | CA  | ALA | A | 73 | 3.077   | −20.002 | 62.684 | 1.00 | 58.90 | C |
| ATOM | 515 | C   | ALA | A | 73 | 3.019   | −18.643 | 61.994 | 1.00 | 65.68 | C |
| ATOM | 516 | O   | ALA | A | 73 | 2.163   | −18.409 | 61.140 | 1.00 | 67.58 | O |
| ATOM | 517 | CB  | ALA | A | 73 | 4.093   | −20.910 | 61.989 | 1.00 | 54.55 | C |
| ATOM | 518 | N   | CYS | A | 74 | 3.922   | −17.747 | 62.375 | 1.00 | 67.83 | N |
| ATOM | 519 | CA  | CYS | A | 74 | 3.908   | −16.381 | 61.858 | 1.00 | 68.48 | C |
| ATOM | 520 | C   | CYS | A | 74 | 3.949   | −16.314 | 60.332 | 1.00 | 61.01 | C |
| ATOM | 521 | O   | CYS | A | 74 | 2.984   | −15.896 | 59.694 | 1.00 | 56.11 | O |
| ATOM | 522 | CB  | CYS | A | 74 | 5.069   | −15.577 | 62.443 | 1.00 | 73.92 | C |
| ATOM | 523 | SG  | CYS | A | 74 | 5.320   | −13.972 | 61.659 | 1.00 | 89.63 | S |
| ATOM | 524 | N   | HIS | A | 75 | 5.070   | −16.729 | 59.753 | 1.00 | 60.21 | N |
| ATOM | 525 | CA  | HIS | A | 75 | 5.288   | −16.586 | 58.317 | 1.00 | 66.41 | C |

TABLE 6-continued

HUMAN A2A ADENOSINE STRUCTURE.PDB FILE
(Table 6: discloses SEQ ID NOS 20-27, respectively, in order of appearance.)

| ATOM | 526 | C | HIS | A | 75 | 4.308 | −17.394 | 57.469 | 1.00 | 68.42 | C |
|---|---|---|---|---|---|---|---|---|---|---|---|
| ATOM | 527 | O | HIS | A | 75 | 3.910 | −16.960 | 56.387 | 1.00 | 67.47 | O |
| ATOM | 528 | CB | HIS | A | 75 | 6.735 | −16.929 | 57.959 | 1.00 | 70.61 | C |
| ATOM | 529 | CG | HIS | A | 75 | 7.728 | −15.934 | 58.471 | 1.00 | 76.99 | C |
| ATOM | 530 | ND1 | HIS | A | 75 | 8.456 | −16.133 | 59.625 | 1.00 | 83.11 | N |
| ATOM | 531 | CD2 | HIS | A | 75 | 8.099 | −14.720 | 57.997 | 1.00 | 77.16 | C |
| ATOM | 532 | CE1 | HIS | A | 75 | 9.239 | −15.091 | 59.834 | 1.00 | 83.85 | C |
| ATOM | 533 | NE2 | HIS | A | 75 | 9.042 | −14.219 | 58.861 | 1.00 | 81.12 | N |
| ATOM | 534 | N | GLY | A | 76 | 3.922 | −18.566 | 57.961 | 1.00 | 69.55 | N |
| ATOM | 535 | CA | GLY | A | 76 | 2.938 | −19.382 | 57.275 | 1.00 | 66.87 | C |
| ATOM | 536 | C | GLY | A | 76 | 1.598 | −18.675 | 57.206 | 1.00 | 68.69 | C |
| ATOM | 537 | O | GLY | A | 76 | 0.879 | −18.773 | 56.211 | 1.00 | 62.20 | O |
| ATOM | 538 | N | CYS | A | 77 | 1.268 | −17.957 | 58.275 | 1.00 | 69.18 | N |
| ATOM | 539 | CA | CYS | A | 77 | 0.031 | −17.190 | 58.345 | 1.00 | 63.36 | C |
| ATOM | 540 | C | CYS | A | 77 | 0.065 | −16.009 | 57.379 | 1.00 | 64.02 | C |
| ATOM | 541 | O | CYS | A | 77 | −0.958 | −15.633 | 56.806 | 1.00 | 67.01 | O |
| ATOM | 542 | CB | CYS | A | 77 | −0.205 | −16.692 | 59.773 | 1.00 | 60.54 | C |
| ATOM | 543 | SG | CYS | A | 77 | −1.577 | −15.528 | 59.946 | 1.00 | 88.66 | S |
| ATOM | 544 | N | LEU | A | 78 | 1.249 | −15.431 | 57.204 | 1.00 | 58.78 | N |
| ATOM | 545 | CA | LEU | A | 78 | 1.419 | −14.275 | 56.331 | 1.00 | 60.78 | C |
| ATOM | 546 | C | LEU | A | 78 | 1.251 | −14.643 | 54.861 | 1.00 | 66.22 | C |
| ATOM | 547 | O | LEU | A | 78 | 0.702 | −13.866 | 54.079 | 1.00 | 62.14 | O |
| ATOM | 548 | CB | LEU | A | 78 | 2.781 | −13.618 | 56.569 | 1.00 | 56.64 | C |
| ATOM | 549 | CG | LEU | A | 78 | 2.884 | −12.806 | 57.863 | 1.00 | 53.72 | C |
| ATOM | 550 | CD1 | LEU | A | 78 | 4.330 | −12.472 | 58.188 | 1.00 | 44.99 | C |
| ATOM | 551 | CD2 | LEU | A | 78 | 2.053 | −11.538 | 57.757 | 1.00 | 57.25 | C |
| ATOM | 552 | N | PHE | A | 79 | 1.719 | −15.830 | 54.488 | 1.00 | 63.13 | N |
| ATOM | 553 | CA | PHE | A | 79 | 1.585 | −16.296 | 53.114 | 1.00 | 58.43 | C |
| ATOM | 554 | C | PHE | A | 79 | 0.117 | −16.431 | 52.718 | 1.00 | 57.93 | C |
| ATOM | 555 | O | PHE | A | 79 | −0.300 | −15.941 | 51.670 | 1.00 | 56.59 | O |
| ATOM | 556 | CB | PHE | A | 79 | 2.310 | −17.628 | 52.918 | 1.00 | 55.48 | C |
| ATOM | 557 | CG | PHE | A | 79 | 2.224 | −18.158 | 51.516 | 1.00 | 55.31 | C |
| ATOM | 558 | CD1 | PHE | A | 79 | 3.085 | −17.698 | 50.533 | 1.00 | 55.74 | C |
| ATOM | 559 | CD2 | PHE | A | 79 | 1.278 | −19.110 | 51.178 | 1.00 | 52.59 | C |
| ATOM | 560 | CE1 | PHE | A | 79 | 3.006 | −18.181 | 49.240 | 1.00 | 49.39 | C |
| ATOM | 561 | CE2 | PHE | A | 79 | 1.194 | −19.596 | 49.887 | 1.00 | 48.73 | C |
| ATOM | 562 | CZ | PHE | A | 79 | 2.059 | −19.131 | 48.918 | 1.00 | 49.02 | C |
| ATOM | 563 | N | ILE | A | 80 | −0.663 | −17.100 | 53.561 | 1.00 | 59.34 | N |
| ATOM | 564 | CA | ILE | A | 80 | −2.089 | −17.273 | 53.310 | 1.00 | 60.27 | C |
| ATOM | 565 | C | ILE | A | 80 | −2.792 | −15.927 | 53.181 | 1.00 | 57.82 | C |
| ATOM | 566 | O | ILE | A | 80 | −3.709 | −15.769 | 52.376 | 1.00 | 53.10 | O |
| ATOM | 567 | CB | ILE | A | 80 | −2.765 | −18.069 | 54.441 | 1.00 | 68.45 | C |
| ATOM | 568 | CG1 | ILE | A | 80 | −2.159 | −19.468 | 54.550 | 1.00 | 76.48 | C |
| ATOM | 569 | CG2 | ILE | A | 80 | −4.266 | −18.156 | 54.209 | 1.00 | 69.15 | C |
| ATOM | 570 | CD1 | ILE | A | 80 | −2.812 | −20.324 | 55.613 | 1.00 | 76.06 | C |
| ATOM | 571 | N | ALA | A | 81 | −2.354 | −14.960 | 53.979 | 1.00 | 55.94 | N |
| ATOM | 572 | CA | ALA | A | 81 | −2.983 | −13.645 | 54.005 | 1.00 | 52.18 | C |
| ATOM | 573 | C | ALA | A | 81 | −2.508 | −12.747 | 52.867 | 1.00 | 54.56 | C |
| ATOM | 574 | O | ALA | A | 81 | −3.265 | −11.915 | 52.369 | 1.00 | 63.21 | O |
| ATOM | 575 | CB | ALA | A | 81 | −2.737 | −12.969 | 55.348 | 1.00 | 48.86 | C |
| ATOM | 576 | N | CYS | A | 82 | −1.257 | −12.924 | 52.453 | 1.00 | 58.95 | N |
| ATOM | 577 | CA | CYS | A | 82 | −0.634 | −12.009 | 51.500 | 1.00 | 59.75 | C |
| ATOM | 578 | C | CYS | A | 82 | −0.597 | −12.513 | 50.058 | 1.00 | 62.46 | C |
| ATOM | 579 | O | CYS | A | 82 | −0.364 | −11.730 | 49.137 | 1.00 | 61.39 | O |
| ATOM | 580 | CB | CYS | A | 82 | 0.783 | −11.648 | 51.955 | 1.00 | 61.48 | C |
| ATOM | 581 | SG | CYS | A | 82 | 0.851 | −10.613 | 53.436 | 1.00 | 66.38 | S |
| ATOM | 582 | N | PHE | A | 83 | −0.820 | −13.808 | 49.856 | 1.00 | 57.25 | N |
| ATOM | 583 | CA | PHE | A | 83 | −0.715 | −14.380 | 48.516 | 1.00 | 52.99 | C |
| ATOM | 584 | C | PHE | A | 83 | −1.604 | −13.658 | 47.511 | 1.00 | 59.19 | C |
| ATOM | 585 | O | PHE | A | 83 | −1.219 | −13.464 | 46.357 | 1.00 | 55.51 | O |
| ATOM | 586 | CB | PHE | A | 83 | −1.041 | −15.874 | 48.519 | 1.00 | 53.72 | C |
| ATOM | 587 | CG | PHE | A | 83 | −0.966 | −16.507 | 47.158 | 1.00 | 55.03 | C |
| ATOM | 588 | CD1 | PHE | A | 83 | 0.253 | −16.663 | 46.520 | 1.00 | 50.93 | C |
| ATOM | 589 | CD2 | PHE | A | 83 | −2.114 | −16.940 | 46.513 | 1.00 | 59.91 | C |
| ATOM | 590 | CE1 | PHE | A | 83 | 0.329 | −17.238 | 45.267 | 1.00 | 52.19 | C |
| ATOM | 591 | CE2 | PHE | A | 83 | −2.045 | −17.519 | 45.260 | 1.00 | 55.73 | C |
| ATOM | 592 | CZ | PHE | A | 83 | −0.822 | −17.668 | 44.636 | 1.00 | 47.31 | C |
| ATOM | 593 | N | VAL | A | 84 | −2.793 | −13.261 | 47.951 | 1.00 | 61.05 | N |
| ATOM | 594 | CA | VAL | A | 84 | −3.729 | −12.565 | 47.078 | 1.00 | 53.61 | C |
| ATOM | 595 | C | VAL | A | 84 | −3.149 | −11.229 | 46.613 | 1.00 | 63.88 | C |
| ATOM | 596 | O | VAL | A | 84 | −3.468 | −10.748 | 45.525 | 1.00 | 62.14 | O |
| ATOM | 597 | CB | VAL | A | 84 | −5.093 | −12.343 | 47.768 | 1.00 | 49.09 | C |
| ATOM | 598 | CG1 | VAL | A | 84 | −4.959 | −11.353 | 48.920 | 1.00 | 44.32 | C |
| ATOM | 599 | CG2 | VAL | A | 84 | −6.131 | −11.872 | 46.761 | 1.00 | 47.44 | C |
| ATOM | 600 | N | LEU | A | 85 | −2.287 | −10.640 | 47.436 | 1.00 | 68.54 | N |
| ATOM | 601 | CA | LEU | A | 85 | −1.637 | −9.382 | 47.087 | 1.00 | 63.38 | C |
| ATOM | 602 | C | LEU | A | 85 | −0.692 | −9.582 | 45.907 | 1.00 | 65.55 | C |

TABLE 6-continued

HUMAN A2A ADENOSINE STRUCTURE.PDB FILE
(Table 6: discloses SEQ ID NOS 20-27, respectively, in order of appearance.)

| ATOM | 603 | O | LEU | A | 85 | −0.505 | −8.682 | 45.088 | 1.00 | 72.16 | O |
|---|---|---|---|---|---|---|---|---|---|---|---|
| ATOM | 604 | CB | LEU | A | 85 | −0.879 | −8.810 | 48.287 | 1.00 | 54.97 | C |
| ATOM | 605 | CG | LEU | A | 85 | −1.708 | −8.588 | 49.554 | 1.00 | 55.41 | C |
| ATOM | 606 | CD1 | LEU | A | 85 | −0.861 | −7.963 | 50.654 | 1.00 | 51.57 | C |
| ATOM | 607 | CD2 | LEU | A | 85 | −2.926 | −7.727 | 49.256 | 1.00 | 50.92 | C |
| ATOM | 608 | N | VAL | A | 86 | −0.098 | −10.768 | 45.828 | 1.00 | 59.46 | N |
| ATOM | 609 | CA | VAL | A | 86 | 0.746 | −11.121 | 44.694 | 1.00 | 61.04 | C |
| ATOM | 610 | C | VAL | A | 86 | −0.075 | −11.091 | 43.411 | 1.00 | 60.72 | C |
| ATOM | 611 | O | VAL | A | 86 | 0.303 | −10.447 | 42.430 | 1.00 | 49.39 | O |
| ATOM | 612 | CB | VAL | A | 86 | 1.356 | −12.524 | 44.863 | 1.00 | 58.19 | C |
| ATOM | 613 | CG1 | VAL | A | 86 | 2.124 | −12.922 | 43.612 | 1.00 | 54.26 | C |
| ATOM | 614 | CG2 | VAL | A | 86 | 2.253 | −12.571 | 46.094 | 1.00 | 51.92 | C |
| ATOM | 615 | N | LEU | A | 87 | −1.207 | −11.787 | 43.431 | 1.00 | 63.38 | N |
| ATOM | 616 | CA | LEU | A | 87 | −2.095 | −11.856 | 42.277 | 1.00 | 54.40 | C |
| ATOM | 617 | C | LEU | A | 87 | −2.586 | −10.475 | 41.852 | 1.00 | 52.89 | C |
| ATOM | 618 | O | LEU | A | 87 | −2.647 | −10.168 | 40.663 | 1.00 | 56.74 | O |
| ATOM | 619 | CB | LEU | A | 87 | −3.288 | −12.765 | 42.580 | 1.00 | 53.50 | C |
| ATOM | 620 | CG | LEU | A | 87 | −2.933 | −14.195 | 42.987 | 1.00 | 52.31 | C |
| ATOM | 621 | CD1 | LEU | A | 87 | −4.185 | −15.047 | 43.113 | 1.00 | 56.23 | C |
| ATOM | 622 | CD2 | LEU | A | 87 | −1.963 | −14.803 | 41.988 | 1.00 | 50.49 | C |
| ATOM | 623 | N | THR | A | 88 | −2.934 | −9.646 | 42.830 | 1.00 | 58.36 | N |
| ATOM | 624 | CA | THR | A | 88 | −3.443 | −8.310 | 42.549 | 1.00 | 64.79 | C |
| ATOM | 625 | C | THR | A | 88 | −2.389 | −7.442 | 41.864 | 1.00 | 56.17 | C |
| ATOM | 626 | O | THR | A | 88 | −2.678 | −6.765 | 40.877 | 1.00 | 49.52 | O |
| ATOM | 627 | CB | THR | A | 88 | −3.925 | −7.610 | 43.832 | 1.00 | 75.77 | C |
| ATOM | 628 | OG1 | THR | A | 88 | −4.774 | −8.497 | 44.570 | 1.00 | 80.09 | O |
| ATOM | 629 | CG2 | THR | A | 88 | −4.695 | −6.343 | 43.491 | 1.00 | 84.70 | C |
| ATOM | 630 | N | GLN | A | 89 | −1.168 | −7.469 | 42.389 | 1.00 | 52.39 | N |
| ATOM | 631 | CA | GLN | A | 89 | −0.081 | −6.683 | 41.818 | 1.00 | 54.11 | C |
| ATOM | 632 | C | GLN | A | 89 | 0.198 | −7.093 | 40.374 | 1.00 | 56.00 | C |
| ATOM | 633 | O | GLN | A | 89 | 0.394 | −6.244 | 39.506 | 1.00 | 48.22 | O |
| ATOM | 634 | CB | GLN | A | 89 | 1.189 | −6.822 | 42.660 | 1.00 | 55.84 | C |
| ATOM | 635 | CG | GLN | A | 89 | 2.188 | −5.703 | 42.432 | 1.00 | 52.12 | C |
| ATOM | 636 | CD | GLN | A | 89 | 1.597 | −4.341 | 42.740 | 1.00 | 59.31 | C |
| ATOM | 637 | OE1 | GLN | A | 89 | 0.969 | −4.146 | 43.781 | 1.00 | 58.17 | O |
| ATOM | 638 | NE2 | GLN | A | 89 | 1.791 | −3.390 | 41.833 | 1.00 | 59.72 | N |
| ATOM | 639 | N | SER | A | 90 | 0.216 | −8.398 | 40.126 | 1.00 | 56.72 | N |
| ATOM | 640 | CA | SER | A | 90 | 0.411 | −8.919 | 38.779 | 1.00 | 50.13 | C |
| ATOM | 641 | C | SER | A | 90 | −0.632 | −8.344 | 37.827 | 1.00 | 59.38 | C |
| ATOM | 642 | O | SER | A | 90 | −0.308 | −7.917 | 36.717 | 1.00 | 61.32 | O |
| ATOM | 643 | CB | SER | A | 90 | 0.335 | −10.447 | 38.781 | 1.00 | 46.14 | C |
| ATOM | 644 | OG | SER | A | 90 | 0.525 | −10.968 | 37.477 | 1.00 | 52.69 | O |
| ATOM | 645 | N | SER | A | 91 | −1.886 | −8.338 | 38.270 | 1.00 | 60.49 | N |
| ATOM | 646 | CA | SER | A | 91 | −2.982 | −7.787 | 37.481 | 1.00 | 56.57 | C |
| ATOM | 647 | C | SER | A | 91 | −2.711 | −6.331 | 37.118 | 1.00 | 49.74 | C |
| ATOM | 648 | O | SER | A | 91 | −2.876 | −5.926 | 35.967 | 1.00 | 50.92 | O |
| ATOM | 649 | CB | SER | A | 91 | −4.302 | −7.897 | 38.248 | 1.00 | 62.44 | C |
| ATOM | 650 | OG | SER | A | 91 | −4.672 | −9.251 | 38.441 | 1.00 | 58.92 | O |
| ATOM | 651 | N | ILE | A | 92 | −2.298 | −5.549 | 38.111 | 1.00 | 46.68 | N |
| ATOM | 652 | CA | ILE | A | 92 | −1.950 | −4.150 | 37.891 | 1.00 | 52.49 | C |
| ATOM | 653 | C | ILE | A | 92 | −0.922 | −4.002 | 36.770 | 1.00 | 58.92 | C |
| ATOM | 654 | O | ILE | A | 92 | −1.103 | −3.199 | 35.855 | 1.00 | 62.73 | O |
| ATOM | 655 | CB | ILE | A | 92 | −1.411 | −3.494 | 39.178 | 1.00 | 57.59 | C |
| ATOM | 656 | CG1 | ILE | A | 92 | −2.566 | −3.137 | 40.114 | 1.00 | 53.53 | C |
| ATOM | 657 | CG2 | ILE | A | 92 | −0.607 | −2.248 | 38.848 | 1.00 | 61.25 | C |
| ATOM | 658 | CD1 | ILE | A | 92 | −3.536 | −2.141 | 39.518 | 1.00 | 60.92 | C |
| ATOM | 659 | N | PHE | A | 93 | 0.152 | −4.784 | 36.844 | 1.00 | 59.44 | N |
| ATOM | 660 | CA | PHE | A | 93 | 1.203 | −4.738 | 35.831 | 1.00 | 56.88 | C |
| ATOM | 661 | C | PHE | A | 93 | 0.677 | −5.106 | 34.445 | 1.00 | 65.10 | C |
| ATOM | 662 | O | PHE | A | 93 | 1.081 | −4.513 | 33.444 | 1.00 | 66.34 | O |
| ATOM | 663 | CB | PHE | A | 93 | 2.370 | −5.653 | 36.210 | 1.00 | 47.96 | C |
| ATOM | 664 | CG | PHE | A | 93 | 3.192 | −5.146 | 37.362 | 1.00 | 56.43 | C |
| ATOM | 665 | CD1 | PHE | A | 93 | 3.475 | −5.965 | 38.444 | 1.00 | 64.13 | C |
| ATOM | 666 | CD2 | PHE | A | 93 | 3.676 | −3.848 | 37.366 | 1.00 | 61.60 | C |
| ATOM | 667 | CE1 | PHE | A | 93 | 4.231 | −5.501 | 39.505 | 1.00 | 62.69 | C |
| ATOM | 668 | CE2 | PHE | A | 93 | 4.431 | −3.377 | 38.424 | 1.00 | 67.20 | C |
| ATOM | 669 | CZ | PHE | A | 93 | 4.710 | −4.205 | 39.495 | 1.00 | 64.16 | C |
| ATOM | 670 | N | SER | A | 94 | −0.221 | −6.085 | 34.393 | 1.00 | 65.57 | N |
| ATOM | 671 | CA | SER | A | 94 | −0.806 | −6.519 | 33.127 | 1.00 | 62.19 | C |
| ATOM | 672 | C | SER | A | 94 | −1.677 | −5.432 | 32.502 | 1.00 | 63.42 | C |
| ATOM | 673 | O | SER | A | 94 | −1.594 | −5.171 | 31.301 | 1.00 | 60.85 | O |
| ATOM | 674 | CB | SER | A | 94 | −1.616 | −7.803 | 33.314 | 1.00 | 57.22 | C |
| ATOM | 675 | OG | SER | A | 94 | −0.766 | −8.934 | 33.410 | 1.00 | 57.89 | O |
| ATOM | 676 | N | LEU | A | 95 | −2.512 | −4.803 | 33.324 | 1.00 | 60.44 | N |
| ATOM | 677 | CA | LEU | A | 95 | −3.386 | −3.733 | 32.857 | 1.00 | 57.55 | C |
| ATOM | 678 | C | LEU | A | 95 | −2.576 | −2.531 | 32.383 | 1.00 | 52.80 | C |
| ATOM | 679 | O | LEU | A | 95 | −2.923 | −1.886 | 31.395 | 1.00 | 47.83 | O |

TABLE 6-continued

HUMAN A2A ADENOSINE STRUCTURE.PDB FILE
(Table 6: discloses SEQ ID NOS 20-27, respectively, in order of appearance.)

| ATOM | 680 | CB | LEU | A | 95 | −4.356 | −3.312 | 33.963 | 1.00 | 53.01 | C |
|---|---|---|---|---|---|---|---|---|---|---|---|
| ATOM | 681 | CG | LEU | A | 95 | −5.379 | −4.362 | 34.399 | 1.00 | 50.87 | C |
| ATOM | 682 | CD1 | LEU | A | 95 | −6.207 | −3.852 | 35.568 | 1.00 | 50.15 | C |
| ATOM | 683 | CD2 | LEU | A | 95 | −6.276 | −4.754 | 33.232 | 1.00 | 40.45 | C |
| ATOM | 684 | N | LEU | A | 96 | −1.494 | −2.237 | 33.095 | 1.00 | 50.06 | N |
| ATOM | 685 | CA | LEU | A | 96 | −0.623 | −1.121 | 32.748 | 1.00 | 51.09 | C |
| ATOM | 686 | C | LEU | A | 96 | 0.064 | −1.359 | 31.404 | 1.00 | 56.60 | C |
| ATOM | 687 | O | LEU | A | 96 | 0.151 | −0.455 | 30.574 | 1.00 | 59.24 | O |
| ATOM | 688 | CB | LEU | A | 96 | 0.415 | −0.900 | 33.852 | 1.00 | 51.51 | C |
| ATOM | 689 | CG | LEU | A | 96 | 1.412 | 0.251 | 33.698 | 1.00 | 59.36 | C |
| ATOM | 690 | CD1 | LEU | A | 96 | 0.708 | 1.547 | 33.329 | 1.00 | 57.37 | C |
| ATOM | 691 | CD2 | LEU | A | 96 | 2.212 | 0.426 | 34.981 | 1.00 | 57.86 | C |
| ATOM | 692 | N | ALA | A | 97 | 0.541 | −2.582 | 31.194 | 1.00 | 54.75 | N |
| ATOM | 693 | CA | ALA | A | 97 | 1.225 | −2.938 | 29.955 | 1.00 | 48.35 | C |
| ATOM | 694 | C | ALA | A | 97 | 0.286 | −2.894 | 28.753 | 1.00 | 53.15 | C |
| ATOM | 695 | O | ALA | A | 97 | 0.710 | −2.599 | 27.636 | 1.00 | 51.29 | O |
| ATOM | 696 | CB | ALA | A | 97 | 1.864 | −4.311 | 30.080 | 1.00 | 48.03 | C |
| ATOM | 697 | N | ILE | A | 98 | −0.988 | −3.194 | 28.985 | 1.00 | 58.97 | N |
| ATOM | 698 | CA | ILE | A | 98 | −1.994 | −3.125 | 27.931 | 1.00 | 48.98 | C |
| ATOM | 699 | C | ILE | A | 98 | −2.240 | −1.678 | 27.525 | 1.00 | 47.93 | C |
| ATOM | 700 | O | ILE | A | 98 | −2.339 | −1.364 | 26.338 | 1.00 | 54.16 | O |
| ATOM | 701 | CB | ILE | A | 98 | −3.324 | −3.763 | 28.374 | 1.00 | 55.37 | C |
| ATOM | 702 | CG1 | ILE | A | 98 | −3.150 | −5.268 | 28.577 | 1.00 | 46.49 | C |
| ATOM | 703 | CG2 | ILE | A | 98 | −4.418 | −3.489 | 27.349 | 1.00 | 52.17 | C |
| ATOM | 704 | CD1 | ILE | A | 98 | −4.388 | −5.958 | 29.102 | 1.00 | 46.43 | C |
| ATOM | 705 | N | ALA | A | 99 | −2.336 | −0.798 | 28.517 | 1.00 | 51.80 | N |
| ATOM | 706 | CA | ALA | A | 99 | −2.524 | 0.626 | 28.265 | 1.00 | 48.61 | C |
| ATOM | 707 | C | ALA | A | 99 | −1.404 | 1.162 | 27.387 | 1.00 | 50.35 | C |
| ATOM | 708 | O | ALA | A | 99 | −1.654 | 1.764 | 26.343 | 1.00 | 51.87 | O |
| ATOM | 709 | CB | ALA | A | 99 | −2.581 | 1.398 | 29.577 | 1.00 | 43.48 | C |
| ATOM | 710 | N | ILE | A | 100 | −0.169 | 0.935 | 27.821 | 1.00 | 57.69 | N |
| ATOM | 711 | CA | ILE | A | 100 | 1.008 | 1.386 | 27.090 | 1.00 | 57.90 | C |
| ATOM | 712 | C | ILE | A | 100 | 1.051 | 0.801 | 25.681 | 1.00 | 63.11 | C |
| ATOM | 713 | O | ILE | A | 100 | 1.325 | 1.512 | 24.713 | 1.00 | 58.89 | O |
| ATOM | 714 | CB | ILE | A | 100 | 2.301 | 1.016 | 27.839 | 1.00 | 62.05 | C |
| ATOM | 715 | CG1 | ILE | A | 100 | 2.333 | 1.706 | 29.206 | 1.00 | 63.82 | C |
| ATOM | 716 | CG2 | ILE | A | 100 | 3.525 | 1.387 | 27.013 | 1.00 | 59.79 | C |
| ATOM | 717 | CD1 | ILE | A | 100 | 3.489 | 1.279 | 30.082 | 1.00 | 68.90 | C |
| ATOM | 718 | N | ASP | A | 101 | 0.776 | −0.495 | 25.572 | 1.00 | 64.12 | N |
| ATOM | 719 | CA | ASP | A | 101 | 0.753 | −1.160 | 24.275 | 1.00 | 60.91 | C |
| ATOM | 720 | C | ASP | A | 101 | −0.187 | −0.438 | 23.320 | 1.00 | 62.05 | C |
| ATOM | 721 | O | ASP | A | 101 | 0.175 | −0.148 | 22.180 | 1.00 | 61.91 | O |
| ATOM | 722 | CB | ASP | A | 101 | 0.318 | −2.619 | 24.419 | 1.00 | 61.47 | C |
| ATOM | 723 | CG | ASP | A | 101 | 0.215 | −3.329 | 23.081 | 1.00 | 67.28 | C |
| ATOM | 724 | OD1 | ASP | A | 101 | 1.262 | −3.532 | 22.432 | 1.00 | 69.92 | O |
| ATOM | 725 | OD2 | ASP | A | 101 | −0.912 | −3.686 | 22.680 | 1.00 | 67.78 | O |
| ATOM | 726 | N | ARG | A | 102 | −1.395 | −0.151 | 23.793 | 1.00 | 55.06 | N |
| ATOM | 727 | CA | ARG | A | 102 | −2.387 | 0.529 | 22.971 | 1.00 | 59.02 | C |
| ATOM | 728 | C | ARG | A | 102 | −1.975 | 1.970 | 22.694 | 1.00 | 70.32 | C |
| ATOM | 729 | O | ARG | A | 102 | −2.400 | 2.566 | 21.704 | 1.00 | 66.53 | O |
| ATOM | 730 | CB | ARG | A | 102 | −3.765 | 0.488 | 23.636 | 1.00 | 62.10 | C |
| ATOM | 731 | CG | ARG | A | 102 | −4.398 | −0.897 | 23.693 | 1.00 | 66.18 | C |
| ATOM | 732 | CD | ARG | A | 102 | −4.608 | −1.477 | 22.302 | 1.00 | 60.89 | C |
| ATOM | 733 | NE | ARG | A | 102 | −3.372 | −2.005 | 21.733 | 1.00 | 65.56 | N |
| ATOM | 734 | CZ | ARG | A | 102 | −3.207 | −2.306 | 20.449 | 1.00 | 58.92 | C |
| ATOM | 735 | NH1 | ARG | A | 102 | −4.202 | −2.128 | 19.591 | 1.00 | 58.23 | N |
| ATOM | 736 | NH2 | ARG | A | 102 | −2.046 | −2.780 | 20.023 | 1.00 | 53.18 | N |
| ATOM | 737 | N | TYR | A | 103 | −1.144 | 2.524 | 23.569 | 1.00 | 72.91 | N |
| ATOM | 738 | CA | TYR | A | 103 | −0.691 | 3.900 | 23.406 | 1.00 | 71.24 | C |
| ATOM | 739 | C | TYR | A | 103 | 0.229 | 4.050 | 22.200 | 1.00 | 68.76 | C |
| ATOM | 740 | O | TYR | A | 103 | −0.051 | 4.825 | 21.287 | 1.00 | 65.89 | O |
| ATOM | 741 | CB | TYR | A | 103 | 0.018 | 4.400 | 24.666 | 1.00 | 66.71 | C |
| ATOM | 742 | CG | TYR | A | 103 | 0.537 | 5.811 | 24.526 | 1.00 | 70.68 | C |
| ATOM | 743 | CD1 | TYR | A | 103 | −0.289 | 6.901 | 24.768 | 1.00 | 73.34 | C |
| ATOM | 744 | CD2 | TYR | A | 103 | 1.847 | 6.055 | 24.138 | 1.00 | 74.95 | C |
| ATOM | 745 | CE1 | TYR | A | 103 | 0.177 | 8.194 | 24.635 | 1.00 | 82.14 | C |
| ATOM | 746 | CE2 | TYR | A | 103 | 2.323 | 7.345 | 24.002 | 1.00 | 84.73 | C |
| ATOM | 747 | CZ | TYR | A | 103 | 1.484 | 8.411 | 24.253 | 1.00 | 92.43 | C |
| ATOM | 748 | OH | TYR | A | 103 | 1.952 | 9.698 | 24.119 | 1.00 | 101.50 | O |
| ATOM | 749 | N | ILE | A | 104 | 1.329 | 3.304 | 22.201 | 1.00 | 67.33 | N |
| ATOM | 750 | CA | ILE | A | 104 | 2.311 | 3.403 | 21.129 | 1.00 | 78.83 | C |
| ATOM | 751 | C | ILE | A | 104 | 1.843 | 2.710 | 19.852 | 1.00 | 78.61 | C |
| ATOM | 752 | O | ILE | A | 104 | 2.579 | 2.642 | 18.870 | 1.00 | 73.74 | O |
| ATOM | 753 | CB | ILE | A | 104 | 3.676 | 2.833 | 21.557 | 1.00 | 86.17 | C |
| ATOM | 754 | CG1 | ILE | A | 104 | 3.559 | 1.347 | 21.893 | 1.00 | 91.16 | C |
| ATOM | 755 | CG2 | ILE | A | 104 | 4.222 | 3.600 | 22.750 | 1.00 | 86.38 | C |
| ATOM | 756 | CD1 | ILE | A | 104 | 4.852 | 0.740 | 22.390 | 1.00 | 96.41 | C |

TABLE 6-continued

HUMAN A2A ADENOSINE STRUCTURE.PDB FILE
(Table 6: discloses SEQ ID NOS 20-27, respectively, in order of appearance.)

| ATOM | 757 | N | ALA | A | 105 | 0.615 | 2.202 | 19.870 | 1.00 | 81.63 | N |
|---|---|---|---|---|---|---|---|---|---|---|---|
| ATOM | 758 | CA | ALA | A | 105 | 0.045 | 1.540 | 18.702 | 1.00 | 83.62 | C |
| ATOM | 759 | C | ALA | A | 105 | −0.940 | 2.455 | 17.984 | 1.00 | 82.08 | C |
| ATOM | 760 | O | ALA | A | 105 | −1.337 | 2.190 | 16.850 | 1.00 | 87.66 | O |
| ATOM | 761 | CB | ALA | A | 105 | −0.637 | 0.242 | 19.107 | 1.00 | 86.61 | C |
| ATOM | 762 | N | ILE | A | 106 | −1.325 | 3.538 | 18.650 | 1.00 | 85.41 | N |
| ATOM | 763 | CA | ILE | A | 106 | −2.329 | 4.446 | 18.108 | 1.00 | 92.73 | C |
| ATOM | 764 | C | ILE | A | 106 | −1.768 | 5.849 | 17.868 | 1.00 | 92.39 | C |
| ATOM | 765 | O | ILE | A | 106 | −2.289 | 6.601 | 17.044 | 1.00 | 90.77 | O |
| ATOM | 766 | CB | ILE | A | 106 | −3.571 | 4.510 | 19.023 | 1.00 | 92.96 | C |
| ATOM | 767 | CG1 | ILE | A | 106 | −4.165 | 3.108 | 19.196 | 1.00 | 86.39 | C |
| ATOM | 768 | CG2 | ILE | A | 106 | −4.610 | 5.467 | 18.459 | 1.00 | 89.28 | C |
| ATOM | 769 | CD1 | ILE | A | 106 | −5.219 | 3.009 | 20.278 | 1.00 | 77.92 | C |
| ATOM | 770 | N | ARG | A | 107 | −0.700 | 6.194 | 18.579 | 1.00 | 94.13 | N |
| ATOM | 771 | CA | ARG | A | 107 | −0.072 | 7.499 | 18.407 | 1.00 | 98.93 | C |
| ATOM | 772 | C | ARG | A | 107 | 1.235 | 7.376 | 17.633 | 1.00 | 93.80 | C |
| ATOM | 773 | O | ARG | A | 107 | 1.663 | 8.317 | 16.963 | 1.00 | 89.93 | O |
| ATOM | 774 | CB | ARG | A | 107 | 0.173 | 8.169 | 19.760 | 1.00 | 113.54 | C |
| ATOM | 775 | CG | ARG | A | 107 | 0.275 | 9.685 | 19.680 | 1.00 | 125.24 | C |
| ATOM | 776 | CD | ARG | A | 107 | 0.731 | 10.291 | 20.997 | 1.00 | 130.99 | C |
| ATOM | 777 | NE | ARG | A | 107 | 2.130 | 9.988 | 21.281 | 1.00 | 135.53 | N |
| ATOM | 778 | CZ | ARG | A | 107 | 3.158 | 10.628 | 20.733 | 1.00 | 134.90 | C |
| ATOM | 779 | NH1 | ARG | A | 107 | 2.945 | 11.608 | 19.865 | 1.00 | 133.69 | N |
| ATOM | 780 | NH2 | ARG | A | 107 | 4.399 | 10.287 | 21.049 | 1.00 | 132.96 | N |
| ATOM | 781 | N | ILE | A | 108 | 1.868 | 6.210 | 17.726 | 1.00 | 93.64 | N |
| ATOM | 782 | CA | ILE | A | 108 | 3.109 | 5.944 | 17.005 | 1.00 | 93.45 | C |
| ATOM | 783 | C | ILE | A | 108 | 3.048 | 4.608 | 16.263 | 1.00 | 88.02 | C |
| ATOM | 784 | O | ILE | A | 108 | 3.827 | 3.696 | 16.558 | 1.00 | 92.18 | O |
| ATOM | 785 | CB | ILE | A | 108 | 4.317 | 5.927 | 17.960 | 1.00 | 100.66 | C |
| ATOM | 786 | CG1 | ILE | A | 108 | 4.179 | 7.020 | 19.022 | 1.00 | 108.02 | C |
| ATOM | 787 | CG2 | ILE | A | 108 | 5.617 | 6.080 | 17.183 | 1.00 | 98.70 | C |
| ATOM | 788 | CD1 | ILE | A | 108 | 5.235 | 6.960 | 20.106 | 1.00 | 111.96 | C |
| ATOM | 789 | N | PRO | A | 109 | 2.129 | 4.487 | 15.294 | 1.00 | 73.44 | N |
| ATOM | 790 | CA | PRO | A | 109 | 1.911 | 3.242 | 14.552 | 1.00 | 73.83 | C |
| ATOM | 791 | C | PRO | A | 109 | 3.099 | 2.845 | 13.678 | 1.00 | 92.11 | C |
| ATOM | 792 | O | PRO | A | 109 | 3.294 | 1.655 | 13.431 | 1.00 | 92.13 | O |
| ATOM | 793 | CB | PRO | A | 109 | 0.702 | 3.583 | 13.663 | 1.00 | 63.67 | C |
| ATOM | 794 | CG | PRO | A | 109 | 0.777 | 5.071 | 13.526 | 1.00 | 59.57 | C |
| ATOM | 795 | CD | PRO | A | 109 | 1.144 | 5.505 | 14.907 | 1.00 | 64.69 | C |
| ATOM | 796 | N | LEU | A | 110 | 3.883 | 3.818 | 13.224 | 1.00 | 104.30 | N |
| ATOM | 797 | CA | LEU | A | 110 | 4.970 | 3.547 | 12.280 | 1.00 | 104.62 | C |
| ATOM | 798 | C | LEU | A | 110 | 6.059 | 2.622 | 12.824 | 1.00 | 109.43 | C |
| ATOM | 799 | O | LEU | A | 110 | 6.735 | 1.941 | 12.053 | 1.00 | 110.68 | O |
| ATOM | 800 | CB | LEU | A | 110 | 5.585 | 4.860 | 11.773 | 1.00 | 99.55 | C |
| ATOM | 801 | CG | LEU | A | 110 | 4.733 | 5.587 | 10.723 | 1.00 | 97.53 | C |
| ATOM | 802 | CD1 | LEU | A | 110 | 5.432 | 6.856 | 10.267 | 1.00 | 100.57 | C |
| ATOM | 803 | CD2 | LEU | A | 110 | 4.455 | 4.660 | 9.554 | 1.00 | 92.50 | C |
| ATOM | 804 | N | ARG | A | 111 | 6.225 | 2.592 | 14.143 | 1.00 | 111.95 | N |
| ATOM | 805 | CA | ARG | A | 111 | 7.278 | 1.784 | 14.738 | 1.00 | 113.96 | C |
| ATOM | 806 | C | ARG | A | 111 | 6.756 | 0.874 | 15.852 | 1.00 | 103.19 | C |
| ATOM | 807 | O | ARG | A | 111 | 7.484 | 0.550 | 16.787 | 1.00 | 102.32 | O |
| ATOM | 808 | CB | ARG | A | 111 | 8.402 | 2.683 | 15.259 | 1.00 | 127.38 | C |
| ATOM | 809 | CG | ARG | A | 111 | 9.190 | 3.384 | 14.161 | 1.00 | 136.53 | C |
| ATOM | 810 | CD | ARG | A | 111 | 10.425 | 4.074 | 14.715 | 1.00 | 143.69 | C |
| ATOM | 811 | NE | ARG | A | 111 | 10.089 | 5.158 | 15.635 | 1.00 | 153.12 | N |
| ATOM | 812 | CZ | ARG | A | 111 | 9.812 | 6.405 | 15.261 | 1.00 | 159.47 | C |
| ATOM | 813 | NH1 | ARG | A | 111 | 9.827 | 6.743 | 13.976 | 1.00 | 160.35 | N |
| ATOM | 814 | NH2 | ARG | A | 111 | 9.517 | 7.318 | 16.178 | 1.00 | 161.15 | N |
| ATOM | 815 | N | TYR | A | 112 | 5.495 | 0.463 | 15.747 | 1.00 | 95.20 | N |
| ATOM | 816 | CA | TYR | A | 112 | 4.880 | −0.379 | 16.774 | 1.00 | 88.47 | C |
| ATOM | 817 | C | TYR | A | 112 | 5.393 | −1.819 | 16.742 | 1.00 | 89.26 | C |
| ATOM | 818 | O | TYR | A | 112 | 5.703 | −2.396 | 17.783 | 1.00 | 85.67 | O |
| ATOM | 819 | CB | TYR | A | 112 | 3.354 | −0.367 | 16.652 | 1.00 | 83.98 | C |
| ATOM | 820 | CG | TYR | A | 112 | 2.678 | −1.427 | 17.492 | 1.00 | 81.13 | C |
| ATOM | 821 | CD1 | TYR | A | 112 | 2.525 | −1.262 | 18.863 | 1.00 | 84.03 | C |
| ATOM | 822 | CD2 | TYR | A | 112 | 2.196 | −2.595 | 16.916 | 1.00 | 82.23 | C |
| ATOM | 823 | CE1 | TYR | A | 112 | 1.911 | −2.229 | 19.636 | 1.00 | 82.84 | C |
| ATOM | 824 | CE2 | TYR | A | 112 | 1.580 | −3.567 | 17.680 | 1.00 | 85.07 | C |
| ATOM | 825 | CZ | TYR | A | 112 | 1.440 | −3.380 | 19.039 | 1.00 | 84.45 | C |
| ATOM | 826 | OH | TYR | A | 112 | 0.826 | −4.347 | 19.803 | 1.00 | 83.19 | O |
| ATOM | 827 | N | ASN | A | 113 | 5.475 | −2.396 | 15.547 | 1.00 | 91.61 | N |
| ATOM | 828 | CA | ASN | A | 113 | 5.908 | −3.784 | 15.403 | 1.00 | 91.99 | C |
| ATOM | 829 | C | ASN | A | 113 | 7.409 | −3.970 | 15.604 | 1.00 | 86.88 | C |
| ATOM | 830 | O | ASN | A | 113 | 7.868 | −5.056 | 15.957 | 1.00 | 83.52 | O |
| ATOM | 831 | CB | ASN | A | 113 | 5.476 | −4.351 | 14.050 | 1.00 | 95.76 | C |
| ATOM | 832 | CG | ASN | A | 113 | 3.996 | −4.679 | 14.003 | 1.00 | 107.24 | C |
| ATOM | 833 | OD1 | ASN | A | 113 | 3.369 | −4.915 | 15.036 | 1.00 | 109.02 | O |

TABLE 6-continued

HUMAN A2A ADENOSINE STRUCTURE.PDB FILE
(Table 6: discloses SEQ ID NOS 20-27, respectively, in order of appearance.)

| ATOM | 834 | ND2 | ASN | A | 113 | 3.431 | −4.699 | 12.802 | 1.00 | 113.64 | N |
|---|---|---|---|---|---|---|---|---|---|---|---|
| ATOM | 835 | N | GLY | A | 114 | 8.169 | −2.904 | 15.379 | 1.00 | 87.59 | N |
| ATOM | 836 | CA | GLY | A | 114 | 9.604 | −2.939 | 15.583 | 1.00 | 94.18 | C |
| ATOM | 837 | C | GLY | A | 114 | 9.975 | −2.670 | 17.029 | 1.00 | 98.41 | C |
| ATOM | 838 | O | GLY | A | 114 | 11.121 | −2.860 | 17.436 | 1.00 | 100.84 | O |
| ATOM | 839 | N | LEU | A | 115 | 8.993 | −2.228 | 17.808 | 1.00 | 93.62 | N |
| ATOM | 840 | CA | LEU | A | 115 | 9.209 | −1.911 | 19.214 | 1.00 | 87.59 | C |
| ATOM | 841 | C | LEU | A | 115 | 8.552 | −2.959 | 20.110 | 1.00 | 86.78 | C |
| ATOM | 842 | O | LEU | A | 115 | 9.178 | −3.484 | 21.032 | 1.00 | 90.76 | O |
| ATOM | 843 | CB | LEU | A | 115 | 8.654 | −0.521 | 19.532 | 1.00 | 87.19 | C |
| ATOM | 844 | CG | LEU | A | 115 | 9.218 | 0.198 | 20.757 | 1.00 | 85.25 | C |
| ATOM | 845 | CD1 | LEU | A | 115 | 10.699 | 0.477 | 20.569 | 1.00 | 87.46 | C |
| ATOM | 846 | CD2 | LEU | A | 115 | 8.459 | 1.490 | 21.013 | 1.00 | 84.95 | C |
| ATOM | 847 | N | VAL | A | 116 | 7.288 | −3.260 | 19.828 | 1.00 | 77.94 | N |
| ATOM | 848 | CA | VAL | A | 116 | 6.538 | −4.250 | 20.592 | 1.00 | 76.88 | C |
| ATOM | 849 | C | VAL | A | 116 | 6.577 | −5.611 | 19.906 | 1.00 | 76.54 | C |
| ATOM | 850 | O | VAL | A | 116 | 5.936 | −5.813 | 18.874 | 1.00 | 70.87 | O |
| ATOM | 851 | CB | VAL | A | 116 | 5.067 | −3.827 | 20.769 | 1.00 | 74.85 | C |
| ATOM | 852 | CG1 | VAL | A | 116 | 4.298 | −4.887 | 21.537 | 1.00 | 68.42 | C |
| ATOM | 853 | CG2 | VAL | A | 116 | 4.982 | −2.486 | 21.475 | 1.00 | 75.76 | C |
| ATOM | 854 | N | THR | A | 117 | 7.331 | −6.541 | 20.484 | 1.00 | 71.30 | N |
| ATOM | 855 | CA | THR | A | 117 | 7.450 | −7.884 | 19.926 | 1.00 | 65.80 | C |
| ATOM | 856 | C | THR | A | 117 | 7.111 | −8.947 | 20.962 | 1.00 | 60.23 | C |
| ATOM | 857 | O | THR | A | 117 | 7.200 | −8.704 | 22.166 | 1.00 | 61.68 | O |
| ATOM | 858 | CB | THR | A | 117 | 8.864 | −8.148 | 19.380 | 1.00 | 64.25 | C |
| ATOM | 859 | OG1 | THR | A | 117 | 9.817 | −8.065 | 20.449 | 1.00 | 65.60 | O |
| ATOM | 860 | CG2 | THR | A | 117 | 9.217 | −7.132 | 18.304 | 1.00 | 57.57 | C |
| ATOM | 861 | N | GLY | A | 118 | 6.722 | −10.126 | 20.484 | 1.00 | 58.84 | N |
| ATOM | 862 | CA | GLY | A | 118 | 6.357 | −11.227 | 21.356 | 1.00 | 56.83 | C |
| ATOM | 863 | C | GLY | A | 118 | 7.448 | −11.582 | 22.345 | 1.00 | 59.65 | C |
| ATOM | 864 | O | GLY | A | 118 | 7.172 | −11.866 | 23.511 | 1.00 | 65.43 | O |
| ATOM | 865 | N | THR | A | 119 | 8.693 | −11.563 | 21.878 | 1.00 | 60.99 | N |
| ATOM | 866 | CA | THR | A | 119 | 9.841 | −11.877 | 22.721 | 1.00 | 63.61 | C |
| ATOM | 867 | C | THR | A | 119 | 9.944 | −10.928 | 23.910 | 1.00 | 62.11 | C |
| ATOM | 868 | O | THR | A | 119 | 10.164 | −11.357 | 25.043 | 1.00 | 60.57 | O |
| ATOM | 869 | CB | THR | A | 119 | 11.154 | −11.809 | 21.925 | 1.00 | 68.54 | C |
| ATOM | 870 | OG1 | THR | A | 119 | 11.114 | −12.758 | 20.851 | 1.00 | 69.43 | O |
| ATOM | 871 | CG2 | THR | A | 119 | 12.343 | −12.112 | 22.828 | 1.00 | 68.23 | C |
| ATOM | 872 | N | ARG | A | 120 | 9.787 | −9.636 | 23.642 | 1.00 | 58.16 | N |
| ATOM | 873 | CA | ARG | A | 120 | 9.893 | −8.621 | 24.683 | 1.00 | 65.76 | C |
| ATOM | 874 | C | ARG | A | 120 | 8.710 | −8.667 | 25.645 | 1.00 | 68.43 | C |
| ATOM | 875 | O | ARG | A | 120 | 8.876 | −8.490 | 26.853 | 1.00 | 69.60 | O |
| ATOM | 876 | CB | ARG | A | 120 | 10.034 | −7.230 | 24.060 | 1.00 | 71.97 | C |
| ATOM | 877 | CG | ARG | A | 120 | 11.309 | −7.071 | 23.250 | 1.00 | 78.55 | C |
| ATOM | 878 | CD | ARG | A | 120 | 11.456 | −5.677 | 22.670 | 1.00 | 83.21 | C |
| ATOM | 879 | NE | ARG | A | 120 | 12.730 | −5.531 | 21.974 | 1.00 | 85.78 | N |
| ATOM | 880 | CZ | ARG | A | 120 | 13.078 | −4.465 | 21.261 | 1.00 | 88.12 | C |
| ATOM | 881 | NH1 | ARG | A | 120 | 14.260 | −4.424 | 20.663 | 1.00 | 90.28 | N |
| ATOM | 882 | NH2 | ARG | A | 120 | 12.243 | −3.442 | 21.143 | 1.00 | 92.85 | N |
| ATOM | 883 | N | ALA | A | 121 | 7.520 | −8.909 | 25.106 | 1.00 | 63.83 | N |
| ATOM | 884 | CA | ALA | A | 121 | 6.324 | −9.029 | 25.931 | 1.00 | 60.03 | C |
| ATOM | 885 | C | ALA | A | 121 | 6.516 | −10.108 | 26.991 | 1.00 | 65.69 | C |
| ATOM | 886 | O | ALA | A | 121 | 6.301 | −9.869 | 28.180 | 1.00 | 65.55 | O |
| ATOM | 887 | CB | ALA | A | 121 | 5.110 | −9.337 | 25.069 | 1.00 | 58.90 | C |
| ATOM | 888 | N | LYS | A | 122 | 6.926 | −11.295 | 26.552 | 1.00 | 65.70 | N |
| ATOM | 889 | CA | LYS | A | 122 | 7.179 | −12.405 | 27.464 | 1.00 | 67.95 | C |
| ATOM | 890 | C | LYS | A | 122 | 8.228 | −12.035 | 28.508 | 1.00 | 68.55 | C |
| ATOM | 891 | O | LYS | A | 122 | 8.132 | −12.437 | 29.668 | 1.00 | 72.17 | O |
| ATOM | 892 | CB | LYS | A | 122 | 7.623 | −13.649 | 26.690 | 1.00 | 71.37 | C |
| ATOM | 893 | CG | LYS | A | 122 | 6.523 | −14.296 | 25.867 | 1.00 | 73.26 | C |
| ATOM | 894 | CD | LYS | A | 122 | 7.056 | −15.466 | 25.057 | 1.00 | 81.69 | C |
| ATOM | 895 | CE | LYS | A | 122 | 5.954 | −16.120 | 24.240 | 1.00 | 94.16 | C |
| ATOM | 896 | NZ | LYS | A | 122 | 6.467 | −17.242 | 23.405 | 1.00 | 98.43 | N |
| ATOM | 897 | N | GLY | A | 123 | 9.230 | −11.267 | 28.090 | 1.00 | 57.35 | N |
| ATOM | 898 | CA | GLY | A | 123 | 10.271 | −10.821 | 28.997 | 1.00 | 59.23 | C |
| ATOM | 899 | C | GLY | A | 123 | 9.714 | −9.933 | 30.092 | 1.00 | 63.70 | C |
| ATOM | 900 | O | GLY | A | 123 | 9.964 | −10.156 | 31.277 | 1.00 | 63.61 | O |
| ATOM | 901 | N | ILE | A | 124 | 8.951 | −8.923 | 29.690 | 1.00 | 63.36 | N |
| ATOM | 902 | CA | ILE | A | 124 | 8.350 | −7.987 | 30.631 | 1.00 | 67.49 | C |
| ATOM | 903 | C | ILE | A | 124 | 7.402 | −8.692 | 31.601 | 1.00 | 70.93 | C |
| ATOM | 904 | O | ILE | A | 124 | 7.356 | −8.363 | 32.787 | 1.00 | 66.42 | O |
| ATOM | 905 | CB | ILE | A | 124 | 7.594 | −6.867 | 29.890 | 1.00 | 64.60 | C |
| ATOM | 906 | CG1 | ILE | A | 124 | 8.578 | −6.008 | 29.091 | 1.00 | 59.98 | C |
| ATOM | 907 | CG2 | ILE | A | 124 | 6.796 | −6.018 | 30.870 | 1.00 | 57.60 | C |
| ATOM | 908 | CD1 | ILE | A | 124 | 7.918 | −5.087 | 28.085 | 1.00 | 56.97 | C |
| ATOM | 909 | N | ILE | A | 125 | 6.652 | −9.663 | 31.089 | 1.00 | 69.67 | N |
| ATOM | 910 | CA | ILE | A | 125 | 5.711 | −10.423 | 31.906 | 1.00 | 66.41 | C |

TABLE 6-continued

HUMAN A2A ADENOSINE STRUCTURE.PDB FILE
(Table 6: discloses SEQ ID NOS 20-27, respectively, in order of appearance.)

| ATOM | 911 | C | ILE | A | 125 | 6.429 | −11.197 | 33.006 | 1.00 | 64.69 | C |
|---|---|---|---|---|---|---|---|---|---|---|---|
| ATOM | 912 | O | ILE | A | 125 | 6.041 | −11.143 | 34.173 | 1.00 | 63.37 | O |
| ATOM | 913 | CB | ILE | A | 125 | 4.889 | −11.405 | 31.050 | 1.00 | 63.12 | C |
| ATOM | 914 | CG1 | ILE | A | 125 | 3.968 | −10.635 | 30.100 | 1.00 | 61.63 | C |
| ATOM | 915 | CG2 | ILE | A | 125 | 4.083 | −12.342 | 31.938 | 1.00 | 56.10 | C |
| ATOM | 916 | CD1 | ILE | A | 125 | 3.402 | −11.476 | 28.975 | 1.00 | 51.66 | C |
| ATOM | 917 | N | ALA | A | 126 | 7.479 | −11.916 | 32.624 | 1.00 | 66.05 | N |
| ATOM | 918 | CA | ALA | A | 126 | 8.261 | −12.697 | 33.575 | 1.00 | 67.52 | C |
| ATOM | 919 | C | ALA | A | 126 | 8.763 | −11.818 | 34.714 | 1.00 | 64.64 | C |
| ATOM | 920 | O | ALA | A | 126 | 8.674 | −12.190 | 35.884 | 1.00 | 67.81 | O |
| ATOM | 921 | CB | ALA | A | 126 | 9.428 | −13.376 | 32.872 | 1.00 | 62.18 | C |
| ATOM | 922 | N | ILE | A | 127 | 9.288 | −10.650 | 34.361 | 1.00 | 63.73 | N |
| ATOM | 923 | CA | ILE | A | 127 | 9.822 | −9.716 | 35.345 | 1.00 | 67.95 | C |
| ATOM | 924 | C | ILE | A | 127 | 8.728 | −9.206 | 36.280 | 1.00 | 66.97 | C |
| ATOM | 925 | O | ILE | A | 127 | 8.937 | −9.082 | 37.487 | 1.00 | 61.28 | O |
| ATOM | 926 | CB | ILE | A | 127 | 10.510 | −8.519 | 34.661 | 1.00 | 70.20 | C |
| ATOM | 927 | CG1 | ILE | A | 127 | 11.572 | −9.010 | 33.677 | 1.00 | 68.52 | C |
| ATOM | 928 | CG2 | ILE | A | 127 | 11.130 | −7.593 | 35.696 | 1.00 | 74.05 | C |
| ATOM | 929 | CD1 | ILE | A | 127 | 12.282 | −7.897 | 32.940 | 1.00 | 72.14 | C |
| ATOM | 930 | N | CYS | A | 128 | 7.559 | −8.918 | 35.717 | 1.00 | 63.06 | N |
| ATOM | 931 | CA | CYS | A | 128 | 6.446 | −8.396 | 36.500 | 1.00 | 54.69 | C |
| ATOM | 932 | C | CYS | A | 128 | 5.929 | −9.405 | 37.523 | 1.00 | 49.73 | C |
| ATOM | 933 | O | CYS | A | 128 | 5.450 | −9.022 | 38.589 | 1.00 | 52.32 | O |
| ATOM | 934 | CB | CYS | A | 128 | 5.312 | −7.932 | 35.585 | 1.00 | 66.50 | C |
| ATOM | 935 | SG | CYS | A | 128 | 5.681 | −6.422 | 34.666 | 1.00 | 74.56 | S |
| ATOM | 936 | N | TRP | A | 129 | 6.023 | −10.691 | 37.201 | 1.00 | 51.13 | N |
| ATOM | 937 | CA | TRP | A | 129 | 5.634 | −11.733 | 38.147 | 1.00 | 52.40 | C |
| ATOM | 938 | C | TRP | A | 129 | 6.621 | −11.815 | 39.309 | 1.00 | 56.96 | C |
| ATOM | 939 | O | TRP | A | 129 | 6.234 | −12.091 | 40.444 | 1.00 | 66.31 | O |
| ATOM | 940 | CB | TRP | A | 129 | 5.504 | −13.092 | 37.453 | 1.00 | 48.49 | C |
| ATOM | 941 | CG | TRP | A | 129 | 4.171 | −13.305 | 36.794 | 1.00 | 51.24 | C |
| ATOM | 942 | CD1 | TRP | A | 129 | 3.890 | −13.210 | 35.462 | 1.00 | 59.03 | C |
| ATOM | 943 | CD2 | TRP | A | 129 | 2.937 | −13.645 | 37.441 | 1.00 | 43.56 | C |
| ATOM | 944 | NE1 | TRP | A | 129 | 2.559 | −13.472 | 35.240 | 1.00 | 57.23 | N |
| ATOM | 945 | CE2 | TRP | A | 129 | 1.953 | −13.742 | 36.438 | 1.00 | 49.30 | C |
| ATOM | 946 | CE3 | TRP | A | 129 | 2.571 | −13.878 | 38.770 | 1.00 | 49.07 | C |
| ATOM | 947 | CZ2 | TRP | A | 129 | 0.626 | −14.061 | 36.722 | 1.00 | 45.75 | C |
| ATOM | 948 | CZ3 | TRP | A | 129 | 1.252 | −14.194 | 39.051 | 1.00 | 46.69 | C |
| ATOM | 949 | CH2 | TRP | A | 129 | 0.296 | −14.283 | 38.031 | 1.00 | 41.88 | C |
| ATOM | 950 | N | VAL | A | 130 | 7.896 | −11.572 | 39.022 | 1.00 | 52.61 | N |
| ATOM | 951 | CA | VAL | A | 130 | 8.919 | −11.549 | 40.059 | 1.00 | 56.34 | C |
| ATOM | 952 | C | VAL | A | 130 | 8.679 | −10.394 | 41.025 | 1.00 | 64.62 | C |
| ATOM | 953 | O | VAL | A | 130 | 8.685 | −10.579 | 42.242 | 1.00 | 67.44 | O |
| ATOM | 954 | CB | VAL | A | 130 | 10.330 | −11.417 | 39.461 | 1.00 | 60.77 | C |
| ATOM | 955 | CG1 | VAL | A | 130 | 11.360 | −11.244 | 40.568 | 1.00 | 56.40 | C |
| ATOM | 956 | CG2 | VAL | A | 130 | 10.656 | −12.629 | 38.604 | 1.00 | 63.46 | C |
| ATOM | 957 | N | LEU | A | 131 | 8.469 | −9.201 | 40.475 | 1.00 | 63.64 | N |
| ATOM | 958 | CA | LEU | A | 131 | 8.192 | −8.021 | 41.287 | 1.00 | 62.11 | C |
| ATOM | 959 | C | LEU | A | 131 | 6.918 | −8.208 | 42.099 | 1.00 | 58.39 | C |
| ATOM | 960 | O | LEU | A | 131 | 6.829 | −7.758 | 43.240 | 1.00 | 62.62 | O |
| ATOM | 961 | CB | LEU | A | 131 | 8.063 | −6.776 | 40.407 | 1.00 | 66.71 | C |
| ATOM | 962 | CG | LEU | A | 131 | 9.301 | −6.326 | 39.633 | 1.00 | 67.88 | C |
| ATOM | 963 | CD1 | LEU | A | 131 | 8.978 | −5.100 | 38.796 | 1.00 | 68.03 | C |
| ATOM | 964 | CD2 | LEU | A | 131 | 10.451 | −6.042 | 40.584 | 1.00 | 73.75 | C |
| ATOM | 965 | N | SER | A | 132 | 5.933 | −8.871 | 41.501 | 1.00 | 54.97 | N |
| ATOM | 966 | CA | SER | A | 132 | 4.658 | −9.114 | 42.167 | 1.00 | 56.03 | C |
| ATOM | 967 | C | SER | A | 132 | 4.842 | −9.945 | 43.435 | 1.00 | 59.03 | C |
| ATOM | 968 | O | SER | A | 132 | 4.230 | −9.663 | 44.465 | 1.00 | 58.03 | O |
| ATOM | 969 | CB | SER | A | 132 | 3.675 | −9.802 | 41.217 | 1.00 | 57.35 | C |
| ATOM | 970 | OG | SER | A | 132 | 3.337 | −8.956 | 40.130 | 1.00 | 56.09 | O |
| ATOM | 971 | N | PHE | A | 133 | 5.686 | −10.969 | 43.354 | 1.00 | 53.41 | N |
| ATOM | 972 | CA | PHE | A | 133 | 6.003 | −11.781 | 44.524 | 1.00 | 57.98 | C |
| ATOM | 973 | C | PHE | A | 133 | 6.777 | −10.967 | 45.557 | 1.00 | 62.28 | C |
| ATOM | 974 | O | PHE | A | 133 | 6.518 | −11.060 | 46.756 | 1.00 | 62.05 | O |
| ATOM | 975 | CB | PHE | A | 133 | 6.801 | −13.025 | 44.125 | 1.00 | 55.72 | C |
| ATOM | 976 | CG | PHE | A | 133 | 5.944 | −14.177 | 43.686 | 1.00 | 59.06 | C |
| ATOM | 977 | CD1 | PHE | A | 133 | 5.632 | −14.357 | 42.348 | 1.00 | 60.09 | C |
| ATOM | 978 | CD2 | PHE | A | 133 | 5.445 | −15.078 | 44.613 | 1.00 | 63.30 | C |
| ATOM | 979 | CE1 | PHE | A | 133 | 4.839 | −15.416 | 41.943 | 1.00 | 62.08 | C |
| ATOM | 980 | CE2 | PHE | A | 133 | 4.651 | −16.138 | 44.216 | 1.00 | 64.41 | C |
| ATOM | 981 | CZ | PHE | A | 133 | 4.348 | −16.307 | 42.879 | 1.00 | 64.42 | C |
| ATOM | 982 | N | ALA | A | 134 | 7.726 | −10.168 | 45.079 | 1.00 | 62.65 | N |
| ATOM | 983 | CA | ALA | A | 134 | 8.536 | −9.328 | 45.953 | 1.00 | 58.86 | C |
| ATOM | 984 | C | ALA | A | 134 | 7.674 | −8.318 | 46.702 | 1.00 | 56.08 | C |
| ATOM | 985 | O | ALA | A | 134 | 7.892 | −8.057 | 47.884 | 1.00 | 57.64 | O |
| ATOM | 986 | CB | ALA | A | 134 | 9.613 | −8.614 | 45.147 | 1.00 | 56.23 | C |
| ATOM | 987 | N | ILE | A | 135 | 6.693 | −7.754 | 46.006 | 1.00 | 59.20 | N |

TABLE 6-continued

HUMAN A2A ADENOSINE STRUCTURE.PDB FILE
(Table 6: discloses SEQ ID NOS 20-27, respectively, in order of appearance.)

| ATOM | 988 | CA | ILE | A | 135 | 5.815 | −6.748 | 46.591 | 1.00 | 62.08 | C |
|---|---|---|---|---|---|---|---|---|---|---|---|
| ATOM | 989 | C | ILE | A | 135 | 4.731 | −7.376 | 47.463 | 1.00 | 59.08 | C |
| ATOM | 990 | O | ILE | A | 135 | 4.510 | −6.950 | 48.597 | 1.00 | 65.05 | O |
| ATOM | 991 | CB | ILE | A | 135 | 5.152 | −5.881 | 45.500 | 1.00 | 65.36 | C |
| ATOM | 992 | CG1 | ILE | A | 135 | 6.211 | −5.073 | 44.746 | 1.00 | 64.34 | C |
| ATOM | 993 | CG2 | ILE | A | 135 | 4.104 | −4.960 | 46.108 | 1.00 | 61.49 | C |
| ATOM | 994 | CD1 | ILE | A | 135 | 5.666 | −4.310 | 43.557 | 1.00 | 64.42 | C |
| ATOM | 995 | N | GLY | A | 136 | 4.060 | −8.392 | 46.931 | 1.00 | 47.67 | N |
| ATOM | 996 | CA | GLY | A | 136 | 2.968 | −9.037 | 47.638 | 1.00 | 48.58 | C |
| ATOM | 997 | C | GLY | A | 136 | 3.391 | −9.763 | 48.902 | 1.00 | 57.36 | C |
| ATOM | 998 | O | GLY | A | 136 | 2.628 | −9.840 | 49.865 | 1.00 | 58.29 | O |
| ATOM | 999 | N | LEU | A | 137 | 4.608 | −10.297 | 48.902 | 1.00 | 66.46 | N |
| ATOM | 1000 | CA | LEU | A | 137 | 5.096 | −11.071 | 50.039 | 1.00 | 63.23 | C |
| ATOM | 1001 | C | LEU | A | 137 | 6.127 | −10.304 | 50.861 | 1.00 | 66.91 | C |
| ATOM | 1002 | O | LEU | A | 137 | 6.957 | −10.903 | 51.544 | 1.00 | 64.37 | O |
| ATOM | 1003 | CB | LEU | A | 137 | 5.681 | −12.404 | 49.569 | 1.00 | 63.17 | C |
| ATOM | 1004 | CG | LEU | A | 137 | 4.679 | −13.392 | 48.968 | 1.00 | 64.82 | C |
| ATOM | 1005 | CD1 | LEU | A | 137 | 5.353 | −14.717 | 48.646 | 1.00 | 62.63 | C |
| ATOM | 1006 | CD2 | LEU | A | 137 | 3.496 | −13.597 | 49.906 | 1.00 | 58.64 | C |
| ATOM | 1007 | N | THR | A | 138 | 6.067 | −8.978 | 50.794 | 1.00 | 72.48 | N |
| ATOM | 1008 | CA | THR | A | 138 | 6.975 | −8.126 | 51.558 | 1.00 | 69.66 | C |
| ATOM | 1009 | C | THR | A | 138 | 6.856 | −8.334 | 53.071 | 1.00 | 61.71 | C |
| ATOM | 1010 | O | THR | A | 138 | 7.867 | −8.362 | 53.773 | 1.00 | 60.72 | O |
| ATOM | 1011 | CB | THR | A | 138 | 6.783 | −6.631 | 51.218 | 1.00 | 65.16 | C |
| ATOM | 1012 | OG1 | THR | A | 138 | 7.358 | −6.354 | 49.935 | 1.00 | 63.90 | O |
| ATOM | 1013 | CG2 | THR | A | 138 | 7.456 | −5.755 | 52.261 | 1.00 | 64.16 | C |
| ATOM | 1014 | N | PRO | A | 139 | 5.620 | −8.472 | 53.582 | 1.00 | 57.22 | N |
| ATOM | 1015 | CA | PRO | A | 139 | 5.457 | −8.731 | 55.018 | 1.00 | 63.21 | C |
| ATOM | 1016 | C | PRO | A | 139 | 6.185 | −10.000 | 55.452 | 1.00 | 68.08 | C |
| ATOM | 1017 | O | PRO | A | 139 | 6.656 | −10.084 | 56.586 | 1.00 | 67.41 | O |
| ATOM | 1018 | CB | PRO | A | 139 | 3.945 | −8.909 | 55.170 | 1.00 | 52.42 | C |
| ATOM | 1019 | CG | PRO | A | 139 | 3.364 | −8.127 | 54.046 | 1.00 | 55.59 | C |
| ATOM | 1020 | CD | PRO | A | 139 | 4.323 | −8.300 | 52.904 | 1.00 | 49.95 | C |
| ATOM | 1021 | N | MET | A | 140 | 6.272 | −10.974 | 54.551 | 1.00 | 73.20 | N |
| ATOM | 1022 | CA | MET | A | 140 | 6.982 | −12.217 | 54.829 | 1.00 | 76.09 | C |
| ATOM | 1023 | C | MET | A | 140 | 8.487 | −12.004 | 54.924 | 1.00 | 82.03 | C |
| ATOM | 1024 | O | MET | A | 140 | 9.203 | −12.822 | 55.500 | 1.00 | 83.70 | O |
| ATOM | 1025 | CB | MET | A | 140 | 6.685 | −13.262 | 53.752 | 1.00 | 70.94 | C |
| ATOM | 1026 | CG | MET | A | 140 | 5.535 | −14.193 | 54.080 | 1.00 | 69.49 | C |
| ATOM | 1027 | SD | MET | A | 140 | 5.659 | −15.729 | 53.147 | 1.00 | 85.83 | S |
| ATOM | 1028 | CE | MET | A | 140 | 7.396 | −16.107 | 53.368 | 1.00 | 82.79 | C |
| ATOM | 1029 | N | LEU | A | 141 | 8.963 | −10.904 | 54.350 | 1.00 | 83.94 | N |
| ATOM | 1030 | CA | LEU | A | 141 | 10.393 | −10.622 | 54.313 | 1.00 | 84.78 | C |
| ATOM | 1031 | C | LEU | A | 141 | 10.873 | −9.915 | 55.578 | 1.00 | 84.45 | C |
| ATOM | 1032 | O | LEU | A | 141 | 12.075 | −9.742 | 55.780 | 1.00 | 83.38 | O |
| ATOM | 1033 | CB | LEU | A | 141 | 10.743 | −9.794 | 53.073 | 1.00 | 84.57 | C |
| ATOM | 1034 | CG | LEU | A | 141 | 10.203 | −10.324 | 51.742 | 1.00 | 84.86 | C |
| ATOM | 1035 | CD1 | LEU | A | 141 | 10.617 | −9.419 | 50.593 | 1.00 | 86.16 | C |
| ATOM | 1036 | CD2 | LEU | A | 141 | 10.668 | −11.749 | 51.497 | 1.00 | 86.17 | C |
| ATOM | 1037 | N | GLY | A | 142 | 9.935 | −9.506 | 56.428 | 1.00 | 79.23 | N |
| ATOM | 1038 | CA | GLY | A | 142 | 10.290 | −8.891 | 57.696 | 1.00 | 80.80 | C |
| ATOM | 1039 | C | GLY | A | 142 | 9.340 | −7.814 | 58.186 | 1.00 | 80.96 | C |
| ATOM | 1040 | O | GLY | A | 142 | 9.326 | −7.488 | 59.374 | 1.00 | 78.36 | O |
| ATOM | 1041 | N | TRP | A | 143 | 8.546 | −7.259 | 57.275 | 1.00 | 76.74 | N |
| ATOM | 1042 | CA | TRP | A | 143 | 7.622 | −6.181 | 57.613 | 1.00 | 68.29 | C |
| ATOM | 1043 | C | TRP | A | 143 | 6.319 | −6.726 | 58.203 | 1.00 | 71.50 | C |
| ATOM | 1044 | O | TRP | A | 143 | 5.253 | −6.584 | 57.602 | 1.00 | 72.95 | O |
| ATOM | 1045 | CB | TRP | A | 143 | 7.314 | −5.346 | 56.368 | 1.00 | 64.17 | C |
| ATOM | 1046 | CG | TRP | A | 143 | 6.819 | −3.961 | 56.662 | 1.00 | 62.07 | C |
| ATOM | 1047 | CD1 | TRP | A | 143 | 6.288 | −3.511 | 57.837 | 1.00 | 60.98 | C |
| ATOM | 1048 | CD2 | TRP | A | 143 | 6.785 | −2.851 | 55.756 | 1.00 | 61.23 | C |
| ATOM | 1049 | NE1 | TRP | A | 143 | 5.940 | −2.186 | 57.722 | 1.00 | 64.65 | N |
| ATOM | 1050 | CE2 | TRP | A | 143 | 6.233 | −1.758 | 56.453 | 1.00 | 65.50 | C |
| ATOM | 1051 | CE3 | TRP | A | 143 | 7.173 | −2.673 | 54.423 | 1.00 | 56.46 | C |
| ATOM | 1052 | CZ2 | TRP | A | 143 | 6.058 | −0.506 | 55.865 | 1.00 | 58.65 | C |
| ATOM | 1053 | CZ3 | TRP | A | 143 | 6.999 | −1.429 | 53.841 | 1.00 | 56.45 | C |
| ATOM | 1054 | CH2 | TRP | A | 143 | 6.446 | −0.363 | 54.561 | 1.00 | 53.43 | C |
| ATOM | 1055 | N | ASN | A | 144 | 6.403 | −7.343 | 59.379 | 1.00 | 66.92 | N |
| ATOM | 1056 | CA | ASN | A | 144 | 5.231 | −7.962 | 60.000 | 1.00 | 75.59 | C |
| ATOM | 1057 | C | ASN | A | 144 | 5.113 | −7.717 | 61.506 | 1.00 | 87.35 | C |
| ATOM | 1058 | O | ASN | A | 144 | 5.944 | −7.030 | 62.100 | 1.00 | 93.88 | O |
| ATOM | 1059 | CB | ASN | A | 144 | 5.199 | −9.463 | 59.708 | 1.00 | 81.45 | C |
| ATOM | 1060 | CG | ASN | A | 144 | 6.464 | −10.170 | 60.150 | 1.00 | 80.28 | C |
| ATOM | 1061 | OD1 | ASN | A | 144 | 7.568 | −9.803 | 59.749 | 1.00 | 82.07 | O |
| ATOM | 1062 | ND2 | ASN | A | 144 | 6.308 | −11.195 | 60.977 | 1.00 | 79.90 | N |
| ATOM | 1063 | N | ASN | A | 145 | 4.079 | −8.295 | 62.115 | 1.00 | 92.12 | N |
| ATOM | 1064 | CA | ASN | A | 145 | 3.756 | −8.029 | 63.517 | 1.00 | 95.13 | C |

TABLE 6-continued

HUMAN A2A ADENOSINE STRUCTURE.PDB FILE
(Table 6: discloses SEQ ID NOS 20-27, respectively, in order of appearance.)

| ATOM | 1065 | C | ASN | A | 145 | 3.725 | −9.256 | 64.428 | 1.00 | 100.95 | C |
|---|---|---|---|---|---|---|---|---|---|---|---|
| ATOM | 1066 | O | ASN | A | 145 | 3.019 | −9.259 | 65.435 | 1.00 | 97.13 | O |
| ATOM | 1067 | CB | ASN | A | 145 | 2.407 | −7.309 | 63.620 | 1.00 | 91.48 | C |
| ATOM | 1068 | CG | ASN | A | 145 | 2.509 | −5.829 | 63.319 | 1.00 | 87.59 | C |
| ATOM | 1069 | OD1 | ASN | A | 145 | 3.601 | −5.297 | 63.124 | 1.00 | 87.87 | O |
| ATOM | 1070 | ND2 | ASN | A | 145 | 1.367 | −5.154 | 63.286 | 1.00 | 84.05 | N |
| ATOM | 1071 | N | CYS | A | 146 | 4.485 | −10.291 | 64.089 | 1.00 | 110.01 | N |
| ATOM | 1072 | CA | CYS | A | 146 | 4.487 | −11.502 | 64.906 | 1.00 | 116.37 | C |
| ATOM | 1073 | C | CYS | A | 146 | 5.882 | −11.946 | 65.346 | 1.00 | 118.97 | C |
| ATOM | 1074 | O | CYS | A | 146 | 6.025 | −12.650 | 66.344 | 1.00 | 122.98 | O |
| ATOM | 1075 | CB | CYS | A | 146 | 3.759 | −12.645 | 64.188 | 1.00 | 117.89 | C |
| ATOM | 1076 | SG | CYS | A | 146 | 3.952 | −12.663 | 62.391 | 1.00 | 97.28 | S |
| ATOM | 1077 | N | GLY | A | 147 | 6.905 | −11.521 | 64.610 | 1.00 | 114.76 | N |
| ATOM | 1078 | CA | GLY | A | 147 | 8.267 | −11.965 | 64.858 | 1.00 | 114.32 | C |
| ATOM | 1079 | C | GLY | A | 147 | 8.875 | −11.540 | 66.189 | 1.00 | 115.40 | C |
| ATOM | 1080 | O | GLY | A | 147 | 10.058 | −11.784 | 66.440 | 1.00 | 115.94 | O |
| ATOM | 1081 | N | GLN | A | 148 | 8.079 | −10.902 | 67.044 | 1.00 | 113.07 | N |
| ATOM | 1082 | CA | GLN | A | 148 | 8.567 | −10.430 | 68.338 | 1.00 | 107.89 | C |
| ATOM | 1083 | C | GLN | A | 148 | 7.638 | −10.822 | 69.482 | 1.00 | 106.38 | C |
| ATOM | 1084 | O | GLN | A | 148 | 7.580 | −10.132 | 70.504 | 1.00 | 108.96 | O |
| ATOM | 1085 | CB | GLN | A | 148 | 8.768 | −8.910 | 68.322 | 1.00 | 109.08 | C |
| ATOM | 1086 | CG | GLN | A | 148 | 9.661 | −8.423 | 67.187 | 1.00 | 118.94 | C |
| ATOM | 1087 | CD | GLN | A | 148 | 9.839 | −6.918 | 67.194 | 1.00 | 125.94 | C |
| ATOM | 1088 | OE1 | GLN | A | 148 | 9.347 | −6.228 | 68.091 | 1.00 | 126.37 | O |
| ATOM | 1089 | NE2 | GLN | A | 148 | 10.546 | −6.398 | 66.192 | 1.00 | 128.16 | N |
| ATOM | 1090 | N | SER | A | 156 | 0.404 | −12.289 | 72.202 | 1.00 | 111.40 | N |
| ATOM | 1091 | CA | SER | A | 156 | −0.282 | −13.281 | 71.371 | 1.00 | 112.40 | C |
| ATOM | 1092 | C | SER | A | 156 | −0.539 | −14.545 | 72.189 | 1.00 | 107.10 | C |
| ATOM | 1093 | O | SER | A | 156 | 0.276 | −15.461 | 72.196 | 1.00 | 104.13 | O |
| ATOM | 1094 | CB | SER | A | 156 | 0.596 | −13.645 | 70.188 | 1.00 | 111.11 | C |
| ATOM | 1095 | OG | SER | A | 156 | 1.652 | −14.476 | 70.673 | 1.00 | 112.97 | O |
| ATOM | 1096 | N | GLN | A | 157 | −1.667 | −14.594 | 72.888 | 1.00 | 100.11 | N |
| ATOM | 1097 | CA | GLN | A | 157 | −1.926 | −15.727 | 73.767 | 1.00 | 94.42 | C |
| ATOM | 1098 | C | GLN | A | 157 | −3.155 | −16.519 | 73.335 | 1.00 | 83.00 | C |
| ATOM | 1099 | O | GLN | A | 157 | −3.948 | −16.067 | 72.517 | 1.00 | 80.27 | O |
| ATOM | 1100 | CB | GLN | A | 157 | −2.061 | −15.267 | 75.222 | 1.00 | 99.49 | C |
| ATOM | 1101 | CG | GLN | A | 157 | −1.568 | −16.284 | 76.241 | 1.00 | 102.47 | C |
| ATOM | 1102 | CD | GLN | A | 157 | −2.217 | −16.109 | 77.595 | 1.00 | 106.85 | C |
| ATOM | 1103 | OE1 | GLN | A | 157 | −3.440 | −16.023 | 77.703 | 1.00 | 105.71 | O |
| ATOM | 1104 | NE2 | GLN | A | 157 | −1.399 | −16.062 | 78.640 | 1.00 | 107.96 | N |
| ATOM | 1105 | N | GLY | A | 158 | −3.296 | −17.713 | 73.899 | 1.00 | 70.83 | N |
| ATOM | 1106 | CA | GLY | A | 158 | −4.361 | −18.620 | 73.510 | 1.00 | 66.83 | C |
| ATOM | 1107 | C | GLY | A | 158 | −3.947 | −19.530 | 72.372 | 1.00 | 62.79 | C |
| ATOM | 1108 | O | GLY | A | 158 | −4.712 | −20.390 | 71.938 | 1.00 | 57.38 | O |
| ATOM | 1109 | N | CYS | A | 159 | −2.720 | −19.346 | 71.894 | 1.00 | 60.35 | N |
| ATOM | 1110 | CA | CYS | A | 159 | −2.212 | −20.099 | 70.749 | 1.00 | 56.16 | C |
| ATOM | 1111 | C | CYS | A | 159 | −0.913 | −20.843 | 71.049 | 1.00 | 59.17 | C |
| ATOM | 1112 | O | CYS | A | 159 | −0.459 | −21.661 | 70.245 | 1.00 | 62.23 | O |
| ATOM | 1113 | CB | CYS | A | 159 | −2.004 | −19.174 | 69.545 | 1.00 | 49.69 | C |
| ATOM | 1114 | SG | CYS | A | 159 | −3.513 | −18.788 | 68.628 | 1.00 | 72.63 | S |
| ATOM | 1115 | N | GLY | A | 160 | −0.317 | −20.564 | 72.203 | 1.00 | 66.01 | N |
| ATOM | 1116 | CA | GLY | A | 160 | 0.970 | −21.143 | 72.543 | 1.00 | 65.87 | C |
| ATOM | 1117 | C | GLY | A | 160 | 2.084 | −20.457 | 71.774 | 1.00 | 66.73 | C |
| ATOM | 1118 | O | GLY | A | 160 | 1.859 | −19.944 | 70.680 | 1.00 | 69.74 | O |
| ATOM | 1119 | N | GLU | A | 161 | 3.286 | −20.445 | 72.340 | 1.00 | 65.22 | N |
| ATOM | 1120 | CA | GLU | A | 161 | 4.407 | −19.747 | 71.717 | 1.00 | 68.91 | C |
| ATOM | 1121 | C | GLU | A | 161 | 4.747 | −20.351 | 70.356 | 1.00 | 65.43 | C |
| ATOM | 1122 | O | GLU | A | 161 | 4.569 | −21.549 | 70.135 | 1.00 | 66.94 | O |
| ATOM | 1123 | CB | GLU | A | 161 | 5.636 | −19.772 | 72.630 | 1.00 | 71.19 | C |
| ATOM | 1124 | CG | GLU | A | 161 | 6.546 | −20.964 | 72.411 | 1.00 | 79.99 | C |
| ATOM | 1125 | CD | GLU | A | 161 | 7.555 | −20.737 | 71.297 | 1.00 | 87.71 | C |
| ATOM | 1126 | OE1 | GLU | A | 161 | 7.966 | −21.727 | 70.655 | 1.00 | 86.91 | O |
| ATOM | 1127 | OE2 | GLU | A | 161 | 7.935 | −19.569 | 71.062 | 1.00 | 81.83 | O |
| ATOM | 1128 | N | GLY | A | 162 | 5.239 | −19.513 | 69.449 | 1.00 | 61.92 | N |
| ATOM | 1129 | CA | GLY | A | 162 | 5.580 | −19.956 | 68.110 | 1.00 | 62.74 | C |
| ATOM | 1130 | C | GLY | A | 162 | 4.385 | −19.899 | 67.179 | 1.00 | 74.95 | C |
| ATOM | 1131 | O | GLY | A | 162 | 4.497 | −20.193 | 65.989 | 1.00 | 82.12 | O |
| ATOM | 1132 | N | GLN | A | 163 | 3.235 | −19.521 | 67.729 | 1.00 | 70.48 | N |
| ATOM | 1133 | CA | GLN | A | 163 | 2.011 | −19.408 | 66.949 | 1.00 | 61.37 | C |
| ATOM | 1134 | C | GLN | A | 163 | 1.238 | −18.150 | 67.316 | 1.00 | 66.77 | C |
| ATOM | 1135 | O | GLN | A | 163 | 1.364 | −17.629 | 68.423 | 1.00 | 66.40 | O |
| ATOM | 1136 | CB | GLN | A | 163 | 1.124 | −20.639 | 67.149 | 1.00 | 56.01 | C |
| ATOM | 1137 | CG | GLN | A | 163 | 1.701 | −21.921 | 66.569 | 1.00 | 57.63 | C |
| ATOM | 1138 | CD | GLN | A | 163 | 0.712 | −23.067 | 66.591 | 1.00 | 63.91 | C |
| ATOM | 1139 | OE1 | GLN | A | 163 | −0.417 | −22.920 | 67.058 | 1.00 | 77.41 | O |
| ATOM | 1140 | NE2 | GLN | A | 163 | 1.131 | −24.219 | 66.083 | 1.00 | 65.43 | N |
| ATOM | 1141 | N | VAL | A | 164 | 0.441 | −17.666 | 66.371 | 1.00 | 68.38 | N |

TABLE 6-continued

HUMAN A2A ADENOSINE STRUCTURE.PDB FILE
(Table 6: discloses SEQ ID NOS 20-27, respectively, in order of appearance.)

| ATOM | 1142 | CA  | VAL | A | 164 | −0.407 | −16.505 | 66.599 | 1.00 | 64.31 | C |
|------|------|-----|-----|---|-----|--------|---------|--------|------|-------|---|
| ATOM | 1143 | C   | VAL | A | 164 | −1.750 | −16.717 | 65.915 | 1.00 | 62.35 | C |
| ATOM | 1144 | O   | VAL | A | 164 | −1.836 | −17.431 | 64.911 | 1.00 | 59.38 | O |
| ATOM | 1145 | CB  | VAL | A | 164 | 0.248  | −15.213 | 66.062 | 1.00 | 64.38 | C |
| ATOM | 1146 | CG1 | VAL | A | 164 | 1.561  | −14.941 | 66.784 | 1.00 | 66.59 | C |
| ATOM | 1147 | CG2 | VAL | A | 164 | 0.472  | −15.312 | 64.562 | 1.00 | 63.12 | C |
| ATOM | 1148 | N   | ALA | A | 165 | −2.797 | −16.118 | 66.470 | 1.00 | 61.77 | N |
| ATOM | 1149 | CA  | ALA | A | 165 | −4.095 | −16.130 | 65.820 | 1.00 | 56.63 | C |
| ATOM | 1150 | C   | ALA | A | 165 | −3.971 | −15.429 | 64.470 | 1.00 | 63.41 | C |
| ATOM | 1151 | O   | ALA | A | 165 | −3.533 | −14.280 | 64.394 | 1.00 | 57.69 | O |
| ATOM | 1152 | CB  | ALA | A | 165 | −5.130 | −15.433 | 66.691 | 1.00 | 49.04 | C |
| ATOM | 1153 | N   | CYS | A | 166 | −4.338 | −16.132 | 63.405 | 1.00 | 64.32 | N |
| ATOM | 1154 | CA  | CYS | A | 166 | −4.200 | −15.593 | 62.058 | 1.00 | 60.34 | C |
| ATOM | 1155 | C   | CYS | A | 166 | −5.343 | −14.641 | 61.704 | 1.00 | 64.43 | C |
| ATOM | 1156 | O   | CYS | A | 166 | −6.267 | −15.006 | 60.974 | 1.00 | 58.57 | O |
| ATOM | 1157 | CB  | CYS | A | 166 | −4.111 | −16.722 | 61.027 | 1.00 | 60.31 | C |
| ATOM | 1158 | SG  | CYS | A | 166 | −3.427 | −16.200 | 59.438 | 1.00 | 79.30 | S |
| ATOM | 1159 | N   | LEU | A | 167 | −5.277 | −13.425 | 62.239 | 1.00 | 65.97 | N |
| ATOM | 1160 | CA  | LEU | A | 167 | −6.210 | −12.364 | 61.866 | 1.00 | 59.40 | C |
| ATOM | 1161 | C   | LEU | A | 167 | −5.485 | −11.335 | 61.004 | 1.00 | 62.14 | C |
| ATOM | 1162 | O   | LEU | A | 167 | −4.439 | −10.812 | 61.395 | 1.00 | 71.58 | O |
| ATOM | 1163 | CB  | LEU | A | 167 | −6.805 | −11.687 | 63.105 | 1.00 | 65.79 | C |
| ATOM | 1164 | CG  | LEU | A | 167 | −7.879 | −12.449 | 63.888 | 1.00 | 66.75 | C |
| ATOM | 1165 | CD1 | LEU | A | 167 | −8.728 | −13.298 | 62.950 | 1.00 | 67.83 | C |
| ATOM | 1166 | CD2 | LEU | A | 167 | −7.272 | −13.293 | 64.998 | 1.00 | 63.93 | C |
| ATOM | 1167 | N   | PHE | A | 168 | −6.043 | −11.050 | 59.832 | 1.00 | 57.68 | N |
| ATOM | 1168 | CA  | PHE | A | 168 | −5.392 | −10.180 | 58.855 | 1.00 | 61.62 | C |
| ATOM | 1169 | C   | PHE | A | 168 | −4.815 | −8.905  | 59.469 | 1.00 | 64.22 | C |
| ATOM | 1170 | O   | PHE | A | 168 | −3.625 | −8.626  | 59.329 | 1.00 | 63.81 | O |
| ATOM | 1171 | CB  | PHE | A | 168 | −6.361 | −9.824  | 57.722 | 1.00 | 60.06 | C |
| ATOM | 1172 | CG  | PHE | A | 168 | −5.702 | −9.158  | 56.547 | 1.00 | 56.89 | C |
| ATOM | 1173 | CD1 | PHE | A | 168 | −5.178 | −9.912  | 55.511 | 1.00 | 57.97 | C |
| ATOM | 1174 | CD2 | PHE | A | 168 | −5.604 | −7.778  | 56.481 | 1.00 | 50.90 | C |
| ATOM | 1175 | CE1 | PHE | A | 168 | −4.570 | −9.303  | 54.430 | 1.00 | 53.39 | C |
| ATOM | 1176 | CE2 | PHE | A | 168 | −4.999 | −7.164  | 55.403 | 1.00 | 51.56 | C |
| ATOM | 1177 | CZ  | PHE | A | 168 | −4.481 | −7.928  | 54.376 | 1.00 | 55.14 | C |
| ATOM | 1178 | N   | GLU | A | 169 | −5.658 | −8.138  | 60.152 | 1.00 | 63.54 | N |
| ATOM | 1179 | CA  | GLU | A | 169 | −5.236 | −6.854  | 60.705 | 1.00 | 64.21 | C |
| ATOM | 1180 | C   | GLU | A | 169 | −4.296 | −7.006  | 61.901 | 1.00 | 64.27 | C |
| ATOM | 1181 | O   | GLU | A | 169 | −3.751 | −6.020  | 62.401 | 1.00 | 59.89 | O |
| ATOM | 1182 | CB  | GLU | A | 169 | −6.452 | −6.003  | 61.084 | 1.00 | 55.80 | C |
| ATOM | 1183 | CG  | GLU | A | 169 | −7.340 | −5.634  | 59.902 | 1.00 | 58.23 | C |
| ATOM | 1184 | CD  | GLU | A | 169 | −8.281 | −4.483  | 60.211 | 1.00 | 67.89 | C |
| ATOM | 1185 | OE1 | GLU | A | 169 | −8.210 | −3.933  | 61.331 | 1.00 | 75.11 | O |
| ATOM | 1186 | OE2 | GLU | A | 169 | −9.091 | −4.125  | 59.330 | 1.00 | 66.46 | O |
| ATOM | 1187 | N   | ASP | A | 170 | −4.105 | −8.242  | 62.351 | 1.00 | 62.92 | N |
| ATOM | 1188 | CA  | ASP | A | 170 | −3.244 | −8.516  | 63.497 | 1.00 | 59.97 | C |
| ATOM | 1189 | C   | ASP | A | 170 | −1.823 | −8.886  | 63.083 | 1.00 | 65.64 | C |
| ATOM | 1190 | O   | ASP | A | 170 | −0.885 | −8.737  | 63.865 | 1.00 | 69.78 | O |
| ATOM | 1191 | CB  | ASP | A | 170 | −3.835 | −9.636  | 64.356 | 1.00 | 62.46 | C |
| ATOM | 1192 | CG  | ASP | A | 170 | −5.020 | −9.178  | 65.178 | 1.00 | 75.69 | C |
| ATOM | 1193 | OD1 | ASP | A | 170 | −5.343 | −7.972  | 65.141 | 1.00 | 83.95 | O |
| ATOM | 1194 | OD2 | ASP | A | 170 | −5.627 | −10.025 | 65.866 | 1.00 | 79.29 | O |
| ATOM | 1195 | N   | VAL | A | 171 | −1.667 | −9.373  | 61.856 | 1.00 | 60.84 | N |
| ATOM | 1196 | CA  | VAL | A | 171 | −0.364 | −9.830  | 61.386 | 1.00 | 61.36 | C |
| ATOM | 1197 | C   | VAL | A | 171 | 0.179  | −8.978  | 60.242 | 1.00 | 65.06 | C |
| ATOM | 1198 | O   | VAL | A | 171 | 1.393  | −8.847  | 60.080 | 1.00 | 65.39 | O |
| ATOM | 1199 | CB  | VAL | A | 171 | −0.404 | −11.312 | 60.954 | 1.00 | 62.30 | C |
| ATOM | 1200 | CG1 | VAL | A | 171 | −0.679 | −12.205 | 62.152 | 1.00 | 50.95 | C |
| ATOM | 1201 | CG2 | VAL | A | 171 | −1.452 | −11.527 | 59.872 | 1.00 | 68.11 | C |
| ATOM | 1202 | N   | VAL | A | 172 | −0.722 | −8.402  | 59.452 | 1.00 | 59.35 | N |
| ATOM | 1203 | CA  | VAL | A | 172 | −0.325 | −7.558  | 58.330 | 1.00 | 59.25 | C |
| ATOM | 1204 | C   | VAL | A | 172 | −0.389 | −6.081  | 58.704 | 1.00 | 62.38 | C |
| ATOM | 1205 | O   | VAL | A | 172 | −1.473 | −5.528  | 58.879 | 1.00 | 67.88 | O |
| ATOM | 1206 | CB  | VAL | A | 172 | −1.216 | −7.800  | 57.096 | 1.00 | 59.89 | C |
| ATOM | 1207 | CG1 | VAL | A | 172 | −0.686 | −7.023  | 55.898 | 1.00 | 46.18 | C |
| ATOM | 1208 | CG2 | VAL | A | 172 | −1.296 | −9.288  | 56.781 | 1.00 | 61.29 | C |
| ATOM | 1209 | N   | PRO | A | 173 | 0.783  | −5.438  | 58.826 | 1.00 | 60.75 | N |
| ATOM | 1210 | CA  | PRO | A | 173 | 0.900  | −4.022  | 59.193 | 1.00 | 54.18 | C |
| ATOM | 1211 | C   | PRO | A | 173 | 0.084  | −3.110  | 58.278 | 1.00 | 57.11 | C |
| ATOM | 1212 | O   | PRO | A | 173 | 0.177  | −3.217  | 57.055 | 1.00 | 63.59 | O |
| ATOM | 1213 | CB  | PRO | A | 173 | 2.394  | −3.740  | 59.014 | 1.00 | 52.86 | C |
| ATOM | 1214 | CG  | PRO | A | 173 | 3.049  | −5.061  | 59.201 | 1.00 | 57.54 | C |
| ATOM | 1215 | CD  | PRO | A | 173 | 2.099  | −6.068  | 58.626 | 1.00 | 61.28 | C |
| ATOM | 1216 | N   | MET | A | 174 | −0.700 | −2.215  | 58.873 | 1.00 | 55.18 | N |
| ATOM | 1217 | CA  | MET | A | 174 | −1.556 | −1.314  | 58.107 | 1.00 | 54.70 | C |
| ATOM | 1218 | C   | MET | A | 174 | −0.770 | −0.258  | 57.339 | 1.00 | 56.48 | C |

TABLE 6-continued

HUMAN A2A ADENOSINE STRUCTURE.PDB FILE
(Table 6: discloses SEQ ID NOS 20-27, respectively, in order of appearance.)

| ATOM | 1219 | O | MET | A | 174 | −1.190 | 0.171 | 56.264 | 1.00 | 63.66 | O |
|---|---|---|---|---|---|---|---|---|---|---|---|
| ATOM | 1220 | CB | MET | A | 174 | −2.594 | −0.649 | 59.010 | 1.00 | 64.19 | C |
| ATOM | 1221 | CG | MET | A | 174 | −3.827 | −1.503 | 59.263 | 1.00 | 80.62 | C |
| ATOM | 1222 | SD | MET | A | 174 | −4.686 | −1.938 | 57.736 | 1.00 | 83.53 | S |
| ATOM | 1223 | CE | MET | A | 174 | −4.860 | −0.325 | 56.985 | 1.00 | 73.80 | C |
| ATOM | 1224 | N | ASN | A | 175 | 0.364 | 0.165 | 57.887 | 1.00 | 60.71 | N |
| ATOM | 1225 | CA | ASN | A | 175 | 1.216 | 1.123 | 57.191 | 1.00 | 66.17 | C |
| ATOM | 1226 | C | ASN | A | 175 | 1.737 | 0.544 | 55.877 | 1.00 | 67.79 | C |
| ATOM | 1227 | O | ASN | A | 175 | 2.000 | 1.275 | 54.922 | 1.00 | 68.29 | O |
| ATOM | 1228 | CB | ASN | A | 175 | 2.368 | 1.605 | 58.082 | 1.00 | 66.08 | C |
| ATOM | 1229 | CG | ASN | A | 175 | 3.259 | 0.473 | 58.556 | 1.00 | 69.42 | C |
| ATOM | 1230 | OD1 | ASN | A | 175 | 2.891 | −0.698 | 58.481 | 1.00 | 80.66 | O |
| ATOM | 1231 | ND2 | ASN | A | 175 | 4.440 | 0.822 | 59.054 | 1.00 | 57.73 | N |
| ATOM | 1232 | N | TYR | A | 176 | 1.873 | −0.777 | 55.835 | 1.00 | 64.10 | N |
| ATOM | 1233 | CA | TYR | A | 176 | 2.216 | −1.469 | 54.602 | 1.00 | 57.17 | C |
| ATOM | 1234 | C | TYR | A | 176 | 1.033 | −1.439 | 53.639 | 1.00 | 56.23 | C |
| ATOM | 1235 | O | TYR | A | 176 | 1.189 | −1.150 | 52.453 | 1.00 | 58.62 | O |
| ATOM | 1236 | CB | TYR | A | 176 | 2.610 | −2.921 | 54.889 | 1.00 | 61.45 | C |
| ATOM | 1237 | CG | TYR | A | 176 | 2.598 | −3.802 | 53.658 | 1.00 | 63.69 | C |
| ATOM | 1238 | CD1 | TYR | A | 176 | 1.463 | −4.523 | 53.307 | 1.00 | 56.39 | C |
| ATOM | 1239 | CD2 | TYR | A | 176 | 3.717 | −3.905 | 52.842 | 1.00 | 61.88 | C |
| ATOM | 1240 | CE1 | TYR | A | 176 | 1.445 | −5.323 | 52.181 | 1.00 | 59.28 | C |
| ATOM | 1241 | CE2 | TYR | A | 176 | 3.709 | −4.703 | 51.715 | 1.00 | 57.78 | C |
| ATOM | 1242 | CZ | TYR | A | 176 | 2.571 | −5.410 | 51.389 | 1.00 | 65.29 | C |
| ATOM | 1243 | OH | TYR | A | 176 | 2.558 | −6.206 | 50.267 | 1.00 | 76.04 | O |
| ATOM | 1244 | N | MET | A | 177 | −0.151 | −1.738 | 54.165 | 1.00 | 54.66 | N |
| ATOM | 1245 | CA | MET | A | 177 | −1.358 | −1.824 | 53.351 | 1.00 | 50.97 | C |
| ATOM | 1246 | C | MET | A | 177 | −1.750 | −0.485 | 52.736 | 1.00 | 59.97 | C |
| ATOM | 1247 | O | MET | A | 177 | −2.261 | −0.434 | 51.618 | 1.00 | 59.12 | O |
| ATOM | 1248 | CB | MET | A | 177 | −2.520 | −2.380 | 54.177 | 1.00 | 45.66 | C |
| ATOM | 1249 | CG | MET | A | 177 | −2.387 | −3.855 | 54.509 | 1.00 | 45.51 | C |
| ATOM | 1250 | SD | MET | A | 177 | −2.208 | −4.878 | 53.030 | 1.00 | 60.18 | S |
| ATOM | 1251 | CE | MET | A | 177 | −3.760 | −4.553 | 52.203 | 1.00 | 62.04 | C |
| ATOM | 1252 | N | VAL | A | 178 | −1.508 | 0.596 | 53.469 | 1.00 | 68.22 | N |
| ATOM | 1253 | CA | VAL | A | 178 | −1.914 | 1.923 | 53.020 | 1.00 | 61.62 | C |
| ATOM | 1254 | C | VAL | A | 178 | −0.839 | 2.623 | 52.191 | 1.00 | 57.36 | C |
| ATOM | 1255 | O | VAL | A | 178 | −1.091 | 3.040 | 51.062 | 1.00 | 55.42 | O |
| ATOM | 1256 | CB | VAL | A | 178 | −2.308 | 2.819 | 54.208 | 1.00 | 61.78 | C |
| ATOM | 1257 | CG1 | VAL | A | 178 | −2.574 | 4.239 | 53.733 | 1.00 | 62.82 | C |
| ATOM | 1258 | CG2 | VAL | A | 178 | −3.529 | 2.248 | 54.914 | 1.00 | 46.74 | C |
| ATOM | 1259 | N | TYR | A | 179 | 0.359 | 2.747 | 52.755 | 1.00 | 59.67 | N |
| ATOM | 1260 | CA | TYR | A | 179 | 1.442 | 3.465 | 52.089 | 1.00 | 59.72 | C |
| ATOM | 1261 | C | TYR | A | 179 | 2.035 | 2.699 | 50.912 | 1.00 | 60.59 | C |
| ATOM | 1262 | O | TYR | A | 179 | 2.060 | 3.195 | 49.787 | 1.00 | 55.02 | O |
| ATOM | 1263 | CB | TYR | A | 179 | 2.547 | 3.822 | 53.085 | 1.00 | 63.83 | C |
| ATOM | 1264 | CG | TYR | A | 179 | 2.148 | 4.896 | 54.067 | 1.00 | 68.94 | C |
| ATOM | 1265 | CD1 | TYR | A | 179 | 2.201 | 4.669 | 55.435 | 1.00 | 75.25 | C |
| ATOM | 1266 | CD2 | TYR | A | 179 | 1.705 | 6.135 | 53.624 | 1.00 | 65.23 | C |
| ATOM | 1267 | CE1 | TYR | A | 179 | 1.833 | 5.650 | 56.336 | 1.00 | 76.87 | C |
| ATOM | 1268 | CE2 | TYR | A | 179 | 1.334 | 7.119 | 54.515 | 1.00 | 68.86 | C |
| ATOM | 1269 | CZ | TYR | A | 179 | 1.400 | 6.873 | 55.869 | 1.00 | 76.23 | C |
| ATOM | 1270 | OH | TYR | A | 179 | 1.029 | 7.854 | 56.755 | 1.00 | 81.33 | O |
| ATOM | 1271 | N | PHE | A | 180 | 2.517 | 1.490 | 51.176 | 1.00 | 73.26 | N |
| ATOM | 1272 | CA | PHE | A | 180 | 3.219 | 0.722 | 50.155 | 1.00 | 72.52 | C |
| ATOM | 1273 | C | PHE | A | 180 | 2.264 | 0.072 | 49.157 | 1.00 | 72.33 | C |
| ATOM | 1274 | O | PHE | A | 180 | 2.359 | 0.307 | 47.953 | 1.00 | 72.48 | O |
| ATOM | 1275 | CB | PHE | A | 180 | 4.126 | −0.329 | 50.798 | 1.00 | 59.61 | C |
| ATOM | 1276 | CG | PHE | A | 180 | 5.168 | −0.875 | 49.869 | 1.00 | 63.52 | C |
| ATOM | 1277 | CD1 | PHE | A | 180 | 6.067 | −0.027 | 49.245 | 1.00 | 70.73 | C |
| ATOM | 1278 | CD2 | PHE | A | 180 | 5.254 | −2.234 | 49.621 | 1.00 | 69.38 | C |
| ATOM | 1279 | CE1 | PHE | A | 180 | 7.030 | −0.524 | 48.387 | 1.00 | 73.13 | C |
| ATOM | 1280 | CE2 | PHE | A | 180 | 6.217 | −2.738 | 48.765 | 1.00 | 71.19 | C |
| ATOM | 1281 | CZ | PHE | A | 180 | 7.105 | −1.881 | 48.148 | 1.00 | 65.78 | C |
| ATOM | 1282 | N | ASN | A | 181 | 1.342 | −0.741 | 49.660 | 1.00 | 67.41 | N |
| ATOM | 1283 | CA | ASN | A | 181 | 0.401 | −1.434 | 48.792 | 1.00 | 71.02 | C |
| ATOM | 1284 | C | ASN | A | 181 | −0.528 | −0.479 | 48.051 | 1.00 | 64.24 | C |
| ATOM | 1285 | O | ASN | A | 181 | −0.493 | −0.397 | 46.825 | 1.00 | 72.23 | O |
| ATOM | 1286 | CB | ASN | A | 181 | −0.412 | −2.465 | 49.578 | 1.00 | 78.04 | C |
| ATOM | 1287 | CG | ASN | A | 181 | −1.188 | −3.404 | 48.675 | 1.00 | 78.10 | C |
| ATOM | 1288 | OD1 | ASN | A | 181 | −2.225 | −3.038 | 48.120 | 1.00 | 77.60 | O |
| ATOM | 1289 | ND2 | ASN | A | 181 | −0.688 | −4.626 | 48.525 | 1.00 | 77.14 | N |
| ATOM | 1290 | N | PHE | A | 182 | −1.355 | 0.248 | 48.795 | 1.00 | 57.68 | N |
| ATOM | 1291 | CA | PHE | A | 182 | −2.356 | 1.106 | 48.172 | 1.00 | 61.54 | C |
| ATOM | 1292 | C | PHE | A | 182 | −1.764 | 2.290 | 47.404 | 1.00 | 62.62 | C |
| ATOM | 1293 | O | PHE | A | 182 | −1.845 | 2.338 | 46.178 | 1.00 | 73.99 | O |
| ATOM | 1294 | CB | PHE | A | 182 | −3.385 | 1.593 | 49.195 | 1.00 | 60.03 | C |
| ATOM | 1295 | CG | PHE | A | 182 | −4.462 | 2.457 | 48.598 | 1.00 | 59.95 | C |

TABLE 6-continued

HUMAN A2A ADENOSINE STRUCTURE.PDB FILE
(Table 6: discloses SEQ ID NOS 20-27, respectively, in order of appearance.)

| ATOM | 1296 | CD1 | PHE | A | 182 | −5.027 | 2.133 | 47.374 | 1.00 | 61.17 | C |
|---|---|---|---|---|---|---|---|---|---|---|---|
| ATOM | 1297 | CD2 | PHE | A | 182 | −4.915 | 3.585 | 49.260 | 1.00 | 59.97 | C |
| ATOM | 1298 | CE1 | PHE | A | 182 | −6.016 | 2.922 | 46.819 | 1.00 | 61.56 | C |
| ATOM | 1299 | CE2 | PHE | A | 182 | −5.906 | 4.378 | 48.710 | 1.00 | 60.08 | C |
| ATOM | 1300 | CZ | PHE | A | 182 | −6.458 | 4.045 | 47.488 | 1.00 | 60.69 | C |
| ATOM | 1301 | N | PHE | A | 183 | −1.170 | 3.238 | 48.121 | 1.00 | 55.81 | N |
| ATOM | 1302 | CA | PHE | A | 183 | −0.698 | 4.473 | 47.496 | 1.00 | 61.65 | C |
| ATOM | 1303 | C | PHE | A | 183 | 0.335 | 4.250 | 46.393 | 1.00 | 61.58 | C |
| ATOM | 1304 | O | PHE | A | 183 | 0.170 | 4.735 | 45.274 | 1.00 | 70.29 | O |
| ATOM | 1305 | CB | PHE | A | 183 | −0.140 | 5.445 | 48.543 | 1.00 | 64.59 | C |
| ATOM | 1306 | CG | PHE | A | 183 | −1.187 | 6.043 | 49.439 | 1.00 | 71.80 | C |
| ATOM | 1307 | CD1 | PHE | A | 183 | −2.462 | 6.300 | 48.963 | 1.00 | 75.59 | C |
| ATOM | 1308 | CD2 | PHE | A | 183 | −0.890 | 6.366 | 50.753 | 1.00 | 70.99 | C |
| ATOM | 1309 | CE1 | PHE | A | 183 | −3.427 | 6.855 | 49.785 | 1.00 | 66.70 | C |
| ATOM | 1310 | CE2 | PHE | A | 183 | −1.850 | 6.923 | 51.578 | 1.00 | 67.93 | C |
| ATOM | 1311 | CZ | PHE | A | 183 | −3.119 | 7.167 | 51.093 | 1.00 | 62.56 | C |
| ATOM | 1312 | N | ALA | A | 184 | 1.394 | 3.514 | 46.709 | 1.00 | 57.06 | N |
| ATOM | 1313 | CA | ALA | A | 184 | 2.518 | 3.367 | 45.789 | 1.00 | 58.06 | C |
| ATOM | 1314 | C | ALA | A | 184 | 2.287 | 2.334 | 44.686 | 1.00 | 62.96 | C |
| ATOM | 1315 | O | ALA | A | 184 | 2.670 | 2.550 | 43.536 | 1.00 | 65.83 | O |
| ATOM | 1316 | CB | ALA | A | 184 | 3.791 | 3.040 | 46.561 | 1.00 | 54.29 | C |
| ATOM | 1317 | N | CYS | A | 185 | 1.661 | 1.215 | 45.036 | 1.00 | 56.66 | N |
| ATOM | 1318 | CA | CYS | A | 185 | 1.569 | 0.082 | 44.118 | 1.00 | 55.19 | C |
| ATOM | 1319 | C | CYS | A | 185 | 0.235 | −0.043 | 43.378 | 1.00 | 59.96 | C |
| ATOM | 1320 | O | CYS | A | 185 | 0.155 | −0.719 | 42.352 | 1.00 | 59.75 | O |
| ATOM | 1321 | CB | CYS | A | 185 | 1.891 | −1.221 | 44.855 | 1.00 | 55.70 | C |
| ATOM | 1322 | SG | CYS | A | 185 | 3.576 | −1.303 | 45.509 | 1.00 | 62.88 | S |
| ATOM | 1323 | N | VAL | A | 186 | −0.806 | 0.605 | 43.889 | 1.00 | 56.67 | N |
| ATOM | 1324 | CA | VAL | A | 186 | −2.122 | 0.523 | 43.263 | 1.00 | 58.12 | C |
| ATOM | 1325 | C | VAL | A | 186 | −2.606 | 1.877 | 42.747 | 1.00 | 60.90 | C |
| ATOM | 1326 | O | VAL | A | 186 | −2.959 | 2.017 | 41.575 | 1.00 | 61.38 | O |
| ATOM | 1327 | CB | VAL | A | 186 | −3.173 | −0.054 | 44.231 | 1.00 | 52.12 | C |
| ATOM | 1328 | CG1 | VAL | A | 186 | −4.548 | −0.076 | 43.574 | 1.00 | 47.03 | C |
| ATOM | 1329 | CG2 | VAL | A | 186 | −2.766 | −1.448 | 44.683 | 1.00 | 51.28 | C |
| ATOM | 1330 | N | LEU | A | 187 | −2.618 | 2.869 | 43.629 | 1.00 | 54.09 | N |
| ATOM | 1331 | CA | LEU | A | 187 | −3.128 | 4.194 | 43.294 | 1.00 | 63.42 | C |
| ATOM | 1332 | C | LEU | A | 187 | −2.351 | 4.839 | 42.146 | 1.00 | 65.18 | C |
| ATOM | 1333 | O | LEU | A | 187 | −2.945 | 5.354 | 41.197 | 1.00 | 59.97 | O |
| ATOM | 1334 | CB | LEU | A | 187 | −3.109 | 5.097 | 44.531 | 1.00 | 65.01 | C |
| ATOM | 1335 | CG | LEU | A | 187 | −3.723 | 6.494 | 44.406 | 1.00 | 63.23 | C |
| ATOM | 1336 | CD1 | LEU | A | 187 | −5.079 | 6.436 | 43.722 | 1.00 | 59.81 | C |
| ATOM | 1337 | CD2 | LEU | A | 187 | −3.839 | 7.147 | 45.775 | 1.00 | 61.29 | C |
| ATOM | 1338 | N | VAL | A | 188 | −1.025 | 4.802 | 42.234 | 1.00 | 60.55 | N |
| ATOM | 1339 | CA | VAL | A | 188 | −0.168 | 5.419 | 41.224 | 1.00 | 59.28 | C |
| ATOM | 1340 | C | VAL | A | 188 | −0.351 | 4.819 | 39.825 | 1.00 | 68.51 | C |
| ATOM | 1341 | O | VAL | A | 188 | −0.502 | 5.556 | 38.851 | 1.00 | 74.08 | O |
| ATOM | 1342 | CB | VAL | A | 188 | 1.322 | 5.376 | 41.633 | 1.00 | 55.93 | C |
| ATOM | 1343 | CG1 | VAL | A | 188 | 2.210 | 5.755 | 40.458 | 1.00 | 58.79 | C |
| ATOM | 1344 | CG2 | VAL | A | 188 | 1.571 | 6.297 | 42.818 | 1.00 | 49.67 | C |
| ATOM | 1345 | N | PRO | A | 189 | −0.329 | 3.479 | 39.718 | 1.00 | 67.42 | N |
| ATOM | 1346 | CA | PRO | A | 189 | −0.566 | 2.835 | 38.421 | 1.00 | 62.87 | C |
| ATOM | 1347 | C | PRO | A | 189 | −1.943 | 3.153 | 37.838 | 1.00 | 63.18 | C |
| ATOM | 1348 | O | PRO | A | 189 | −2.050 | 3.392 | 36.636 | 1.00 | 64.19 | O |
| ATOM | 1349 | CB | PRO | A | 189 | −0.467 | 1.343 | 38.750 | 1.00 | 68.30 | C |
| ATOM | 1350 | CG | PRO | A | 189 | 0.411 | 1.285 | 39.947 | 1.00 | 67.94 | C |
| ATOM | 1351 | CD | PRO | A | 189 | 0.064 | 2.502 | 40.749 | 1.00 | 67.68 | C |
| ATOM | 1352 | N | LEU | A | 190 | −2.976 | 3.153 | 38.676 | 1.00 | 59.02 | N |
| ATOM | 1353 | CA | LEU | A | 190 | −4.333 | 3.444 | 38.216 | 1.00 | 64.13 | C |
| ATOM | 1354 | C | LEU | A | 190 | −4.454 | 4.841 | 37.610 | 1.00 | 64.10 | C |
| ATOM | 1355 | O | LEU | A | 190 | −5.047 | 5.013 | 36.546 | 1.00 | 62.95 | O |
| ATOM | 1356 | CB | LEU | A | 190 | −5.345 | 3.273 | 39.352 | 1.00 | 66.37 | C |
| ATOM | 1357 | CG | LEU | A | 190 | −5.760 | 1.839 | 39.684 | 1.00 | 66.79 | C |
| ATOM | 1358 | CD1 | LEU | A | 190 | −6.728 | 1.818 | 40.858 | 1.00 | 68.63 | C |
| ATOM | 1359 | CD2 | LEU | A | 190 | −6.377 | 1.164 | 38.467 | 1.00 | 65.21 | C |
| ATOM | 1360 | N | LEU | A | 191 | −3.897 | 5.836 | 38.293 | 1.00 | 65.09 | N |
| ATOM | 1361 | CA | LEU | A | 191 | −3.911 | 7.204 | 37.783 | 1.00 | 66.12 | C |
| ATOM | 1362 | C | LEU | A | 191 | −3.065 | 7.314 | 36.521 | 1.00 | 64.56 | C |
| ATOM | 1363 | O | LEU | A | 191 | −3.392 | 8.068 | 35.603 | 1.00 | 56.85 | O |
| ATOM | 1364 | CB | LEU | A | 191 | −3.414 | 8.188 | 38.844 | 1.00 | 65.00 | C |
| ATOM | 1365 | CG | LEU | A | 191 | −4.337 | 8.405 | 40.047 | 1.00 | 70.15 | C |
| ATOM | 1366 | CD1 | LEU | A | 191 | −3.940 | 9.659 | 40.809 | 1.00 | 70.66 | C |
| ATOM | 1367 | CD2 | LEU | A | 191 | −5.794 | 8.478 | 39.608 | 1.00 | 69.85 | C |
| ATOM | 1368 | N | LEU | A | 192 | −1.975 | 6.555 | 36.483 | 1.00 | 66.12 | N |
| ATOM | 1369 | CA | LEU | A | 192 | −1.107 | 6.519 | 35.315 | 1.00 | 62.98 | C |
| ATOM | 1370 | C | LEU | A | 192 | −1.847 | 5.907 | 34.130 | 1.00 | 61.93 | C |
| ATOM | 1371 | O | LEU | A | 192 | −1.710 | 6.367 | 32.998 | 1.00 | 66.81 | O |
| ATOM | 1372 | CB | LEU | A | 192 | 0.163 | 5.724 | 35.617 | 1.00 | 68.96 | C |

TABLE 6-continued

HUMAN A2A ADENOSINE STRUCTURE.PDB FILE
(Table 6: discloses SEQ ID NOS 20-27, respectively, in order of appearance.)

| ATOM | 1373 | CG  | LEU | A | 192 | 1.253   | 5.763  | 34.547 | 1.00 | 83.35  | C |
|------|------|-----|-----|---|-----|---------|--------|--------|------|--------|---|
| ATOM | 1374 | CD1 | LEU | A | 192 | 1.642   | 7.200  | 34.240 | 1.00 | 86.74  | C |
| ATOM | 1375 | CD2 | LEU | A | 192 | 2.466   | 4.959  | 34.992 | 1.00 | 88.80  | C |
| ATOM | 1376 | N   | MET | A | 193 | −2.634  | 4.870  | 34.401 | 1.00 | 62.18  | N |
| ATOM | 1377 | CA  | MET | A | 193 | −3.447  | 4.235  | 33.369 | 1.00 | 59.56  | C |
| ATOM | 1378 | C   | MET | A | 193 | −4.597  | 5.137  | 32.935 | 1.00 | 59.47  | C |
| ATOM | 1379 | O   | MET | A | 193 | −5.082  | 5.041  | 31.808 | 1.00 | 61.31  | O |
| ATOM | 1380 | CB  | MET | A | 193 | −3.987  | 2.888  | 33.854 | 1.00 | 61.23  | C |
| ATOM | 1381 | CG  | MET | A | 193 | −2.996  | 1.744  | 33.719 | 1.00 | 72.09  | C |
| ATOM | 1382 | SD  | MET | A | 193 | −3.674  | 0.150  | 34.221 | 1.00 | 72.44  | S |
| ATOM | 1383 | CE  | MET | A | 193 | −3.505  | 0.246  | 36.002 | 1.00 | 49.34  | C |
| ATOM | 1384 | N   | LEU | A | 194 | −5.032  | 6.011  | 33.835 | 1.00 | 55.36  | N |
| ATOM | 1385 | CA  | LEU | A | 194 | −6.098  | 6.952  | 33.522 | 1.00 | 50.67  | C |
| ATOM | 1386 | C   | LEU | A | 194 | −5.593  | 8.018  | 32.560 | 1.00 | 53.56  | C |
| ATOM | 1387 | O   | LEU | A | 194 | −6.285  | 8.394  | 31.614 | 1.00 | 60.12  | O |
| ATOM | 1388 | CB  | LEU | A | 194 | −6.639  | 7.600  | 34.797 | 1.00 | 57.62  | C |
| ATOM | 1389 | CG  | LEU | A | 194 | −7.751  | 8.635  | 34.613 | 1.00 | 64.63  | C |
| ATOM | 1390 | CD1 | LEU | A | 194 | −8.880  | 8.074  | 33.760 | 1.00 | 56.30  | C |
| ATOM | 1391 | CD2 | LEU | A | 194 | −8.278  | 9.100  | 35.963 | 1.00 | 67.95  | C |
| ATOM | 1392 | N   | GLY | A | 195 | −4.379  | 8.499  | 32.806 | 1.00 | 55.54  | N |
| ATOM | 1393 | CA  | GLY | A | 195 | −3.775  | 9.507  | 31.956 | 1.00 | 58.98  | C |
| ATOM | 1394 | C   | GLY | A | 195 | −3.492  | 8.991  | 30.559 | 1.00 | 58.15  | C |
| ATOM | 1395 | O   | GLY | A | 195 | −3.694  | 9.698  | 29.572 | 1.00 | 57.74  | O |
| ATOM | 1396 | N   | VAL | A | 196 | −3.024  | 7.750  | 30.474 | 1.00 | 55.91  | N |
| ATOM | 1397 | CA  | VAL | A | 196 | −2.691  | 7.143  | 29.190 | 1.00 | 51.58  | C |
| ATOM | 1398 | C   | VAL | A | 196 | −3.923  | 6.951  | 28.310 | 1.00 | 51.36  | C |
| ATOM | 1399 | O   | VAL | A | 196 | −3.912  | 7.306  | 27.131 | 1.00 | 53.56  | O |
| ATOM | 1400 | CB  | VAL | A | 196 | −1.985  | 5.787  | 29.369 | 1.00 | 50.58  | C |
| ATOM | 1401 | CG1 | VAL | A | 196 | −1.747  | 5.134  | 28.018 | 1.00 | 50.07  | C |
| ATOM | 1402 | CG2 | VAL | A | 196 | −0.677  | 5.969  | 30.120 | 1.00 | 51.69  | C |
| ATOM | 1403 | N   | TYR | A | 197 | −4.981  | 6.386  | 28.882 | 1.00 | 48.78  | N |
| ATOM | 1404 | CA  | TYR | A | 197 | −6.213  | 6.167  | 28.133 | 1.00 | 53.66  | C |
| ATOM | 1405 | C   | TYR | A | 197 | −6.853  | 7.482  | 27.710 | 1.00 | 56.74  | C |
| ATOM | 1406 | O   | TYR | A | 197 | −7.323  | 7.614  | 26.580 | 1.00 | 62.83  | O |
| ATOM | 1407 | CB  | TYR | A | 197 | −7.203  | 5.313  | 28.930 | 1.00 | 58.80  | C |
| ATOM | 1408 | CG  | TYR | A | 197 | −7.000  | 3.826  | 28.738 | 1.00 | 61.57  | C |
| ATOM | 1409 | CD1 | TYR | A | 197 | −7.207  | 3.234  | 27.497 | 1.00 | 59.49  | C |
| ATOM | 1410 | CD2 | TYR | A | 197 | −6.603  | 3.014  | 29.793 | 1.00 | 53.77  | C |
| ATOM | 1411 | CE1 | TYR | A | 197 | −7.022  | 1.876  | 27.312 | 1.00 | 63.51  | C |
| ATOM | 1412 | CE2 | TYR | A | 197 | −6.416  | 1.654  | 29.616 | 1.00 | 60.47  | C |
| ATOM | 1413 | CZ  | TYR | A | 197 | −6.627  | 1.091  | 28.373 | 1.00 | 64.49  | C |
| ATOM | 1414 | OH  | TYR | A | 197 | −6.444  | −0.260 | 28.190 | 1.00 | 63.18  | O |
| ATOM | 1415 | N   | LEU | A | 198 | −6.864  | 8.454  | 28.616 | 1.00 | 54.86  | N |
| ATOM | 1416 | CA  | LEU | A | 198 | −7.392  | 9.774  | 28.300 | 1.00 | 59.87  | C |
| ATOM | 1417 | C   | LEU | A | 198 | −6.676  | 10.381 | 27.098 | 1.00 | 63.56  | C |
| ATOM | 1418 | O   | LEU | A | 198 | −7.308  | 10.977 | 26.227 | 1.00 | 62.39  | O |
| ATOM | 1419 | CB  | LEU | A | 198 | −7.288  | 10.707 | 29.507 | 1.00 | 65.95  | C |
| ATOM | 1420 | CG  | LEU | A | 198 | −8.371  | 10.534 | 30.574 | 1.00 | 79.11  | C |
| ATOM | 1421 | CD1 | LEU | A | 198 | −8.174  | 11.528 | 31.710 | 1.00 | 80.77  | C |
| ATOM | 1422 | CD2 | LEU | A | 198 | −9.756  | 10.684 | 29.958 | 1.00 | 75.76  | C |
| ATOM | 1423 | N   | ARG | A | 199 | −5.356  | 10.224 | 27.053 | 1.00 | 61.45  | N |
| ATOM | 1424 | CA  | ARG | A | 199 | −4.567  | 10.746 | 25.941 | 1.00 | 64.31  | C |
| ATOM | 1425 | C   | ARG | A | 199 | −4.863  | 9.997  | 24.641 | 1.00 | 63.00  | C |
| ATOM | 1426 | O   | ARG | A | 199 | −4.855  | 10.585 | 23.559 | 1.00 | 57.26  | O |
| ATOM | 1427 | CB  | ARG | A | 199 | −3.071  | 10.697 | 26.262 | 1.00 | 67.13  | C |
| ATOM | 1428 | CG  | ARG | A | 199 | −2.198  | 11.282 | 25.165 | 1.00 | 81.51  | C |
| ATOM | 1429 | CD  | ARG | A | 199 | −0.813  | 11.638 | 25.674 | 1.00 | 96.32  | C |
| ATOM | 1430 | NE  | ARG | A | 199 | −0.037  | 12.348 | 24.661 | 1.00 | 108.06 | N |
| ATOM | 1431 | CZ  | ARG | A | 199 | 1.160   | 12.885 | 24.875 | 1.00 | 115.00 | C |
| ATOM | 1432 | NH1 | ARG | A | 199 | 1.724   | 12.796 | 26.072 | 1.00 | 113.90 | N |
| ATOM | 1433 | NH2 | ARG | A | 199 | 1.793   | 13.512 | 23.892 | 1.00 | 118.37 | N |
| ATOM | 1434 | N   | ILE | A | 200 | −5.127  | 8.700  | 24.753 | 1.00 | 65.48  | N |
| ATOM | 1435 | CA  | ILE | A | 200 | −5.502  | 7.903  | 23.592 | 1.00 | 69.12  | C |
| ATOM | 1436 | C   | ILE | A | 200 | −6.825  | 8.399  | 23.014 | 1.00 | 65.45  | C |
| ATOM | 1437 | O   | ILE | A | 200 | −6.962  | 8.566  | 21.802 | 1.00 | 54.79  | O |
| ATOM | 1438 | CB  | ILE | A | 200 | −5.626  | 6.408  | 23.946 | 1.00 | 76.83  | C |
| ATOM | 1439 | CG1 | ILE | A | 200 | −4.259  | 5.829  | 24.317 | 1.00 | 75.54  | C |
| ATOM | 1440 | CG2 | ILE | A | 200 | −6.231  | 5.631  | 22.786 | 1.00 | 79.38  | C |
| ATOM | 1441 | CD1 | ILE | A | 200 | −4.312  | 4.385  | 24.772 | 1.00 | 65.44  | C |
| ATOM | 1442 | N   | PHE | A | 201 | −7.793  | 8.643  | 23.893 | 1.00 | 69.70  | N |
| ATOM | 1443 | CA  | PHE | A | 201 | −9.119  | 9.085  | 23.472 | 1.00 | 69.83  | C |
| ATOM | 1444 | C   | PHE | A | 201 | −9.089  | 10.482 | 22.858 | 1.00 | 65.70  | C |
| ATOM | 1445 | O   | PHE | A | 201 | −9.659  | 10.712 | 21.792 | 1.00 | 72.46  | O |
| ATOM | 1446 | CB  | PHE | A | 201 | −10.101 | 9.048  | 24.646 | 1.00 | 72.76  | C |
| ATOM | 1447 | CG  | PHE | A | 201 | −10.261 | 7.687  | 25.260 | 1.00 | 78.84  | C |
| ATOM | 1448 | CD1 | PHE | A | 201 | −10.304 | 7.531  | 26.636 | 1.00 | 84.18  | C |
| ATOM | 1449 | CD2 | PHE | A | 201 | −10.360 | 6.560  | 24.461 | 1.00 | 82.93  | C |

TABLE 6-continued

HUMAN A2A ADENOSINE STRUCTURE.PDB FILE
(Table 6: discloses SEQ ID NOS 20-27, respectively, in order of appearance.)

| | | | | | | | | | | | |
|---|---|---|---|---|---|---|---|---|---|---|---|
| ATOM | 1450 | CE1 | PHE | A | 201 | −10.450 | 6.279 | 27.203 | 1.00 | 83.93 | C |
| ATOM | 1451 | CE2 | PHE | A | 201 | −10.505 | 5.305 | 25.021 | 1.00 | 87.07 | C |
| ATOM | 1452 | CZ | PHE | A | 201 | −10.549 | 5.165 | 26.394 | 1.00 | 86.46 | C |
| ATOM | 1453 | N | LEU | A | 202 | −8.424 | 11.411 | 23.536 | 1.00 | 65.99 | N |
| ATOM | 1454 | CA | LEU | A | 202 | −8.326 | 12.787 | 23.059 | 1.00 | 65.94 | C |
| ATOM | 1455 | C | LEU | A | 202 | −7.702 | 12.854 | 21.668 | 1.00 | 65.29 | C |
| ATOM | 1456 | O | LEU | A | 202 | −7.996 | 13.761 | 20.890 | 1.00 | 55.81 | O |
| ATOM | 1457 | CB | LEU | A | 202 | −7.519 | 13.639 | 24.043 | 1.00 | 61.52 | C |
| ATOM | 1458 | CG | LEU | A | 202 | −8.162 | 13.865 | 25.414 | 1.00 | 63.19 | C |
| ATOM | 1459 | CD1 | LEU | A | 202 | −7.183 | 14.521 | 26.378 | 1.00 | 54.16 | C |
| ATOM | 1460 | CD2 | LEU | A | 202 | −9.426 | 14.699 | 25.278 | 1.00 | 63.22 | C |
| ATOM | 1461 | N | ALA | A | 203 | −6.844 | 11.886 | 21.360 | 1.00 | 66.53 | N |
| ATOM | 1462 | CA | ALA | A | 203 | −6.160 | 11.848 | 20.073 | 1.00 | 67.52 | C |
| ATOM | 1463 | C | ALA | A | 203 | −7.101 | 11.433 | 18.945 | 1.00 | 65.46 | C |
| ATOM | 1464 | O | ALA | A | 203 | −6.902 | 11.807 | 17.790 | 1.00 | 71.44 | O |
| ATOM | 1465 | CB | ALA | A | 203 | −4.958 | 10.915 | 20.137 | 1.00 | 76.22 | C |
| ATOM | 1466 | N | ALA | A | 204 | −8.126 | 10.659 | 19.285 | 1.00 | 63.70 | N |
| ATOM | 1467 | CA | ALA | A | 204 | −9.109 | 10.219 | 18.302 | 1.00 | 62.18 | C |
| ATOM | 1468 | C | ALA | A | 204 | −10.167 | 11.292 | 18.085 | 1.00 | 64.65 | C |
| ATOM | 1469 | O | ALA | A | 204 | −11.004 | 11.184 | 17.188 | 1.00 | 65.71 | O |
| ATOM | 1470 | CB | ALA | A | 204 | −9.756 | 8.917 | 18.742 | 1.00 | 66.97 | C |
| ATOM | 1471 | N | ARG | A | 205 | −10.123 | 12.327 | 18.916 | 1.00 | 65.50 | N |
| ATOM | 1472 | CA | ARG | A | 205 | −11.076 | 13.424 | 18.825 | 1.00 | 64.94 | C |
| ATOM | 1473 | C | ARG | A | 205 | −10.382 | 14.705 | 18.383 | 1.00 | 60.03 | C |
| ATOM | 1474 | O | ARG | A | 205 | −10.940 | 15.795 | 18.497 | 1.00 | 63.90 | O |
| ATOM | 1475 | CB | ARG | A | 205 | −11.773 | 13.633 | 20.170 | 1.00 | 75.01 | C |
| ATOM | 1476 | CG | ARG | A | 205 | −12.585 | 12.434 | 20.629 | 1.00 | 86.23 | C |
| ATOM | 1477 | CD | ARG | A | 205 | −13.927 | 12.370 | 19.918 | 1.00 | 90.41 | C |
| ATOM | 1478 | NE | ARG | A | 205 | −14.907 | 13.251 | 20.545 | 1.00 | 92.87 | N |
| ATOM | 1479 | CZ | ARG | A | 205 | −15.865 | 12.835 | 21.367 | 1.00 | 91.26 | C |
| ATOM | 1480 | NH1 | ARG | A | 205 | −15.983 | 11.545 | 21.652 | 1.00 | 90.17 | N |
| ATOM | 1481 | NH2 | ARG | A | 205 | −16.712 | 13.707 | 21.897 | 1.00 | 91.03 | N |
| ATOM | 1482 | N | ARG | A | 206 | −9.161 | 14.566 | 17.875 | 1.00 | 53.21 | N |
| ATOM | 1483 | CA | ARG | A | 206 | −8.394 | 15.716 | 17.415 | 1.00 | 58.22 | C |
| ATOM | 1484 | C | ARG | A | 206 | −9.059 | 16.364 | 16.204 | 1.00 | 60.50 | C |
| ATOM | 1485 | O | ARG | A | 206 | −9.722 | 15.694 | 15.413 | 1.00 | 55.35 | O |
| ATOM | 1486 | CB | ARG | A | 206 | −6.960 | 15.308 | 17.072 | 1.00 | 58.28 | C |
| ATOM | 1487 | CG | ARG | A | 206 | −6.839 | 14.476 | 15.807 | 1.00 | 62.04 | C |
| ATOM | 1488 | CD | ARG | A | 206 | −5.397 | 14.393 | 15.337 | 1.00 | 62.69 | C |
| ATOM | 1489 | NE | ARG | A | 206 | −4.572 | 13.595 | 16.237 | 1.00 | 68.82 | N |
| ATOM | 1490 | CZ | ARG | A | 206 | −4.200 | 12.343 | 15.993 | 1.00 | 78.59 | C |
| ATOM | 1491 | NH1 | ARG | A | 206 | −3.448 | 11.689 | 16.868 | 1.00 | 84.01 | N |
| ATOM | 1492 | NH2 | ARG | A | 206 | −4.578 | 11.745 | 14.871 | 1.00 | 78.81 | N |
| ATOM | 1493 | N | GLN | A | 207 | −8.875 | 17.673 | 16.070 | 1.00 | 65.00 | N |
| ATOM | 1494 | CA | GLN | A | 207 | −9.440 | 18.427 | 14.957 | 1.00 | 61.28 | C |
| ATOM | 1495 | C | GLN | A | 207 | −8.716 | 18.092 | 13.656 | 1.00 | 61.20 | C |
| ATOM | 1496 | O | GLN | A | 207 | −7.486 | 18.114 | 13.599 | 1.00 | 62.58 | O |
| ATOM | 1497 | CB | GLN | A | 207 | −9.346 | 19.924 | 15.246 | 1.00 | 59.32 | C |
| ATOM | 1498 | CG | GLN | A | 207 | −10.010 | 20.811 | 14.215 | 1.00 | 66.69 | C |
| ATOM | 1499 | CD | GLN | A | 207 | −9.989 | 22.270 | 14.622 | 1.00 | 72.68 | C |
| ATOM | 1500 | OE1 | GLN | A | 207 | −9.229 | 22.667 | 15.506 | 1.00 | 77.80 | O |
| ATOM | 1501 | NE2 | GLN | A | 207 | −10.826 | 23.076 | 13.982 | 1.00 | 73.65 | N |
| ATOM | 1502 | N | LEU | A | 208 | −9.480 | 17.785 | 12.613 | 1.00 | 58.37 | N |
| ATOM | 1503 | CA | LEU | A | 208 | −8.898 | 17.347 | 11.347 | 1.00 | 60.11 | C |
| ATOM | 1504 | C | LEU | A | 208 | −8.603 | 18.497 | 10.386 | 1.00 | 56.35 | C |
| ATOM | 1505 | O | LEU | A | 208 | −9.305 | 19.509 | 10.368 | 1.00 | 56.10 | O |
| ATOM | 1506 | CB | LEU | A | 208 | −9.789 | 16.301 | 10.668 | 1.00 | 54.72 | C |
| ATOM | 1507 | CG | LEU | A | 208 | −9.887 | 14.946 | 11.375 | 1.00 | 52.42 | C |
| ATOM | 1508 | CD1 | LEU | A | 208 | −10.804 | 14.004 | 10.617 | 1.00 | 55.68 | C |
| ATOM | 1509 | CD2 | LEU | A | 208 | −8.509 | 14.326 | 11.545 | 1.00 | 53.54 | C |
| ATOM | 1510 | N | ASN | A | 1002 | −7.552 | 18.320 | 9.591 | 1.00 | 57.40 | N |
| ATOM | 1511 | CA | ASN | A | 1002 | −7.123 | 19.309 | 8.611 | 1.00 | 50.58 | C |
| ATOM | 1512 | C | ASN | A | 1002 | −6.152 | 18.677 | 7.620 | 1.00 | 52.71 | C |
| ATOM | 1513 | O | ASN | A | 1002 | −5.853 | 17.487 | 7.712 | 1.00 | 62.40 | O |
| ATOM | 1514 | CB | ASN | A | 1002 | −6.478 | 20.513 | 9.303 | 1.00 | 52.37 | C |
| ATOM | 1515 | CG | ASN | A | 1002 | −5.353 | 20.115 | 10.241 | 1.00 | 54.04 | C |
| ATOM | 1516 | OD1 | ASN | A | 1002 | −4.466 | 19.342 | 9.876 | 1.00 | 58.56 | O |
| ATOM | 1517 | ND2 | ASN | A | 1002 | −5.382 | 20.649 | 11.457 | 1.00 | 43.77 | N |
| ATOM | 1518 | N | ILE | A | 1003 | −5.659 | 19.468 | 6.674 | 1.00 | 55.19 | N |
| ATOM | 1519 | CA | ILE | A | 1003 | −4.779 | 18.940 | 5.635 | 1.00 | 54.09 | C |
| ATOM | 1520 | C | ILE | A | 1003 | −3.527 | 18.273 | 6.211 | 1.00 | 53.49 | C |
| ATOM | 1521 | O | ILE | A | 1003 | −3.006 | 17.320 | 5.632 | 1.00 | 49.31 | O |
| ATOM | 1522 | CB | ILE | A | 1003 | −4.386 | 20.024 | 4.604 | 1.00 | 60.60 | C |
| ATOM | 1523 | CG1 | ILE | A | 1003 | −3.570 | 19.408 | 3.463 | 1.00 | 57.53 | C |
| ATOM | 1524 | CG2 | ILE | A | 1003 | −3.629 | 21.163 | 5.277 | 1.00 | 52.48 | C |
| ATOM | 1525 | CD1 | ILE | A | 1003 | −3.351 | 20.344 | 2.295 | 1.00 | 49.85 | C |
| ATOM | 1526 | N | PHE | A | 1004 | −3.053 | 18.765 | 7.353 | 1.00 | 57.04 | N |

TABLE 6-continued

HUMAN A2A ADENOSINE STRUCTURE.PDB FILE
(Table 6: discloses SEQ ID NOS 20-27, respectively, in order of appearance.)

| ATOM | 1527 | CA | PHE | A | 1004 | −1.886 | 18.173 | 8.005 | 1.00 | 58.69 | C |
|---|---|---|---|---|---|---|---|---|---|---|---|
| ATOM | 1528 | C | PHE | A | 1004 | −2.206 | 16.805 | 8.602 | 1.00 | 60.13 | C |
| ATOM | 1529 | O | PHE | A | 1004 | −1.445 | 15.850 | 8.434 | 1.00 | 59.59 | O |
| ATOM | 1530 | CB | PHE | A | 1004 | −1.327 | 19.098 | 9.088 | 1.00 | 53.02 | C |
| ATOM | 1531 | CG | PHE | A | 1004 | −0.257 | 18.461 | 9.933 | 1.00 | 61.63 | C |
| ATOM | 1532 | CD1 | PHE | A | 1004 | 1.041 | 18.342 | 9.460 | 1.00 | 58.63 | C |
| ATOM | 1533 | CD2 | PHE | A | 1004 | −0.550 | 17.974 | 11.197 | 1.00 | 64.89 | C |
| ATOM | 1534 | CE1 | PHE | A | 1004 | 2.026 | 17.754 | 10.234 | 1.00 | 59.07 | C |
| ATOM | 1535 | CE2 | PHE | A | 1004 | 0.432 | 17.383 | 11.976 | 1.00 | 56.22 | C |
| ATOM | 1536 | CZ | PHE | A | 1004 | 1.721 | 17.274 | 11.493 | 1.00 | 54.14 | C |
| ATOM | 1537 | N | GLU | A | 1005 | −3.332 | 16.714 | 9.302 | 1.00 | 54.04 | N |
| ATOM | 1538 | CA | GLU | A | 1005 | −3.753 | 15.451 | 9.895 | 1.00 | 50.95 | C |
| ATOM | 1539 | C | GLU | A | 1005 | −4.181 | 14.483 | 8.799 | 1.00 | 49.35 | C |
| ATOM | 1540 | O | GLU | A | 1005 | −4.190 | 13.267 | 8.994 | 1.00 | 60.90 | O |
| ATOM | 1541 | CB | GLU | A | 1005 | −4.899 | 15.672 | 10.885 | 1.00 | 49.68 | C |
| ATOM | 1542 | CG | GLU | A | 1005 | −4.648 | 16.785 | 11.894 | 1.00 | 54.56 | C |
| ATOM | 1543 | CD | GLU | A | 1005 | −3.534 | 16.457 | 12.876 | 1.00 | 67.59 | C |
| ATOM | 1544 | OE1 | GLU | A | 1005 | −3.226 | 15.260 | 13.058 | 1.00 | 64.83 | O |
| ATOM | 1545 | OE2 | GLU | A | 1005 | −2.970 | 17.399 | 13.474 | 1.00 | 74.63 | O |
| ATOM | 1546 | N | MET | A | 1006 | −4.529 | 15.038 | 7.643 | 1.00 | 46.22 | N |
| ATOM | 1547 | CA | MET | A | 1006 | −4.948 | 14.245 | 6.494 | 1.00 | 50.79 | C |
| ATOM | 1548 | C | MET | A | 1006 | −3.789 | 13.426 | 5.931 | 1.00 | 54.17 | C |
| ATOM | 1549 | O | MET | A | 1006 | −3.897 | 12.212 | 5.767 | 1.00 | 56.71 | O |
| ATOM | 1550 | CB | MET | A | 1006 | −5.517 | 15.155 | 5.405 | 1.00 | 48.87 | C |
| ATOM | 1551 | CG | MET | A | 1006 | −6.042 | 14.419 | 4.187 | 1.00 | 45.14 | C |
| ATOM | 1552 | SD | MET | A | 1006 | −6.340 | 15.533 | 2.798 | 1.00 | 57.45 | S |
| ATOM | 1553 | CE | MET | A | 1006 | −7.410 | 14.520 | 1.775 | 1.00 | 50.85 | C |
| ATOM | 1554 | N | LEU | A | 1007 | −2.679 | 14.095 | 5.634 | 1.00 | 53.46 | N |
| ATOM | 1555 | CA | LEU | A | 1007 | −1.511 | 13.407 | 5.091 | 1.00 | 59.73 | C |
| ATOM | 1556 | C | LEU | A | 1007 | −0.693 | 12.702 | 6.167 | 1.00 | 60.91 | C |
| ATOM | 1557 | O | LEU | A | 1007 | 0.115 | 11.825 | 5.865 | 1.00 | 64.13 | O |
| ATOM | 1558 | CB | LEU | A | 1007 | −0.631 | 14.360 | 4.281 | 1.00 | 49.37 | C |
| ATOM | 1559 | CG | LEU | A | 1007 | −1.161 | 14.638 | 2.874 | 1.00 | 50.71 | C |
| ATOM | 1560 | CD1 | LEU | A | 1007 | −2.169 | 15.779 | 2.895 | 1.00 | 49.29 | C |
| ATOM | 1561 | CD2 | LEU | A | 1007 | −0.020 | 14.947 | 1.928 | 1.00 | 62.29 | C |
| ATOM | 1562 | N | ARG | A | 1008 | −0.904 | 13.085 | 7.421 | 1.00 | 55.54 | N |
| ATOM | 1563 | CA | ARG | A | 1008 | −0.285 | 12.381 | 8.534 | 1.00 | 51.78 | C |
| ATOM | 1564 | C | ARG | A | 1008 | −0.785 | 10.941 | 8.549 | 1.00 | 54.08 | C |
| ATOM | 1565 | O | ARG | A | 1008 | −0.087 | 10.031 | 8.994 | 1.00 | 59.46 | O |
| ATOM | 1566 | CB | ARG | A | 1008 | −0.618 | 13.072 | 9.856 | 1.00 | 55.69 | C |
| ATOM | 1567 | CG | ARG | A | 1008 | −0.030 | 12.395 | 11.083 | 1.00 | 56.42 | C |
| ATOM | 1568 | CD | ARG | A | 1008 | −0.378 | 13.159 | 12.352 | 1.00 | 61.69 | C |
| ATOM | 1569 | NE | ARG | A | 1008 | 0.066 | 12.463 | 13.557 | 1.00 | 70.50 | N |
| ATOM | 1570 | CZ | ARG | A | 1008 | −0.150 | 12.899 | 14.794 | 1.00 | 72.61 | C |
| ATOM | 1571 | NH1 | ARG | A | 1008 | −0.806 | 14.034 | 14.995 | 1.00 | 71.04 | N |
| ATOM | 1572 | NH2 | ARG | A | 1008 | 0.290 | 12.201 | 15.832 | 1.00 | 78.23 | N |
| ATOM | 1573 | N | ILE | A | 1009 | −2.001 | 10.748 | 8.046 | 1.00 | 55.91 | N |
| ATOM | 1574 | CA | ILE | A | 1009 | −2.625 | 9.431 | 7.990 | 1.00 | 54.99 | C |
| ATOM | 1575 | C | ILE | A | 1009 | −2.272 | 8.700 | 6.698 | 1.00 | 60.77 | C |
| ATOM | 1576 | O | ILE | A | 1009 | −2.126 | 7.477 | 6.686 | 1.00 | 69.04 | O |
| ATOM | 1577 | CB | ILE | A | 1009 | −4.159 | 9.539 | 8.101 | 1.00 | 59.77 | C |
| ATOM | 1578 | CG1 | ILE | A | 1009 | −4.562 | 9.989 | 9.507 | 1.00 | 55.21 | C |
| ATOM | 1579 | CG2 | ILE | A | 1009 | −4.819 | 8.214 | 7.757 | 1.00 | 61.35 | C |
| ATOM | 1580 | CD1 | ILE | A | 1009 | −6.056 | 10.152 | 9.689 | 1.00 | 58.71 | C |
| ATOM | 1581 | N | ASP | A | 1010 | −2.133 | 9.454 | 5.612 | 1.00 | 58.39 | N |
| ATOM | 1582 | CA | ASP | A | 1010 | −1.835 | 8.870 | 4.308 | 1.00 | 55.69 | C |
| ATOM | 1583 | C | ASP | A | 1010 | −0.342 | 8.629 | 4.096 | 1.00 | 57.23 | C |
| ATOM | 1584 | O | ASP | A | 1010 | 0.046 | 7.671 | 3.427 | 1.00 | 55.67 | O |
| ATOM | 1585 | CB | ASP | A | 1010 | −2.384 | 9.752 | 3.182 | 1.00 | 58.24 | C |
| ATOM | 1586 | CG | ASP | A | 1010 | −3.879 | 9.588 | 2.988 | 1.00 | 59.78 | C |
| ATOM | 1587 | OD1 | ASP | A | 1010 | −4.441 | 8.590 | 3.485 | 1.00 | 62.57 | O |
| ATOM | 1588 | OD2 | ASP | A | 1010 | −4.492 | 10.457 | 2.334 | 1.00 | 62.77 | O |
| ATOM | 1589 | N | GLU | A | 1011 | 0.490 | 9.496 | 4.664 | 1.00 | 59.41 | N |
| ATOM | 1590 | CA | GLU | A | 1011 | 1.934 | 9.408 | 4.456 | 1.00 | 69.06 | C |
| ATOM | 1591 | C | GLU | A | 1011 | 2.725 | 9.165 | 5.743 | 1.00 | 73.98 | C |
| ATOM | 1592 | O | GLU | A | 1011 | 3.880 | 8.746 | 5.696 | 1.00 | 87.32 | O |
| ATOM | 1593 | CB | GLU | A | 1011 | 2.457 | 10.654 | 3.736 | 1.00 | 74.32 | C |
| ATOM | 1594 | CG | GLU | A | 1011 | 1.989 | 10.773 | 2.293 | 1.00 | 79.53 | C |
| ATOM | 1595 | CD | GLU | A | 1011 | 2.776 | 11.805 | 1.507 | 1.00 | 84.42 | C |
| ATOM | 1596 | OE1 | GLU | A | 1011 | 3.777 | 12.324 | 2.045 | 1.00 | 84.07 | O |
| ATOM | 1597 | OE2 | GLU | A | 1011 | 2.396 | 12.092 | 0.352 | 1.00 | 77.44 | O |
| ATOM | 1598 | N | GLY | A | 1012 | 2.105 | 9.433 | 6.887 | 1.00 | 68.52 | N |
| ATOM | 1599 | CA | GLY | A | 1012 | 2.732 | 9.162 | 8.169 | 1.00 | 61.41 | C |
| ATOM | 1600 | C | GLY | A | 1012 | 3.533 | 10.321 | 8.731 | 1.00 | 66.01 | C |
| ATOM | 1601 | O | GLY | A | 1012 | 3.872 | 11.264 | 8.016 | 1.00 | 65.86 | O |
| ATOM | 1602 | N | LEU | A | 1013 | 3.837 | 10.247 | 10.024 | 1.00 | 68.92 | N |
| ATOM | 1603 | CA | LEU | A | 1013 | 4.603 | 11.291 | 10.695 | 1.00 | 72.70 | C |

TABLE 6-continued

HUMAN A2A ADENOSINE STRUCTURE.PDB FILE
(Table 6: discloses SEQ ID NOS 20-27, respectively, in order of appearance.)

| ATOM | 1604 | C | LEU | A | 1013 | 5.881 | 10.738 | 11.325 | 1.00 | 75.09 | C |
|---|---|---|---|---|---|---|---|---|---|---|---|
| ATOM | 1605 | O | LEU | A | 1013 | 5.849 | 9.756 | 12.067 | 1.00 | 73.25 | O |
| ATOM | 1606 | CB | LEU | A | 1013 | 3.750 | 11.986 | 11.759 | 1.00 | 69.24 | C |
| ATOM | 1607 | CG | LEU | A | 1013 | 4.437 | 13.105 | 12.545 | 1.00 | 68.88 | C |
| ATOM | 1608 | CD1 | LEU | A | 1013 | 4.975 | 14.171 | 11.604 | 1.00 | 59.51 | C |
| ATOM | 1609 | CD2 | LEU | A | 1013 | 3.486 | 13.716 | 13.563 | 1.00 | 67.50 | C |
| ATOM | 1610 | N | ARG | A | 1014 | 7.004 | 11.381 | 11.021 | 1.00 | 79.98 | N |
| ATOM | 1611 | CA | ARG | A | 1014 | 8.301 | 10.977 | 11.550 | 1.00 | 75.43 | C |
| ATOM | 1612 | C | ARG | A | 1014 | 8.993 | 12.164 | 12.208 | 1.00 | 65.69 | C |
| ATOM | 1613 | O | ARG | A | 1014 | 9.090 | 13.238 | 11.615 | 1.00 | 67.46 | O |
| ATOM | 1614 | CB | ARG | A | 1014 | 9.182 | 10.430 | 10.428 | 1.00 | 78.94 | C |
| ATOM | 1615 | CG | ARG | A | 1014 | 8.720 | 9.103 | 9.853 | 1.00 | 86.38 | C |
| ATOM | 1616 | CD | ARG | A | 1014 | 9.219 | 7.941 | 10.691 | 1.00 | 97.21 | C |
| ATOM | 1617 | NE | ARG | A | 1014 | 9.348 | 6.721 | 9.899 | 1.00 | 106.77 | N |
| ATOM | 1618 | CZ | ARG | A | 1014 | 9.987 | 5.630 | 10.307 | 1.00 | 116.22 | C |
| ATOM | 1619 | NH1 | ARG | A | 1014 | 10.057 | 4.566 | 9.517 | 1.00 | 120.57 | N |
| ATOM | 1620 | NH2 | ARG | A | 1014 | 10.559 | 5.601 | 11.503 | 1.00 | 119.85 | N |
| ATOM | 1621 | N | LEU | A | 1015 | 9.472 | 11.972 | 13.432 | 1.00 | 60.33 | N |
| ATOM | 1622 | CA | LEU | A | 1015 | 10.158 | 13.041 | 14.149 | 1.00 | 70.48 | C |
| ATOM | 1623 | C | LEU | A | 1015 | 11.665 | 12.803 | 14.186 | 1.00 | 74.17 | C |
| ATOM | 1624 | O | LEU | A | 1015 | 12.424 | 13.633 | 14.687 | 1.00 | 78.22 | O |
| ATOM | 1625 | CB | LEU | A | 1015 | 9.593 | 13.198 | 15.562 | 1.00 | 73.22 | C |
| ATOM | 1626 | CG | LEU | A | 1015 | 8.105 | 13.551 | 15.624 | 1.00 | 69.50 | C |
| ATOM | 1627 | CD1 | LEU | A | 1015 | 7.699 | 13.936 | 17.038 | 1.00 | 67.65 | C |
| ATOM | 1628 | CD2 | LEU | A | 1015 | 7.781 | 14.673 | 14.651 | 1.00 | 65.05 | C |
| ATOM | 1629 | N | LYS | A | 1016 | 12.086 | 11.663 | 13.649 | 1.00 | 70.51 | N |
| ATOM | 1630 | CA | LYS | A | 1016 | 13.502 | 11.352 | 13.503 | 1.00 | 75.16 | C |
| ATOM | 1631 | C | LYS | A | 1016 | 13.825 | 11.125 | 12.031 | 1.00 | 67.66 | C |
| ATOM | 1632 | O | LYS | A | 1016 | 13.064 | 10.470 | 11.317 | 1.00 | 65.42 | O |
| ATOM | 1633 | CB | LYS | A | 1016 | 13.866 | 10.103 | 14.306 | 1.00 | 88.31 | C |
| ATOM | 1634 | CG | LYS | A | 1016 | 13.565 | 10.193 | 15.791 | 1.00 | 96.33 | C |
| ATOM | 1635 | CD | LYS | A | 1016 | 13.897 | 8.880 | 16.487 | 1.00 | 105.15 | C |
| ATOM | 1636 | CE | LYS | A | 1016 | 13.522 | 8.915 | 17.959 | 1.00 | 110.63 | C |
| ATOM | 1637 | NZ | LYS | A | 1016 | 13.792 | 7.611 | 18.627 | 1.00 | 110.59 | N |
| ATOM | 1638 | N | ILE | A | 1017 | 14.952 | 11.664 | 11.579 | 1.00 | 65.18 | N |
| ATOM | 1639 | CA | ILE | A | 1017 | 15.377 | 11.485 | 10.195 | 1.00 | 67.57 | C |
| ATOM | 1640 | C | ILE | A | 1017 | 15.390 | 10.006 | 9.815 | 1.00 | 69.53 | C |
| ATOM | 1641 | O | ILE | A | 1017 | 15.910 | 9.171 | 10.554 | 1.00 | 72.59 | O |
| ATOM | 1642 | CB | ILE | A | 1017 | 16.773 | 12.086 | 9.945 | 1.00 | 65.22 | C |
| ATOM | 1643 | CG1 | ILE | A | 1017 | 16.789 | 13.571 | 10.315 | 1.00 | 71.50 | C |
| ATOM | 1644 | CG2 | ILE | A | 1017 | 17.184 | 11.894 | 8.494 | 1.00 | 55.83 | C |
| ATOM | 1645 | CD1 | ILE | A | 1017 | 18.071 | 14.281 | 9.938 | 1.00 | 69.99 | C |
| ATOM | 1646 | N | TYR | A | 1018 | 14.812 | 9.692 | 8.659 | 1.00 | 69.36 | N |
| ATOM | 1647 | CA | TYR | A | 1018 | 14.752 | 8.320 | 8.171 | 1.00 | 68.77 | C |
| ATOM | 1648 | C | TYR | A | 1018 | 15.037 | 8.285 | 6.674 | 1.00 | 66.91 | C |
| ATOM | 1649 | O | TYR | A | 1018 | 15.095 | 9.327 | 6.024 | 1.00 | 66.87 | O |
| ATOM | 1650 | CB | TYR | A | 1018 | 13.372 | 7.718 | 8.446 | 1.00 | 78.58 | C |
| ATOM | 1651 | CG | TYR | A | 1018 | 12.266 | 8.325 | 7.608 | 1.00 | 79.77 | C |
| ATOM | 1652 | CD1 | TYR | A | 1018 | 11.863 | 7.732 | 6.419 | 1.00 | 72.41 | C |
| ATOM | 1653 | CD2 | TYR | A | 1018 | 11.630 | 9.496 | 8.004 | 1.00 | 76.71 | C |
| ATOM | 1654 | CE1 | TYR | A | 1018 | 10.856 | 8.285 | 5.647 | 1.00 | 72.69 | C |
| ATOM | 1655 | CE2 | TYR | A | 1018 | 10.621 | 10.056 | 7.240 | 1.00 | 70.99 | C |
| ATOM | 1656 | CZ | TYR | A | 1018 | 10.238 | 9.447 | 6.063 | 1.00 | 75.69 | C |
| ATOM | 1657 | OH | TYR | A | 1018 | 9.235 | 10.002 | 5.300 | 1.00 | 76.97 | O |
| ATOM | 1658 | N | LYS | A | 1019 | 15.213 | 7.085 | 6.130 | 1.00 | 71.74 | N |
| ATOM | 1659 | CA | LYS | A | 1019 | 15.422 | 6.919 | 4.695 | 1.00 | 78.92 | C |
| ATOM | 1660 | C | LYS | A | 1019 | 14.120 | 6.531 | 4.003 | 1.00 | 80.68 | C |
| ATOM | 1661 | O | LYS | A | 1019 | 13.407 | 5.642 | 4.466 | 1.00 | 87.51 | O |
| ATOM | 1662 | CB | LYS | A | 1019 | 16.487 | 5.856 | 4.421 | 1.00 | 83.84 | C |
| ATOM | 1663 | CG | LYS | A | 1019 | 17.904 | 6.272 | 4.774 | 1.00 | 82.05 | C |
| ATOM | 1664 | CD | LYS | A | 1019 | 18.907 | 5.256 | 4.248 | 1.00 | 88.19 | C |
| ATOM | 1665 | CE | LYS | A | 1019 | 20.338 | 5.675 | 4.544 | 1.00 | 93.03 | C |
| ATOM | 1666 | NZ | LYS | A | 1019 | 21.321 | 4.738 | 3.933 | 1.00 | 90.39 | N |
| ATOM | 1667 | N | ASP | A | 1020 | 13.813 | 7.194 | 2.892 | 1.00 | 79.28 | N |
| ATOM | 1668 | CA | ASP | A | 1020 | 12.596 | 6.889 | 2.148 | 1.00 | 84.03 | C |
| ATOM | 1669 | C | ASP | A | 1020 | 12.754 | 5.603 | 1.341 | 1.00 | 95.26 | C |
| ATOM | 1670 | O | ASP | A | 1020 | 13.744 | 4.887 | 1.489 | 1.00 | 94.50 | O |
| ATOM | 1671 | CB | ASP | A | 1020 | 12.186 | 8.060 | 1.245 | 1.00 | 74.92 | C |
| ATOM | 1672 | CG | ASP | A | 1020 | 13.154 | 8.290 | 0.100 | 1.00 | 80.06 | C |
| ATOM | 1673 | OD1 | ASP | A | 1020 | 14.103 | 7.495 | −0.057 | 1.00 | 85.47 | O |
| ATOM | 1674 | OD2 | ASP | A | 1020 | 12.962 | 9.271 | −0.650 | 1.00 | 82.79 | O |
| ATOM | 1675 | N | THR | A | 1021 | 11.775 | 5.318 | 0.488 | 1.00 | 100.19 | N |
| ATOM | 1676 | CA | THR | A | 1021 | 11.778 | 4.091 | −0.303 | 1.00 | 100.11 | C |
| ATOM | 1677 | C | THR | A | 1021 | 12.995 | 3.986 | −1.219 | 1.00 | 98.92 | C |
| ATOM | 1678 | O | THR | A | 1021 | 13.434 | 2.886 | −1.556 | 1.00 | 105.20 | O |
| ATOM | 1679 | CB | THR | A | 1021 | 10.497 | 3.967 | −1.147 | 1.00 | 97.91 | C |
| ATOM | 1680 | OG1 | THR | A | 1021 | 10.309 | 5.166 | −1.910 | 1.00 | 100.68 | O |

TABLE 6-continued

HUMAN A2A ADENOSINE STRUCTURE.PDB FILE
(Table 6: discloses SEQ ID NOS 20-27, respectively, in order of appearance.)

| ATOM | 1681 | CG2 | THR | A | 1021 | 9.290 | 3.749 | −0.248 | 1.00 | 91.55 | C |
|---|---|---|---|---|---|---|---|---|---|---|---|
| ATOM | 1682 | N | GLU | A | 1022 | 13.538 | 5.131 | −1.619 | 1.00 | 93.43 | N |
| ATOM | 1683 | CA | GLU | A | 1022 | 14.695 | 5.155 | −2.507 | 1.00 | 91.02 | C |
| ATOM | 1684 | C | GLU | A | 1022 | 15.978 | 5.566 | −1.787 | 1.00 | 90.06 | C |
| ATOM | 1685 | O | GLU | A | 1022 | 16.953 | 5.972 | −2.420 | 1.00 | 90.21 | O |
| ATOM | 1686 | CB | GLU | A | 1022 | 14.433 | 6.063 | −3.710 | 1.00 | 91.40 | C |
| ATOM | 1687 | CG | GLU | A | 1022 | 13.601 | 7.289 | −3.390 | 1.00 | 99.93 | C |
| ATOM | 1688 | CD | GLU | A | 1022 | 13.022 | 7.933 | −4.632 | 1.00 | 106.60 | C |
| ATOM | 1689 | OE1 | GLU | A | 1022 | 13.657 | 7.838 | −5.704 | 1.00 | 102.38 | O |
| ATOM | 1690 | OE2 | GLU | A | 1022 | 11.930 | 8.532 | −4.537 | 1.00 | 112.97 | O |
| ATOM | 1691 | N | GLY | A | 1023 | 15.967 | 5.458 | −0.463 | 1.00 | 90.17 | N |
| ATOM | 1692 | CA | GLY | A | 1023 | 17.157 | 5.685 | 0.337 | 1.00 | 94.97 | C |
| ATOM | 1693 | C | GLY | A | 1023 | 17.601 | 7.131 | 0.450 | 1.00 | 94.39 | C |
| ATOM | 1694 | O | GLY | A | 1023 | 18.798 | 7.412 | 0.522 | 1.00 | 94.16 | O |
| ATOM | 1695 | N | TYR | A | 1024 | 16.641 | 8.050 | 0.466 | 1.00 | 92.80 | N |
| ATOM | 1696 | CA | TYR | A | 1024 | 16.945 | 9.463 | 0.662 | 1.00 | 85.63 | C |
| ATOM | 1697 | C | TYR | A | 1024 | 16.502 | 9.923 | 2.044 | 1.00 | 78.14 | C |
| ATOM | 1698 | O | TYR | A | 1024 | 15.406 | 9.593 | 2.495 | 1.00 | 79.69 | O |
| ATOM | 1699 | CB | TYR | A | 1024 | 16.279 | 10.323 | −0.413 | 1.00 | 86.57 | C |
| ATOM | 1700 | CG | TYR | A | 1024 | 16.826 | 10.100 | −1.802 | 1.00 | 94.51 | C |
| ATOM | 1701 | CD1 | TYR | A | 1024 | 15.976 | 9.924 | −2.884 | 1.00 | 99.25 | C |
| ATOM | 1702 | CD2 | TYR | A | 1024 | 18.195 | 10.056 | −2.030 | 1.00 | 100.23 | C |
| ATOM | 1703 | CE1 | TYR | A | 1024 | 16.472 | 9.718 | −4.157 | 1.00 | 105.55 | C |
| ATOM | 1704 | CE2 | TYR | A | 1024 | 18.701 | 9.850 | −3.298 | 1.00 | 106.10 | C |
| ATOM | 1705 | CZ | TYR | A | 1024 | 17.835 | 9.682 | −4.358 | 1.00 | 109.96 | C |
| ATOM | 1706 | OH | TYR | A | 1024 | 18.335 | 9.476 | −5.623 | 1.00 | 113.27 | O |
| ATOM | 1707 | N | TYR | A | 1025 | 17.359 | 10.686 | 2.713 | 1.00 | 72.90 | N |
| ATOM | 1708 | CA | TYR | A | 1025 | 17.050 | 11.174 | 4.050 | 1.00 | 69.83 | C |
| ATOM | 1709 | C | TYR | A | 1025 | 15.827 | 12.086 | 4.048 | 1.00 | 65.99 | C |
| ATOM | 1710 | O | TYR | A | 1025 | 15.754 | 13.051 | 3.286 | 1.00 | 60.39 | O |
| ATOM | 1711 | CB | TYR | A | 1025 | 18.263 | 11.873 | 4.664 | 1.00 | 68.72 | C |
| ATOM | 1712 | CG | TYR | A | 1025 | 19.390 | 10.919 | 4.992 | 1.00 | 71.48 | C |
| ATOM | 1713 | CD1 | TYR | A | 1025 | 20.561 | 10.910 | 4.246 | 1.00 | 72.69 | C |
| ATOM | 1714 | CD2 | TYR | A | 1025 | 19.274 | 10.017 | 6.041 | 1.00 | 70.08 | C |
| ATOM | 1715 | CE1 | TYR | A | 1025 | 21.588 | 10.034 | 4.542 | 1.00 | 71.64 | C |
| ATOM | 1716 | CE2 | TYR | A | 1025 | 20.295 | 9.139 | 6.344 | 1.00 | 72.05 | C |
| ATOM | 1717 | CZ | TYR | A | 1025 | 21.449 | 9.151 | 5.592 | 1.00 | 79.14 | C |
| ATOM | 1718 | OH | TYR | A | 1025 | 22.467 | 8.276 | 5.894 | 1.00 | 90.30 | O |
| ATOM | 1719 | N | THR | A | 1026 | 14.871 | 11.761 | 4.912 | 1.00 | 63.11 | N |
| ATOM | 1720 | CA | THR | A | 1026 | 13.581 | 12.436 | 4.953 | 1.00 | 63.07 | C |
| ATOM | 1721 | C | THR | A | 1026 | 13.149 | 12.624 | 6.402 | 1.00 | 62.42 | C |
| ATOM | 1722 | O | THR | A | 1026 | 13.626 | 11.920 | 7.291 | 1.00 | 61.41 | O |
| ATOM | 1723 | CB | THR | A | 1026 | 12.510 | 11.597 | 4.227 | 1.00 | 65.22 | C |
| ATOM | 1724 | OG1 | THR | A | 1026 | 12.962 | 11.277 | 2.905 | 1.00 | 69.47 | O |
| ATOM | 1725 | CG2 | THR | A | 1026 | 11.193 | 12.351 | 4.139 | 1.00 | 70.50 | C |
| ATOM | 1726 | N | ILE | A | 1027 | 12.251 | 13.575 | 6.641 | 1.00 | 67.05 | N |
| ATOM | 1727 | CA | ILE | A | 1027 | 11.686 | 13.761 | 7.975 | 1.00 | 65.98 | C |
| ATOM | 1728 | C | ILE | A | 1027 | 10.305 | 14.417 | 7.912 | 1.00 | 61.47 | C |
| ATOM | 1729 | O | ILE | A | 1027 | 9.890 | 14.907 | 6.861 | 1.00 | 54.44 | O |
| ATOM | 1730 | CB | ILE | A | 1027 | 12.628 | 14.573 | 8.892 | 1.00 | 56.72 | C |
| ATOM | 1731 | CG1 | ILE | A | 1027 | 12.312 | 14.291 | 10.364 | 1.00 | 51.50 | C |
| ATOM | 1732 | CG2 | ILE | A | 1027 | 12.539 | 16.060 | 8.573 | 1.00 | 45.36 | C |
| ATOM | 1733 | CD1 | ILE | A | 1027 | 13.381 | 14.761 | 11.324 | 1.00 | 51.60 | C |
| ATOM | 1734 | N | GLY | A | 1028 | 9.597 | 14.414 | 9.039 | 1.00 | 57.98 | N |
| ATOM | 1735 | CA | GLY | A | 1028 | 8.250 | 14.952 | 9.099 | 1.00 | 55.26 | C |
| ATOM | 1736 | C | GLY | A | 1028 | 7.290 | 14.131 | 8.260 | 1.00 | 58.08 | C |
| ATOM | 1737 | O | GLY | A | 1028 | 7.284 | 12.903 | 8.335 | 1.00 | 67.01 | O |
| ATOM | 1738 | N | ILE | A | 1029 | 6.477 | 14.810 | 7.457 | 1.00 | 55.02 | N |
| ATOM | 1739 | CA | ILE | A | 1029 | 5.586 | 14.123 | 6.529 | 1.00 | 56.46 | C |
| ATOM | 1740 | C | ILE | A | 1029 | 6.159 | 14.150 | 5.116 | 1.00 | 54.10 | C |
| ATOM | 1741 | O | ILE | A | 1029 | 5.890 | 15.068 | 4.342 | 1.00 | 61.26 | O |
| ATOM | 1742 | CB | ILE | A | 1029 | 4.169 | 14.738 | 6.527 | 1.00 | 60.32 | C |
| ATOM | 1743 | CG1 | ILE | A | 1029 | 3.541 | 14.634 | 7.918 | 1.00 | 66.95 | C |
| ATOM | 1744 | CG2 | ILE | A | 1029 | 3.286 | 14.048 | 5.494 | 1.00 | 52.13 | C |
| ATOM | 1745 | CD1 | ILE | A | 1029 | 2.112 | 15.123 | 7.981 | 1.00 | 71.18 | C |
| ATOM | 1746 | N | GLY | A | 1030 | 6.967 | 13.143 | 4.797 | 1.00 | 54.04 | N |
| ATOM | 1747 | CA | GLY | A | 1030 | 7.533 | 12.996 | 3.468 | 1.00 | 45.95 | C |
| ATOM | 1748 | C | GLY | A | 1030 | 8.373 | 14.168 | 2.993 | 1.00 | 53.75 | C |
| ATOM | 1749 | O | GLY | A | 1030 | 8.474 | 14.416 | 1.792 | 1.00 | 66.78 | O |
| ATOM | 1750 | N | HIS | A | 1031 | 8.983 | 14.888 | 3.930 | 1.00 | 53.64 | N |
| ATOM | 1751 | CA | HIS | A | 1031 | 9.819 | 16.031 | 3.579 | 1.00 | 62.35 | C |
| ATOM | 1752 | C | HIS | A | 1031 | 11.274 | 15.623 | 3.359 | 1.00 | 67.02 | C |
| ATOM | 1753 | O | HIS | A | 1031 | 12.033 | 15.457 | 4.315 | 1.00 | 66.73 | O |
| ATOM | 1754 | CB | HIS | A | 1031 | 9.736 | 17.113 | 4.658 | 1.00 | 67.56 | C |
| ATOM | 1755 | CG | HIS | A | 1031 | 10.494 | 18.359 | 4.321 | 1.00 | 67.34 | C |
| ATOM | 1756 | ND1 | HIS | A | 1031 | 9.888 | 19.477 | 3.787 | 1.00 | 67.75 | N |
| ATOM | 1757 | CD2 | HIS | A | 1031 | 11.808 | 18.663 | 4.436 | 1.00 | 65.25 | C |

TABLE 6-continued

HUMAN A2A ADENOSINE STRUCTURE.PDB FILE
(Table 6: discloses SEQ ID NOS 20-27, respectively, in order of appearance.)

| ATOM | 1758 | CE1 | HIS | A | 1031 | 10.796 | 20.416 | 3.591 | 1.00 | 66.66 | C |
|---|---|---|---|---|---|---|---|---|---|---|---|
| ATOM | 1759 | NE2 | HIS | A | 1031 | 11.969 | 19.948 | 3.978 | 1.00 | 64.71 | N |
| ATOM | 1760 | N | LEU | A | 1032 | 11.659 | 15.467 | 2.096 | 1.00 | 69.19 | N |
| ATOM | 1761 | CA | LEU | A | 1032 | 13.023 | 15.077 | 1.754 | 1.00 | 70.04 | C |
| ATOM | 1762 | C | LEU | A | 1032 | 14.023 | 16.187 | 2.071 | 1.00 | 68.84 | C |
| ATOM | 1763 | O | LEU | A | 1032 | 13.802 | 17.352 | 1.739 | 1.00 | 67.03 | O |
| ATOM | 1764 | CB | LEU | A | 1032 | 13.117 | 14.672 | 0.280 | 1.00 | 79.43 | C |
| ATOM | 1765 | CG | LEU | A | 1032 | 14.511 | 14.366 | −0.278 | 1.00 | 86.39 | C |
| ATOM | 1766 | CD1 | LEU | A | 1032 | 14.444 | 13.291 | −1.352 | 1.00 | 90.55 | C |
| ATOM | 1767 | CD2 | LEU | A | 1032 | 15.178 | 15.627 | −0.815 | 1.00 | 85.41 | C |
| ATOM | 1768 | N | LEU | A | 1033 | 15.124 | 15.813 | 2.714 | 1.00 | 65.64 | N |
| ATOM | 1769 | CA | LEU | A | 1033 | 16.146 | 16.773 | 3.114 | 1.00 | 65.91 | C |
| ATOM | 1770 | C | LEU | A | 1033 | 17.253 | 16.896 | 2.072 | 1.00 | 71.02 | C |
| ATOM | 1771 | O | LEU | A | 1033 | 17.614 | 18.000 | 1.668 | 1.00 | 76.14 | O |
| ATOM | 1772 | CB | LEU | A | 1033 | 16.739 | 16.381 | 4.468 | 1.00 | 63.46 | C |
| ATOM | 1773 | CG | LEU | A | 1033 | 15.787 | 16.482 | 5.661 | 1.00 | 60.37 | C |
| ATOM | 1774 | CD1 | LEU | A | 1033 | 16.412 | 15.872 | 6.904 | 1.00 | 60.73 | C |
| ATOM | 1775 | CD2 | LEU | A | 1033 | 15.403 | 17.932 | 5.909 | 1.00 | 65.47 | C |
| ATOM | 1776 | N | THR | A | 1034 | 17.788 | 15.758 | 1.642 | 1.00 | 71.63 | N |
| ATOM | 1777 | CA | THR | A | 1034 | 18.877 | 15.744 | 0.672 | 1.00 | 68.38 | C |
| ATOM | 1778 | C | THR | A | 1034 | 19.046 | 14.362 | 0.050 | 1.00 | 69.57 | C |
| ATOM | 1779 | O | THR | A | 1034 | 18.684 | 13.350 | 0.651 | 1.00 | 62.66 | O |
| ATOM | 1780 | CB | THR | A | 1034 | 20.212 | 16.173 | 1.318 | 1.00 | 66.96 | C |
| ATOM | 1781 | OG1 | THR | A | 1034 | 21.254 | 16.159 | 0.334 | 1.00 | 64.01 | O |
| ATOM | 1782 | CG2 | THR | A | 1034 | 20.583 | 15.231 | 2.454 | 1.00 | 56.21 | C |
| ATOM | 1783 | N | LYS | A | 1035 | 19.599 | 14.328 | −1.158 | 1.00 | 77.67 | N |
| ATOM | 1784 | CA | LYS | A | 1035 | 19.866 | 13.070 | −1.846 | 1.00 | 73.48 | C |
| ATOM | 1785 | C | LYS | A | 1035 | 21.298 | 12.615 | −1.593 | 1.00 | 61.50 | C |
| ATOM | 1786 | O | LYS | A | 1035 | 21.736 | 11.589 | −2.111 | 1.00 | 60.21 | O |
| ATOM | 1787 | CB | LYS | A | 1035 | 19.611 | 13.219 | −3.346 | 1.00 | 77.83 | C |
| ATOM | 1788 | CG | LYS | A | 1035 | 18.138 | 13.248 | −3.722 | 1.00 | 85.90 | C |
| ATOM | 1789 | CD | LYS | A | 1035 | 17.893 | 14.172 | −4.901 | 1.00 | 92.99 | C |
| ATOM | 1790 | CE | LYS | A | 1035 | 18.228 | 15.611 | −4.534 | 1.00 | 99.27 | C |
| ATOM | 1791 | NZ | LYS | A | 1035 | 18.022 | 16.546 | −5.674 | 1.00 | 100.21 | N |
| ATOM | 1792 | N | SER | A | 1036 | 22.022 | 13.389 | −0.791 | 1.00 | 58.80 | N |
| ATOM | 1793 | CA | SER | A | 1036 | 23.392 | 13.056 | −0.428 | 1.00 | 65.52 | C |
| ATOM | 1794 | C | SER | A | 1036 | 23.420 | 11.855 | 0.511 | 1.00 | 74.00 | C |
| ATOM | 1795 | O | SER | A | 1036 | 22.556 | 11.720 | 1.377 | 1.00 | 81.62 | O |
| ATOM | 1796 | CB | SER | A | 1036 | 24.076 | 14.255 | 0.230 | 1.00 | 71.90 | C |
| ATOM | 1797 | OG | SER | A | 1036 | 25.359 | 13.907 | 0.716 | 1.00 | 80.84 | O |
| ATOM | 1798 | N | PRO | A | 1037 | 24.420 | 10.978 | 0.340 | 1.00 | 74.48 | N |
| ATOM | 1799 | CA | PRO | A | 1037 | 24.557 | 9.743 | 1.120 | 1.00 | 72.50 | C |
| ATOM | 1800 | C | PRO | A | 1037 | 25.121 | 10.003 | 2.512 | 1.00 | 76.82 | C |
| ATOM | 1801 | O | PRO | A | 1037 | 25.831 | 9.155 | 3.051 | 1.00 | 84.85 | O |
| ATOM | 1802 | CB | PRO | A | 1037 | 25.569 | 8.921 | 0.306 | 1.00 | 64.80 | C |
| ATOM | 1803 | CG | PRO | A | 1037 | 25.774 | 9.674 | −0.983 | 1.00 | 65.29 | C |
| ATOM | 1804 | CD | PRO | A | 1037 | 25.472 | 11.095 | −0.679 | 1.00 | 67.78 | C |
| ATOM | 1805 | N | SER | A | 1038 | 24.809 | 11.160 | 3.084 | 1.00 | 72.80 | N |
| ATOM | 1806 | CA | SER | A | 1038 | 25.357 | 11.531 | 4.383 | 1.00 | 68.55 | C |
| ATOM | 1807 | C | SER | A | 1038 | 24.282 | 11.962 | 5.374 | 1.00 | 67.20 | C |
| ATOM | 1808 | O | SER | A | 1038 | 23.650 | 13.005 | 5.205 | 1.00 | 68.75 | O |
| ATOM | 1809 | CB | SER | A | 1038 | 26.395 | 12.645 | 4.224 | 1.00 | 70.73 | C |
| ATOM | 1810 | OG | SER | A | 1038 | 26.754 | 13.188 | 5.483 | 1.00 | 69.18 | O |
| ATOM | 1811 | N | LEU | A | 1039 | 24.085 | 11.153 | 6.410 | 1.00 | 60.38 | N |
| ATOM | 1812 | CA | LEU | A | 1039 | 23.189 | 11.510 | 7.500 | 1.00 | 59.67 | C |
| ATOM | 1813 | C | LEU | A | 1039 | 23.616 | 12.848 | 8.094 | 1.00 | 63.11 | C |
| ATOM | 1814 | O | LEU | A | 1039 | 22.782 | 13.689 | 8.430 | 1.00 | 66.11 | O |
| ATOM | 1815 | CB | LEU | A | 1039 | 23.210 | 10.429 | 8.579 | 1.00 | 57.26 | C |
| ATOM | 1816 | CG | LEU | A | 1039 | 22.373 | 10.705 | 9.828 | 1.00 | 64.93 | C |
| ATOM | 1817 | CD1 | LEU | A | 1039 | 20.894 | 10.777 | 9.475 | 1.00 | 65.26 | C |
| ATOM | 1818 | CD2 | LEU | A | 1039 | 22.625 | 9.642 | 10.886 | 1.00 | 66.58 | C |
| ATOM | 1819 | N | ASN | A | 1040 | 24.927 | 13.029 | 8.218 | 1.00 | 68.07 | N |
| ATOM | 1820 | CA | ASN | A | 1040 | 25.503 | 14.274 | 8.709 | 1.00 | 66.58 | C |
| ATOM | 1821 | C | ASN | A | 1040 | 25.013 | 15.469 | 7.898 | 1.00 | 65.15 | C |
| ATOM | 1822 | O | ASN | A | 1040 | 24.574 | 16.474 | 8.457 | 1.00 | 64.58 | O |
| ATOM | 1823 | CB | ASN | A | 1040 | 27.033 | 14.194 | 8.670 | 1.00 | 69.42 | C |
| ATOM | 1824 | CG | ASN | A | 1040 | 27.702 | 15.453 | 9.188 | 1.00 | 67.67 | C |
| ATOM | 1825 | OD1 | ASN | A | 1040 | 27.055 | 16.316 | 9.779 | 1.00 | 69.99 | O |
| ATOM | 1826 | ND2 | ASN | A | 1040 | 29.008 | 15.562 | 8.967 | 1.00 | 68.91 | N |
| ATOM | 1827 | N | ALA | A | 1041 | 25.086 | 15.349 | 6.575 | 1.00 | 68.84 | N |
| ATOM | 1828 | CA | ALA | A | 1041 | 24.627 | 16.406 | 5.680 | 1.00 | 71.51 | C |
| ATOM | 1829 | C | ALA | A | 1041 | 23.125 | 16.636 | 5.822 | 1.00 | 73.67 | C |
| ATOM | 1830 | O | ALA | A | 1041 | 22.658 | 17.775 | 5.815 | 1.00 | 76.45 | O |
| ATOM | 1831 | CB | ALA | A | 1041 | 24.979 | 16.072 | 4.238 | 1.00 | 68.72 | C |
| ATOM | 1832 | N | ALA | A | 1042 | 22.374 | 15.546 | 5.950 | 1.00 | 69.30 | N |
| ATOM | 1833 | CA | ALA | A | 1042 | 20.929 | 15.627 | 6.122 | 1.00 | 67.49 | C |
| ATOM | 1834 | C | ALA | A | 1042 | 20.571 | 16.427 | 7.369 | 1.00 | 66.07 | C |

TABLE 6-continued

HUMAN A2A ADENOSINE STRUCTURE.PDB FILE
(Table 6: discloses SEQ ID NOS 20-27, respectively, in order of appearance.)

| ATOM | 1835 | O | ALA | A | 1042 | 19.672 | 17.267 | 7.340 | 1.00 | 62.31 | O |
|------|------|-----|-----|---|------|--------|--------|--------|------|-------|---|
| ATOM | 1836 | CB | ALA | A | 1042 | 20.324 | 14.235 | 6.196 | 1.00 | 66.75 | C |
| ATOM | 1837 | N | LYS | A | 1043 | 21.279 | 16.163 | 8.462 | 1.00 | 58.42 | N |
| ATOM | 1838 | CA | LYS | A | 1043 | 21.016 | 16.849 | 9.721 | 1.00 | 64.00 | C |
| ATOM | 1839 | C | LYS | A | 1043 | 21.312 | 18.344 | 9.620 | 1.00 | 65.56 | C |
| ATOM | 1840 | O | LYS | A | 1043 | 20.650 | 19.162 | 10.257 | 1.00 | 66.25 | O |
| ATOM | 1841 | CB | LYS | A | 1043 | 21.833 | 16.228 | 10.855 | 1.00 | 63.36 | C |
| ATOM | 1842 | CG | LYS | A | 1043 | 21.459 | 14.797 | 11.201 | 1.00 | 63.17 | C |
| ATOM | 1843 | CD | LYS | A | 1043 | 22.234 | 14.314 | 12.416 | 1.00 | 67.07 | C |
| ATOM | 1844 | CE | LYS | A | 1043 | 21.892 | 12.874 | 12.761 | 1.00 | 73.16 | C |
| ATOM | 1845 | NZ | LYS | A | 1043 | 22.570 | 12.424 | 14.009 | 1.00 | 71.24 | N |
| ATOM | 1846 | N | SER | A | 1044 | 22.311 | 18.694 | 8.817 | 1.00 | 66.30 | N |
| ATOM | 1847 | CA | SER | A | 1044 | 22.686 | 20.090 | 8.631 | 1.00 | 65.13 | C |
| ATOM | 1848 | C | SER | A | 1044 | 21.609 | 20.826 | 7.846 | 1.00 | 70.13 | C |
| ATOM | 1849 | O | SER | A | 1044 | 21.309 | 21.986 | 8.123 | 1.00 | 74.77 | O |
| ATOM | 1850 | CB | SER | A | 1044 | 24.032 | 20.195 | 7.914 | 1.00 | 69.62 | C |
| ATOM | 1851 | OG | SER | A | 1044 | 25.024 | 19.434 | 8.583 | 1.00 | 72.49 | O |
| ATOM | 1852 | N | GLU | A | 1045 | 21.034 | 20.141 | 6.862 | 1.00 | 71.24 | N |
| ATOM | 1853 | CA | GLU | A | 1045 | 19.923 | 20.693 | 6.098 | 1.00 | 74.35 | C |
| ATOM | 1854 | C | GLU | A | 1045 | 18.726 | 20.927 | 7.010 | 1.00 | 69.93 | C |
| ATOM | 1855 | O | GLU | A | 1045 | 18.011 | 21.920 | 6.874 | 1.00 | 67.44 | O |
| ATOM | 1856 | CB | GLU | A | 1045 | 19.534 | 19.748 | 4.958 | 1.00 | 77.46 | C |
| ATOM | 1857 | CG | GLU | A | 1045 | 20.571 | 19.640 | 3.854 | 1.00 | 79.90 | C |
| ATOM | 1858 | CD | GLU | A | 1045 | 20.689 | 20.914 | 3.038 | 1.00 | 82.50 | C |
| ATOM | 1859 | OE1 | GLU | A | 1045 | 19.785 | 21.769 | 3.135 | 1.00 | 85.49 | O |
| ATOM | 1860 | OE2 | GLU | A | 1045 | 21.684 | 21.057 | 2.297 | 1.00 | 83.20 | O |
| ATOM | 1861 | N | LEU | A | 1046 | 18.518 | 20.005 | 7.944 | 1.00 | 68.76 | N |
| ATOM | 1862 | CA | LEU | A | 1046 | 17.402 | 20.091 | 8.877 | 1.00 | 72.48 | C |
| ATOM | 1863 | C | LEU | A | 1046 | 17.539 | 21.304 | 9.793 | 1.00 | 69.88 | C |
| ATOM | 1864 | O | LEU | A | 1046 | 16.583 | 22.052 | 9.990 | 1.00 | 65.23 | O |
| ATOM | 1865 | CB | LEU | A | 1046 | 17.302 | 18.809 | 9.708 | 1.00 | 78.23 | C |
| ATOM | 1866 | CG | LEU | A | 1046 | 16.103 | 18.686 | 10.652 | 1.00 | 73.85 | C |
| ATOM | 1867 | CD1 | LEU | A | 1046 | 14.797 | 18.812 | 9.883 | 1.00 | 70.02 | C |
| ATOM | 1868 | CD2 | LEU | A | 1046 | 16.155 | 17.370 | 11.411 | 1.00 | 73.33 | C |
| ATOM | 1869 | N | ASP | A | 1047 | 18.734 | 21.494 | 10.346 | 1.00 | 66.78 | N |
| ATOM | 1870 | CA | ASP | A | 1047 | 18.993 | 22.615 | 11.243 | 1.00 | 69.47 | C |
| ATOM | 1871 | C | ASP | A | 1047 | 18.819 | 23.960 | 10.540 | 1.00 | 76.57 | C |
| ATOM | 1872 | O | ASP | A | 1047 | 18.485 | 24.963 | 11.172 | 1.00 | 78.82 | O |
| ATOM | 1873 | CB | ASP | A | 1047 | 20.397 | 22.510 | 11.842 | 1.00 | 75.25 | C |
| ATOM | 1874 | CG | ASP | A | 1047 | 20.536 | 21.343 | 12.799 | 1.00 | 83.59 | C |
| ATOM | 1875 | OD1 | ASP | A | 1047 | 19.553 | 20.590 | 12.966 | 1.00 | 87.38 | O |
| ATOM | 1876 | OD2 | ASP | A | 1047 | 21.627 | 21.180 | 13.387 | 1.00 | 78.59 | O |
| ATOM | 1877 | N | LYS | A | 1048 | 19.048 | 23.974 | 9.231 | 1.00 | 73.83 | N |
| ATOM | 1878 | CA | LYS | A | 1048 | 18.880 | 25.186 | 8.438 | 1.00 | 76.01 | C |
| ATOM | 1879 | C | LYS | A | 1048 | 17.403 | 25.538 | 8.288 | 1.00 | 80.45 | C |
| ATOM | 1880 | O | LYS | A | 1048 | 17.022 | 26.707 | 8.355 | 1.00 | 80.97 | O |
| ATOM | 1881 | CB | LYS | A | 1048 | 19.523 | 25.014 | 7.060 | 1.00 | 83.10 | C |
| ATOM | 1882 | CG | LYS | A | 1048 | 19.306 | 26.190 | 6.121 | 1.00 | 93.96 | C |
| ATOM | 1883 | CD | LYS | A | 1048 | 19.865 | 25.899 | 4.737 | 1.00 | 102.83 | C |
| ATOM | 1884 | CE | LYS | A | 1048 | 19.643 | 27.069 | 3.790 | 1.00 | 107.02 | C |
| ATOM | 1885 | NZ | LYS | A | 1048 | 20.187 | 26.792 | 2.431 | 1.00 | 109.15 | N |
| ATOM | 1886 | N | ALA | A | 1049 | 16.574 | 24.518 | 8.090 | 1.00 | 79.94 | N |
| ATOM | 1887 | CA | ALA | A | 1049 | 15.140 | 24.716 | 7.902 | 1.00 | 69.83 | C |
| ATOM | 1888 | C | ALA | A | 1049 | 14.427 | 25.015 | 9.218 | 1.00 | 69.42 | C |
| ATOM | 1889 | O | ALA | A | 1049 | 13.528 | 25.853 | 9.269 | 1.00 | 60.97 | O |
| ATOM | 1890 | CB | ALA | A | 1049 | 14.523 | 23.498 | 7.229 | 1.00 | 61.47 | C |
| ATOM | 1891 | N | ILE | A | 1050 | 14.831 | 24.325 | 10.280 | 1.00 | 74.66 | N |
| ATOM | 1892 | CA | ILE | A | 1050 | 14.196 | 24.488 | 11.583 | 1.00 | 80.09 | C |
| ATOM | 1893 | C | ILE | A | 1050 | 14.699 | 25.736 | 12.303 | 1.00 | 88.48 | C |
| ATOM | 1894 | O | ILE | A | 1050 | 13.936 | 26.423 | 12.982 | 1.00 | 96.01 | O |
| ATOM | 1895 | CB | ILE | A | 1050 | 14.425 | 23.257 | 12.481 | 1.00 | 77.76 | C |
| ATOM | 1896 | CG1 | ILE | A | 1050 | 14.083 | 21.971 | 11.726 | 1.00 | 70.73 | C |
| ATOM | 1897 | CG2 | ILE | A | 1050 | 13.603 | 23.369 | 13.758 | 1.00 | 77.51 | C |
| ATOM | 1898 | CD1 | ILE | A | 1050 | 12.640 | 21.884 | 11.284 | 1.00 | 60.96 | C |
| ATOM | 1899 | N | GLY | A | 1051 | 15.987 | 26.025 | 12.152 | 1.00 | 88.61 | N |
| ATOM | 1900 | CA | GLY | A | 1051 | 16.583 | 27.187 | 12.784 | 1.00 | 87.42 | C |
| ATOM | 1901 | C | GLY | A | 1051 | 17.140 | 26.887 | 14.163 | 1.00 | 86.47 | C |
| ATOM | 1902 | O | GLY | A | 1051 | 17.148 | 27.751 | 15.041 | 1.00 | 86.08 | O |
| ATOM | 1903 | N | ARG | A | 1052 | 17.606 | 25.656 | 14.353 | 1.00 | 79.96 | N |
| ATOM | 1904 | CA | ARG | A | 1052 | 18.213 | 25.251 | 15.615 | 1.00 | 79.05 | C |
| ATOM | 1905 | C | ARG | A | 1052 | 18.925 | 23.912 | 15.472 | 1.00 | 78.75 | C |
| ATOM | 1906 | O | ARG | A | 1052 | 18.735 | 23.197 | 14.490 | 1.00 | 85.14 | O |
| ATOM | 1907 | CB | ARG | A | 1052 | 17.157 | 25.147 | 16.716 | 1.00 | 73.95 | C |
| ATOM | 1908 | CG | ARG | A | 1052 | 16.327 | 23.874 | 16.653 | 1.00 | 66.70 | C |
| ATOM | 1909 | CD | ARG | A | 1052 | 15.555 | 23.652 | 17.944 | 1.00 | 64.28 | C |
| ATOM | 1910 | NE | ARG | A | 1052 | 14.650 | 22.509 | 17.850 | 1.00 | 68.44 | N |
| ATOM | 1911 | CZ | ARG | A | 1052 | 14.977 | 21.265 | 18.186 | 1.00 | 77.48 | C |

TABLE 6-continued

HUMAN A2A ADENOSINE STRUCTURE.PDB FILE
(Table 6: discloses SEQ ID NOS 20-27, respectively, in order of appearance.)

| ATOM | 1912 | NH1 | ARG | A | 1052 | 16.194 | 20.997 | 18.641 | 1.00 | 82.58 | N |
|---|---|---|---|---|---|---|---|---|---|---|---|
| ATOM | 1913 | NH2 | ARG | A | 1052 | 14.088 | 20.289 | 18.066 | 1.00 | 75.98 | N |
| ATOM | 1914 | N | ASN | A | 1053 | 19.746 | 23.578 | 16.462 | 1.00 | 73.30 | N |
| ATOM | 1915 | CA | ASN | A | 1053 | 20.421 | 22.289 | 16.494 | 1.00 | 77.68 | C |
| ATOM | 1916 | C | ASN | A | 1053 | 19.455 | 21.184 | 16.906 | 1.00 | 83.86 | C |
| ATOM | 1917 | O | ASN | A | 1053 | 19.102 | 21.062 | 18.079 | 1.00 | 89.66 | O |
| ATOM | 1918 | CB | ASN | A | 1053 | 21.606 | 22.334 | 17.457 | 1.00 | 84.67 | C |
| ATOM | 1919 | CG | ASN | A | 1053 | 22.454 | 21.083 | 17.393 | 1.00 | 95.60 | C |
| ATOM | 1920 | OD1 | ASN | A | 1053 | 22.977 | 20.728 | 16.335 | 1.00 | 103.08 | O |
| ATOM | 1921 | ND2 | ASN | A | 1053 | 22.602 | 20.407 | 18.527 | 1.00 | 93.66 | N |
| ATOM | 1922 | N | THR | A | 1054 | 19.032 | 20.379 | 15.937 | 1.00 | 82.14 | N |
| ATOM | 1923 | CA | THR | A | 1054 | 18.020 | 19.355 | 16.176 | 1.00 | 74.70 | C |
| ATOM | 1924 | C | THR | A | 1054 | 18.623 | 18.013 | 16.574 | 1.00 | 70.81 | C |
| ATOM | 1925 | O | THR | A | 1054 | 17.989 | 17.225 | 17.276 | 1.00 | 76.52 | O |
| ATOM | 1926 | CB | THR | A | 1054 | 17.139 | 19.139 | 14.931 | 1.00 | 72.46 | C |
| ATOM | 1927 | OG1 | THR | A | 1054 | 17.929 | 18.576 | 13.875 | 1.00 | 78.51 | O |
| ATOM | 1928 | CG2 | THR | A | 1054 | 16.538 | 20.458 | 14.466 | 1.00 | 65.15 | C |
| ATOM | 1929 | N | ASN | A | 1055 | 19.845 | 17.756 | 16.117 | 1.00 | 71.05 | N |
| ATOM | 1930 | CA | ASN | A | 1055 | 20.501 | 16.474 | 16.353 | 1.00 | 78.59 | C |
| ATOM | 1931 | C | ASN | A | 1055 | 19.770 | 15.327 | 15.661 | 1.00 | 72.00 | C |
| ATOM | 1932 | O | ASN | A | 1055 | 19.958 | 14.161 | 16.004 | 1.00 | 72.01 | O |
| ATOM | 1933 | CB | ASN | A | 1055 | 20.635 | 16.194 | 17.853 | 1.00 | 91.78 | C |
| ATOM | 1934 | CG | ASN | A | 1055 | 21.533 | 17.195 | 18.557 | 1.00 | 94.50 | C |
| ATOM | 1935 | OD1 | ASN | A | 1055 | 22.476 | 17.722 | 17.968 | 1.00 | 88.19 | O |
| ATOM | 1936 | ND2 | ASN | A | 1055 | 21.246 | 17.458 | 19.827 | 1.00 | 97.32 | N |
| ATOM | 1937 | N | GLY | A | 1056 | 18.934 | 15.670 | 14.685 | 1.00 | 79.23 | N |
| ATOM | 1938 | CA | GLY | A | 1056 | 18.203 | 14.680 | 13.915 | 1.00 | 77.94 | C |
| ATOM | 1939 | C | GLY | A | 1056 | 16.801 | 14.417 | 14.432 | 1.00 | 76.68 | C |
| ATOM | 1940 | O | GLY | A | 1056 | 16.134 | 13.484 | 13.985 | 1.00 | 78.26 | O |
| ATOM | 1941 | N | VAL | A | 1057 | 16.351 | 15.242 | 15.373 | 1.00 | 73.54 | N |
| ATOM | 1942 | CA | VAL | A | 1057 | 15.035 | 15.065 | 15.981 | 1.00 | 71.81 | C |
| ATOM | 1943 | C | VAL | A | 1057 | 14.295 | 16.390 | 16.142 | 1.00 | 74.80 | C |
| ATOM | 1944 | O | VAL | A | 1057 | 14.836 | 17.354 | 16.684 | 1.00 | 72.84 | O |
| ATOM | 1945 | CB | VAL | A | 1057 | 15.140 | 14.381 | 17.359 | 1.00 | 74.93 | C |
| ATOM | 1946 | CG1 | VAL | A | 1057 | 13.798 | 14.412 | 18.074 | 1.00 | 75.20 | C |
| ATOM | 1947 | CG2 | VAL | A | 1057 | 15.641 | 12.952 | 17.207 | 1.00 | 77.14 | C |
| ATOM | 1948 | N | ILE | A | 1058 | 13.053 | 16.429 | 15.669 | 1.00 | 78.97 | N |
| ATOM | 1949 | CA | ILE | A | 1058 | 12.223 | 17.624 | 15.782 | 1.00 | 78.10 | C |
| ATOM | 1950 | C | ILE | A | 1058 | 10.928 | 17.330 | 16.535 | 1.00 | 66.57 | C |
| ATOM | 1951 | O | ILE | A | 1058 | 10.592 | 16.171 | 16.784 | 1.00 | 60.95 | O |
| ATOM | 1952 | CB | ILE | A | 1058 | 11.877 | 18.202 | 14.397 | 1.00 | 77.66 | C |
| ATOM | 1953 | CG1 | ILE | A | 1058 | 11.229 | 17.128 | 13.520 | 1.00 | 72.84 | C |
| ATOM | 1954 | CG2 | ILE | A | 1058 | 13.123 | 18.758 | 13.725 | 1.00 | 72.77 | C |
| ATOM | 1955 | CD1 | ILE | A | 1058 | 10.750 | 17.639 | 12.178 | 1.00 | 61.77 | C |
| ATOM | 1956 | N | THR | A | 1059 | 10.203 | 18.383 | 16.898 | 1.00 | 58.60 | N |
| ATOM | 1957 | CA | THR | A | 1059 | 8.926 | 18.227 | 17.586 | 1.00 | 62.26 | C |
| ATOM | 1958 | C | THR | A | 1059 | 7.780 | 18.129 | 16.586 | 1.00 | 64.79 | C |
| ATOM | 1959 | O | THR | A | 1059 | 7.954 | 18.415 | 15.401 | 1.00 | 64.65 | O |
| ATOM | 1960 | CB | THR | A | 1059 | 8.650 | 19.395 | 18.552 | 1.00 | 69.44 | C |
| ATOM | 1961 | OG1 | THR | A | 1059 | 8.545 | 20.618 | 17.812 | 1.00 | 73.51 | O |
| ATOM | 1962 | CG2 | THR | A | 1059 | 9.770 | 19.518 | 19.572 | 1.00 | 72.03 | C |
| ATOM | 1963 | N | LYS | A | 1060 | 6.611 | 17.717 | 17.067 | 1.00 | 70.45 | N |
| ATOM | 1964 | CA | LYS | A | 1060 | 5.428 | 17.637 | 16.219 | 1.00 | 66.59 | C |
| ATOM | 1965 | C | LYS | A | 1060 | 5.152 | 18.986 | 15.576 | 1.00 | 66.61 | C |
| ATOM | 1966 | O | LYS | A | 1060 | 4.941 | 19.081 | 14.367 | 1.00 | 70.77 | O |
| ATOM | 1967 | CB | LYS | A | 1060 | 4.208 | 17.200 | 17.028 | 1.00 | 72.87 | C |
| ATOM | 1968 | CG | LYS | A | 1060 | 2.888 | 17.594 | 16.383 | 1.00 | 80.24 | C |
| ATOM | 1969 | CD | LYS | A | 1060 | 1.711 | 17.355 | 17.310 | 1.00 | 85.69 | C |
| ATOM | 1970 | CE | LYS | A | 1060 | 0.509 | 18.178 | 16.880 | 1.00 | 86.21 | C |
| ATOM | 1971 | NZ | LYS | A | 1060 | 0.251 | 18.057 | 15.419 | 1.00 | 86.92 | N |
| ATOM | 1972 | N | ASP | A | 1061 | 5.155 | 20.029 | 16.399 | 1.00 | 67.98 | N |
| ATOM | 1973 | CA | ASP | A | 1061 | 4.915 | 21.385 | 15.927 | 1.00 | 73.37 | C |
| ATOM | 1974 | C | ASP | A | 1061 | 5.832 | 21.731 | 14.760 | 1.00 | 68.27 | C |
| ATOM | 1975 | O | ASP | A | 1061 | 5.371 | 22.189 | 13.715 | 1.00 | 66.95 | O |
| ATOM | 1976 | CB | ASP | A | 1061 | 5.111 | 22.383 | 17.071 | 1.00 | 88.29 | C |
| ATOM | 1977 | CG | ASP | A | 1061 | 4.756 | 23.806 | 16.677 | 1.00 | 101.24 | C |
| ATOM | 1978 | OD1 | ASP | A | 1061 | 5.065 | 24.212 | 15.537 | 1.00 | 107.74 | O |
| ATOM | 1979 | OD2 | ASP | A | 1061 | 4.172 | 24.523 | 17.515 | 1.00 | 102.03 | O |
| ATOM | 1980 | N | GLU | A | 1062 | 7.131 | 21.507 | 14.942 | 1.00 | 75.41 | N |
| ATOM | 1981 | CA | GLU | A | 1062 | 8.120 | 21.839 | 13.921 | 1.00 | 79.87 | C |
| ATOM | 1982 | C | GLU | A | 1062 | 7.898 | 21.064 | 12.626 | 1.00 | 74.97 | C |
| ATOM | 1983 | O | GLU | A | 1062 | 8.163 | 21.574 | 11.536 | 1.00 | 74.35 | O |
| ATOM | 1984 | CB | GLU | A | 1062 | 9.536 | 21.600 | 14.448 | 1.00 | 81.59 | C |
| ATOM | 1985 | CG | GLU | A | 1062 | 9.965 | 22.588 | 15.518 | 1.00 | 85.62 | C |
| ATOM | 1986 | CD | GLU | A | 1062 | 11.292 | 22.222 | 16.150 | 1.00 | 84.49 | C |
| ATOM | 1987 | OE1 | GLU | A | 1062 | 11.628 | 21.019 | 16.177 | 1.00 | 86.95 | O |
| ATOM | 1988 | OE2 | GLU | A | 1062 | 11.996 | 23.137 | 16.626 | 1.00 | 77.53 | O |

TABLE 6-continued

HUMAN A2A ADENOSINE STRUCTURE.PDB FILE
(Table 6: discloses SEQ ID NOS 20-27, respectively, in order of appearance.)

| ATOM | 1989 | N | ALA | A | 1063 | 7.415 | 19.832 | 12.749 | 1.00 | 64.21 | N |
|---|---|---|---|---|---|---|---|---|---|---|---|
| ATOM | 1990 | CA | ALA | A | 1063 | 7.103 | 19.018 | 11.581 | 1.00 | 65.21 | C |
| ATOM | 1991 | C | ALA | A | 1063 | 5.929 | 19.620 | 10.819 | 1.00 | 69.70 | C |
| ATOM | 1992 | O | ALA | A | 1063 | 5.836 | 19.493 | 9.598 | 1.00 | 68.56 | O |
| ATOM | 1993 | CB | ALA | A | 1063 | 6.793 | 17.587 | 11.993 | 1.00 | 54.62 | C |
| ATOM | 1994 | N | GLU | A | 1064 | 5.036 | 20.282 | 11.549 | 1.00 | 66.00 | N |
| ATOM | 1995 | CA | GLU | A | 1064 | 3.866 | 20.908 | 10.949 | 1.00 | 69.72 | C |
| ATOM | 1996 | C | GLU | A | 1064 | 4.249 | 22.151 | 10.154 | 1.00 | 73.69 | C |
| ATOM | 1997 | O | GLU | A | 1064 | 3.717 | 22.392 | 9.070 | 1.00 | 85.44 | O |
| ATOM | 1998 | CB | GLU | A | 1064 | 2.831 | 21.258 | 12.019 | 1.00 | 74.07 | C |
| ATOM | 1999 | CG | GLU | A | 1064 | 1.489 | 21.702 | 11.459 | 1.00 | 81.92 | C |
| ATOM | 2000 | CD | GLU | A | 1064 | 0.378 | 21.647 | 12.489 | 1.00 | 88.62 | C |
| ATOM | 2001 | OE1 | GLU | A | 1064 | 0.688 | 21.554 | 13.697 | 1.00 | 88.82 | O |
| ATOM | 2002 | OE2 | GLU | A | 1064 | −0.806 | 21.694 | 12.092 | 1.00 | 87.09 | O |
| ATOM | 2003 | N | LYS | A | 1065 | 5.173 | 22.939 | 10.693 | 1.00 | 64.49 | N |
| ATOM | 2004 | CA | LYS | A | 1065 | 5.652 | 24.129 | 9.998 | 1.00 | 64.57 | C |
| ATOM | 2005 | C | LYS | A | 1065 | 6.322 | 23.770 | 8.675 | 1.00 | 68.05 | C |
| ATOM | 2006 | O | LYS | A | 1065 | 6.155 | 24.471 | 7.678 | 1.00 | 70.67 | O |
| ATOM | 2007 | CB | LYS | A | 1065 | 6.596 | 24.942 | 10.886 | 1.00 | 73.97 | C |
| ATOM | 2008 | CG | LYS | A | 1065 | 5.874 | 25.898 | 11.824 | 1.00 | 85.47 | C |
| ATOM | 2009 | CD | LYS | A | 1065 | 6.833 | 26.606 | 12.768 | 1.00 | 94.02 | C |
| ATOM | 2010 | CE | LYS | A | 1065 | 7.287 | 25.686 | 13.889 | 1.00 | 99.46 | C |
| ATOM | 2011 | NZ | LYS | A | 1065 | 8.041 | 26.424 | 14.941 | 1.00 | 102.10 | N |
| ATOM | 2012 | N | LEU | A | 1066 | 7.075 | 22.675 | 8.665 | 1.00 | 70.04 | N |
| ATOM | 2013 | CA | LEU | A | 1066 | 7.685 | 22.191 | 7.432 | 1.00 | 66.35 | C |
| ATOM | 2014 | C | LEU | A | 1066 | 6.611 | 21.771 | 6.434 | 1.00 | 63.34 | C |
| ATOM | 2015 | O | LEU | A | 1066 | 6.706 | 22.066 | 5.244 | 1.00 | 62.98 | O |
| ATOM | 2016 | CB | LEU | A | 1066 | 8.625 | 21.018 | 7.713 | 1.00 | 74.11 | C |
| ATOM | 2017 | CG | LEU | A | 1066 | 10.007 | 21.351 | 8.276 | 1.00 | 76.06 | C |
| ATOM | 2018 | CD1 | LEU | A | 1066 | 10.738 | 20.079 | 8.678 | 1.00 | 76.86 | C |
| ATOM | 2019 | CD2 | LEU | A | 1066 | 10.820 | 22.147 | 7.265 | 1.00 | 71.32 | C |
| ATOM | 2020 | N | PHE | A | 1067 | 5.588 | 21.083 | 6.931 | 1.00 | 66.17 | N |
| ATOM | 2021 | CA | PHE | A | 1067 | 4.493 | 20.622 | 6.085 | 1.00 | 65.88 | C |
| ATOM | 2022 | C | PHE | A | 1067 | 3.721 | 21.793 | 5.485 | 1.00 | 62.56 | C |
| ATOM | 2023 | O | PHE | A | 1067 | 3.364 | 21.774 | 4.306 | 1.00 | 63.34 | O |
| ATOM | 2024 | CB | PHE | A | 1067 | 3.547 | 19.712 | 6.873 | 1.00 | 68.68 | C |
| ATOM | 2025 | CG | PHE | A | 1067 | 2.373 | 19.224 | 6.073 | 1.00 | 69.93 | C |
| ATOM | 2026 | CD1 | PHE | A | 1067 | 2.497 | 18.129 | 5.234 | 1.00 | 70.67 | C |
| ATOM | 2027 | CD2 | PHE | A | 1067 | 1.145 | 19.862 | 6.159 | 1.00 | 71.48 | C |
| ATOM | 2028 | CE1 | PHE | A | 1067 | 1.419 | 17.678 | 4.494 | 1.00 | 67.93 | C |
| ATOM | 2029 | CE2 | PHE | A | 1067 | 0.063 | 19.415 | 5.422 | 1.00 | 73.70 | C |
| ATOM | 2030 | CZ | PHE | A | 1067 | 0.200 | 18.322 | 4.589 | 1.00 | 68.07 | C |
| ATOM | 2031 | N | ASN | A | 1068 | 3.465 | 22.812 | 6.299 | 1.00 | 64.04 | N |
| ATOM | 2032 | CA | ASN | A | 1068 | 2.779 | 24.008 | 5.822 | 1.00 | 66.05 | C |
| ATOM | 2033 | C | ASN | A | 1068 | 3.508 | 24.641 | 4.644 | 1.00 | 66.08 | C |
| ATOM | 2034 | O | ASN | A | 1068 | 2.891 | 24.993 | 3.638 | 1.00 | 71.39 | O |
| ATOM | 2035 | CB | ASN | A | 1068 | 2.606 | 25.024 | 6.952 | 1.00 | 71.52 | C |
| ATOM | 2036 | CG | ASN | A | 1068 | 1.512 | 24.632 | 7.922 | 1.00 | 78.35 | C |
| ATOM | 2037 | OD1 | ASN | A | 1068 | 0.908 | 23.565 | 7.797 | 1.00 | 76.98 | O |
| ATOM | 2038 | ND2 | ASN | A | 1068 | 1.247 | 25.495 | 8.897 | 1.00 | 80.57 | N |
| ATOM | 2039 | N | GLN | A | 1069 | 4.824 | 24.779 | 4.773 | 1.00 | 68.06 | N |
| ATOM | 2040 | CA | GLN | A | 1069 | 5.655 | 25.292 | 3.690 | 1.00 | 70.50 | C |
| ATOM | 2041 | C | GLN | A | 1069 | 5.510 | 24.442 | 2.431 | 1.00 | 66.20 | C |
| ATOM | 2042 | O | GLN | A | 1069 | 5.408 | 24.971 | 1.324 | 1.00 | 68.34 | O |
| ATOM | 2043 | CB | GLN | A | 1069 | 7.123 | 25.353 | 4.121 | 1.00 | 87.72 | C |
| ATOM | 2044 | CG | GLN | A | 1069 | 7.618 | 26.746 | 4.498 | 1.00 | 105.25 | C |
| ATOM | 2045 | CD | GLN | A | 1069 | 6.863 | 27.357 | 5.664 | 1.00 | 118.67 | C |
| ATOM | 2046 | OE1 | GLN | A | 1069 | 6.164 | 26.663 | 6.401 | 1.00 | 125.68 | O |
| ATOM | 2047 | NE2 | GLN | A | 1069 | 7.006 | 28.666 | 5.839 | 1.00 | 120.47 | N |
| ATOM | 2048 | N | ASP | A | 1070 | 5.500 | 23.124 | 2.606 | 1.00 | 63.34 | N |
| ATOM | 2049 | CA | ASP | A | 1070 | 5.362 | 22.201 | 1.484 | 1.00 | 61.95 | C |
| ATOM | 2050 | C | ASP | A | 1070 | 4.026 | 22.376 | 0.770 | 1.00 | 61.58 | C |
| ATOM | 2051 | O | ASP | A | 1070 | 3.944 | 22.246 | −0.450 | 1.00 | 65.02 | O |
| ATOM | 2052 | CB | ASP | A | 1070 | 5.519 | 20.753 | 1.951 | 1.00 | 67.85 | C |
| ATOM | 2053 | CG | ASP | A | 1070 | 6.966 | 20.376 | 2.207 | 1.00 | 71.24 | C |
| ATOM | 2054 | OD1 | ASP | A | 1070 | 7.839 | 21.264 | 2.112 | 1.00 | 66.70 | O |
| ATOM | 2055 | OD2 | ASP | A | 1070 | 7.229 | 19.190 | 2.499 | 1.00 | 75.17 | O |
| ATOM | 2056 | N | VAL | A | 1071 | 2.980 | 22.665 | 1.536 | 1.00 | 61.41 | N |
| ATOM | 2057 | CA | VAL | A | 1071 | 1.657 | 22.875 | 0.964 | 1.00 | 56.84 | C |
| ATOM | 2058 | C | VAL | A | 1071 | 1.626 | 24.149 | 0.128 | 1.00 | 58.17 | C |
| ATOM | 2059 | O | VAL | A | 1071 | 1.147 | 24.146 | −1.006 | 1.00 | 58.46 | O |
| ATOM | 2060 | CB | VAL | A | 1071 | 0.572 | 22.953 | 2.056 | 1.00 | 62.46 | C |
| ATOM | 2061 | CG1 | VAL | A | 1071 | −0.742 | 23.436 | 1.465 | 1.00 | 67.79 | C |
| ATOM | 2062 | CG2 | VAL | A | 1071 | 0.395 | 21.599 | 2.723 | 1.00 | 55.46 | C |
| ATOM | 2063 | N | ASP | A | 1072 | 2.145 | 25.235 | 0.694 | 1.00 | 63.22 | N |
| ATOM | 2064 | CA | ASP | A | 1072 | 2.189 | 26.519 | 0.002 | 1.00 | 63.71 | C |
| ATOM | 2065 | C | ASP | A | 1072 | 2.844 | 26.391 | −1.368 | 1.00 | 69.86 | C |

TABLE 6-continued

HUMAN A2A ADENOSINE STRUCTURE.PDB FILE
(Table 6: discloses SEQ ID NOS 20-27, respectively, in order of appearance.)

| ATOM | 2066 | O | ASP | A | 1072 | 2.357 | 26.946 | −2.354 | 1.00 | 78.53 | O |
|---|---|---|---|---|---|---|---|---|---|---|---|
| ATOM | 2067 | CB | ASP | A | 1072 | 2.935 | 27.558 | 0.841 | 1.00 | 65.50 | C |
| ATOM | 2068 | CG | ASP | A | 1072 | 2.155 | 27.985 | 2.068 | 1.00 | 74.41 | C |
| ATOM | 2069 | OD1 | ASP | A | 1072 | 1.000 | 27.536 | 2.226 | 1.00 | 78.58 | O |
| ATOM | 2070 | OD2 | ASP | A | 1072 | 2.697 | 28.772 | 2.873 | 1.00 | 79.03 | O |
| ATOM | 2071 | N | ALA | A | 1073 | 3.951 | 25.657 | −1.422 | 1.00 | 62.49 | N |
| ATOM | 2072 | CA | ALA | A | 1073 | 4.676 | 25.457 | −2.670 | 1.00 | 65.69 | C |
| ATOM | 2073 | C | ALA | A | 1073 | 3.828 | 24.697 | −3.683 | 1.00 | 70.18 | C |
| ATOM | 2074 | O | ALA | A | 1073 | 3.760 | 25.072 | −4.854 | 1.00 | 77.10 | O |
| ATOM | 2075 | CB | ALA | A | 1073 | 5.982 | 24.722 | −2.411 | 1.00 | 66.04 | C |
| ATOM | 2076 | N | ALA | A | 1074 | 3.182 | 23.629 | −3.224 | 1.00 | 64.77 | N |
| ATOM | 2077 | CA | ALA | A | 1074 | 2.332 | 22.815 | −4.085 | 1.00 | 58.33 | C |
| ATOM | 2078 | C | ALA | A | 1074 | 1.184 | 23.637 | −4.661 | 1.00 | 58.51 | C |
| ATOM | 2079 | O | ALA | A | 1074 | 0.842 | 23.506 | −5.835 | 1.00 | 52.13 | O |
| ATOM | 2080 | CB | ALA | A | 1074 | 1.797 | 21.615 | −3.318 | 1.00 | 60.57 | C |
| ATOM | 2081 | N | VAL | A | 1075 | 0.592 | 24.483 | −3.825 | 1.00 | 65.54 | N |
| ATOM | 2082 | CA | VAL | A | 1075 | −0.501 | 25.343 | −4.259 | 1.00 | 65.91 | C |
| ATOM | 2083 | C | VAL | A | 1075 | −0.025 | 26.311 | −5.337 | 1.00 | 66.58 | C |
| ATOM | 2084 | O | VAL | A | 1075 | −0.728 | 26.555 | −6.319 | 1.00 | 69.82 | O |
| ATOM | 2085 | CB | VAL | A | 1075 | −1.105 | 26.135 | −3.082 | 1.00 | 63.54 | C |
| ATOM | 2086 | CG1 | VAL | A | 1075 | −2.136 | 27.132 | −3.583 | 1.00 | 59.94 | C |
| ATOM | 2087 | CG2 | VAL | A | 1075 | −1.725 | 25.186 | −2.069 | 1.00 | 57.71 | C |
| ATOM | 2088 | N | ARG | A | 1076 | 1.173 | 26.857 | −5.152 | 1.00 | 60.22 | N |
| ATOM | 2089 | CA | ARG | A | 1076 | 1.758 | 27.757 | −6.140 | 1.00 | 59.77 | C |
| ATOM | 2090 | C | ARG | A | 1076 | 2.010 | 27.038 | −7.463 | 1.00 | 61.59 | C |
| ATOM | 2091 | O | ARG | A | 1076 | 1.793 | 27.601 | −8.537 | 1.00 | 60.13 | O |
| ATOM | 2092 | CB | ARG | A | 1076 | 3.049 | 28.387 | −5.611 | 1.00 | 65.41 | C |
| ATOM | 2093 | CG | ARG | A | 1076 | 2.817 | 29.650 | −4.795 | 1.00 | 76.36 | C |
| ATOM | 2094 | CD | ARG | A | 1076 | 4.118 | 30.364 | −4.455 | 1.00 | 79.99 | C |
| ATOM | 2095 | NE | ARG | A | 1076 | 4.744 | 29.837 | −3.245 | 1.00 | 86.97 | N |
| ATOM | 2096 | CZ | ARG | A | 1076 | 5.820 | 29.057 | −3.237 | 1.00 | 81.16 | C |
| ATOM | 2097 | NH1 | ARG | A | 1076 | 6.398 | 28.713 | −4.379 | 1.00 | 81.38 | N |
| ATOM | 2098 | NH2 | ARG | A | 1076 | 6.320 | 28.626 | −2.087 | 1.00 | 67.17 | N |
| ATOM | 2099 | N | GLY | A | 1077 | 2.463 | 25.792 | −7.379 | 1.00 | 60.84 | N |
| ATOM | 2100 | CA | GLY | A | 1077 | 2.676 | 24.986 | −8.565 | 1.00 | 56.43 | C |
| ATOM | 2101 | C | GLY | A | 1077 | 1.369 | 24.720 | −9.286 | 1.00 | 55.73 | C |
| ATOM | 2102 | O | GLY | A | 1077 | 1.301 | 24.771 | −10.514 | 1.00 | 58.21 | O |
| ATOM | 2103 | N | ILE | A | 1078 | 0.326 | 24.436 | −8.514 | 1.00 | 54.99 | N |
| ATOM | 2104 | CA | ILE | A | 1078 | −0.992 | 24.161 | −9.071 | 1.00 | 62.60 | C |
| ATOM | 2105 | C | ILE | A | 1078 | −1.557 | 25.370 | −9.811 | 1.00 | 60.35 | C |
| ATOM | 2106 | O | ILE | A | 1078 | −2.206 | 25.228 | −10.848 | 1.00 | 63.52 | O |
| ATOM | 2107 | CB | ILE | A | 1078 | −1.984 | 23.728 | −7.974 | 1.00 | 63.43 | C |
| ATOM | 2108 | CG1 | ILE | A | 1078 | −1.637 | 22.324 | −7.471 | 1.00 | 69.61 | C |
| ATOM | 2109 | CG2 | ILE | A | 1078 | −3.413 | 23.774 | −8.497 | 1.00 | 49.86 | C |
| ATOM | 2110 | CD1 | ILE | A | 1078 | −2.514 | 21.847 | −6.332 | 1.00 | 72.57 | C |
| ATOM | 2111 | N | LEU | A | 1079 | −1.299 | 26.560 | −9.277 | 1.00 | 55.01 | N |
| ATOM | 2112 | CA | LEU | A | 1079 | −1.830 | 27.789 | −9.857 | 1.00 | 55.86 | C |
| ATOM | 2113 | C | LEU | A | 1079 | −1.100 | 28.216 | −11.130 | 1.00 | 64.61 | C |
| ATOM | 2114 | O | LEU | A | 1079 | −1.632 | 28.989 | −11.925 | 1.00 | 78.56 | O |
| ATOM | 2115 | CB | LEU | A | 1079 | −1.813 | 28.917 | −8.824 | 1.00 | 53.25 | C |
| ATOM | 2116 | CG | LEU | A | 1079 | −2.824 | 28.754 | −7.687 | 1.00 | 61.68 | C |
| ATOM | 2117 | CD1 | LEU | A | 1079 | −2.551 | 29.741 | −6.563 | 1.00 | 57.50 | C |
| ATOM | 2118 | CD2 | LEU | A | 1079 | −4.246 | 28.904 | −8.211 | 1.00 | 59.69 | C |
| ATOM | 2119 | N | ARG | A | 1080 | 0.116 | 27.711 | −11.321 | 1.00 | 61.54 | N |
| ATOM | 2120 | CA | ARG | A | 1080 | 0.877 | 27.998 | −12.534 | 1.00 | 58.97 | C |
| ATOM | 2121 | C | ARG | A | 1080 | 0.452 | 27.082 | −13.680 | 1.00 | 66.91 | C |
| ATOM | 2122 | O | ARG | A | 1080 | 0.714 | 27.370 | −14.849 | 1.00 | 63.24 | O |
| ATOM | 2123 | CB | ARG | A | 1080 | 2.380 | 27.850 | −12.282 | 1.00 | 55.15 | C |
| ATOM | 2124 | CG | ARG | A | 1080 | 2.951 | 28.843 | −11.285 | 1.00 | 66.50 | C |
| ATOM | 2125 | CD | ARG | A | 1080 | 4.472 | 28.797 | −11.279 | 1.00 | 78.98 | C |
| ATOM | 2126 | NE | ARG | A | 1080 | 4.986 | 27.528 | −10.772 | 1.00 | 91.02 | N |
| ATOM | 2127 | CZ | ARG | A | 1080 | 5.436 | 27.345 | −9.535 | 1.00 | 92.75 | C |
| ATOM | 2128 | NH1 | ARG | A | 1080 | 5.442 | 28.352 | −8.672 | 1.00 | 85.53 | N |
| ATOM | 2129 | NH2 | ARG | A | 1080 | 5.885 | 26.155 | −9.159 | 1.00 | 95.14 | N |
| ATOM | 2130 | N | ASN | A | 1081 | −0.200 | 25.976 | −13.339 | 1.00 | 68.55 | N |
| ATOM | 2131 | CA | ASN | A | 1081 | −0.651 | 25.021 | −14.343 | 1.00 | 67.01 | C |
| ATOM | 2132 | C | ASN | A | 1081 | −2.013 | 25.402 | −14.917 | 1.00 | 68.88 | C |
| ATOM | 2133 | O | ASN | A | 1081 | −2.981 | 25.586 | −14.178 | 1.00 | 67.22 | O |
| ATOM | 2134 | CB | ASN | A | 1081 | −0.681 | 23.606 | −13.764 | 1.00 | 61.04 | C |
| ATOM | 2135 | CG | ASN | A | 1081 | −0.871 | 22.547 | −14.828 | 1.00 | 62.36 | C |
| ATOM | 2136 | OD1 | ASN | A | 1081 | −1.890 | 22.521 | −15.518 | 1.00 | 66.42 | O |
| ATOM | 2137 | ND2 | ASN | A | 1081 | 0.110 | 21.662 | −14.966 | 1.00 | 59.60 | N |
| ATOM | 2138 | N | ALA | A | 1082 | −2.078 | 25.515 | −16.240 | 1.00 | 73.35 | N |
| ATOM | 2139 | CA | ALA | A | 1082 | −3.275 | 26.003 | −16.922 | 1.00 | 65.65 | C |
| ATOM | 2140 | C | ALA | A | 1082 | −4.461 | 25.044 | −16.830 | 1.00 | 66.30 | C |
| ATOM | 2141 | O | ALA | A | 1082 | −5.612 | 25.459 | −16.965 | 1.00 | 64.14 | O |
| ATOM | 2142 | CB | ALA | A | 1082 | −2.959 | 26.322 | −18.379 | 1.00 | 59.91 | C |

TABLE 6-continued

HUMAN A2A ADENOSINE STRUCTURE.PDB FILE
(Table 6: discloses SEQ ID NOS 20-27, respectively, in order of appearance.)

| ATOM | 2143 | N   | LYS | A | 1083 | -4.179  | 23.764 | -16.605 | 1.00 | 72.58 | N |
| ---- | ---- | --- | --- | - | ---- | ------- | ------ | ------- | ---- | ----- | - |
| ATOM | 2144 | CA  | LYS | A | 1083 | -5.238  | 22.767 | -16.484 | 1.00 | 76.68 | C |
| ATOM | 2145 | C   | LYS | A | 1083 | -5.780  | 22.691 | -15.061 | 1.00 | 73.64 | C |
| ATOM | 2146 | O   | LYS | A | 1083 | -6.990  | 22.600 | -14.850 | 1.00 | 70.29 | O |
| ATOM | 2147 | CB  | LYS | A | 1083 | -4.738  | 21.388 | -16.921 | 1.00 | 80.21 | C |
| ATOM | 2148 | CG  | LYS | A | 1083 | -4.428  | 21.278 | -18.403 | 1.00 | 88.39 | C |
| ATOM | 2149 | CD  | LYS | A | 1083 | -4.245  | 19.827 | -18.821 | 1.00 | 92.04 | C |
| ATOM | 2150 | CE  | LYS | A | 1083 | -5.524  | 19.028 | -18.618 | 1.00 | 88.61 | C |
| ATOM | 2151 | NZ  | LYS | A | 1083 | -5.398  | 17.638 | -19.137 | 1.00 | 90.29 | N |
| ATOM | 2152 | N   | LEU | A | 1084 | -4.877  | 22.736 | -14.088 | 1.00 | 73.01 | N |
| ATOM | 2153 | CA  | LEU | A | 1084 | -5.248  | 22.551 | -12.689 | 1.00 | 72.81 | C |
| ATOM | 2154 | C   | LEU | A | 1084 | -5.884  | 23.788 | -12.056 | 1.00 | 70.07 | C |
| ATOM | 2155 | O   | LEU | A | 1084 | -6.763  | 23.670 | -11.203 | 1.00 | 73.42 | O |
| ATOM | 2156 | CB  | LEU | A | 1084 | -4.032  | 22.103 | -11.873 | 1.00 | 68.36 | C |
| ATOM | 2157 | CG  | LEU | A | 1084 | -3.449  | 20.743 | -12.263 | 1.00 | 63.16 | C |
| ATOM | 2158 | CD1 | LEU | A | 1084 | -2.250  | 20.397 | -11.396 | 1.00 | 63.56 | C |
| ATOM | 2159 | CD2 | LEU | A | 1084 | -4.515  | 19.665 | -12.162 | 1.00 | 65.73 | C |
| ATOM | 2160 | N   | LYS | A | 1085 | -5.443  | 24.970 | -12.475 | 1.00 | 63.18 | N |
| ATOM | 2161 | CA  | LYS | A | 1085 | -5.919  | 26.214 | -11.869 | 1.00 | 63.63 | C |
| ATOM | 2162 | C   | LYS | A | 1085 | -7.445  | 26.368 | -11.869 | 1.00 | 65.06 | C |
| ATOM | 2163 | O   | LYS | A | 1085 | -8.039  | 26.633 | -10.823 | 1.00 | 66.73 | O |
| ATOM | 2164 | CB  | LYS | A | 1085 | -5.258  | 27.435 | -12.517 | 1.00 | 55.87 | C |
| ATOM | 2165 | CG  | LYS | A | 1085 | -5.651  | 28.751 | -11.862 | 1.00 | 57.59 | C |
| ATOM | 2166 | CD  | LYS | A | 1085 | -4.742  | 29.887 | -12.291 | 1.00 | 69.71 | C |
| ATOM | 2167 | CE  | LYS | A | 1085 | -5.017  | 31.140 | -11.476 | 1.00 | 70.63 | C |
| ATOM | 2168 | NZ  | LYS | A | 1085 | -6.441  | 31.564 | -11.577 | 1.00 | 71.44 | N |
| ATOM | 2169 | N   | PRO | A | 1086 | -8.086  | 26.203 | -13.038 | 1.00 | 65.83 | N |
| ATOM | 2170 | CA  | PRO | A | 1086 | -9.540  | 26.394 | -13.108 | 1.00 | 63.71 | C |
| ATOM | 2171 | C   | PRO | A | 1086 | -10.284 | 25.476 | -12.144 | 1.00 | 64.91 | C |
| ATOM | 2172 | O   | PRO | A | 1086 | -11.263 | 25.893 | -11.525 | 1.00 | 66.12 | O |
| ATOM | 2173 | CB  | PRO | A | 1086 | -9.875  | 26.014 | -14.555 | 1.00 | 54.10 | C |
| ATOM | 2174 | CG  | PRO | A | 1086 | -8.601  | 26.190 | -15.303 | 1.00 | 55.16 | C |
| ATOM | 2175 | CD  | PRO | A | 1086 | -7.517  | 25.818 | -14.341 | 1.00 | 61.12 | C |
| ATOM | 2176 | N   | VAL | A | 1087 | -9.815  | 24.239 | -12.023 | 1.00 | 58.50 | N |
| ATOM | 2177 | CA  | VAL | A | 1087 | -10.452 | 23.253 | -11.159 | 1.00 | 59.96 | C |
| ATOM | 2178 | C   | VAL | A | 1087 | -10.213 | 23.573 | -9.686  | 1.00 | 62.37 | C |
| ATOM | 2179 | O   | VAL | A | 1087 | -11.143 | 23.563 | -8.880  | 1.00 | 67.88 | O |
| ATOM | 2180 | CB  | VAL | A | 1087 | -9.941  | 21.831 | -11.457 | 1.00 | 57.84 | C |
| ATOM | 2181 | CG1 | VAL | A | 1087 | -10.628 | 20.820 | -10.554 | 1.00 | 61.27 | C |
| ATOM | 2182 | CG2 | VAL | A | 1087 | -10.165 | 21.483 | -12.921 | 1.00 | 56.50 | C |
| ATOM | 2183 | N   | TYR | A | 1088 | -8.961  | 23.856 | -9.342  | 1.00 | 54.70 | N |
| ATOM | 2184 | CA  | TYR | A | 1088 | -8.602  | 24.173 | -7.966  | 1.00 | 60.12 | C |
| ATOM | 2185 | C   | TYR | A | 1088 | -9.402  | 25.361 | -7.440  | 1.00 | 61.96 | C |
| ATOM | 2186 | O   | TYR | A | 1088 | -9.913  | 25.333 | -6.320  | 1.00 | 66.10 | O |
| ATOM | 2187 | CB  | TYR | A | 1088 | -7.101  | 24.457 | -7.855  | 1.00 | 59.30 | C |
| ATOM | 2188 | CG  | TYR | A | 1088 | -6.655  | 24.833 | -6.461  | 1.00 | 58.53 | C |
| ATOM | 2189 | CD1 | TYR | A | 1088 | -6.388  | 23.858 | -5.508  | 1.00 | 53.91 | C |
| ATOM | 2190 | CD2 | TYR | A | 1088 | -6.504  | 26.165 | -6.095  | 1.00 | 62.09 | C |
| ATOM | 2191 | CE1 | TYR | A | 1088 | -5.981  | 24.198 | -4.230  | 1.00 | 56.16 | C |
| ATOM | 2192 | CE2 | TYR | A | 1088 | -6.098  | 26.514 | -4.819  | 1.00 | 60.36 | C |
| ATOM | 2193 | CZ  | TYR | A | 1088 | -5.838  | 25.528 | -3.892  | 1.00 | 63.20 | C |
| ATOM | 2194 | OH  | TYR | A | 1088 | -5.434  | 25.874 | -2.622  | 1.00 | 70.94 | O |
| ATOM | 2195 | N   | ASP | A | 1089 | -9.510  | 26.402 | -8.258  | 1.00 | 59.15 | N |
| ATOM | 2196 | CA  | ASP | A | 1089 | -10.205 | 27.621 | -7.860  | 1.00 | 62.19 | C |
| ATOM | 2197 | C   | ASP | A | 1089 | -11.694 | 27.399 | -7.608  | 1.00 | 62.05 | C |
| ATOM | 2198 | O   | ASP | A | 1089 | -12.310 | 28.126 | -6.832  | 1.00 | 63.54 | O |
| ATOM | 2199 | CB  | ASP | A | 1089 | -10.008 | 28.718 | -8.910  | 1.00 | 71.62 | C |
| ATOM | 2200 | CG  | ASP | A | 1089 | -8.624  | 29.337 | -8.854  | 1.00 | 81.19 | C |
| ATOM | 2201 | OD1 | ASP | A | 1089 | -7.876  | 29.038 | -7.900  | 1.00 | 76.32 | O |
| ATOM | 2202 | OD2 | ASP | A | 1089 | -8.286  | 30.127 | -9.761  | 1.00 | 87.61 | O |
| ATOM | 2203 | N   | SER | A | 1090 | -12.268 | 26.391 | -8.259  | 1.00 | 62.45 | N |
| ATOM | 2204 | CA  | SER | A | 1090 | -13.703 | 26.138 | -8.154  | 1.00 | 60.96 | C |
| ATOM | 2205 | C   | SER | A | 1090 | -14.061 | 25.261 | -6.957  | 1.00 | 70.82 | C |
| ATOM | 2206 | O   | SER | A | 1090 | -15.232 | 25.135 | -6.600  | 1.00 | 75.14 | O |
| ATOM | 2207 | CB  | SER | A | 1090 | -14.231 | 25.497 | -9.439  | 1.00 | 64.89 | C |
| ATOM | 2208 | OG  | SER | A | 1090 | -13.832 | 24.140 | -9.536  | 1.00 | 72.06 | O |
| ATOM | 2209 | N   | LEU | A | 1091 | -13.050 | 24.657 | -6.340  | 1.00 | 71.49 | N |
| ATOM | 2210 | CA  | LEU | A | 1091 | -13.278 | 23.728 | -5.237  | 1.00 | 64.87 | C |
| ATOM | 2211 | C   | LEU | A | 1091 | -13.365 | 24.431 | -3.886  | 1.00 | 59.56 | C |
| ATOM | 2212 | O   | LEU | A | 1091 | -12.867 | 25.544 | -3.718  | 1.00 | 63.51 | O |
| ATOM | 2213 | CB  | LEU | A | 1091 | -12.175 | 22.669 | -5.196  | 1.00 | 61.09 | C |
| ATOM | 2214 | CG  | LEU | A | 1091 | -12.068 | 21.740 | -6.406  | 1.00 | 56.62 | C |
| ATOM | 2215 | CD1 | LEU | A | 1091 | -10.853 | 20.832 | -6.278  | 1.00 | 58.23 | C |
| ATOM | 2216 | CD2 | LEU | A | 1091 | -13.339 | 20.922 | -6.572  | 1.00 | 54.13 | C |
| ATOM | 2217 | N   | ASP | A | 1092 | -14.006 | 23.770 | -2.927  | 1.00 | 58.90 | N |
| ATOM | 2218 | CA  | ASP | A | 1092 | -14.045 | 24.257 | -1.554  | 1.00 | 58.25 | C |
| ATOM | 2219 | C   | ASP | A | 1092 | -12.768 | 23.847 | -0.826  | 1.00 | 51.70 | C |

TABLE 6-continued

HUMAN A2A ADENOSINE STRUCTURE.PDB FILE
(Table 6: discloses SEQ ID NOS 20-27, respectively, in order of appearance.)

| ATOM | 2220 | O | ASP | A | 1092 | −11.955 | 23.098 | −1.366 | 1.00 | 59.19 | O |
|---|---|---|---|---|---|---|---|---|---|---|---|
| ATOM | 2221 | CB | ASP | A | 1092 | −15.276 | 23.723 | −0.818 | 1.00 | 65.12 | C |
| ATOM | 2222 | CG | ASP | A | 1092 | −15.416 | 22.216 | −0.928 | 1.00 | 79.92 | C |
| ATOM | 2223 | OD1 | ASP | A | 1092 | −15.686 | 21.723 | −2.043 | 1.00 | 85.35 | O |
| ATOM | 2224 | OD2 | ASP | A | 1092 | −15.271 | 21.526 | 0.104 | 1.00 | 86.82 | O |
| ATOM | 2225 | N | ALA | A | 1093 | −12.600 | 24.334 | 0.399 | 1.00 | 47.80 | N |
| ATOM | 2226 | CA | ALA | A | 1093 | −11.363 | 24.127 | 1.150 | 1.00 | 56.35 | C |
| ATOM | 2227 | C | ALA | A | 1093 | −11.005 | 22.653 | 1.338 | 1.00 | 64.43 | C |
| ATOM | 2228 | O | ALA | A | 1093 | −9.847 | 22.264 | 1.177 | 1.00 | 70.72 | O |
| ATOM | 2229 | CB | ALA | A | 1093 | −11.436 | 24.833 | 2.498 | 1.00 | 54.20 | C |
| ATOM | 2230 | N | VAL | A | 1094 | −11.996 | 21.839 | 1.681 | 1.00 | 59.12 | N |
| ATOM | 2231 | CA | VAL | A | 1094 | −11.757 | 20.423 | 1.945 | 1.00 | 59.35 | C |
| ATOM | 2232 | C | VAL | A | 1094 | −11.419 | 19.652 | 0.670 | 1.00 | 61.16 | C |
| ATOM | 2233 | O | VAL | A | 1094 | −10.522 | 18.809 | 0.667 | 1.00 | 62.93 | O |
| ATOM | 2234 | CB | VAL | A | 1094 | −12.955 | 19.766 | 2.668 | 1.00 | 53.78 | C |
| ATOM | 2235 | CG1 | VAL | A | 1094 | −12.835 | 18.251 | 2.639 | 1.00 | 52.45 | C |
| ATOM | 2236 | CG2 | VAL | A | 1094 | −13.044 | 20.266 | 4.102 | 1.00 | 46.27 | C |
| ATOM | 2237 | N | ARG | A | 1095 | −12.133 | 19.946 | −0.412 | 1.00 | 60.52 | N |
| ATOM | 2238 | CA | ARG | A | 1095 | −11.884 | 19.276 | −1.685 | 1.00 | 54.77 | C |
| ATOM | 2239 | C | ARG | A | 1095 | −10.543 | 19.697 | −2.282 | 1.00 | 49.77 | C |
| ATOM | 2240 | O | ARG | A | 1095 | −9.923 | 18.943 | −3.032 | 1.00 | 53.54 | O |
| ATOM | 2241 | CB | ARG | A | 1095 | −13.026 | 19.532 | −2.672 | 1.00 | 49.27 | C |
| ATOM | 2242 | CG | ARG | A | 1095 | −14.321 | 18.823 | −2.302 | 1.00 | 53.82 | C |
| ATOM | 2243 | CD | ARG | A | 1095 | −15.376 | 18.974 | −3.386 | 1.00 | 56.86 | C |
| ATOM | 2244 | NE | ARG | A | 1095 | −16.539 | 18.124 | −3.139 | 1.00 | 56.74 | N |
| ATOM | 2245 | CZ | ARG | A | 1095 | −17.651 | 18.530 | −2.533 | 1.00 | 53.19 | C |
| ATOM | 2246 | NH1 | ARG | A | 1095 | −17.761 | 19.782 | −2.111 | 1.00 | 47.16 | N |
| ATOM | 2247 | NH2 | ARG | A | 1095 | −18.656 | 17.685 | −2.351 | 1.00 | 52.18 | N |
| ATOM | 2248 | N | ARG | A | 1096 | −10.097 | 20.901 | −1.943 | 1.00 | 49.25 | N |
| ATOM | 2249 | CA | ARG | A | 1096 | −8.783 | 21.370 | −2.370 | 1.00 | 57.10 | C |
| ATOM | 2250 | C | ARG | A | 1096 | −7.685 | 20.530 | −1.726 | 1.00 | 60.70 | C |
| ATOM | 2251 | O | ARG | A | 1096 | −6.678 | 20.212 | −2.360 | 1.00 | 58.87 | O |
| ATOM | 2252 | CB | ARG | A | 1096 | −8.597 | 22.850 | −2.024 | 1.00 | 52.82 | C |
| ATOM | 2253 | CG | ARG | A | 1096 | −9.406 | 23.792 | −2.900 | 1.00 | 52.13 | C |
| ATOM | 2254 | CD | ARG | A | 1096 | −9.190 | 25.245 | −2.515 | 1.00 | 53.26 | C |
| ATOM | 2255 | NE | ARG | A | 1096 | −9.801 | 26.150 | −3.485 | 1.00 | 57.97 | N |
| ATOM | 2256 | CZ | ARG | A | 1096 | −9.704 | 27.474 | −3.438 | 1.00 | 67.10 | C |
| ATOM | 2257 | NH1 | ARG | A | 1096 | −9.019 | 28.057 | −2.464 | 1.00 | 71.95 | N |
| ATOM | 2258 | NH2 | ARG | A | 1096 | −10.292 | 28.216 | −4.366 | 1.00 | 70.27 | N |
| ATOM | 2259 | N | ALA | A | 1097 | −7.891 | 20.168 | −0.465 | 1.00 | 55.05 | N |
| ATOM | 2260 | CA | ALA | A | 1097 | −6.936 | 19.342 | 0.261 | 1.00 | 55.29 | C |
| ATOM | 2261 | C | ALA | A | 1097 | −6.781 | 17.974 | −0.402 | 1.00 | 57.91 | C |
| ATOM | 2262 | O | ALA | A | 1097 | −5.687 | 17.406 | −0.431 | 1.00 | 51.38 | O |
| ATOM | 2263 | CB | ALA | A | 1097 | −7.363 | 19.191 | 1.716 | 1.00 | 48.61 | C |
| ATOM | 2264 | N | ALA | A | 1098 | −7.881 | 17.452 | −0.935 | 1.00 | 54.42 | N |
| ATOM | 2265 | CA | ALA | A | 1098 | −7.861 | 16.170 | −1.630 | 1.00 | 54.61 | C |
| ATOM | 2266 | C | ALA | A | 1098 | −7.103 | 16.268 | −2.953 | 1.00 | 62.12 | C |
| ATOM | 2267 | O | ALA | A | 1098 | −6.486 | 15.300 | −3.399 | 1.00 | 59.64 | O |
| ATOM | 2268 | CB | ALA | A | 1098 | −9.278 | 15.670 | −1.861 | 1.00 | 49.88 | C |
| ATOM | 2269 | N | LEU | A | 1099 | −7.152 | 17.440 | −3.580 | 1.00 | 60.87 | N |
| ATOM | 2270 | CA | LEU | A | 1099 | −6.424 | 17.665 | −4.823 | 1.00 | 62.58 | C |
| ATOM | 2271 | C | LEU | A | 1099 | −4.938 | 17.859 | −4.537 | 1.00 | 57.55 | C |
| ATOM | 2272 | O | LEU | A | 1099 | −4.084 | 17.378 | −5.283 | 1.00 | 55.25 | O |
| ATOM | 2273 | CB | LEU | A | 1099 | −6.983 | 18.877 | −5.571 | 1.00 | 65.42 | C |
| ATOM | 2274 | CG | LEU | A | 1099 | −6.433 | 19.099 | −6.982 | 1.00 | 61.85 | C |
| ATOM | 2275 | CD1 | LEU | A | 1099 | −6.831 | 17.954 | −7.898 | 1.00 | 49.29 | C |
| ATOM | 2276 | CD2 | LEU | A | 1099 | −6.913 | 20.428 | −7.543 | 1.00 | 68.36 | C |
| ATOM | 2277 | N | ILE | A | 1100 | −4.636 | 18.567 | −3.454 | 1.00 | 51.77 | N |
| ATOM | 2278 | CA | ILE | A | 1100 | −3.259 | 18.750 | −3.016 | 1.00 | 61.30 | C |
| ATOM | 2279 | C | ILE | A | 1100 | −2.667 | 17.410 | −2.583 | 1.00 | 70.54 | C |
| ATOM | 2280 | O | ILE | A | 1100 | −1.484 | 17.140 | −2.798 | 1.00 | 63.42 | O |
| ATOM | 2281 | CB | ILE | A | 1100 | −3.168 | 19.763 | −1.860 | 1.00 | 61.75 | C |
| ATOM | 2282 | CG1 | ILE | A | 1100 | −3.610 | 21.149 | −2.336 | 1.00 | 54.02 | C |
| ATOM | 2283 | CG2 | ILE | A | 1100 | −1.753 | 19.819 | −1.305 | 1.00 | 61.84 | C |
| ATOM | 2284 | CD1 | ILE | A | 1100 | −3.812 | 22.147 | −1.216 | 1.00 | 45.45 | C |
| ATOM | 2285 | N | ASN | A | 1101 | −3.504 | 16.573 | −1.978 | 1.00 | 67.91 | N |
| ATOM | 2286 | CA | ASN | A | 1101 | −3.103 | 15.225 | −1.593 | 1.00 | 60.85 | C |
| ATOM | 2287 | C | ASN | A | 1101 | −2.599 | 14.433 | −2.796 | 1.00 | 53.19 | C |
| ATOM | 2288 | O | ASN | A | 1101 | −1.566 | 13.768 | −2.726 | 1.00 | 53.45 | O |
| ATOM | 2289 | CB | ASN | A | 1101 | −4.274 | 14.496 | −0.926 | 1.00 | 60.93 | C |
| ATOM | 2290 | CG | ASN | A | 1101 | −3.875 | 13.158 | −0.327 | 1.00 | 55.99 | C |
| ATOM | 2291 | OD1 | ASN | A | 1101 | −3.113 | 12.397 | −0.923 | 1.00 | 58.87 | O |
| ATOM | 2292 | ND2 | ASN | A | 1101 | −4.402 | 12.861 | 0.855 | 1.00 | 49.68 | N |
| ATOM | 2293 | N | MET | A | 1102 | −3.330 | 14.515 | −3.904 | 1.00 | 52.46 | N |
| ATOM | 2294 | CA | MET | A | 1102 | −2.955 | 13.805 | −5.123 | 1.00 | 54.25 | C |
| ATOM | 2295 | C | MET | A | 1102 | −1.652 | 14.331 | −5.722 | 1.00 | 55.65 | C |
| ATOM | 2296 | O | MET | A | 1102 | −0.833 | 13.558 | −6.218 | 1.00 | 52.94 | O |

TABLE 6-continued

HUMAN A2A ADENOSINE STRUCTURE.PDB FILE
(Table 6: discloses SEQ ID NOS 20-27, respectively, in order of appearance.)

| ATOM | 2297 | CB | MET | A | 1102 | −4.079 | 13.878 | −6.155 | 1.00 | 48.69 | C |
|---|---|---|---|---|---|---|---|---|---|---|---|
| ATOM | 2298 | CG | MET | A | 1102 | −5.332 | 13.123 | −5.752 | 1.00 | 48.99 | C |
| ATOM | 2299 | SD | MET | A | 1102 | −6.631 | 13.212 | −6.999 | 1.00 | 72.28 | S |
| ATOM | 2300 | CE | MET | A | 1102 | −5.804 | 12.472 | −8.405 | 1.00 | 60.39 | C |
| ATOM | 2301 | N | VAL | A | 1103 | −1.463 | 15.646 | −5.676 | 1.00 | 57.59 | N |
| ATOM | 2302 | CA | VAL | A | 1103 | −0.237 | 16.254 | −6.182 | 1.00 | 63.01 | C |
| ATOM | 2303 | C | VAL | A | 1103 | 0.974 | 15.820 | −5.357 | 1.00 | 61.51 | C |
| ATOM | 2304 | O | VAL | A | 1103 | 2.060 | 15.609 | −5.898 | 1.00 | 56.54 | O |
| ATOM | 2305 | CB | VAL | A | 1103 | −0.327 | 17.796 | −6.206 | 1.00 | 57.23 | C |
| ATOM | 2306 | CG1 | VAL | A | 1103 | 1.026 | 18.404 | −6.546 | 1.00 | 49.64 | C |
| ATOM | 2307 | CG2 | VAL | A | 1103 | −1.386 | 18.251 | −7.199 | 1.00 | 43.12 | C |
| ATOM | 2308 | N | PHE | A | 1104 | 0.781 | 15.684 | −4.048 | 1.00 | 61.65 | N |
| ATOM | 2309 | CA | PHE | A | 1104 | 1.851 | 15.234 | −3.160 | 1.00 | 62.20 | C |
| ATOM | 2310 | C | PHE | A | 1104 | 2.295 | 13.810 | −3.480 | 1.00 | 67.68 | C |
| ATOM | 2311 | O | PHE | A | 1104 | 3.414 | 13.412 | −3.155 | 1.00 | 69.60 | O |
| ATOM | 2312 | CB | PHE | A | 1104 | 1.419 | 15.319 | −1.694 | 1.00 | 59.39 | C |
| ATOM | 2313 | CG | PHE | A | 1104 | 1.712 | 16.644 | −1.049 | 1.00 | 70.31 | C |
| ATOM | 2314 | CD1 | PHE | A | 1104 | 0.767 | 17.267 | −0.250 | 1.00 | 71.41 | C |
| ATOM | 2315 | CD2 | PHE | A | 1104 | 2.933 | 17.268 | −1.243 | 1.00 | 73.47 | C |
| ATOM | 2316 | CE1 | PHE | A | 1104 | 1.036 | 18.484 | 0.347 | 1.00 | 70.55 | C |
| ATOM | 2317 | CE2 | PHE | A | 1104 | 3.207 | 18.486 | −0.652 | 1.00 | 74.84 | C |
| ATOM | 2318 | CZ | PHE | A | 1104 | 2.257 | 19.095 | 0.145 | 1.00 | 72.20 | C |
| ATOM | 2319 | N | GLN | A | 1105 | 1.414 | 13.048 | −4.120 | 1.00 | 58.94 | N |
| ATOM | 2320 | CA | GLN | A | 1105 | 1.682 | 11.642 | −4.397 | 1.00 | 59.40 | C |
| ATOM | 2321 | C | GLN | A | 1105 | 2.139 | 11.389 | −5.834 | 1.00 | 68.82 | C |
| ATOM | 2322 | O | GLN | A | 1105 | 3.074 | 10.622 | −6.068 | 1.00 | 71.56 | O |
| ATOM | 2323 | CB | GLN | A | 1105 | 0.444 | 10.798 | −4.087 | 1.00 | 57.92 | C |
| ATOM | 2324 | CG | GLN | A | 1105 | 0.624 | 9.313 | −4.343 | 1.00 | 61.43 | C |
| ATOM | 2325 | CD | GLN | A | 1105 | −0.620 | 8.511 | −4.018 | 1.00 | 67.01 | C |
| ATOM | 2326 | OE1 | GLN | A | 1105 | −1.583 | 9.037 | −3.460 | 1.00 | 76.19 | O |
| ATOM | 2327 | NE2 | GLN | A | 1105 | −0.606 | 7.230 | −4.366 | 1.00 | 63.30 | N |
| ATOM | 2328 | N | MET | A | 1106 | 1.483 | 12.037 | −6.792 | 1.00 | 66.24 | N |
| ATOM | 2329 | CA | MET | A | 1106 | 1.725 | 11.750 | −8.204 | 1.00 | 62.03 | C |
| ATOM | 2330 | C | MET | A | 1106 | 2.453 | 12.875 | −8.934 | 1.00 | 65.48 | C |
| ATOM | 2331 | O | MET | A | 1106 | 3.003 | 12.667 | −10.015 | 1.00 | 74.98 | O |
| ATOM | 2332 | CB | MET | A | 1106 | 0.404 | 11.455 | −8.916 | 1.00 | 67.53 | C |
| ATOM | 2333 | CG | MET | A | 1106 | −0.543 | 10.570 | −8.127 | 1.00 | 77.13 | C |
| ATOM | 2334 | SD | MET | A | 1106 | −2.033 | 10.192 | −9.062 | 1.00 | 102.30 | S |
| ATOM | 2335 | CE | MET | A | 1106 | −2.364 | 11.786 | −9.804 | 1.00 | 87.58 | C |
| ATOM | 2336 | N | GLY | A | 1107 | 2.450 | 14.066 | −8.347 | 1.00 | 65.36 | N |
| ATOM | 2337 | CA | GLY | A | 1107 | 3.044 | 15.221 | −8.990 | 1.00 | 61.19 | C |
| ATOM | 2338 | C | GLY | A | 1107 | 2.018 | 15.983 | −9.805 | 1.00 | 59.33 | C |
| ATOM | 2339 | O | GLY | A | 1107 | 0.970 | 15.444 | −10.162 | 1.00 | 61.28 | O |
| ATOM | 2340 | N | GLU | A | 1108 | 2.327 | 17.237 | −10.111 | 1.00 | 61.54 | N |
| ATOM | 2341 | CA | GLU | A | 1108 | 1.379 | 18.126 | −10.775 | 1.00 | 64.65 | C |
| ATOM | 2342 | C | GLU | A | 1108 | 1.094 | 17.713 | −12.215 | 1.00 | 61.24 | C |
| ATOM | 2343 | O | GLU | A | 1108 | −0.026 | 17.865 | −12.704 | 1.00 | 64.27 | O |
| ATOM | 2344 | CB | GLU | A | 1108 | 1.887 | 19.565 | −10.714 | 1.00 | 67.92 | C |
| ATOM | 2345 | CG | GLU | A | 1108 | 2.636 | 19.866 | −9.427 | 1.00 | 79.36 | C |
| ATOM | 2346 | CD | GLU | A | 1108 | 2.476 | 21.299 | −8.979 | 1.00 | 91.71 | C |
| ATOM | 2347 | OE1 | GLU | A | 1108 | 1.811 | 22.070 | −9.700 | 1.00 | 102.95 | O |
| ATOM | 2348 | OE2 | GLU | A | 1108 | 3.009 | 21.652 | −7.905 | 1.00 | 85.96 | O |
| ATOM | 2349 | N | THR | A | 1109 | 2.111 | 17.190 | −12.891 | 1.00 | 64.73 | N |
| ATOM | 2350 | CA | THR | A | 1109 | 1.942 | 16.690 | −14.249 | 1.00 | 65.31 | C |
| ATOM | 2351 | C | THR | A | 1109 | 1.096 | 15.421 | −14.240 | 1.00 | 68.01 | C |
| ATOM | 2352 | O | THR | A | 1109 | 0.330 | 15.164 | −15.170 | 1.00 | 73.32 | O |
| ATOM | 2353 | CB | THR | A | 1109 | 3.299 | 16.400 | −14.916 | 1.00 | 64.81 | C |
| ATOM | 2354 | OG1 | THR | A | 1109 | 4.024 | 17.625 | −15.079 | 1.00 | 63.14 | O |
| ATOM | 2355 | CG2 | THR | A | 1109 | 3.100 | 15.751 | −16.276 | 1.00 | 62.62 | C |
| ATOM | 2356 | N | GLY | A | 1110 | 1.235 | 14.636 | −13.177 | 1.00 | 60.00 | N |
| ATOM | 2357 | CA | GLY | A | 1110 | 0.473 | 13.411 | −13.027 | 1.00 | 54.91 | C |
| ATOM | 2358 | C | GLY | A | 1110 | −1.015 | 13.665 | −12.877 | 1.00 | 62.39 | C |
| ATOM | 2359 | O | GLY | A | 1110 | −1.832 | 13.032 | −13.546 | 1.00 | 69.38 | O |
| ATOM | 2360 | N | VAL | A | 1111 | −1.369 | 14.596 | −11.997 | 1.00 | 65.76 | N |
| ATOM | 2361 | CA | VAL | A | 1111 | −2.769 | 14.923 | −11.759 | 1.00 | 67.26 | C |
| ATOM | 2362 | C | VAL | A | 1111 | −3.397 | 15.554 | −12.997 | 1.00 | 66.07 | C |
| ATOM | 2363 | O | VAL | A | 1111 | −4.560 | 15.301 | −13.314 | 1.00 | 60.96 | O |
| ATOM | 2364 | CB | VAL | A | 1111 | −2.935 | 15.880 | −10.563 | 1.00 | 59.99 | C |
| ATOM | 2365 | CG1 | VAL | A | 1111 | −4.410 | 16.085 | −10.249 | 1.00 | 57.17 | C |
| ATOM | 2366 | CG2 | VAL | A | 1111 | −2.202 | 15.339 | −9.349 | 1.00 | 55.73 | C |
| ATOM | 2367 | N | ALA | A | 1112 | −2.615 | 16.372 | −13.696 | 1.00 | 67.42 | N |
| ATOM | 2368 | CA | ALA | A | 1112 | −3.090 | 17.066 | −14.889 | 1.00 | 66.27 | C |
| ATOM | 2369 | C | ALA | A | 1112 | −3.486 | 16.096 | −16.001 | 1.00 | 69.14 | C |
| ATOM | 2370 | O | ALA | A | 1112 | −4.085 | 16.495 | −16.999 | 1.00 | 65.25 | O |
| ATOM | 2371 | CB | ALA | A | 1112 | −2.038 | 18.047 | −15.387 | 1.00 | 59.35 | C |
| ATOM | 2372 | N | GLY | A | 1113 | −3.148 | 14.823 | −15.822 | 1.00 | 79.96 | N |
| ATOM | 2373 | CA | GLY | A | 1113 | −3.483 | 13.799 | −16.795 | 1.00 | 77.36 | C |

TABLE 6-continued

HUMAN A2A ADENOSINE STRUCTURE.PDB FILE
(Table 6: discloses SEQ ID NOS 20-27, respectively, in order of appearance.)

| ATOM | 2374 | C   | GLY | A | 1113 | −4.925  | 13.335 | −16.692 | 1.00 | 83.69  | C |
| ---- | ---- | --- | --- | - | ---- | ------- | ------ | ------- | ---- | ------ | - |
| ATOM | 2375 | O   | GLY | A | 1113 | −5.461  | 12.742 | −17.628 | 1.00 | 87.05  | O |
| ATOM | 2376 | N   | PHE | A | 1114 | −5.552  | 13.601 | −15.550 | 1.00 | 82.49  | N |
| ATOM | 2377 | CA  | PHE | A | 1114 | −6.952  | 13.246 | −15.340 | 1.00 | 75.42  | C |
| ATOM | 2378 | C   | PHE | A | 1114 | −7.875  | 14.272 | −15.987 | 1.00 | 72.67  | C |
| ATOM | 2379 | O   | PHE | A | 1114 | −8.647  | 14.941 | −15.300 | 1.00 | 71.62  | O |
| ATOM | 2380 | CB  | PHE | A | 1114 | −7.263  | 13.149 | −13.844 | 1.00 | 76.33  | C |
| ATOM | 2381 | CG  | PHE | A | 1114 | −6.618  | 11.979 | −13.162 | 1.00 | 76.97  | C |
| ATOM | 2382 | CD1 | PHE | A | 1114 | −7.296  | 10.778 | −13.030 | 1.00 | 79.65  | C |
| ATOM | 2383 | CD2 | PHE | A | 1114 | −5.334  | 12.078 | −12.652 | 1.00 | 70.64  | C |
| ATOM | 2384 | CE1 | PHE | A | 1114 | −6.707  | 9.698  | −12.401 | 1.00 | 74.39  | C |
| ATOM | 2385 | CE2 | PHE | A | 1114 | −4.739  | 11.000 | −12.024 | 1.00 | 70.90  | C |
| ATOM | 2386 | CZ  | PHE | A | 1114 | −5.427  | 9.809  | −11.898 | 1.00 | 70.81  | C |
| ATOM | 2387 | N   | THR | A | 1115 | −7.804  | 14.384 | −17.310 | 1.00 | 68.40  | N |
| ATOM | 2388 | CA  | THR | A | 1115 | −8.569  | 15.392 | −18.040 | 1.00 | 69.79  | C |
| ATOM | 2389 | C   | THR | A | 1115 | −10.074 | 15.321 | −17.777 | 1.00 | 68.85  | C |
| ATOM | 2390 | O   | THR | A | 1115 | −10.717 | 16.340 | −17.524 | 1.00 | 72.68  | O |
| ATOM | 2391 | CB  | THR | A | 1115 | −8.320  | 15.291 | −19.560 | 1.00 | 73.52  | C |
| ATOM | 2392 | OG1 | THR | A | 1115 | −6.922  | 15.454 | −19.830 | 1.00 | 68.56  | O |
| ATOM | 2393 | CG2 | THR | A | 1115 | −9.102  | 16.366 | −20.299 | 1.00 | 73.33  | C |
| ATOM | 2394 | N   | ASN | A | 1116 | −10.634 | 14.118 | −17.842 | 1.00 | 68.27  | N |
| ATOM | 2395 | CA  | ASN | A | 1116 | −12.075 | 13.937 | −17.689 | 1.00 | 69.21  | C |
| ATOM | 2396 | C   | ASN | A | 1116 | −12.567 | 14.060 | −16.249 | 1.00 | 66.93  | C |
| ATOM | 2397 | O   | ASN | A | 1116 | −13.571 | 14.722 | −15.987 | 1.00 | 73.12  | O |
| ATOM | 2398 | CB  | ASN | A | 1116 | −12.520 | 12.603 | −18.295 | 1.00 | 78.40  | C |
| ATOM | 2399 | CG  | ASN | A | 1116 | −12.571 | 12.643 | −19.812 | 1.00 | 82.74  | C |
| ATOM | 2400 | OD1 | ASN | A | 1116 | −12.940 | 13.659 | −20.406 | 1.00 | 77.44  | O |
| ATOM | 2401 | ND2 | ASN | A | 1116 | −12.205 | 11.536 | −20.447 | 1.00 | 84.64  | N |
| ATOM | 2402 | N   | SER | A | 1117 | −11.864 | 13.420 | −15.319 | 1.00 | 70.09  | N |
| ATOM | 2403 | CA  | SER | A | 1117 | −12.235 | 13.488 | −13.909 | 1.00 | 67.37  | C |
| ATOM | 2404 | C   | SER | A | 1117 | −12.169 | 14.921 | −13.390 | 1.00 | 67.38  | C |
| ATOM | 2405 | O   | SER | A | 1117 | −13.051 | 15.362 | −12.651 | 1.00 | 70.95  | O |
| ATOM | 2406 | CB  | SER | A | 1117 | −11.342 | 12.575 | −13.065 | 1.00 | 69.45  | C |
| ATOM | 2407 | OG  | SER | A | 1117 | −11.642 | 11.209 | −13.299 | 1.00 | 74.98  | O |
| ATOM | 2408 | N   | LEU | A | 1118 | −11.122 | 15.644 | −13.779 | 1.00 | 63.57  | N |
| ATOM | 2409 | CA  | LEU | A | 1118 | −10.974 | 17.043 | −13.393 | 1.00 | 64.09  | C |
| ATOM | 2410 | C   | LEU | A | 1118 | −12.187 | 17.852 | −13.839 | 1.00 | 70.05  | C |
| ATOM | 2411 | O   | LEU | A | 1118 | −12.769 | 18.603 | −13.058 | 1.00 | 74.96  | O |
| ATOM | 2412 | CB  | LEU | A | 1118 | −9.699  | 17.638 | −13.995 | 1.00 | 65.91  | C |
| ATOM | 2413 | CG  | LEU | A | 1118 | −8.356  | 17.167 | −13.428 | 1.00 | 67.56  | C |
| ATOM | 2414 | CD1 | LEU | A | 1118 | −7.206  | 17.659 | −14.297 | 1.00 | 62.29  | C |
| ATOM | 2415 | CD2 | LEU | A | 1118 | −8.178  | 17.620 | −11.985 | 1.00 | 57.62  | C |
| ATOM | 2416 | N   | ARG | A | 1119 | −12.560 | 17.684 | −15.104 | 1.00 | 73.71  | N |
| ATOM | 2417 | CA  | ARG | A | 1119 | −13.696 | 18.392 | −15.685 | 1.00 | 70.74  | C |
| ATOM | 2418 | C   | ARG | A | 1119 | −14.976 | 18.205 | −14.873 | 1.00 | 70.08  | C |
| ATOM | 2419 | O   | ARG | A | 1119 | −15.683 | 19.172 | −14.582 | 1.00 | 73.09  | O |
| ATOM | 2420 | CB  | ARG | A | 1119 | −13.902 | 17.945 | −17.134 | 1.00 | 72.88  | C |
| ATOM | 2421 | CG  | ARG | A | 1119 | −15.312 | 18.122 | −17.665 | 1.00 | 80.58  | C |
| ATOM | 2422 | CD  | ARG | A | 1119 | −15.339 | 17.934 | −19.174 | 1.00 | 88.70  | C |
| ATOM | 2423 | NE  | ARG | A | 1119 | −16.569 | 17.295 | −19.630 | 1.00 | 97.97  | N |
| ATOM | 2424 | CZ  | ARG | A | 1119 | −16.673 | 16.000 | −19.915 | 1.00 | 102.54 | C |
| ATOM | 2425 | NH1 | ARG | A | 1119 | −17.831 | 15.502 | −20.324 | 1.00 | 105.15 | N |
| ATOM | 2426 | NH2 | ARG | A | 1119 | −15.618 | 15.204 | −19.795 | 1.00 | 94.37  | N |
| ATOM | 2427 | N   | MET | A | 1120 | −15.267 | 16.962 | −14.504 | 1.00 | 68.79  | N |
| ATOM | 2428 | CA  | MET | A | 1120 | −16.442 | 16.665 | −13.694 | 1.00 | 67.28  | C |
| ATOM | 2429 | C   | MET | A | 1120 | −16.357 | 17.367 | −12.344 | 1.00 | 70.93  | C |
| ATOM | 2430 | O   | MET | A | 1120 | −17.359 | 17.855 | −11.821 | 1.00 | 72.23  | O |
| ATOM | 2431 | CB  | MET | A | 1120 | −16.587 | 15.157 | −13.491 | 1.00 | 62.61  | C |
| ATOM | 2432 | CG  | MET | A | 1120 | −16.637 | 14.365 | −14.783 | 1.00 | 60.63  | C |
| ATOM | 2433 | SD  | MET | A | 1120 | −16.686 | 12.587 | −14.497 | 1.00 | 109.64 | S |
| ATOM | 2434 | CE  | MET | A | 1120 | −16.539 | 11.973 | −16.173 | 1.00 | 272.52 | C |
| ATOM | 2435 | N   | LEU | A | 1121 | −15.153 | 17.414 | −11.784 | 1.00 | 71.12  | N |
| ATOM | 2436 | CA  | LEU | A | 1121 | −14.935 | 18.065 | −10.498 | 1.00 | 66.74  | C |
| ATOM | 2437 | C   | LEU | A | 1121 | −15.293 | 19.546 | −10.558 | 1.00 | 67.05  | C |
| ATOM | 2438 | O   | LEU | A | 1121 | −15.886 | 20.084 | −9.622  | 1.00 | 72.61  | O |
| ATOM | 2439 | CB  | LEU | A | 1121 | −13.489 | 17.879 | −10.035 | 1.00 | 68.01  | C |
| ATOM | 2440 | CG  | LEU | A | 1121 | −13.137 | 16.487 | −9.504  | 1.00 | 64.05  | C |
| ATOM | 2441 | CD1 | LEU | A | 1121 | −11.635 | 16.332 | −9.323  | 1.00 | 59.67  | C |
| ATOM | 2442 | CD2 | LEU | A | 1121 | −13.864 | 16.214 | −8.197  | 1.00 | 70.14  | C |
| ATOM | 2443 | N   | GLN | A | 1122 | −14.937 | 20.202 | −11.659 | 1.00 | 61.58  | N |
| ATOM | 2444 | CA  | GLN | A | 1122 | −15.258 | 21.615 | −11.829 | 1.00 | 68.03  | C |
| ATOM | 2445 | C   | GLN | A | 1122 | −16.740 | 21.815 | −12.135 | 1.00 | 68.74  | C |
| ATOM | 2446 | O   | GLN | A | 1122 | −17.304 | 22.873 | −11.858 | 1.00 | 61.30  | O |
| ATOM | 2447 | CB  | GLN | A | 1122 | −14.399 | 22.253 | −12.920 | 1.00 | 73.07  | C |
| ATOM | 2448 | CG  | GLN | A | 1122 | −14.663 | 23.740 | −13.098 | 1.00 | 79.50  | C |
| ATOM | 2449 | CD  | GLN | A | 1122 | −13.583 | 24.440 | −13.895 | 1.00 | 87.39  | C |
| ATOM | 2450 | OE1 | GLN | A | 1122 | −12.909 | 23.828 | −14.723 | 1.00 | 89.22  | O |

TABLE 6-continued

HUMAN A2A ADENOSINE STRUCTURE.PDB FILE
(Table 6: discloses SEQ ID NOS 20-27, respectively, in order of appearance.)

| ATOM | 2451 | NE2 | GLN | A | 1122 | −13.415 | 25.735 | −13.649 | 1.00 | 92.14 | N |
|---|---|---|---|---|---|---|---|---|---|---|---|
| ATOM | 2452 | N | GLN | A | 1123 | −17.366 | 20.792 | −12.707 | 1.00 | 73.35 | N |
| ATOM | 2453 | CA | GLN | A | 1123 | −18.801 | 20.825 | −12.958 | 1.00 | 82.05 | C |
| ATOM | 2454 | C | GLN | A | 1123 | −19.562 | 20.393 | −11.710 | 1.00 | 83.17 | C |
| ATOM | 2455 | O | GLN | A | 1123 | −20.784 | 20.249 | −11.732 | 1.00 | 88.88 | O |
| ATOM | 2456 | CB | GLN | A | 1123 | −19.163 | 19.929 | −14.144 | 1.00 | 83.42 | C |
| ATOM | 2457 | CG | GLN | A | 1123 | −18.787 | 20.511 | −15.497 | 1.00 | 87.16 | C |
| ATOM | 2458 | CD | GLN | A | 1123 | −19.068 | 19.556 | −16.642 | 1.00 | 95.91 | C |
| ATOM | 2459 | OE1 | GLN | A | 1123 | −18.946 | 18.341 | −16.495 | 1.00 | 100.47 | O |
| ATOM | 2460 | NE2 | GLN | A | 1123 | −19.442 | 20.105 | −17.793 | 1.00 | 98.85 | N |
| ATOM | 2461 | N | LYS | A | 1124 | −18.823 | 20.191 | −10.623 | 1.00 | 74.22 | N |
| ATOM | 2462 | CA | LYS | A | 1124 | −19.401 | 19.772 | −9.349 | 1.00 | 71.30 | C |
| ATOM | 2463 | C | LYS | A | 1124 | −20.210 | 18.482 | −9.475 | 1.00 | 69.02 | C |
| ATOM | 2464 | O | LYS | A | 1124 | −21.147 | 18.245 | −8.712 | 1.00 | 68.45 | O |
| ATOM | 2465 | CB | LYS | A | 1124 | −20.257 | 20.890 | −8.747 | 1.00 | 67.75 | C |
| ATOM | 2466 | CG | LYS | A | 1124 | −19.491 | 22.179 | −8.512 | 1.00 | 68.73 | C |
| ATOM | 2467 | CD | LYS | A | 1124 | −20.238 | 23.108 | −7.571 | 1.00 | 75.88 | C |
| ATOM | 2468 | CE | LYS | A | 1124 | −19.508 | 24.434 | −7.424 | 1.00 | 85.73 | C |
| ATOM | 2469 | NZ | LYS | A | 1124 | −18.068 | 24.238 | −7.097 | 1.00 | 90.75 | N |
| ATOM | 2470 | N | ARG | A | 1125 | −19.840 | 17.656 | −10.447 | 1.00 | 65.31 | N |
| ATOM | 2471 | CA | ARG | A | 1125 | −20.449 | 16.345 | −10.612 | 1.00 | 70.08 | C |
| ATOM | 2472 | C | ARG | A | 1125 | −19.680 | 15.342 | −9.760 | 1.00 | 76.69 | C |
| ATOM | 2473 | O | ARG | A | 1125 | −19.014 | 14.444 | −10.278 | 1.00 | 83.98 | O |
| ATOM | 2474 | CB | ARG | A | 1125 | −20.435 | 15.937 | −12.086 | 1.00 | 69.85 | C |
| ATOM | 2475 | CG | ARG | A | 1125 | −21.117 | 16.948 | −12.997 | 1.00 | 75.17 | C |
| ATOM | 2476 | CD | ARG | A | 1125 | −20.701 | 16.784 | −14.451 | 1.00 | 78.01 | C |
| ATOM | 2477 | NE | ARG | A | 1125 | −21.343 | 15.642 | −15.094 | 1.00 | 82.50 | N |
| ATOM | 2478 | CZ | ARG | A | 1125 | −21.239 | 15.362 | −16.390 | 1.00 | 91.10 | C |
| ATOM | 2479 | NH1 | ARG | A | 1125 | −21.857 | 14.303 | −16.894 | 1.00 | 94.57 | N |
| ATOM | 2480 | NH2 | ARG | A | 1125 | −20.518 | 16.142 | −17.183 | 1.00 | 91.49 | N |
| ATOM | 2481 | N | TRP | A | 1126 | −19.779 | 15.515 | −8.446 | 1.00 | 75.05 | N |
| ATOM | 2482 | CA | TRP | A | 1126 | −18.982 | 14.753 | −7.489 | 1.00 | 71.36 | C |
| ATOM | 2483 | C | TRP | A | 1126 | −19.069 | 13.243 | −7.691 | 1.00 | 71.60 | C |
| ATOM | 2484 | O | TRP | A | 1126 | −18.049 | 12.556 | −7.714 | 1.00 | 76.93 | O |
| ATOM | 2485 | CB | TRP | A | 1126 | −19.388 | 15.111 | −6.056 | 1.00 | 62.81 | C |
| ATOM | 2486 | CG | TRP | A | 1126 | −19.553 | 16.586 | −5.823 | 1.00 | 56.10 | C |
| ATOM | 2487 | CD1 | TRP | A | 1126 | −20.665 | 17.221 | −5.349 | 1.00 | 52.22 | C |
| ATOM | 2488 | CD2 | TRP | A | 1126 | −18.578 | 17.610 | −6.061 | 1.00 | 54.90 | C |
| ATOM | 2489 | NE1 | TRP | A | 1126 | −20.440 | 18.575 | −5.271 | 1.00 | 50.72 | N |
| ATOM | 2490 | CE2 | TRP | A | 1126 | −19.167 | 18.840 | −5.703 | 1.00 | 58.29 | C |
| ATOM | 2491 | CE3 | TRP | A | 1126 | −17.263 | 17.606 | −6.540 | 1.00 | 51.51 | C |
| ATOM | 2492 | CZ2 | TRP | A | 1126 | −18.488 | 20.053 | −5.807 | 1.00 | 53.26 | C |
| ATOM | 2493 | CZ3 | TRP | A | 1126 | −16.591 | 18.811 | −6.645 | 1.00 | 54.02 | C |
| ATOM | 2494 | CH2 | TRP | A | 1126 | −17.204 | 20.018 | −6.280 | 1.00 | 56.66 | C |
| ATOM | 2495 | N | ASP | A | 1127 | −20.287 | 12.731 | −7.833 | 1.00 | 73.28 | N |
| ATOM | 2496 | CA | ASP | A | 1127 | −20.495 | 11.292 | −7.960 | 1.00 | 78.32 | C |
| ATOM | 2497 | C | ASP | A | 1127 | −19.901 | 10.727 | −9.248 | 1.00 | 74.61 | C |
| ATOM | 2498 | O | ASP | A | 1127 | −19.312 | 9.644 | −9.245 | 1.00 | 62.79 | O |
| ATOM | 2499 | CB | ASP | A | 1127 | −21.982 | 10.947 | −7.853 | 1.00 | 82.22 | C |
| ATOM | 2500 | CG | ASP | A | 1127 | −22.507 | 11.078 | −6.436 | 1.00 | 91.84 | C |
| ATOM | 2501 | OD1 | ASP | A | 1127 | −21.683 | 11.120 | −5.497 | 1.00 | 88.14 | O |
| ATOM | 2502 | OD2 | ASP | A | 1127 | −23.741 | 11.139 | −6.258 | 1.00 | 100.36 | O |
| ATOM | 2503 | N | GLU | A | 1128 | −20.056 | 11.459 | −10.346 | 1.00 | 80.14 | N |
| ATOM | 2504 | CA | GLU | A | 1128 | −19.481 | 11.037 | −11.618 | 1.00 | 87.94 | C |
| ATOM | 2505 | C | GLU | A | 1128 | −17.960 | 11.010 | −11.535 | 1.00 | 87.34 | C |
| ATOM | 2506 | O | GLU | A | 1128 | −17.323 | 10.042 | −11.949 | 1.00 | 88.16 | O |
| ATOM | 2507 | CB | GLU | A | 1128 | −19.927 | 11.960 | −12.751 | 1.00 | 103.85 | C |
| ATOM | 2508 | CG | GLU | A | 1128 | −21.400 | 11.856 | −13.098 | 1.00 | 114.47 | C |
| ATOM | 2509 | CD | GLU | A | 1128 | −21.693 | 12.315 | −14.512 | 1.00 | 125.25 | C |
| ATOM | 2510 | OE1 | GLU | A | 1128 | −22.802 | 12.836 | −14.752 | 1.00 | 131.49 | O |
| ATOM | 2511 | OE2 | GLU | A | 1128 | −20.811 | 12.156 | −15.383 | 1.00 | 126.90 | O |
| ATOM | 2512 | N | ALA | A | 1129 | −17.387 | 12.083 | −10.998 | 1.00 | 81.99 | N |
| ATOM | 2513 | CA | ALA | A | 1129 | −15.943 | 12.173 | −10.819 | 1.00 | 70.31 | C |
| ATOM | 2514 | C | ALA | A | 1129 | −15.428 | 10.978 | −10.031 | 1.00 | 64.42 | C |
| ATOM | 2515 | O | ALA | A | 1129 | −14.402 | 10.392 | −10.374 | 1.00 | 71.73 | O |
| ATOM | 2516 | CB | ALA | A | 1129 | −15.579 | 13.469 | −10.112 | 1.00 | 70.98 | C |
| ATOM | 2517 | N | ALA | A | 1130 | −16.153 | 10.621 | −8.975 | 1.00 | 66.81 | N |
| ATOM | 2518 | CA | ALA | A | 1130 | −15.771 | 9.508 | −8.113 | 1.00 | 67.03 | C |
| ATOM | 2519 | C | ALA | A | 1130 | −15.667 | 8.205 | −8.896 | 1.00 | 72.79 | C |
| ATOM | 2520 | O | ALA | A | 1130 | −14.662 | 7.497 | −8.809 | 1.00 | 76.61 | O |
| ATOM | 2521 | CB | ALA | A | 1130 | −16.763 | 9.362 | −6.967 | 1.00 | 64.32 | C |
| ATOM | 2522 | N | VAL | A | 1131 | −16.711 | 7.894 | −9.657 | 1.00 | 74.95 | N |
| ATOM | 2523 | CA | VAL | A | 1131 | −16.737 | 6.681 | −10.466 | 1.00 | 74.08 | C |
| ATOM | 2524 | C | VAL | A | 1131 | −15.550 | 6.637 | −11.421 | 1.00 | 72.71 | C |
| ATOM | 2525 | O | VAL | A | 1131 | −14.905 | 5.601 | −11.582 | 1.00 | 78.08 | O |
| ATOM | 2526 | CB | VAL | A | 1131 | −18.037 | 6.580 | −11.284 | 1.00 | 71.59 | C |
| ATOM | 2527 | CG1 | VAL | A | 1131 | −18.046 | 5.305 | −12.114 | 1.00 | 66.62 | C |

TABLE 6-continued

HUMAN A2A ADENOSINE STRUCTURE.PDB FILE
(Table 6: discloses SEQ ID NOS 20-27, respectively, in order of appearance.)

| ATOM | 2528 | CG2 | VAL | A | 1131 | −19.247 | 6.635 | −10.367 | 1.00 | 72.99 | C |
|---|---|---|---|---|---|---|---|---|---|---|---|
| ATOM | 2529 | N | ASN | A | 1132 | −15.267 | 7.774 | −12.047 | 1.00 | 70.07 | N |
| ATOM | 2530 | CA | ASN | A | 1132 | −14.192 | 7.869 | −13.025 | 1.00 | 70.36 | C |
| ATOM | 2531 | C | ASN | A | 1132 | −12.819 | 7.689 | −12.382 | 1.00 | 72.11 | C |
| ATOM | 2532 | O | ASN | A | 1132 | −11.981 | 6.938 | −12.882 | 1.00 | 66.71 | O |
| ATOM | 2533 | CB | ASN | A | 1132 | −14.262 | 9.211 | −13.756 | 1.00 | 73.01 | C |
| ATOM | 2534 | CG | ASN | A | 1132 | −13.852 | 9.105 | −15.209 | 1.00 | 84.01 | C |
| ATOM | 2535 | OD1 | ASN | A | 1132 | −14.049 | 8.071 | −15.847 | 1.00 | 90.19 | O |
| ATOM | 2536 | ND2 | ASN | A | 1132 | −13.286 | 10.180 | −15.744 | 1.00 | 89.81 | N |
| ATOM | 2537 | N | LEU | A | 1133 | −12.598 | 8.382 | −11.268 | 1.00 | 67.08 | N |
| ATOM | 2538 | CA | LEU | A | 1133 | −11.345 | 8.276 | −10.530 | 1.00 | 61.37 | C |
| ATOM | 2539 | C | LEU | A | 1133 | −11.093 | 6.844 | −10.073 | 1.00 | 72.18 | C |
| ATOM | 2540 | O | LEU | A | 1133 | −9.946 | 6.428 | −9.911 | 1.00 | 68.43 | O |
| ATOM | 2541 | CB | LEU | A | 1133 | −11.360 | 9.209 | −9.318 | 1.00 | 56.95 | C |
| ATOM | 2542 | CG | LEU | A | 1133 | −11.175 | 10.702 | −9.592 | 1.00 | 58.68 | C |
| ATOM | 2543 | CD1 | LEU | A | 1133 | −11.617 | 11.522 | −8.391 | 1.00 | 58.98 | C |
| ATOM | 2544 | CD2 | LEU | A | 1133 | −9.727 | 11.006 | −9.958 | 1.00 | 57.03 | C |
| ATOM | 2545 | N | ALA | A | 1134 | −12.173 | 6.097 | −9.865 | 1.00 | 79.13 | N |
| ATOM | 2546 | CA | ALA | A | 1134 | −12.078 | 4.721 | −9.388 | 1.00 | 78.45 | C |
| ATOM | 2547 | C | ALA | A | 1134 | −11.562 | 3.778 | −10.472 | 1.00 | 80.63 | C |
| ATOM | 2548 | O | ALA | A | 1134 | −11.103 | 2.674 | −10.179 | 1.00 | 78.78 | O |
| ATOM | 2549 | CB | ALA | A | 1134 | −13.428 | 4.248 | −8.870 | 1.00 | 77.07 | C |
| ATOM | 2550 | N | LYS | A | 1135 | −11.638 | 4.222 | −11.723 | 1.00 | 82.35 | N |
| ATOM | 2551 | CA | LYS | A | 1135 | −11.201 | 3.411 | −12.853 | 1.00 | 84.56 | C |
| ATOM | 2552 | C | LYS | A | 1135 | −9.736 | 3.663 | −13.200 | 1.00 | 85.69 | C |
| ATOM | 2553 | O | LYS | A | 1135 | −9.228 | 3.138 | −14.190 | 1.00 | 88.49 | O |
| ATOM | 2554 | CB | LYS | A | 1135 | −12.066 | 3.701 | −14.082 | 1.00 | 88.73 | C |
| ATOM | 2555 | CG | LYS | A | 1135 | −13.563 | 3.599 | −13.845 | 1.00 | 92.67 | C |
| ATOM | 2556 | CD | LYS | A | 1135 | −14.330 | 3.968 | −15.106 | 1.00 | 97.36 | C |
| ATOM | 2557 | CE | LYS | A | 1135 | −15.832 | 3.889 | −14.892 | 1.00 | 107.44 | C |
| ATOM | 2558 | NZ | LYS | A | 1135 | −16.582 | 4.239 | −16.130 | 1.00 | 113.83 | N |
| ATOM | 2559 | N | SER | A | 1136 | −9.061 | 4.465 | −12.384 | 1.00 | 79.73 | N |
| ATOM | 2560 | CA | SER | A | 1136 | −7.692 | 4.877 | −12.683 | 1.00 | 80.17 | C |
| ATOM | 2561 | C | SER | A | 1136 | −6.652 | 3.844 | −12.257 | 1.00 | 79.95 | C |
| ATOM | 2562 | O | SER | A | 1136 | −6.946 | 2.926 | −11.491 | 1.00 | 75.26 | O |
| ATOM | 2563 | CB | SER | A | 1136 | −7.383 | 6.229 | −12.031 | 1.00 | 76.43 | C |
| ATOM | 2564 | OG | SER | A | 1136 | −7.331 | 6.119 | −10.619 | 1.00 | 74.25 | O |
| ATOM | 2565 | N | ARG | A | 1137 | −5.435 | 4.005 | −12.769 | 1.00 | 80.53 | N |
| ATOM | 2566 | CA | ARG | A | 1137 | −4.314 | 3.161 | −12.377 | 1.00 | 79.92 | C |
| ATOM | 2567 | C | ARG | A | 1137 | −3.818 | 3.582 | −11.000 | 1.00 | 75.95 | C |
| ATOM | 2568 | O | ARG | A | 1137 | −3.226 | 2.790 | −10.268 | 1.00 | 80.00 | O |
| ATOM | 2569 | CB | ARG | A | 1137 | −3.182 | 3.266 | −13.401 | 1.00 | 89.43 | C |
| ATOM | 2570 | CG | ARG | A | 1137 | −1.940 | 2.463 | −13.042 | 1.00 | 103.96 | C |
| ATOM | 2571 | CD | ARG | A | 1137 | −2.237 | 0.972 | −12.997 | 1.00 | 117.47 | C |
| ATOM | 2572 | NE | ARG | A | 1137 | −1.085 | 0.194 | −12.544 | 1.00 | 124.93 | N |
| ATOM | 2573 | CZ | ARG | A | 1137 | −0.924 | −0.251 | −11.302 | 1.00 | 129.57 | C |
| ATOM | 2574 | NH1 | ARG | A | 1137 | 0.156 | −0.951 | −10.981 | 1.00 | 129.25 | N |
| ATOM | 2575 | NH2 | ARG | A | 1137 | −1.843 | 0.000 | −10.379 | 1.00 | 132.12 | N |
| ATOM | 2576 | N | TRP | A | 1138 | −4.065 | 4.842 | −10.657 | 1.00 | 73.47 | N |
| ATOM | 2577 | CA | TRP | A | 1138 | −3.722 | 5.365 | −9.341 | 1.00 | 65.21 | C |
| ATOM | 2578 | C | TRP | A | 1138 | −4.509 | 4.635 | −8.260 | 1.00 | 68.50 | C |
| ATOM | 2579 | O | TRP | A | 1138 | −3.954 | 4.231 | −7.236 | 1.00 | 66.19 | O |
| ATOM | 2580 | CB | TRP | A | 1138 | −3.995 | 6.870 | −9.286 | 1.00 | 58.78 | C |
| ATOM | 2581 | CG | TRP | A | 1138 | −4.172 | 7.420 | −7.901 | 1.00 | 66.32 | C |
| ATOM | 2582 | CD1 | TRP | A | 1138 | −3.254 | 7.412 | −6.890 | 1.00 | 66.55 | C |
| ATOM | 2583 | CD2 | TRP | A | 1138 | −5.334 | 8.081 | −7.381 | 1.00 | 66.73 | C |
| ATOM | 2584 | NE1 | TRP | A | 1138 | −3.777 | 8.017 | −5.771 | 1.00 | 67.36 | N |
| ATOM | 2585 | CE2 | TRP | A | 1138 | −5.052 | 8.436 | −6.047 | 1.00 | 63.72 | C |
| ATOM | 2586 | CE3 | TRP | A | 1138 | −6.587 | 8.401 | −7.914 | 1.00 | 62.36 | C |
| ATOM | 2587 | CZ2 | TRP | A | 1138 | −5.976 | 9.097 | −5.238 | 1.00 | 59.13 | C |
| ATOM | 2588 | CZ3 | TRP | A | 1138 | −7.503 | 9.057 | −7.109 | 1.00 | 58.68 | C |
| ATOM | 2589 | CH2 | TRP | A | 1138 | −7.193 | 9.397 | −5.787 | 1.00 | 55.75 | C |
| ATOM | 2590 | N | TYR | A | 1139 | −5.805 | 4.461 | −8.498 | 1.00 | 69.54 | N |
| ATOM | 2591 | CA | TYR | A | 1139 | −6.667 | 3.755 | −7.560 | 1.00 | 72.07 | C |
| ATOM | 2592 | C | TYR | A | 1139 | −6.254 | 2.294 | −7.437 | 1.00 | 77.48 | C |
| ATOM | 2593 | O | TYR | A | 1139 | −6.181 | 1.749 | −6.336 | 1.00 | 87.38 | O |
| ATOM | 2594 | CB | TYR | A | 1139 | −8.129 | 3.850 | −8.001 | 1.00 | 77.29 | C |
| ATOM | 2595 | CG | TYR | A | 1139 | −9.083 | 3.105 | −7.097 | 1.00 | 83.46 | C |
| ATOM | 2596 | CD1 | TYR | A | 1139 | −9.593 | 3.703 | −5.953 | 1.00 | 84.09 | C |
| ATOM | 2597 | CD2 | TYR | A | 1139 | −9.470 | 1.804 | −7.384 | 1.00 | 91.59 | C |
| ATOM | 2598 | CE1 | TYR | A | 1139 | −10.464 | 3.025 | −5.121 | 1.00 | 92.44 | C |
| ATOM | 2599 | CE2 | TYR | A | 1139 | −10.340 | 1.118 | −6.558 | 1.00 | 96.30 | C |
| ATOM | 2600 | CZ | TYR | A | 1139 | −10.834 | 1.734 | −5.428 | 1.00 | 97.54 | C |
| ATOM | 2601 | OH | TYR | A | 1139 | −11.701 | 1.056 | −4.601 | 1.00 | 101.62 | O |
| ATOM | 2602 | N | ASN | A | 1140 | −5.985 | 1.666 | −8.576 | 1.00 | 80.11 | N |
| ATOM | 2603 | CA | ASN | A | 1140 | −5.578 | 0.268 | −8.607 | 1.00 | 83.43 | C |
| ATOM | 2604 | C | ASN | A | 1140 | −4.304 | 0.018 | −7.805 | 1.00 | 86.62 | C |

TABLE 6-continued

HUMAN A2A ADENOSINE STRUCTURE.PDB FILE
(Table 6: discloses SEQ ID NOS 20-27, respectively, in order of appearance.)

| ATOM | 2605 | O | ASN | A | 1140 | -4.093 | -1.075 | -7.278 | 1.00 | 88.68 | O |
|---|---|---|---|---|---|---|---|---|---|---|---|
| ATOM | 2606 | CB | ASN | A | 1140 | -5.378 | -0.188 | -10.054 | 1.00 | 88.68 | C |
| ATOM | 2607 | CG | ASN | A | 1140 | -5.097 | -1.672 | -10.162 | 1.00 | 98.33 | C |
| ATOM | 2608 | OD1 | ASN | A | 1140 | -5.874 | -2.499 | -9.686 | 1.00 | 105.29 | O |
| ATOM | 2609 | ND2 | ASN | A | 1140 | -3.984 | -2.018 | -10.799 | 1.00 | 100.64 | N |
| ATOM | 2610 | N | GLN | A | 1141 | -3.461 | 1.041 | -7.713 | 1.00 | 84.80 | N |
| ATOM | 2611 | CA | GLN | A | 1141 | -2.164 | 0.912 | -7.058 | 1.00 | 81.98 | C |
| ATOM | 2612 | C | GLN | A | 1141 | -2.263 | 1.099 | -5.545 | 1.00 | 83.07 | C |
| ATOM | 2613 | O | GLN | A | 1141 | -1.714 | 0.306 | -4.779 | 1.00 | 92.44 | O |
| ATOM | 2614 | CB | GLN | A | 1141 | -1.169 | 1.906 | -7.659 | 1.00 | 91.77 | C |
| ATOM | 2615 | CG | GLN | A | 1141 | 0.284 | 1.612 | -7.333 | 1.00 | 102.05 | C |
| ATOM | 2616 | CD | GLN | A | 1141 | 1.241 | 2.309 | -8.281 | 1.00 | 108.23 | C |
| ATOM | 2617 | OE1 | GLN | A | 1141 | 0.853 | 2.742 | -9.366 | 1.00 | 105.17 | O |
| ATOM | 2618 | NE2 | GLN | A | 1141 | 2.501 | 2.417 | -7.876 | 1.00 | 113.29 | N |
| ATOM | 2619 | N | THR | A | 1142 | -2.961 | 2.147 | -5.119 | 1.00 | 74.16 | N |
| ATOM | 2620 | CA | THR | A | 1142 | -3.159 | 2.409 | -3.695 | 1.00 | 70.75 | C |
| ATOM | 2621 | C | THR | A | 1142 | -4.636 | 2.636 | -3.382 | 1.00 | 78.63 | C |
| ATOM | 2622 | O | THR | A | 1142 | -5.064 | 3.770 | -3.176 | 1.00 | 84.80 | O |
| ATOM | 2623 | CB | THR | A | 1142 | -2.344 | 3.629 | -3.219 | 1.00 | 66.58 | C |
| ATOM | 2624 | OG1 | THR | A | 1142 | -2.717 | 4.785 | -3.978 | 1.00 | 66.56 | O |
| ATOM | 2625 | CG2 | THR | A | 1142 | -0.852 | 3.376 | -3.388 | 1.00 | 56.52 | C |
| ATOM | 2626 | N | PRO | A | 1143 | -5.418 | 1.545 | -3.341 | 1.00 | 81.27 | N |
| ATOM | 2627 | CA | PRO | A | 1143 | -6.876 | 1.577 | -3.172 | 1.00 | 75.67 | C |
| ATOM | 2628 | C | PRO | A | 1143 | -7.329 | 2.239 | -1.874 | 1.00 | 68.97 | C |
| ATOM | 2629 | O | PRO | A | 1143 | -8.319 | 2.967 | -1.876 | 1.00 | 72.77 | O |
| ATOM | 2630 | CB | PRO | A | 1143 | -7.258 | 0.092 | -3.161 | 1.00 | 78.86 | C |
| ATOM | 2631 | CG | PRO | A | 1143 | -6.143 | -0.595 | -3.869 | 1.00 | 81.26 | C |
| ATOM | 2632 | CD | PRO | A | 1143 | -4.914 | 0.171 | -3.493 | 1.00 | 82.87 | C |
| ATOM | 2633 | N | ASN | A | 1144 | -6.618 | 1.984 | -0.781 | 1.00 | 64.01 | N |
| ATOM | 2634 | CA | ASN | A | 1144 | -6.994 | 2.537 | 0.516 | 1.00 | 68.96 | C |
| ATOM | 2635 | C | ASN | A | 1144 | -6.842 | 4.056 | 0.585 | 1.00 | 69.73 | C |
| ATOM | 2636 | O | ASN | A | 1144 | -7.751 | 4.759 | 1.027 | 1.00 | 73.42 | O |
| ATOM | 2637 | CB | ASN | A | 1144 | -6.198 | 1.865 | 1.636 | 1.00 | 66.22 | C |
| ATOM | 2638 | CG | ASN | A | 1144 | -6.504 | 0.386 | 1.758 | 1.00 | 69.32 | C |
| ATOM | 2639 | OD1 | ASN | A | 1144 | -7.648 | -0.040 | 1.589 | 1.00 | 70.95 | O |
| ATOM | 2640 | ND2 | ASN | A | 1144 | -5.483 | -0.408 | 2.055 | 1.00 | 74.92 | N |
| ATOM | 2641 | N | ARG | A | 1145 | -5.691 | 4.557 | 0.149 | 1.00 | 64.15 | N |
| ATOM | 2642 | CA | ARG | A | 1145 | -5.449 | 5.994 | 0.133 | 1.00 | 57.15 | C |
| ATOM | 2643 | C | ARG | A | 1145 | -6.384 | 6.687 | -0.853 | 1.00 | 55.27 | C |
| ATOM | 2644 | O | ARG | A | 1145 | -7.016 | 7.692 | -0.524 | 1.00 | 54.09 | O |
| ATOM | 2645 | CB | ARG | A | 1145 | -3.990 | 6.293 | -0.221 | 1.00 | 55.30 | C |
| ATOM | 2646 | CG | ARG | A | 1145 | -3.679 | 7.777 | -0.354 | 1.00 | 54.05 | C |
| ATOM | 2647 | CD | ARG | A | 1145 | -2.181 | 8.034 | -0.430 | 1.00 | 52.51 | C |
| ATOM | 2648 | NE | ARG | A | 1145 | -1.878 | 9.463 | -0.416 | 1.00 | 62.37 | N |
| ATOM | 2649 | CZ | ARG | A | 1145 | -0.648 | 9.968 | -0.409 | 1.00 | 64.77 | C |
| ATOM | 2650 | NH1 | ARG | A | 1145 | 0.404 | 9.160 | -0.412 | 1.00 | 75.79 | N |
| ATOM | 2651 | NH2 | ARG | A | 1145 | -0.469 | 11.282 | -0.397 | 1.00 | 51.28 | N |
| ATOM | 2652 | N | ALA | A | 1146 | -6.471 | 6.138 | -2.060 | 1.00 | 61.50 | N |
| ATOM | 2653 | CA | ALA | A | 1146 | -7.312 | 6.707 | -3.108 | 1.00 | 61.91 | C |
| ATOM | 2654 | C | ALA | A | 1146 | -8.784 | 6.717 | -2.708 | 1.00 | 64.09 | C |
| ATOM | 2655 | O | ALA | A | 1146 | -9.503 | 7.674 | -2.998 | 1.00 | 75.03 | O |
| ATOM | 2656 | CB | ALA | A | 1146 | -7.120 | 5.951 | -4.415 | 1.00 | 52.79 | C |
| ATOM | 2657 | N | LYS | A | 1147 | -9.226 | 5.648 | -2.055 | 1.00 | 59.77 | N |
| ATOM | 2658 | CA | LYS | A | 1147 | -10.618 | 5.533 | -1.634 | 1.00 | 61.60 | C |
| ATOM | 2659 | C | LYS | A | 1147 | -10.986 | 6.634 | -0.644 | 1.00 | 61.82 | C |
| ATOM | 2660 | O | LYS | A | 1147 | -12.112 | 7.134 | -0.650 | 1.00 | 66.82 | O |
| ATOM | 2661 | CB | LYS | A | 1147 | -10.886 | 4.154 | -1.026 | 1.00 | 74.76 | C |
| ATOM | 2662 | CG | LYS | A | 1147 | -12.350 | 3.879 | -0.732 | 1.00 | 89.83 | C |
| ATOM | 2663 | CD | LYS | A | 1147 | -12.571 | 2.431 | -0.327 | 1.00 | 103.23 | C |
| ATOM | 2664 | CE | LYS | A | 1147 | -14.042 | 2.153 | -0.057 | 1.00 | 111.04 | C |
| ATOM | 2665 | NZ | LYS | A | 1147 | -14.293 | 0.716 | 0.244 | 1.00 | 110.51 | N |
| ATOM | 2666 | N | ARG | A | 1148 | -10.031 | 7.009 | 0.203 | 1.00 | 49.88 | N |
| ATOM | 2667 | CA | ARG | A | 1148 | -10.244 | 8.088 | 1.160 | 1.00 | 60.19 | C |
| ATOM | 2668 | C | ARG | A | 1148 | -10.282 | 9.443 | 0.462 | 1.00 | 59.00 | C |
| ATOM | 2669 | O | ARG | A | 1148 | -11.135 | 10.281 | 0.758 | 1.00 | 56.07 | O |
| ATOM | 2670 | CB | ARG | A | 1148 | -9.156 | 8.087 | 2.236 | 1.00 | 63.82 | C |
| ATOM | 2671 | CG | ARG | A | 1148 | -9.321 | 7.010 | 3.295 | 1.00 | 53.31 | C |
| ATOM | 2672 | CD | ARG | A | 1148 | -8.343 | 7.215 | 4.442 | 1.00 | 55.62 | C |
| ATOM | 2673 | NE | ARG | A | 1148 | -6.955 | 7.072 | 4.011 | 1.00 | 60.50 | N |
| ATOM | 2674 | CZ | ARG | A | 1148 | -6.285 | 5.925 | 4.027 | 1.00 | 67.27 | C |
| ATOM | 2675 | NH1 | ARG | A | 1148 | -6.876 | 4.818 | 4.454 | 1.00 | 66.92 | N |
| ATOM | 2676 | NH2 | ARG | A | 1148 | -5.024 | 5.884 | 3.617 | 1.00 | 61.65 | N |
| ATOM | 2677 | N | VAL | A | 1149 | -9.349 | 9.652 | -0.462 | 1.00 | 53.90 | N |
| ATOM | 2678 | CA | VAL | A | 1149 | -9.290 | 10.892 | -1.227 | 1.00 | 46.34 | C |
| ATOM | 2679 | C | VAL | A | 1149 | -10.569 | 11.103 | -2.029 | 1.00 | 56.23 | C |
| ATOM | 2680 | O | VAL | A | 1149 | -11.103 | 12.210 | -2.087 | 1.00 | 59.39 | O |
| ATOM | 2681 | CB | VAL | A | 1149 | -8.093 | 10.901 | -2.191 | 1.00 | 50.28 | C |

TABLE 6-continued

HUMAN A2A ADENOSINE STRUCTURE.PDB FILE
(Table 6: discloses SEQ ID NOS 20-27, respectively, in order of appearance.)

| ATOM | 2682 | CG1 | VAL | A | 1149 | −8.109 | 12.160 | −3.046 | 1.00 | 52.16 | C |
|---|---|---|---|---|---|---|---|---|---|---|---|
| ATOM | 2683 | CG2 | VAL | A | 1149 | −6.787 | 10.788 | −1.417 | 1.00 | 54.62 | C |
| ATOM | 2684 | N | ILE | A | 1150 | −11.056 | 10.031 | −2.645 | 1.00 | 64.09 | N |
| ATOM | 2685 | CA | ILE | A | 1150 | −12.266 | 10.092 | −3.458 | 1.00 | 67.54 | C |
| ATOM | 2686 | C | ILE | A | 1150 | −13.495 | 10.411 | −2.609 | 1.00 | 66.26 | C |
| ATOM | 2687 | O | ILE | A | 1150 | −14.348 | 11.205 | −3.008 | 1.00 | 59.60 | O |
| ATOM | 2688 | CB | ILE | A | 1150 | −12.489 | 8.776 | −4.231 | 1.00 | 68.99 | C |
| ATOM | 2689 | CG1 | ILE | A | 1150 | −11.375 | 8.574 | −5.262 | 1.00 | 63.66 | C |
| ATOM | 2690 | CG2 | ILE | A | 1150 | −13.847 | 8.777 | −4.912 | 1.00 | 67.65 | C |
| ATOM | 2691 | CD1 | ILE | A | 1150 | −11.494 | 7.285 | −6.045 | 1.00 | 60.75 | C |
| ATOM | 2692 | N | THR | A | 1151 | −13.577 | 9.792 | −1.435 | 1.00 | 65.25 | N |
| ATOM | 2693 | CA | THR | A | 1151 | −14.662 | 10.067 | −0.499 | 1.00 | 60.60 | C |
| ATOM | 2694 | C | THR | A | 1151 | −14.667 | 11.543 | −0.113 | 1.00 | 57.87 | C |
| ATOM | 2695 | O | THR | A | 1151 | −15.721 | 12.133 | 0.121 | 1.00 | 70.20 | O |
| ATOM | 2696 | CB | THR | A | 1151 | −14.544 | 9.205 | 0.774 | 1.00 | 65.32 | C |
| ATOM | 2697 | OG1 | THR | A | 1151 | −14.723 | 7.823 | 0.438 | 1.00 | 61.51 | O |
| ATOM | 2698 | CG2 | THR | A | 1151 | −15.592 | 9.610 | 1.804 | 1.00 | 66.20 | C |
| ATOM | 2699 | N | THR | A | 1152 | −13.479 | 12.135 | −0.053 | 1.00 | 57.71 | N |
| ATOM | 2700 | CA | THR | A | 1152 | −13.337 | 13.548 | 0.276 | 1.00 | 60.97 | C |
| ATOM | 2701 | C | THR | A | 1152 | −13.888 | 14.427 | −0.846 | 1.00 | 57.37 | C |
| ATOM | 2702 | O | THR | A | 1152 | −14.475 | 15.478 | −0.588 | 1.00 | 52.14 | O |
| ATOM | 2703 | CB | THR | A | 1152 | −11.863 | 13.913 | 0.547 | 1.00 | 63.82 | C |
| ATOM | 2704 | OG1 | THR | A | 1152 | −11.327 | 13.034 | 1.544 | 1.00 | 70.01 | O |
| ATOM | 2705 | CG2 | THR | A | 1152 | −11.742 | 15.352 | 1.026 | 1.00 | 51.81 | C |
| ATOM | 2706 | N | PHE | A | 1153 | −13.694 | 13.991 | −2.089 | 1.00 | 61.62 | N |
| ATOM | 2707 | CA | PHE | A | 1153 | −14.252 | 14.688 | −3.246 | 1.00 | 65.28 | C |
| ATOM | 2708 | C | PHE | A | 1153 | −15.774 | 14.561 | −3.274 | 1.00 | 63.37 | C |
| ATOM | 2709 | O | PHE | A | 1153 | −16.485 | 15.520 | −3.570 | 1.00 | 54.96 | O |
| ATOM | 2710 | CB | PHE | A | 1153 | −13.668 | 14.135 | −4.549 | 1.00 | 62.83 | C |
| ATOM | 2711 | CG | PHE | A | 1153 | −12.306 | 14.678 | −4.891 | 1.00 | 60.26 | C |
| ATOM | 2712 | CD1 | PHE | A | 1153 | −12.067 | 16.042 | −4.887 | 1.00 | 55.39 | C |
| ATOM | 2713 | CD2 | PHE | A | 1153 | −11.273 | 13.823 | −5.245 | 1.00 | 59.43 | C |
| ATOM | 2714 | CE1 | PHE | A | 1153 | −10.817 | 16.543 | −5.210 | 1.00 | 58.69 | C |
| ATOM | 2715 | CE2 | PHE | A | 1153 | −10.023 | 14.318 | −5.572 | 1.00 | 57.71 | C |
| ATOM | 2716 | CZ | PHE | A | 1153 | −9.795 | 15.679 | −5.555 | 1.00 | 58.36 | C |
| ATOM | 2717 | N | ARG | A | 1154 | −16.262 | 13.364 | −2.967 | 1.00 | 59.14 | N |
| ATOM | 2718 | CA | ARG | A | 1154 | −17.692 | 13.081 | −2.941 | 1.00 | 64.04 | C |
| ATOM | 2719 | C | ARG | A | 1154 | −18.437 | 13.954 | −1.937 | 1.00 | 70.56 | C |
| ATOM | 2720 | O | ARG | A | 1154 | −19.396 | 14.643 | −2.286 | 1.00 | 62.30 | O |
| ATOM | 2721 | CB | ARG | A | 1154 | −17.923 | 11.608 | −2.595 | 1.00 | 68.25 | C |
| ATOM | 2722 | CG | ARG | A | 1154 | −17.793 | 10.657 | −3.770 | 1.00 | 78.87 | C |
| ATOM | 2723 | CD | ARG | A | 1154 | −19.144 | 10.097 | −4.178 | 1.00 | 84.33 | C |
| ATOM | 2724 | NE | ARG | A | 1154 | −19.489 | 8.909 | −3.401 | 1.00 | 88.22 | N |
| ATOM | 2725 | CZ | ARG | A | 1154 | −20.657 | 8.278 | −3.470 | 1.00 | 93.03 | C |
| ATOM | 2726 | NH1 | ARG | A | 1154 | −21.611 | 8.725 | −4.276 | 1.00 | 94.35 | N |
| ATOM | 2727 | NH2 | ARG | A | 1154 | −20.876 | 7.202 | −2.726 | 1.00 | 93.11 | N |
| ATOM | 2728 | N | THR | A | 1155 | −17.981 | 13.918 | −0.689 | 1.00 | 74.01 | N |
| ATOM | 2729 | CA | THR | A | 1155 | −18.716 | 14.509 | 0.423 | 1.00 | 62.69 | C |
| ATOM | 2730 | C | THR | A | 1155 | −18.280 | 15.931 | 0.756 | 1.00 | 64.45 | C |
| ATOM | 2731 | O | THR | A | 1155 | −19.099 | 16.761 | 1.152 | 1.00 | 68.53 | O |
| ATOM | 2732 | CB | THR | A | 1155 | −18.559 | 13.651 | 1.688 | 1.00 | 64.46 | C |
| ATOM | 2733 | OG1 | THR | A | 1155 | −17.194 | 13.690 | 2.122 | 1.00 | 66.24 | O |
| ATOM | 2734 | CG2 | THR | A | 1155 | −18.952 | 12.209 | 1.401 | 1.00 | 63.74 | C |
| ATOM | 2735 | N | GLY | A | 1156 | −16.990 | 16.209 | 0.604 | 1.00 | 63.43 | N |
| ATOM | 2736 | CA | GLY | A | 1156 | −16.451 | 17.504 | 0.976 | 1.00 | 52.38 | C |
| ATOM | 2737 | C | GLY | A | 1156 | −16.272 | 17.619 | 2.478 | 1.00 | 59.38 | C |
| ATOM | 2738 | O | GLY | A | 1156 | −16.257 | 18.720 | 3.029 | 1.00 | 65.43 | O |
| ATOM | 2739 | N | THR | A | 1157 | −16.144 | 16.473 | 3.140 | 1.00 | 60.48 | N |
| ATOM | 2740 | CA | THR | A | 1157 | −15.913 | 16.428 | 4.581 | 1.00 | 59.84 | C |
| ATOM | 2741 | C | THR | A | 1157 | −14.654 | 15.619 | 4.889 | 1.00 | 62.03 | C |
| ATOM | 2742 | O | THR | A | 1157 | −13.999 | 15.108 | 3.980 | 1.00 | 54.89 | O |
| ATOM | 2743 | CB | THR | A | 1157 | −17.102 | 15.796 | 5.328 | 1.00 | 60.37 | C |
| ATOM | 2744 | OG1 | THR | A | 1157 | −17.213 | 14.412 | 4.973 | 1.00 | 61.50 | O |
| ATOM | 2745 | CG2 | THR | A | 1157 | −18.399 | 16.511 | 4.979 | 1.00 | 57.26 | C |
| ATOM | 2746 | N | TRP | A | 1158 | −14.322 | 15.504 | 6.172 | 1.00 | 62.65 | N |
| ATOM | 2747 | CA | TRP | A | 1158 | −13.158 | 14.731 | 6.597 | 1.00 | 50.99 | C |
| ATOM | 2748 | C | TRP | A | 1158 | −13.567 | 13.332 | 7.050 | 1.00 | 55.09 | C |
| ATOM | 2749 | O | TRP | A | 1158 | −12.792 | 12.634 | 7.703 | 1.00 | 53.77 | O |
| ATOM | 2750 | CB | TRP | A | 1158 | −12.424 | 15.438 | 7.739 | 1.00 | 49.70 | C |
| ATOM | 2751 | CG | TRP | A | 1158 | −11.927 | 16.819 | 7.410 | 1.00 | 53.10 | C |
| ATOM | 2752 | CD1 | TRP | A | 1158 | −12.463 | 18.003 | 7.828 | 1.00 | 48.59 | C |
| ATOM | 2753 | CD2 | TRP | A | 1158 | −10.788 | 17.156 | 6.606 | 1.00 | 52.69 | C |
| ATOM | 2754 | NE1 | TRP | A | 1158 | −11.733 | 19.056 | 7.331 | 1.00 | 47.52 | N |
| ATOM | 2755 | CE2 | TRP | A | 1158 | −10.699 | 18.564 | 6.578 | 1.00 | 51.49 | C |
| ATOM | 2756 | CE3 | TRP | A | 1158 | −9.836 | 16.406 | 5.906 | 1.00 | 54.55 | C |
| ATOM | 2757 | CZ2 | TRP | A | 1158 | −9.697 | 19.236 | 5.878 | 1.00 | 54.10 | C |
| ATOM | 2758 | CZ3 | TRP | A | 1158 | −8.842 | 17.076 | 5.209 | 1.00 | 56.12 | C |

TABLE 6-continued

HUMAN A2A ADENOSINE STRUCTURE.PDB FILE
(Table 6: discloses SEQ ID NOS 20-27, respectively, in order of appearance.)

| ATOM | 2759 | CH2 | TRP | A | 1158 | −8.781 | 18.477 | 5.201 | 1.00 | 54.28 | C |
|---|---|---|---|---|---|---|---|---|---|---|---|
| ATOM | 2760 | N | ASP | A | 1159 | −14.785 | 12.931 | 6.698 | 1.00 | 65.51 | N |
| ATOM | 2761 | CA | ASP | A | 1159 | −15.348 | 11.656 | 7.142 | 1.00 | 64.81 | C |
| ATOM | 2762 | C | ASP | A | 1159 | −14.380 | 10.482 | 7.040 | 1.00 | 63.07 | C |
| ATOM | 2763 | O | ASP | A | 1159 | −14.143 | 9.777 | 8.021 | 1.00 | 65.38 | O |
| ATOM | 2764 | CB | ASP | A | 1159 | −16.624 | 11.333 | 6.361 | 1.00 | 72.61 | C |
| ATOM | 2765 | CG | ASP | A | 1159 | −17.812 | 12.150 | 6.822 | 1.00 | 82.71 | C |
| ATOM | 2766 | OD1 | ASP | A | 1159 | −17.631 | 13.026 | 7.695 | 1.00 | 86.35 | O |
| ATOM | 2767 | OD2 | ASP | A | 1159 | −18.927 | 11.911 | 6.313 | 1.00 | 86.00 | O |
| ATOM | 2768 | N | ALA | A | 1160 | −13.831 | 10.273 | 5.847 | 1.00 | 61.75 | N |
| ATOM | 2769 | CA | ALA | A | 1160 | −12.965 | 9.126 | 5.588 | 1.00 | 62.25 | C |
| ATOM | 2770 | C | ALA | A | 1160 | −11.776 | 9.063 | 6.543 | 1.00 | 59.90 | C |
| ATOM | 2771 | O | ALA | A | 1160 | −11.276 | 7.982 | 6.855 | 1.00 | 64.16 | O |
| ATOM | 2772 | CB | ALA | A | 1160 | −12.487 | 9.138 | 4.141 | 1.00 | 57.82 | C |
| ATOM | 2773 | N | TYR | A | 1161 | −11.326 | 10.223 | 7.007 | 1.00 | 46.32 | N |
| ATOM | 2774 | CA | TYR | A | 1161 | −10.160 | 10.285 | 7.878 | 1.00 | 56.11 | C |
| ATOM | 2775 | C | TYR | A | 1161 | −10.552 | 10.249 | 9.353 | 1.00 | 64.26 | C |
| ATOM | 2776 | O | TYR | A | 1161 | −9.767 | 9.828 | 10.203 | 1.00 | 63.26 | O |
| ATOM | 2777 | CB | TYR | A | 1161 | −9.314 | 11.518 | 7.551 | 1.00 | 51.64 | C |
| ATOM | 2778 | CG | TYR | A | 1161 | −8.725 | 11.472 | 6.159 | 1.00 | 48.58 | C |
| ATOM | 2779 | CD1 | TYR | A | 1161 | −7.438 | 10.995 | 5.944 | 1.00 | 52.84 | C |
| ATOM | 2780 | CD2 | TYR | A | 1161 | −9.463 | 11.884 | 5.057 | 1.00 | 51.32 | C |
| ATOM | 2781 | CE1 | TYR | A | 1161 | −6.899 | 10.941 | 4.673 | 1.00 | 56.31 | C |
| ATOM | 2782 | CE2 | TYR | A | 1161 | −8.932 | 11.833 | 3.782 | 1.00 | 50.11 | C |
| ATOM | 2783 | CZ | TYR | A | 1161 | −7.650 | 11.361 | 3.596 | 1.00 | 53.47 | C |
| ATOM | 2784 | OH | TYR | A | 1161 | −7.118 | 11.308 | 2.328 | 1.00 | 61.20 | O |
| ATOM | 2785 | N | ARG | A | 222 | −11.775 | 10.677 | 9.647 | 1.00 | 63.22 | N |
| ATOM | 2786 | CA | ARG | A | 222 | −12.290 | 10.630 | 11.008 | 1.00 | 54.85 | C |
| ATOM | 2787 | C | ARG | A | 222 | −12.676 | 9.199 | 11.369 | 1.00 | 55.79 | C |
| ATOM | 2788 | O | ARG | A | 222 | −12.618 | 8.803 | 12.533 | 1.00 | 59.44 | O |
| ATOM | 2789 | CB | ARG | A | 222 | −13.496 | 11.559 | 11.158 | 1.00 | 47.89 | C |
| ATOM | 2790 | CG | ARG | A | 222 | −13.821 | 11.937 | 12.594 | 1.00 | 44.51 | C |
| ATOM | 2791 | CD | ARG | A | 222 | −14.998 | 12.896 | 12.650 | 1.00 | 57.47 | C |
| ATOM | 2792 | NE | ARG | A | 222 | −14.928 | 13.901 | 11.592 | 1.00 | 64.41 | N |
| ATOM | 2793 | CZ | ARG | A | 222 | −14.362 | 15.094 | 11.731 | 1.00 | 67.61 | C |
| ATOM | 2794 | NH1 | ARG | A | 222 | −14.343 | 15.944 | 10.714 | 1.00 | 70.49 | N |
| ATOM | 2795 | NH2 | ARG | A | 222 | −13.814 | 15.439 | 12.887 | 1.00 | 76.31 | N |
| ATOM | 2796 | N | SER | A | 223 | −13.067 | 8.427 | 10.359 | 1.00 | 64.48 | N |
| ATOM | 2797 | CA | SER | A | 223 | −13.426 | 7.025 | 10.553 | 1.00 | 61.21 | C |
| ATOM | 2798 | C | SER | A | 223 | −12.208 | 6.202 | 10.949 | 1.00 | 55.59 | C |
| ATOM | 2799 | O | SER | A | 223 | −12.293 | 5.325 | 11.807 | 1.00 | 66.27 | O |
| ATOM | 2800 | CB | SER | A | 223 | −14.053 | 6.445 | 9.283 | 1.00 | 63.78 | C |
| ATOM | 2801 | OG | SER | A | 223 | −15.348 | 6.975 | 9.063 | 1.00 | 73.65 | O |
| ATOM | 2802 | N | THR | A | 224 | −11.078 | 6.488 | 10.312 | 1.00 | 59.77 | N |
| ATOM | 2803 | CA | THR | A | 224 | −9.833 | 5.790 | 10.605 | 1.00 | 61.54 | C |
| ATOM | 2804 | C | THR | A | 224 | −9.468 | 5.912 | 12.080 | 1.00 | 64.45 | C |
| ATOM | 2805 | O | THR | A | 224 | −9.091 | 4.932 | 12.720 | 1.00 | 71.97 | O |
| ATOM | 2806 | CB | THR | A | 224 | −8.672 | 6.335 | 9.756 | 1.00 | 65.38 | C |
| ATOM | 2807 | OG1 | THR | A | 224 | −8.951 | 6.118 | 8.367 | 1.00 | 66.37 | O |
| ATOM | 2808 | CG2 | THR | A | 224 | −7.371 | 5.638 | 10.122 | 1.00 | 72.97 | C |
| ATOM | 2809 | N | LEU | A | 225 | −9.588 | 7.122 | 12.615 | 1.00 | 68.66 | N |
| ATOM | 2810 | CA | LEU | A | 225 | −9.235 | 7.385 | 14.005 | 1.00 | 73.76 | C |
| ATOM | 2811 | C | LEU | A | 225 | −10.215 | 6.742 | 14.985 | 1.00 | 70.02 | C |
| ATOM | 2812 | O | LEU | A | 225 | −9.818 | 6.275 | 16.052 | 1.00 | 69.10 | O |
| ATOM | 2813 | CB | LEU | A | 225 | −9.154 | 8.893 | 14.258 | 1.00 | 74.09 | C |
| ATOM | 2814 | CG | LEU | A | 225 | −8.155 | 9.679 | 13.406 | 1.00 | 67.08 | C |
| ATOM | 2815 | CD1 | LEU | A | 225 | −8.248 | 11.168 | 13.704 | 1.00 | 63.25 | C |
| ATOM | 2816 | CD2 | LEU | A | 225 | −6.738 | 9.171 | 13.630 | 1.00 | 63.08 | C |
| ATOM | 2817 | N | GLN | A | 226 | −11.494 | 6.719 | 14.619 | 1.00 | 68.18 | N |
| ATOM | 2818 | CA | GLN | A | 226 | −12.534 | 6.208 | 15.510 | 1.00 | 74.09 | C |
| ATOM | 2819 | C | GLN | A | 226 | −12.592 | 4.682 | 15.562 | 1.00 | 87.21 | C |
| ATOM | 2820 | O | GLN | A | 226 | −13.175 | 4.109 | 16.483 | 1.00 | 93.97 | O |
| ATOM | 2821 | CB | GLN | A | 226 | −13.902 | 6.788 | 15.137 | 1.00 | 79.24 | C |
| ATOM | 2822 | CG | GLN | A | 226 | −14.149 | 8.182 | 15.698 | 1.00 | 92.86 | C |
| ATOM | 2823 | CD | GLN | A | 226 | −15.426 | 8.812 | 15.175 | 1.00 | 103.30 | C |
| ATOM | 2824 | OE1 | GLN | A | 226 | −16.013 | 8.338 | 14.201 | 1.00 | 101.78 | O |
| ATOM | 2825 | NE2 | GLN | A | 226 | −15.861 | 9.889 | 15.818 | 1.00 | 106.94 | N |
| ATOM | 2826 | N | LYS | A | 227 | −11.990 | 4.029 | 14.575 | 1.00 | 93.48 | N |
| ATOM | 2827 | CA | LYS | A | 227 | −11.891 | 2.574 | 14.580 | 1.00 | 99.60 | C |
| ATOM | 2828 | C | LYS | A | 227 | −10.575 | 2.157 | 15.222 | 1.00 | 97.48 | C |
| ATOM | 2829 | O | LYS | A | 227 | −10.461 | 1.078 | 15.803 | 1.00 | 93.64 | O |
| ATOM | 2830 | CB | LYS | A | 227 | −11.977 | 2.021 | 13.156 | 1.00 | 105.62 | C |
| ATOM | 2831 | CG | LYS | A | 227 | −13.293 | 2.310 | 12.452 | 1.00 | 113.43 | C |
| ATOM | 2832 | CD | LYS | A | 227 | −13.339 | 1.654 | 11.081 | 1.00 | 121.57 | C |
| ATOM | 2833 | CE | LYS | A | 227 | −14.691 | 1.854 | 10.415 | 1.00 | 126.74 | C |
| ATOM | 2834 | NZ | LYS | A | 227 | −14.764 | 1.183 | 9.087 | 1.00 | 125.91 | N |
| ATOM | 2835 | N | GLU | A | 228 | −9.586 | 3.037 | 15.115 | 1.00 | 99.97 | N |

TABLE 6-continued

HUMAN A2A ADENOSINE STRUCTURE.PDB FILE
(Table 6: discloses SEQ ID NOS 20-27, respectively, in order of appearance.)

| ATOM | 2836 | CA  | GLU | A | 228 | −8.250  | 2.792  | 15.640 | 1.00 | 102.09 | C |
|------|------|-----|-----|---|-----|---------|--------|--------|------|--------|---|
| ATOM | 2837 | C   | GLU | A | 228 | −8.217  | 3.003  | 17.153 | 1.00 | 95.46  | C |
| ATOM | 2838 | O   | GLU | A | 228 | −7.149  | 3.043  | 17.761 | 1.00 | 97.03  | O |
| ATOM | 2839 | CB  | GLU | A | 228 | −7.256  | 3.732  | 14.951 | 1.00 | 110.17 | C |
| ATOM | 2840 | CG  | GLU | A | 228 | −5.793  | 3.347  | 15.081 | 1.00 | 116.21 | C |
| ATOM | 2841 | CD  | GLU | A | 228 | −4.899  | 4.177  | 14.175 | 1.00 | 121.31 | C |
| ATOM | 2842 | OE1 | GLU | A | 228 | −5.392  | 4.661  | 13.133 | 1.00 | 122.62 | O |
| ATOM | 2843 | OE2 | GLU | A | 228 | −3.704  | 4.342  | 14.501 | 1.00 | 121.41 | O |
| ATOM | 2844 | N   | VAL | A | 229 | −9.397  | 3.131  | 17.754 | 1.00 | 89.29  | N |
| ATOM | 2845 | CA  | VAL | A | 229 | −9.511  | 3.446  | 19.176 | 1.00 | 87.67  | C |
| ATOM | 2846 | C   | VAL | A | 229 | −10.665 | 2.692  | 19.841 | 1.00 | 94.90  | C |
| ATOM | 2847 | O   | VAL | A | 229 | −10.672 | 2.495  | 21.057 | 1.00 | 100.49 | O |
| ATOM | 2848 | CB  | VAL | A | 229 | −9.673  | 4.973  | 19.393 | 1.00 | 74.61  | C |
| ATOM | 2849 | CG1 | VAL | A | 229 | −10.374 | 5.271  | 20.710 | 1.00 | 79.78  | C |
| ATOM | 2850 | CG2 | VAL | A | 229 | −8.320  | 5.666  | 19.329 | 1.00 | 71.97  | C |
| ATOM | 2851 | N   | HIS | A | 230 | −11.631 | 2.262  | 19.035 | 1.00 | 94.88  | N |
| ATOM | 2852 | CA  | HIS | A | 230 | −12.804 | 1.554  | 19.544 | 1.00 | 93.82  | C |
| ATOM | 2853 | C   | HIS | A | 230 | −12.439 | 0.366  | 20.434 | 1.00 | 88.38  | C |
| ATOM | 2854 | O   | HIS | A | 230 | −13.137 | 0.068  | 21.403 | 1.00 | 85.57  | O |
| ATOM | 2855 | CB  | HIS | A | 230 | −13.693 | 1.089  | 18.388 | 1.00 | 101.70 | C |
| ATOM | 2856 | CG  | HIS | A | 230 | −14.795 | 0.167  | 18.806 | 1.00 | 110.55 | C |
| ATOM | 2857 | ND1 | HIS | A | 230 | −15.886 | 0.591  | 19.534 | 1.00 | 113.44 | N |
| ATOM | 2858 | CD2 | HIS | A | 230 | −14.977 | −1.159 | 18.594 | 1.00 | 113.59 | C |
| ATOM | 2859 | CE1 | HIS | A | 230 | −16.691 | −0.433 | 19.755 | 1.00 | 114.04 | C |
| ATOM | 2860 | NE2 | HIS | A | 230 | −16.162 | −1.506 | 19.195 | 1.00 | 115.00 | N |
| ATOM | 2861 | N   | ALA | A | 231 | −11.346 | −0.311 | 20.099 | 1.00 | 83.31  | N |
| ATOM | 2862 | CA  | ALA | A | 231 | −10.897 | −1.466 | 20.869 | 1.00 | 73.51  | C |
| ATOM | 2863 | C   | ALA | A | 231 | −10.318 | −1.045 | 22.217 | 1.00 | 67.57  | C |
| ATOM | 2864 | O   | ALA | A | 231 | −10.462 | −1.754 | 23.214 | 1.00 | 63.31  | O |
| ATOM | 2865 | CB  | ALA | A | 231 | −9.874  | −2.268 | 20.075 | 1.00 | 70.46  | C |
| ATOM | 2866 | N   | ALA | A | 232 | −9.666  | 0.112  | 22.242 | 1.00 | 62.86  | N |
| ATOM | 2867 | CA  | ALA | A | 232 | −9.054  | 0.617  | 23.465 | 1.00 | 58.92  | C |
| ATOM | 2868 | C   | ALA | A | 232 | −10.106 | 1.015  | 24.499 | 1.00 | 63.13  | C |
| ATOM | 2869 | O   | ALA | A | 232 | −9.813  | 1.103  | 25.692 | 1.00 | 62.57  | O |
| ATOM | 2870 | CB  | ALA | A | 232 | −8.133  | 1.788  | 23.156 | 1.00 | 56.61  | C |
| ATOM | 2871 | N   | LYS | A | 233 | −11.330 | 1.258  | 24.041 | 1.00 | 69.07  | N |
| ATOM | 2872 | CA  | LYS | A | 233 | −12.415 | 1.559  | 24.964 | 1.00 | 76.63  | C |
| ATOM | 2873 | C   | LYS | A | 233 | −12.798 | 0.302  | 25.738 | 1.00 | 72.76  | C |
| ATOM | 2874 | O   | LYS | A | 233 | −13.029 | 0.352  | 26.947 | 1.00 | 67.54  | O |
| ATOM | 2875 | CB  | LYS | A | 233 | −13.633 | 2.121  | 24.230 | 1.00 | 85.44  | C |
| ATOM | 2876 | CG  | LYS | A | 233 | −14.674 | 2.714  | 25.169 | 1.00 | 96.75  | C |
| ATOM | 2877 | CD  | LYS | A | 233 | −16.029 | 2.875  | 24.501 | 1.00 | 98.56  | C |
| ATOM | 2878 | CE  | LYS | A | 233 | −17.081 | 3.308  | 25.512 | 1.00 | 93.74  | C |
| ATOM | 2879 | NZ  | LYS | A | 233 | −18.444 | 3.366  | 24.917 | 1.00 | 92.86  | N |
| ATOM | 2880 | N   | SER | A | 234 | −12.859 | −0.824 | 25.032 | 1.00 | 66.51  | N |
| ATOM | 2881 | CA  | SER | A | 234 | −13.153 | −2.111 | 25.652 | 1.00 | 58.02  | C |
| ATOM | 2882 | C   | SER | A | 234 | −12.181 | −2.393 | 26.791 | 1.00 | 55.39  | C |
| ATOM | 2883 | O   | SER | A | 234 | −12.586 | −2.758 | 27.895 | 1.00 | 55.03  | O |
| ATOM | 2884 | CB  | SER | A | 234 | −13.064 | −3.236 | 24.619 | 1.00 | 64.77  | C |
| ATOM | 2885 | OG  | SER | A | 234 | −13.873 | −2.969 | 23.488 | 1.00 | 67.08  | O |
| ATOM | 2886 | N   | LEU | A | 235 | −10.893 | −2.218 | 26.513 | 1.00 | 49.24  | N |
| ATOM | 2887 | CA  | LEU | A | 235 | −9.844  | −2.486 | 27.491 | 1.00 | 56.30  | C |
| ATOM | 2888 | C   | LEU | A | 235 | −9.870  | −1.488 | 28.646 | 1.00 | 60.55  | C |
| ATOM | 2889 | O   | LEU | A | 235 | −9.561  | −1.838 | 29.784 | 1.00 | 62.35  | O |
| ATOM | 2890 | CB  | LEU | A | 235 | −8.473  | −2.475 | 26.813 | 1.00 | 58.60  | C |
| ATOM | 2891 | CG  | LEU | A | 235 | −8.301  | −3.468 | 25.659 | 1.00 | 64.45  | C |
| ATOM | 2892 | CD1 | LEU | A | 235 | −7.050  | −3.159 | 24.851 | 1.00 | 67.68  | C |
| ATOM | 2893 | CD2 | LEU | A | 235 | −8.274  | −4.899 | 26.177 | 1.00 | 62.86  | C |
| ATOM | 2894 | N   | ALA | A | 236 | −10.237 | −0.245 | 28.350 | 1.00 | 65.50  | N |
| ATOM | 2895 | CA  | ALA | A | 236 | −10.314 | 0.791  | 29.375 | 1.00 | 65.44  | C |
| ATOM | 2896 | C   | ALA | A | 236 | −11.406 | 0.471  | 30.392 | 1.00 | 66.83  | C |
| ATOM | 2897 | O   | ALA | A | 236 | −11.276 | 0.775  | 31.580 | 1.00 | 63.16  | O |
| ATOM | 2898 | CB  | ALA | A | 236 | −10.554 | 2.152  | 28.741 | 1.00 | 58.67  | C |
| ATOM | 2899 | N   | ILE | A | 237 | −12.484 | −0.144 | 29.916 | 1.00 | 61.25  | N |
| ATOM | 2900 | CA  | ILE | A | 237 | −13.571 | −0.575 | 30.784 | 1.00 | 58.85  | C |
| ATOM | 2901 | C   | ILE | A | 237 | −13.067 | −1.595 | 31.799 | 1.00 | 61.27  | C |
| ATOM | 2902 | O   | ILE | A | 237 | −13.527 | −1.632 | 32.940 | 1.00 | 62.54  | O |
| ATOM | 2903 | CB  | ILE | A | 237 | −14.729 | −1.177 | 29.965 | 1.00 | 63.78  | C |
| ATOM | 2904 | CG1 | ILE | A | 237 | −15.422 | −0.080 | 29.154 | 1.00 | 67.34  | C |
| ATOM | 2905 | CG2 | ILE | A | 237 | −15.725 | −1.885 | 30.874 | 1.00 | 59.36  | C |
| ATOM | 2906 | CD1 | ILE | A | 237 | −16.417 | −0.598 | 28.141 | 1.00 | 65.54  | C |
| ATOM | 2907 | N   | ILE | A | 238 | −12.110 | −2.417 | 31.377 | 1.00 | 54.13  | N |
| ATOM | 2908 | CA  | ILE | A | 238 | −11.506 | −3.413 | 32.254 | 1.00 | 50.65  | C |
| ATOM | 2909 | C   | ILE | A | 238 | −10.858 | −2.764 | 33.474 | 1.00 | 54.49  | C |
| ATOM | 2910 | O   | ILE | A | 238 | −10.987 | −3.261 | 34.592 | 1.00 | 52.88  | O |
| ATOM | 2911 | CB  | ILE | A | 238 | −10.443 | −4.243 | 31.512 | 1.00 | 63.67  | C |
| ATOM | 2912 | CG1 | ILE | A | 238 | −11.053 | −4.929 | 30.288 | 1.00 | 65.11  | C |

TABLE 6-continued

HUMAN A2A ADENOSINE STRUCTURE.PDB FILE
(Table 6: discloses SEQ ID NOS 20-27, respectively, in order of appearance.)

| ATOM | 2913 | CG2 | ILE | A | 238 | −9.819  | −5.269 | 32.447 | 1.00 | 67.31 | C |
|------|------|-----|-----|---|-----|---------|--------|--------|------|-------|---|
| ATOM | 2914 | CD1 | ILE | A | 238 | −12.018 | −6.042 | 30.624 | 1.00 | 57.47 | C |
| ATOM | 2915 | N   | VAL | A | 239 | −10.158 | −1.655 | 33.255 | 1.00 | 58.50 | N |
| ATOM | 2916 | CA  | VAL | A | 239 | −9.477  | −0.957 | 34.340 | 1.00 | 57.59 | C |
| ATOM | 2917 | C   | VAL | A | 239 | −10.471 | −0.282 | 35.280 | 1.00 | 60.82 | C |
| ATOM | 2918 | O   | VAL | A | 239 | −10.279 | −0.269 | 36.495 | 1.00 | 69.52 | O |
| ATOM | 2919 | CB  | VAL | A | 239 | −8.495  | 0.109  | 33.813 | 1.00 | 56.53 | C |
| ATOM | 2920 | CG1 | VAL | A | 239 | −7.679  | 0.688  | 34.962 | 1.00 | 52.49 | C |
| ATOM | 2921 | CG2 | VAL | A | 239 | −7.581  | −0.482 | 32.751 | 1.00 | 47.11 | C |
| ATOM | 2922 | N   | GLY | A | 240 | −11.530 | 0.283  | 34.708 | 1.00 | 56.92 | N |
| ATOM | 2923 | CA  | GLY | A | 240 | −12.555 | 0.949  | 35.491 | 1.00 | 53.42 | C |
| ATOM | 2924 | C   | GLY | A | 240 | −13.228 | 0.010  | 36.473 | 1.00 | 55.72 | C |
| ATOM | 2925 | O   | GLY | A | 240 | −13.550 | 0.396  | 37.597 | 1.00 | 58.38 | O |
| ATOM | 2926 | N   | LEU | A | 241 | −13.437 | −1.231 | 36.046 | 1.00 | 56.22 | N |
| ATOM | 2927 | CA  | LEU | A | 241 | −14.073 | −2.234 | 36.893 | 1.00 | 53.25 | C |
| ATOM | 2928 | C   | LEU | A | 241 | −13.127 | −2.721 | 37.986 | 1.00 | 52.70 | C |
| ATOM | 2929 | O   | LEU | A | 241 | −13.542 | −2.934 | 39.126 | 1.00 | 53.95 | O |
| ATOM | 2930 | CB  | LEU | A | 241 | −14.577 | −3.406 | 36.050 | 1.00 | 50.95 | C |
| ATOM | 2931 | CG  | LEU | A | 241 | −15.793 | −3.087 | 35.176 | 1.00 | 56.54 | C |
| ATOM | 2932 | CD1 | LEU | A | 241 | −16.031 | −4.179 | 34.148 | 1.00 | 61.81 | C |
| ATOM | 2933 | CD2 | LEU | A | 241 | −17.033 | −2.873 | 36.033 | 1.00 | 53.32 | C |
| ATOM | 2934 | N   | PHE | A | 242 | −11.857 | −2.893 | 37.637 | 1.00 | 52.97 | N |
| ATOM | 2935 | CA  | PHE | A | 242 | −10.845 | −3.248 | 38.626 | 1.00 | 57.03 | C |
| ATOM | 2936 | C   | PHE | A | 242 | −10.835 | −2.225 | 39.757 | 1.00 | 50.20 | C |
| ATOM | 2937 | O   | PHE | A | 242 | −10.903 | −2.582 | 40.933 | 1.00 | 52.63 | O |
| ATOM | 2938 | CB  | PHE | A | 242 | −9.461  | −3.326 | 37.979 | 1.00 | 61.25 | C |
| ATOM | 2939 | CG  | PHE | A | 242 | −8.366  | −3.710 | 38.935 | 1.00 | 61.49 | C |
| ATOM | 2940 | CD1 | PHE | A | 242 | −7.961  | −5.030 | 39.050 | 1.00 | 57.01 | C |
| ATOM | 2941 | CD2 | PHE | A | 242 | −7.745  | −2.752 | 39.721 | 1.00 | 60.29 | C |
| ATOM | 2942 | CE1 | PHE | A | 242 | −6.956  | −5.388 | 39.929 | 1.00 | 59.54 | C |
| ATOM | 2943 | CE2 | PHE | A | 242 | −6.740  | −3.104 | 40.604 | 1.00 | 56.46 | C |
| ATOM | 2944 | CZ  | PHE | A | 242 | −6.344  | −4.424 | 40.707 | 1.00 | 60.63 | C |
| ATOM | 2945 | N   | ALA | A | 243 | −10.750 | −0.949 | 39.388 | 1.00 | 53.71 | N |
| ATOM | 2946 | CA  | ALA | A | 243 | −10.740 | 0.140  | 40.360 | 1.00 | 51.85 | C |
| ATOM | 2947 | C   | ALA | A | 243 | −11.982 | 0.108  | 41.240 | 1.00 | 57.86 | C |
| ATOM | 2948 | O   | ALA | A | 243 | −11.899 | 0.271  | 42.456 | 1.00 | 62.06 | O |
| ATOM | 2949 | CB  | ALA | A | 243 | −10.634 | 1.478  | 39.648 | 1.00 | 47.00 | C |
| ATOM | 2950 | N   | LEU | A | 244 | −13.134 | −0.104 | 40.614 | 1.00 | 56.95 | N |
| ATOM | 2951 | CA  | LEU | A | 244 | −14.403 | −0.139 | 41.328 | 1.00 | 59.28 | C |
| ATOM | 2952 | C   | LEU | A | 244 | −14.451 | −1.279 | 42.344 | 1.00 | 58.13 | C |
| ATOM | 2953 | O   | LEU | A | 244 | −14.981 | −1.119 | 43.443 | 1.00 | 56.58 | O |
| ATOM | 2954 | CB  | LEU | A | 244 | −15.560 | −0.274 | 40.336 | 1.00 | 63.16 | C |
| ATOM | 2955 | CG  | LEU | A | 244 | −16.968 | −0.045 | 40.883 | 1.00 | 71.96 | C |
| ATOM | 2956 | CD1 | LEU | A | 244 | −17.124 | 1.389  | 41.368 | 1.00 | 73.10 | C |
| ATOM | 2957 | CD2 | LEU | A | 244 | −18.009 | −0.377 | 39.825 | 1.00 | 77.80 | C |
| ATOM | 2958 | N   | CYS | A | 245 | −13.890 | −2.425 | 41.973 | 1.00 | 56.88 | N |
| ATOM | 2959 | CA  | CYS | A | 245 | −13.943 | −3.617 | 42.816 | 1.00 | 53.36 | C |
| ATOM | 2960 | C   | CYS | A | 245 | −12.944 | −3.597 | 43.974 | 1.00 | 56.84 | C |
| ATOM | 2961 | O   | CYS | A | 245 | −13.134 | −4.295 | 44.971 | 1.00 | 56.12 | O |
| ATOM | 2962 | CB  | CYS | A | 245 | −13.727 | −4.879 | 41.974 | 1.00 | 51.05 | C |
| ATOM | 2963 | SG  | CYS | A | 245 | −15.093 | −5.300 | 40.862 | 1.00 | 71.51 | S |
| ATOM | 2964 | N   | TRP | A | 246 | −11.886 | −2.802 | 43.845 | 1.00 | 62.05 | N |
| ATOM | 2965 | CA  | TRP | A | 246 | −10.810 | −2.816 | 44.836 | 1.00 | 58.73 | C |
| ATOM | 2966 | C   | TRP | A | 246 | −10.731 | −1.573 | 45.717 | 1.00 | 53.00 | C |
| ATOM | 2967 | O   | TRP | A | 246 | −10.282 | −1.649 | 46.860 | 1.00 | 66.02 | O |
| ATOM | 2968 | CB  | TRP | A | 246 | −9.459  | −3.066 | 44.161 | 1.00 | 49.83 | C |
| ATOM | 2969 | CG  | TRP | A | 246 | −9.238  | −4.503 | 43.819 | 1.00 | 55.02 | C |
| ATOM | 2970 | CD1 | TRP | A | 246 | −9.386  | −5.088 | 42.595 | 1.00 | 52.27 | C |
| ATOM | 2971 | CD2 | TRP | A | 246 | −8.842  | −5.547 | 44.718 | 1.00 | 55.69 | C |
| ATOM | 2972 | NE1 | TRP | A | 246 | −9.100  | −6.430 | 42.675 | 1.00 | 56.58 | N |
| ATOM | 2973 | CE2 | TRP | A | 246 | −8.763  | −6.736 | 43.967 | 1.00 | 60.63 | C |
| ATOM | 2974 | CE3 | TRP | A | 246 | −8.542  | −5.589 | 46.083 | 1.00 | 47.83 | C |
| ATOM | 2975 | CZ2 | TRP | A | 246 | −8.398  | −7.956 | 44.536 | 1.00 | 57.03 | C |
| ATOM | 2976 | CZ3 | TRP | A | 246 | −8.178  | −6.799 | 46.645 | 1.00 | 54.20 | C |
| ATOM | 2977 | CH2 | TRP | A | 246 | −8.110  | −7.966 | 45.874 | 1.00 | 49.71 | C |
| ATOM | 2978 | N   | LEU | A | 247 | −11.160 | −0.431 | 45.191 | 1.00 | 47.85 | N |
| ATOM | 2979 | CA  | LEU | A | 247 | −11.084 | 0.818  | 45.946 | 1.00 | 56.76 | C |
| ATOM | 2980 | C   | LEU | A | 247 | −11.787 | 0.768  | 47.308 | 1.00 | 53.51 | C |
| ATOM | 2981 | O   | LEU | A | 247 | −11.209 | 1.180  | 48.312 | 1.00 | 51.99 | O |
| ATOM | 2982 | CB  | LEU | A | 247 | −11.585 | 2.002  | 45.112 | 1.00 | 56.86 | C |
| ATOM | 2983 | CG  | LEU | A | 247 | −10.563 | 2.572  | 44.125 | 1.00 | 62.68 | C |
| ATOM | 2984 | CD1 | LEU | A | 247 | −11.165 | 3.706  | 43.310 | 1.00 | 65.61 | C |
| ATOM | 2985 | CD2 | LEU | A | 247 | −9.313  | 3.037  | 44.860 | 1.00 | 64.98 | C |
| ATOM | 2986 | N   | PRO | A | 248 | −13.033 | 0.263  | 47.348 | 1.00 | 50.58 | N |
| ATOM | 2987 | CA  | PRO | A | 248 | −13.748 | 0.185  | 48.629 | 1.00 | 54.33 | C |
| ATOM | 2988 | C   | PRO | A | 248 | −12.893 | −0.404 | 49.751 | 1.00 | 58.13 | C |
| ATOM | 2989 | O   | PRO | A | 248 | −12.811 | 0.180  | 50.831 | 1.00 | 61.00 | O |

TABLE 6-continued

HUMAN A2A ADENOSINE STRUCTURE.PDB FILE
(Table 6: discloses SEQ ID NOS 20-27, respectively, in order of appearance.)

| ATOM | 2990 | CB  | PRO | A | 248 | −14.921 | −0.741 | 48.311 | 1.00 | 53.67 | C |
| ---- | ---- | --- | --- | - | --- | ------- | ------ | ------ | ---- | ----- | - |
| ATOM | 2991 | CG  | PRO | A | 248 | −15.196 | −0.493 | 46.870 | 1.00 | 54.83 | C |
| ATOM | 2992 | CD  | PRO | A | 248 | −13.859 | −0.221 | 46.227 | 1.00 | 50.82 | C |
| ATOM | 2993 | N   | LEU | A | 249 | −12.261 | −1.544 | 49.495 | 1.00 | 60.08 | N |
| ATOM | 2994 | CA  | LEU | A | 249 | −11.425 | −2.190 | 50.499 | 1.00 | 57.57 | C |
| ATOM | 2995 | C   | LEU | A | 249 | −10.244 | −1.305 | 50.898 | 1.00 | 58.63 | C |
| ATOM | 2996 | O   | LEU | A | 249 | −9.921  | −1.184 | 52.081 | 1.00 | 56.45 | O |
| ATOM | 2997 | CB  | LEU | A | 249 | −10.934 | −3.548 | 49.990 | 1.00 | 61.18 | C |
| ATOM | 2998 | CG  | LEU | A | 249 | −10.316 | −4.500 | 51.017 | 1.00 | 53.65 | C |
| ATOM | 2999 | CD1 | LEU | A | 249 | −11.125 | −4.505 | 52.305 | 1.00 | 48.86 | C |
| ATOM | 3000 | CD2 | LEU | A | 249 | −10.203 | −5.908 | 50.444 | 1.00 | 42.89 | C |
| ATOM | 3001 | N   | HIS | A | 250 | −9.606  | −0.685 | 49.909 | 1.00 | 56.86 | N |
| ATOM | 3002 | CA  | HIS | A | 250 | −8.469  | 0.196  | 50.163 | 1.00 | 55.17 | C |
| ATOM | 3003 | C   | HIS | A | 250 | −8.866  | 1.403  | 51.006 | 1.00 | 63.80 | C |
| ATOM | 3004 | O   | HIS | A | 250 | −8.135  | 1.810  | 51.909 | 1.00 | 64.24 | O |
| ATOM | 3005 | CB  | HIS | A | 250 | −7.849  | 0.675  | 48.850 | 1.00 | 48.72 | C |
| ATOM | 3006 | CG  | HIS | A | 250 | −7.085  | −0.383 | 48.119 | 1.00 | 50.95 | C |
| ATOM | 3007 | ND1 | HIS | A | 250 | −5.943  | −0.961 | 48.627 | 1.00 | 59.40 | N |
| ATOM | 3008 | CD2 | HIS | A | 250 | −7.293  | −0.958 | 46.911 | 1.00 | 55.60 | C |
| ATOM | 3009 | CE1 | HIS | A | 250 | −5.483  | −1.854 | 47.767 | 1.00 | 57.33 | C |
| ATOM | 3010 | NE2 | HIS | A | 250 | −6.284  | −1.870 | 46.718 | 1.00 | 60.80 | N |
| ATOM | 3011 | N   | ILE | A | 251 | −10.024 | 1.977  | 50.699 | 1.00 | 66.61 | N |
| ATOM | 3012 | CA  | ILE | A | 251 | −10.500 | 3.163  | 51.400 | 1.00 | 69.77 | C |
| ATOM | 3013 | C   | ILE | A | 251 | −10.815 | 2.855  | 52.860 | 1.00 | 68.61 | C |
| ATOM | 3014 | O   | ILE | A | 251 | −10.497 | 3.643  | 53.751 | 1.00 | 63.38 | O |
| ATOM | 3015 | CB  | ILE | A | 251 | −11.743 | 3.762  | 50.714 | 1.00 | 73.55 | C |
| ATOM | 3016 | CG1 | ILE | A | 251 | −11.443 | 4.065  | 49.245 | 1.00 | 76.67 | C |
| ATOM | 3017 | CG2 | ILE | A | 251 | −12.195 | 5.023  | 51.437 | 1.00 | 70.80 | C |
| ATOM | 3018 | CD1 | ILE | A | 251 | −12.633 | 4.593  | 48.472 | 1.00 | 83.10 | C |
| ATOM | 3019 | N   | ILE | A | 252 | −11.437 | 1.704  | 53.098 | 1.00 | 66.56 | N |
| ATOM | 3020 | CA  | ILE | A | 252 | −11.742 | 1.268  | 54.457 | 1.00 | 58.35 | C |
| ATOM | 3021 | C   | ILE | A | 252 | −10.462 | 1.104  | 55.274 | 1.00 | 63.00 | C |
| ATOM | 3022 | O   | ILE | A | 252 | −10.417 | 1.455  | 56.453 | 1.00 | 66.64 | O |
| ATOM | 3023 | CB  | ILE | A | 252 | −12.530 | −0.052 | 54.464 | 1.00 | 49.93 | C |
| ATOM | 3024 | CG1 | ILE | A | 252 | −13.925 | 0.161  | 53.877 | 1.00 | 48.84 | C |
| ATOM | 3025 | CG2 | ILE | A | 252 | −12.633 | −0.604 | 55.875 | 1.00 | 46.06 | C |
| ATOM | 3026 | CD1 | ILE | A | 252 | −14.764 | −1.098 | 53.831 | 1.00 | 44.16 | C |
| ATOM | 3027 | N   | ASN | A | 253 | −9.423  | 0.569  | 54.641 | 1.00 | 58.47 | N |
| ATOM | 3028 | CA  | ASN | A | 253 | −8.125  | 0.442  | 55.292 | 1.00 | 51.43 | C |
| ATOM | 3029 | C   | ASN | A | 253 | −7.597  | 1.802  | 55.737 | 1.00 | 57.18 | C |
| ATOM | 3030 | O   | ASN | A | 253 | −7.055  | 1.940  | 56.834 | 1.00 | 55.26 | O |
| ATOM | 3031 | CB  | ASN | A | 253 | −7.119  | −0.239 | 54.362 | 1.00 | 54.71 | C |
| ATOM | 3032 | CG  | ASN | A | 253 | −7.341  | −1.736 | 54.258 | 1.00 | 61.98 | C |
| ATOM | 3033 | OD1 | ASN | A | 253 | −8.046  | −2.329 | 55.073 | 1.00 | 66.43 | O |
| ATOM | 3034 | ND2 | ASN | A | 253 | −6.734  | −2.355 | 53.254 | 1.00 | 61.89 | N |
| ATOM | 3035 | N   | CYS | A | 254 | −7.766  | 2.803  | 54.879 | 1.00 | 55.71 | N |
| ATOM | 3036 | CA  | CYS | A | 254 | −7.315  | 4.158  | 55.176 | 1.00 | 58.66 | C |
| ATOM | 3037 | C   | CYS | A | 254 | −8.019  | 4.726  | 56.405 | 1.00 | 64.06 | C |
| ATOM | 3038 | O   | CYS | A | 254 | −7.388  | 5.357  | 57.252 | 1.00 | 58.54 | O |
| ATOM | 3039 | CB  | CYS | A | 254 | −7.531  | 5.073  | 53.968 | 1.00 | 53.92 | C |
| ATOM | 3040 | SG  | CYS | A | 254 | −6.517  | 4.654  | 52.531 | 1.00 | 64.49 | S |
| ATOM | 3041 | N   | PHE | A | 255 | −9.327  | 4.503  | 56.495 | 1.00 | 63.30 | N |
| ATOM | 3042 | CA  | PHE | A | 255 | −10.099 | 4.925  | 57.661 | 1.00 | 66.97 | C |
| ATOM | 3043 | C   | PHE | A | 255 | −9.546  | 4.321  | 58.942 | 1.00 | 66.28 | C |
| ATOM | 3044 | O   | PHE | A | 255 | −9.179  | 5.035  | 59.878 | 1.00 | 67.75 | O |
| ATOM | 3045 | CB  | PHE | A | 255 | −11.572 | 4.538  | 57.501 | 1.00 | 76.04 | C |
| ATOM | 3046 | CG  | PHE | A | 255 | −12.398 | 5.571  | 56.783 | 1.00 | 87.32 | C |
| ATOM | 3047 | CD1 | PHE | A | 255 | −12.154 | 5.875  | 55.453 | 1.00 | 88.11 | C |
| ATOM | 3048 | CD2 | PHE | A | 255 | −13.432 | 6.227  | 57.434 | 1.00 | 87.19 | C |
| ATOM | 3049 | CE1 | PHE | A | 255 | −12.917 | 6.822  | 54.790 | 1.00 | 86.46 | C |
| ATOM | 3050 | CE2 | PHE | A | 255 | −14.199 | 7.174  | 56.776 | 1.00 | 90.16 | C |
| ATOM | 3051 | CZ  | PHE | A | 255 | −13.940 | 7.471  | 55.451 | 1.00 | 87.09 | C |
| ATOM | 3052 | N   | THR | A | 256 | −9.510  | 2.993  | 58.979 | 1.00 | 63.39 | N |
| ATOM | 3053 | CA  | THR | A | 256 | −8.965  | 2.266  | 60.111 | 1.00 | 62.41 | C |
| ATOM | 3054 | C   | THR | A | 256 | −7.596  | 2.810  | 60.418 | 1.00 | 61.04 | C |
| ATOM | 3055 | O   | THR | A | 256 | −7.298  | 3.123  | 61.556 | 1.00 | 61.76 | O |
| ATOM | 3056 | CB  | THR | A | 256 | −8.810  | 0.762  | 59.806 | 1.00 | 65.65 | C |
| ATOM | 3057 | OG1 | THR | A | 256 | −10.077 | 0.227  | 59.397 | 1.00 | 75.23 | O |
| ATOM | 3058 | CG2 | THR | A | 256 | −8.272  | 0.017  | 61.030 | 1.00 | 57.49 | C |
| ATOM | 3059 | N   | PHE | A | 257 | −6.746  | 2.919  | 59.411 | 1.00 | 57.43 | N |
| ATOM | 3060 | CA  | PHE | A | 257 | −5.420  | 3.428  | 59.649 | 1.00 | 60.42 | C |
| ATOM | 3061 | C   | PHE | A | 257 | −5.300  | 4.856  | 60.222 | 1.00 | 68.32 | C |
| ATOM | 3062 | O   | PHE | A | 257 | −4.646  | 5.052  | 61.263 | 1.00 | 67.03 | O |
| ATOM | 3063 | CB  | PHE | A | 257 | −4.624  | 3.425  | 58.356 | 1.00 | 61.65 | C |
| ATOM | 3064 | CG  | PHE | A | 257 | −3.129  | 3.605  | 58.553 | 1.00 | 60.88 | C |
| ATOM | 3065 | CD1 | PHE | A | 257 | −2.457  | 4.625  | 57.895 | 1.00 | 62.58 | C |
| ATOM | 3066 | CD2 | PHE | A | 257 | −2.396  | 2.738  | 59.351 | 1.00 | 65.29 | C |

TABLE 6-continued

HUMAN A2A ADENOSINE STRUCTURE.PDB FILE
(Table 6: discloses SEQ ID NOS 20-27, respectively, in order of appearance.)

| ATOM | 3067 | CE1 | PHE | A | 257 | −1.084 | 4.801 | 58.055 | 1.00 | 64.53 | C |
|---|---|---|---|---|---|---|---|---|---|---|---|
| ATOM | 3068 | CE2 | PHE | A | 257 | −1.026 | 2.907 | 59.516 | 1.00 | 63.61 | C |
| ATOM | 3069 | CZ | PHE | A | 257 | −0.365 | 3.937 | 58.870 | 1.00 | 62.25 | C |
| ATOM | 3070 | N | PHE | A | 258 | −5.989 | 5.811 | 59.600 | 1.00 | 70.62 | N |
| ATOM | 3071 | CA | PHE | A | 258 | −5.833 | 7.229 | 59.892 | 1.00 | 70.28 | C |
| ATOM | 3072 | C | PHE | A | 258 | −6.705 | 7.669 | 61.074 | 1.00 | 71.13 | C |
| ATOM | 3073 | O | PHE | A | 258 | −6.415 | 8.683 | 61.684 | 1.00 | 77.95 | O |
| ATOM | 3074 | CB | PHE | A | 258 | −6.105 | 8.120 | 58.661 | 1.00 | 68.91 | C |
| ATOM | 3075 | CG | PHE | A | 258 | −5.030 | 8.047 | 57.627 | 1.00 | 64.33 | C |
| ATOM | 3076 | CD1 | PHE | A | 258 | −5.313 | 7.633 | 56.338 | 1.00 | 56.40 | C |
| ATOM | 3077 | CD2 | PHE | A | 258 | −3.714 | 8.336 | 57.961 | 1.00 | 55.61 | C |
| ATOM | 3078 | CE1 | PHE | A | 258 | −4.319 | 7.544 | 55.393 | 1.00 | 55.10 | C |
| ATOM | 3079 | CE2 | PHE | A | 258 | −2.711 | 8.245 | 57.013 | 1.00 | 55.98 | C |
| ATOM | 3080 | CZ | PHE | A | 258 | −3.019 | 7.849 | 55.731 | 1.00 | 56.46 | C |
| ATOM | 3081 | N | CYS | A | 259 | −7.757 | 6.922 | 61.389 | 1.00 | 64.15 | N |
| ATOM | 3082 | CA | CYS | A | 259 | −8.599 | 7.266 | 62.537 | 1.00 | 69.23 | C |
| ATOM | 3083 | C | CYS | A | 259 | −8.664 | 6.097 | 63.508 | 1.00 | 73.08 | C |
| ATOM | 3084 | O | CYS | A | 259 | −9.649 | 5.353 | 63.526 | 1.00 | 60.95 | O |
| ATOM | 3085 | CB | CYS | A | 259 | −10.016 | 7.641 | 62.090 | 1.00 | 76.04 | C |
| ATOM | 3086 | SG | CYS | A | 259 | −11.014 | 8.532 | 63.314 | 1.00 | 116.36 | S |
| ATOM | 3087 | N | PRO | A | 260 | −7.610 | 5.929 | 64.318 | 1.00 | 82.55 | N |
| ATOM | 3088 | CA | PRO | A | 260 | −7.395 | 4.767 | 65.187 | 1.00 | 85.53 | C |
| ATOM | 3089 | C | PRO | A | 260 | −8.511 | 4.559 | 66.206 | 1.00 | 88.89 | C |
| ATOM | 3090 | O | PRO | A | 260 | −8.921 | 3.421 | 66.432 | 1.00 | 86.25 | O |
| ATOM | 3091 | CB | PRO | A | 260 | −6.087 | 5.109 | 65.911 | 1.00 | 90.07 | C |
| ATOM | 3092 | CG | PRO | A | 260 | −5.415 | 6.114 | 65.041 | 1.00 | 92.31 | C |
| ATOM | 3093 | CD | PRO | A | 260 | −6.520 | 6.910 | 64.429 | 1.00 | 88.02 | C |
| ATOM | 3094 | N | ASP | A | 261 | −8.991 | 5.641 | 66.810 | 1.00 | 96.10 | N |
| ATOM | 3095 | CA | ASP | A | 261 | −9.975 | 5.531 | 67.883 | 1.00 | 105.20 | C |
| ATOM | 3096 | C | ASP | A | 261 | −11.417 | 5.743 | 67.423 | 1.00 | 108.40 | C |
| ATOM | 3097 | O | ASP | A | 261 | −12.277 | 6.134 | 68.212 | 1.00 | 110.57 | O |
| ATOM | 3098 | CB | ASP | A | 261 | −9.634 | 6.484 | 69.034 | 1.00 | 112.67 | C |
| ATOM | 3099 | CG | ASP | A | 261 | −9.600 | 7.935 | 68.600 | 1.00 | 119.70 | C |
| ATOM | 3100 | OD1 | ASP | A | 261 | −10.062 | 8.237 | 67.479 | 1.00 | 122.59 | O |
| ATOM | 3101 | OD2 | ASP | A | 261 | −9.112 | 8.776 | 69.384 | 1.00 | 120.66 | O |
| ATOM | 3102 | N | CYS | A | 262 | −11.676 | 5.488 | 66.145 | 1.00 | 106.67 | N |
| ATOM | 3103 | CA | CYS | A | 262 | −13.041 | 5.484 | 65.634 | 1.00 | 98.77 | C |
| ATOM | 3104 | C | CYS | A | 262 | −13.572 | 4.058 | 65.659 | 1.00 | 98.45 | C |
| ATOM | 3105 | O | CYS | A | 262 | −12.797 | 3.103 | 65.648 | 1.00 | 96.66 | O |
| ATOM | 3106 | CB | CYS | A | 262 | −13.092 | 6.036 | 64.211 | 1.00 | 93.04 | C |
| ATOM | 3107 | SG | CYS | A | 262 | −12.743 | 7.799 | 64.087 | 1.00 | 150.04 | S |
| ATOM | 3108 | N | SER | A | 263 | −14.892 | 3.914 | 65.699 | 1.00 | 100.70 | N |
| ATOM | 3109 | CA | SER | A | 263 | −15.500 | 2.589 | 65.689 | 1.00 | 99.62 | C |
| ATOM | 3110 | C | SER | A | 263 | −15.206 | 1.894 | 64.364 | 1.00 | 88.02 | C |
| ATOM | 3111 | O | SER | A | 263 | −15.559 | 2.398 | 63.298 | 1.00 | 83.87 | O |
| ATOM | 3112 | CB | SER | A | 263 | −17.010 | 2.676 | 65.929 | 1.00 | 98.59 | C |
| ATOM | 3113 | OG | SER | A | 263 | −17.646 | 3.451 | 64.928 | 1.00 | 101.70 | O |
| ATOM | 3114 | N | HIS | A | 264 | −14.550 | 0.741 | 64.439 | 1.00 | 80.43 | N |
| ATOM | 3115 | CA | HIS | A | 264 | −14.152 | 0.005 | 63.245 | 1.00 | 73.18 | C |
| ATOM | 3116 | C | HIS | A | 264 | −15.355 | −0.349 | 62.375 | 1.00 | 71.92 | C |
| ATOM | 3117 | O | HIS | A | 264 | −16.475 | −0.476 | 62.868 | 1.00 | 74.56 | O |
| ATOM | 3118 | CB | HIS | A | 264 | −13.393 | −1.268 | 63.630 | 1.00 | 69.10 | C |
| ATOM | 3119 | CG | HIS | A | 264 | −12.692 | −1.924 | 62.481 | 1.00 | 66.84 | C |
| ATOM | 3120 | ND1 | HIS | A | 264 | −13.353 | −2.688 | 61.543 | 1.00 | 57.95 | N |
| ATOM | 3121 | CD2 | HIS | A | 264 | −11.387 | −1.931 | 62.120 | 1.00 | 63.05 | C |
| ATOM | 3122 | CE1 | HIS | A | 264 | −12.486 | −3.134 | 60.651 | 1.00 | 54.47 | C |
| ATOM | 3123 | NE2 | HIS | A | 264 | −11.286 | −2.690 | 60.979 | 1.00 | 62.11 | N |
| ATOM | 3124 | N | ALA | A | 265 | −15.114 | −0.502 | 61.077 | 1.00 | 72.64 | N |
| ATOM | 3125 | CA | ALA | A | 265 | −16.159 | −0.912 | 60.149 | 1.00 | 66.14 | C |
| ATOM | 3126 | C | ALA | A | 265 | −16.736 | −2.260 | 60.568 | 1.00 | 63.94 | C |
| ATOM | 3127 | O | ALA | A | 265 | −15.990 | −3.186 | 60.889 | 1.00 | 59.55 | O |
| ATOM | 3128 | CB | ALA | A | 265 | −15.610 | −0.984 | 58.735 | 1.00 | 57.93 | C |
| ATOM | 3129 | N | PRO | A | 266 | −18.071 | −2.373 | 60.568 | 1.00 | 60.88 | N |
| ATOM | 3130 | CA | PRO | A | 266 | −18.739 | −3.617 | 60.964 | 1.00 | 61.26 | C |
| ATOM | 3131 | C | PRO | A | 266 | −18.298 | −4.791 | 60.095 | 1.00 | 68.46 | C |
| ATOM | 3132 | O | PRO | A | 266 | −17.888 | −4.588 | 58.951 | 1.00 | 66.26 | O |
| ATOM | 3133 | CB | PRO | A | 266 | −20.226 | −3.314 | 60.740 | 1.00 | 63.31 | C |
| ATOM | 3134 | CG | PRO | A | 266 | −20.270 | −2.098 | 59.875 | 1.00 | 63.38 | C |
| ATOM | 3135 | CD | PRO | A | 266 | −19.020 | −1.331 | 60.141 | 1.00 | 62.42 | C |
| ATOM | 3136 | N | LEU | A | 267 | −18.386 | −6.002 | 60.637 | 1.00 | 73.04 | N |
| ATOM | 3137 | CA | LEU | A | 267 | −17.934 | −7.196 | 59.931 | 1.00 | 68.76 | C |
| ATOM | 3138 | C | LEU | A | 267 | −18.657 | −7.409 | 58.606 | 1.00 | 73.92 | C |
| ATOM | 3139 | O | LEU | A | 267 | −18.049 | −7.843 | 57.628 | 1.00 | 76.91 | O |
| ATOM | 3140 | CB | LEU | A | 267 | −18.089 | −8.438 | 60.811 | 1.00 | 74.70 | C |
| ATOM | 3141 | CG | LEU | A | 267 | −17.278 | −8.465 | 62.105 | 1.00 | 87.75 | C |
| ATOM | 3142 | CD1 | LEU | A | 267 | −17.136 | −9.895 | 62.602 | 1.00 | 93.88 | C |
| ATOM | 3143 | CD2 | LEU | A | 267 | −15.914 | −7.840 | 61.890 | 1.00 | 88.32 | C |

TABLE 6-continued

HUMAN A2A ADENOSINE STRUCTURE.PDB FILE
(Table 6: discloses SEQ ID NOS 20-27, respectively, in order of appearance.)

| ATOM | 3144 | N | TRP | A | 268 | −19.953 | −7.112 | 58.574 | 1.00 | 75.29 | N |
|---|---|---|---|---|---|---|---|---|---|---|---|
| ATOM | 3145 | CA | TRP | A | 268 | −20.738 | −7.305 | 57.358 | 1.00 | 72.96 | C |
| ATOM | 3146 | C | TRP | A | 268 | −20.199 | −6.449 | 56.216 | 1.00 | 68.67 | C |
| ATOM | 3147 | O | TRP | A | 268 | −20.115 | −6.904 | 55.076 | 1.00 | 70.33 | O |
| ATOM | 3148 | CB | TRP | A | 268 | −22.226 | −7.020 | 57.600 | 1.00 | 71.74 | C |
| ATOM | 3149 | CG | TRP | A | 268 | −22.551 | −5.571 | 57.818 | 1.00 | 72.86 | C |
| ATOM | 3150 | CD1 | TRP | A | 268 | −22.734 | −4.943 | 59.016 | 1.00 | 72.03 | C |
| ATOM | 3151 | CD2 | TRP | A | 268 | −22.738 | −4.571 | 56.809 | 1.00 | 69.70 | C |
| ATOM | 3152 | NE1 | TRP | A | 268 | −23.018 | −3.614 | 58.816 | 1.00 | 72.90 | N |
| ATOM | 3153 | CE2 | TRP | A | 268 | −23.026 | −3.360 | 57.470 | 1.00 | 68.79 | C |
| ATOM | 3154 | CE3 | TRP | A | 268 | −22.686 | −4.581 | 55.410 | 1.00 | 68.51 | C |
| ATOM | 3155 | CZ2 | TRP | A | 268 | −23.262 | −2.171 | 56.781 | 1.00 | 63.90 | C |
| ATOM | 3156 | CZ3 | TRP | A | 268 | −22.919 | −3.399 | 54.728 | 1.00 | 67.40 | C |
| ATOM | 3157 | CH2 | TRP | A | 268 | −23.205 | −2.211 | 55.414 | 1.00 | 68.89 | C |
| ATOM | 3158 | N | LEU | A | 269 | −19.827 | −5.211 | 56.528 | 1.00 | 61.76 | N |
| ATOM | 3159 | CA | LEU | A | 269 | −19.253 | −4.318 | 55.529 | 1.00 | 66.77 | C |
| ATOM | 3160 | C | LEU | A | 269 | −17.882 | −4.817 | 55.097 | 1.00 | 70.22 | C |
| ATOM | 3161 | O | LEU | A | 269 | −17.525 | −4.755 | 53.920 | 1.00 | 68.84 | O |
| ATOM | 3162 | CB | LEU | A | 269 | −19.139 | −2.893 | 56.075 | 1.00 | 60.72 | C |
| ATOM | 3163 | CG | LEU | A | 269 | −18.371 | −1.905 | 55.191 | 1.00 | 60.57 | C |
| ATOM | 3164 | CD1 | LEU | A | 269 | −18.995 | −1.813 | 53.805 | 1.00 | 59.88 | C |
| ATOM | 3165 | CD2 | LEU | A | 269 | −18.301 | −0.533 | 55.842 | 1.00 | 57.44 | C |
| ATOM | 3166 | N | MET | A | 270 | −17.118 | −5.319 | 56.060 | 1.00 | 69.40 | N |
| ATOM | 3167 | CA | MET | A | 270 | −15.766 | −5.786 | 55.795 | 1.00 | 66.60 | C |
| ATOM | 3168 | C | MET | A | 270 | −15.766 | −6.934 | 54.790 | 1.00 | 64.78 | C |
| ATOM | 3169 | O | MET | A | 270 | −15.067 | −6.886 | 53.778 | 1.00 | 70.55 | O |
| ATOM | 3170 | CB | MET | A | 270 | −15.090 | −6.221 | 57.096 | 1.00 | 68.62 | C |
| ATOM | 3171 | CG | MET | A | 270 | −13.621 | −5.860 | 57.165 | 1.00 | 75.47 | C |
| ATOM | 3172 | SD | MET | A | 270 | −13.379 | −4.076 | 57.266 | 1.00 | 69.50 | S |
| ATOM | 3173 | CE | MET | A | 270 | −11.601 | −3.970 | 57.080 | 1.00 | 77.08 | C |
| ATOM | 3174 | N | TYR | A | 271 | −16.559 | −7.964 | 55.069 | 1.00 | 58.09 | N |
| ATOM | 3175 | CA | TYR | A | 271 | −16.615 | −9.132 | 54.197 | 1.00 | 63.50 | C |
| ATOM | 3176 | C | TYR | A | 271 | −17.362 | −8.845 | 52.899 | 1.00 | 61.99 | C |
| ATOM | 3177 | O | TYR | A | 271 | −17.279 | −9.615 | 51.943 | 1.00 | 66.32 | O |
| ATOM | 3178 | CB | TYR | A | 271 | −17.221 | −10.332 | 54.931 | 1.00 | 65.57 | C |
| ATOM | 3179 | CG | TYR | A | 271 | −16.272 | −10.942 | 55.937 | 1.00 | 72.21 | C |
| ATOM | 3180 | CD1 | TYR | A | 271 | −15.270 | −11.813 | 55.531 | 1.00 | 76.07 | C |
| ATOM | 3181 | CD2 | TYR | A | 271 | −16.364 | −10.632 | 57.287 | 1.00 | 74.68 | C |
| ATOM | 3182 | CE1 | TYR | A | 271 | −14.392 | −12.366 | 56.441 | 1.00 | 79.02 | C |
| ATOM | 3183 | CE2 | TYR | A | 271 | −15.489 | −11.181 | 58.206 | 1.00 | 80.17 | C |
| ATOM | 3184 | CZ | TYR | A | 271 | −14.505 | −12.048 | 57.777 | 1.00 | 82.39 | C |
| ATOM | 3185 | OH | TYR | A | 271 | −13.631 | −12.599 | 58.686 | 1.00 | 86.30 | O |
| ATOM | 3186 | N | LEU | A | 272 | −18.080 | −7.729 | 52.866 | 1.00 | 58.87 | N |
| ATOM | 3187 | CA | LEU | A | 272 | −18.768 | −7.311 | 51.652 | 1.00 | 61.48 | C |
| ATOM | 3188 | C | LEU | A | 272 | −17.763 | −6.709 | 50.676 | 1.00 | 63.21 | C |
| ATOM | 3189 | O | LEU | A | 272 | −17.865 | −6.901 | 49.465 | 1.00 | 63.88 | O |
| ATOM | 3190 | CB | LEU | A | 272 | −19.875 | −6.308 | 51.980 | 1.00 | 63.94 | C |
| ATOM | 3191 | CG | LEU | A | 272 | −20.917 | −6.032 | 50.893 | 1.00 | 71.79 | C |
| ATOM | 3192 | CD1 | LEU | A | 272 | −22.254 | −5.654 | 51.514 | 1.00 | 78.35 | C |
| ATOM | 3193 | CD2 | LEU | A | 272 | −20.438 | −4.952 | 49.933 | 1.00 | 78.54 | C |
| ATOM | 3194 | N | ALA | A | 273 | −16.787 | −5.985 | 51.214 | 1.00 | 65.29 | N |
| ATOM | 3195 | CA | ALA | A | 273 | −15.734 | −5.393 | 50.399 | 1.00 | 65.95 | C |
| ATOM | 3196 | C | ALA | A | 273 | −14.786 | −6.473 | 49.892 | 1.00 | 62.33 | C |
| ATOM | 3197 | O | ALA | A | 273 | −14.212 | −6.356 | 48.809 | 1.00 | 58.46 | O |
| ATOM | 3198 | CB | ALA | A | 273 | −14.974 | −4.345 | 51.194 | 1.00 | 69.13 | C |
| ATOM | 3199 | N | ILE | A | 274 | −14.629 | −7.527 | 50.687 | 1.00 | 70.67 | N |
| ATOM | 3200 | CA | ILE | A | 274 | −13.780 | −8.654 | 50.319 | 1.00 | 66.36 | C |
| ATOM | 3201 | C | ILE | A | 274 | −14.413 | −9.482 | 49.202 | 1.00 | 60.04 | C |
| ATOM | 3202 | O | ILE | A | 274 | −13.742 | −9.855 | 48.241 | 1.00 | 57.42 | O |
| ATOM | 3203 | CB | ILE | A | 274 | −13.480 | −9.550 | 51.535 | 1.00 | 63.35 | C |
| ATOM | 3204 | CG1 | ILE | A | 274 | −12.554 | −8.819 | 52.511 | 1.00 | 54.86 | C |
| ATOM | 3205 | CG2 | ILE | A | 274 | −12.860 | −10.864 | 51.091 | 1.00 | 61.51 | C |
| ATOM | 3206 | CD1 | ILE | A | 274 | −12.396 | −9.515 | 53.846 | 1.00 | 52.45 | C |
| ATOM | 3207 | N | VAL | A | 275 | −15.707 | −9.761 | 49.329 | 1.00 | 51.59 | N |
| ATOM | 3208 | CA | VAL | A | 275 | −16.438 | −10.478 | 48.289 | 1.00 | 55.45 | C |
| ATOM | 3209 | C | VAL | A | 275 | −16.405 | −9.700 | 46.977 | 1.00 | 60.96 | C |
| ATOM | 3210 | O | VAL | A | 275 | −16.211 | −10.274 | 45.903 | 1.00 | 63.73 | O |
| ATOM | 3211 | CB | VAL | A | 275 | −17.906 | −10.723 | 48.693 | 1.00 | 58.12 | C |
| ATOM | 3212 | CG1 | VAL | A | 275 | −18.697 | −11.279 | 47.517 | 1.00 | 56.24 | C |
| ATOM | 3213 | CG2 | VAL | A | 275 | −17.979 | −11.666 | 49.883 | 1.00 | 52.83 | C |
| ATOM | 3214 | N | LEU | A | 276 | −16.591 | −8.389 | 47.076 | 1.00 | 62.28 | N |
| ATOM | 3215 | CA | LEU | A | 276 | −16.586 | −7.512 | 45.909 | 1.00 | 55.72 | C |
| ATOM | 3216 | C | LEU | A | 276 | −15.272 | −7.592 | 45.134 | 1.00 | 56.54 | C |
| ATOM | 3217 | O | LEU | A | 276 | −15.271 | −7.709 | 43.907 | 1.00 | 53.88 | O |
| ATOM | 3218 | CB | LEU | A | 276 | −16.862 | −6.068 | 46.338 | 1.00 | 60.34 | C |
| ATOM | 3219 | CG | LEU | A | 276 | −16.746 | −4.977 | 45.273 | 1.00 | 58.30 | C |
| ATOM | 3220 | CD1 | LEU | A | 276 | −17.644 | −5.280 | 44.082 | 1.00 | 51.32 | C |

TABLE 6-continued

HUMAN A2A ADENOSINE STRUCTURE.PDB FILE
(Table 6: discloses SEQ ID NOS 20-27, respectively, in order of appearance.)

| ATOM | 3221 | CD2 | LEU | A | 276 | −17.084 | −3.622 | 45.874 | 1.00 | 51.37 | C |
|---|---|---|---|---|---|---|---|---|---|---|---|
| ATOM | 3222 | N | SER | A | 277 | −14.154 | −7.530 | 45.852 | 1.00 | 54.17 | N |
| ATOM | 3223 | CA | SER | A | 277 | −12.841 | −7.559 | 45.218 | 1.00 | 55.56 | C |
| ATOM | 3224 | C | SER | A | 277 | −12.603 | −8.874 | 44.481 | 1.00 | 59.78 | C |
| ATOM | 3225 | O | SER | A | 277 | −11.899 | −8.910 | 43.471 | 1.00 | 64.00 | O |
| ATOM | 3226 | CB | SER | A | 277 | −11.735 | −7.324 | 46.250 | 1.00 | 52.24 | C |
| ATOM | 3227 | OG | SER | A | 277 | −11.650 | −8.403 | 47.164 | 1.00 | 53.55 | O |
| ATOM | 3228 | N | HIS | A | 278 | −13.194 | −9.952 | 44.989 | 1.00 | 59.02 | N |
| ATOM | 3229 | CA | HIS | A | 278 | −13.048 | −11.266 | 44.370 | 1.00 | 61.28 | C |
| ATOM | 3230 | C | HIS | A | 278 | −13.870 | −11.380 | 43.093 | 1.00 | 58.63 | C |
| ATOM | 3231 | O | HIS | A | 278 | −13.520 | −12.134 | 42.185 | 1.00 | 51.04 | O |
| ATOM | 3232 | CB | HIS | A | 278 | −13.449 | −12.376 | 45.344 | 1.00 | 65.43 | C |
| ATOM | 3233 | CG | HIS | A | 278 | −12.540 | −12.501 | 46.525 | 1.00 | 67.86 | C |
| ATOM | 3234 | ND1 | HIS | A | 278 | −12.995 | −12.832 | 47.782 | 1.00 | 67.54 | N |
| ATOM | 3235 | CD2 | HIS | A | 278 | −11.202 | −12.329 | 46.641 | 1.00 | 74.86 | C |
| ATOM | 3236 | CE1 | HIS | A | 278 | −11.974 | −12.867 | 48.621 | 1.00 | 75.63 | C |
| ATOM | 3237 | NE2 | HIS | A | 278 | −10.876 | −12.564 | 47.954 | 1.00 | 77.19 | N |
| ATOM | 3238 | N | THR | A | 279 | −14.968 | −10.633 | 43.031 | 1.00 | 59.28 | N |
| ATOM | 3239 | CA | THR | A | 279 | −15.844 | −10.652 | 41.867 | 1.00 | 63.73 | C |
| ATOM | 3240 | C | THR | A | 279 | −15.120 | −10.105 | 40.640 | 1.00 | 61.31 | C |
| ATOM | 3241 | O | THR | A | 279 | −15.466 | −10.429 | 39.502 | 1.00 | 57.13 | O |
| ATOM | 3242 | CB | THR | A | 279 | −17.134 | −9.843 | 42.122 | 1.00 | 72.10 | C |
| ATOM | 3243 | OG1 | THR | A | 279 | −17.865 | −10.435 | 43.204 | 1.00 | 63.41 | O |
| ATOM | 3244 | CG2 | THR | A | 279 | −18.012 | −9.825 | 40.881 | 1.00 | 80.19 | C |
| ATOM | 3245 | N | ASN | A | 280 | −14.103 | −9.284 | 40.882 | 1.00 | 56.25 | N |
| ATOM | 3246 | CA | ASN | A | 280 | −13.321 | −8.689 | 39.805 | 1.00 | 58.40 | C |
| ATOM | 3247 | C | ASN | A | 280 | −12.632 | −9.731 | 38.929 | 1.00 | 63.48 | C |
| ATOM | 3248 | O | ASN | A | 280 | −12.240 | −9.443 | 37.798 | 1.00 | 70.65 | O |
| ATOM | 3249 | CB | ASN | A | 280 | −12.281 | −7.722 | 40.374 | 1.00 | 55.54 | C |
| ATOM | 3250 | CG | ASN | A | 280 | −11.432 | −7.081 | 39.294 | 1.00 | 61.10 | C |
| ATOM | 3251 | OD1 | ASN | A | 280 | −10.209 | −7.212 | 39.291 | 1.00 | 68.02 | O |
| ATOM | 3252 | ND2 | ASN | A | 280 | −12.081 | −6.389 | 38.364 | 1.00 | 56.63 | N |
| ATOM | 3253 | N | SER | A | 281 | −12.484 | −10.942 | 39.456 | 1.00 | 60.18 | N |
| ATOM | 3254 | CA | SER | A | 281 | −11.821 | −12.015 | 38.725 | 1.00 | 59.56 | C |
| ATOM | 3255 | C | SER | A | 281 | −12.802 | −12.799 | 37.858 | 1.00 | 61.03 | C |
| ATOM | 3256 | O | SER | A | 281 | −12.443 | −13.813 | 37.259 | 1.00 | 64.30 | O |
| ATOM | 3257 | CB | SER | A | 281 | −11.101 | −12.956 | 39.691 | 1.00 | 59.85 | C |
| ATOM | 3258 | OG | SER | A | 281 | −10.035 | −12.289 | 40.346 | 1.00 | 59.65 | O |
| ATOM | 3259 | N | VAL | A | 282 | −14.038 | −12.318 | 37.788 | 1.00 | 58.12 | N |
| ATOM | 3260 | CA | VAL | A | 282 | −15.079 | −12.993 | 37.025 | 1.00 | 64.59 | C |
| ATOM | 3261 | C | VAL | A | 282 | −15.547 | −12.167 | 35.827 | 1.00 | 60.34 | C |
| ATOM | 3262 | O | VAL | A | 282 | −15.970 | −12.719 | 34.812 | 1.00 | 60.47 | O |
| ATOM | 3263 | CB | VAL | A | 282 | −16.301 | −13.303 | 37.915 | 1.00 | 68.02 | C |
| ATOM | 3264 | CG1 | VAL | A | 282 | −17.359 | −14.060 | 37.126 | 1.00 | 74.18 | C |
| ATOM | 3265 | CG2 | VAL | A | 282 | −15.875 | −14.093 | 39.142 | 1.00 | 65.29 | C |
| ATOM | 3266 | N | VAL | A | 283 | −15.455 | −10.846 | 35.949 | 1.00 | 56.58 | N |
| ATOM | 3267 | CA | VAL | A | 283 | −16.075 | −9.930 | 34.990 | 1.00 | 55.89 | C |
| ATOM | 3268 | C | VAL | A | 283 | −15.399 | −9.853 | 33.619 | 1.00 | 59.63 | C |
| ATOM | 3269 | O | VAL | A | 283 | −16.071 | −9.657 | 32.606 | 1.00 | 58.80 | O |
| ATOM | 3270 | CB | VAL | A | 283 | −16.187 | −8.504 | 35.574 | 1.00 | 51.46 | C |
| ATOM | 3271 | CG1 | VAL | A | 283 | −17.233 | −8.466 | 36.678 | 1.00 | 46.59 | C |
| ATOM | 3272 | CG2 | VAL | A | 283 | −14.839 | −8.034 | 36.097 | 1.00 | 46.82 | C |
| ATOM | 3273 | N | ASN | A | 284 | −14.078 | −10.003 | 33.587 | 1.00 | 59.43 | N |
| ATOM | 3274 | CA | ASN | A | 284 | −13.316 | −9.827 | 32.350 | 1.00 | 58.91 | C |
| ATOM | 3275 | C | ASN | A | 284 | −13.806 | −10.646 | 31.149 | 1.00 | 59.42 | C |
| ATOM | 3276 | O | ASN | A | 284 | −14.026 | −10.091 | 30.072 | 1.00 | 56.86 | O |
| ATOM | 3277 | CB | ASN | A | 284 | −11.820 | −10.062 | 32.587 | 1.00 | 64.06 | C |
| ATOM | 3278 | CG | ASN | A | 284 | −11.172 | −8.939 | 33.371 | 1.00 | 59.03 | C |
| ATOM | 3279 | OD1 | ASN | A | 284 | −11.850 | −8.030 | 33.851 | 1.00 | 60.87 | O |
| ATOM | 3280 | ND2 | ASN | A | 284 | −9.851 | −8.994 | 33.504 | 1.00 | 52.55 | N |
| ATOM | 3281 | N | PRO | A | 285 | −13.970 | −11.968 | 31.324 | 1.00 | 58.83 | N |
| ATOM | 3282 | CA | PRO | A | 285 | −14.420 | −12.801 | 30.202 | 1.00 | 59.51 | C |
| ATOM | 3283 | C | PRO | A | 285 | −15.742 | −12.309 | 29.612 | 1.00 | 64.98 | C |
| ATOM | 3284 | O | PRO | A | 285 | −15.917 | −12.343 | 28.393 | 1.00 | 69.54 | O |
| ATOM | 3285 | CB | PRO | A | 285 | −14.605 | −14.180 | 30.843 | 1.00 | 57.41 | C |
| ATOM | 3286 | CG | PRO | A | 285 | −13.697 | −14.173 | 32.023 | 1.00 | 56.69 | C |
| ATOM | 3287 | CD | PRO | A | 285 | −13.722 | −12.764 | 32.539 | 1.00 | 55.55 | C |
| ATOM | 3288 | N | PHE | A | 286 | −16.654 | −11.860 | 30.470 | 1.00 | 62.03 | N |
| ATOM | 3289 | CA | PHE | A | 286 | −17.950 | −11.357 | 30.023 | 1.00 | 66.17 | C |
| ATOM | 3290 | C | PHE | A | 286 | −17.789 | −10.122 | 29.145 | 1.00 | 62.53 | C |
| ATOM | 3291 | O | PHE | A | 286 | −18.522 | −9.937 | 28.174 | 1.00 | 64.75 | O |
| ATOM | 3292 | CB | PHE | A | 286 | −18.847 | −11.034 | 31.221 | 1.00 | 65.80 | C |
| ATOM | 3293 | CG | PHE | A | 286 | −19.409 | −12.249 | 31.906 | 1.00 | 66.00 | C |
| ATOM | 3294 | CD1 | PHE | A | 286 | −18.751 | −12.822 | 32.982 | 1.00 | 63.52 | C |
| ATOM | 3295 | CD2 | PHE | A | 286 | −20.595 | −12.817 | 31.473 | 1.00 | 67.24 | C |
| ATOM | 3296 | CE1 | PHE | A | 286 | −19.267 | −13.939 | 33.613 | 1.00 | 68.78 | C |
| ATOM | 3297 | CE2 | PHE | A | 286 | −21.115 | −13.935 | 32.101 | 1.00 | 65.33 | C |

TABLE 6-continued

HUMAN A2A ADENOSINE STRUCTURE.PDB FILE
(Table 6: discloses SEQ ID NOS 20-27, respectively, in order of appearance.)

| ATOM | 3298 | CZ | PHE | A | 286 | −20.451 | −14.496 | 33.171 | 1.00 | 69.42 | C |
|---|---|---|---|---|---|---|---|---|---|---|---|
| ATOM | 3299 | N | ILE | A | 287 | −16.823 | −9.280 | 29.495 | 1.00 | 59.29 | N |
| ATOM | 3300 | CA | ILE | A | 287 | −16.561 | −8.055 | 28.750 | 1.00 | 60.52 | C |
| ATOM | 3301 | C | ILE | A | 287 | −16.008 | −8.349 | 27.358 | 1.00 | 66.84 | C |
| ATOM | 3302 | O | ILE | A | 287 | −16.424 | −7.735 | 26.375 | 1.00 | 74.69 | O |
| ATOM | 3303 | CB | ILE | A | 287 | −15.589 | −7.145 | 29.515 | 1.00 | 64.57 | C |
| ATOM | 3304 | CG1 | ILE | A | 287 | −16.139 | −6.861 | 30.913 | 1.00 | 63.24 | C |
| ATOM | 3305 | CG2 | ILE | A | 287 | −15.358 | −5.850 | 28.750 | 1.00 | 64.66 | C |
| ATOM | 3306 | CD1 | ILE | A | 287 | −15.083 | −6.504 | 31.922 | 1.00 | 70.55 | C |
| ATOM | 3307 | N | TYR | A | 288 | −15.072 | −9.289 | 27.275 | 1.00 | 69.29 | N |
| ATOM | 3308 | CA | TYR | A | 288 | −14.516 | −9.687 | 25.988 | 1.00 | 65.51 | C |
| ATOM | 3309 | C | TYR | A | 288 | −15.621 | −10.195 | 25.067 | 1.00 | 68.22 | C |
| ATOM | 3310 | O | TYR | A | 288 | −15.616 | −9.926 | 23.866 | 1.00 | 64.34 | O |
| ATOM | 3311 | CB | TYR | A | 288 | −13.449 | −10.771 | 26.159 | 1.00 | 54.27 | C |
| ATOM | 3312 | CG | TYR | A | 288 | −12.305 | −10.390 | 27.072 | 1.00 | 57.57 | C |
| ATOM | 3313 | CD1 | TYR | A | 288 | −11.762 | −9.115 | 27.042 | 1.00 | 65.41 | C |
| ATOM | 3314 | CD2 | TYR | A | 288 | −11.756 | −11.315 | 27.950 | 1.00 | 61.99 | C |
| ATOM | 3315 | CE1 | TYR | A | 288 | −10.713 | −8.765 | 27.872 | 1.00 | 70.11 | C |
| ATOM | 3316 | CE2 | TYR | A | 288 | −10.706 | −10.976 | 28.782 | 1.00 | 61.62 | C |
| ATOM | 3317 | CZ | TYR | A | 288 | −10.188 | −9.700 | 28.739 | 1.00 | 68.27 | C |
| ATOM | 3318 | OH | TYR | A | 288 | −9.142 | −9.354 | 29.565 | 1.00 | 65.39 | O |
| ATOM | 3319 | N | ALA | A | 289 | −16.567 | −10.931 | 25.641 | 1.00 | 71.89 | N |
| ATOM | 3320 | CA | ALA | A | 289 | −17.669 | −11.501 | 24.875 | 1.00 | 65.85 | C |
| ATOM | 3321 | C | ALA | A | 289 | −18.582 | −10.419 | 24.304 | 1.00 | 69.72 | C |
| ATOM | 3322 | O | ALA | A | 289 | −18.965 | −10.472 | 23.134 | 1.00 | 66.15 | O |
| ATOM | 3323 | CB | ALA | A | 289 | −18.465 | −12.472 | 25.735 | 1.00 | 49.46 | C |
| ATOM | 3324 | N | TYR | A | 290 | −18.924 | −9.436 | 25.132 | 1.00 | 65.07 | N |
| ATOM | 3325 | CA | TYR | A | 290 | −19.839 | −8.374 | 24.725 | 1.00 | 76.34 | C |
| ATOM | 3326 | C | TYR | A | 290 | −19.234 | −7.391 | 23.725 | 1.00 | 75.32 | C |
| ATOM | 3327 | O | TYR | A | 290 | −19.890 | −7.001 | 22.759 | 1.00 | 74.69 | O |
| ATOM | 3328 | CB | TYR | A | 290 | −20.354 | −7.604 | 25.944 | 1.00 | 85.34 | C |
| ATOM | 3329 | CG | TYR | A | 290 | −21.489 | −8.283 | 26.676 | 1.00 | 100.57 | C |
| ATOM | 3330 | CD1 | TYR | A | 290 | −22.657 | −8.634 | 26.012 | 1.00 | 105.71 | C |
| ATOM | 3331 | CD2 | TYR | A | 290 | −21.401 | −8.556 | 28.034 | 1.00 | 110.70 | C |
| ATOM | 3332 | CE1 | TYR | A | 290 | −23.700 | −9.250 | 26.678 | 1.00 | 109.30 | C |
| ATOM | 3333 | CE2 | TYR | A | 290 | −22.439 | −9.172 | 28.709 | 1.00 | 113.10 | C |
| ATOM | 3334 | CZ | TYR | A | 290 | −23.586 | −9.516 | 28.025 | 1.00 | 110.15 | C |
| ATOM | 3335 | OH | TYR | A | 290 | −24.622 | −10.128 | 28.692 | 1.00 | 108.86 | O |
| ATOM | 3336 | N | ARG | A | 291 | −17.987 | −6.990 | 23.957 | 1.00 | 70.17 | N |
| ATOM | 3337 | CA | ARG | A | 291 | −17.407 | −5.882 | 23.201 | 1.00 | 70.63 | C |
| ATOM | 3338 | C | ARG | A | 291 | −16.383 | −6.289 | 22.145 | 1.00 | 67.32 | C |
| ATOM | 3339 | O | ARG | A | 291 | −16.150 | −5.549 | 21.190 | 1.00 | 71.30 | O |
| ATOM | 3340 | CB | ARG | A | 291 | −16.798 | −4.847 | 24.151 | 1.00 | 75.59 | C |
| ATOM | 3341 | CG | ARG | A | 291 | −17.736 | −4.406 | 25.261 | 1.00 | 76.34 | C |
| ATOM | 3342 | CD | ARG | A | 291 | −17.363 | −3.033 | 25.793 | 1.00 | 82.64 | C |
| ATOM | 3343 | NE | ARG | A | 291 | −17.908 | −1.957 | 24.969 | 1.00 | 89.34 | N |
| ATOM | 3344 | CZ | ARG | A | 291 | −17.265 | −1.390 | 23.954 | 1.00 | 94.49 | C |
| ATOM | 3345 | NH1 | ARG | A | 291 | −16.046 | −1.792 | 23.629 | 1.00 | 90.92 | N |
| ATOM | 3346 | NH2 | ARG | A | 291 | −17.842 | −0.417 | 23.262 | 1.00 | 100.91 | N |
| ATOM | 3347 | N | ILE | A | 292 | −15.769 | −7.455 | 22.311 | 1.00 | 67.04 | N |
| ATOM | 3348 | CA | ILE | A | 292 | −14.772 | −7.912 | 21.345 | 1.00 | 63.61 | C |
| ATOM | 3349 | C | ILE | A | 292 | −15.295 | −9.067 | 20.496 | 1.00 | 71.59 | C |
| ATOM | 3350 | O | ILE | A | 292 | −15.572 | −10.154 | 20.999 | 1.00 | 75.25 | O |
| ATOM | 3351 | CB | ILE | A | 292 | −13.446 | −8.301 | 22.020 | 1.00 | 58.94 | C |
| ATOM | 3352 | CG1 | ILE | A | 292 | −12.979 | −7.180 | 22.950 | 1.00 | 59.71 | C |
| ATOM | 3353 | CG2 | ILE | A | 292 | −12.387 | −8.599 | 20.969 | 1.00 | 47.29 | C |
| ATOM | 3354 | CD1 | ILE | A | 292 | −11.564 | −7.352 | 23.455 | 1.00 | 63.50 | C |
| ATOM | 3355 | N | ARG | A | 293 | −15.416 | −8.811 | 19.198 | 1.00 | 80.32 | N |
| ATOM | 3356 | CA | ARG | A | 293 | −16.036 | −9.744 | 18.263 | 1.00 | 81.56 | C |
| ATOM | 3357 | C | ARG | A | 293 | −15.274 | −11.063 | 18.111 | 1.00 | 73.75 | C |
| ATOM | 3358 | O | ARG | A | 293 | −15.871 | −12.140 | 18.167 | 1.00 | 64.51 | O |
| ATOM | 3359 | CB | ARG | A | 293 | −16.206 | −9.066 | 16.901 | 1.00 | 86.33 | C |
| ATOM | 3360 | CG | ARG | A | 293 | −16.739 | −9.965 | 15.804 | 1.00 | 93.96 | C |
| ATOM | 3361 | CD | ARG | A | 293 | −16.782 | −9.220 | 14.480 | 1.00 | 104.85 | C |
| ATOM | 3362 | NE | ARG | A | 293 | −16.744 | −10.130 | 13.339 | 1.00 | 115.28 | N |
| ATOM | 3363 | CZ | ARG | A | 293 | −15.636 | −10.707 | 12.885 | 1.00 | 117.34 | C |
| ATOM | 3364 | NH1 | ARG | A | 293 | −14.474 | −10.474 | 13.480 | 1.00 | 115.03 | N |
| ATOM | 3365 | NH2 | ARG | A | 293 | −15.688 | −11.521 | 11.839 | 1.00 | 117.81 | N |
| ATOM | 3366 | N | GLU | A | 294 | −13.961 | −10.979 | 17.920 | 1.00 | 71.43 | N |
| ATOM | 3367 | CA | GLU | A | 294 | −13.154 | −12.171 | 17.670 | 1.00 | 70.71 | C |
| ATOM | 3368 | C | GLU | A | 294 | −13.092 | −13.104 | 18.885 | 1.00 | 69.04 | C |
| ATOM | 3369 | O | GLU | A | 294 | −12.837 | −14.300 | 18.741 | 1.00 | 70.01 | O |
| ATOM | 3370 | CB | GLU | A | 294 | −11.743 | −11.790 | 17.206 | 1.00 | 77.58 | C |
| ATOM | 3371 | CG | GLU | A | 294 | −10.964 | −12.934 | 16.557 | 1.00 | 87.68 | C |
| ATOM | 3372 | CD | GLU | A | 294 | −11.184 | −13.028 | 15.055 | 1.00 | 94.15 | C |
| ATOM | 3373 | OE1 | GLU | A | 294 | −11.220 | −11.972 | 14.390 | 1.00 | 102.95 | O |
| ATOM | 3374 | OE2 | GLU | A | 294 | −11.306 | −14.159 | 14.536 | 1.00 | 88.18 | O |

TABLE 6-continued

HUMAN A2A ADENOSINE STRUCTURE.PDB FILE
(Table 6: discloses SEQ ID NOS 20-27, respectively, in order of appearance.)

| ATOM | 3375 | N | PHE | A | 295 | −13.317 | −12.556 | 20.077 | 1.00 | 65.53 | N |
|---|---|---|---|---|---|---|---|---|---|---|---|
| ATOM | 3376 | CA | PHE | A | 295 | −13.416 | −13.376 | 21.282 | 1.00 | 58.28 | C |
| ATOM | 3377 | C | PHE | A | 295 | −14.772 | −14.065 | 21.330 | 1.00 | 66.01 | C |
| ATOM | 3378 | O | PHE | A | 295 | −14.863 | −15.276 | 21.531 | 1.00 | 67.76 | O |
| ATOM | 3379 | CB | PHE | A | 295 | −13.225 | −12.532 | 22.546 | 1.00 | 54.43 | C |
| ATOM | 3380 | CG | PHE | A | 295 | −11.796 | −12.427 | 23.000 | 1.00 | 61.07 | C |
| ATOM | 3381 | CD1 | PHE | A | 295 | −11.181 | −13.488 | 23.646 | 1.00 | 65.14 | C |
| ATOM | 3382 | CD2 | PHE | A | 295 | −11.071 | −11.266 | 22.791 | 1.00 | 58.98 | C |
| ATOM | 3383 | CE1 | PHE | A | 295 | −9.866 | −13.395 | 24.067 | 1.00 | 61.07 | C |
| ATOM | 3384 | CE2 | PHE | A | 295 | −9.756 | −11.166 | 23.210 | 1.00 | 60.30 | C |
| ATOM | 3385 | CZ | PHE | A | 295 | −9.153 | −12.231 | 23.849 | 1.00 | 58.30 | C |
| ATOM | 3386 | N | ARG | A | 296 | −15.825 | −13.276 | 21.140 | 1.00 | 61.80 | N |
| ATOM | 3387 | CA | ARG | A | 296 | −17.193 | −13.776 | 21.163 | 1.00 | 62.20 | C |
| ATOM | 3388 | C | ARG | A | 296 | −17.389 | −14.945 | 20.198 | 1.00 | 65.25 | C |
| ATOM | 3389 | O | ARG | A | 296 | −17.998 | −15.956 | 20.548 | 1.00 | 66.81 | O |
| ATOM | 3390 | CB | ARG | A | 296 | −18.168 | −12.643 | 20.831 | 1.00 | 64.51 | C |
| ATOM | 3391 | CG | ARG | A | 296 | −19.635 | −13.035 | 20.882 | 1.00 | 69.78 | C |
| ATOM | 3392 | CD | ARG | A | 296 | −20.543 | −11.810 | 20.794 | 1.00 | 70.98 | C |
| ATOM | 3393 | NE | ARG | A | 296 | −20.388 | −11.085 | 19.534 | 1.00 | 72.95 | N |
| ATOM | 3394 | CZ | ARG | A | 296 | −19.688 | −9.962 | 19.395 | 1.00 | 72.01 | C |
| ATOM | 3395 | NH1 | ARG | A | 296 | −19.604 | −9.375 | 18.208 | 1.00 | 64.97 | N |
| ATOM | 3396 | NH2 | ARG | A | 296 | −19.073 | −9.425 | 20.440 | 1.00 | 72.68 | N |
| ATOM | 3397 | N | GLN | A | 297 | −16.866 | −14.804 | 18.985 | 1.00 | 62.87 | N |
| ATOM | 3398 | CA | GLN | A | 297 | −17.005 | −15.846 | 17.973 | 1.00 | 63.27 | C |
| ATOM | 3399 | C | GLN | A | 297 | −16.233 | −17.111 | 18.339 | 1.00 | 62.10 | C |
| ATOM | 3400 | O | GLN | A | 297 | −16.684 | −18.222 | 18.061 | 1.00 | 56.97 | O |
| ATOM | 3401 | CB | GLN | A | 297 | −16.562 | −15.329 | 16.602 | 1.00 | 71.42 | C |
| ATOM | 3402 | CG | GLN | A | 297 | −17.526 | −14.334 | 15.978 | 1.00 | 83.47 | C |
| ATOM | 3403 | CD | GLN | A | 297 | −17.069 | −13.852 | 14.615 | 1.00 | 91.02 | C |
| ATOM | 3404 | OE1 | GLN | A | 297 | −15.887 | −13.929 | 14.279 | 1.00 | 94.57 | O |
| ATOM | 3405 | NE2 | GLN | A | 297 | −18.008 | −13.349 | 13.821 | 1.00 | 90.28 | N |
| ATOM | 3406 | N | THR | A | 298 | −15.071 | −16.940 | 18.960 | 1.00 | 66.11 | N |
| ATOM | 3407 | CA | THR | A | 298 | −14.259 | −18.079 | 19.370 | 1.00 | 60.32 | C |
| ATOM | 3408 | C | THR | A | 298 | −14.892 | −18.796 | 20.559 | 1.00 | 61.09 | C |
| ATOM | 3409 | O | THR | A | 298 | −14.816 | −20.020 | 20.668 | 1.00 | 60.48 | O |
| ATOM | 3410 | CB | THR | A | 298 | −12.821 | −17.659 | 19.724 | 1.00 | 59.44 | C |
| ATOM | 3411 | OG1 | THR | A | 298 | −12.229 | −16.988 | 18.605 | 1.00 | 61.44 | O |
| ATOM | 3412 | CG2 | THR | A | 298 | −11.983 | −18.879 | 20.075 | 1.00 | 54.14 | C |
| ATOM | 3413 | N | PHE | A | 299 | −15.520 | −18.030 | 21.446 | 1.00 | 61.13 | N |
| ATOM | 3414 | CA | PHE | A | 299 | −16.214 | −18.612 | 22.588 | 1.00 | 61.43 | C |
| ATOM | 3415 | C | PHE | A | 299 | −17.369 | −19.496 | 22.127 | 1.00 | 69.99 | C |
| ATOM | 3416 | O | PHE | A | 299 | −17.487 | −20.647 | 22.552 | 1.00 | 69.95 | O |
| ATOM | 3417 | CB | PHE | A | 299 | −16.725 | −17.526 | 23.537 | 1.00 | 55.14 | C |
| ATOM | 3418 | CG | PHE | A | 299 | −15.636 | −16.784 | 24.258 | 1.00 | 58.19 | C |
| ATOM | 3419 | CD1 | PHE | A | 299 | −14.375 | −17.338 | 24.398 | 1.00 | 58.68 | C |
| ATOM | 3420 | CD2 | PHE | A | 299 | −15.883 | −15.541 | 24.817 | 1.00 | 60.11 | C |
| ATOM | 3421 | CE1 | PHE | A | 299 | −13.374 | −16.657 | 25.066 | 1.00 | 58.66 | C |
| ATOM | 3422 | CE2 | PHE | A | 299 | −14.887 | −14.857 | 25.490 | 1.00 | 65.03 | C |
| ATOM | 3423 | CZ | PHE | A | 299 | −13.631 | −15.416 | 25.614 | 1.00 | 61.60 | C |
| ATOM | 3424 | N | ARG | A | 300 | −18.221 | −18.954 | 21.260 | 1.00 | 64.87 | N |
| ATOM | 3425 | CA | ARG | A | 300 | −19.321 | −19.728 | 20.691 | 1.00 | 69.72 | C |
| ATOM | 3426 | C | ARG | A | 300 | −18.828 | −21.043 | 20.103 | 1.00 | 70.15 | C |
| ATOM | 3427 | O | ARG | A | 300 | −19.433 | −22.094 | 20.313 | 1.00 | 67.05 | O |
| ATOM | 3428 | CB | ARG | A | 300 | −20.048 | −18.931 | 19.607 | 1.00 | 76.69 | C |
| ATOM | 3429 | CG | ARG | A | 300 | −21.392 | −18.376 | 20.035 | 1.00 | 86.88 | C |
| ATOM | 3430 | CD | ARG | A | 300 | −22.287 | −18.144 | 18.829 | 1.00 | 91.46 | C |
| ATOM | 3431 | NE | ARG | A | 300 | −21.705 | −17.181 | 17.901 | 1.00 | 87.22 | N |
| ATOM | 3432 | CZ | ARG | A | 300 | −21.814 | −15.864 | 18.033 | 1.00 | 86.03 | C |
| ATOM | 3433 | NH1 | ARG | A | 300 | −22.483 | −15.354 | 19.059 | 1.00 | 92.89 | N |
| ATOM | 3434 | NH2 | ARG | A | 300 | −21.254 | −15.056 | 17.144 | 1.00 | 75.92 | N |
| ATOM | 3435 | N | LYS | A | 301 | −17.728 | −20.972 | 19.361 | 1.00 | 69.60 | N |
| ATOM | 3436 | CA | LYS | A | 301 | −17.153 | −22.144 | 18.715 | 1.00 | 71.56 | C |
| ATOM | 3437 | C | LYS | A | 301 | −16.710 | −23.177 | 19.744 | 1.00 | 68.82 | C |
| ATOM | 3438 | O | LYS | A | 301 | −16.936 | −24.374 | 19.572 | 1.00 | 68.48 | O |
| ATOM | 3439 | CB | LYS | A | 301 | −15.962 | −21.735 | 17.848 | 1.00 | 79.63 | C |
| ATOM | 3440 | CG | LYS | A | 301 | −15.271 | −22.892 | 17.148 | 1.00 | 85.03 | C |
| ATOM | 3441 | CD | LYS | A | 301 | −13.883 | −22.491 | 16.677 | 1.00 | 95.12 | C |
| ATOM | 3442 | CE | LYS | A | 301 | −13.921 | −21.198 | 15.875 | 1.00 | 102.40 | C |
| ATOM | 3443 | NZ | LYS | A | 301 | −12.554 | −20.679 | 15.589 | 1.00 | 100.76 | N |
| ATOM | 3444 | N | ILE | A | 302 | −16.077 | −22.705 | 20.813 | 1.00 | 63.47 | N |
| ATOM | 3445 | CA | ILE | A | 302 | −15.558 | −23.588 | 21.851 | 1.00 | 67.91 | C |
| ATOM | 3446 | C | ILE | A | 302 | −16.682 | −24.247 | 22.642 | 1.00 | 68.98 | C |
| ATOM | 3447 | O | ILE | A | 302 | −16.663 | −25.455 | 22.881 | 1.00 | 71.20 | O |
| ATOM | 3448 | CB | ILE | A | 302 | −14.629 | −22.831 | 22.822 | 1.00 | 68.50 | C |
| ATOM | 3449 | CG1 | ILE | A | 302 | −13.359 | −22.378 | 22.098 | 1.00 | 59.47 | C |
| ATOM | 3450 | CG2 | ILE | A | 302 | −14.283 | −23.702 | 24.020 | 1.00 | 55.95 | C |
| ATOM | 3451 | CD1 | ILE | A | 302 | −12.365 | −21.674 | 22.992 | 1.00 | 56.73 | C |

TABLE 6-continued

HUMAN A2A ADENOSINE STRUCTURE.PDB FILE
(Table 6: discloses SEQ ID NOS 20-27, respectively, in order of appearance.)

| ATOM | 3452 | N | ILE | A | 303 | −17.660 | −23.446 | 23.047 | 1.00 | 67.06 | N |
|---|---|---|---|---|---|---|---|---|---|---|---|
| ATOM | 3453 | CA | ILE | A | 303 | −18.774 | −23.945 | 23.842 | 1.00 | 66.18 | C |
| ATOM | 3454 | C | ILE | A | 303 | −19.618 | −24.951 | 23.064 | 1.00 | 71.40 | C |
| ATOM | 3455 | O | ILE | A | 303 | −20.005 | −25.992 | 23.595 | 1.00 | 76.63 | O |
| ATOM | 3456 | CB | ILE | A | 303 | −19.660 | −22.791 | 24.351 | 1.00 | 66.28 | C |
| ATOM | 3457 | CG1 | ILE | A | 303 | −18.863 | −21.901 | 25.307 | 1.00 | 68.36 | C |
| ATOM | 3458 | CG2 | ILE | A | 303 | −20.904 | −23.332 | 25.038 | 1.00 | 65.78 | C |
| ATOM | 3459 | CD1 | ILE | A | 303 | −19.660 | −20.756 | 25.890 | 1.00 | 67.48 | C |
| ATOM | 3460 | N | ARG | A | 304 | −19.891 | −24.647 | 21.800 | 1.00 | 74.11 | N |
| ATOM | 3461 | CA | ARG | A | 304 | −20.729 | −25.516 | 20.981 | 1.00 | 75.45 | C |
| ATOM | 3462 | C | ARG | A | 304 | −20.014 | −26.773 | 20.489 | 1.00 | 74.61 | C |
| ATOM | 3463 | O | ARG | A | 304 | −20.600 | −27.854 | 20.461 | 1.00 | 73.65 | O |
| ATOM | 3464 | CB | ARG | A | 304 | −21.341 | −24.736 | 19.812 | 1.00 | 76.96 | C |
| ATOM | 3465 | CG | ARG | A | 304 | −22.727 | −24.203 | 20.133 | 1.00 | 87.23 | C |
| ATOM | 3466 | CD | ARG | A | 304 | −23.068 | −22.925 | 19.386 | 1.00 | 92.33 | C |
| ATOM | 3467 | NE | ARG | A | 304 | −24.231 | −22.277 | 19.989 | 1.00 | 101.86 | N |
| ATOM | 3468 | CZ | ARG | A | 304 | −24.817 | −21.181 | 19.516 | 1.00 | 103.97 | C |
| ATOM | 3469 | NH1 | ARG | A | 304 | −25.869 | −20.670 | 20.141 | 1.00 | 98.37 | N |
| ATOM | 3470 | NH2 | ARG | A | 304 | −24.354 | −20.598 | 18.419 | 1.00 | 105.11 | N |
| ATOM | 3471 | N | SER | A | 305 | −18.747 | −26.635 | 20.117 | 1.00 | 77.95 | N |
| ATOM | 3472 | CA | SER | A | 305 | −18.000 | −27.764 | 19.572 | 1.00 | 82.94 | C |
| ATOM | 3473 | C | SER | A | 305 | −17.352 | −28.649 | 20.637 | 1.00 | 80.18 | C |
| ATOM | 3474 | O | SER | A | 305 | −17.592 | −29.855 | 20.673 | 1.00 | 81.74 | O |
| ATOM | 3475 | CB | SER | A | 305 | −16.951 | −27.284 | 18.565 | 1.00 | 89.74 | C |
| ATOM | 3476 | OG | SER | A | 305 | −17.557 | −26.887 | 17.348 | 1.00 | 91.81 | O |
| ATOM | 3477 | N | HIS | A | 306 | −16.537 | −28.051 | 21.501 | 1.00 | 77.09 | N |
| ATOM | 3478 | CA | HIS | A | 306 | −15.743 | −28.826 | 22.454 | 1.00 | 77.23 | C |
| ATOM | 3479 | C | HIS | A | 306 | −16.439 | −29.072 | 23.793 | 1.00 | 75.01 | C |
| ATOM | 3480 | O | HIS | A | 306 | −16.175 | −30.071 | 24.457 | 1.00 | 74.86 | O |
| ATOM | 3481 | CB | HIS | A | 306 | −14.384 | −28.162 | 22.690 | 1.00 | 77.17 | C |
| ATOM | 3482 | CG | HIS | A | 306 | −13.657 | −27.813 | 21.431 | 1.00 | 88.23 | C |
| ATOM | 3483 | ND1 | HIS | A | 306 | −13.664 | −26.542 | 20.896 | 1.00 | 99.08 | N |
| ATOM | 3484 | CD2 | HIS | A | 306 | −12.906 | −28.568 | 20.595 | 1.00 | 93.77 | C |
| ATOM | 3485 | CE1 | HIS | A | 306 | −12.946 | −26.529 | 19.788 | 1.00 | 99.06 | C |
| ATOM | 3486 | NE2 | HIS | A | 306 | −12.476 | −27.747 | 19.582 | 1.00 | 96.06 | N |
| ATOM | 3487 | N | VAL | A | 307 | −17.320 | −28.163 | 24.191 | 1.00 | 68.66 | N |
| ATOM | 3488 | CA | VAL | A | 307 | −17.978 | −28.270 | 25.491 | 1.00 | 62.67 | C |
| ATOM | 3489 | C | VAL | A | 307 | −19.256 | −29.103 | 25.432 | 1.00 | 69.88 | C |
| ATOM | 3490 | O | VAL | A | 307 | −19.410 | −30.068 | 26.178 | 1.00 | 73.85 | O |
| ATOM | 3491 | CB | VAL | A | 307 | −18.260 | −26.879 | 26.099 | 1.00 | 56.26 | C |
| ATOM | 3492 | CG1 | VAL | A | 307 | −19.165 | −26.999 | 27.314 | 1.00 | 48.63 | C |
| ATOM | 3493 | CG2 | VAL | A | 307 | −16.956 | −26.186 | 26.469 | 1.00 | 52.95 | C |
| ATOM | 3494 | N | LEU | A | 308 | −20.175 | −28.725 | 24.553 | 1.00 | 80.85 | N |
| ATOM | 3495 | CA | LEU | A | 308 | −21.364 | −29.522 | 24.324 | 1.00 | 92.67 | C |
| ATOM | 3496 | C | LEU | A | 308 | −20.998 | −30.704 | 23.454 | 1.00 | 107.73 | C |
| ATOM | 3497 | O | LEU | A | 308 | −21.699 | −31.715 | 23.435 | 1.00 | 111.66 | O |
| ATOM | 3498 | CB | LEU | A | 308 | −22.461 | −28.668 | 23.673 | 1.00 | 86.67 | C |
| ATOM | 3499 | CG | LEU | A | 308 | −23.432 | −27.973 | 24.646 | 1.00 | 84.53 | C |
| ATOM | 3500 | CD1 | LEU | A | 308 | −22.791 | −27.762 | 25.997 | 1.00 | 78.57 | C |
| ATOM | 3501 | CD2 | LEU | A | 308 | −23.883 | −26.652 | 24.058 | 1.00 | 83.22 | C |
| ATOM | 2227 | N | ARG | A | 309 | −19.878 | −30.584 | 22.758 | 1.00 | 115.37 | N |
| ATOM | 2228 | CA | ARG | A | 309 | −19.477 | −31.616 | 21.824 | 1.00 | 114.52 | C |
| ATOM | 2229 | C | ARG | A | 309 | −20.459 | −31.736 | 20.690 | 1.00 | 110.36 | C |
| ATOM | 2237 | O | ARG | A | 309 | −20.645 | −32.827 | 20.154 | 1.00 | 107.74 | O |
| ATOM | 2230 | CB | ARG | A | 309 | −19.368 | −32.969 | 22.507 | 1.00 | 112.30 | C |
| ATOM | 2231 | CG | ARG | A | 309 | −18.201 | −33.061 | 23.453 | 1.00 | 103.01 | C |
| ATOM | 2232 | CD | ARG | A | 309 | −16.877 | −32.644 | 22.807 | 1.00 | 104.12 | C |
| ATOM | 2233 | NE | ARG | A | 309 | −16.070 | −33.794 | 22.388 | 1.00 | 113.70 | N |
| ATOM | 2234 | CZ | ARG | A | 309 | −14.862 | −33.698 | 21.840 | 1.00 | 125.17 | C |
| ATOM | 2235 | NH1 | ARG | A | 309 | −14.333 | −32.500 | 21.621 | 1.00 | 130.11 | N |
| ATOM | 2236 | NH2 | ARG | A | 309 | −14.194 | −34.792 | 21.497 | 1.00 | 126.66 | N |
| ATOM | 3513 | N | GLN | A | 310 | −21.100 | −30.616 | 20.366 | 1.00 | 111.32 | N |
| ATOM | 3514 | CA | GLN | A | 310 | −22.030 | −30.506 | 19.246 | 1.00 | 113.48 | C |
| ATOM | 3515 | C | GLN | A | 310 | −23.336 | −29.820 | 19.651 | 1.00 | 112.38 | C |
| ATOM | 3516 | O | GLN | A | 310 | −23.606 | −28.679 | 19.263 | 1.00 | 107.05 | O |
| ATOM | 3517 | CB | GLN | A | 310 | −22.314 | −31.870 | 18.620 | 1.00 | 118.22 | C |
| ATOM | 3518 | CG | GLN | A | 310 | −22.486 | −31.839 | 17.115 | 1.00 | 120.97 | C |
| ATOM | 3519 | CD | GLN | A | 310 | −21.312 | −31.188 | 16.403 | 1.00 | 120.49 | C |
| ATOM | 3520 | OE1 | GLN | A | 310 | −20.703 | −30.245 | 16.912 | 1.00 | 119.20 | O |
| ATOM | 3521 | NE2 | GLN | A | 310 | −20.989 | −31.690 | 15.215 | 1.00 | 118.40 | N |
| TER | 3522 | | GLN | A | 310 | | | | | | |
| HETATM | 3523 | C1 | ZMA | A | 401 | −10.992 | −8.796 | 60.617 | 1.00 | 104.51 | C |
| HETATM | 3524 | C2 | ZMA | A | 401 | −11.241 | −8.297 | 61.889 | 1.00 | 106.65 | C |
| HETATM | 3525 | C3 | ZMA | A | 401 | −11.984 | −7.133 | 62.045 | 1.00 | 104.03 | C |
| HETATM | 3526 | C4 | ZMA | A | 401 | −12.231 | −6.638 | 63.286 | 1.00 | 109.18 | O |
| HETATM | 3527 | C5 | ZMA | A | 401 | −12.476 | −6.469 | 60.928 | 1.00 | 95.90 | C |
| HETATM | 3528 | C6 | ZMA | A | 401 | −12.230 | −6.969 | 59.657 | 1.00 | 93.55 | C |

TABLE 6-continued

HUMAN A2A ADENOSINE STRUCTURE.PDB FILE
(Table 6: discloses SEQ ID NOS 20-27, respectively, in order of appearance.)

| HETATM | 3529 | C7  | ZMA | A | 401 | −11.492 | −8.135  | 59.501 | 1.00 | 91.84  | C |
|--------|------|-----|-----|---|-----|---------|---------|--------|------|--------|---|
| HETATM | 3530 | C8  | ZMA | A | 401 | −11.208 | −8.677  | 58.101 | 1.00 | 72.50  | C |
| HETATM | 3531 | C9  | ZMA | A | 401 | −9.746  | −9.104  | 58.006 | 1.00 | 56.96  | C |
| HETATM | 3532 | N10 | ZMA | A | 401 | −9.420  | −9.544  | 56.644 | 1.00 | 49.16  | N |
| HETATM | 3533 | C11 | ZMA | A | 401 | −8.953  | −8.593  | 55.842 | 1.00 | 53.12  | C |
| HETATM | 3534 | N12 | ZMA | A | 401 | −8.585  | −8.857  | 54.578 | 1.00 | 51.75  | N |
| HETATM | 3535 | N13 | ZMA | A | 401 | −8.833  | −7.359  | 56.358 | 1.00 | 54.15  | N |
| HETATM | 3536 | C14 | ZMA | A | 401 | −8.365  | −6.342  | 55.626 | 1.00 | 57.39  | C |
| HETATM | 3537 | N15 | ZMA | A | 401 | −8.266  | −5.125  | 56.156 | 1.00 | 58.08  | N |
| HETATM | 3538 | N16 | ZMA | A | 401 | −7.981  | −6.582  | 54.309 | 1.00 | 52.32  | N |
| HETATM | 3539 | N17 | ZMA | A | 401 | −7.525  | −5.852  | 53.428 | 1.00 | 49.90  | N |
| HETATM | 3540 | C18 | ZMA | A | 401 | −8.104  | −7.874  | 53.800 | 1.00 | 47.64  | C |
| HETATM | 3541 | N19 | ZMA | A | 401 | −7.676  | −7.829  | 52.544 | 1.00 | 53.04  | N |
| HETATM | 3542 | C20 | ZMA | A | 401 | −7.313  | −6.565  | 52.320 | 1.00 | 51.81  | C |
| HETATM | 3543 | C21 | ZMA | A | 401 | −6.809  | −6.054  | 51.131 | 1.00 | 49.80  | C |
| HETATM | 3544 | C22 | ZMA | A | 401 | −6.554  | −6.688  | 49.991 | 1.00 | 47.99  | C |
| HETATM | 3545 | C23 | ZMA | A | 401 | −6.081  | −5.796  | 49.121 | 1.00 | 53.65  | C |
| HETATM | 3546 | C24 | ZMA | A | 401 | −6.034  | −4.598  | 49.703 | 1.00 | 50.25  | C |
| HETATM | 3547 | O25 | ZMA | A | 401 | −6.492  | −4.739  | 50.984 | 1.00 | 51.60  | O |
| HETATM | 3548 | C1  | STE | A | 402 | −1.046  | −19.906 | 26.269 | 1.00 | 101.96 | C |
| HETATM | 3549 | O1  | STE | A | 402 | −2.118  | −20.474 | 26.029 | 1.00 | 102.79 | O |
| HETATM | 3550 | O2  | STE | A | 402 | −0.204  | −19.579 | 25.428 | 1.00 | 104.67 | O |
| HETATM | 3551 | C2  | STE | A | 402 | −0.729  | −19.550 | 27.709 | 1.00 | 95.33  | C |
| HETATM | 3552 | C3  | STE | A | 402 | −1.574  | −20.321 | 28.715 | 1.00 | 89.62  | C |
| HETATM | 3553 | C4  | STE | A | 402 | −1.071  | −20.087 | 30.137 | 1.00 | 79.90  | C |
| HETATM | 3554 | C5  | STE | A | 402 | −2.210  | −20.089 | 31.126 | 1.00 | 76.48  | C |
| HETATM | 3555 | C6  | STE | A | 402 | −1.759  | −20.748 | 32.401 | 1.00 | 80.09  | C |
| HETATM | 3556 | C7  | STE | A | 402 | −2.794  | −20.596 | 33.492 | 1.00 | 80.87  | C |
| HETATM | 3557 | C8  | STE | A | 402 | −2.128  | −20.715 | 34.853 | 1.00 | 85.07  | C |
| HETATM | 3558 | C9  | STE | A | 402 | −3.140  | −21.015 | 35.946 | 1.00 | 84.90  | C |
| HETATM | 3559 | C10 | STE | A | 402 | −2.471  | −21.555 | 37.199 | 1.00 | 84.71  | C |
| HETATM | 3560 | C11 | STE | A | 402 | −3.435  | −21.496 | 38.371 | 1.00 | 78.33  | C |
| HETATM | 3561 | C12 | STE | A | 402 | −3.300  | −22.696 | 39.292 | 1.00 | 77.12  | C |
| HETATM | 3562 | C13 | STE | A | 402 | −2.601  | −22.325 | 40.583 | 1.00 | 78.65  | C |
| HETATM | 3563 | C14 | STE | A | 402 | −2.992  | −23.264 | 41.711 | 1.00 | 89.02  | C |
| HETATM | 3564 | C15 | STE | A | 402 | −2.591  | −24.716 | 41.436 | 1.00 | 96.19  | C |
| HETATM | 3565 | C16 | STE | A | 402 | −2.905  | −25.630 | 42.614 | 1.00 | 93.19  | C |
| HETATM | 3566 | C17 | STE | A | 402 | −1.785  | −26.625 | 42.842 | 1.00 | 91.32  | C |
| HETATM | 3567 | C18 | STE | A | 402 | −0.942  | −26.260 | 44.054 | 1.00 | 92.30  | C |
| HETATM | 3568 | C1  | STE | A | 403 | 2.094   | −15.536 | 27.760 | 1.00 | 95.00  | C |
| HETATM | 3569 | O1  | STE | A | 403 | 1.634   | −15.661 | 26.622 | 1.00 | 93.81  | O |
| HETATM | 3570 | O2  | STE | A | 403 | 3.214   | −15.136 | 28.033 | 1.00 | 94.58  | O |
| HETATM | 3571 | C2  | STE | A | 403 | 1.234   | −15.919 | 28.942 | 1.00 | 92.42  | C |
| HETATM | 3572 | C3  | STE | A | 403 | 2.079   | −15.994 | 30.201 | 1.00 | 81.66  | C |
| HETATM | 3573 | C4  | STE | A | 403 | 1.459   | −16.895 | 31.248 | 1.00 | 70.47  | C |
| HETATM | 3574 | C5  | STE | A | 403 | 1.973   | −16.537 | 32.624 | 1.00 | 64.66  | C |
| HETATM | 3575 | C6  | STE | A | 403 | 1.270   | −17.363 | 33.677 | 1.00 | 69.35  | C |
| HETATM | 3576 | C7  | STE | A | 403 | 2.021   | −17.249 | 34.975 | 1.00 | 77.72  | C |
| HETATM | 3577 | C8  | STE | A | 403 | 1.190   | −17.752 | 36.135 | 1.00 | 91.26  | C |
| HETATM | 3578 | C9  | STE | A | 403 | 2.067   | −17.815 | 37.367 | 1.00 | 96.45  | C |
| HETATM | 3579 | C10 | STE | A | 403 | 3.484   | −17.447 | 36.957 | 1.00 | 96.09  | C |
| HETATM | 3580 | C11 | STE | A | 403 | 4.480   | −17.662 | 38.082 | 1.00 | 92.60  | C |
| HETATM | 3581 | C12 | STE | A | 403 | 5.858   | −17.424 | 37.530 | 1.00 | 90.95  | C |
| HETATM | 3582 | C13 | STE | A | 403 | 5.691   | −16.968 | 36.100 | 1.00 | 96.43  | C |
| HETATM | 3583 | C14 | STE | A | 403 | 7.001   | −16.997 | 35.326 | 1.00 | 98.01  | C |
| HETATM | 3584 | C15 | STE | A | 403 | 6.760   | −17.508 | 33.912 | 1.00 | 93.82  | C |
| HETATM | 3585 | C16 | STE | A | 403 | 6.664   | −16.379 | 32.898 | 1.00 | 88.04  | C |
| HETATM | 3586 | C17 | STE | A | 403 | 6.587   | −16.970 | 31.505 | 1.00 | 84.21  | C |
| HETATM | 3587 | C18 | STE | A | 403 | 6.655   | −15.899 | 30.432 | 1.00 | 81.40  | C |
| HETATM | 3588 | C1  | STE | A | 404 | −3.153  | −27.554 | 60.261 | 1.00 | 103.30 | C |
| HETATM | 3589 | O1  | STE | A | 404 | −3.529  | −28.476 | 59.547 | 1.00 | 109.79 | O |
| HETATM | 3590 | O2  | STE | A | 404 | −2.690  | −27.688 | 61.393 | 1.00 | 104.10 | O |
| HETATM | 3591 | C2  | STE | A | 404 | −3.247  | −26.158 | 59.677 | 1.00 | 102.90 | C |
| HETATM | 3592 | C3  | STE | A | 404 | −3.762  | −26.201 | 58.238 | 1.00 | 101.88 | C |
| HETATM | 3593 | C4  | STE | A | 404 | −3.659  | −24.839 | 57.554 | 1.00 | 98.59  | C |
| HETATM | 3594 | C5  | STE | A | 404 | −4.563  | −24.744 | 56.330 | 1.00 | 91.91  | C |
| HETATM | 3595 | C6  | STE | A | 404 | −3.844  | −24.106 | 55.159 | 1.00 | 87.51  | C |
| HETATM | 3596 | C7  | STE | A | 404 | −4.829  | −23.479 | 54.190 | 1.00 | 88.98  | C |
| HETATM | 3597 | C8  | STE | A | 404 | −5.435  | −24.525 | 53.268 | 1.00 | 93.83  | C |
| HETATM | 3598 | C9  | STE | A | 404 | −5.568  | −24.029 | 51.829 | 1.00 | 94.43  | C |
| HETATM | 3599 | C10 | STE | A | 404 | −6.379  | −24.985 | 50.965 | 1.00 | 88.89  | C |
| HETATM | 3600 | C11 | STE | A | 404 | −5.803  | −25.169 | 49.565 | 1.00 | 87.37  | C |
| HETATM | 3601 | C12 | STE | A | 404 | −6.926  | −25.384 | 48.569 | 1.00 | 88.79  | C |
| HETATM | 3602 | C13 | STE | A | 404 | −6.499  | −26.077 | 47.286 | 1.00 | 92.60  | C |
| HETATM | 3603 | C14 | STE | A | 404 | −7.391  | −25.619 | 46.131 | 1.00 | 92.44  | C |
| HETATM | 3604 | C15 | STE | A | 404 | −8.219  | −26.742 | 45.516 | 1.00 | 89.47  | C |
| HETATM | 3605 | C16 | STE | A | 404 | −9.211  | −26.219 | 44.473 | 1.00 | 87.54  | C |

TABLE 6-continued

HUMAN A2A ADENOSINE STRUCTURE.PDB FILE
(Table 6: discloses SEQ ID NOS 20-27, respectively, in order of appearance.)

| HETATM | 3606 | C17 | STE | A | 404 | −10.544 | −25.833 | 45.105 | 1.00 | 87.34 | C |
|---|---|---|---|---|---|---|---|---|---|---|---|
| HETATM | 3607 | C18 | STE | A | 404 | −11.596 | −25.386 | 44.090 | 1.00 | 89.75 | C |
| HETATM | 3608 | C1 | STE | A | 405 | 0.152 | −23.528 | 58.196 | 1.00 | 111.30 | C |
| HETATM | 3609 | O1 | STE | A | 405 | −0.397 | −24.603 | 58.468 | 1.00 | 110.51 | O |
| HETATM | 3610 | O2 | STE | A | 405 | 1.288 | −23.176 | 58.523 | 1.00 | 109.34 | O |
| HETATM | 3611 | C2 | STE | A | 405 | −0.636 | −22.544 | 57.379 | 1.00 | 110.04 | C |
| HETATM | 3612 | C3 | STE | A | 405 | 0.092 | −22.221 | 56.093 | 1.00 | 104.17 | C |
| HETATM | 3613 | C4 | STE | A | 405 | 0.265 | −23.452 | 55.238 | 1.00 | 99.26 | C |
| HETATM | 3614 | C5 | STE | A | 405 | 1.325 | −23.189 | 54.196 | 1.00 | 95.55 | C |
| HETATM | 3615 | C6 | STE | A | 405 | 0.675 | −22.754 | 52.908 | 1.00 | 95.95 | C |
| HETATM | 3616 | C7 | STE | A | 405 | −0.185 | −23.862 | 52.352 | 1.00 | 94.84 | C |
| HETATM | 3617 | C8 | STE | A | 405 | −0.125 | −23.885 | 50.837 | 1.00 | 96.47 | C |
| HETATM | 3618 | C9 | STE | A | 405 | −1.337 | −24.617 | 50.305 | 1.00 | 100.46 | C |
| HETATM | 3619 | C10 | STE | A | 405 | −1.074 | −25.145 | 48.916 | 1.00 | 103.76 | C |
| HETATM | 3620 | C11 | STE | A | 405 | 0.168 | −24.495 | 48.340 | 1.00 | 109.11 | C |
| HETATM | 3621 | C12 | STE | A | 405 | 0.141 | −24.617 | 46.825 | 1.00 | 115.54 | C |
| HETATM | 3622 | C13 | STE | A | 405 | 1.293 | −23.853 | 46.197 | 1.00 | 118.55 | C |
| HETATM | 3623 | C14 | STE | A | 405 | 0.982 | −22.369 | 46.115 | 1.00 | 117.71 | C |
| HETATM | 3624 | C15 | STE | A | 405 | 2.032 | −21.637 | 45.292 | 1.00 | 115.56 | C |
| HETATM | 3625 | C16 | STE | A | 405 | 1.465 | −21.223 | 43.950 | 1.00 | 115.41 | C |
| HETATM | 3626 | C17 | STE | A | 405 | 1.803 | −22.236 | 42.876 | 1.00 | 119.40 | C |
| HETATM | 3627 | C18 | STE | A | 405 | 1.285 | −21.764 | 41.521 | 1.00 | 121.54 | C |
| HETATM | 3628 | C1 | STE | A | 406 | −20.891 | −16.658 | 25.051 | 1.00 | 114.47 | C |
| HETATM | 3629 | O1 | STE | A | 406 | −21.979 | −17.227 | 24.883 | 1.00 | 113.81 | O |
| HETATM | 3630 | O2 | STE | A | 406 | −20.005 | −16.531 | 24.201 | 1.00 | 120.50 | O |
| HETATM | 3631 | C2 | STE | A | 406 | −20.650 | −16.009 | 26.398 | 1.00 | 105.97 | C |
| HETATM | 3632 | C3 | STE | A | 406 | −19.392 | −16.484 | 27.101 | 1.00 | 94.17 | C |
| HETATM | 3633 | C4 | STE | A | 406 | −19.595 | −16.363 | 28.606 | 1.00 | 88.47 | C |
| HETATM | 3634 | C5 | STE | A | 406 | −18.551 | −15.501 | 29.283 | 1.00 | 84.32 | C |
| HETATM | 3635 | C6 | STE | A | 406 | −17.889 | −16.272 | 30.404 | 1.00 | 84.58 | C |
| HETATM | 3636 | C7 | STE | A | 406 | −18.833 | −17.282 | 31.044 | 1.00 | 83.94 | C |
| HETATM | 3637 | C8 | STE | A | 406 | −18.047 | −18.291 | 31.866 | 1.00 | 84.78 | C |
| HETATM | 3638 | C9 | STE | A | 406 | −18.937 | −19.293 | 32.581 | 1.00 | 94.09 | C |
| HETATM | 3639 | C10 | STE | A | 406 | −19.734 | −20.139 | 31.598 | 1.00 | 101.66 | C |
| HETATM | 3640 | C11 | STE | A | 406 | −19.111 | −21.519 | 31.398 | 1.00 | 102.56 | C |
| HETATM | 3641 | C12 | STE | A | 406 | −18.779 | −21.810 | 29.936 | 1.00 | 98.89 | C |
| HETATM | 3642 | C13 | STE | A | 406 | −18.055 | −23.146 | 29.786 | 1.00 | 94.04 | C |
| HETATM | 3643 | C14 | STE | A | 406 | −16.542 | −22.999 | 29.854 | 1.00 | 84.78 | C |
| HETATM | 3644 | C15 | STE | A | 406 | −15.874 | −24.343 | 29.625 | 1.00 | 82.44 | C |
| HETATM | 3645 | C16 | STE | A | 406 | −14.484 | −24.391 | 30.239 | 1.00 | 82.54 | C |
| HETATM | 3646 | C17 | STE | A | 406 | −13.974 | −25.820 | 30.413 | 1.00 | 86.31 | C |
| HETATM | 3647 | C18 | STE | A | 406 | −15.032 | −26.777 | 30.967 | 1.00 | 89.29 | C |
| HETATM | 3648 | S | SO4 | A | 407 | −16.013 | 17.889 | 8.618 | 1.00 | 71.08 | S |
| HETATM | 3649 | O1 | SO4 | A | 407 | −15.772 | 18.606 | 7.369 | 1.00 | 70.79 | O |
| HETATM | 3650 | O2 | SO4 | A | 407 | −17.363 | 18.170 | 9.099 | 1.00 | 74.80 | O |
| HETATM | 3651 | O3 | SO4 | A | 407 | −15.870 | 16.454 | 8.388 | 1.00 | 69.56 | O |
| HETATM | 3652 | O4 | SO4 | A | 407 | −15.045 | 18.330 | 9.618 | 1.00 | 70.02 | O |
| HETATM | 3653 | S | SO4 | A | 408 | −21.572 | −11.702 | 15.804 | 1.00 | 103.32 | S |
| HETATM | 3654 | O1 | SO4 | A | 408 | −20.339 | −12.039 | 15.098 | 1.00 | 95.44 | O |
| HETATM | 3655 | O2 | SO4 | A | 408 | −22.722 | −12.153 | 15.025 | 1.00 | 98.95 | O |
| HETATM | 3656 | O3 | SO4 | A | 408 | −21.583 | −12.357 | 17.108 | 1.00 | 106.55 | O |
| HETATM | 3657 | O4 | SO4 | A | 408 | −21.648 | −10.256 | 15.992 | 1.00 | 111.08 | O |
| HETATM | 3658 | S | SO4 | A | 409 | −1.181 | 13.819 | 19.630 | 1.00 | 161.08 | S |
| HETATM | 3659 | O1 | SO4 | A | 409 | 0.240 | 13.789 | 19.297 | 1.00 | 160.17 | O |
| HETATM | 3660 | O2 | SO4 | A | 409 | −1.947 | 14.230 | 18.457 | 1.00 | 155.72 | O |
| HETATM | 3661 | O3 | SO4 | A | 409 | −1.611 | 12.489 | 20.052 | 1.00 | 163.96 | O |
| HETATM | 3662 | O4 | SO4 | A | 409 | −1.405 | 14.770 | 20.715 | 1.00 | 161.31 | O |
| HETATM | 3663 | S | SO4 | A | 410 | 7.972 | −18.865 | 62.180 | 1.00 | 120.92 | S |
| HETATM | 3664 | O1 | SO4 | A | 410 | 9.335 | −19.359 | 62.016 | 1.00 | 120.10 | O |
| HETATM | 3665 | O2 | SO4 | A | 410 | 7.149 | −19.327 | 61.066 | 1.00 | 121.73 | O |
| HETATM | 3666 | O3 | SO4 | A | 410 | 7.421 | −19.370 | 63.435 | 1.00 | 126.13 | O |
| HETATM | 3667 | O4 | SO4 | A | 410 | 7.981 | −17.405 | 62.209 | 1.00 | 117.47 | O |
| HETATM | 3668 | S | SO4 | A | 411 | −2.727 | 1.729 | 0.249 | 1.00 | 90.85 | S |
| HETATM | 3669 | O1 | SO4 | A | 411 | −1.641 | 1.037 | −0.437 | 1.00 | 93.45 | O |
| HETATM | 3670 | O2 | SO4 | A | 411 | −3.903 | 1.753 | −0.615 | 1.00 | 84.30 | O |
| HETATM | 3671 | O3 | SO4 | A | 411 | −3.047 | 1.025 | 1.487 | 1.00 | 94.36 | O |
| HETATM | 3672 | O4 | SO4 | A | 411 | −2.316 | 3.097 | 0.556 | 1.00 | 85.38 | O |
| HETATM | 3673 | S | SO4 | A | 412 | −9.473 | 10.595 | −16.897 | 1.00 | 125.46 | S |
| HETATM | 3674 | O1 | SO4 | A | 412 | −9.342 | 10.984 | −15.496 | 1.00 | 123.21 | O |
| HETATM | 3675 | O2 | SO4 | A | 412 | −8.433 | 9.627 | −17.233 | 1.00 | 129.64 | O |
| HETATM | 3676 | O3 | SO4 | A | 412 | −10.785 | 9.994 | −17.117 | 1.00 | 125.41 | O |
| HETATM | 3677 | O4 | SO4 | A | 412 | −9.327 | 11.772 | −17.748 | 1.00 | 124.48 | O |
| HETATM | 3678 | S | SO4 | A | 413 | 8.313 | 27.080 | −6.220 | 1.00 | 135.28 | S |
| HETATM | 3679 | O1 | SO4 | A | 413 | 9.329 | 26.447 | −7.057 | 1.00 | 136.47 | O |
| HETATM | 3680 | O2 | SO4 | A | 413 | 7.125 | 26.232 | −6.170 | 1.00 | 135.42 | O |
| HETATM | 3681 | O3 | SO4 | A | 413 | 8.841 | 27.259 | −4.871 | 1.00 | 134.96 | O |
| HETATM | 3682 | O4 | SO4 | A | 413 | 7.961 | 28.381 | −6.781 | 1.00 | 133.33 | O |

TABLE 6-continued

HUMAN A2A ADENOSINE STRUCTURE.PDB FILE
(Table 6: discloses SEQ ID NOS 20-27, respectively, in order of appearance.)

| HETATM | 3683 | O | HOH | A | 501 | −4.003 | −15.002 | 49.894 | 1.00 | 39.38 | O |
|---|---|---|---|---|---|---|---|---|---|---|---|
| HETATM | 3684 | O | HOH | A | 502 | −13.677 | −3.697 | 47.669 | 1.00 | 56.51 | O |
| HETATM | 3685 | O | HOH | A | 503 | 4.543 | 14.639 | 0.918 | 1.00 | 61.93 | O |
| HETATM | 3686 | O | HOH | A | 504 | −9.158 | −12.000 | 33.321 | 1.00 | 49.62 | O |
| HETATM | 3687 | O | HOH | A | 505 | −5.127 | −1.172 | 51.443 | 1.00 | 46.10 | O |
| HETATM | 3688 | O | HOH | A | 506 | −17.101 | 19.986 | 5.313 | 1.00 | 51.47 | O |
| HETATM | 3689 | O | HOH | A | 507 | −5.526 | −1.444 | 30.482 | 1.00 | 66.44 | O |
| HETATM | 3690 | O | HOH | A | 508 | 6.640 | 17.769 | 7.739 | 1.00 | 44.24 | O |
| HETATM | 3691 | O | HOH | A | 509 | −7.997 | −11.369 | 30.954 | 1.00 | 54.25 | O |
| HETATM | 3692 | O | HOH | A | 510 | −3.644 | 10.800 | −3.036 | 1.00 | 58.38 | O |
| HETATM | 3693 | O | HOH | A | 511 | 6.256 | 17.895 | 5.014 | 1.00 | 57.31 | O |
| HETATM | 3694 | O | HOH | A | 512 | −11.483 | −5.432 | 35.855 | 1.00 | 55.90 | O |
| HETATM | 3695 | O | HOH | A | 513 | −7.564 | −3.600 | 29.891 | 1.00 | 63.07 | O |
| HETATM | 3696 | O | HOH | A | 514 | −6.981 | −14.619 | 50.159 | 1.00 | 62.37 | O |
| HETATM | 3697 | O | HOH | A | 515 | −20.577 | 15.269 | −20.283 | 1.00 | 70.43 | O |
| HETATM | 3698 | O | HOH | A | 516 | 22.234 | 6.137 | 7.747 | 1.00 | 71.40 | O |
| HETATM | 3699 | O | HOH | A | 517 | 1.310 | 10.014 | 14.672 | 1.00 | 75.11 | O |
| HETATM | 3700 | O | HOH | A | 518 | −14.139 | −2.114 | 0.075 | 1.00 | 90.93 | O |
| HETATM | 3701 | O | HOH | A | 519 | −12.282 | −4.739 | 64.998 | 1.00 | 81.01 | O |
| HETATM | 3702 | O | HOH | A | 520 | −12.042 | 14.729 | 14.732 | 1.00 | 57.68 | O |
| HETATM | 3703 | O | HOH | A | 521 | 11.352 | 11.509 | 0.390 | 1.00 | 75.94 | O |
| HETATM | 3704 | O | HOH | A | 522 | −5.987 | −12.917 | 52.690 | 1.00 | 58.26 | O |
| HETATM | 3705 | O | HOH | A | 523 | −3.607 | −14.642 | 12.010 | 1.00 | 71.00 | O |
| HETATM | 3706 | O | HOH | A | 524 | 6.119 | 16.982 | 0.205 | 1.00 | 67.99 | O |
| HETATM | 3707 | O | HOH | A | 525 | −15.752 | 22.470 | −8.387 | 1.00 | 84.60 | O |
| HETATM | 3708 | O | HOH | A | 526 | −16.644 | 9.344 | 19.939 | 1.00 | 85.78 | O |
| HETATM | 3709 | O | HOH | A | 527 | −6.739 | 16.284 | 20.625 | 1.00 | 58.78 | O |
| HETATM | 3710 | O | HOH | A | 528 | −11.834 | −13.848 | 54.529 | 1.00 | 65.53 | O |
| HETATM | 3711 | O | HOH | A | 529 | 23.206 | 13.737 | 16.558 | 1.00 | 88.35 | O |
| HETATM | 3712 | O | HOH | A | 530 | −4.087 | 15.393 | 21.026 | 1.00 | 66.04 | O |
| HETATM | 3713 | O | HOH | A | 531 | −9.101 | −27.460 | 21.785 | 1.00 | 68.34 | O |
| HETATM | 3714 | O | HOH | A | 532 | −4.878 | −5.438 | 20.147 | 1.00 | 70.43 | O |
| HETATM | 3715 | O | HOH | A | 533 | −1.895 | 5.381 | 2.984 | 1.00 | 67.30 | O |
| HETATM | 3716 | O | HOH | A | 534 | 11.438 | 26.901 | 12.887 | 1.00 | 69.64 | O |
| HETATM | 3717 | O | HOH | A | 535 | −25.023 | −20.750 | 22.895 | 1.00 | 86.87 | O |
| HETATM | 3718 | O | HOH | A | 536 | 20.060 | 24.828 | 0.145 | 1.00 | 77.10 | O |
| HETATM | 3719 | O | HOH | A | 537 | −19.015 | 13.447 | −21.620 | 1.00 | 86.21 | O |
| HETATM | 3720 | O | HOH | A | 538 | −11.732 | 5.370 | 6.172 | 1.00 | 52.59 | O |
| HETATM | 3721 | O | HOH | A | 539 | −26.040 | 11.567 | −5.365 | 1.00 | 78.01 | O |
| HETATM | 3722 | O | HOH | A | 540 | 5.684 | 21.233 | −2.210 | 1.00 | 78.48 | O |
| HETATM | 3723 | O | HOH | A | 541 | −23.416 | −15.905 | 21.628 | 1.00 | 95.02 | O |
| HETATM | 3724 | O | HOH | A | 542 | −3.985 | 6.785 | −13.345 | 1.00 | 76.20 | O |
| HETATM | 3725 | O | HOH | A | 543 | −9.218 | 3.319 | 5.440 | 1.00 | 68.46 | O |
| HETATM | 3726 | O | HOH | A | 544 | 0.454 | −4.371 | 14.142 | 1.00 | 84.88 | O |
| HETATM | 3727 | O | HOH | A | 545 | 25.820 | 8.802 | 7.267 | 1.00 | 71.66 | O |
| HETATM | 3728 | O | HOH | A | 546 | −14.172 | 8.871 | 18.981 | 1.00 | 79.02 | O |
| HETATM | 3729 | O | HOH | A | 547 | 9.629 | 26.876 | −9.684 | 1.00 | 85.70 | O |
| HETATM | 3730 | O | HOH | A | 548 | −19.426 | 19.780 | 1.690 | 1.00 | 70.13 | O |
| HETATM | 3731 | O | HOH | A | 549 | 17.981 | 11.242 | 14.713 | 1.00 | 101.85 | O |
| HETATM | 3732 | O | HOH | A | 550 | −8.855 | −12.246 | 49.850 | 1.00 | 87.52 | O |
| HETATM | 3733 | O | HOH | A | 551 | −3.487 | 12.915 | 12.787 | 1.00 | 81.37 | O |
| HETATM | 3734 | O | HOH | A | 552 | −21.157 | 19.523 | −1.468 | 1.00 | 65.04 | O |
| HETATM | 3735 | O | HOH | A | 553 | −7.444 | 23.927 | 2.102 | 1.00 | 72.96 | O |
| HETATM | 3736 | O | HOH | A | 554 | 6.527 | 18.082 | −13.999 | 1.00 | 72.46 | O |
| HETATM | 3737 | O | HOH | A | 555 | 2.725 | 27.302 | 9.910 | 1.00 | 83.25 | O |
| HETATM | 3738 | O | HOH | A | 556 | 2.815 | 8.178 | 12.101 | 1.00 | 65.16 | O |
| HETATM | 3739 | O | HOH | A | 557 | −9.767 | −27.548 | 18.960 | 1.00 | 83.73 | O |
| HETATM | 3740 | O | HOH | A | 558 | −17.662 | −33.104 | 19.064 | 1.00 | 74.19 | O |
| HETATM | 3741 | O | HOH | A | 559 | −7.905 | −10.299 | 51.015 | 1.00 | 78.06 | O |
| HETATM | 3742 | O | HOH | A | 560 | −15.668 | −5.885 | 18.003 | 1.00 | 64.11 | O |
| HETATM | 3743 | O | HOH | A | 561 | 4.221 | 13.041 | 23.505 | 1.00 | 87.64 | O |
| HETATM | 3744 | O | HOH | A | 562 | −22.907 | −19.674 | 24.204 | 1.00 | 100.51 | O |
| HETATM | 3745 | O | HOH | A | 563 | −0.184 | 15.944 | −18.355 | 1.00 | 71.91 | O |
| HETATM | 3746 | O | HOH | A | 564 | 0.221 | −18.844 | 22.399 | 1.00 | 81.90 | O |
| HETATM | 3747 | O | HOH | A | 565 | −3.535 | −5.067 | 46.532 | 1.00 | 66.18 | O |
| HETATM | 3748 | O | HOH | A | 566 | −13.528 | 12.732 | 3.850 | 1.00 | 60.28 | O |
| HETATM | 3749 | O | HOH | A | 567 | −8.923 | −11.777 | 53.200 | 1.00 | 80.35 | O |
| HETATM | 3750 | O | HOH | A | 568 | −14.577 | −0.624 | 66.710 | 1.00 | 70.25 | O |
| HETATM | 3751 | O | HOH | A | 569 | 0.504 | −5.917 | 11.422 | 1.00 | 78.91 | O |
| HETATM | 3753 | O | HOH | A | 570 | −0.067 | −16.797 | 24.142 | 1.00 | 84.56 | O |
| HETATM | 3754 | O | HOH | A | 571 | −17.836 | −31.472 | 17.241 | 1.00 | 86.10 | O |
| HETATM | 3755 | O | HOH | A | 572 | −5.995 | −2.407 | −6.585 | 1.00 | 77.37 | O |
| HETATM | 3756 | O | HOH | A | 573 | −8.006 | −8.469 | 64.051 | 1.00 | 62.98 | O |
| HETATM | 3757 | O | HOH | A | 574 | −3.976 | 3.933 | 11.250 | 1.00 | 92.23 | O |
| HETATM | 3758 | O | HOH | A | 575 | −2.323 | −14.391 | 68.855 | 1.00 | 65.14 | O |
| HETATM | 3759 | O | HOH | A | 576 | −7.912 | −8.676 | 61.443 | 1.00 | 75.17 | O |
| CONECT | 507 | 1114 | | | | | | | | | |

TABLE 6-continued

HUMAN A2A ADENOSINE STRUCTURE.PDB FILE
(Table 6: discloses SEQ ID NOS 20-27, respectively, in order of appearance.)

| | | | | |
|---|---|---|---|---|
| CONECT | 523 | 1076 | | |
| CONECT | 543 | 1158 | | |
| CONECT | 1076 | 523 | | |
| CONECT | 1114 | 507 | | |
| CONECT | 1158 | 543 | | |
| CONECT | 3086 | 3107 | | |
| CONECT | 3107 | 3086 | | |
| CONECT | 3523 | 3524 | 3529 | |
| CONECT | 3524 | 3523 | 3525 | |
| CONECT | 3525 | 3524 | 3526 | 3527 |
| CONECT | 3526 | 3525 | | |
| CONECT | 3527 | 3525 | 3528 | |
| CONECT | 3528 | 3527 | 3529 | |
| CONECT | 3529 | 3523 | 3528 | 3530 |
| CONECT | 3530 | 3529 | 3531 | |
| CONECT | 3531 | 3530 | 3532 | |
| CONECT | 3532 | 3531 | 3533 | |
| CONECT | 3533 | 3532 | 3534 | 3535 |
| CONECT | 3534 | 3533 | 3540 | |
| CONECT | 3535 | 3533 | 3536 | |
| CONECT | 3536 | 3535 | 3537 | 3538 |
| CONECT | 3537 | 3536 | | |
| CONECT | 3538 | 3536 | 3539 | 3540 |
| CONECT | 3539 | 3538 | 3542 | |
| CONECT | 3540 | 3534 | 3538 | 3541 |
| CONECT | 3541 | 3540 | 3542 | |
| CONECT | 3542 | 3539 | 3541 | 3543 |
| CONECT | 3543 | 3542 | 3544 | 3547 |
| CONECT | 3544 | 3543 | 3545 | |
| CONECT | 3545 | 3544 | 3546 | |
| CONECT | 3546 | 3545 | 3547 | |
| CONECT | 3547 | 3543 | 3546 | |
| CONECT | 3548 | 3549 | 3550 | 3551 |
| CONECT | 3549 | 3548 | | |
| CONECT | 3550 | 3548 | | |
| CONECT | 3551 | 3548 | 3552 | |
| CONECT | 3552 | 3551 | 3553 | |
| CONECT | 3553 | 3552 | 3554 | |
| CONECT | 3554 | 3553 | 3555 | |
| CONECT | 3555 | 3554 | 3556 | |
| CONECT | 3556 | 3555 | 3557 | |
| CONECT | 3557 | 3556 | 3558 | |
| CONECT | 3558 | 3557 | 3559 | |
| CONECT | 3559 | 3558 | 3560 | |
| CONECT | 3560 | 3559 | 3561 | |
| CONECT | 3561 | 3560 | 3562 | |
| CONECT | 3562 | 3561 | 3563 | |
| CONECT | 3563 | 3562 | 3564 | |
| CONECT | 3564 | 3563 | 3565 | |
| CONECT | 3565 | 3564 | 3566 | |
| CONECT | 3566 | 3565 | 3567 | |
| CONECT | 3567 | 3566 | | |
| CONECT | 3568 | 3569 | 3570 | 3571 |
| CONECT | 3569 | 3568 | | |
| CONECT | 3570 | 3568 | | |
| CONECT | 3571 | 3568 | 3572 | |
| CONECT | 3572 | 3571 | 3573 | |
| CONECT | 3573 | 3572 | 3574 | |
| CONECT | 3574 | 3573 | 3575 | |
| CONECT | 3575 | 3574 | 3576 | |
| CONECT | 3576 | 3575 | 3577 | |
| CONECT | 3577 | 3576 | 3578 | |
| CONECT | 3578 | 3577 | 3579 | |
| CONECT | 3579 | 3578 | 3580 | |
| CONECT | 3580 | 3579 | 3581 | |
| CONECT | 3581 | 3580 | 3582 | |
| CONECT | 3582 | 3581 | 3583 | |
| CONECT | 3583 | 3582 | 3584 | |
| CONECT | 3584 | 3583 | 3585 | |
| CONECT | 3585 | 3584 | 3586 | |
| CONECT | 3586 | 3585 | 3587 | |
| CONECT | 3587 | 3586 | | |
| CONECT | 3588 | 3589 | 3590 | 3591 |
| CONECT | 3589 | 3588 | | |
| CONECT | 3590 | 3588 | | |
| CONECT | 3591 | 3588 | 3592 | |
| CONECT | 3592 | 3591 | 3593 | |

TABLE 6-continued

HUMAN A2A ADENOSINE STRUCTURE.PDB FILE
(Table 6: discloses SEQ ID NOS 20-27, respectively, in order of appearance.)

| | | | | | |
|---|---|---|---|---|---|
| CONECT | 3593 | 3592 | 3594 | | |
| CONECT | 3594 | 3593 | 3595 | | |
| CONECT | 3595 | 3594 | 3596 | | |
| CONECT | 3596 | 3595 | 3597 | | |
| CONECT | 3597 | 3596 | 3598 | | |
| CONECT | 3598 | 3597 | 3599 | | |
| CONECT | 3599 | 3598 | 3600 | | |
| CONECT | 3600 | 3599 | 3601 | | |
| CONECT | 3601 | 3600 | 3602 | | |
| CONECT | 3602 | 3601 | 3603 | | |
| CONECT | 3603 | 3602 | 3604 | | |
| CONECT | 3604 | 3603 | 3605 | | |
| CONECT | 3605 | 3604 | 3606 | | |
| CONECT | 3606 | 3605 | 3607 | | |
| CONECT | 3607 | 3606 | | | |
| CONECT | 3608 | 3609 | 3610 | 3611 | |
| CONECT | 3609 | 3608 | | | |
| CONECT | 3610 | 3608 | | | |
| CONECT | 3611 | 3608 | 3612 | | |
| CONECT | 3612 | 3611 | 3613 | | |
| CONECT | 3613 | 3612 | 3614 | | |
| CONECT | 3614 | 3613 | 3615 | | |
| CONECT | 3615 | 3614 | 3616 | | |
| CONECT | 3616 | 3615 | 3617 | | |
| CONECT | 3617 | 3616 | 3618 | | |
| CONECT | 3618 | 3617 | 3619 | | |
| CONECT | 3619 | 3618 | 3620 | | |
| CONECT | 3620 | 3619 | 3621 | | |
| CONECT | 3621 | 3620 | 3622 | | |
| CONECT | 3622 | 3621 | 3623 | | |
| CONECT | 3623 | 3622 | 3624 | | |
| CONECT | 3624 | 3623 | 3625 | | |
| CONECT | 3625 | 3624 | 3626 | | |
| CONECT | 3626 | 3625 | 3627 | | |
| CONECT | 3627 | 3626 | | | |
| CONECT | 3628 | 3629 | 3630 | 3631 | |
| CONECT | 3629 | 3628 | | | |
| CONECT | 3630 | 3628 | | | |
| CONECT | 3631 | 3628 | 3632 | | |
| CONECT | 3632 | 3631 | 3633 | | |
| CONECT | 3633 | 3632 | 3634 | | |
| CONECT | 3634 | 3633 | 3635 | | |
| CONECT | 3635 | 3634 | 3636 | | |
| CONECT | 3636 | 3635 | 3637 | | |
| CONECT | 3637 | 3636 | 3638 | | |
| CONECT | 3638 | 3637 | 3639 | | |
| CONECT | 3639 | 3638 | 3640 | | |
| CONECT | 3640 | 3639 | 3641 | | |
| CONECT | 3641 | 3640 | 3642 | | |
| CONECT | 3642 | 3641 | 3643 | | |
| CONECT | 3643 | 3642 | 3644 | | |
| CONECT | 3644 | 3643 | 3645 | | |
| CONECT | 3645 | 3644 | 3646 | | |
| CONECT | 3646 | 3645 | 3647 | | |
| CONECT | 3647 | 3646 | | | |
| CONECT | 3648 | 3649 | 3650 | 3651 | 3652 |
| CONECT | 3649 | 3648 | | | |
| CONECT | 3650 | 3648 | | | |
| CONECT | 3651 | 3648 | | | |
| CONECT | 3652 | 3648 | | | |
| CONECT | 3653 | 3654 | 3655 | 3656 | 3657 |
| CONECT | 3654 | 3653 | | | |
| CONECT | 3655 | 3653 | | | |
| CONECT | 3656 | 3653 | | | |
| CONECT | 3657 | 3653 | | | |
| CONECT | 3658 | 3659 | 3660 | 3661 | 3662 |
| CONECT | 3659 | 3658 | | | |
| CONECT | 3660 | 3658 | | | |
| CONECT | 3661 | 3658 | | | |
| CONECT | 3662 | 3658 | | | |
| CONECT | 3663 | 3664 | 3665 | 3666 | 3667 |
| CONECT | 3664 | 3663 | | | |
| CONECT | 3665 | 3663 | | | |
| CONECT | 3666 | 3663 | | | |
| CONECT | 3667 | 3663 | | | |
| CONECT | 3668 | 3669 | 3670 | 3671 | 3672 |
| CONECT | 3669 | 3668 | | | |

TABLE 6-continued

HUMAN A2A ADENOSINE STRUCTURE.PDB FILE
(Table 6: discloses SEQ ID NOS 20-27, respectively, in order of appearance.)

| | | | | | | | | | | | |
|---|---|---|---|---|---|---|---|---|---|---|---|
| CONECT | 3670 | 3668 | | | | | | | | | |
| CONECT | 3671 | 3668 | | | | | | | | | |
| CONECT | 3672 | 3668 | | | | | | | | | |
| CONECT | 3673 | 3674 | 3675 | 3676 | 3677 | | | | | | |
| CONECT | 3674 | 3673 | | | | | | | | | |
| CONECT | 3675 | 3673 | | | | | | | | | |
| CONECT | 3676 | 3673 | | | | | | | | | |
| CONECT | 3677 | 3673 | | | | | | | | | |
| CONECT | 3678 | 3679 | 3680 | 3681 | 3682 | | | | | | |
| CONECT | 3679 | 3678 | | | | | | | | | |
| CONECT | 3680 | 3678 | | | | | | | | | |
| CONECT | 3681 | 3678 | | | | | | | | | |
| CONECT | 3682 | 3678 | | | | | | | | | |
| MASTER | | 313 | 0 | 13 | 25 | 5 | 0 | 18 | 6 | 3758 | 1 | 168 | 38 |
| END | | | | | | | | | | | | |

INFORMAL SEQUENCE LISTING

| SEQ ID NO: | DESCRIPTION | SEQUENCE |
|---|---|---|
| SEQ ID NO: 1 | $A_{2A}$ Adenosine receptor with T4 lysozyme replacing the 3$^{rd}$ cytoplasmic loop | MKTIIALSYIFCLVFADYKDDDDAMGQPVGAPPIMGSSVYITVELAIAVLAILGWLVCW AVWLNSNLQNVTNYFWSLAAADIAVGVLAIPFAITISTGFCMCHGCLFIACFVLVLTQ SSIFSLLAIAIDRYIAIRIPLRYNGLVTGTRAKGIIAICWVLSFAIGLTPMLGWNNCGQP KEGKNHSQGCGEGQVACLFEDWPMNYMVYFNFFACVLVPLLLMLGVYLRIFLMRRQLN IFEMLRIDEGLRLKIYKDTEGYYTIGIGHLLTKSPSLNMKSELDKAIGRNTNGVITKDE AEKLFNQDVDMVRGILRNAKLKPVYDSLDAVR~LINMVFQMGETGVAGFTNSLRMLQ QKRWDEMVNLAKSRWYNQTPNRAKRVITTFRTGTWDAYRSTLQKEVHMKSLAIIVGLF ALCWLPLHIINCFTFFCPDCSHAPLWLMYLAIVLSHTNSVPFIYAYRIREFRQTFRKI IRSHVLRQQEPFKAHHHHHHHHHH |
| SEQ ID NO: 2 | ADORA2A; $A_{2A}$ adenosine receptor; P29274; protein sequence | MPIMGSSVYITVELAIAVLAILGNVLVCWAVWLNSNLQNVTNYFVVSLAAADIAVGVLAI PFAITISTGFCAACHGCLFIACFVLVLTQSSIFSLLAIAIDRYIAIRIPLRYNGLVTGTR AKGIIAICWVLSFAIGLTPMLGWNNCGQPKEGKNHSQGCGEGQVACLFEDVVPMNYMVYF NFFACVLVPLLLMLGVYLRIFLAARRQLKQMESQPLPGERARSTLQKEVHAAKSLAIIVG LFALCWLPLHIINCFTFFCPDCSHAPLWLMYLAIVLSHTNSVVNPFIYAYRIREFRQTFR KIIRSHVLRQQEPFKAAGTSARVLAAHGSDGEQVSLRLNGHPPGVWANGSAPHPERRPNG YALGLVSGGSAQESQGNTGLPDVELLSHELKGVCPEPPGLDDPLAQDGAGVS |
| SEQ ID NO: 3 | Human β2 adrenergic receptor; protein sequence | MGQPGNGSAFLLAPNRSHAPDHDVTQQRDEVWVVGMGIVMSLIV LAIVFGNVLVITAIAKFERLQTVTNYFITSLACADLVMGLAVVPFGAAHILMKMWTFG NFWCEFWTSIDVLCVTASIETLCVIAVDRYFAITSPFKYQSLLTKNKARVIILMVWIV SGLTSFLPIQMHWYRATHQEAINCYANETCCDFFTNQAYAIASSIVSFYVPLVIMVFV YSRVFQEAKRQLQKIDKSEGRFHVQNLSQVEQDGRTGHGLRRSSKFCLKEHKALKTLG IIMGTFTLCWLPFFIVNIVHVIQDNLIRKEVYILLNWIGYVNSGFNPLIYCRSPDFRI AFQELLCLRRSSLKAYGNGYSSNGNTGEQSGYHVEQEKENKLLCEDLPGTEDFVGHQG TVPSDNIDSQGRNCSTNDSLL |
| SEQ ID NO: 4 | TACR1; tachykinin receptor 1; NM_001058; protein sequence | MDNVLPVDSDLSPNISTNTSEPNQFVQPAWQIVLWAAAYTVIVV TSVVGNVVVMWIILAHKRMRTVTNYFLVNLAFAEASMAAFNTVVNFTYAVHNEWYYGL FYCKFHNFFPIAAVFASIYSMTAVAFDRYMAIIHPLQPRLSATATKVVICVIWVLALL LAFPQGYYSTTETMPSRVVCMIEWPEHPNKIYEKVYHICVTVLIYFLPLLVIGYAYTV VGITLWASEIPGDSSDRYHEQVSAKRKVVKMMIVVVCTFAICWLPFHIFFLLPYINPD LYLKKFIQQVYLAIMWLAMSSTMYNPIIYCCLNDRFRLGFKHAFRCCPFISAGDYEGL EMKSTRYLQTQGSVYKVSRLETTISTVVGAHEEEPEDGPKATPSSLDLTSNCSSRSDS KTMTESFSFSSNVLS |
| SEQ ID NO: 5 | ADRA1A; adrenergic, alpha-1A-, receptor; NM_000680; protein sequence | MVFLSGNASDSSNCTQPPAPVNISKAILLGVILGGLILFGVLGN ILVILSVACHRHLHSVTHYYIVNLAVADLLLTSTVLPFSAIFEVLGYWAFGRVFCNIW AAVDVLCCTASIMGLCIISIDRYIGVSYPLRYPTIVTQRRGLMALLCVWALSLVISIG PLFGWRQPAPEDETICQINEEPGYVLFSALGSFYLPLAIILVMYCRVYVVAKRESRGL KSGLKTDKSDSEQVTLRIHRKNAPAGGSGMASAKTKTHFSVRLLKFSREKKAAKTLGI VVGCFVLCWLPFFLVMPIGSFFPDFKPSETVFKIVFWLGYLNSCINPIIYPCSSQEFK KAFQNVLRIQCLCRKQSSKHALGYTLHPPSQAVEGQHKDMVRIPVGSRETFYRISKTD GVCEWKFFSSMPRGSARITVSKDQSSCTTARVRSKSFLQVCCCVGPSTPSLDKNHQVP TIKVHTISLSENGEEV |
| SEQ ID NO: 6 | CHRM1; cholinergic receptor, muscarinic 1; | MNTSAPPAVSPNITVLAPGKGPWQVAFIGITTGLLSLATVTGNL LVLISFKVNTELKTVNNYFLLSLACADLIIGTFSMNLYTTYLLMGHWALGTLACDLWL ALDYVASNASVMNLLLISFDRYFSVTRPLSYRAKRTPRRAALMIGLAWLVSFVLWAPA ILFWQYLVGERTVLAGQCYIQFLSQPIITFGTAMAAFYLPVTVMCTLYWRIYRETENR |

INFORMAL SEQUENCE LISTING

| SEQ ID NO: | DESCRIPTION | SEQUENCE |
|---|---|---|
| | NM_000738; protein sequence | ARELAALQGSETPGKGGGSSSSSERSQPGAEGSPETPPGRCCRCCRAPRLLQAYSWKE EEEEDEGSMESLTSSEGEEPGSEVVIKMPMVDPEAQAPTKQPPRSSPNTVKRPTKKGR DRAGKGQKPRGKEQLAKRKTFSLVKEKKAARTLSAILLAFILTWTPYNIMVLVSTFCK DCVPETLWELGYWLCYVNSTINPMCYALCNKAFRDTFRLLLLCRWDKRRWRKIPKRPG SVHRTPSRQC |
| SEQ ID NO: 7 | DRD2; dopamine receptor D2; NM_000795; protein sequence | MDPLNLSWYDDDLERQNWSRPFNGSDGKADRPHYNYYATLLTLL IAVIVEGNVLVCMAVSREKALQTTTNYLIVSLAVADLLVATLVMPWVVYLEVVGEWKE SRIHCDIFVTLDVMMCTASILNLCAISIDRYTAVAMPMLYNTRYSSKRRVTVMISIVW VLSFTISCPLLFGLNNADQNECIIANPAFVVYSSIVSFYVPFIVTLLVYIKIYIVLRR RRKRVNTKRSSRAFRAHLRAPLKGNCTHPEDMKLCTVIMKSNGSFPVNRRRVEAARRA QELEMEMLSSTSPPERTRYSPIPPSHHQLTLPDPSHHGLHSTPDSPAKPEKNGHAKDH PKIAKIFEIQTMPNGKTRTSLKTMSRRKLSQQKEKKATQMLAIVLGVFIICWLPFFIT HILNIHCDCNIPPVLYSAFTWLGYVNSAVNPIIYTTFNIEFRKAFLKILHC |
| SEQ ID NO: 8 | EDG1; endothelial differentiation, sphingolipidG- protein-coupled receptor, 1; NM_001400; protein sequence | MGPTSVPLVKAHRSSVSDYVNYDIIVRHYNYTGKLNISADKENS IKLTSVVFILICCFIILENIFVLLTIWKTKKFHRPMYYFIGNLALSDLLAGVAYTANL LLSGATTYKLTPAQWFLREGSMFVALSASVFSLLAIAIERYITMLKMKLHNGSNNFRL FLLISACWVISLILGGLPIMGWNCISALSSCSTVLPLYHKHYILFCTTVPILLLLSIV ILYCRIYSLVRTRSRRLTFRKNISKASRSSEKSLALLKTVIIVLSVFIACWAPLFILL LLDVGCKVKTCDILFRAEYFLVLAVLNSGTNPIIYTLTNKEMRRAFIRIMSCCKCPSG DSAGKFKRPIIAGMEFSRSKSDNSSHPQKDEGDNPETIMSSGNVNSSS |
| SEQ ID NO: 9 | HTR1A; 5- hydroxytryptamine (serotonin) receptor 1A; NM_000524; protein sequence | MDVLSPGQGNNTTSPPAPFETGGNTTGISDVTVSYQVITSLLLG TLIFCAVLGNACVVAAIALERSLQNVANYLIGSLAVTDLMVSVLVLPMAALYQVLNKW TLGQVTCDLFIALDVLCCTSSILHLCAIALDRYWAITDPIDYVNKRTPRRAAALISLT WLIGFLISIPPMLGWRTPEDRSDPDACTISKDHGYTIYSTFGAFYIPLLLMLVLYGRI FRAARFRIRKTVKKVEKTGADTRHGASPAPQPKKSVNGESGSRNWRLGVESKAGGALC ANGAVRQGDDGAALEVIEVHRVGNSKEHLPLPSEAGPTPCAPASFERKNERNAEAKRK MALARERKTVKTLGIIMGTFILCWLPFFIVALVLPFCESSCHMPTLLGAIINWLGYSN SLLNPVIYAYFNKDFQNAFKKIIKCKFCRQ |
| SEQ ID NO: 10 | MC2R; melanocortin 2 receptor (adrenocorticotropi c hormone); NM_000529; protein sequence | MKHIINSYENINNTARNNSDCPRVVLPEEIFFTISIVGVLENLI VLLAVFKNKNLQAPMYFFICSLAISDMLGSLYKILENILIILRNMGYLKPRGSFETTA DDIIDSLFVLSLLGSIFSLSVIAADRYITIFHALRYHSIVTMRRTVVVLTVIWTFCTG TGITMVIFSHHVPTVITFTSLFPLMLVFILCLYVHMFLLARSHTRKISTLPRANMKGA ITLTILLGVFIFCWAPFVLHVLLMTFCPSNPYCACYMSLFQVNGMLIMCNAVIDPFIY AFRSPELRDAFKKMIFCSRYW |
| SEQ ID NO: 11 | NTSR1; neurotensin receptor 1; NM_002531; protein sequence | MRLNSSAPGTPGTPAADPFQRAQAGLEEALLAPGFGNASGNASE RVLAAPSSELDVNTDIYSKVLVTAVYLALFVVGTVGNTVTAFTLARKKSLQSLQSTVH YHLGSLALSDLLTLLLAMPVELYNFIWVHHPWAFGDAGCRGYYFLRDACTYATALNVA SLSVERYLAICHPPFKAKTLMSRSRTKKFISAIWLASALLAVPMLFTMGEQNASGQH AGGLVCTPTIHTATVKVVIQVNTFMSFIFPMVVISVLTIIANKLTVMVRQAAEQGQV CTVGGEHSTFSMAIEPGRVQALRHGVRVLRAVVIAFVVCWLPYHVRRLMFCYISDEQW TPFLYDFYHYFYMVTNALFYVSSTINPILYNLVSANFRHIFLATLACLCPVWRRRKR PAFSRKADSVSSNHTLSSNATRETLY |
| SEQ ID NO: 12 | OXTR; oxytocin receptor; NM_000916; protein sequence | MEGALAANWSAEAANASAAPPGAEGNRTAGPPRRNEALARVEVA VLCLILLLALSGNACVLLALRTTRQKHSRLFFFMKHLSIADLVVAVFQVLPQLLWDIT FRFYGPDLLCRLVKYLQVVGMFASTYLLLLMSLDRCLAICQPLRSLRRRTDRLAVLAT WLGCLVASAPQVHIFSLREVADGVFDCWAVFIQPWGPKAYITWITLAVYIVPVIVLAA CYGLISFKIWQNLRLKTAAAAAAEAPEGAAAGDGGRVALARVSSVKLISKAKIRTVKM TFIIVLAFIVCWTPFFFVQMWSVWDANAPKEASAFIIVMLLASLNSCCNPWIYMLFTG HLFHELVQRFLCCSASYLKGRRLGETSASKKSNSSSFVLSHRSSSQRSCSQPSTA |

We claim:

1. A crystalline form of a human $A_{2A}$ adenosine receptor protein in complex with (4-(2-[7-amino-2-(2-furyl)-[1,2,4]triazolo-[2,3-a][1,3,5]triazin-5-ylamino]ethyl)-phenol (ZM241385), wherein the human $A_{2A}$ adenosine receptor protein comprises the amino acid sequence of SEQ ID NO: 1 and the crystalline form is of space group $P2_1$ and has unit cell dimensions of a=47.7±0.5 Angstroms, b=76.9±0.5 Angstroms, and c=86.8±0.5 Angstroms, and β=101.3°.

2. The crystalline form of claim 1, wherein said human $A_{2A}$ adenosine receptor protein comprises a binding pocket I site, and wherein said binding pocket I comprises a plurality of amino acid residues selected from the group consisting of $Phe168^{5.29}$, $Ile274^{7.39}$, $Glu169^{5.30}$, $Leu249^{6.51}$, and $Asn253^{6.55}$.

3. The crystalline form of claim 1, wherein said human $A_{2A}$ adenosine receptor protein comprises a binding pocket II site, and wherein said binding pocket II comprises amino acid residues $Phe62^{2.60}$, $Ile66^{2.64}$, $Ile80^{3.28}$, $Val84^{3.32}$, $Phe168^{5.29}$, $Leu249^{6.51}$, $Ile274^{7.39}$ and $His278^{7.43}$.

4. The crystalline form of claim 1, wherein said human $A_{2A}$ adenosine receptor protein comprises a binding pocket III site, and wherein said binding pocket III site comprises a plurality of amino acid residues selected from the group consisting of $Leu48^{2.46}$, $Ala51^{2.49}$, $Asp52^{2.50}$, $Val55^{2.53}$, $Val84^{3.32}$, $Leu87^{3.35}$, $Thr88^{3.36}$, $Ser91^{3.39}$, $Leu95^{3.43}$, $Ile238^{6.40}$, $Phe242^{6.44}$, $Trp246^{6.48}$, $Ser277^{7.42}$, $His278^{7.43}$, $Asn280^{7.45}$, $Ser281^{7.46}$ and $Asn284^{7.49}$.

* * * * *

UNITED STATES PATENT AND TRADEMARK OFFICE
CERTIFICATE OF CORRECTION

PATENT NO. : 8,536,306 B2  
APPLICATION NO. : 13/121923  
DATED : September 17, 2013  
INVENTOR(S) : Raymond C. Stevens et al.

Page 1 of 1

It is certified that error appears in the above-identified patent and that said Letters Patent is hereby corrected as shown below:

On the Title Page, Item (56)

Page 3, Right Column, Line 12, after "Adrenergic Receptor Activation" delete "," and insert --: Modulation Of The Proline Kink In Transmembrane 6 By A Rotamer Toggle Switch--.

Page 3, Right Column, Line 13, after "Oct. 25, 2002, pp. 40989-" delete "10996" and insert --40996--.

Signed and Sealed this  
Twenty-first Day of October, 2014

Michelle K. Lee  
*Deputy Director of the United States Patent and Trademark Office*

SEQUENCE LISTING

<160> NUMBER OF SEQ ID NOS: 36

<210> SEQ ID NO 1
<211> LENGTH: 490
<212> TYPE: PRT
<213> ORGANISM: Artificial Sequence
<220> FEATURE:
<223> OTHER INFORMATION: Description of Artificial Sequence: Synthetic polypeptide -continued

<400> SEQUENCE: 1

```
Met Lys Thr Ile Ile Ala Leu Ser Tyr Ile Phe Cys Leu Val Phe Ala
1               5                   10                  15

Asp Tyr Lys Asp Asp Asp Ala Met Gly Gln Pro Val Gly Ala Pro
            20                  25                  30

Pro Ile Met Gly Ser Ser Val Tyr Ile Thr Val Glu Leu Ala Ile Ala
            35                  40                  45

Val Leu Ala Ile Leu Gly Trp Leu Val Cys Trp Ala Val Trp Leu Asn
50                  55                  60

Ser Asn Leu Gln Asn Val Thr Asn Tyr Phe Trp Ser Leu Ala Ala Ala
65                  70                  75                  80

Asp Ile Ala Val Gly Val Leu Ala Ile Pro Phe Ala Ile Thr Ile Ser
                85                  90                  95

Thr Gly Phe Cys Met Cys His Gly Cys Leu Phe Ile Ala Cys Phe Val
            100                 105                 110

Leu Val Leu Thr Gln Ser Ser Ile Phe Ser Leu Leu Ala Ile Ala Ile
            115                 120                 125

Asp Arg Tyr Ile Ala Ile Arg Ile Pro Leu Arg Tyr Asn Gly Leu Val
130                 135                 140

Thr Gly Thr Arg Ala Lys Gly Ile Ile Ala Ile Cys Trp Val Leu Ser
145                 150                 155                 160

Phe Ala Ile Gly Leu Thr Pro Met Leu Gly Trp Asn Asn Cys Gly Gln
                165                 170                 175

Pro Lys Glu Gly Lys Asn His Ser Gln Gly Cys Gly Glu Gly Gln Val
            180                 185                 190

Ala Cys Leu Phe Glu Asp Trp Pro Met Asn Tyr Met Val Tyr Phe Asn
            195                 200                 205

Phe Phe Ala Cys Val Leu Val Pro Leu Leu Leu Met Leu Gly Val Tyr
210                 215                 220

Leu Arg Ile Phe Leu Met Arg Arg Gln Leu Asn Ile Phe Glu Met Leu
225                 230                 235                 240

Arg Ile Asp Glu Gly Leu Arg Leu Lys Ile Tyr Lys Asp Thr Glu Gly
                245                 250                 255

Tyr Tyr Thr Ile Gly Ile Gly His Leu Leu Thr Lys Ser Pro Ser Leu
            260                 265                 270

Asn Met Lys Ser Glu Leu Asp Lys Ala Ile Gly Arg Asn Thr Asn Gly
            275                 280                 285

Val Ile Thr Lys Asp Glu Ala Glu Lys Leu Phe Asn Gln Asp Val Asp
290                 295                 300

Met Val Arg Gly Ile Leu Arg Asn Ala Lys Leu Lys Pro Val Tyr Asp
305                 310                 315                 320

Ser Leu Asp Ala Val Arg Leu Ile Asn Met Val Phe Gln Met Gly Glu
                325                 330                 335

Thr Gly Val Ala Gly Phe Thr Asn Ser Leu Arg Met Leu Gln Gln Lys
            340                 345                 350

Arg Trp Asp Glu Met Val Asn Leu Ala Lys Ser Arg Trp Tyr Asn Gln
            355                 360                 365

Thr Pro Asn Arg Ala Lys Arg Val Ile Thr Thr Phe Arg Thr Gly Thr
370                 375                 380

Trp Asp Ala Tyr Arg Ser Thr Leu Gln Lys Glu Val His Met Lys Ser
385                 390                 395                 400

Leu Ala Ile Ile Val Gly Leu Phe Ala Leu Cys Trp Leu Pro Leu His
                405                 410                 415
```

```
Ile Ile Asn Cys Phe Thr Phe Phe Cys Pro Asp Cys Ser His Ala Pro
            420                 425                 430

Leu Trp Leu Met Tyr Leu Ala Ile Val Leu Ser His Thr Asn Ser Val
            435                 440                 445

Pro Phe Ile Tyr Ala Tyr Arg Ile Arg Glu Phe Arg Gln Thr Phe Arg
            450                 455                 460

Lys Ile Ile Arg Ser His Val Leu Arg Gln Gln Glu Pro Phe Lys Ala
465                 470                 475                 480

His His His His His His His His His
                485                 490

<210> SEQ ID NO 2
<211> LENGTH: 412
<212> TYPE: PRT
<213> ORGANISM: Homo sapiens

<400> SEQUENCE: 2

Met Pro Ile Met Gly Ser Ser Val Tyr Ile Thr Val Glu Leu Ala Ile
1               5                   10                  15

Ala Val Leu Ala Ile Leu Gly Asn Val Leu Val Cys Trp Ala Val Trp
            20                  25                  30

Leu Asn Ser Asn Leu Gln Asn Val Thr Asn Tyr Phe Val Val Ser Leu
            35                  40                  45

Ala Ala Ala Asp Ile Ala Val Gly Val Leu Ala Ile Pro Phe Ala Ile
        50                  55                  60

Thr Ile Ser Thr Gly Phe Cys Ala Ala Cys His Gly Cys Leu Phe Ile
65                  70                  75                  80

Ala Cys Phe Val Leu Val Leu Thr Gln Ser Ser Ile Phe Ser Leu Leu
                85                  90                  95

Ala Ile Ala Ile Asp Arg Tyr Ile Ala Ile Arg Ile Pro Leu Arg Tyr
            100                 105                 110

Asn Gly Leu Val Thr Gly Thr Arg Ala Lys Gly Ile Ile Ala Ile Cys
            115                 120                 125

Trp Val Leu Ser Phe Ala Ile Gly Leu Thr Pro Met Leu Gly Trp Asn
        130                 135                 140

Asn Cys Gly Gln Pro Lys Glu Gly Lys Asn His Ser Gln Gly Cys Gly
145                 150                 155                 160

Glu Gly Gln Val Ala Cys Leu Phe Glu Asp Val Val Pro Met Asn Tyr
                165                 170                 175

Met Val Tyr Phe Asn Phe Phe Ala Cys Val Leu Val Pro Leu Leu Leu
            180                 185                 190

Met Leu Gly Val Tyr Leu Arg Ile Phe Leu Ala Ala Arg Arg Gln Leu
            195                 200                 205

Lys Gln Met Glu Ser Gln Pro Leu Pro Gly Glu Arg Ala Arg Ser Thr
        210                 215                 220

Leu Gln Lys Glu Val His Ala Ala Lys Ser Leu Ala Ile Ile Val Gly
225                 230                 235                 240

Leu Phe Ala Leu Cys Trp Leu Pro Leu His Ile Ile Asn Cys Phe Thr
                245                 250                 255

Phe Phe Cys Pro Asp Cys Ser His Ala Pro Leu Trp Leu Met Tyr Leu
            260                 265                 270

Ala Ile Val Leu Ser His Thr Asn Ser Val Val Asn Pro Phe Ile Tyr
            275                 280                 285

Ala Tyr Arg Ile Arg Glu Phe Arg Gln Thr Phe Arg Lys Ile Ile Arg
        290                 295                 300
```

```
Ser His Val Leu Arg Gln Gln Glu Pro Phe Lys Ala Ala Gly Thr Ser
305                 310                 315                 320

Ala Arg Val Leu Ala Ala His Gly Ser Asp Gly Glu Gln Val Ser Leu
            325                 330                 335

Arg Leu Asn Gly His Pro Pro Gly Val Trp Ala Asn Gly Ser Ala Pro
        340                 345                 350

His Pro Glu Arg Arg Pro Asn Gly Tyr Ala Leu Gly Leu Val Ser Gly
    355                 360                 365

Gly Ser Ala Gln Glu Ser Gln Gly Asn Thr Gly Leu Pro Asp Val Glu
370                 375                 380

Leu Leu Ser His Glu Leu Lys Gly Val Cys Pro Glu Pro Pro Gly Leu
385                 390                 395                 400

Asp Asp Pro Leu Ala Gln Asp Gly Ala Gly Val Ser
            405                 410

<210> SEQ ID NO 3
<211> LENGTH: 413
<212> TYPE: PRT
<213> ORGANISM: Homo sapiens

<400> SEQUENCE: 3

Met Gly Gln Pro Gly Asn Gly Ser Ala Phe Leu Leu Ala Pro Asn Arg
1               5                   10                  15

Ser His Ala Pro Asp His Asp Val Thr Gln Gln Arg Asp Glu Val Trp
            20                  25                  30

Val Val Gly Met Gly Ile Val Met Ser Leu Ile Val Leu Ala Ile Val
        35                  40                  45

Phe Gly Asn Val Leu Val Ile Thr Ala Ile Ala Lys Phe Glu Arg Leu
    50                  55                  60

Gln Thr Val Thr Asn Tyr Phe Ile Thr Ser Leu Ala Cys Ala Asp Leu
65                  70                  75                  80

Val Met Gly Leu Ala Val Val Pro Phe Gly Ala Ala His Ile Leu Met
                85                  90                  95

Lys Met Trp Thr Phe Gly Asn Phe Trp Cys Glu Phe Trp Thr Ser Ile
            100                 105                 110

Asp Val Leu Cys Val Thr Ala Ser Ile Glu Thr Leu Cys Val Ile Ala
        115                 120                 125

Val Asp Arg Tyr Phe Ala Ile Thr Ser Pro Phe Lys Tyr Gln Ser Leu
    130                 135                 140

Leu Thr Lys Asn Lys Ala Arg Val Ile Ile Leu Met Val Trp Ile Val
145                 150                 155                 160

Ser Gly Leu Thr Ser Phe Leu Pro Ile Gln Met His Trp Tyr Arg Ala
                165                 170                 175

Thr His Gln Glu Ala Ile Asn Cys Tyr Ala Asn Glu Thr Cys Cys Asp
            180                 185                 190

Phe Phe Thr Asn Gln Ala Tyr Ala Ile Ala Ser Ser Ile Val Ser Phe
        195                 200                 205

Tyr Val Pro Leu Val Ile Met Val Phe Val Tyr Ser Arg Val Phe Gln
    210                 215                 220

Glu Ala Lys Arg Gln Leu Gln Lys Ile Asp Lys Ser Glu Gly Arg Phe
225                 230                 235                 240

His Val Gln Asn Leu Ser Gln Val Glu Gln Asp Gly Arg Thr Gly His
                245                 250                 255

Gly Leu Arg Arg Ser Ser Lys Phe Cys Leu Lys Glu His Lys Ala Leu
            260                 265                 270
```

```
Lys Thr Leu Gly Ile Ile Met Gly Thr Phe Thr Leu Cys Trp Leu Pro
            275                 280                 285

Phe Phe Ile Val Asn Ile Val His Val Ile Gln Asp Asn Leu Ile Arg
        290                 295                 300

Lys Glu Val Tyr Ile Leu Leu Asn Trp Ile Gly Tyr Val Asn Ser Gly
305                 310                 315                 320

Phe Asn Pro Leu Ile Tyr Cys Arg Ser Pro Asp Phe Arg Ile Ala Phe
                325                 330                 335

Gln Glu Leu Leu Cys Leu Arg Arg Ser Ser Leu Lys Ala Tyr Gly Asn
                340                 345                 350

Gly Tyr Ser Ser Asn Gly Asn Thr Gly Glu Gln Ser Gly Tyr His Val
            355                 360                 365

Glu Gln Glu Lys Glu Asn Lys Leu Leu Cys Glu Asp Leu Pro Gly Thr
        370                 375                 380

Glu Asp Phe Val Gly His Gln Gly Thr Val Pro Ser Asp Asn Ile Asp
385                 390                 395                 400

Ser Gln Gly Arg Asn Cys Ser Thr Asn Asp Ser Leu Leu
                405                 410

<210> SEQ ID NO 4
<211> LENGTH: 407
<212> TYPE: PRT
<213> ORGANISM: Homo sapiens

<400> SEQUENCE: 4

Met Asp Asn Val Leu Pro Val Asp Ser Asp Leu Ser Pro Asn Ile Ser
1               5                   10                  15

Thr Asn Thr Ser Glu Pro Asn Gln Phe Val Gln Pro Ala Trp Gln Ile
            20                  25                  30

Val Leu Trp Ala Ala Ala Tyr Thr Val Ile Val Val Thr Ser Val Val
        35                  40                  45

Gly Asn Val Val Val Met Trp Ile Ile Leu Ala His Lys Arg Met Arg
    50                  55                  60

Thr Val Thr Asn Tyr Phe Leu Val Asn Leu Ala Phe Ala Glu Ala Ser
65                  70                  75                  80

Met Ala Ala Phe Asn Thr Val Val Asn Phe Thr Tyr Ala Val His Asn
                85                  90                  95

Glu Trp Tyr Tyr Gly Leu Phe Tyr Cys Lys Phe His Asn Phe Phe Pro
            100                 105                 110

Ile Ala Ala Val Phe Ala Ser Ile Tyr Ser Met Thr Ala Val Ala Phe
        115                 120                 125

Asp Arg Tyr Met Ala Ile Ile His Pro Leu Gln Pro Arg Leu Ser Ala
    130                 135                 140

Thr Ala Thr Lys Val Val Ile Cys Val Ile Trp Val Leu Ala Leu Leu
145                 150                 155                 160

Leu Ala Phe Pro Gln Gly Tyr Tyr Ser Thr Thr Glu Thr Met Pro Ser
                165                 170                 175

Arg Val Val Cys Met Ile Glu Trp Pro Glu His Pro Asn Lys Ile Tyr
            180                 185                 190

Glu Lys Val Tyr His Ile Cys Val Thr Val Leu Ile Tyr Phe Leu Pro
        195                 200                 205

Leu Leu Val Ile Gly Tyr Ala Tyr Thr Val Val Gly Ile Thr Leu Trp
    210                 215                 220

Ala Ser Glu Ile Pro Gly Asp Ser Ser Asp Arg Tyr His Glu Gln Val
225                 230                 235                 240
```

```
Ser Ala Lys Arg Lys Val Val Lys Met Met Ile Val Val Cys Thr
            245                 250                 255

Phe Ala Ile Cys Trp Leu Pro Phe His Ile Phe Phe Leu Leu Pro Tyr
            260                 265                 270

Ile Asn Pro Asp Leu Tyr Leu Lys Lys Phe Ile Gln Gln Val Tyr Leu
            275                 280                 285

Ala Ile Met Trp Leu Ala Met Ser Ser Thr Met Tyr Asn Pro Ile Ile
            290                 295                 300

Tyr Cys Cys Leu Asn Asp Arg Phe Arg Leu Gly Phe Lys His Ala Phe
305                 310                 315                 320

Arg Cys Cys Pro Phe Ile Ser Ala Gly Asp Tyr Glu Gly Leu Glu Met
                325                 330                 335

Lys Ser Thr Arg Tyr Leu Gln Thr Gln Gly Ser Val Tyr Lys Val Ser
                340                 345                 350

Arg Leu Glu Thr Thr Ile Ser Thr Val Val Gly Ala His Glu Glu Glu
                355                 360                 365

Pro Glu Asp Gly Pro Lys Ala Thr Pro Ser Ser Leu Asp Leu Thr Ser
            370                 375                 380

Asn Cys Ser Ser Arg Ser Asp Ser Lys Thr Met Thr Glu Ser Phe Ser
385                 390                 395                 400

Phe Ser Ser Asn Val Leu Ser
                405

<210> SEQ ID NO 5
<211> LENGTH: 466
<212> TYPE: PRT
<213> ORGANISM: Homo sapiens

<400> SEQUENCE: 5

Met Val Phe Leu Ser Gly Asn Ala Ser Asp Ser Ser Asn Cys Thr Gln
1               5                   10                  15

Pro Pro Ala Pro Val Asn Ile Ser Lys Ala Ile Leu Leu Gly Val Ile
            20                  25                  30

Leu Gly Gly Leu Ile Leu Phe Gly Val Leu Gly Asn Ile Leu Val Ile
        35                  40                  45

Leu Ser Val Ala Cys His Arg His Leu His Ser Val Thr His Tyr Tyr
    50                  55                  60

Ile Val Asn Leu Ala Val Ala Asp Leu Leu Leu Thr Ser Thr Val Leu
65                  70                  75                  80

Pro Phe Ser Ala Ile Phe Glu Val Leu Gly Tyr Trp Ala Phe Gly Arg
                85                  90                  95

Val Phe Cys Asn Ile Trp Ala Ala Val Asp Val Leu Cys Cys Thr Ala
            100                 105                 110

Ser Ile Met Gly Leu Cys Ile Ile Ser Ile Asp Arg Tyr Ile Gly Val
        115                 120                 125

Ser Tyr Pro Leu Arg Tyr Pro Thr Ile Val Thr Gln Arg Arg Gly Leu
    130                 135                 140

Met Ala Leu Leu Cys Val Trp Ala Leu Ser Leu Val Ile Ser Ile Gly
145                 150                 155                 160

Pro Leu Phe Gly Trp Arg Gln Pro Ala Pro Glu Asp Glu Thr Ile Cys
                165                 170                 175

Gln Ile Asn Glu Glu Pro Gly Tyr Val Leu Phe Ser Ala Leu Gly Ser
            180                 185                 190

Phe Tyr Leu Pro Leu Ala Ile Ile Leu Val Met Tyr Cys Arg Val Tyr
        195                 200                 205
```

```
Val Val Ala Lys Arg Glu Ser Arg Gly Leu Lys Ser Gly Leu Lys Thr
    210                 215                 220

Asp Lys Ser Asp Ser Glu Gln Val Thr Leu Arg Ile His Arg Lys Asn
225                 230                 235                 240

Ala Pro Ala Gly Gly Ser Gly Met Ala Ser Ala Lys Thr Lys Thr His
                245                 250                 255

Phe Ser Val Arg Leu Leu Lys Phe Ser Arg Glu Lys Lys Ala Ala Lys
                260                 265                 270

Thr Leu Gly Ile Val Val Gly Cys Phe Val Leu Cys Trp Leu Pro Phe
            275                 280                 285

Phe Leu Val Met Pro Ile Gly Ser Phe Phe Pro Asp Phe Lys Pro Ser
    290                 295                 300

Glu Thr Val Phe Lys Ile Val Phe Trp Leu Gly Tyr Leu Asn Ser Cys
305                 310                 315                 320

Ile Asn Pro Ile Ile Tyr Pro Cys Ser Ser Gln Glu Phe Lys Lys Ala
                325                 330                 335

Phe Gln Asn Val Leu Arg Ile Gln Cys Leu Cys Arg Lys Gln Ser Ser
                340                 345                 350

Lys His Ala Leu Gly Tyr Thr Leu His Pro Pro Ser Gln Ala Val Glu
            355                 360                 365

Gly Gln His Lys Asp Met Val Arg Ile Pro Val Gly Ser Arg Glu Thr
    370                 375                 380

Phe Tyr Arg Ile Ser Lys Thr Asp Gly Val Cys Glu Trp Lys Phe Phe
385                 390                 395                 400

Ser Ser Met Pro Arg Gly Ser Ala Arg Ile Thr Val Ser Lys Asp Gln
                405                 410                 415

Ser Ser Cys Thr Thr Ala Arg Val Arg Ser Lys Ser Phe Leu Gln Val
                420                 425                 430

Cys Cys Cys Val Gly Pro Ser Thr Pro Ser Leu Asp Lys Asn His Gln
            435                 440                 445

Val Pro Thr Ile Lys Val His Thr Ile Ser Leu Ser Glu Asn Gly Glu
    450                 455                 460

Glu Val
465

<210> SEQ ID NO 6
<211> LENGTH: 460
<212> TYPE: PRT
<213> ORGANISM: Homo sapiens

<400> SEQUENCE: 6

Met Asn Thr Ser Ala Pro Pro Ala Val Ser Pro Asn Ile Thr Val Leu
1               5                   10                  15

Ala Pro Gly Lys Gly Pro Trp Gln Val Ala Phe Ile Gly Ile Thr Thr
                20                  25                  30

Gly Leu Leu Ser Leu Ala Thr Val Thr Gly Asn Leu Leu Val Leu Ile
            35                  40                  45

Ser Phe Lys Val Asn Thr Glu Leu Lys Thr Val Asn Asn Tyr Phe Leu
    50                  55                  60

Leu Ser Leu Ala Cys Ala Asp Leu Ile Ile Gly Thr Phe Ser Met Asn
65                  70                  75                  80

Leu Tyr Thr Thr Tyr Leu Leu Met Gly His Trp Ala Leu Gly Thr Leu
                85                  90                  95

Ala Cys Asp Leu Trp Leu Ala Leu Asp Tyr Val Ala Ser Asn Ala Ser
            100                 105                 110
```

```
Val Met Asn Leu Leu Leu Ile Ser Phe Asp Arg Tyr Phe Ser Val Thr
    115                 120                 125

Arg Pro Leu Ser Tyr Arg Ala Lys Arg Thr Pro Arg Arg Ala Ala Leu
    130                 135                 140

Met Ile Gly Leu Ala Trp Leu Val Ser Phe Val Leu Trp Ala Pro Ala
145                 150                 155                 160

Ile Leu Phe Trp Gln Tyr Leu Val Gly Glu Arg Thr Val Leu Ala Gly
                165                 170                 175

Gln Cys Tyr Ile Gln Phe Leu Ser Gln Pro Ile Ile Thr Phe Gly Thr
                180                 185                 190

Ala Met Ala Ala Phe Tyr Leu Pro Val Thr Val Met Cys Thr Leu Tyr
        195                 200                 205

Trp Arg Ile Tyr Arg Glu Thr Glu Asn Arg Ala Arg Glu Leu Ala Ala
    210                 215                 220

Leu Gln Gly Ser Glu Thr Pro Gly Lys Gly Gly Gly Ser Ser Ser Ser
225                 230                 235                 240

Ser Glu Arg Ser Gln Pro Gly Ala Glu Gly Ser Pro Glu Thr Pro Pro
                245                 250                 255

Gly Arg Cys Cys Arg Cys Cys Arg Ala Pro Arg Leu Leu Gln Ala Tyr
                260                 265                 270

Ser Trp Lys Glu Glu Glu Glu Asp Glu Gly Ser Met Glu Ser Leu
        275                 280                 285

Thr Ser Ser Glu Gly Glu Glu Pro Gly Ser Glu Val Val Ile Lys Met
    290                 295                 300

Pro Met Val Asp Pro Glu Ala Gln Ala Pro Thr Lys Gln Pro Pro Arg
305                 310                 315                 320

Ser Ser Pro Asn Thr Val Lys Arg Pro Thr Lys Lys Gly Arg Asp Arg
                325                 330                 335

Ala Gly Lys Gly Gln Lys Pro Arg Gly Lys Glu Gln Leu Ala Lys Arg
                340                 345                 350

Lys Thr Phe Ser Leu Val Lys Glu Lys Lys Ala Ala Arg Thr Leu Ser
        355                 360                 365

Ala Ile Leu Leu Ala Phe Ile Leu Thr Trp Thr Pro Tyr Asn Ile Met
    370                 375                 380

Val Leu Val Ser Thr Phe Cys Lys Asp Cys Val Pro Glu Thr Leu Trp
385                 390                 395                 400

Glu Leu Gly Tyr Trp Leu Cys Tyr Val Asn Ser Thr Ile Asn Pro Met
                405                 410                 415

Cys Tyr Ala Leu Cys Asn Lys Ala Phe Arg Asp Thr Phe Arg Leu Leu
                420                 425                 430

Leu Leu Cys Arg Trp Asp Lys Arg Arg Trp Arg Lys Ile Pro Lys Arg
        435                 440                 445

Pro Gly Ser Val His Arg Thr Pro Ser Arg Gln Cys
    450                 455                 460

<210> SEQ ID NO 7
<211> LENGTH: 443
<212> TYPE: PRT
<213> ORGANISM: Homo sapiens

<400> SEQUENCE: 7

Met Asp Pro Leu Asn Leu Ser Trp Tyr Asp Asp Asp Leu Glu Arg Gln
1               5                   10                  15

Asn Trp Ser Arg Pro Phe Asn Gly Ser Asp Gly Lys Ala Asp Arg Pro
            20                  25                  30
```

```
His Tyr Asn Tyr Tyr Ala Thr Leu Leu Thr Leu Leu Ile Ala Val Ile
         35                  40                  45

Val Phe Gly Asn Val Leu Val Cys Met Ala Val Ser Arg Glu Lys Ala
 50                  55                  60

Leu Gln Thr Thr Thr Asn Tyr Leu Ile Val Ser Leu Ala Val Ala Asp
 65                  70                  75                  80

Leu Leu Val Ala Thr Leu Val Met Pro Trp Val Val Tyr Leu Glu Val
                 85                  90                  95

Val Gly Glu Trp Lys Phe Ser Arg Ile His Cys Asp Ile Phe Val Thr
            100                 105                 110

Leu Asp Val Met Met Cys Thr Ala Ser Ile Leu Asn Leu Cys Ala Ile
            115                 120                 125

Ser Ile Asp Arg Tyr Thr Ala Val Ala Met Pro Met Leu Tyr Asn Thr
            130                 135                 140

Arg Tyr Ser Ser Lys Arg Arg Val Thr Val Met Ile Ser Ile Val Trp
145                 150                 155                 160

Val Leu Ser Phe Thr Ile Ser Cys Pro Leu Leu Phe Gly Leu Asn Asn
                165                 170                 175

Ala Asp Gln Asn Glu Cys Ile Ile Ala Asn Pro Ala Phe Val Val Tyr
            180                 185                 190

Ser Ser Ile Val Ser Phe Tyr Val Pro Phe Ile Val Thr Leu Leu Val
            195                 200                 205

Tyr Ile Lys Ile Tyr Ile Val Leu Arg Arg Arg Arg Lys Arg Val Asn
            210                 215                 220

Thr Lys Arg Ser Ser Arg Ala Phe Arg Ala His Leu Arg Ala Pro Leu
225                 230                 235                 240

Lys Gly Asn Cys Thr His Pro Glu Asp Met Lys Leu Cys Thr Val Ile
                245                 250                 255

Met Lys Ser Asn Gly Ser Phe Pro Val Asn Arg Arg Arg Val Glu Ala
            260                 265                 270

Ala Arg Arg Ala Gln Glu Leu Glu Met Glu Met Leu Ser Ser Thr Ser
            275                 280                 285

Pro Pro Glu Arg Thr Arg Tyr Ser Pro Ile Pro Pro Ser His His Gln
            290                 295                 300

Leu Thr Leu Pro Asp Pro Ser His His Gly Leu His Ser Thr Pro Asp
305                 310                 315                 320

Ser Pro Ala Lys Pro Glu Lys Asn Gly His Ala Lys Asp His Pro Lys
                325                 330                 335

Ile Ala Lys Ile Phe Glu Ile Gln Thr Met Pro Asn Gly Lys Thr Arg
            340                 345                 350

Thr Ser Leu Lys Thr Met Ser Arg Arg Lys Leu Ser Gln Gln Lys Glu
            355                 360                 365

Lys Lys Ala Thr Gln Met Leu Ala Ile Val Leu Gly Val Phe Ile Ile
            370                 375                 380

Cys Trp Leu Pro Phe Phe Ile Thr His Ile Leu Asn Ile His Cys Asp
385                 390                 395                 400

Cys Asn Ile Pro Pro Val Leu Tyr Ser Ala Phe Thr Trp Leu Gly Tyr
                405                 410                 415

Val Asn Ser Ala Val Asn Pro Ile Ile Tyr Thr Thr Phe Asn Ile Glu
            420                 425                 430

Phe Arg Lys Ala Phe Leu Lys Ile Leu His Cys
            435                 440
```

```
<210> SEQ ID NO 8
<211> LENGTH: 382
<212> TYPE: PRT
<213> ORGANISM: Homo sapiens

<400> SEQUENCE: 8

Met Gly Pro Thr Ser Val Pro Leu Val Lys Ala His Arg Ser Ser Val
1               5                   10                  15

Ser Asp Tyr Val Asn Tyr Asp Ile Ile Val Arg His Tyr Asn Tyr Thr
            20                  25                  30

Gly Lys Leu Asn Ile Ser Ala Asp Lys Glu Asn Ser Ile Lys Leu Thr
        35                  40                  45

Ser Val Val Phe Ile Leu Ile Cys Cys Phe Ile Ile Leu Glu Asn Ile
    50                  55                  60

Phe Val Leu Leu Thr Ile Trp Lys Thr Lys Phe His Arg Pro Met
65                  70                  75                  80

Tyr Tyr Phe Ile Gly Asn Leu Ala Leu Ser Asp Leu Leu Ala Gly Val
                85                  90                  95

Ala Tyr Thr Ala Asn Leu Leu Leu Ser Gly Ala Thr Thr Tyr Lys Leu
            100                 105                 110

Thr Pro Ala Gln Trp Phe Leu Arg Glu Gly Ser Met Phe Val Ala Leu
        115                 120                 125

Ser Ala Ser Val Phe Ser Leu Leu Ala Ile Ala Ile Glu Arg Tyr Ile
    130                 135                 140

Thr Met Leu Lys Met Lys Leu His Asn Gly Ser Asn Asn Phe Arg Leu
145                 150                 155                 160

Phe Leu Leu Ile Ser Ala Cys Trp Val Ile Ser Leu Ile Leu Gly Gly
                165                 170                 175

Leu Pro Ile Met Gly Trp Asn Cys Ile Ser Ala Leu Ser Ser Cys Ser
            180                 185                 190

Thr Val Leu Pro Leu Tyr His Lys His Tyr Ile Leu Phe Cys Thr Thr
        195                 200                 205

Val Phe Thr Leu Leu Leu Leu Ser Ile Val Ile Leu Tyr Cys Arg Ile
    210                 215                 220

Tyr Ser Leu Val Arg Thr Arg Ser Arg Arg Leu Thr Phe Arg Lys Asn
225                 230                 235                 240

Ile Ser Lys Ala Ser Arg Ser Ser Glu Lys Ser Leu Ala Leu Leu Lys
                245                 250                 255

Thr Val Ile Ile Val Leu Ser Val Phe Ile Ala Cys Trp Ala Pro Leu
            260                 265                 270

Phe Ile Leu Leu Leu Leu Asp Val Gly Cys Lys Val Lys Thr Cys Asp
        275                 280                 285

Ile Leu Phe Arg Ala Glu Tyr Phe Leu Val Leu Ala Val Leu Asn Ser
    290                 295                 300

Gly Thr Asn Pro Ile Ile Tyr Thr Leu Thr Asn Lys Glu Met Arg Arg
305                 310                 315                 320

Ala Phe Ile Arg Ile Met Ser Cys Cys Lys Cys Pro Ser Gly Asp Ser
                325                 330                 335

Ala Gly Lys Phe Lys Arg Pro Ile Ile Ala Gly Met Glu Phe Ser Arg
            340                 345                 350

Ser Lys Ser Asp Asn Ser Ser His Pro Gln Lys Asp Glu Gly Asp Asn
        355                 360                 365

Pro Glu Thr Ile Met Ser Ser Gly Asn Val Asn Ser Ser Ser
    370                 375                 380
```

```
<210> SEQ ID NO 9
<211> LENGTH: 422
<212> TYPE: PRT
<213> ORGANISM: Homo sapiens

<400> SEQUENCE: 9

Met Asp Val Leu Ser Pro Gly Gln Gly Asn Asn Thr Thr Ser Pro Pro
1               5                   10                  15

Ala Pro Phe Glu Thr Gly Gly Asn Thr Thr Gly Ile Ser Asp Val Thr
            20                  25                  30

Val Ser Tyr Gln Val Ile Thr Ser Leu Leu Leu Gly Thr Leu Ile Phe
        35                  40                  45

Cys Ala Val Leu Gly Asn Ala Cys Val Val Ala Ala Ile Ala Leu Glu
    50                  55                  60

Arg Ser Leu Gln Asn Val Ala Asn Tyr Leu Ile Gly Ser Leu Ala Val
65                  70                  75                  80

Thr Asp Leu Met Val Ser Val Leu Val Leu Pro Met Ala Ala Leu Tyr
                85                  90                  95

Gln Val Leu Asn Lys Trp Thr Leu Gly Gln Val Thr Cys Asp Leu Phe
            100                 105                 110

Ile Ala Leu Asp Val Leu Cys Cys Thr Ser Ser Ile Leu His Leu Cys
        115                 120                 125

Ala Ile Ala Leu Asp Arg Tyr Trp Ala Ile Thr Asp Pro Ile Asp Tyr
    130                 135                 140

Val Asn Lys Arg Thr Pro Arg Arg Ala Ala Ala Leu Ile Ser Leu Thr
145                 150                 155                 160

Trp Leu Ile Gly Phe Leu Ile Ser Ile Pro Pro Met Leu Gly Trp Arg
                165                 170                 175

Thr Pro Glu Asp Arg Ser Asp Pro Asp Ala Cys Thr Ile Ser Lys Asp
            180                 185                 190

His Gly Tyr Thr Ile Tyr Ser Thr Phe Gly Ala Phe Tyr Ile Pro Leu
        195                 200                 205

Leu Leu Met Leu Val Leu Tyr Gly Arg Ile Phe Arg Ala Ala Arg Phe
    210                 215                 220

Arg Ile Arg Lys Thr Val Lys Lys Val Glu Lys Thr Gly Ala Asp Thr
225                 230                 235                 240

Arg His Gly Ala Ser Pro Ala Pro Gln Pro Lys Lys Ser Val Asn Gly
                245                 250                 255

Glu Ser Gly Ser Arg Asn Trp Arg Leu Gly Val Glu Ser Lys Ala Gly
            260                 265                 270

Gly Ala Leu Cys Ala Asn Gly Ala Val Arg Gln Gly Asp Asp Gly Ala
        275                 280                 285

Ala Leu Glu Val Ile Glu Val His Arg Val Gly Asn Ser Lys Glu His
    290                 295                 300

Leu Pro Leu Pro Ser Glu Ala Gly Pro Thr Pro Cys Ala Pro Ala Ser
305                 310                 315                 320

Phe Glu Arg Lys Asn Glu Arg Asn Ala Glu Ala Lys Arg Lys Met Ala
                325                 330                 335

Leu Ala Arg Glu Arg Lys Thr Val Lys Thr Leu Gly Ile Ile Met Gly
            340                 345                 350

Thr Phe Ile Leu Cys Trp Leu Pro Phe Phe Ile Val Ala Leu Val Leu
        355                 360                 365

Pro Phe Cys Glu Ser Ser Cys His Met Pro Thr Leu Leu Gly Ala Ile
    370                 375                 380

Ile Asn Trp Leu Gly Tyr Ser Asn Ser Leu Leu Asn Pro Val Ile Tyr
```

```
                385                 390                 395                 400
Ala Tyr Phe Asn Lys Asp Phe Gln Asn Ala Phe Lys Lys Ile Ile Lys
                    405                 410                 415

Cys Lys Phe Cys Arg Gln
            420

<210> SEQ ID NO 10
<211> LENGTH: 297
<212> TYPE: PRT
<213> ORGANISM: Homo sapiens

<400> SEQUENCE: 10

Met Lys His Ile Ile Asn Ser Tyr Glu Asn Ile Asn Thr Ala Arg
1               5                   10                  15

Asn Asn Ser Asp Cys Pro Arg Val Val Leu Pro Glu Glu Ile Phe Phe
                20                  25                  30

Thr Ile Ser Ile Val Gly Val Leu Glu Asn Leu Ile Val Leu Leu Ala
                35                  40                  45

Val Phe Lys Asn Lys Asn Leu Gln Ala Pro Met Tyr Phe Phe Ile Cys
        50                  55                  60

Ser Leu Ala Ile Ser Asp Met Leu Gly Ser Leu Tyr Lys Ile Leu Glu
65                  70                  75                  80

Asn Ile Leu Ile Ile Leu Arg Asn Met Gly Tyr Leu Lys Pro Arg Gly
                85                  90                  95

Ser Phe Glu Thr Thr Ala Asp Asp Ile Ile Asp Ser Leu Phe Val Leu
            100                 105                 110

Ser Leu Leu Gly Ser Ile Phe Ser Leu Ser Val Ile Ala Ala Asp Arg
        115                 120                 125

Tyr Ile Thr Ile Phe His Ala Leu Arg Tyr His Ser Ile Val Thr Met
    130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro Thr Val Ile
                165                 170                 175

Thr Phe Thr Ser Leu Phe Pro Leu Met Leu Val Phe Ile Leu Cys Leu
            180                 185                 190

Tyr Val His Met Phe Leu Leu Ala Arg Ser His Thr Arg Lys Ile Ser
        195                 200                 205

Thr Leu Pro Arg Ala Asn Met Lys Gly Ala Ile Thr Leu Thr Ile Leu
    210                 215                 220

Leu Gly Val Phe Ile Phe Cys Trp Ala Pro Phe Val Leu His Val Leu
225                 230                 235                 240

Leu Met Thr Phe Cys Pro Ser Asn Pro Tyr Cys Ala Cys Tyr Met Ser
                245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
        275                 280                 285

Lys Met Ile Phe Cys Ser Arg Tyr Trp
    290                 295

<210> SEQ ID NO 11
<211> LENGTH: 418
<212> TYPE: PRT
<213> ORGANISM: Homo sapiens

<400> SEQUENCE: 11
```

```
Met Arg Leu Asn Ser Ser Ala Pro Gly Thr Pro Gly Thr Pro Ala Ala
1               5                   10                  15

Asp Pro Phe Gln Arg Ala Gln Ala Gly Leu Glu Ala Leu Leu Ala
            20                  25                  30

Pro Gly Phe Gly Asn Ala Ser Gly Asn Ala Ser Glu Arg Val Leu Ala
            35                  40                  45

Ala Pro Ser Ser Glu Leu Asp Val Asn Thr Asp Ile Tyr Ser Lys Val
50                  55                  60

Leu Val Thr Ala Val Tyr Leu Ala Leu Phe Val Val Gly Thr Val Gly
65                  70                  75                  80

Asn Thr Val Thr Ala Phe Thr Leu Ala Arg Lys Lys Ser Leu Gln Ser
                85                  90                  95

Leu Gln Ser Thr Val His Tyr His Leu Gly Ser Leu Ala Leu Ser Asp
            100                 105                 110

Leu Leu Thr Leu Leu Leu Ala Met Pro Val Glu Leu Tyr Asn Phe Ile
            115                 120                 125

Trp Val His His Pro Trp Ala Phe Gly Asp Ala Gly Cys Arg Gly Tyr
        130                 135                 140

Tyr Phe Leu Arg Asp Ala Cys Thr Tyr Ala Thr Ala Leu Asn Val Ala
145                 150                 155                 160

Ser Leu Ser Val Glu Arg Tyr Leu Ala Ile Cys His Pro Phe Lys Ala
                165                 170                 175

Lys Thr Leu Met Ser Arg Ser Arg Thr Lys Lys Phe Ile Ser Ala Ile
            180                 185                 190

Trp Leu Ala Ser Ala Leu Leu Ala Val Pro Met Leu Phe Thr Met Gly
        195                 200                 205

Glu Gln Asn Arg Ser Ala Asp Gly Gln His Ala Gly Gly Leu Val Cys
210                 215                 220

Thr Pro Thr Ile His Thr Ala Thr Val Lys Val Val Ile Gln Val Asn
225                 230                 235                 240

Thr Phe Met Ser Phe Ile Phe Pro Met Val Val Ile Ser Val Leu Asn
                245                 250                 255

Thr Ile Ile Ala Asn Lys Leu Thr Val Met Val Arg Gln Ala Ala Glu
            260                 265                 270

Gln Gly Gln Val Cys Thr Val Gly Gly Glu His Ser Thr Phe Ser Met
        275                 280                 285

Ala Ile Glu Pro Gly Arg Val Gln Ala Leu Arg His Gly Val Arg Val
290                 295                 300

Leu Arg Ala Val Val Ile Ala Phe Val Val Cys Trp Leu Pro Tyr His
305                 310                 315                 320

Val Arg Arg Leu Met Phe Cys Tyr Ile Ser Asp Glu Gln Trp Thr Pro
                325                 330                 335

Phe Leu Tyr Asp Phe Tyr His Tyr Phe Tyr Met Val Thr Asn Ala Leu
            340                 345                 350

Phe Tyr Val Ser Ser Thr Ile Asn Pro Ile Leu Tyr Asn Leu Val Ser
        355                 360                 365

Ala Asn Phe Arg His Ile Phe Leu Ala Thr Leu Ala Cys Leu Cys Pro
370                 375                 380

Val Trp Arg Arg Arg Lys Arg Pro Ala Phe Ser Arg Lys Ala Asp
385                 390                 395                 400

Ser Val Ser Ser Asn His Thr Leu Ser Ser Asn Ala Thr Arg Glu Thr
                405                 410                 415

Leu Tyr
```

<210> SEQ ID NO 12
<211> LENGTH: 389
<212> TYPE: PRT
<213> ORGANISM: Homo sapiens

<400> SEQUENCE: 12

Met Glu Gly Ala Leu Ala Ala Asn Trp Ser Ala Glu Ala Ala Asn Ala
1               5                   10                  15

Ser Ala Ala Pro Pro Gly Ala Glu Gly Asn Arg Thr Ala Gly Pro Pro
            20                  25                  30

Arg Arg Asn Glu Ala Leu Ala Arg Val Glu Val Ala Val Leu Cys Leu
        35                  40                  45

Ile Leu Leu Leu Ala Leu Ser Gly Asn Ala Cys Val Leu Leu Ala Leu
50                  55                  60

Arg Thr Thr Arg Gln Lys His Ser Arg Leu Phe Phe Met Lys His
65                  70                  75                  80

Leu Ser Ile Ala Asp Leu Val Val Ala Val Phe Gln Val Leu Pro Gln
                85                  90                  95

Leu Leu Trp Asp Ile Thr Phe Arg Phe Tyr Gly Pro Asp Leu Leu Cys
            100                 105                 110

Arg Leu Val Lys Tyr Leu Gln Val Val Gly Met Phe Ala Ser Thr Tyr
        115                 120                 125

Leu Leu Leu Leu Met Ser Leu Asp Arg Cys Leu Ala Ile Cys Gln Pro
130                 135                 140

Leu Arg Ser Leu Arg Arg Arg Thr Asp Arg Leu Ala Val Leu Ala Thr
145                 150                 155                 160

Trp Leu Gly Cys Leu Val Ala Ser Ala Pro Gln Val His Ile Phe Ser
                165                 170                 175

Leu Arg Glu Val Ala Asp Gly Val Phe Asp Cys Trp Ala Val Phe Ile
            180                 185                 190

Gln Pro Trp Gly Pro Lys Ala Tyr Ile Thr Trp Ile Thr Leu Ala Val
        195                 200                 205

Tyr Ile Val Pro Val Ile Val Leu Ala Ala Cys Tyr Gly Leu Ile Ser
210                 215                 220

Phe Lys Ile Trp Gln Asn Leu Arg Leu Lys Thr Ala Ala Ala Ala Ala
225                 230                 235                 240

Ala Glu Ala Pro Glu Gly Ala Ala Ala Gly Asp Gly Gly Arg Val Ala
                245                 250                 255

Leu Ala Arg Val Ser Ser Val Lys Leu Ile Ser Lys Ala Lys Ile Arg
            260                 265                 270

Thr Val Lys Met Thr Phe Ile Ile Val Leu Ala Phe Ile Val Cys Trp
        275                 280                 285

Thr Pro Phe Phe Phe Val Gln Met Trp Ser Val Trp Asp Ala Asn Ala
290                 295                 300

Pro Lys Glu Ala Ser Ala Phe Ile Ile Val Met Leu Leu Ala Ser Leu
305                 310                 315                 320

Asn Ser Cys Cys Asn Pro Trp Ile Tyr Met Leu Phe Thr Gly His Leu
                325                 330                 335

Phe His Glu Leu Val Gln Arg Phe Leu Cys Cys Ser Ala Ser Tyr Leu
            340                 345                 350

Lys Gly Arg Arg Leu Gly Glu Thr Ser Ala Ser Lys Lys Ser Asn Ser
        355                 360                 365

Ser Ser Phe Val Leu Ser His Arg Ser Ser Ser Gln Arg Ser Cys Ser
370                 375                 380

```
Gln Pro Ser Thr Ala
385

<210> SEQ ID NO 13
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ggcgcgccgc ccatcatggg ctcctcggtg tacatca                               37

<210> SEQ ID NO 14
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aggccggccg gacactcctg ctccatcctg ggc                                   33

<210> SEQ ID NO 15
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggatccatga agacgatcat cgccctgagc tacatcttct g                          41

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aagcttctaa tggtgatggt gatggtgatg gtgatggtga gg                         42

<210> SEQ ID NO 17
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
aagctttcag tgatggtgat ggtgatggtg atggtggtgt gccttgaaag gttc            54

<210> SEQ ID NO 18
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
```

```
gctagcatga agacgatcat cgccctgagc tacatcttct g                    41
```

<210> SEQ ID NO 19
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19

```
aagctttcag tgatggtgat ggtgatggtg atggtggt                        38
```

<210> SEQ ID NO 20
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: mat_peptide
<222> LOCATION: (15)..(17)

<400> SEQUENCE: 20

```
Asp Tyr Lys Asp Asp Asp Asp Ala Met Gly Gln Pro Val Gly Ala Pro
            -10                 -5                  -1   1
Pro
```

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

```
Pro Lys Glu Gly Lys Asn His
1               5
```

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

```
Gln Glu Pro Phe Lys Ala His His His His His His His His His His
1               5                   10                  15
```

<210> SEQ ID NO 23
<211> LENGTH: 488
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Asp Tyr Lys Asp Asp Asp Asp Ala Met Gly Gln Pro Val Gly Ala Pro
1               5                   10                  15

Pro Ile Met Gly Ser Ser Val Tyr Ile Thr Val Glu Leu Ala Ile Ala
            20                  25                  30

Val Leu Ala Ile Leu Gly Asn Val Leu Val Cys Trp Ala Val Trp Leu
```

```
            35                  40                  45
Asn Ser Asn Leu Gln Asn Val Thr Asn Tyr Phe Val Ser Leu Ala
 50                  55                  60
Ala Ala Asp Ile Ala Val Gly Val Leu Ala Ile Pro Phe Ala Ile Thr
 65                  70                  75                  80
Ile Ser Thr Gly Phe Cys Ala Ala Cys His Gly Cys Leu Phe Ile Ala
                 85                  90                  95
Cys Phe Val Leu Val Leu Thr Gln Ser Ser Ile Phe Ser Leu Leu Ala
                100                 105                 110
Ile Ala Ile Asp Arg Tyr Ile Ala Ile Arg Ile Pro Leu Arg Tyr Asn
                115                 120                 125
Gly Leu Val Thr Gly Thr Arg Ala Lys Gly Ile Ala Ile Cys Trp
130                 135                 140
Val Leu Ser Phe Ala Ile Gly Leu Thr Pro Met Leu Gly Trp Asn Asn
145                 150                 155                 160
Cys Gly Gln Pro Lys Glu Gly Lys Asn His Ser Gln Gly Cys Gly Glu
                165                 170                 175
Gly Gln Val Ala Cys Leu Phe Glu Asp Val Val Pro Met Asn Tyr Met
                180                 185                 190
Val Tyr Phe Asn Phe Phe Ala Cys Val Leu Val Pro Leu Leu Leu Met
                195                 200                 205
Leu Gly Val Tyr Leu Arg Ile Phe Leu Ala Ala Arg Arg Gln Leu Asn
                210                 215                 220
Ile Phe Glu Met Leu Arg Ile Asp Gly Leu Arg Leu Lys Ile Tyr
225                 230                 235                 240
Lys Asp Thr Glu Gly Tyr Tyr Thr Ile Gly Ile Gly His Leu Leu Thr
                245                 250                 255
Lys Ser Pro Ser Leu Asn Ala Ala Lys Ser Glu Leu Asp Lys Ala Ile
                260                 265                 270
Gly Arg Asn Thr Asn Gly Val Ile Thr Lys Asp Glu Ala Glu Lys Leu
                275                 280                 285
Phe Asn Gln Asp Val Asp Ala Ala Val Arg Gly Ile Leu Arg Asn Ala
290                 295                 300
Lys Leu Lys Pro Val Tyr Asp Ser Leu Asp Ala Val Arg Arg Ala Ala
305                 310                 315                 320
Leu Ile Asn Met Val Phe Gln Met Gly Glu Thr Gly Val Ala Gly Phe
                325                 330                 335
Thr Asn Ser Leu Arg Met Leu Gln Gln Lys Arg Trp Asp Glu Ala Ala
                340                 345                 350
Val Asn Leu Ala Lys Ser Arg Trp Tyr Asn Gln Thr Pro Asn Arg Ala
                355                 360                 365
Lys Arg Val Ile Thr Thr Phe Arg Thr Gly Thr Trp Asp Ala Tyr Arg
370                 375                 380
Ser Thr Leu Gln Lys Glu Val His Ala Ala Lys Ser Leu Ala Ile Ile
385                 390                 395                 400
Val Gly Leu Phe Ala Leu Cys Trp Leu Pro Leu His Ile Ile Asn Cys
                405                 410                 415
Phe Thr Phe Phe Cys Pro Asp Cys Ser His Ala Pro Leu Trp Leu Met
                420                 425                 430
Tyr Leu Ala Ile Val Leu Ser His Thr Asn Ser Val Val Asn Pro Phe
                435                 440                 445
Ile Tyr Ala Tyr Arg Ile Arg Glu Phe Arg Gln Thr Phe Arg Lys Ile
                450                 455                 460
```

```
Ile Arg Ser His Val Leu Arg Gln Gln Glu Pro Phe Lys Ala His His
465                 470                 475                 480

His His His His His His His His
                485

<210> SEQ ID NO 24
<211> LENGTH: 146
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Ile Met Gly Ser Ser Val Tyr Ile Thr Val Glu Leu Ala Ile Ala Val
1               5                   10                  15

Leu Ala Ile Leu Gly Asn Val Leu Val Cys Trp Ala Val Trp Leu Asn
                20                  25                  30

Ser Asn Leu Gln Asn Val Thr Asn Tyr Phe Val Val Ser Leu Ala Ala
            35                  40                  45

Ala Asp Ile Ala Val Gly Val Leu Ala Ile Pro Phe Ala Ile Thr Ile
50                  55                  60

Ser Thr Gly Phe Cys Ala Ala Cys His Gly Cys Leu Phe Ile Ala Cys
65                  70                  75                  80

Phe Val Leu Val Leu Thr Gln Ser Ser Ile Phe Ser Leu Leu Ala Ile
                85                  90                  95

Ala Ile Asp Arg Tyr Ile Ala Ile Arg Ile Pro Leu Arg Tyr Asn Gly
            100                 105                 110

Leu Val Thr Gly Thr Arg Ala Lys Gly Ile Ile Ala Ile Cys Trp Val
        115                 120                 125

Leu Ser Phe Ala Ile Gly Leu Thr Pro Met Leu Gly Trp Asn Asn Cys
130                 135                 140

Gly Gln
145

<210> SEQ ID NO 25
<211> LENGTH: 53
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser Gln Gly Cys Gly Glu Gly Gln Val Ala Cys Leu Phe Glu Asp Val
1               5                   10                  15

Val Pro Met Asn Tyr Met Val Tyr Phe Asn Phe Phe Ala Cys Val Leu
                20                  25                  30

Val Pro Leu Leu Leu Met Leu Gly Val Tyr Leu Arg Ile Phe Leu Ala
            35                  40                  45

Ala Arg Arg Gln Leu
    50

<210> SEQ ID NO 26
<211> LENGTH: 160
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26
```

```
Asn Ile Phe Glu Met Leu Arg Ile Asp Glu Gly Leu Arg Leu Lys Ile
1               5                   10                  15

Tyr Lys Asp Thr Glu Gly Tyr Tyr Thr Ile Gly Ile Gly His Leu Leu
            20                  25                  30

Thr Lys Ser Pro Ser Leu Asn Ala Ala Lys Ser Glu Leu Asp Lys Ala
        35                  40                  45

Ile Gly Arg Asn Thr Asn Gly Val Ile Thr Lys Asp Glu Ala Glu Lys
50                  55                  60

Leu Phe Asn Gln Asp Val Asp Ala Ala Val Arg Gly Ile Leu Arg Asn
65                  70                  75                  80

Ala Lys Leu Lys Pro Val Tyr Asp Ser Leu Asp Ala Val Arg Arg Ala
            85                  90                  95

Ala Leu Ile Asn Met Val Phe Gln Met Gly Glu Thr Gly Val Ala Gly
            100                 105                 110

Phe Thr Asn Ser Leu Arg Met Leu Gln Gln Lys Arg Trp Asp Glu Ala
            115                 120                 125

Ala Val Asn Leu Ala Lys Ser Arg Trp Tyr Asn Gln Thr Pro Asn Arg
130                 135                 140

Ala Lys Arg Val Ile Thr Thr Phe Arg Thr Gly Thr Trp Asp Ala Tyr
145                 150                 155                 160

<210> SEQ ID NO 27
<211> LENGTH: 89
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Arg Ser Thr Leu Gln Lys Glu Val His Ala Ala Lys Ser Leu Ala Ile
1               5                   10                  15

Ile Val Gly Leu Phe Ala Leu Cys Trp Leu Pro Leu His Ile Ile Asn
            20                  25                  30

Cys Phe Thr Phe Phe Cys Pro Asp Cys Ser His Ala Pro Leu Trp Leu
        35                  40                  45

Met Tyr Leu Ala Ile Val Leu Ser His Thr Asn Ser Val Val Asn Pro
50                  55                  60

Phe Ile Tyr Ala Tyr Arg Ile Arg Glu Phe Arg Gln Thr Phe Arg Lys
65                  70                  75                  80

Ile Ile Arg Ser His Val Leu Arg Gln
            85

<210> SEQ ID NO 28
<211> LENGTH: 503
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Met Lys Thr Ile Ile Ala Leu Ser Tyr Ile Phe Cys Leu Val Phe Ala
1               5                   10                  15

Asp Tyr Lys Asp Asp Asp Ala Met Gly Gln Pro Val Gly Ala Pro
            20                  25                  30

Pro Ile Met Gly Ser Ser Val Tyr Ile Thr Val Glu Leu Ala Ile Ala
        35                  40                  45
```

-continued

```
Val Leu Ala Ile Leu Gly Asn Val Leu Val Cys Trp Ala Val Trp Leu
    50                  55                  60

Asn Ser Asn Leu Gln Asn Val Thr Asn Tyr Phe Val Val Ser Leu Ala
 65                  70                  75                  80

Ala Ala Asp Ile Ala Val Gly Val Leu Ala Ile Pro Phe Ala Ile Thr
                 85                  90                  95

Ile Ser Thr Gly Phe Cys Ala Ala Cys His Gly Cys Leu Phe Ile Ala
                100                 105                 110

Cys Phe Val Leu Val Leu Thr Gln Ser Ser Ile Phe Ser Leu Leu Ala
            115                 120                 125

Ile Ala Ile Asp Arg Tyr Ile Ala Ile Arg Ile Pro Leu Arg Tyr Asn
        130                 135                 140

Gly Leu Val Thr Gly Thr Arg Ala Lys Gly Ile Ile Ala Ile Cys Trp
145                 150                 155                 160

Val Leu Ser Phe Ala Ile Gly Leu Thr Pro Met Leu Gly Trp Asn Asn
                165                 170                 175

Cys Gly Gln Pro Lys Glu Gly Lys Asn His Ser Gln Gly Cys Gly Glu
                180                 185                 190

Gly Gln Val Ala Cys Leu Phe Glu Asp Trp Pro Met Asn Tyr Met Val
            195                 200                 205

Tyr Phe Asn Phe Phe Ala Cys Val Leu Val Pro Leu Leu Leu Met Leu
    210                 215                 220

Gly Val Tyr Leu Arg Ile Phe Leu Ala Ala Arg Arg Gln Leu Asn Ile
225                 230                 235                 240

Phe Glu Met Leu Arg Ile Asp Glu Gly Leu Arg Leu Lys Ile Tyr Lys
                245                 250                 255

Asp Thr Glu Gly Tyr Tyr Thr Ile Gly Ile Gly His Leu Leu Thr Lys
                260                 265                 270

Ser Pro Ser Leu Asn Ala Ala Lys Ser Glu Leu Asp Lys Ala Ile Gly
            275                 280                 285

Arg Asn Thr Asn Gly Val Ile Thr Lys Asp Glu Ala Glu Lys Leu Phe
        290                 295                 300

Asn Gln Asp Val Asp Ala Ala Val Arg Gly Ile Leu Arg Asn Ala Lys
305                 310                 315                 320

Leu Lys Pro Val Tyr Asp Ser Leu Asp Ala Val Arg Arg Ala Ala Leu
                325                 330                 335

Ile Asn Met Val Phe Gln Met Gly Glu Thr Gly Val Ala Gly Phe Thr
            340                 345                 350

Asn Ser Leu Arg Met Leu Gln Gln Lys Arg Trp Asp Glu Ala Ala Val
        355                 360                 365

Asn Leu Ala Lys Ser Arg Trp Tyr Asn Gln Thr Pro Asn Arg Ala Lys
    370                 375                 380

Arg Val Ile Thr Thr Phe Arg Thr Gly Thr Trp Asp Ala Tyr Arg Ser
385                 390                 395                 400

Thr Leu Gln Lys Glu Val His Ala Ala Lys Ser Leu Ala Ile Ile Val
                405                 410                 415

Gly Leu Phe Ala Leu Cys Trp Leu Pro Leu His Ile Ile Asn Cys Phe
            420                 425                 430

Thr Phe Phe Cys Pro Asp Cys Ser His Ala Pro Leu Trp Leu Met Tyr
        435                 440                 445

Leu Ala Ile Val Leu Ser His Thr Asn Ser Val Val Asn Pro Phe Ile
    450                 455                 460

Tyr Ala Tyr Arg Ile Arg Glu Phe Arg Gln Thr Phe Arg Lys Ile Ile
465                 470                 475                 480
```

Arg Ser His Val Leu Arg Gln Gln Glu Pro Phe Lys Ala His His
            485                 490                 495
His His His His His His
        500

<210> SEQ ID NO 29
<211> LENGTH: 326
<212> TYPE: PRT
<213> ORGANISM: Homo sapiens

<400> SEQUENCE: 29

Met Pro Pro Ser Ile Ser Ala Phe Gln Ala Ala Tyr Ile Gly Ile Glu
1               5                   10                  15

Val Leu Ile Ala Leu Val Ser Val Pro Gly Asn Val Leu Val Ile Trp
            20                  25                  30

Ala Val Lys Val Asn Gln Ala Leu Arg Asp Ala Thr Phe Cys Phe Ile
            35                  40                  45

Val Ser Leu Ala Val Ala Asp Val Ala Val Gly Ala Leu Val Ile Pro
        50                  55                  60

Leu Ala Ile Leu Ile Asn Ile Gly Pro Gln Thr Tyr Phe His Thr Cys
65                  70                  75                  80

Leu Met Val Ala Cys Pro Val Leu Ile Leu Thr Gln Ser Ser Ile Leu
            85                  90                  95

Ala Leu Leu Ala Ile Ala Val Asp Arg Tyr Leu Arg Val Lys Ile Pro
            100                 105                 110

Leu Arg Tyr Lys Met Val Val Thr Pro Arg Arg Ala Ala Val Ala Ile
            115                 120                 125

Ala Gly Cys Trp Ile Leu Ser Phe Val Val Gly Leu Thr Pro Met Phe
130                 135                 140

Gly Trp Asn Asn Leu Ser Ala Val Glu Arg Ala Trp Ala Ala Asn Gly
145                 150                 155                 160

Ser Met Gly Glu Pro Val Ile Lys Cys Glu Phe Glu Lys Val Ile Ser
            165                 170                 175

Met Glu Tyr Met Val Tyr Phe Asn Phe Phe Val Trp Val Leu Pro Pro
            180                 185                 190

Leu Leu Leu Met Val Leu Ile Tyr Leu Glu Val Phe Tyr Leu Ile Arg
            195                 200                 205

Lys Gln Leu Asn Lys Lys Val Ser Ala Ser Ser Gly Asp Pro Gln Lys
            210                 215                 220

Tyr Tyr Gly Lys Glu Leu Lys Ile Ala Lys Ser Leu Ala Leu Ile Leu
225                 230                 235                 240

Phe Leu Phe Ala Leu Ser Trp Leu Pro Leu His Ile Leu Asn Cys Ile
            245                 250                 255

Thr Leu Phe Cys Pro Ser Cys His Lys Pro Ser Ile Leu Thr Tyr Ile
            260                 265                 270

Ala Ile Phe Leu Thr His Gly Asn Ser Ala Met Asn Pro Ile Val Tyr
            275                 280                 285

Ala Phe Arg Ile Gln Lys Phe Arg Val Thr Phe Leu Lys Ile Trp Asn
            290                 295                 300

Asp His Phe Arg Cys Gln Pro Ala Pro Pro Ile Asp Glu Asp Leu Pro
305                 310                 315                 320

Glu Glu Arg Pro Asp Asp
            325

<210> SEQ ID NO 30

<211> LENGTH: 332
<212> TYPE: PRT
<213> ORGANISM: Homo sapiens

<400> SEQUENCE: 30

```
Met Leu Leu Glu Thr Gln Asp Ala Leu Tyr Val Ala Leu Glu Leu Val
1               5                   10                  15

Ile Ala Ala Leu Ser Val Ala Gly Asn Val Leu Val Cys Ala Ala Val
            20                  25                  30

Gly Thr Ala Asn Thr Leu Gln Thr Pro Thr Asn Tyr Phe Leu Val Ser
        35                  40                  45

Leu Ala Ala Ala Asp Val Ala Val Gly Leu Phe Ala Ile Pro Phe Ala
    50                  55                  60

Ile Thr Ile Ser Leu Gly Phe Cys Thr Asp Phe Tyr Gly Cys Leu Phe
65                  70                  75                  80

Leu Ala Cys Phe Val Leu Val Leu Thr Gln Ser Ser Ile Phe Ser Leu
                85                  90                  95

Leu Ala Val Ala Val Asp Arg Tyr Leu Ala Ile Cys Val Pro Leu Arg
            100                 105                 110

Tyr Lys Ser Leu Val Thr Gly Thr Arg Ala Arg Gly Val Ile Ala Val
        115                 120                 125

Leu Trp Val Leu Ala Phe Gly Ile Gly Leu Thr Pro Phe Leu Gly Trp
    130                 135                 140

Asn Ser Lys Asp Ser Ala Thr Asn Asn Cys Thr Glu Pro Trp Asp Gly
145                 150                 155                 160

Thr Thr Asn Glu Ser Cys Cys Leu Val Lys Cys Leu Phe Glu Asn Val
                165                 170                 175

Val Pro Met Ser Tyr Met Val Tyr Phe Asn Phe Phe Gly Cys Val Leu
            180                 185                 190

Pro Pro Leu Leu Ile Met Leu Val Ile Tyr Ile Lys Ile Phe Leu Val
        195                 200                 205

Ala Cys Arg Gln Leu Gln Arg Thr Glu Leu Met Asp His Ser Arg Thr
    210                 215                 220

Thr Leu Gln Arg Glu Ile His Ala Ala Lys Ser Leu Ala Met Ile Val
225                 230                 235                 240

Gly Ile Phe Ala Leu Cys Trp Leu Pro Val His Ala Val Asn Cys Val
                245                 250                 255

Thr Leu Phe Gln Pro Ala Gln Gly Lys Asn Lys Pro Lys Trp Ala Met
            260                 265                 270

Asn Met Ala Ile Leu Leu Ser His Ala Asn Ser Val Val Asn Pro Ile
        275                 280                 285

Val Tyr Ala Tyr Arg Asn Arg Asp Phe Arg Tyr Thr Phe His Lys Ile
    290                 295                 300

Ile Ser Arg Tyr Leu Leu Cys Gln Ala Asp Val Lys Ser Gly Asn Gly
305                 310                 315                 320

Gln Ala Gly Val Gln Pro Ala Leu Gly Val Gly Leu
                325                 330
```

<210> SEQ ID NO 31
<211> LENGTH: 318
<212> TYPE: PRT
<213> ORGANISM: Homo sapiens

<400> SEQUENCE: 31

```
Met Pro Asn Asn Ser Thr Ala Leu Ser Leu Ala Asn Val Thr Tyr Ile
1               5                   10                  15
```

```
Thr Met Glu Ile Phe Ile Gly Leu Cys Ala Ile Val Gly Asn Val Leu
             20                  25                  30

Val Ile Cys Val Val Lys Leu Asn Pro Ser Leu Gln Thr Thr Thr Phe
             35                  40                  45

Tyr Phe Ile Val Ser Leu Ala Leu Ala Asp Ile Ala Val Gly Val Leu
 50                  55                  60

Val Met Pro Leu Ala Ile Val Val Ser Leu Gly Ile Thr Ile His Phe
 65                  70                  75                  80

Tyr Ser Cys Leu Phe Met Thr Cys Leu Leu Leu Ile Phe Thr His Ala
                 85                  90                  95

Ser Ile Met Ser Leu Leu Ala Ile Ala Val Asp Arg Tyr Leu Arg Val
             100                 105                 110

Lys Leu Thr Val Arg Tyr Lys Arg Val Thr Thr His Arg Arg Ile Trp
         115                 120                 125

Leu Ala Leu Gly Leu Cys Trp Leu Val Ser Phe Leu Val Gly Leu Thr
     130                 135                 140

Pro Met Phe Gly Trp Asn Met Lys Leu Thr Ser Glu Tyr His Arg Asn
145                 150                 155                 160

Val Thr Phe Leu Ser Cys Gln Phe Val Ser Val Met Arg Met Asp Tyr
                165                 170                 175

Met Val Tyr Phe Ser Phe Leu Thr Trp Ile Phe Ile Pro Leu Val Val
            180                 185                 190

Met Cys Ala Ile Tyr Leu Asp Ile Phe Tyr Ile Ile Arg Asn Lys Leu
        195                 200                 205

Ser Leu Asn Leu Ser Asn Ser Lys Glu Thr Gly Ala Phe Tyr Gly Arg
    210                 215                 220

Glu Phe Lys Thr Ala Lys Ser Leu Phe Leu Val Leu Phe Leu Phe Ala
225                 230                 235                 240

Leu Ser Trp Leu Pro Leu Ser Ile Ile Asn Cys Ile Ile Tyr Phe Asn
                245                 250                 255

Gly Glu Val Pro Gln Leu Val Leu Tyr Met Gly Ile Leu Leu Ser His
            260                 265                 270

Ala Asn Ser Met Met Asn Pro Ile Val Tyr Ala Tyr Lys Ile Lys Lys
        275                 280                 285

Phe Lys Glu Thr Tyr Leu Leu Ile Leu Lys Ala Cys Val Val Cys His
290                 295                 300

Pro Ser Asp Ser Leu Asp Thr Ser Ile Glu Lys Asn Ser Glu
305                 310                 315

<210> SEQ ID NO 32
<211> LENGTH: 410
<212> TYPE: PRT
<213> ORGANISM: Rattus norvegicus

<400> SEQUENCE: 32

Met Gly Ser Ser Val Tyr Ile Thr Val Glu Leu Ala Ile Ala Val Leu
1               5                   10                  15

Ala Ile Leu Gly Asn Val Leu Val Cys Trp Ala Val Trp Ile Asn Ser
            20                  25                  30

Asn Leu Gln Asn Val Thr Asn Phe Phe Val Val Ser Leu Ala Ala Ala
        35                  40                  45

Asp Ile Ala Val Gly Val Leu Ala Ile Pro Phe Ala Ile Thr Ile Ser
    50                  55                  60

Thr Gly Phe Cys Ala Ala Cys His Gly Cys Leu Phe Phe Ala Cys Phe
65                  70                  75                  80
```

```
Val Leu Val Leu Thr Gln Ser Ser Ile Phe Ser Leu Ala Ile Ala
            85                  90                  95

Ile Asp Arg Tyr Ile Ala Ile Arg Ile Pro Leu Arg Tyr Asn Gly Leu
                100                 105                 110

Val Thr Gly Val Arg Ala Lys Gly Ile Ala Ile Cys Trp Val Leu
            115                 120                 125

Ser Phe Ala Ile Gly Leu Thr Pro Met Leu Gly Trp Asn Asn Cys Ser
    130                 135                 140

Gln Lys Asp Gly Asn Ser Thr Lys Thr Cys Gly Glu Gly Arg Val Thr
145                 150                 155                 160

Cys Leu Phe Glu Asp Val Val Pro Met Asn Tyr Met Val Tyr Tyr Asn
                165                 170                 175

Phe Phe Ala Phe Val Leu Leu Pro Leu Leu Leu Met Leu Ala Ile Tyr
                180                 185                 190

Leu Arg Ile Phe Leu Ala Ala Arg Arg Gln Leu Lys Gln Met Glu Ser
                195                 200                 205

Gln Pro Leu Pro Gly Glu Arg Thr Arg Ser Thr Leu Gln Lys Glu Val
        210                 215                 220

His Ala Ala Lys Ser Leu Ala Ile Ile Val Gly Leu Phe Ala Leu Cys
225                 230                 235                 240

Trp Leu Pro Leu His Ile Ile Asn Cys Phe Thr Phe Phe Cys Ser Thr
                245                 250                 255

Cys Arg His Ala Pro Pro Trp Leu Met Tyr Leu Ala Ile Ile Leu Ser
                260                 265                 270

His Ser Asn Ser Val Val Asn Pro Phe Ile Tyr Ala Tyr Arg Ile Arg
            275                 280                 285

Glu Phe Arg Gln Thr Phe Arg Lys Ile Ile Arg Thr His Val Leu Arg
290                 295                 300

Arg Gln Glu Pro Phe Gln Ala Gly Gly Ser Ser Ala Trp Ala Leu Ala
305                 310                 315                 320

Ala His Ser Thr Glu Gly Glu Gln Val Ser Leu Arg Leu Asn Gly His
                325                 330                 335

Pro Leu Gly Val Trp Ala Asn Gly Ser Ala Thr His Ser Gly Arg Arg
            340                 345                 350

Pro Asn Gly Tyr Thr Leu Gly Leu Gly Gly Gly Ser Ala Gln Gly
            355                 360                 365

Ser Pro Arg Asp Val Glu Leu Pro Thr Gln Glu Arg Gln Glu Gly Gln
    370                 375                 380

Glu His Pro Gly Leu Arg Gly His Leu Val Gln Ala Arg Val Gly Ala
385                 390                 395                 400

Ser Ser Trp Ser Ser Glu Phe Ala Pro Ser
                405                 410

<210> SEQ ID NO 33
<211> LENGTH: 410
<212> TYPE: PRT
<213> ORGANISM: Mus musculus

<400> SEQUENCE: 33

Met Gly Ser Ser Val Tyr Ile Met Val Glu Leu Ala Ile Ala Val Leu
1               5                   10                  15

Ala Ile Leu Gly Asn Val Leu Val Cys Trp Ala Val Trp Ile Asn Ser
            20                  25                  30

Asn Leu Gln Asn Val Thr Asn Phe Phe Val Val Ser Leu Ala Ala Ala
        35                  40                  45
```

Asp Ile Ala Val Gly Val Leu Ala Ile Pro Phe Ala Ile Thr Ile Ser
     50                  55                  60

Thr Gly Phe Cys Ala Ala Cys His Gly Cys Leu Phe Phe Ala Cys Phe
 65                  70                  75                  80

Val Leu Val Leu Thr Gln Ser Ser Ile Phe Ser Leu Leu Ala Ile Ala
                 85                  90                  95

Ile Asp Arg Tyr Ile Ala Ile Arg Ile Pro Leu Arg Tyr Asn Gly Leu
                100                 105                 110

Val Thr Gly Met Arg Ala Lys Gly Ile Ile Ala Ile Cys Trp Val Leu
            115                 120                 125

Ser Phe Ala Ile Gly Leu Thr Pro Met Leu Gly Trp Asn Asn Cys Ser
    130                 135                 140

Gln Lys Asp Glu Asn Ser Thr Lys Thr Cys Gly Glu Gly Arg Val Thr
145                 150                 155                 160

Cys Leu Phe Glu Asp Val Val Pro Met Asn Tyr Met Val Tyr Tyr Asn
                165                 170                 175

Phe Phe Ala Phe Val Leu Leu Pro Leu Leu Met Leu Ala Ile Tyr
                180                 185                 190

Leu Arg Ile Phe Leu Ala Ala Arg Arg Gln Leu Lys Gln Met Glu Ser
    195                 200                 205

Gln Pro Leu Pro Gly Glu Arg Thr Arg Ser Thr Leu Gln Lys Glu Val
    210                 215                 220

His Ala Ala Lys Ser Leu Ala Ile Ile Val Gly Leu Phe Ala Leu Cys
225                 230                 235                 240

Trp Leu Pro Leu His Ile Ile Asn Cys Phe Thr Phe Phe Cys Ser Thr
                245                 250                 255

Cys Gln His Ala Pro Pro Trp Leu Met Tyr Leu Ala Ile Ile Leu Ser
                260                 265                 270

His Ser Asn Ser Val Val Asn Pro Phe Ile Tyr Ala Tyr Arg Ile Arg
    275                 280                 285

Glu Phe Arg Gln Thr Phe Arg Lys Ile Ile Arg Thr His Val Leu Arg
    290                 295                 300

Arg Gln Glu Pro Phe Arg Ala Gly Gly Ser Ser Ala Trp Ala Leu Ala
305                 310                 315                 320

Ala His Ser Thr Glu Gly Glu Gln Val Ser Leu Arg Leu Asn Gly His
                325                 330                 335

Pro Leu Gly Val Trp Ala Asn Gly Ser Ala Pro His Ser Gly Arg Arg
                340                 345                 350

Pro Asn Gly Tyr Thr Leu Gly Pro Gly Gly Gly Ser Thr Gln Gly
                355                 360                 365

Ser Pro Gly Asp Val Glu Leu Leu Thr Gln His Gln Glu Gly Gln
370                 375                 380

Glu His Pro Gly Leu Gly Asp His Leu Ala Gln Gly Arg Val Gly Thr
385                 390                 395                 400

Ala Ser Trp Ser Ser Glu Phe Ala Pro Ser
                405                 410

<210> SEQ ID NO 34
<211> LENGTH: 409
<212> TYPE: PRT
<213> ORGANISM: Macaca mulatta

<400> SEQUENCE: 34

Met Gly Ser Ser Val Tyr Ile Thr Val Glu Leu Ala Ile Ala Val Leu
 1               5                  10                  15

Ala Ile Leu Gly Asn Val Leu Val Cys Trp Ala Val Trp Leu Asn Ser
            20                  25                  30

Asn Leu Gln Asn Val Thr Asn Tyr Phe Val Val Ser Leu Ala Ala Ala
        35                  40                  45

Asp Ile Ala Val Gly Val Leu Ala Ile Pro Phe Ala Ile Thr Ile Ser
50                  55                  60

Thr Gly Phe Cys Ala Ala Cys His Gly Cys Leu Phe Ile Ala Cys Phe
65                  70                  75                  80

Val Leu Val Leu Thr Gln Ser Ser Ile Phe Ser Leu Ala Ile Ala
                85                  90                  95

Ile Asp Arg Tyr Ile Ala Ile Arg Ile Pro Leu Arg Tyr Asn Gly Leu
                100                 105                 110

Val Thr Gly Thr Arg Ala Lys Gly Ile Ala Ile Cys Trp Val Leu
            115                 120                 125

Ser Phe Ala Ile Gly Leu Thr Pro Met Leu Gly Trp Asn Asn Cys Gly
    130                 135                 140

Gln Pro Lys Glu Gly Lys Asn His Ser Gln Gly Cys Gly Glu Gly Gln
145                 150                 155                 160

Val Ala Cys Leu Phe Glu Asp Val Val Pro Met Asn Tyr Met Val Tyr
                165                 170                 175

Phe Asn Phe Phe Ala Cys Val Leu Val Pro Leu Leu Leu Met Leu Gly
                180                 185                 190

Val Tyr Leu Arg Ile Phe Leu Ala Ala Arg Arg Gln Leu Lys Gln Met
            195                 200                 205

Glu Ser Gln Pro Leu Pro Gly Glu Arg Ala Arg Ser Thr Leu Gln Lys
    210                 215                 220

Glu Val His Ala Ala Lys Ser Leu Ala Ile Ile Val Gly Leu Phe Ala
225                 230                 235                 240

Leu Cys Trp Leu Pro Leu His Ile Ile Asn Cys Phe Thr Phe Phe Cys
                245                 250                 255

Pro Asp Cys Asn His Ala Pro Leu Trp Leu Met Tyr Leu Ala Ile Val
                260                 265                 270

Leu Ser His Thr Asn Ser Val Val Asn Pro Phe Ile Tyr Ala Tyr Arg
            275                 280                 285

Ile Arg Glu Phe Arg Gln Thr Phe Arg Lys Ile Ile Arg Ser His Val
    290                 295                 300

Leu Arg Gln Gln Glu Pro Phe Lys Ala Ala Gly Thr Ser Ala Arg Val
305                 310                 315                 320

Leu Ala Ala His Gly Ser Asp Gly Glu Gln Val Ser Leu Arg Leu Asn
                325                 330                 335

Gly His Pro Pro Gly Val Trp Ala Asn Gly Ser Ala Pro His Pro Glu
                340                 345                 350

Arg Arg Pro Asn Gly Tyr Ala Leu Gly Leu Val Ser Gly Gly Ser Thr
            355                 360                 365

Gln Glu Ser Gln Gly Asn Thr Ser Leu Pro Asp Val Glu Leu Leu Ser
    370                 375                 380

His Glu Leu Lys Gly Val Cys Pro Glu Pro Gly Leu Asp Asp Pro
385                 390                 395                 400

Leu Ala Gln Gly Gly Ala Gly Val Ser
                405

<210> SEQ ID NO 35
<211> LENGTH: 442
<212> TYPE: PRT
<213> ORGANISM: Danio rerio

<400> SEQUENCE: 35

```
Met Leu Asn Asn Val Phe Asp Val Leu Tyr Met Ile Leu Glu Leu Leu
1               5                   10                  15

Ile Ala Leu Leu Ser Val Leu Gly Asn Val Leu Val Cys Trp Ala Val
            20                  25                  30

Gly Leu Asn Ser Asn Leu Gln Ser Ile Thr Asn Phe Phe Val Val Ser
                35                  40                  45

Leu Ala Val Ala Asp Ile Ala Val Gly Val Leu Ala Ile Pro Phe Ser
        50                  55                  60

Ile Val Ile Ser Thr Gly Phe Cys Ala Asn Phe Tyr Gly Cys Leu Phe
65                  70                  75                  80

Ile Ala Cys Phe Val Leu Val Leu Thr Gln Ser Ser Ile Phe Ser Leu
                85                  90                  95

Leu Ala Ile Ala Ile Asp Arg Tyr Ile Ala Ile Lys Ile Pro Leu Arg
            100                 105                 110

Tyr Asn Ser Leu Val Thr Gly Gln Arg Ala Arg Gly Ile Ile Ala Ile
                115                 120                 125

Cys Trp Val Leu Ser Val Ile Ile Gly Leu Thr Pro Met Leu Gly Trp
            130                 135                 140

His Lys Ala Arg Leu Gln Glu Gly His Asn Gly Thr Cys Pro Pro Gly
145                 150                 155                 160

Met Met Glu Cys Leu Phe Glu Glu Val Val Met Asp Tyr Met Val
                165                 170                 175

Tyr Phe Asn Phe Phe Ala Cys Val Leu Val Pro Leu Leu Leu Met Leu
            180                 185                 190

Ala Ile Tyr Leu Arg Ile Phe Met Ala Ala Arg His Gln Leu Lys Cys
            195                 200                 205

Ile Glu Ser Lys Ala Ile Pro Cys Glu Leu Lys Ser Arg Ser Thr Leu
            210                 215                 220

Gln Lys Glu Val His Ala Ala Lys Ser Leu Ala Ile Ile Val Gly Leu
225                 230                 235                 240

Phe Ala Val Cys Trp Leu Pro Leu His Ile Ile Asn Cys Phe Thr Leu
            245                 250                 255

Phe Cys Pro Glu Cys Glu Arg Pro Pro Ala Leu Ile Met Tyr Leu Ala
            260                 265                 270

Ile Ile Leu Ser His Ala Asn Ser Val Val Asn Pro Phe Ile Tyr Ala
            275                 280                 285

Tyr Arg Ile Arg Glu Phe Arg His Thr Phe Arg Lys Ile Val Arg Tyr
            290                 295                 300

His Ile Leu Gly Arg Arg Glu Pro Leu Ser Cys Asn Gly Ser Thr Arg
305                 310                 315                 320

Thr Ser Thr Arg Thr Ser Val Ala Asp Ser Leu Arg Ile Lys Val Asn
            325                 330                 335

Gly Leu Val Arg Glu Leu Tyr Ala Glu Gln Ser Ser Thr Ser Ser
            340                 345                 350

Cys Glu Ser Ala Glu Pro Gly His Thr His Arg Pro Val Ser Thr Glu
            355                 360                 365

Asn Ser Ile Leu Asp Asn Gln Pro Ile Glu Ile Ser Asn Ser His Arg
            370                 375                 380

His Thr Ala Leu Arg His Pro Glu Ser Pro Leu Thr Gly Asn Asn Glu
385                 390                 395                 400

Gly Leu Ala Cys Arg Lys His Ala Gly Leu Asp Ile Thr Asp Gly Lys
            405                 410                 415
```

```
Asp Leu Ser Ser Pro Leu His Ile Lys Ser Ala Leu Tyr Val Gln Thr
            420                 425                 430

Ala His Cys Val Glu Leu Thr Glu Val Ser
        435                 440

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      10xHis tag

<400> SEQUENCE: 36

His His His His His His His His His His
1               5                   10
```